US012453560B2

(12) United States Patent
Skolnick et al.

(10) Patent No.: US 12,453,560 B2
(45) Date of Patent: Oct. 28, 2025

(54) MEDICAL CUTTING DEVICES HAVING STATIC COMPONENTS, WORKING BLADE BODIES, RAILS, STRUTS, CHANNELS FOR FLUID AND GAS FLOW, AND HAND-PIECE AND ROBOTIC ARM ATTACHMENT CAPABILITIES

(71) Applicant: Innovations 4 Surgery, LLC, Chapel Hill, NC (US)

(72) Inventors: Edward Skolnick, Denville, NJ (US); Antoine Kaeslin, Jersey City, NJ (US)

(73) Assignee: Innovations 4 Surgery, LLC, Chapel Hill, NC (US)

( * ) Notice: Subject to any disclaimer, the term of this patent is extended or adjusted under 35 U.S.C. 154(b) by 0 days.

(21) Appl. No.: 18/759,961

(22) Filed: Jun. 30, 2024

(65) Prior Publication Data

US 2025/0000519 A1 Jan. 2, 2025

Related U.S. Application Data

(60) Provisional application No. 63/619,549, filed on Jan. 10, 2024, provisional application No. 63/542,630, (Continued)

(51) Int. Cl.
*A61B 17/14* (2006.01)
*A61B 17/32* (2006.01)

(52) U.S. Cl.
CPC ............ *A61B 17/142* (2016.11); *A61B 17/32* (2013.01)

(58) Field of Classification Search
CPC ....... A61B 17/14; A61B 17/142; A61B 17/32; A61B 17/320068; A61B 2017/320074;
(Continued)

(56) References Cited

U.S. PATENT DOCUMENTS 1,368,842 A 2/1921 Roeling
3,786,814 A 1/1974 Armao
(Continued)

FOREIGN PATENT DOCUMENTS

AU 2021216849 A1 9/2022
CN 112998802 A 3/2022
(Continued)

OTHER PUBLICATIONS

PCT Search Report and Written Opinion for PCT International Application No. PCT/US2024/036305.
(Continued)

*Primary Examiner* — Eric S Gibson
(74) *Attorney, Agent, or Firm* — Olive Law Group, PLLC

(57) ABSTRACT

Medical cutting devices having static components, working blade bodies, rails, struts, channels for fluid and gas flow, and hand-piece and robotic arm attachment capabilities are disclosed. According to an aspect, a cutting device includes a working blade body being configured for operable connection to a source of movement. The cutting device also includes a static component being configured for operable connection to the source of movement. The static component comprises at least one rail, wherein the at least one rail extends substantially the same length as the working blade body.

45 Claims, 225 Drawing Sheets

Related U.S. Application Data filed on Oct. 5, 2023, provisional application No. 63/530,782, filed on Aug. 4, 2023, provisional application No. 63/524,631, filed on Jul. 1, 2023.

(58) Field of Classification Search
CPC ....... A61B 2017/320075; A61B 2017/320082; A61B 2017/320088
See application file for complete search history.

(56) References Cited

U.S. PATENT DOCUMENTS

| | | | |
|---|---|---|---|
| 3,805,787 A | 4/1974 | Banko | |
| 4,008,720 A | 2/1977 | Brinckmann | |
| 4,491,132 A | 1/1985 | Aikins | |
| 5,087,261 A | 2/1992 | Leif | |
| 5,122,142 A | 6/1992 | Pascaloff | |
| 5,188,102 A | 2/1993 | Idemoto | |
| 5,248,296 A | 9/1993 | Alliger | |
| 5,261,922 A | 11/1993 | Hood | |
| 5,318,570 A | 6/1994 | Hood | |
| 5,322,055 A | 6/1994 | Davison et al. | |
| 5,624,393 A | 4/1997 | Diamond | |
| 5,728,130 A | 3/1998 | Ishikawa | |
| 5,989,275 A | 11/1999 | Estabrook | |
| 6,033,375 A | 3/2000 | Brumbach | |
| 6,379,371 B1 | 4/2002 | Novak | |
| 6,443,969 B1 | 9/2002 | Novak | |
| 7,497,860 B2 * | 3/2009 | Carusillo | A61B 17/142 606/86 R |
| 7,638,958 B2 | 12/2009 | Philipp | |
| 7,704,254 B2 * | 4/2010 | Walen | A61B 34/20 606/82 |
| 8,323,285 B2 * | 12/2012 | Walen | A61B 17/142 606/82 |
| 8,343,178 B2 | 1/2013 | Novak | |
| 8,348,880 B2 | 1/2013 | Messerly | |
| D680,218 S | 4/2013 | Darian | |
| 8,608,745 B2 | 12/2013 | Guzman et al. | |
| 8,628,534 B2 | 1/2014 | Jones | |
| 8,961,536 B2 | 2/2015 | Nikou et al. | |
| 9,320,528 B2 | 4/2016 | Voic | |
| 9,439,655 B2 * | 9/2016 | Cosgrove | A61B 17/142 |
| 9,554,809 B2 | 1/2017 | Lark et al. | |
| 9,559,624 B2 | 1/2017 | Philipp | |
| 10,004,517 B2 | 6/2018 | Philipp | |
| 10,022,131 B1 | 7/2018 | Burley et al. | |
| 10,238,415 B2 | 3/2019 | Naono | |
| 10,314,595 B2 | 6/2019 | Lark et al. | |
| 10,517,610 B2 | 12/2019 | Philipp et al. | |
| 10,531,929 B2 | 1/2020 | Widenhouse et al. | |
| 10,687,824 B2 * | 6/2020 | Shiels | A61B 17/142 |
| 10,695,074 B2 | 6/2020 | Carusillo | |
| 10,702,296 B2 | 7/2020 | Boudreaux et al. | |
| 11,439,411 B2 | 9/2022 | Forstein et al. | |
| 11,471,168 B2 * | 10/2022 | Lark | A61B 17/1628 |
| 11,490,898 B2 | 11/2022 | Gisler | |
| 11,534,182 B2 | 12/2022 | Xie | |
| 11,540,841 B2 | 1/2023 | Carusillo | |
| 11,812,973 B2 * | 11/2023 | Sieh | A61B 17/142 |
| 11,812,977 B2 | 11/2023 | Carusillo | |
| 12,011,182 B2 * | 6/2024 | Lark | A61B 17/1615 |
| 2003/0204199 A1 | 10/2003 | Novak | |
| 2005/0273127 A1 | 12/2005 | Novak | |
| 2007/0083209 A1 * | 4/2007 | Schenberger | A61B 17/142 606/82 |
| 2008/0009848 A1 | 1/2008 | Paraschiv | |
| 2010/0064525 A1 * | 3/2010 | Walen | A61B 34/20 30/144 |
| 2010/0292701 A1 * | 11/2010 | Fisher | A61B 17/142 606/82 |
| 2012/0172786 A1 | 7/2012 | Mackool | |
| 2013/0060278 A1 | 3/2013 | Bozung | |
| 2013/0204285 A1 | 8/2013 | Gouery | |
| 2015/0005771 A1 | 1/2015 | Voic | |
| 2015/0088137 A1 | 3/2015 | Manna | |
| 2016/0089155 A1 | 3/2016 | Lark et al. | |
| 2017/0056052 A1 | 3/2017 | Dickerson | |
| 2017/0340339 A1 | 11/2017 | Madan | |
| 2017/0340344 A1 | 11/2017 | Boudreaux et al. | |
| 2017/0340345 A1 | 11/2017 | Yates | |
| 2017/0348007 A1 | 12/2017 | Shiels | |
| 2018/0064448 A1 * | 3/2018 | Mac an Tuile | A61B 17/14 |
| 2018/0344346 A1 | 12/2018 | Naono | |
| 2019/0021745 A1 * | 1/2019 | Shiels | A61B 17/142 |
| 2021/0100561 A1 * | 4/2021 | Sieh | A61B 17/142 |
| 2021/0121195 A1 | 4/2021 | Richards | |
| 2021/0186525 A1 * | 6/2021 | Lark | A61B 17/1615 |
| 2021/0322029 A1 | 10/2021 | McGinley et al. | |
| 2022/0192754 A1 | 6/2022 | Bonny et al. | |
| 2022/0257263 A1 | 8/2022 | Chappuis et al. | |
| 2022/0338935 A1 | 10/2022 | Bell | |
| 2022/0387049 A1 * | 12/2022 | Lark | A61B 17/1628 |
| 2023/0190302 A1 * | 6/2023 | Lark | A61B 17/1644 |
| 2023/0190303 A1 | 6/2023 | Lark et al. | |
| 2023/0190304 A1 | 6/2023 | Lark et al. | |
| 2023/0190325 A1 | 6/2023 | Lark et al. | |
| 2023/0190327 A1 * | 6/2023 | Lark | A61B 17/14 |
| 2025/0000519 A1 * | 1/2025 | Skolnick | G16H 40/63 |

FOREIGN PATENT DOCUMENTS

| | | | |
|---|---|---|---|
| CN | 115227332 | A | 10/2022 |
| DE | 10 2008 063 239 | A1 | 6/2010 |
| EP | 3808304 | A1 | 4/2021 |
| EP | 3926639 | A1 | 12/2021 |
| JP | 2021118881 | A | 10/2021 |
| KR | 102511541 | B1 | 6/2017 |
| WO | 2010132216 | A1 | 11/2010 |
| WO | 2019/213241 | A1 | 11/2019 |
| WO | 2020210782 | A1 | 10/2020 |
| WO | 2021074720 | A1 | 4/2021 |
| WO | 2023/122295 | A2 | 6/2023 |
| WO | 2024044365 | A1 | 2/2024 |

OTHER PUBLICATIONS

Notice of Allowance for U.S. Appl. No. 14/700,189 dated Jan. 20, 2017.
Notice of Allowance for U.S. Appl. No. 15/407,411 dated Jul. 18, 2019.
Office Action for U.S. Appl. No. 14/700,189 dated Aug. 18, 2016.
Amendment in Response to Office Action for U.S. Appl. No. 14/700,189 dated Sep. 17, 2016.
Office Action for U.S. Appl. No. 15/407,411 dated Jan. 17, 2017.
Amendment in Response to Office Action for U.S. Appl. No. 15/407,411 dated Mar. 19, 2019.
Office Action for U.S. Appl. No. 17/128,098 dated May 27, 2022.
Search Report for PCT International Application PCT/US2022/053856.
Written Opinion for PCT International Application PCT/US2022/053856.
U.S. Appl. No. 18/759,961, filed Jun. 30, 2024.
U.S. Appl. No. 18/759,963, filed Jun. 30, 2024.
U.S. Appl. No. 18/759,972, filed Jun. 30, 2024.
U.S. Appl. No. 18/759,974, filed Jun. 30, 2024.
U.S. Appl. No. 18/759,977, filed Jun. 30, 2024.
PCT International Application No. PCT/US2024/036305.
Office Action for U.S. Appl. No. 18/087,749 dated Mar. 6, 2025.
Office Action for U.S. Appl. No. 18/087,741 dated Feb. 21, 2025.

* cited by examiner

Bending Down

Front View

Bending Up

Front View

Positive Torsion and Bending Up
Front View

Clinical Cutting Example (Tibia)

During execution of cutting, acquire strain gauge & location data to demonstrate deviations from planned resection.

Example of real-time strain gauge data used to generate the kinematics of the blade edge.

Clinical Cutting Example (Tibia)

Generate individual instances of blade kinematics based on sensor data.

Front View (Blade Edge)

Front View (Bone Cutting Section)

Clinical Cutting Example (Tibia)

Surface map the response of all cutting instances to generate real-time resulting 3D surface trajectory relative to planned cutting trajectory. Provide surface mapped data to robotic/navigation system and user.

Clinical Cutting Example (Tibia)

Post-op, analyze data to determine consistent trends in cutting error relative to other data sets and use for real-time corrections in future applications. Data could demonstrate a pattern across multiple data sets where there is a consistent anatomic specific region of skiving.

Depth Detection

Depth of bone detected from using transmitted and received audio waves.

MEDICAL CUTTING DEVICES HAVING STATIC COMPONENTS, WORKING BLADE BODIES, RAILS, STRUTS, CHANNELS FOR FLUID AND GAS FLOW, AND HAND-PIECE AND ROBOTIC ARM ATTACHMENT CAPABILITIES

CROSS REFERENCE TO RELATED APPLICATIONS

This application claims priority to U.S. Provisional Patent Application No. 63/524,631, filed Jul. 1, 2023, U.S. Provisional Patent Application No. 63/530,782, filed Aug. 4, 2023, U.S. Provisional Patent Application No. 63/542,630, filed Oct. 5, 2023, and U.S. Provisional Patent Application No. 63/619,549, filed Jan. 10, 2024; the content of which is incorporated herein by reference in its entirety.

TECHNICAL FIELD

The presently disclosed subject matter relates generally to medical devices. Particularly, the presently disclosed subject matter relates to medical cutting devices having static components, working blade bodies, rails, struts, channels for fluid and gas flow, and hand-piece and robotic arm attachment capabilities.

BACKGROUND

In orthopedic procedures, oscillating saw blades encounter several challenges that impact surgical outcomes. These blades often produce cuts that are inconsistent and may result in uneven surfaces, affecting the fit and alignment of implants. Additionally, the phenomenon of skiving can lead to deviations from the intended cutting path, potentially causing damage to surrounding tissues. Traditional saw blades lack the precision required for intricate cuts in complex anatomical areas, which can compromise surgical accuracy. Moreover, the high-speed oscillation of these blades generates heat, increasing the risk of thermal necrosis in bone and soft tissues, which may lead to post-operative complications. Operation of these blades generates significant vibration, which can be disruptive and affect the surgeon's ability to maintain steady control during the procedure. Addressing these issues is crucial for improving surgical outcomes and patient safety in orthopedic surgery through advancements in blade design, surgical techniques, and the integration of innovative technologies.

Traditional oscillating and reciprocating bone saws have employed a variety of different measures to address disadvantages of heat generation while cutting. This includes adding features to the blade itself (e.g., cutouts, protrusions, etc.) to allow for increased debris removal. It also includes surgeons resorting to externally applying saline. However, each of these methods have been ineffective at resolving the problem.

A majority of saw blades used for small/large bone osteotomies (i.e., for completing boney cuts in total knee procedures) are disposable requiring the use of a new one for each procedure. This makes clinicians/hospital administrators very sensitive to pricing when purchasing these devices for their surgery centers. Although saw blades are relatively inexpensive (i.e., they've become a very commoditized product), there is little room for premium products to come into the market without having this cost sensitivity in mind.

Precision of cuts is of critical importance when carrying out procedures such as joint replacements. In a majority of traditional cases, cutting guides are used which help to stabilize the blade and keep it on a prescribed plane. Even with the use of cutting guides, blades can deflect based on user bias and/or based on interaction with the bone that changes with each patient. Standard blades can also cause misalignment of the guide itself by disrupting the pinned connections that allow for fixation to the patients bone. These changes are typically imperceptible to the user during the procedure and lead to inconsistencies that influence implant alignment, implant fixation, and patient satisfaction.

Robotic platforms in combination with navigation systems allow for solving some of the problems caused by more manually based cutting guides. The goal of these enabled technologies is to provide a more consistent and accurate results based on a plan. However, all robotic systems (e.g. whether robotic arms, hand-held robotics, and/or micro-robotic guides) use basic saw blades (e.g., the blades all lack any enabling technology) and lack the ability to understand what is happening inside the cut during the cutting process (e.g. skiving). Therefore, robotic systems lack the ability to provide feedback to the user relating to the cutting process and/or provide real-time output functionality through the robotic/navigation systems. For that reason, concerns persist relating to providing sufficient surgeon haptics, increasing precision, optimizing cutting efficiency, maintaining tissue integrity, and ensuring the long-term fixation of implants.

There is also an emergence of AR/VR systems being incorporated into the operating room to support visual feedback to surgeons in combination with navigation and robotics. This feedback has been useful in providing information that would typically be on a screen adjacent to the workspace and allows for execution of procedures without taking eyes off a patient. However, there is still limited interactive feedback and haptics that derive from the cutting plane and with respect to the cutting device.

Common challenges with manually driven drills in orthopedic procedures include deviations from the planned path, inconsistent drill depth, and the inability to provide real-time feedback on bone density or drill positioning. These issues can lead to inaccuracies, potential damage to surrounding tissues, and suboptimal implant fixation.

Robotic platforms in combination with navigation systems allow for solving some of the problems caused by more manually based drilling guides. The goal of these enabled technologies is to provide more consistent and accurate results based on a plan. However, all robotic systems (e.g., whether robotic arms, hand-held robotics, and/or micro-robotic guides) use basic drilling devices (e.g., the drills all lack any enabling technology) and lack the ability to understand what is happening inside the drill site during the drilling process (e.g., deviations or depth control). Therefore, robotic systems lack the ability to provide feedback to the user relating to the drilling process and/or provide real-time output functionality through the robotic/navigation systems. For that reason, concerns persist relating to providing sufficient surgeon haptics, increasing precision, optimizing drilling efficiency, maintaining tissue integrity, and ensuring the long-term fixation of implants.

Machine learning and predictive analytics hold significant promise for enhancing surgical planning and execution in orthopedic procedures. By analyzing vast amounts of surgical data, these technologies can predict optimal cutting paths, blade usage, and potential complications, thereby reducing inconsistencies and improving implant alignment. Machine learning algorithms can be trained to recognize patterns in surgical procedures, providing real-time feedback and adjustments to ensure precision. Predictive analytics can forecast the outcomes of different surgical approaches, enabling surgeons to make more informed decisions and customize procedures to individual patient anatomies. However, there is still limited data coming from the cutting plane and the cutting devices themselves throughout the execution of the cutting process to inform these models. This gap hinders the ability to fully leverage these technologies, as real-time data from the cutting plane and cutting devices is crucial for further enhancing the accuracy and effectiveness of machine learning and predictive analytics in surgical applications. This challenge is also present in drilling devices used in orthopedics, where precise control and feedback are critical for successful outcomes. Despite this gap in generating real-time data from within the cutting site, the future integration of advanced data analytics can lead to more accurate cuts, reduced surgical times, and improved overall patient outcomes.

For at least the aforementioned reasons, there is a need for improved surgical devices and techniques.

BRIEF DESCRIPTION OF THE DRAWINGS

Figure 1:
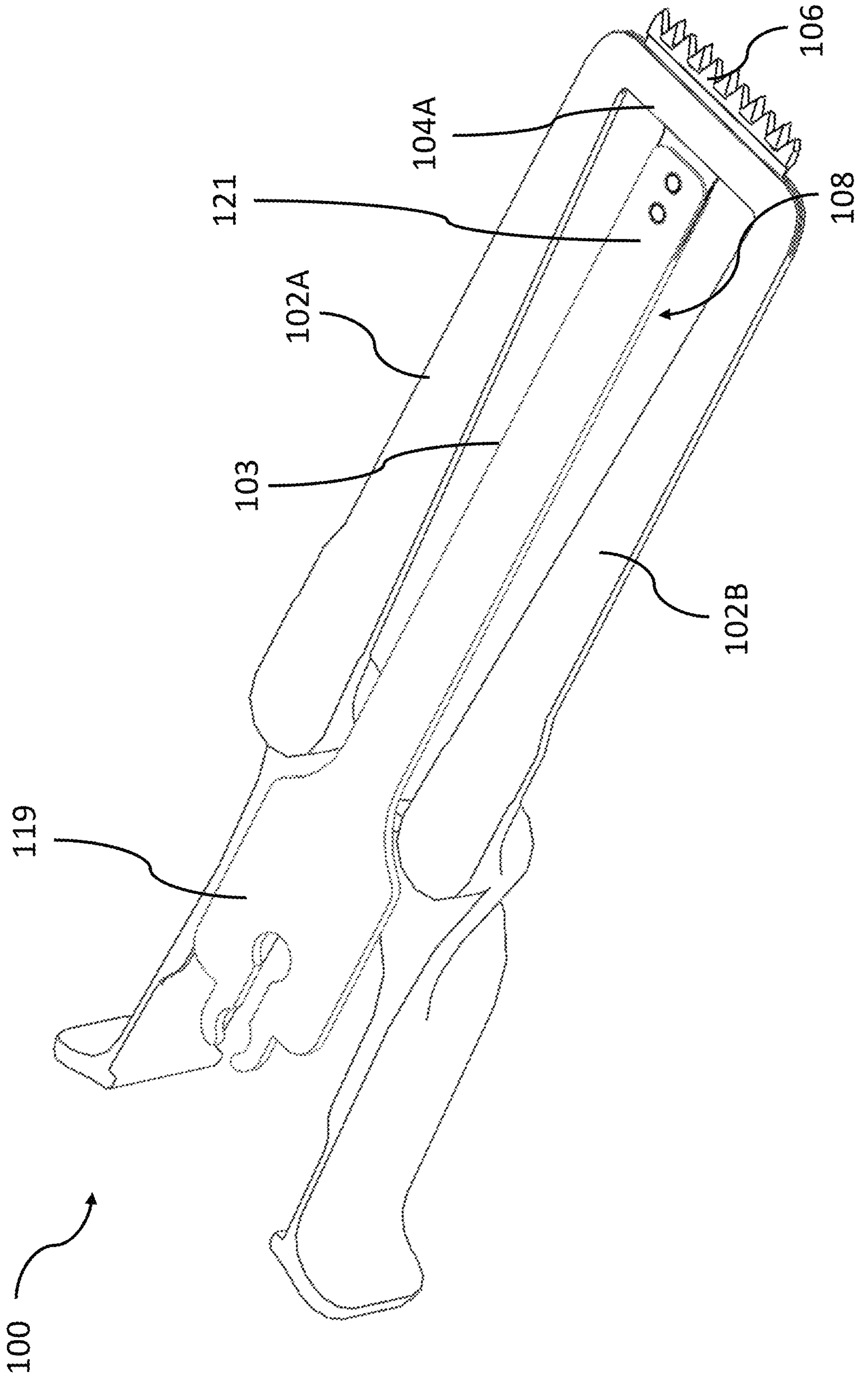
Figure 2:
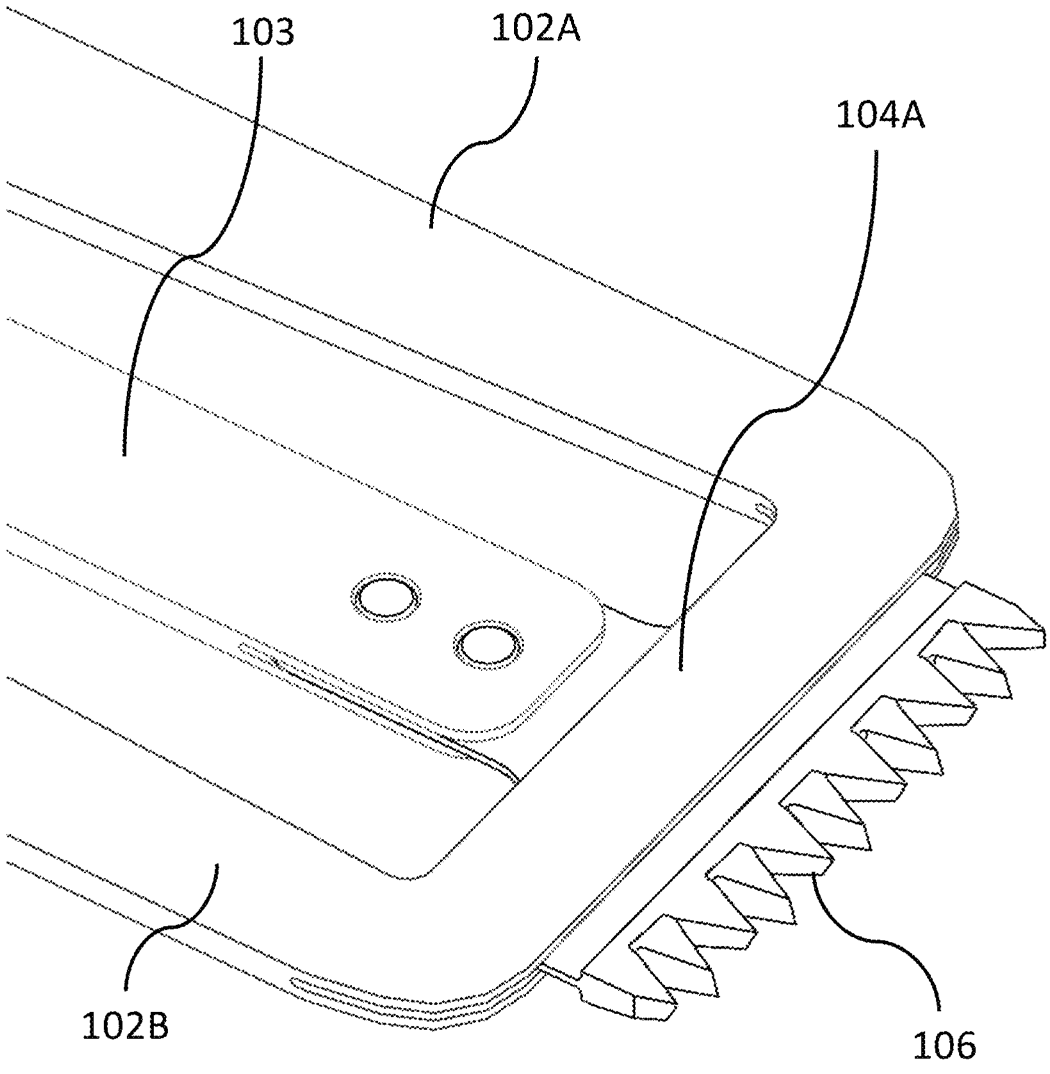
Figure 3:
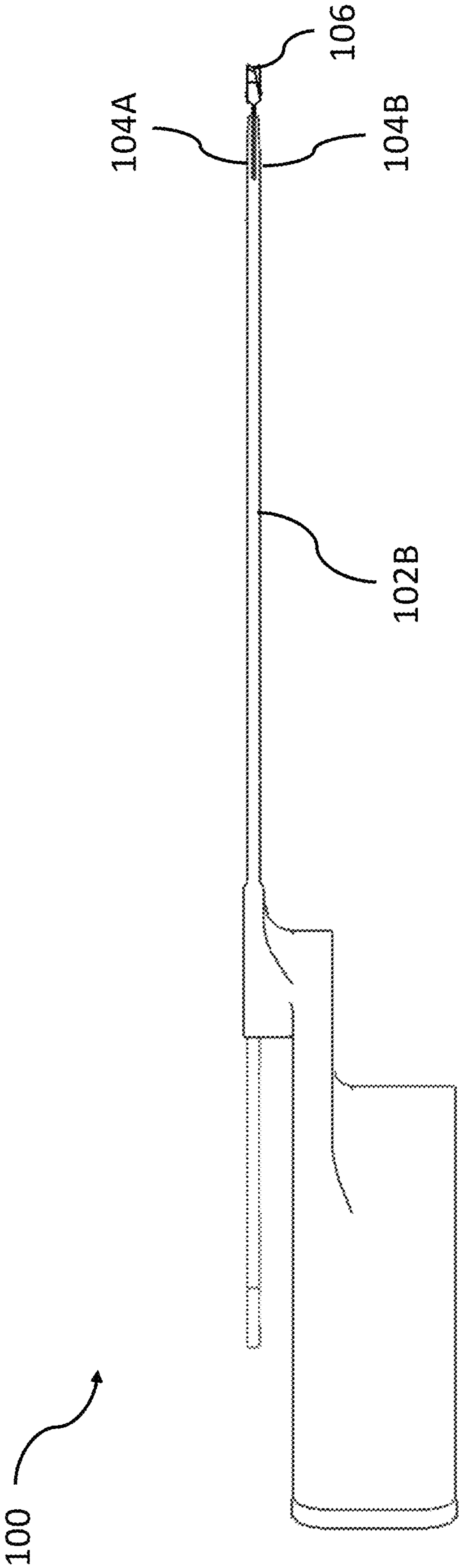
Figure 4A:
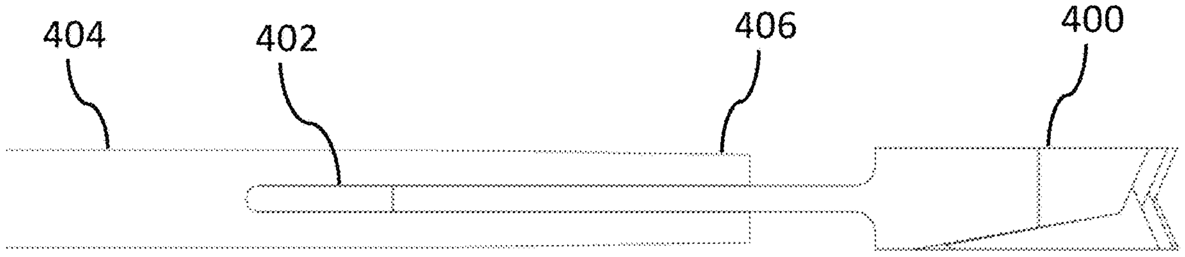
Figure 4B:
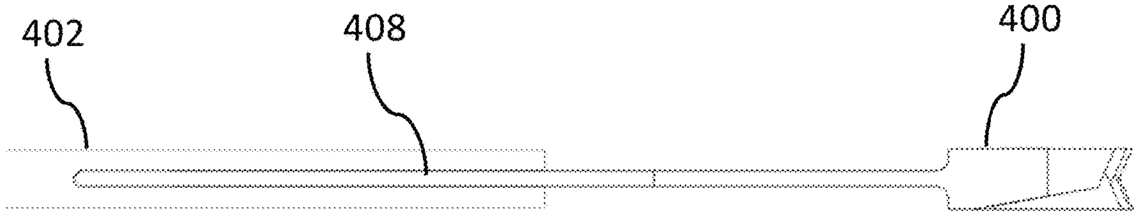
Figure 4C:
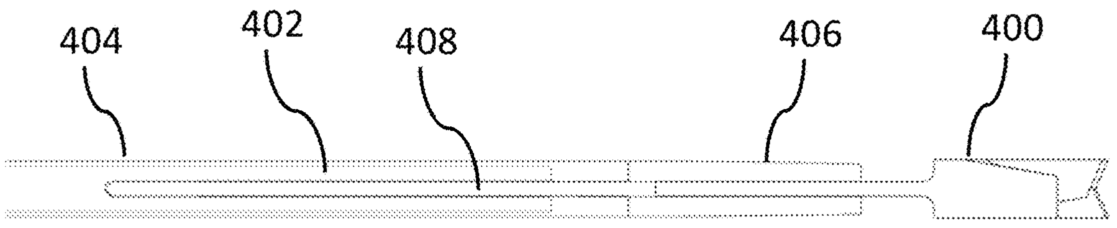
Figure 5:
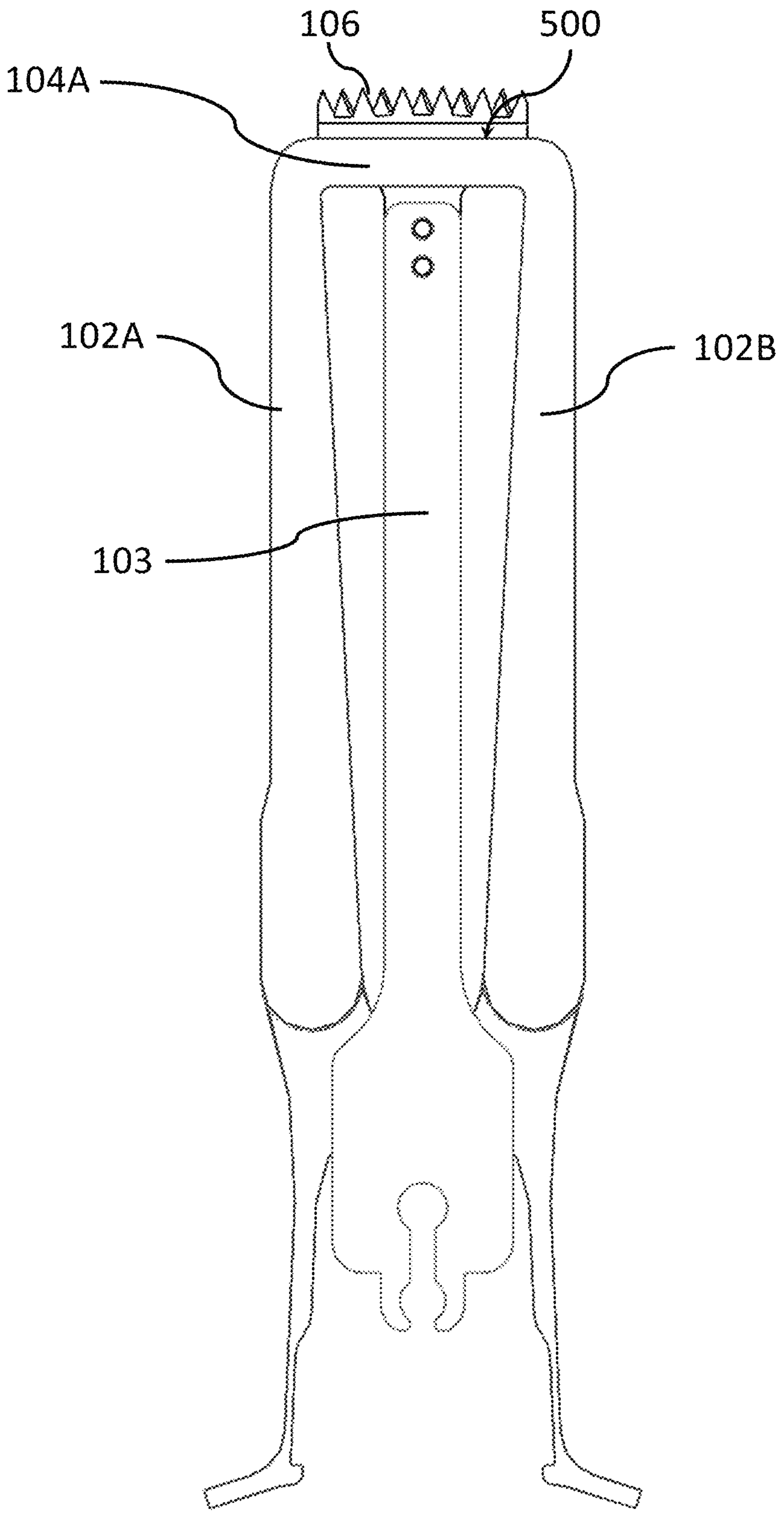
Figure 6:
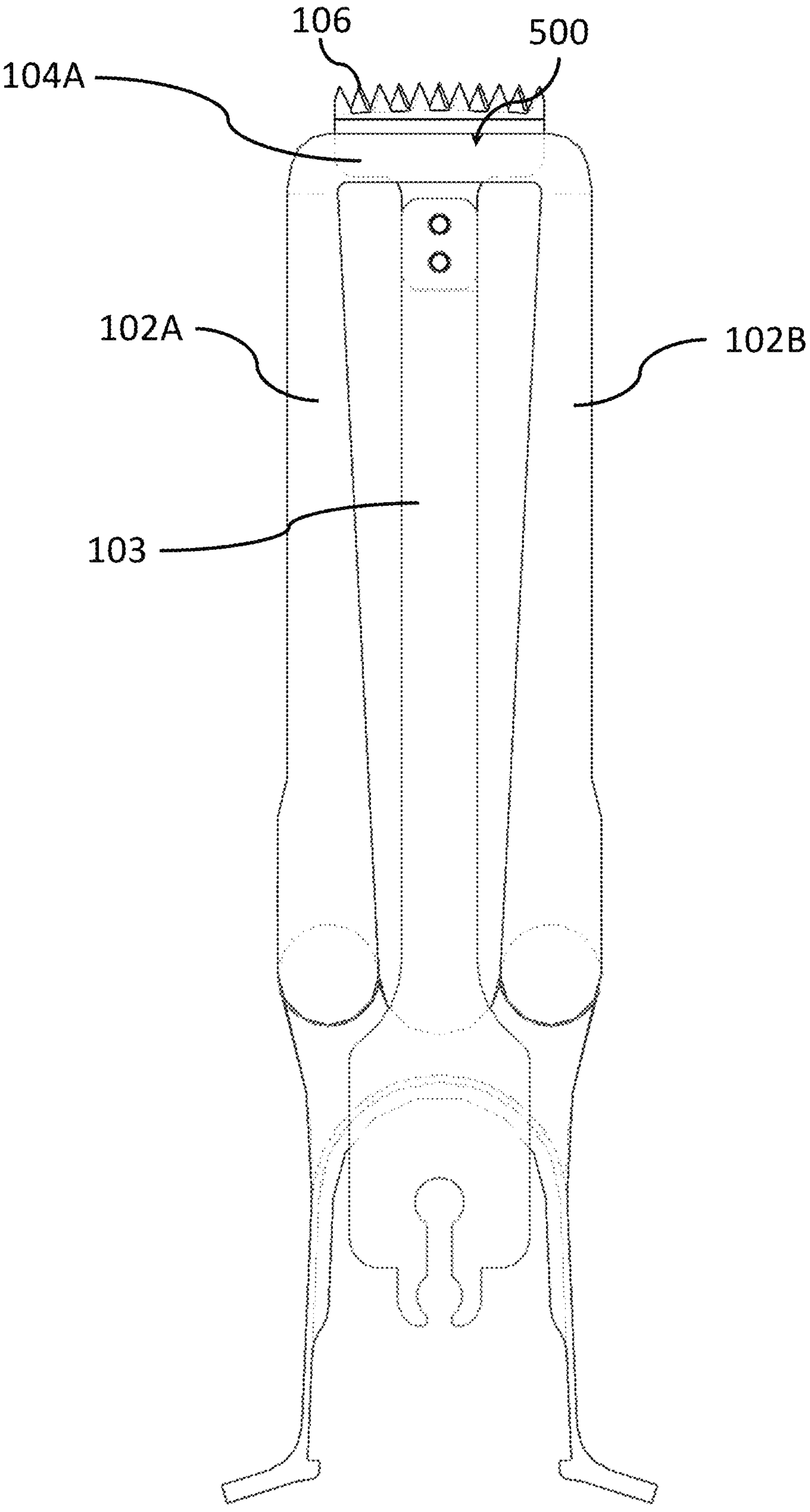
Figure 7:
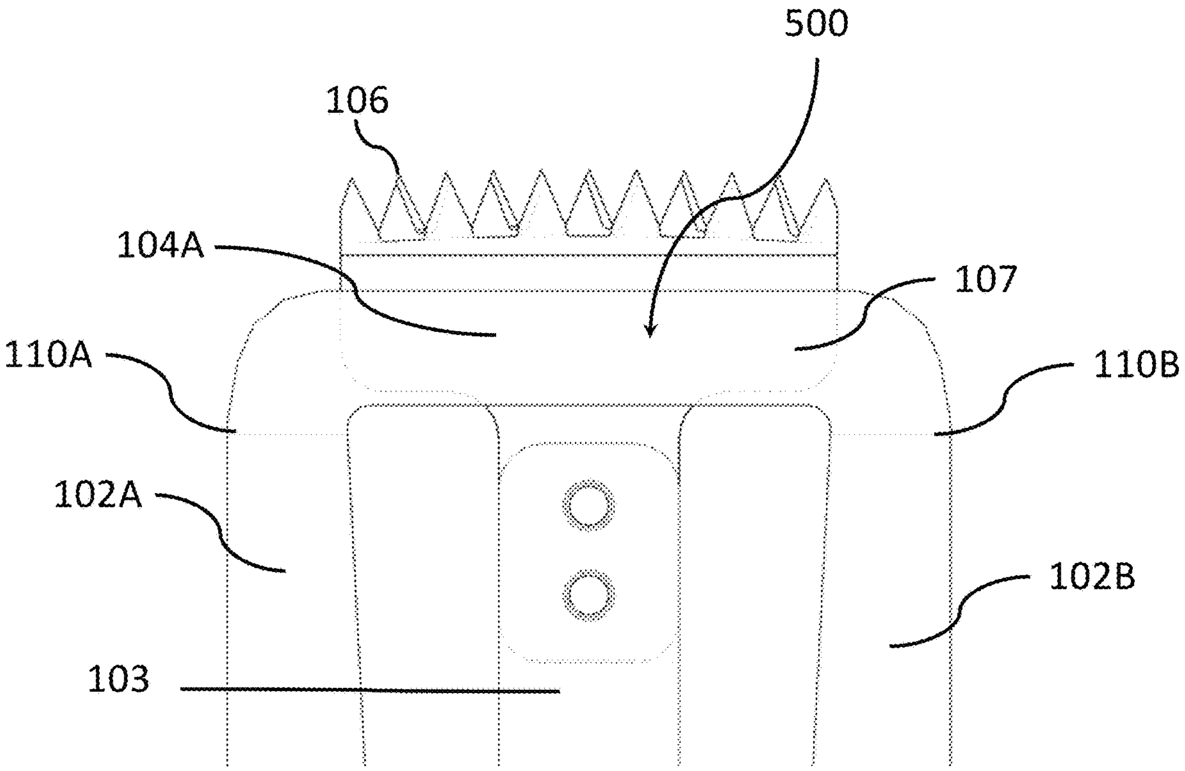
Figure 8:
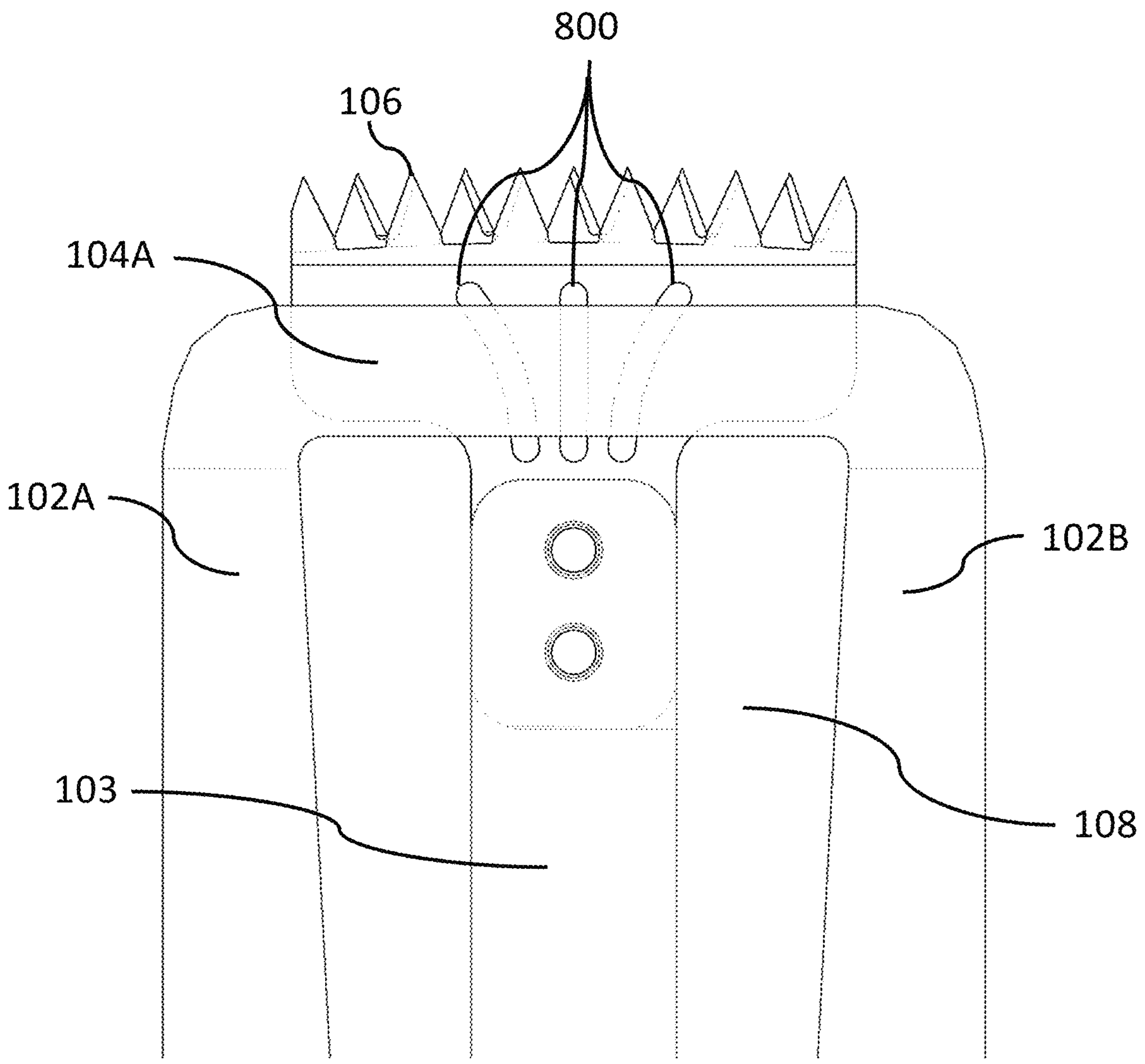
Figure 9A:
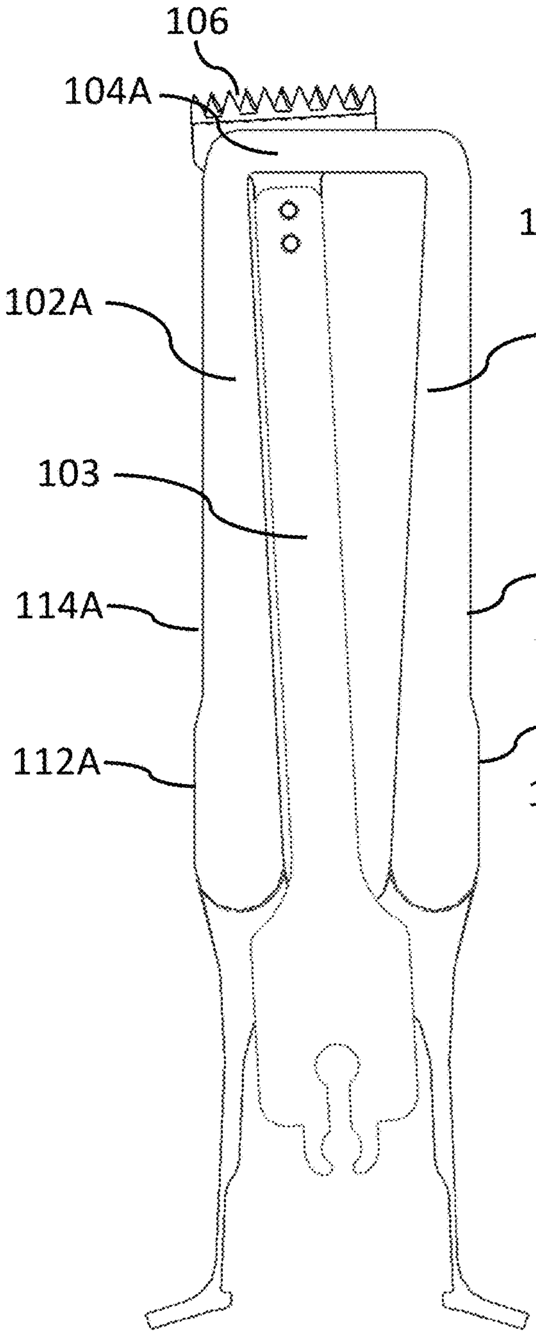
Figure 9B:
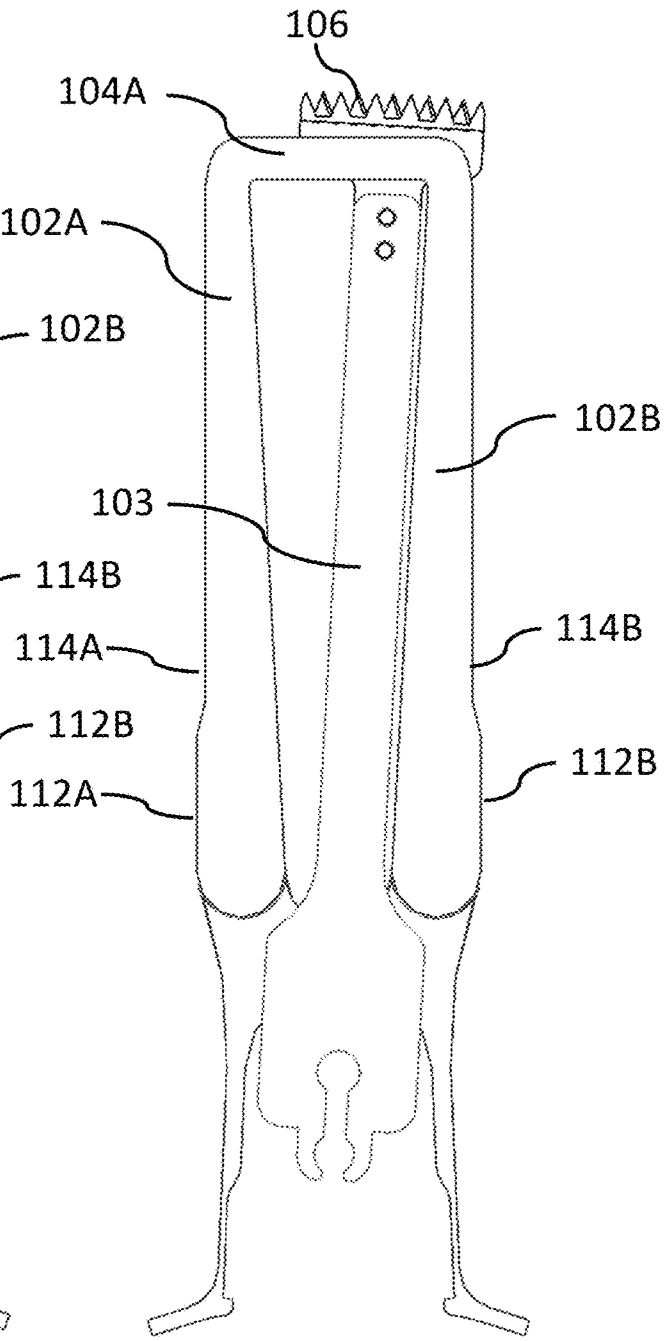
Figure 10A:
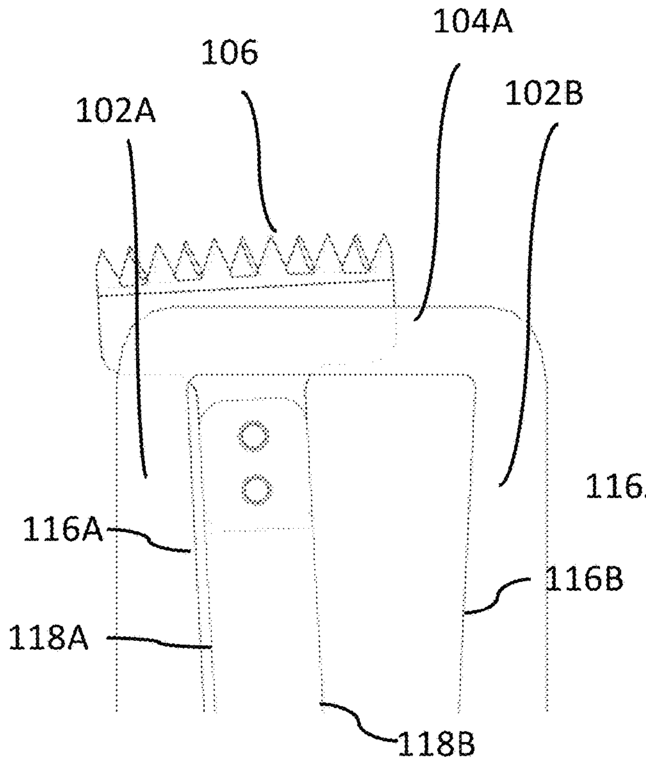
Figure 10B:
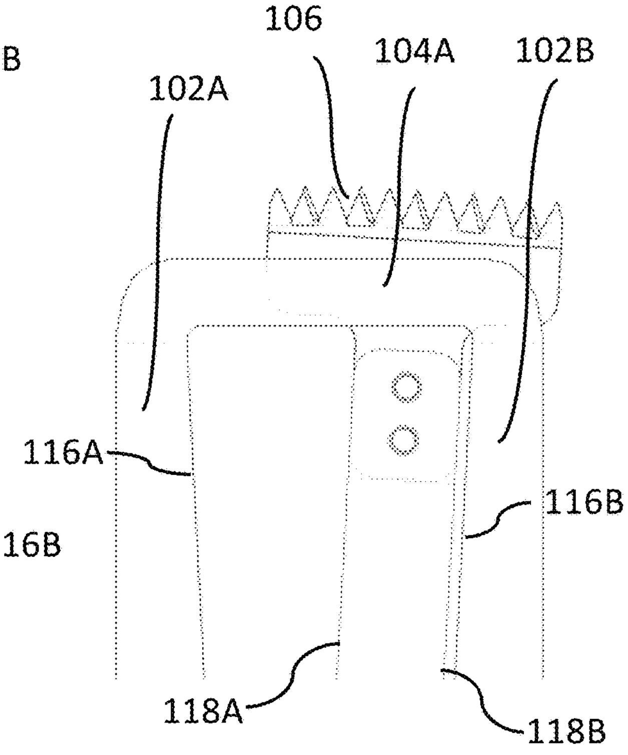
Figure 12:
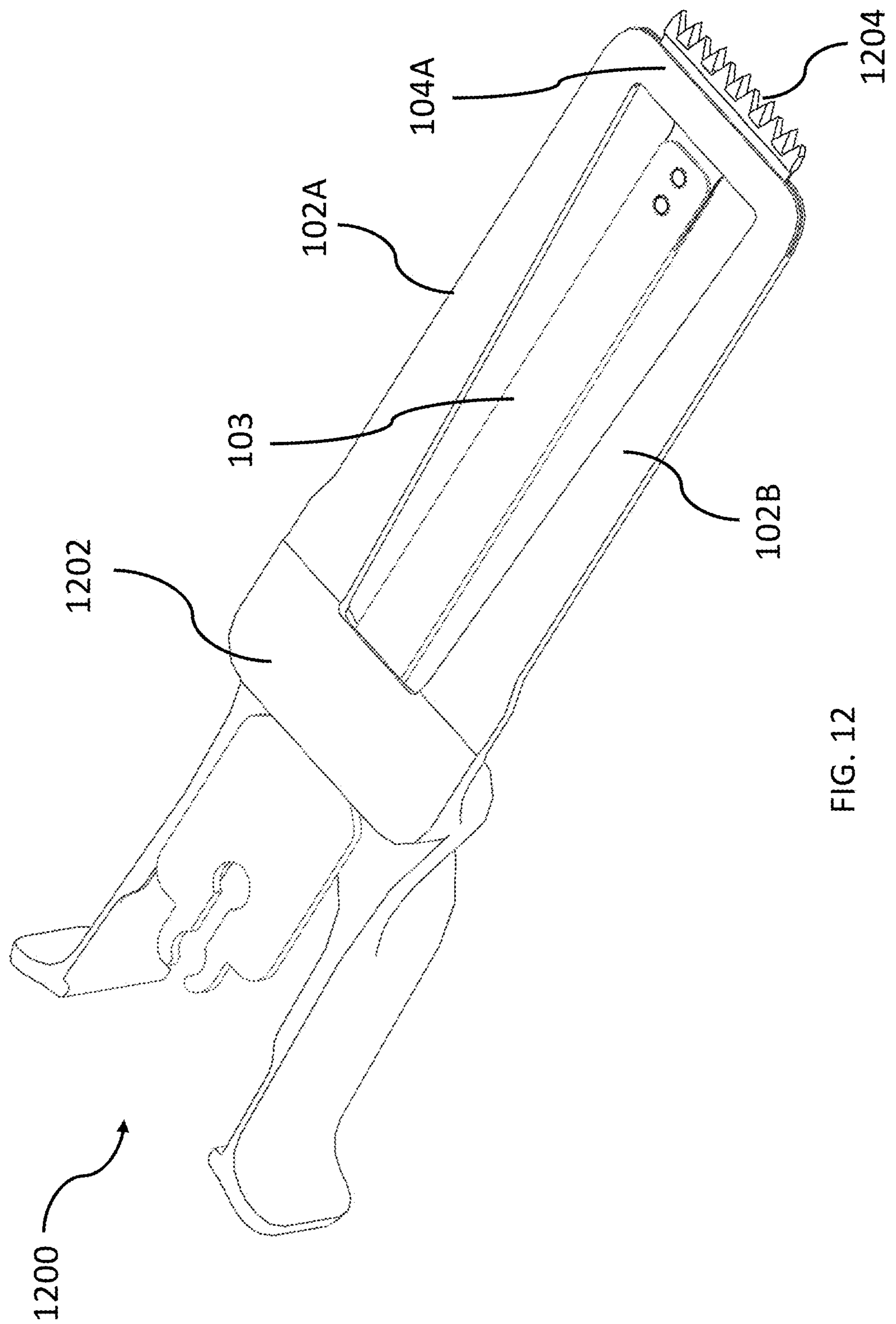
Figure 13:
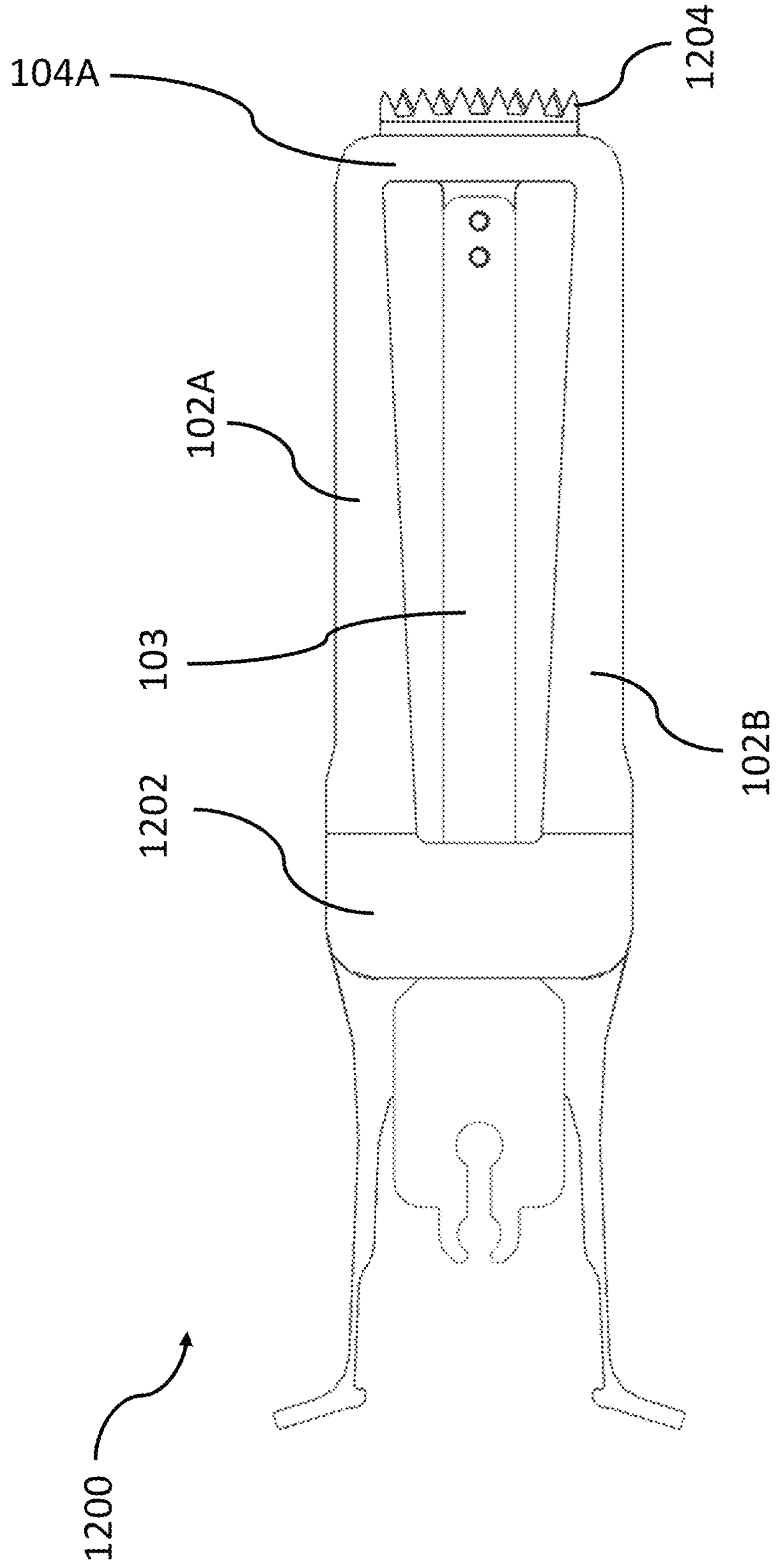
Figure 14:
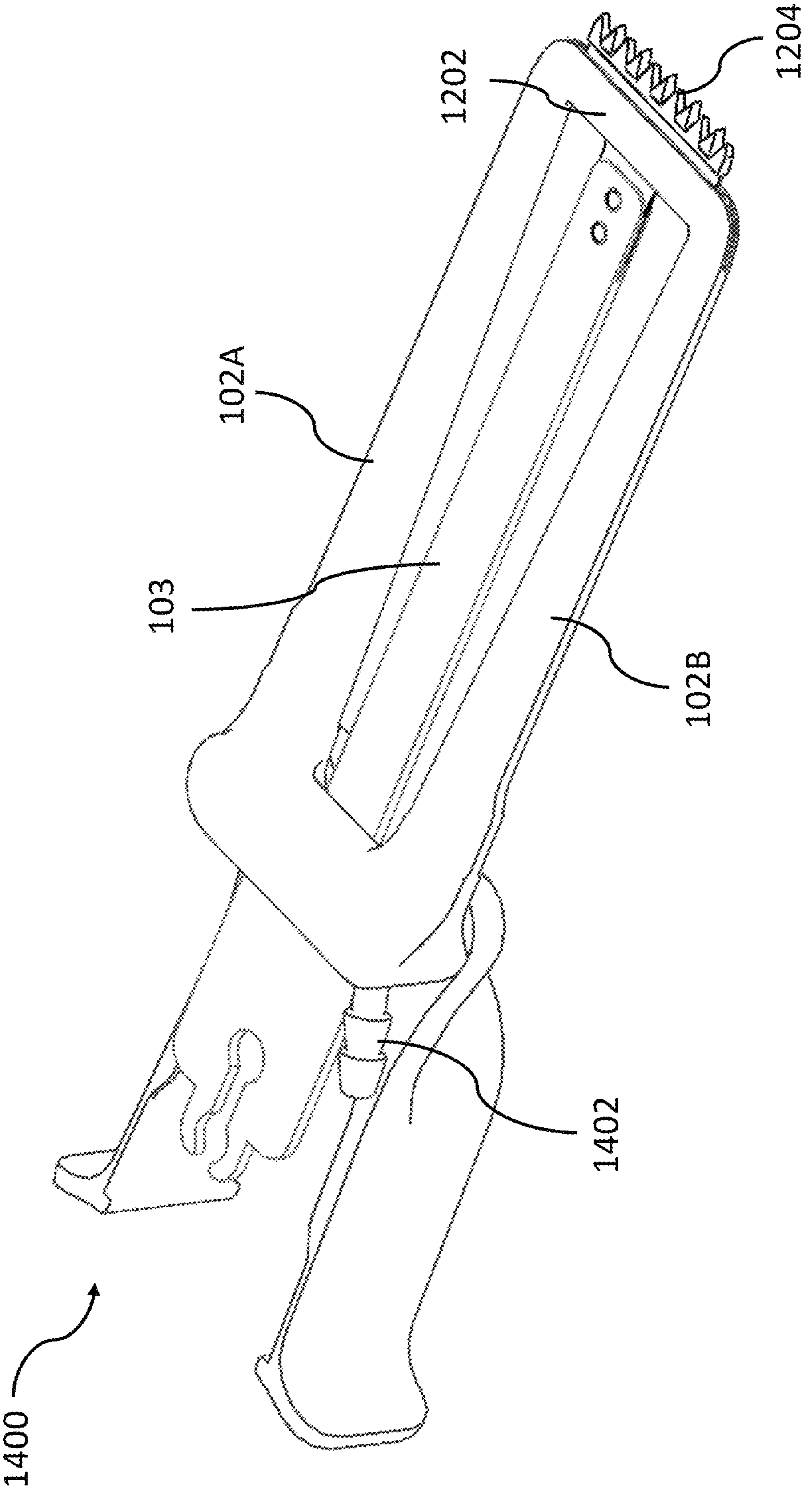
Figure 15:
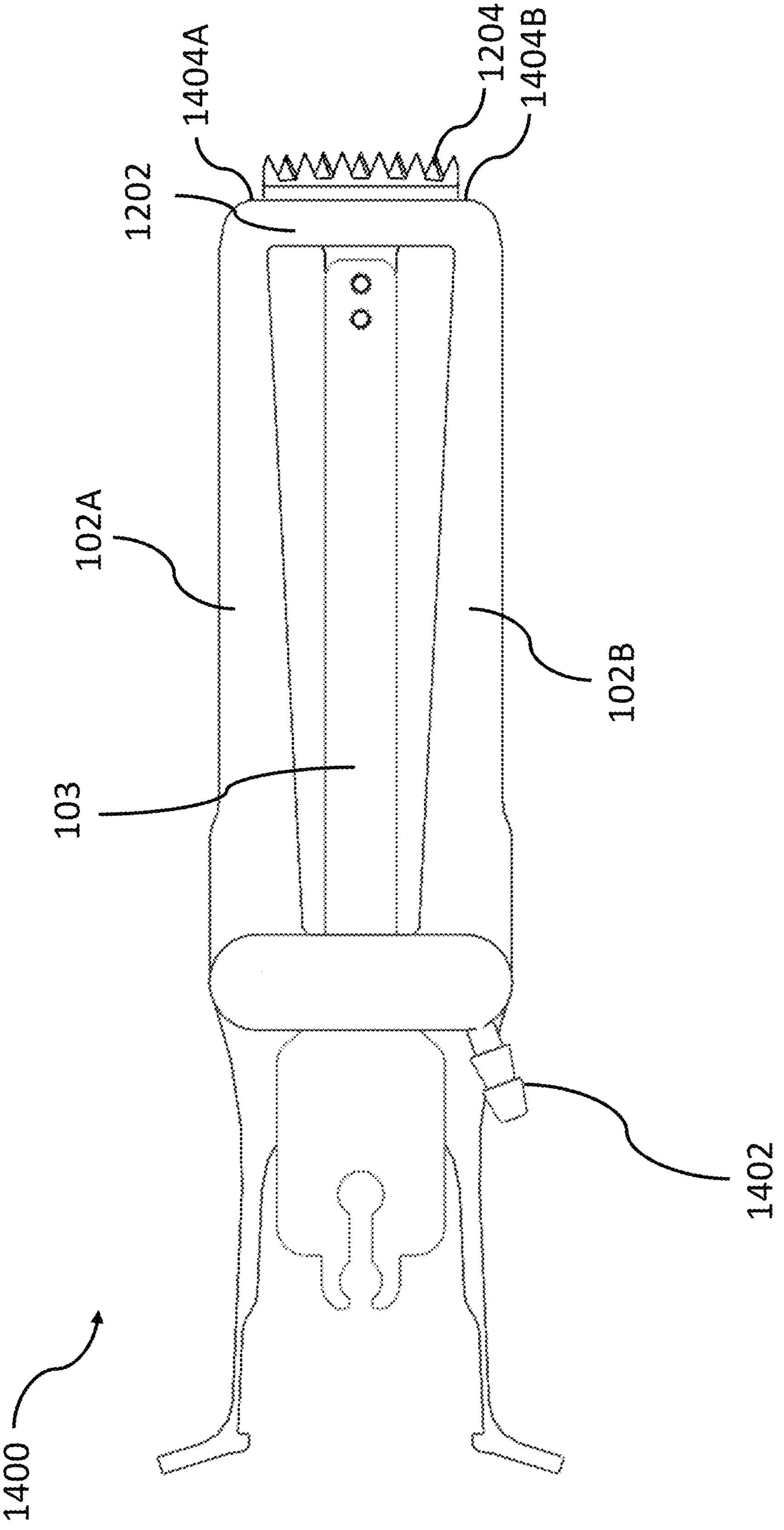
Figure 16:
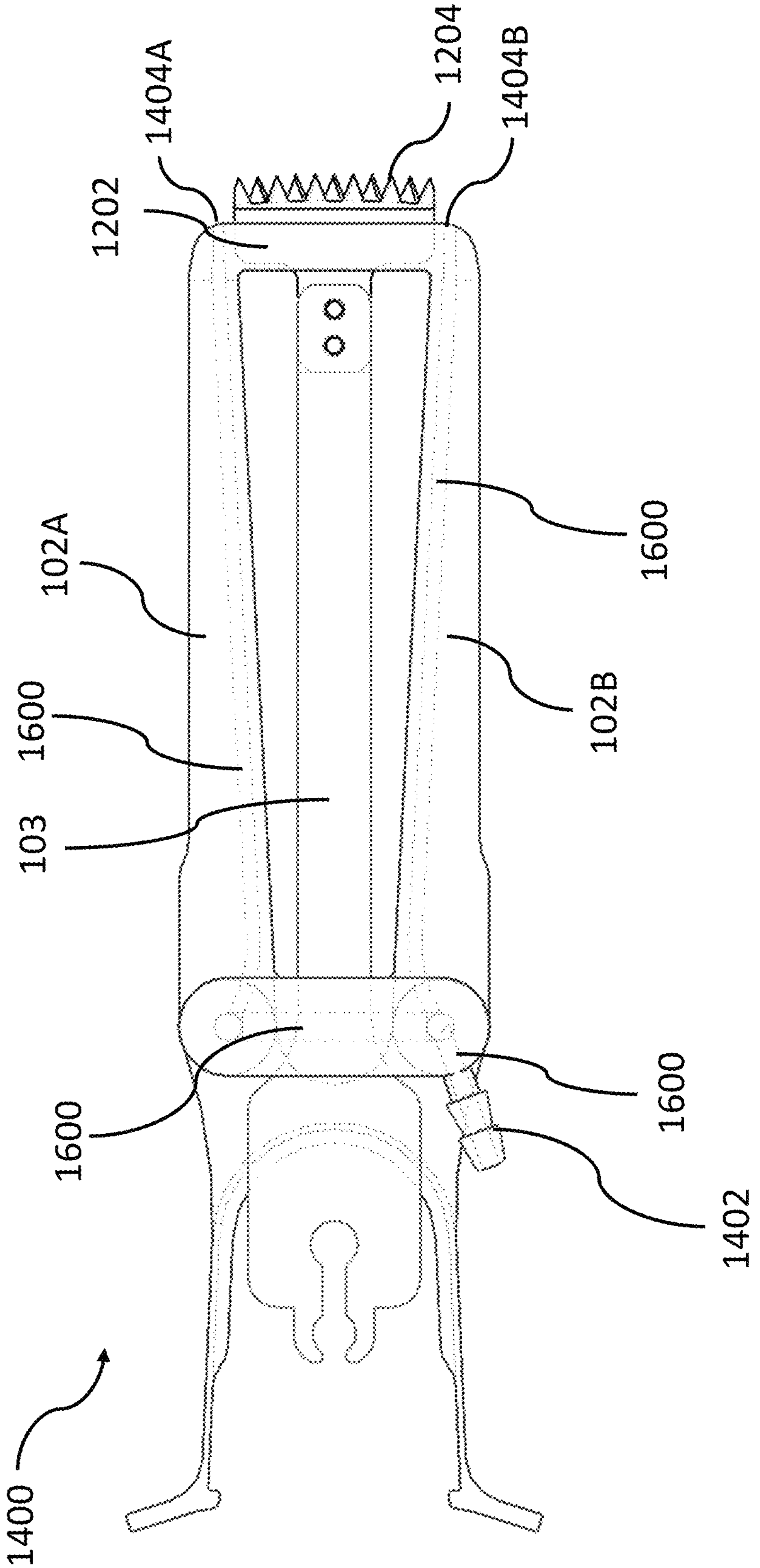
Figure 17:
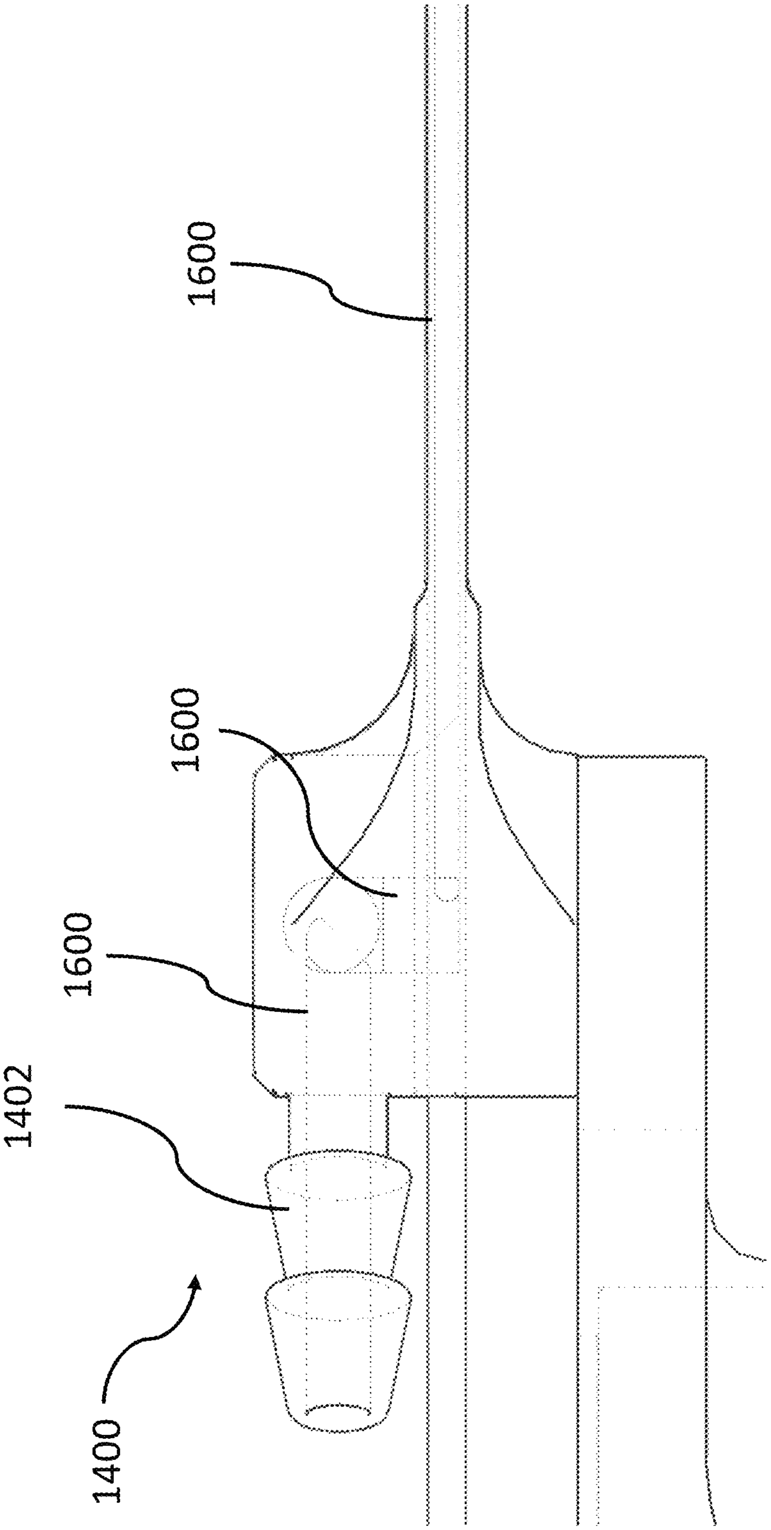
Figure 18:
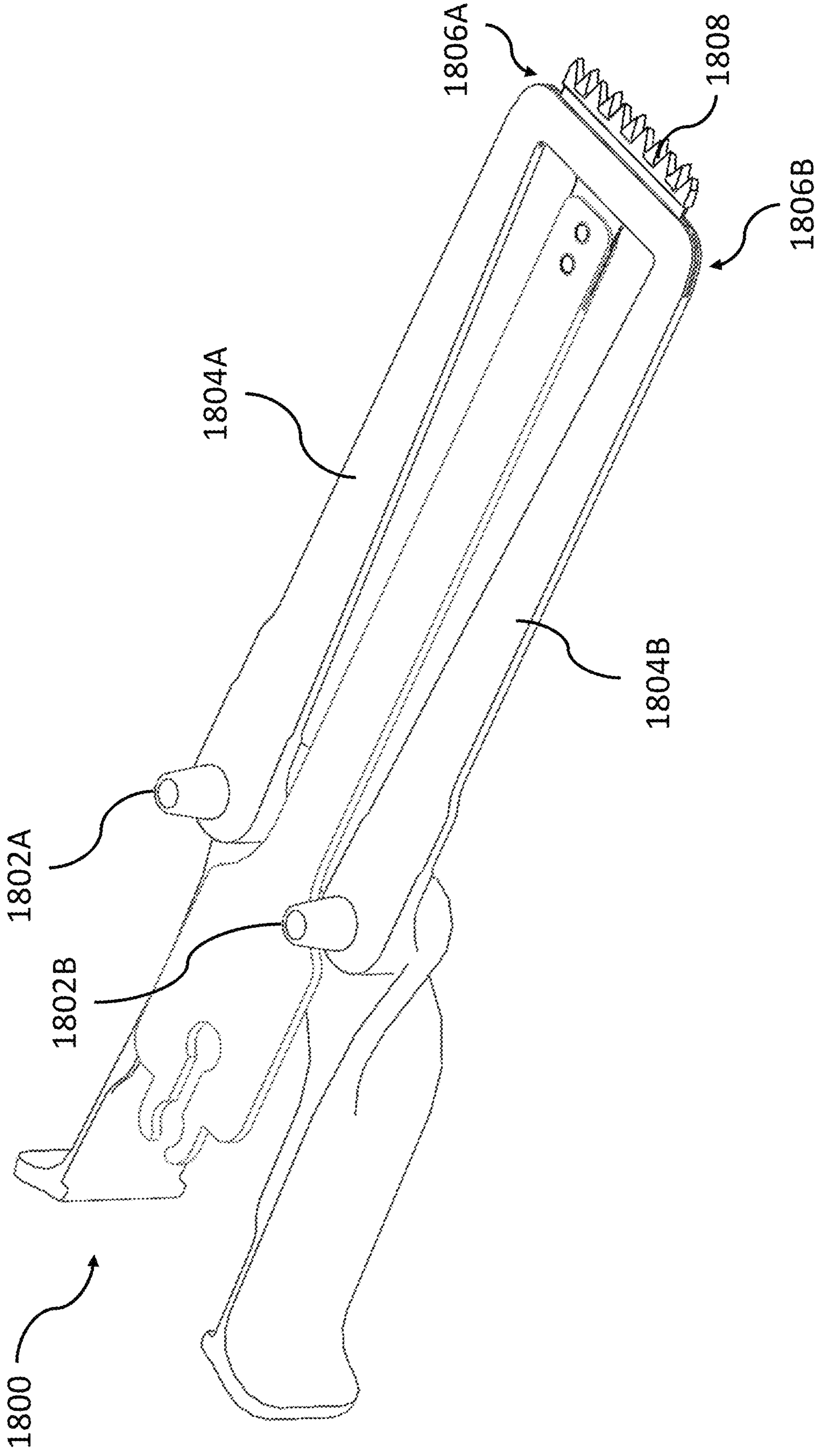
Figure 19:
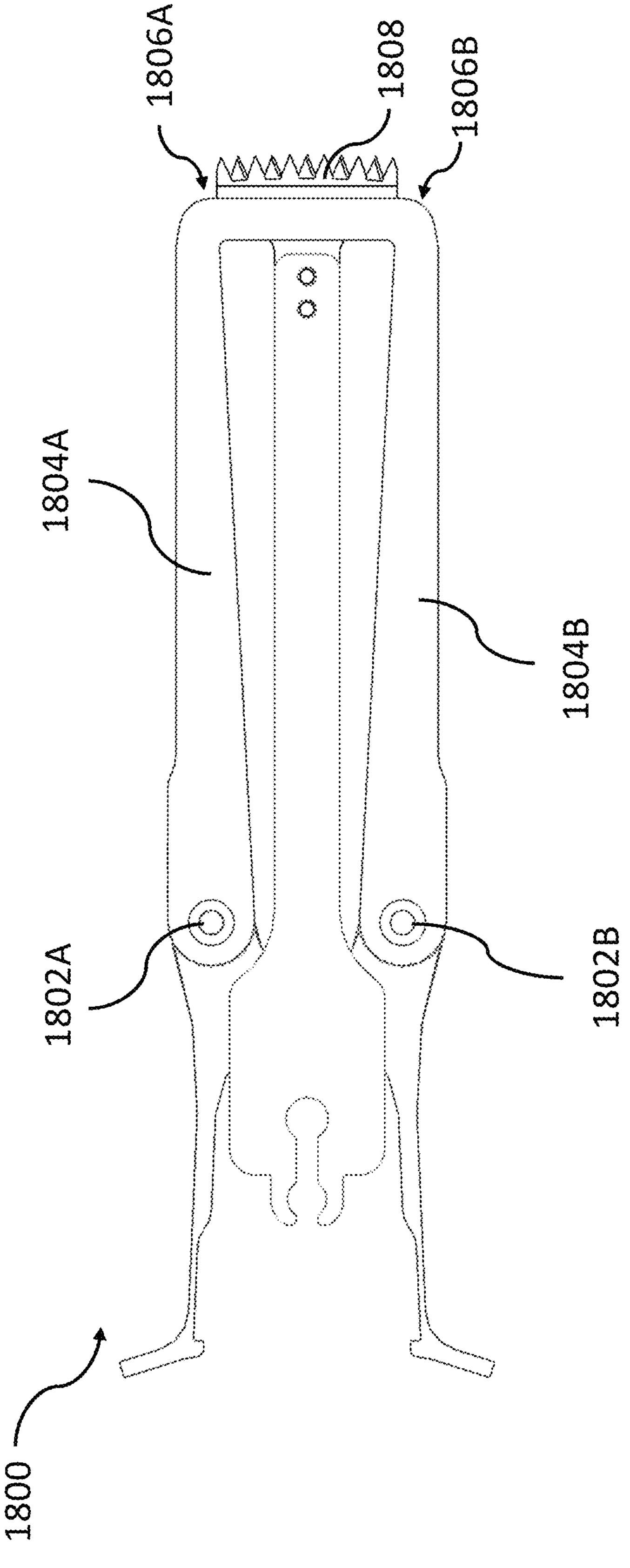
Figure 20:
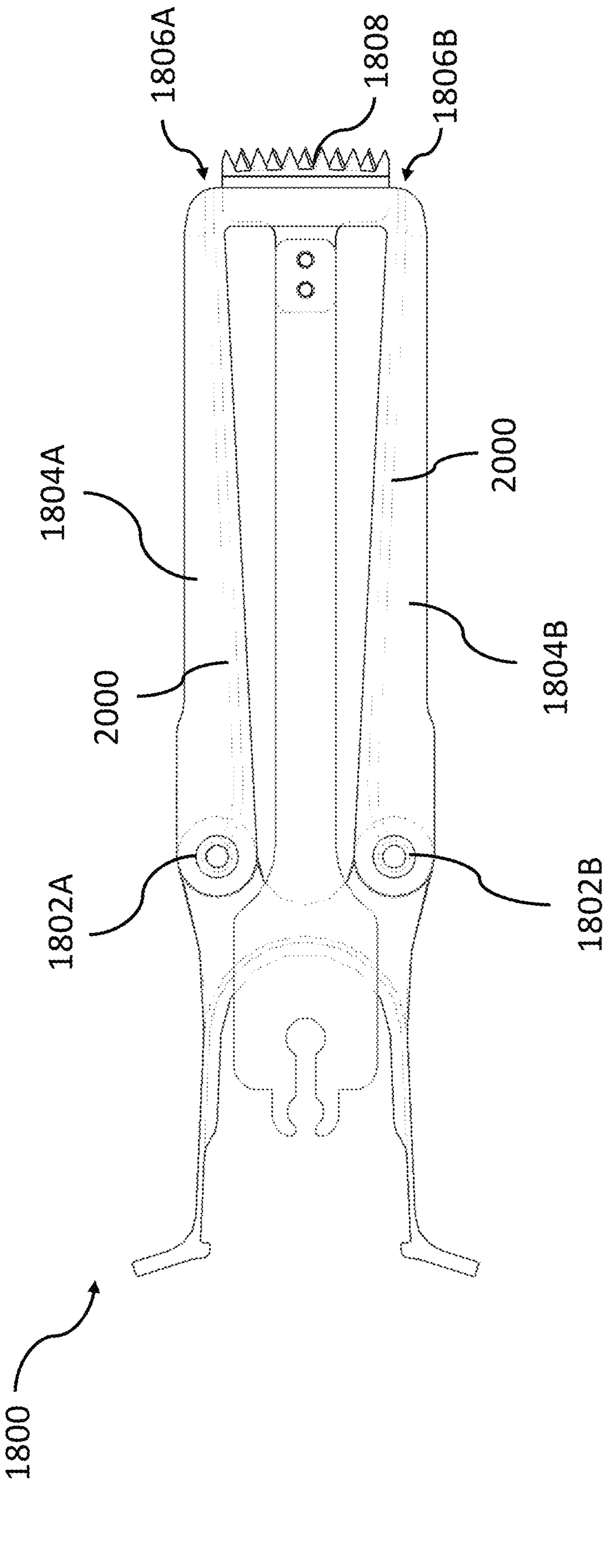
Figure 21:
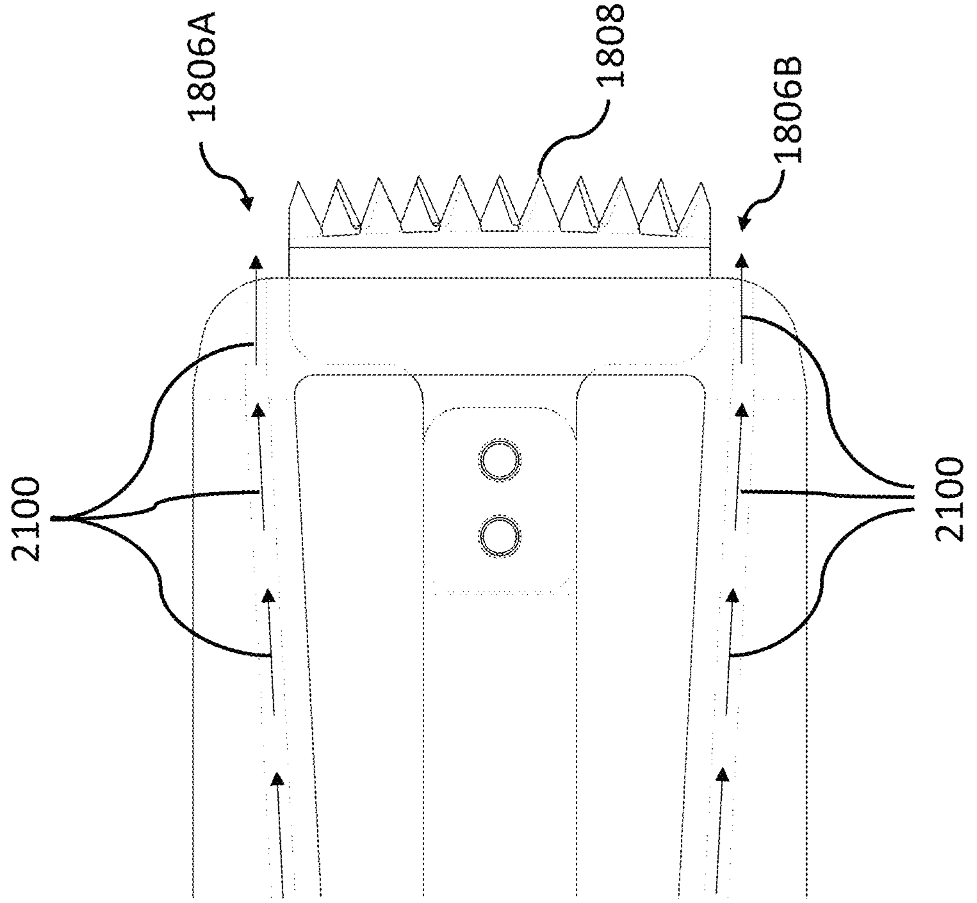
Figure 22:
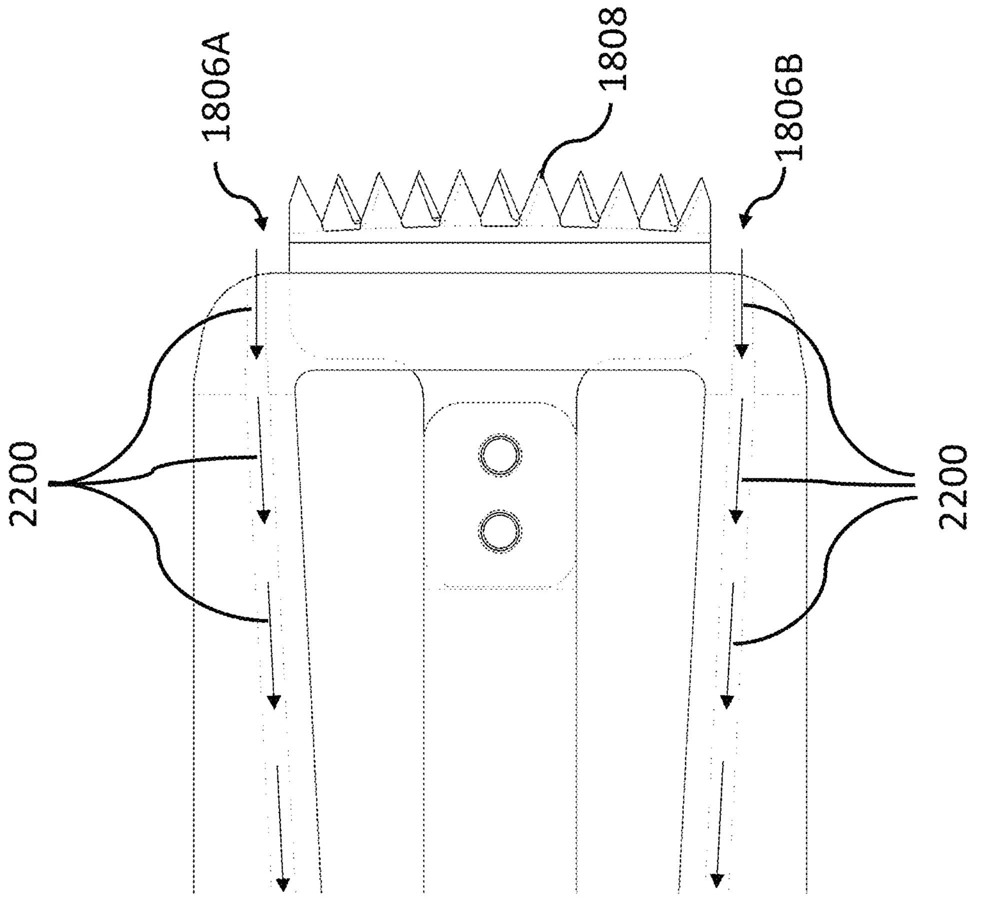
Figure 23:
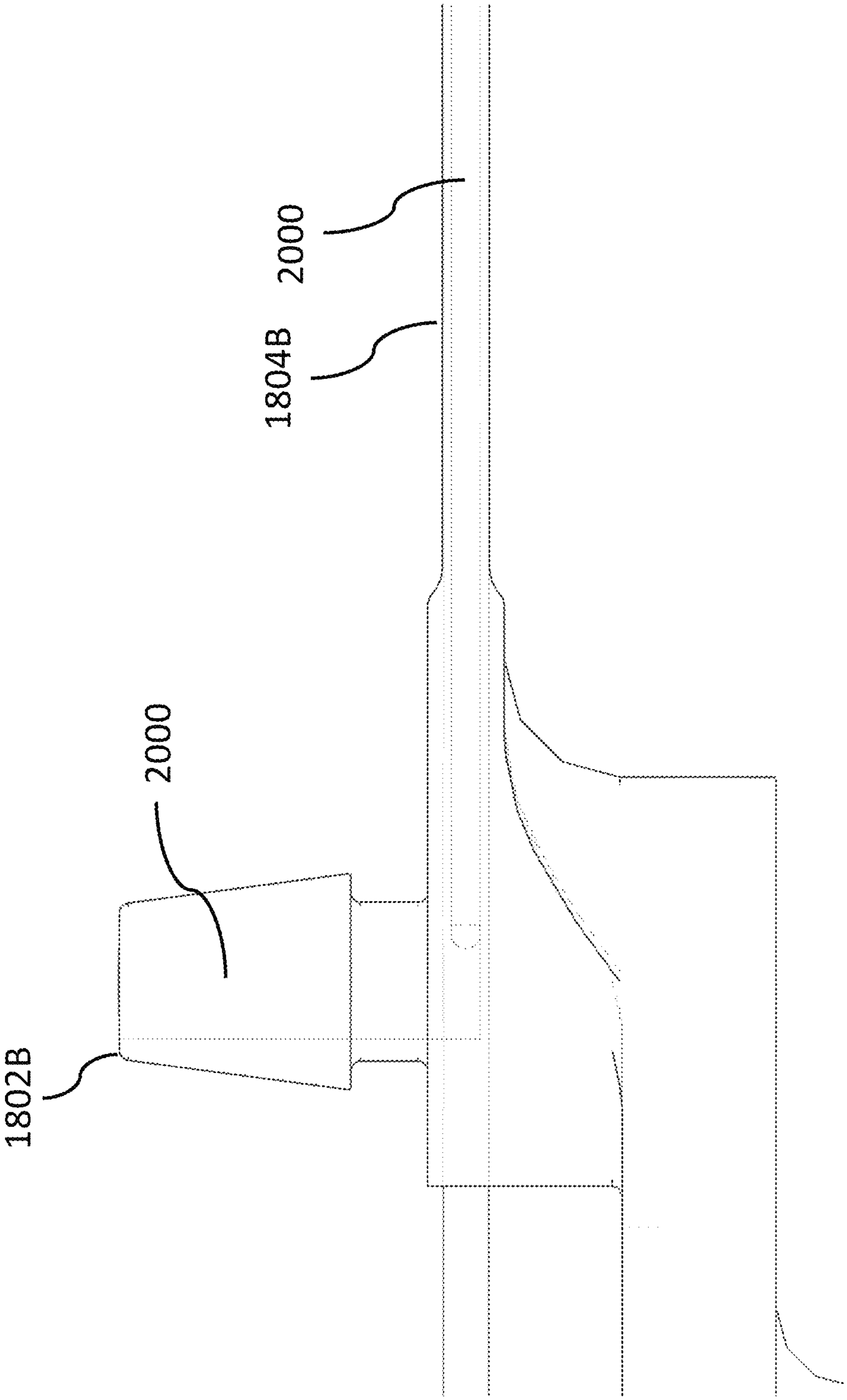
Figure 24:
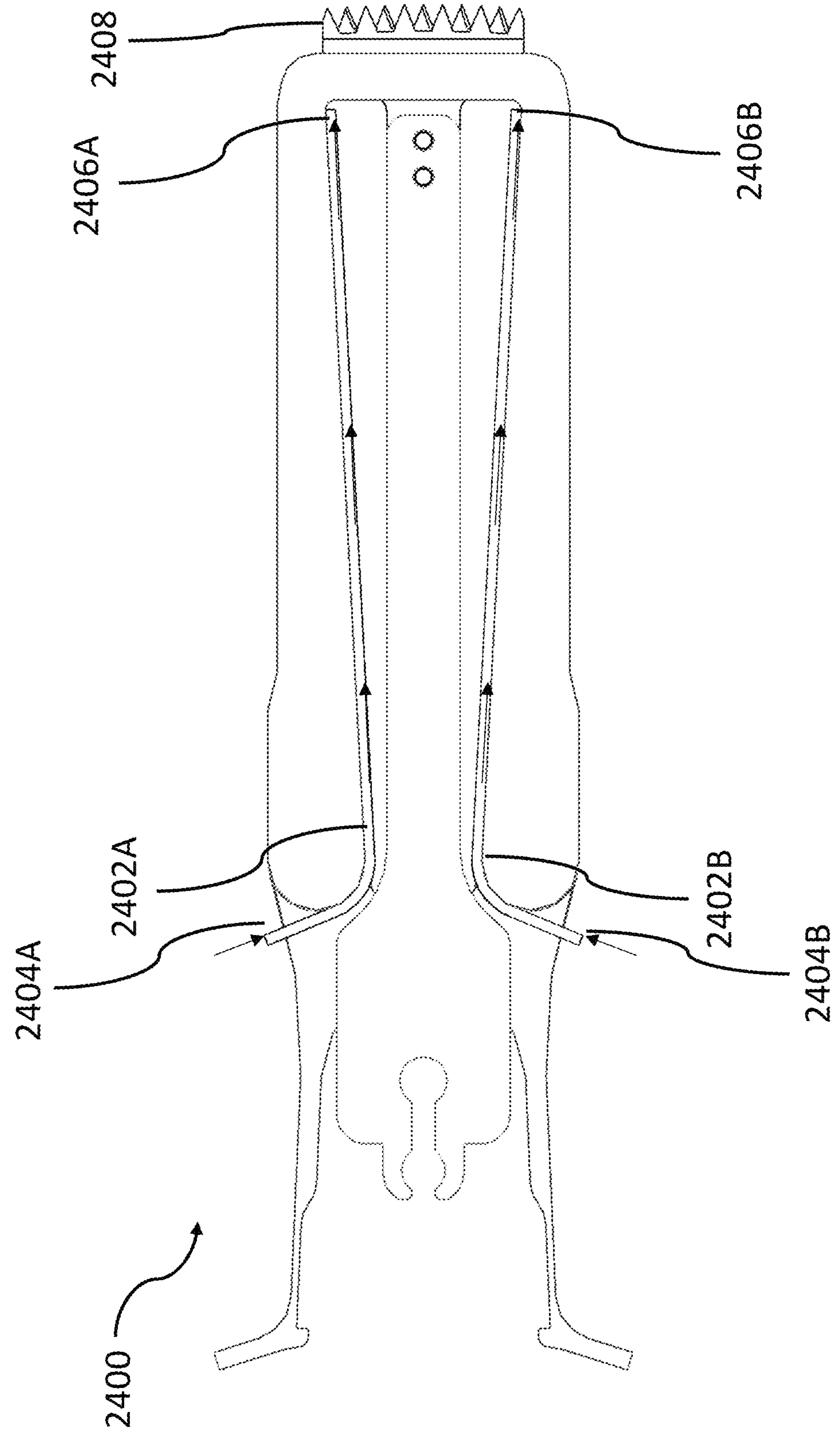
Figure 25:
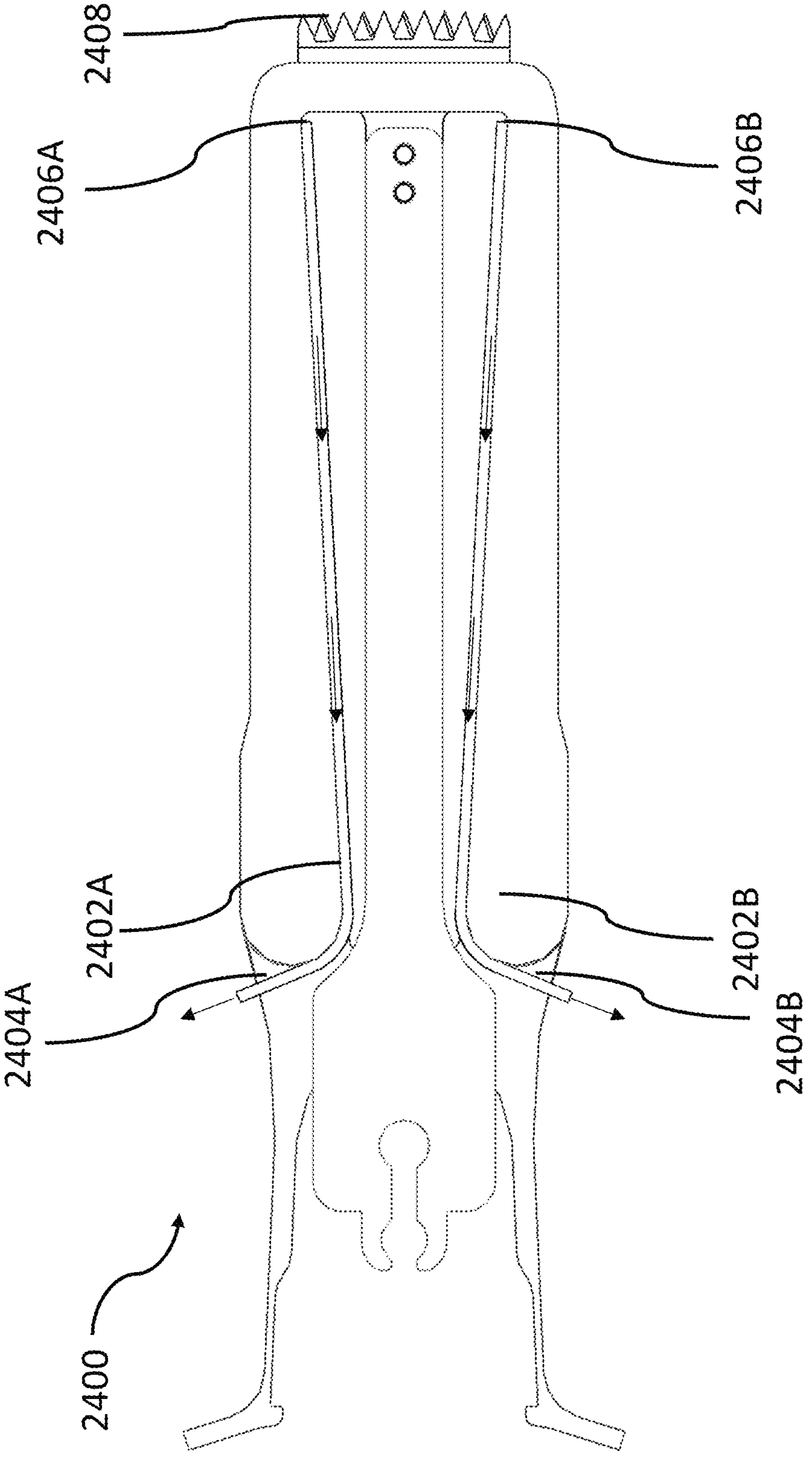
Figure 26:
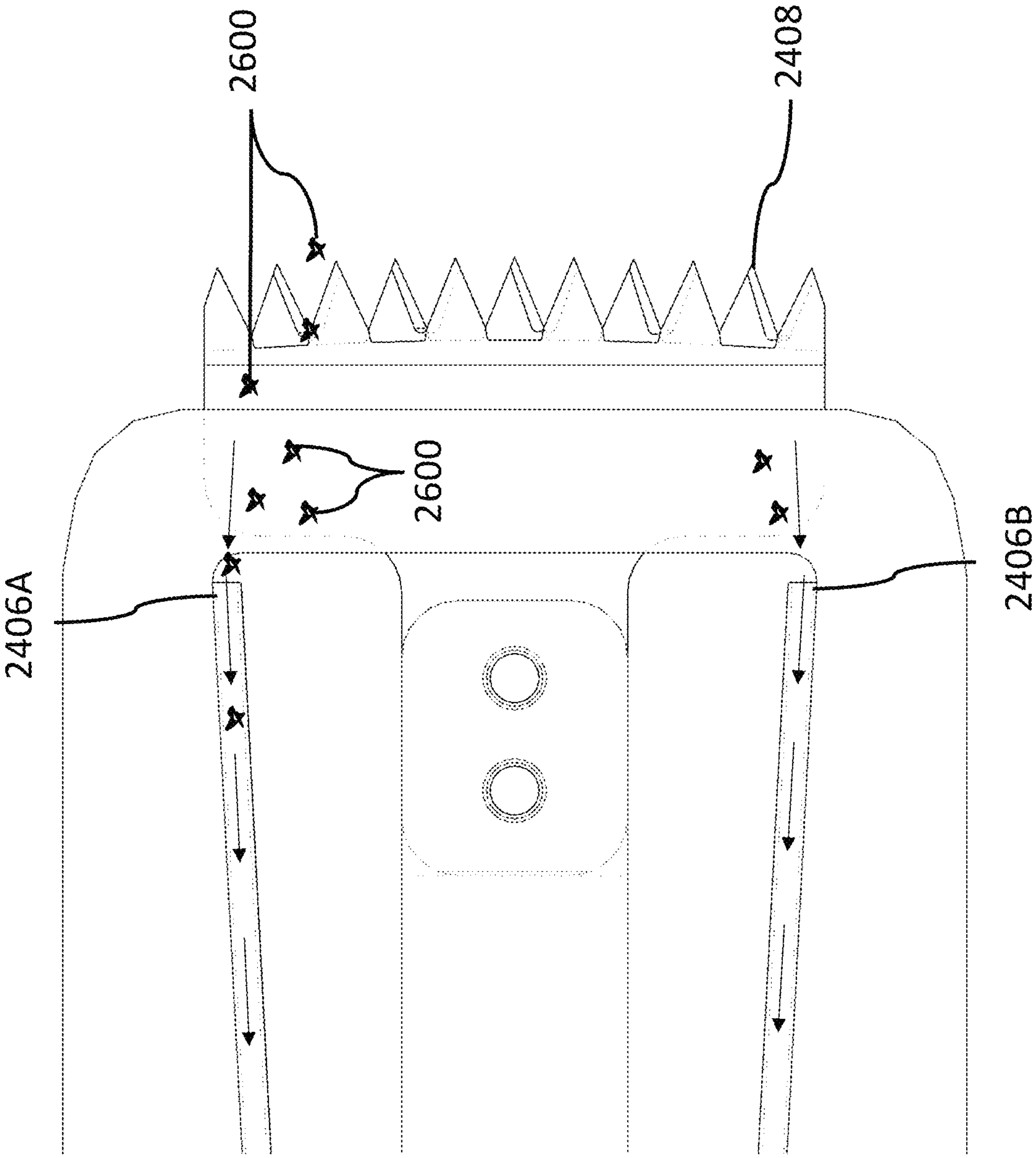
Figure 31:
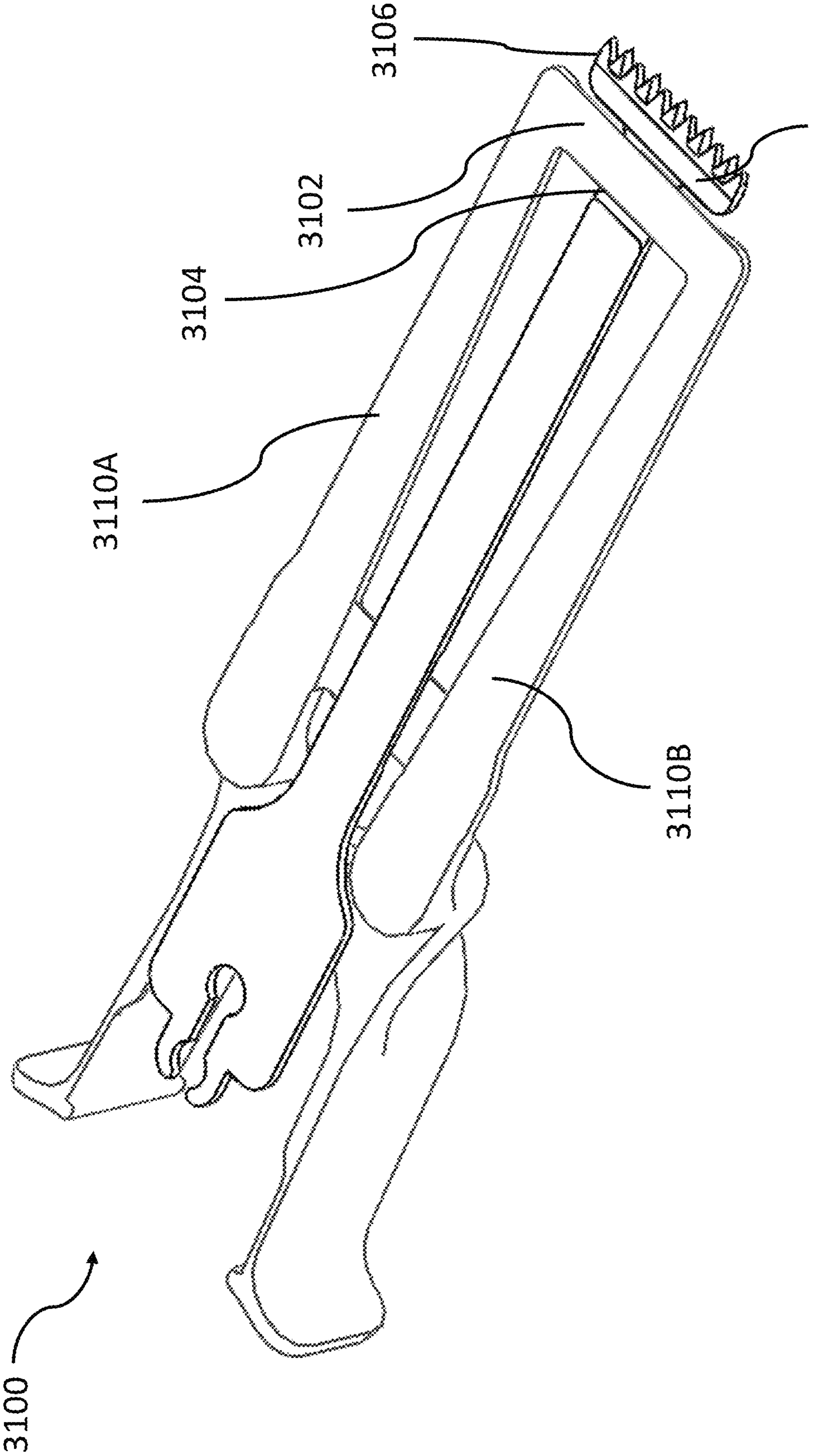
Figure 32A:
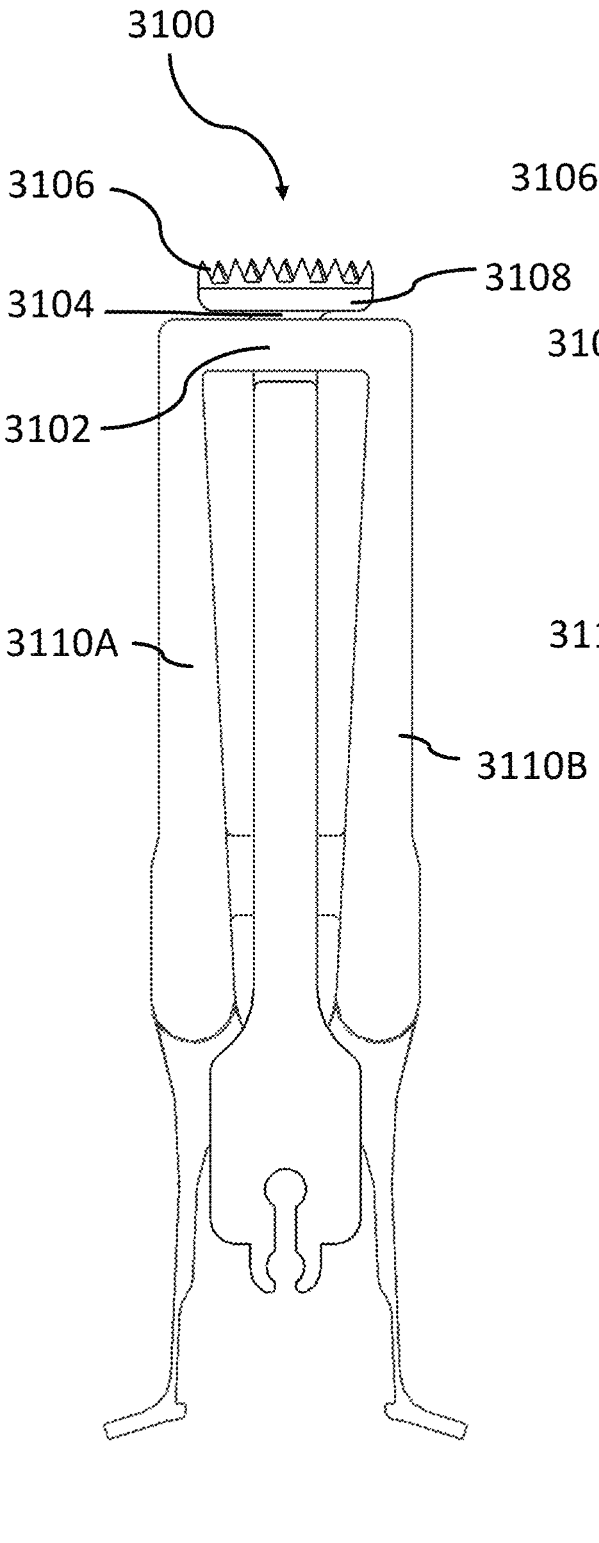
Figure 32B:
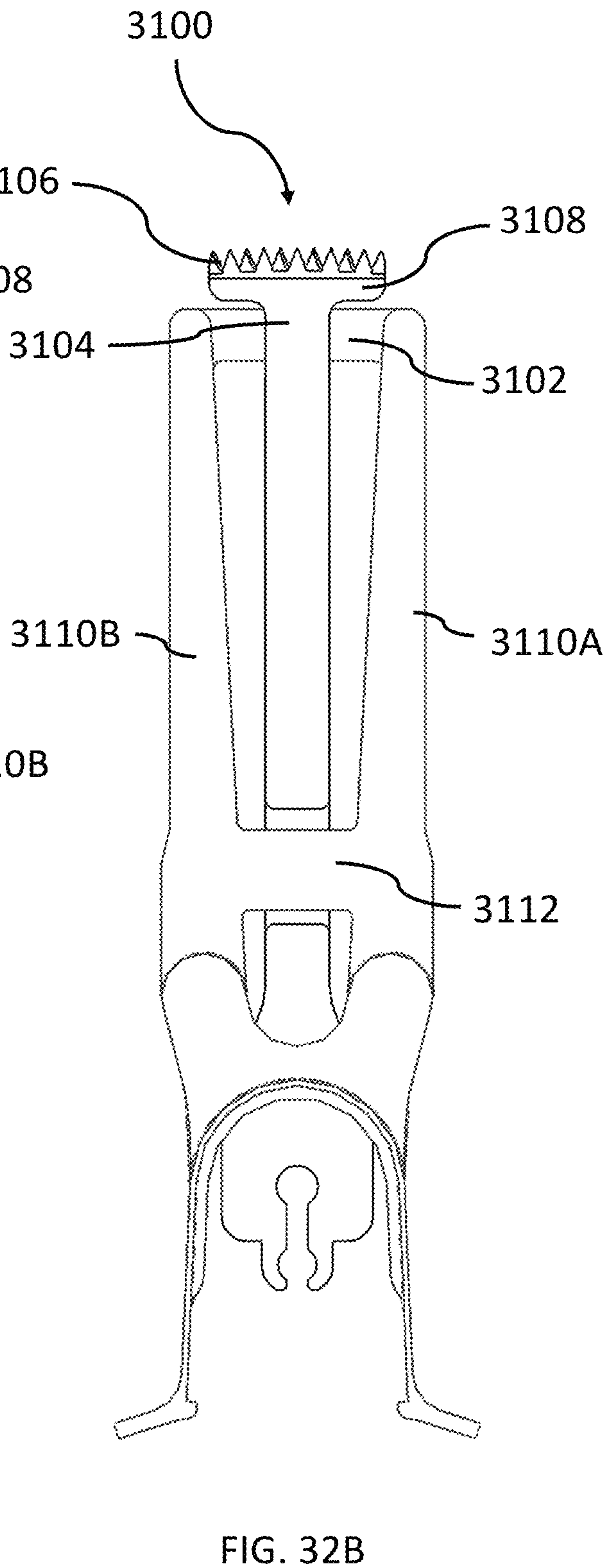
Figure 33:
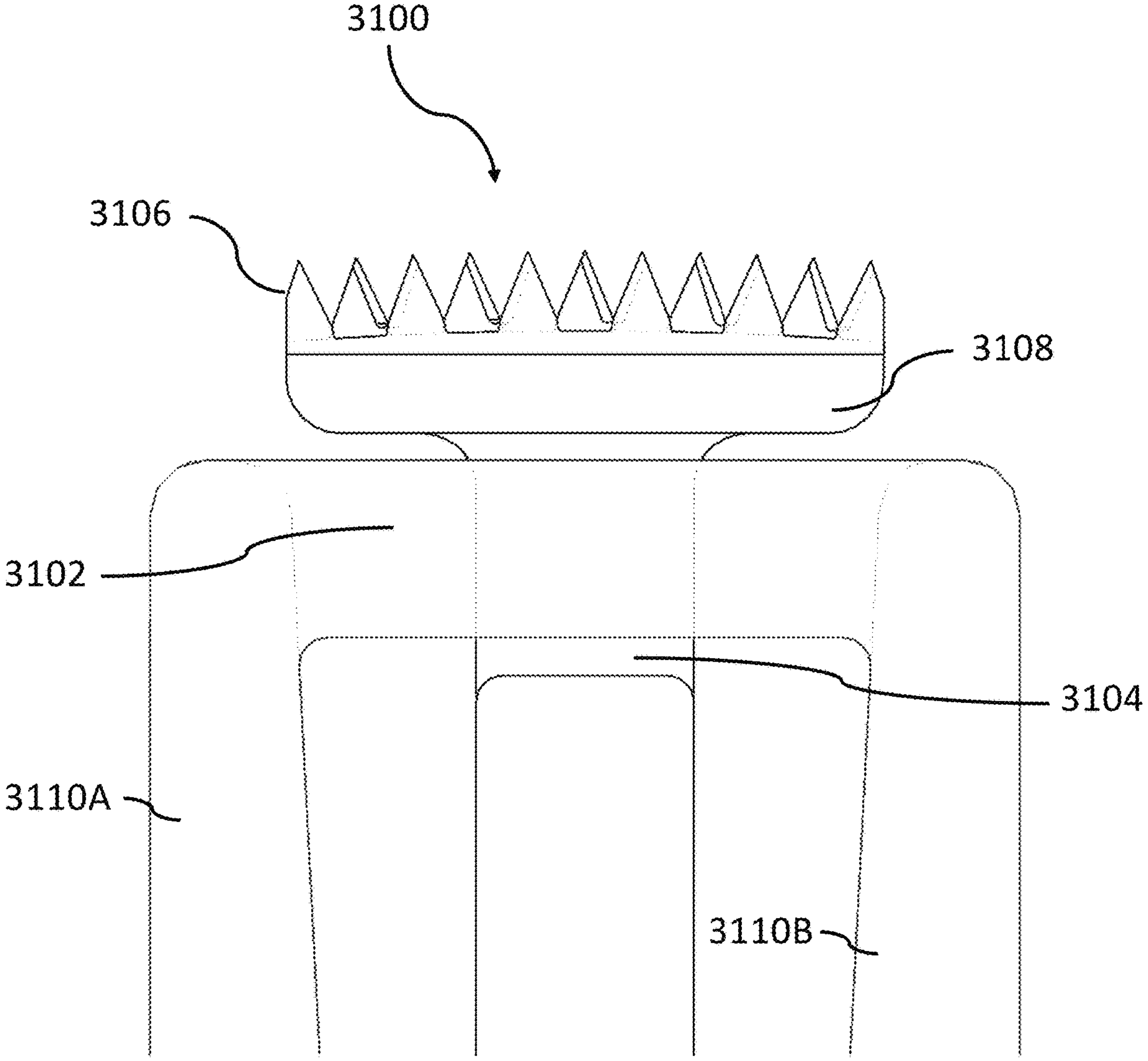
Figure 34A:
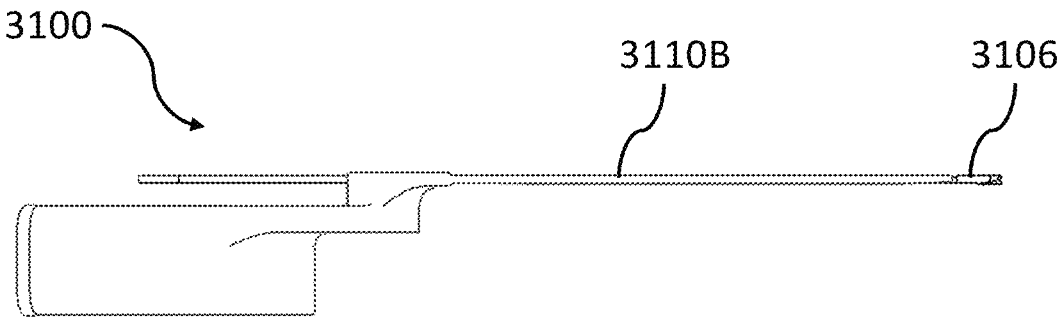
Figure 34B:
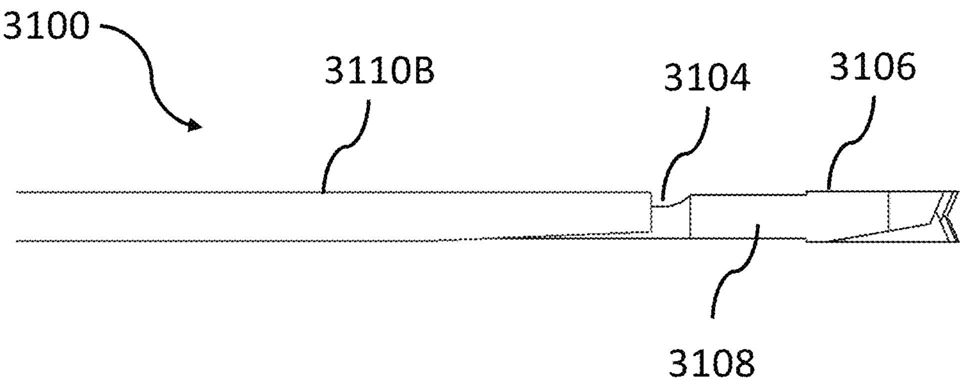
Figure 35A:
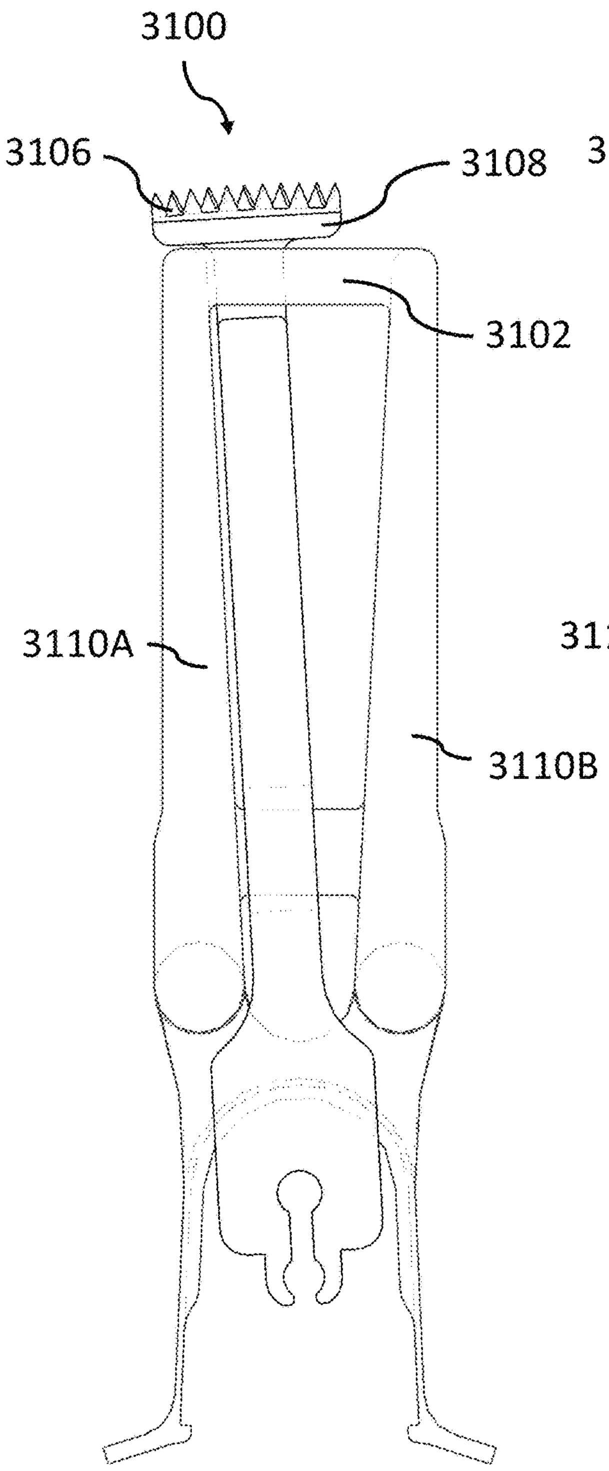
Figure 35B:
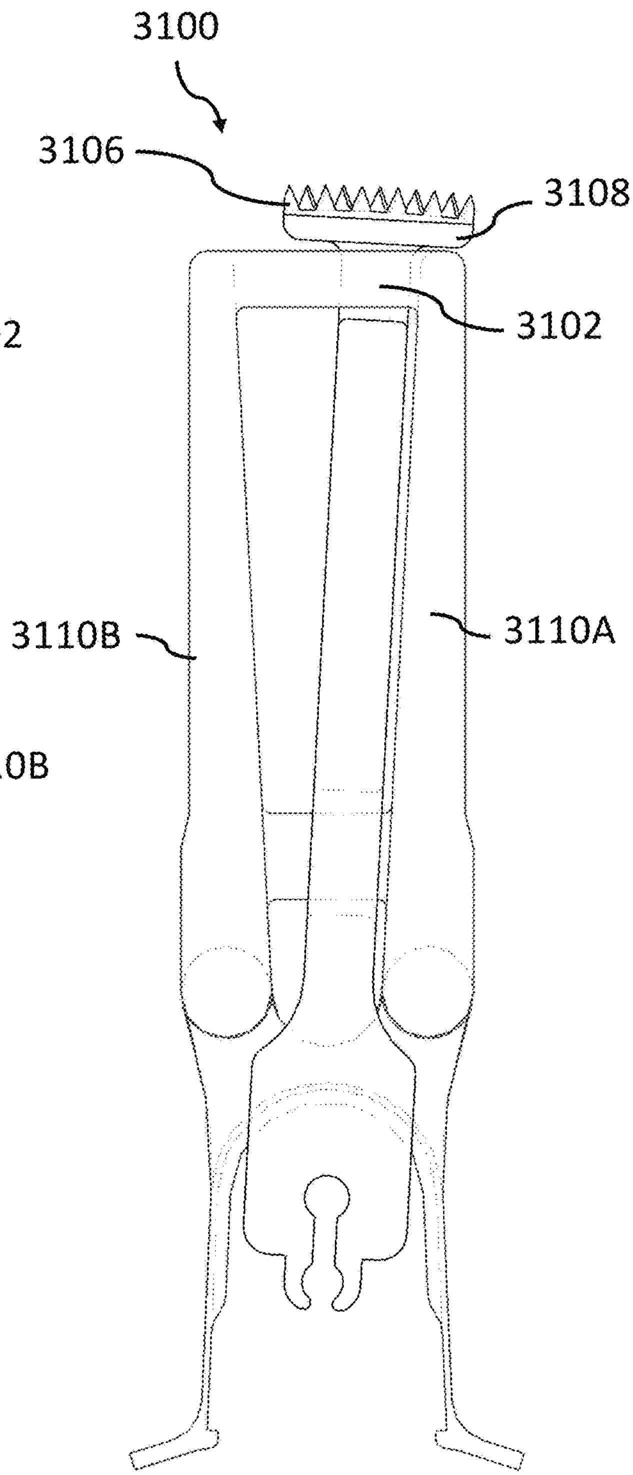
Figure 36:
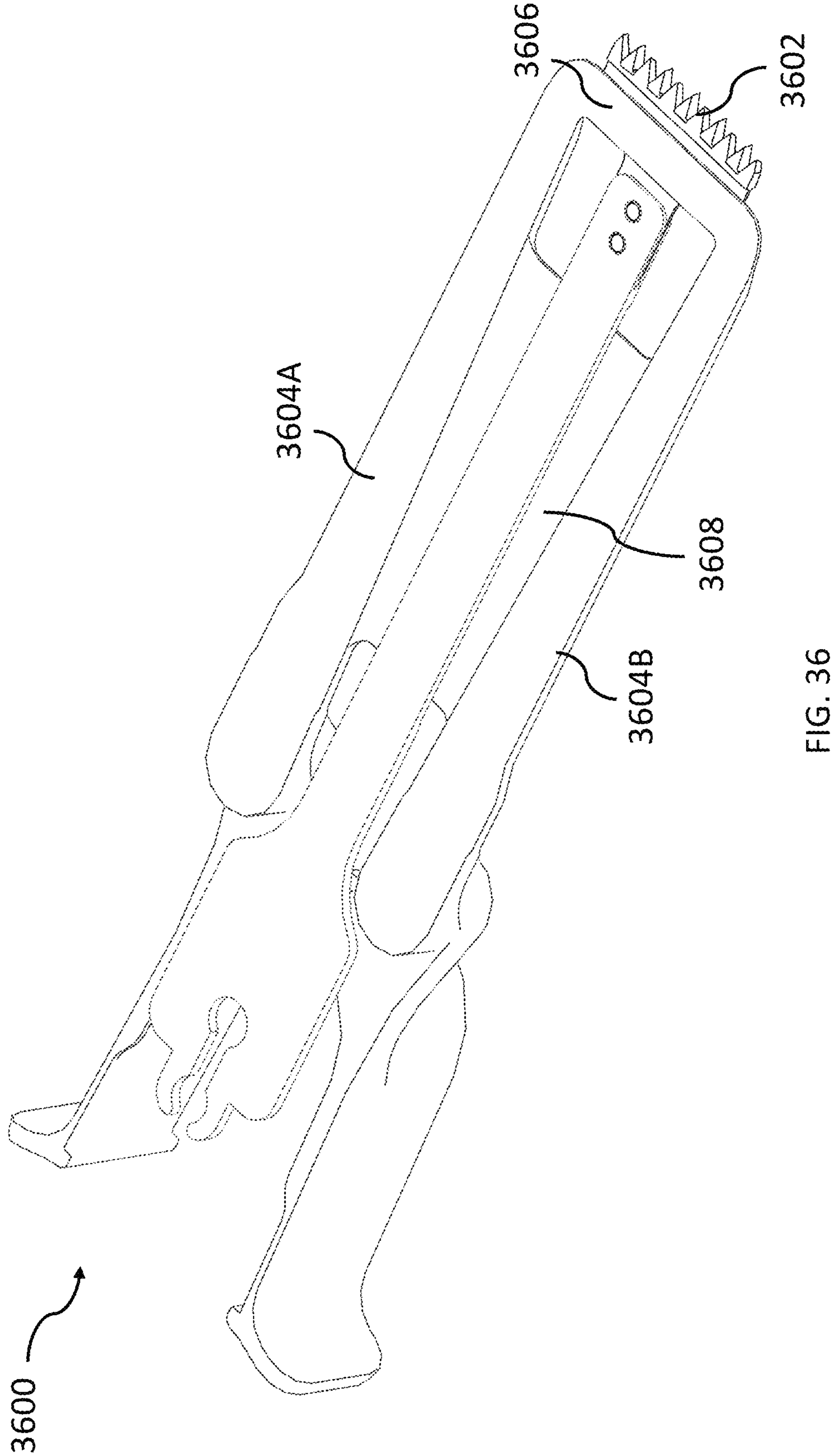
Figure 37A:
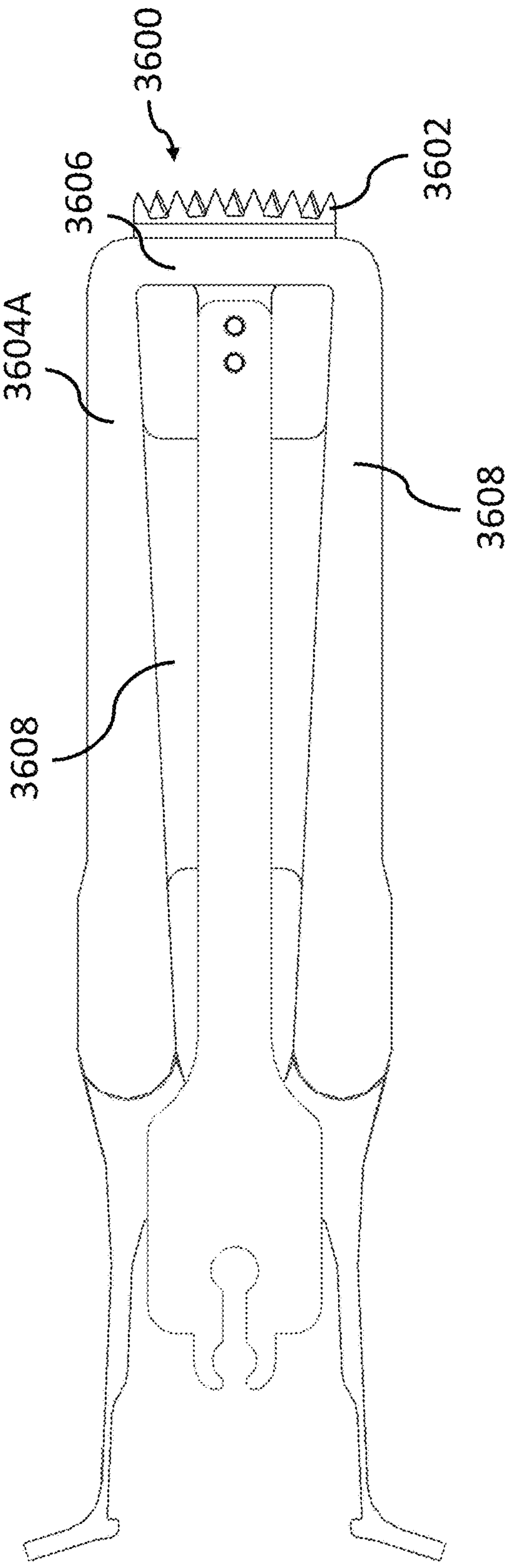
Figure 37B:
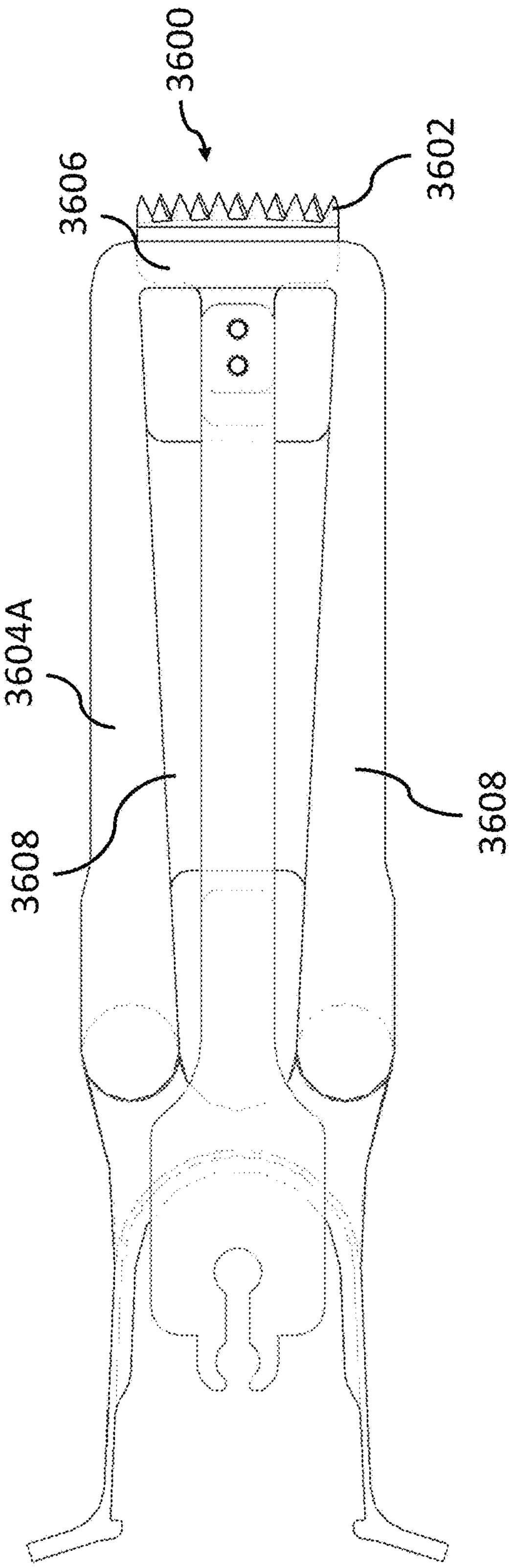
Figure 38:
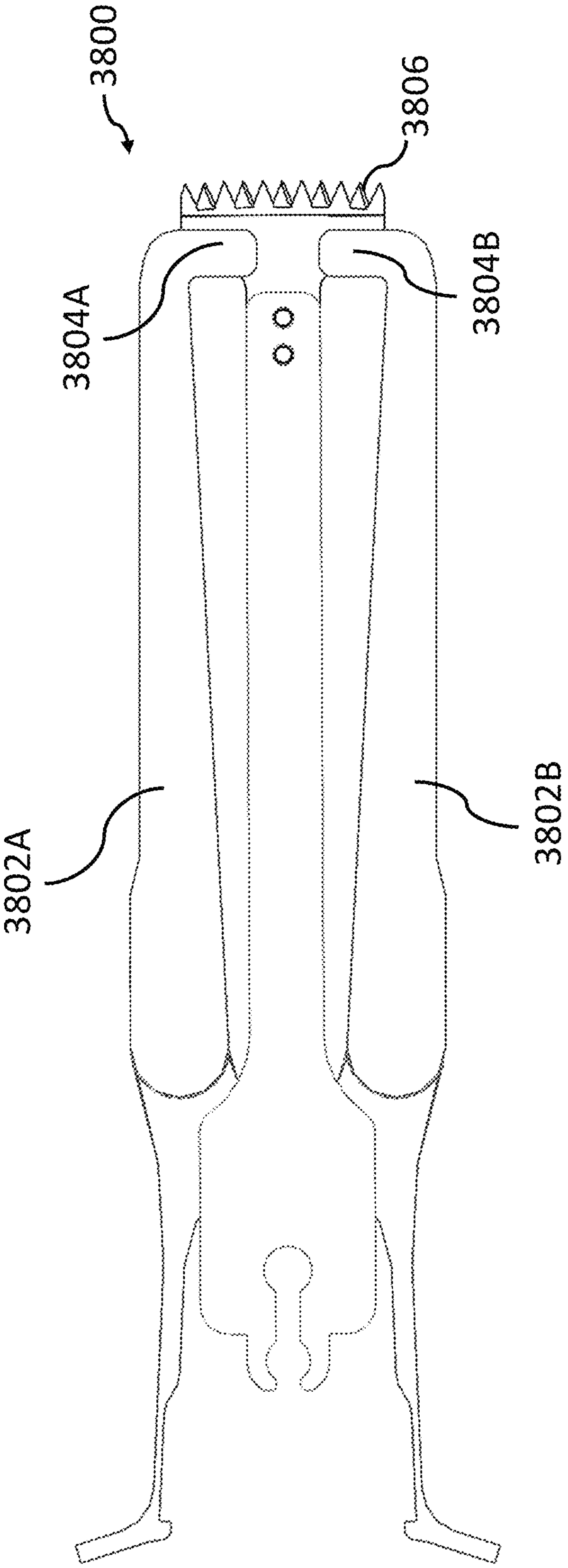
Figure 39:
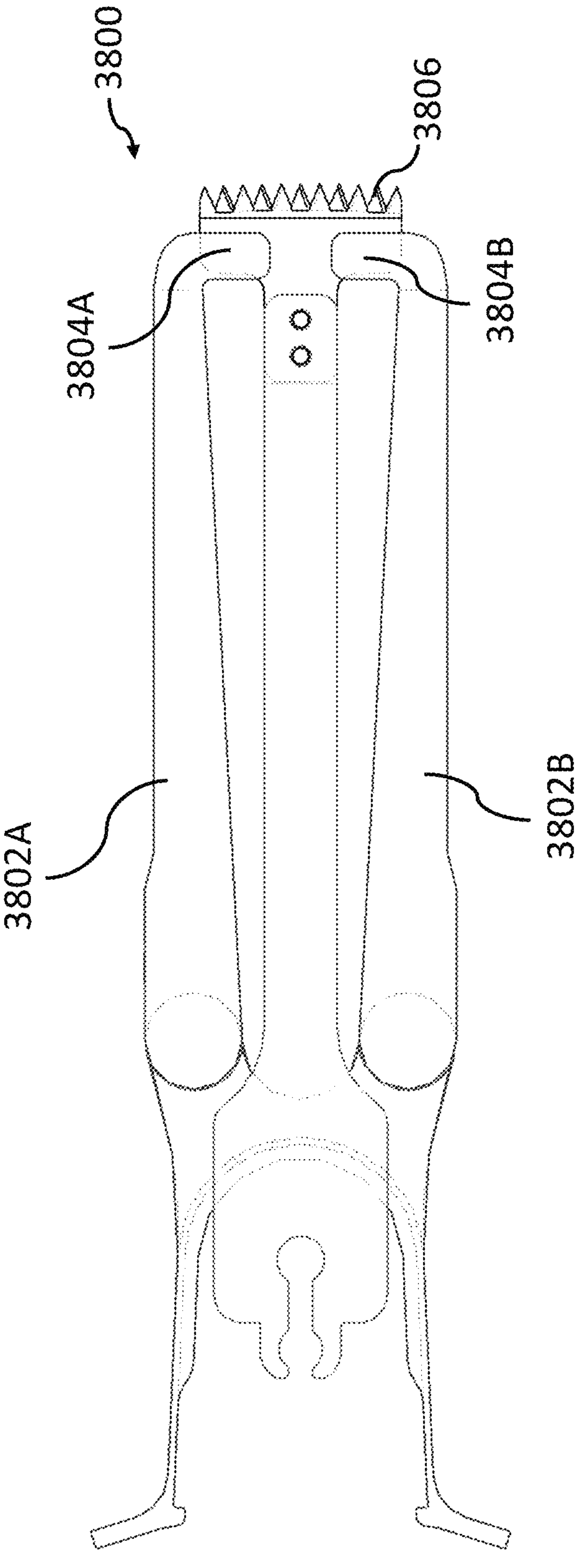
Figure 40:
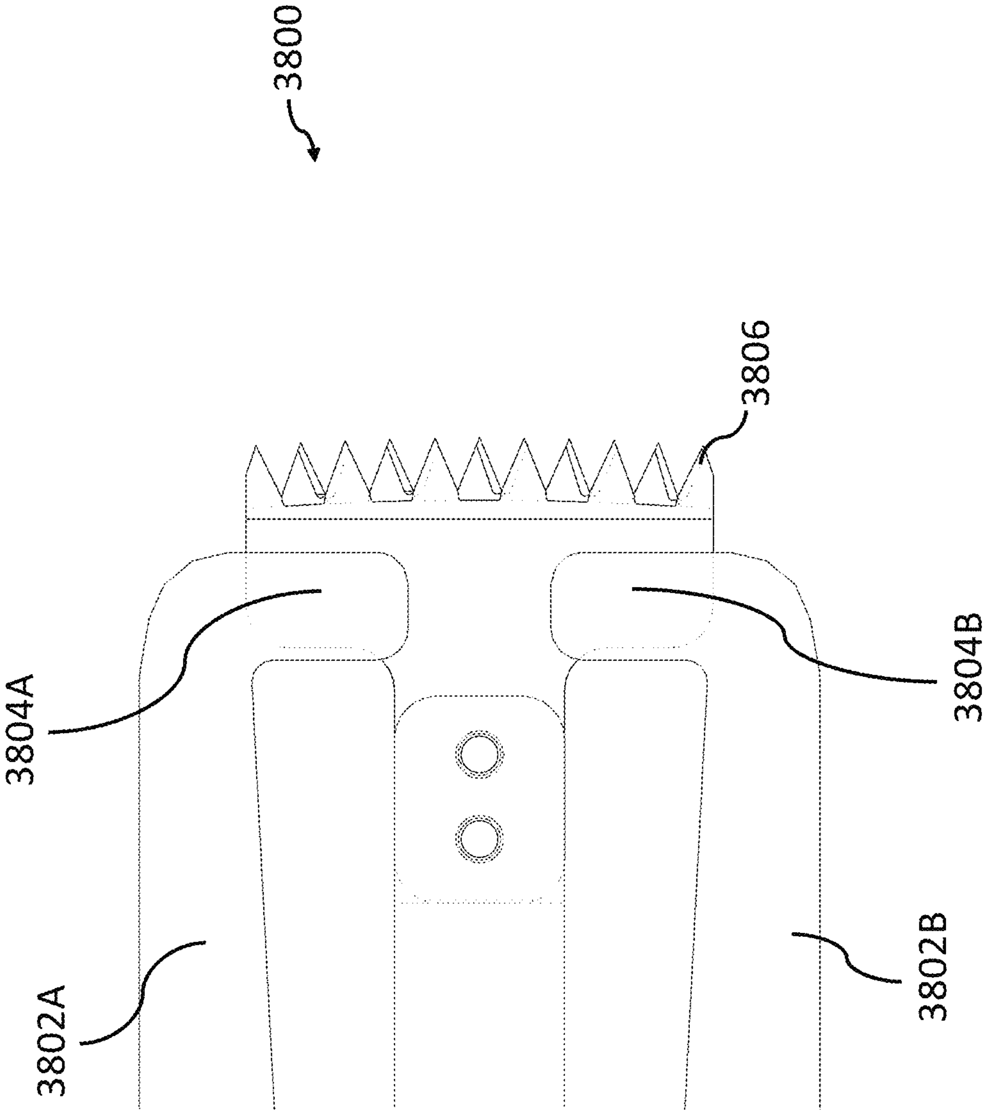
Figure 41A:
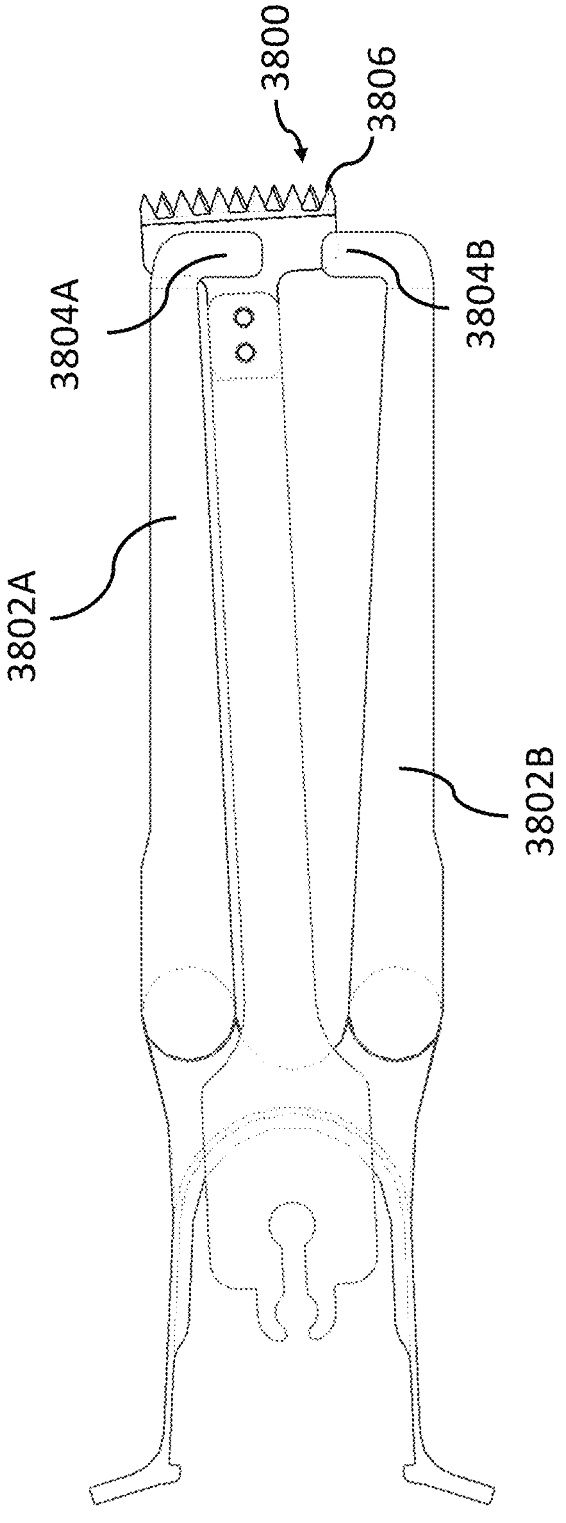
Figure 41B:
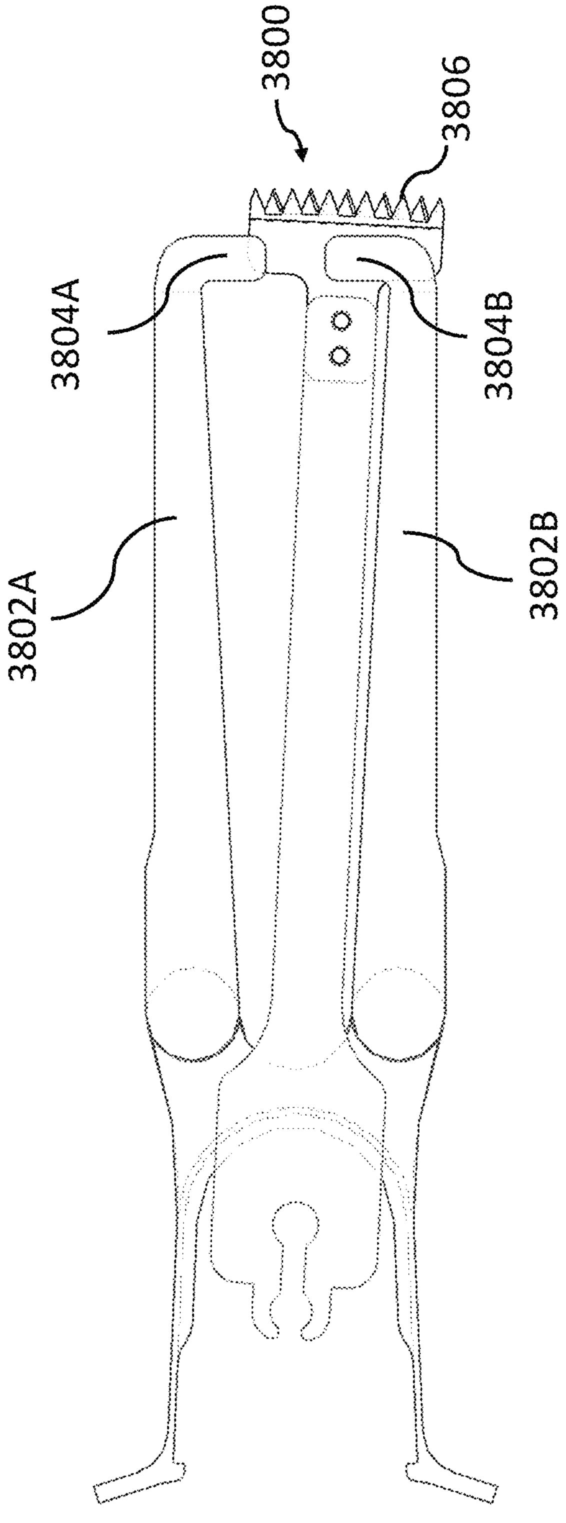
Figure 42:
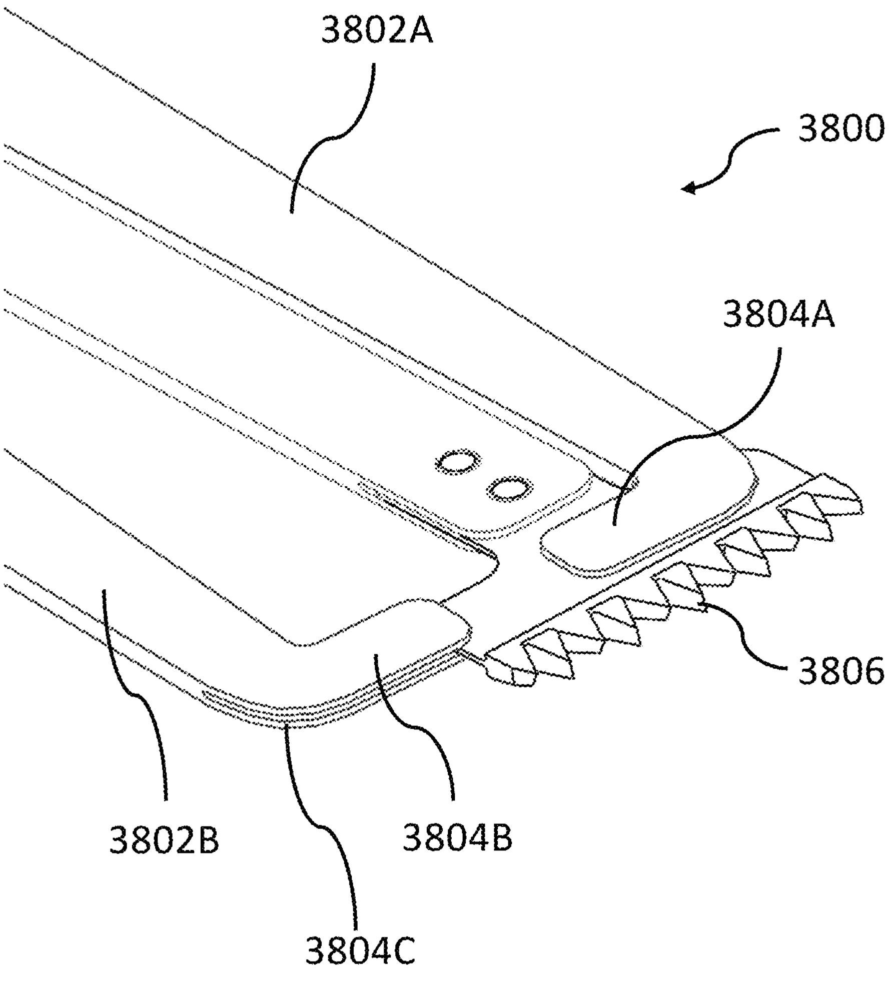
Figure 43:
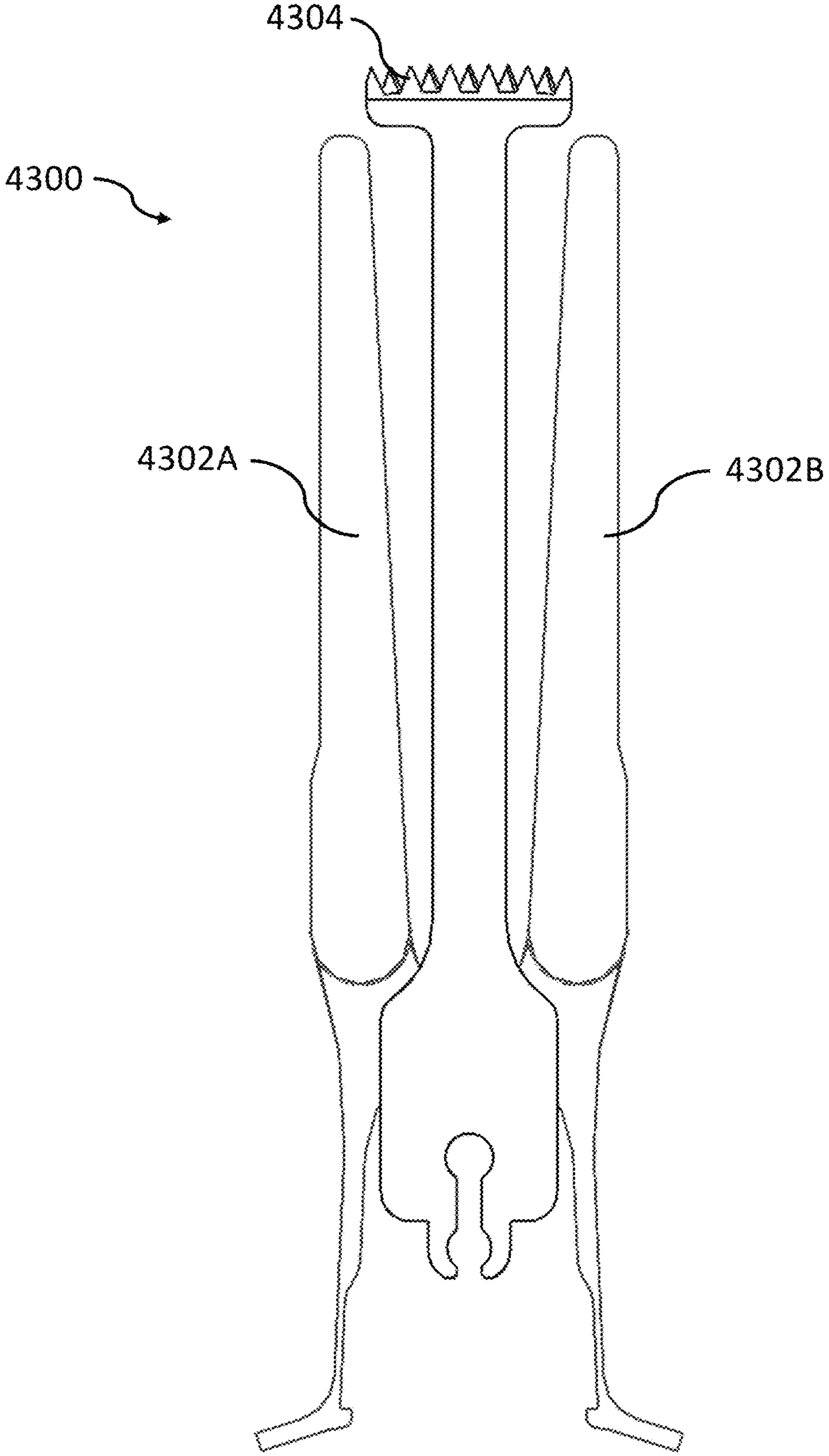
Figure 44A:
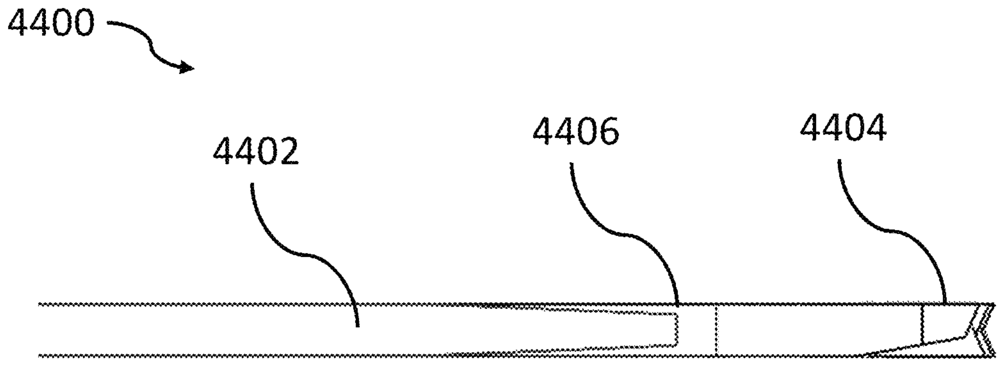
Figure 44B:
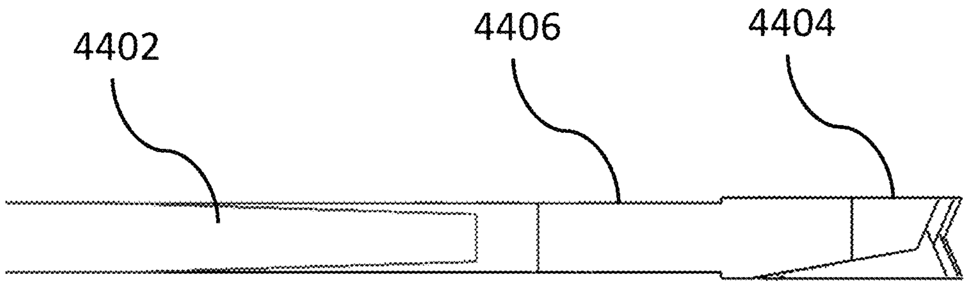
Figure 44C:
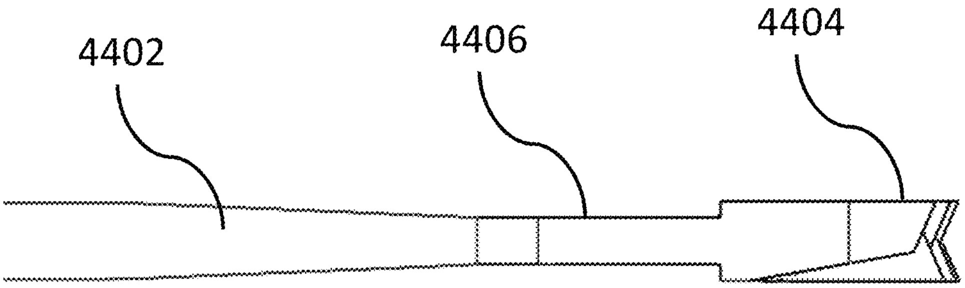
Figure 45:
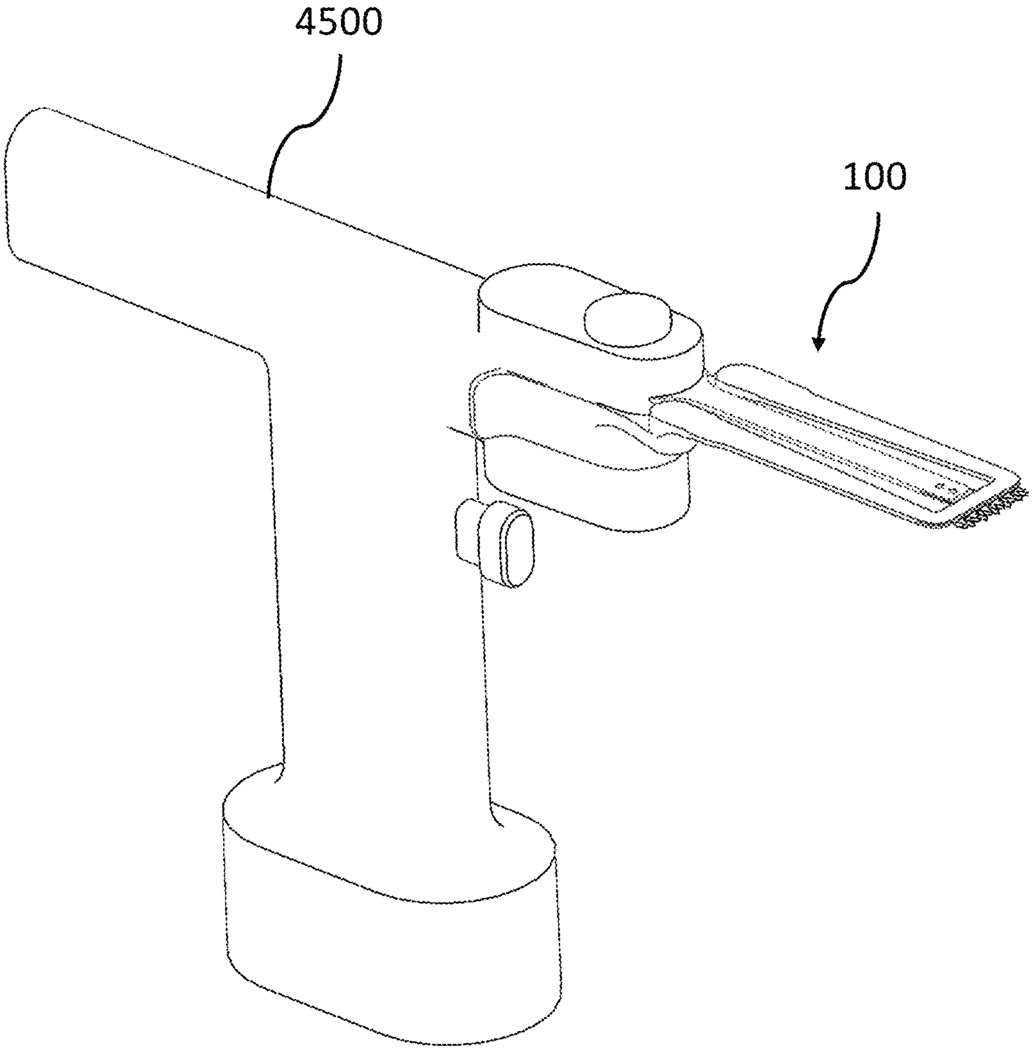
Figure 46:
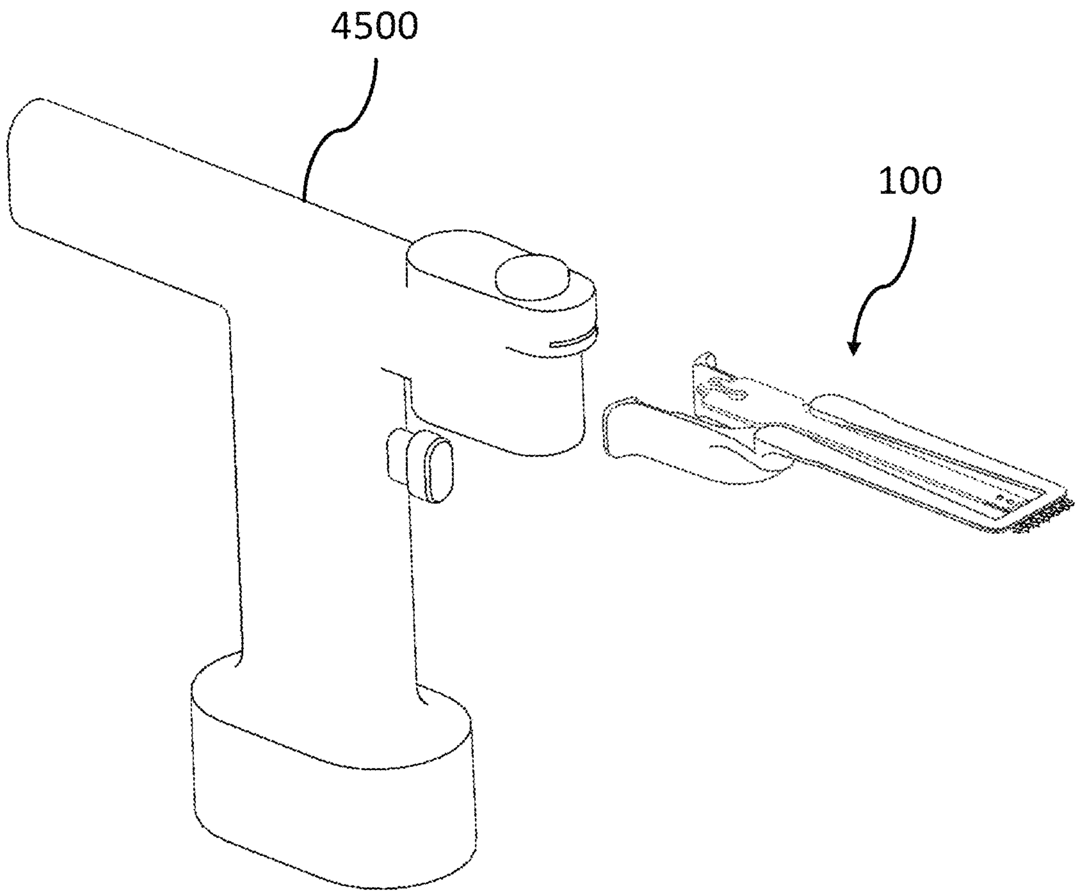
Figure 47:
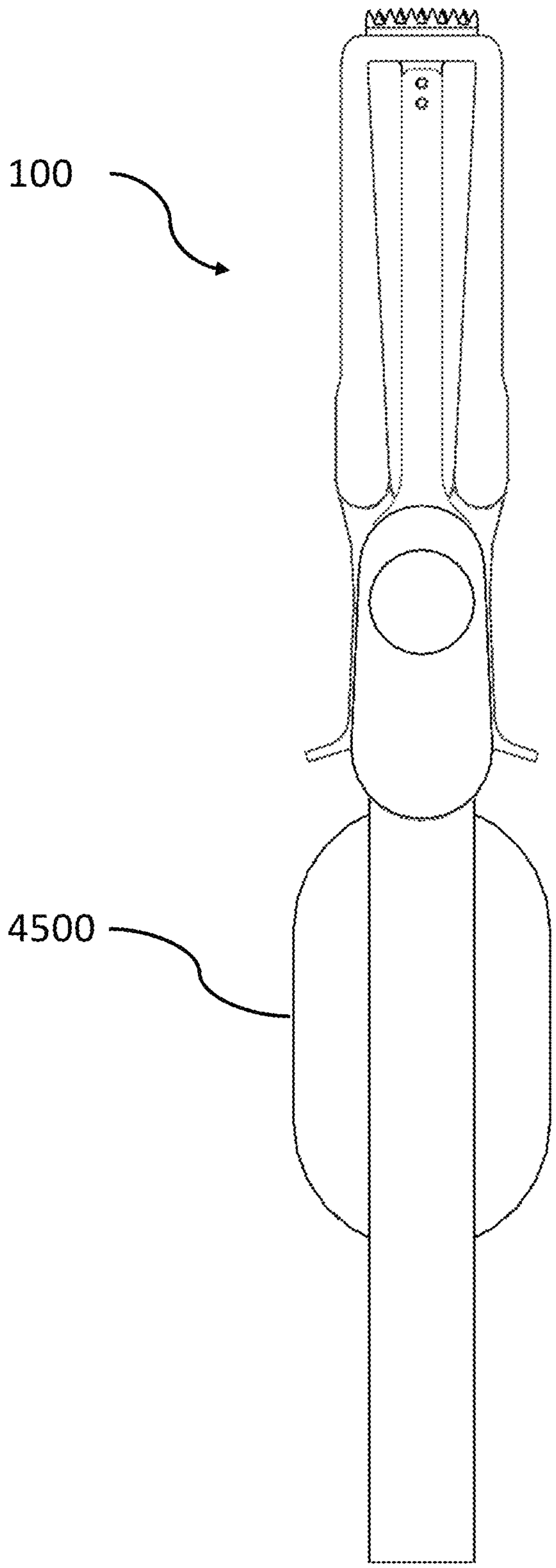
Figure 48A:
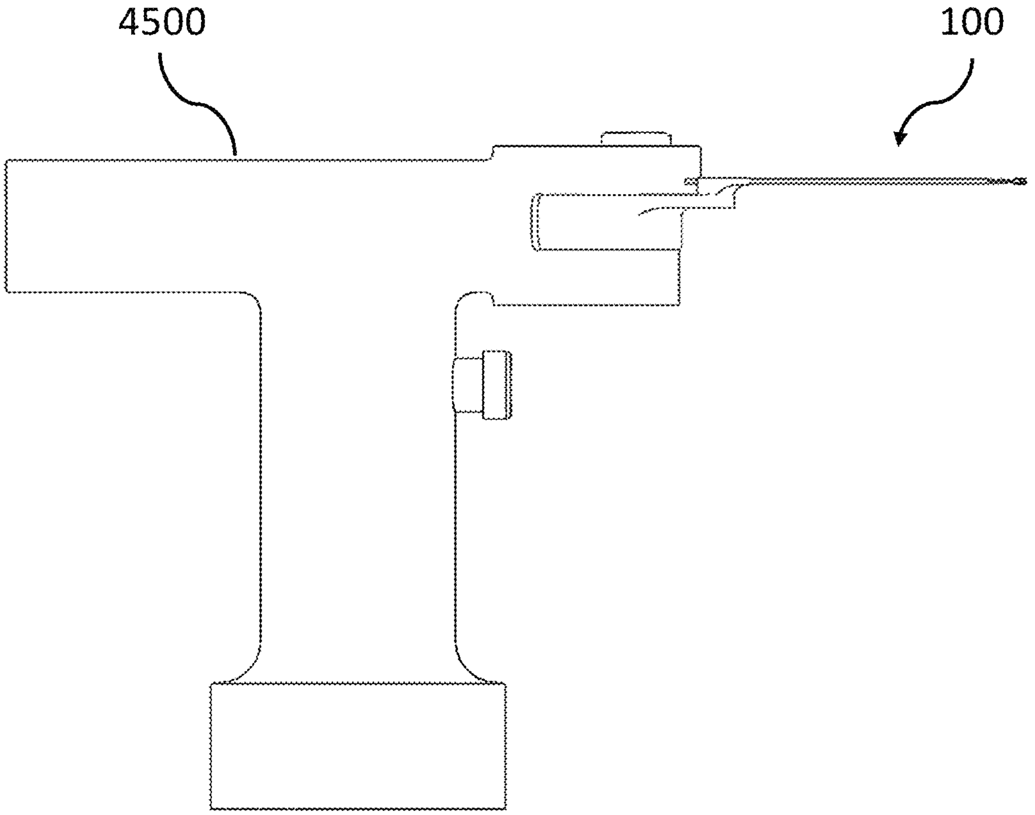
Figure 48B:
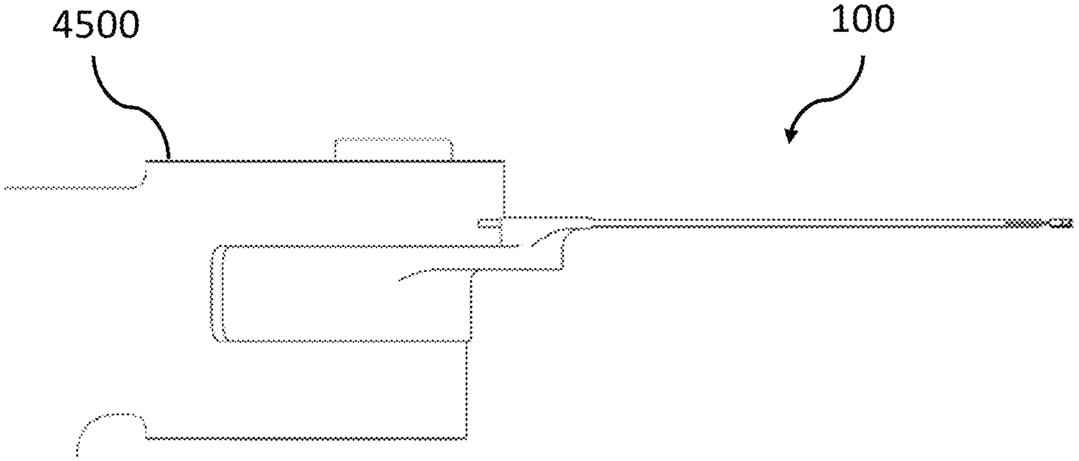
Figure 49:
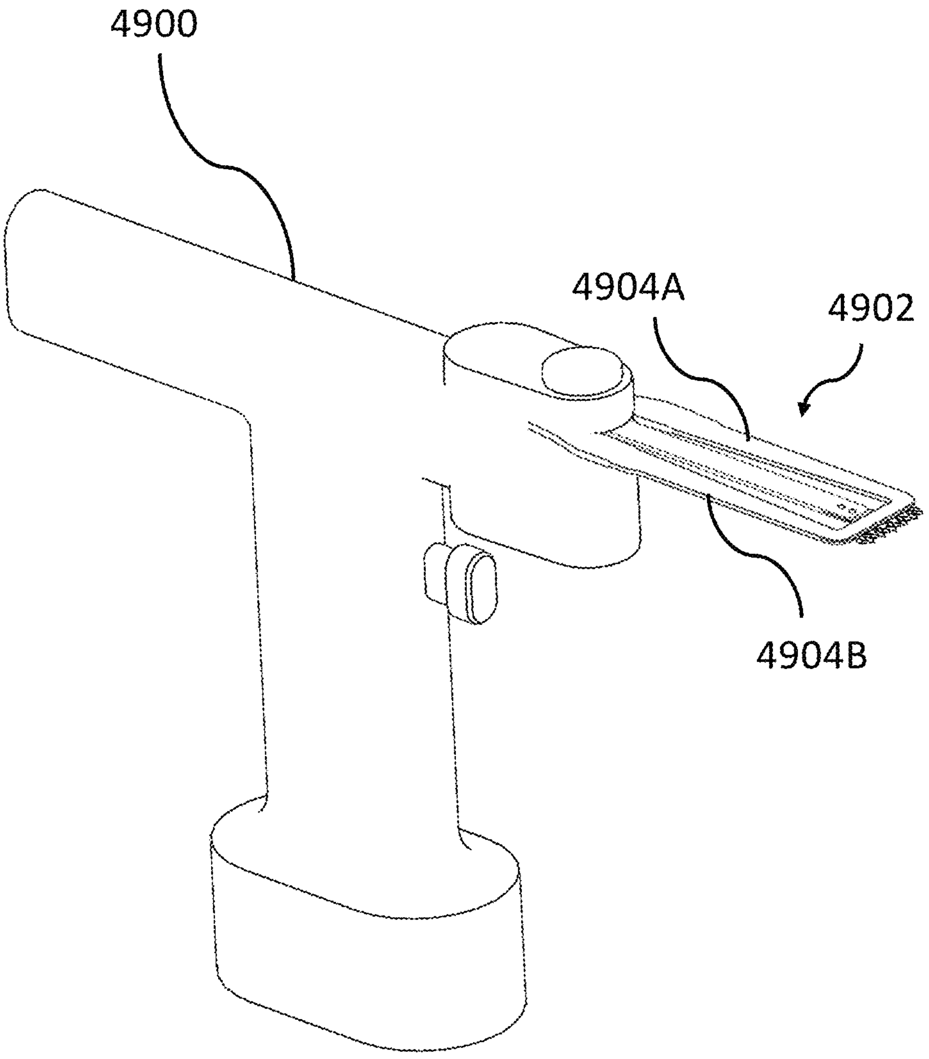
Figure 50:
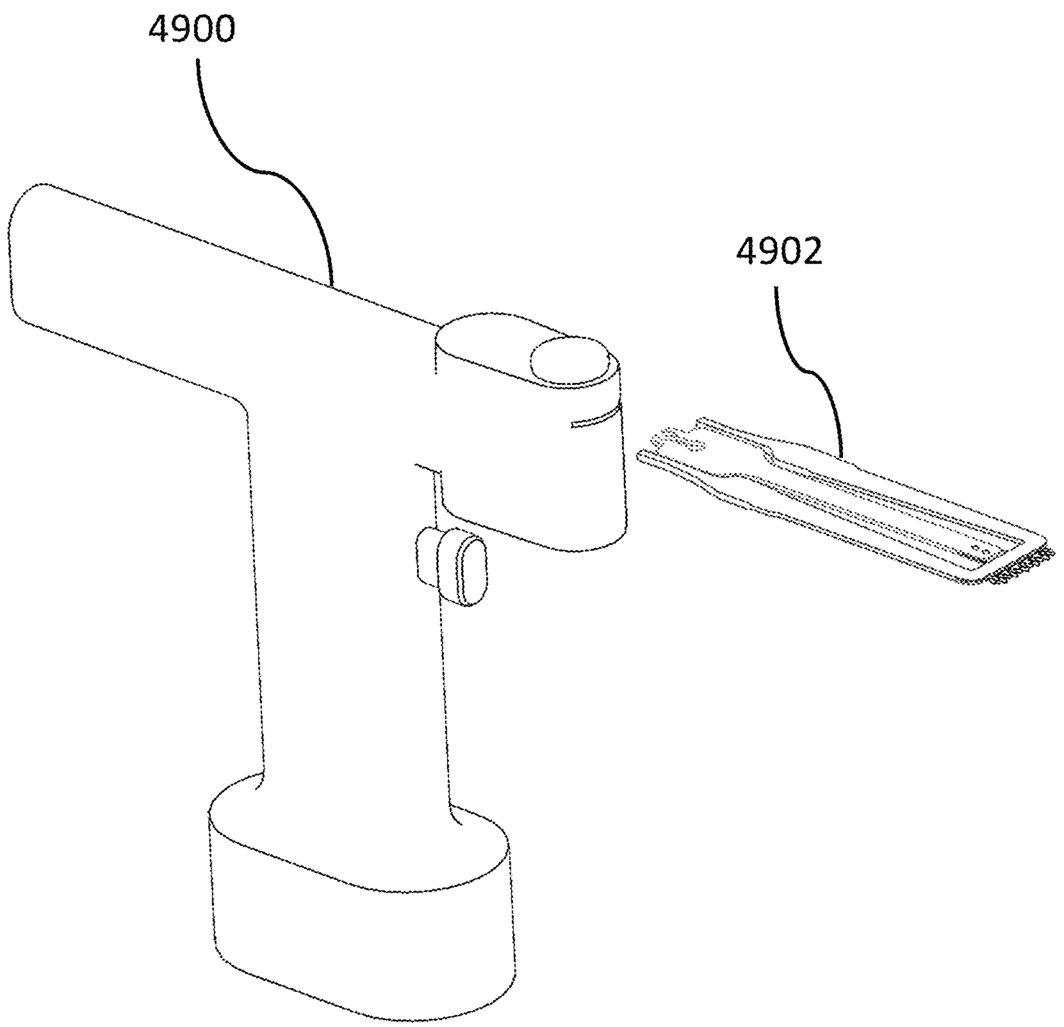
Figure 51:
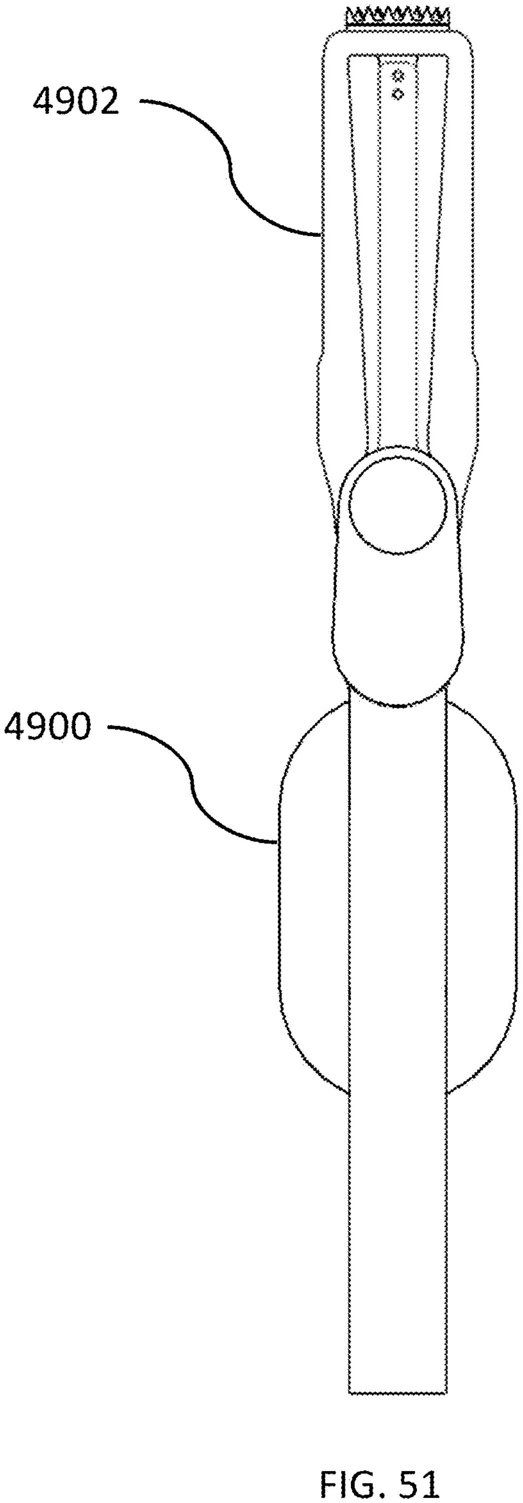
Figure 52:
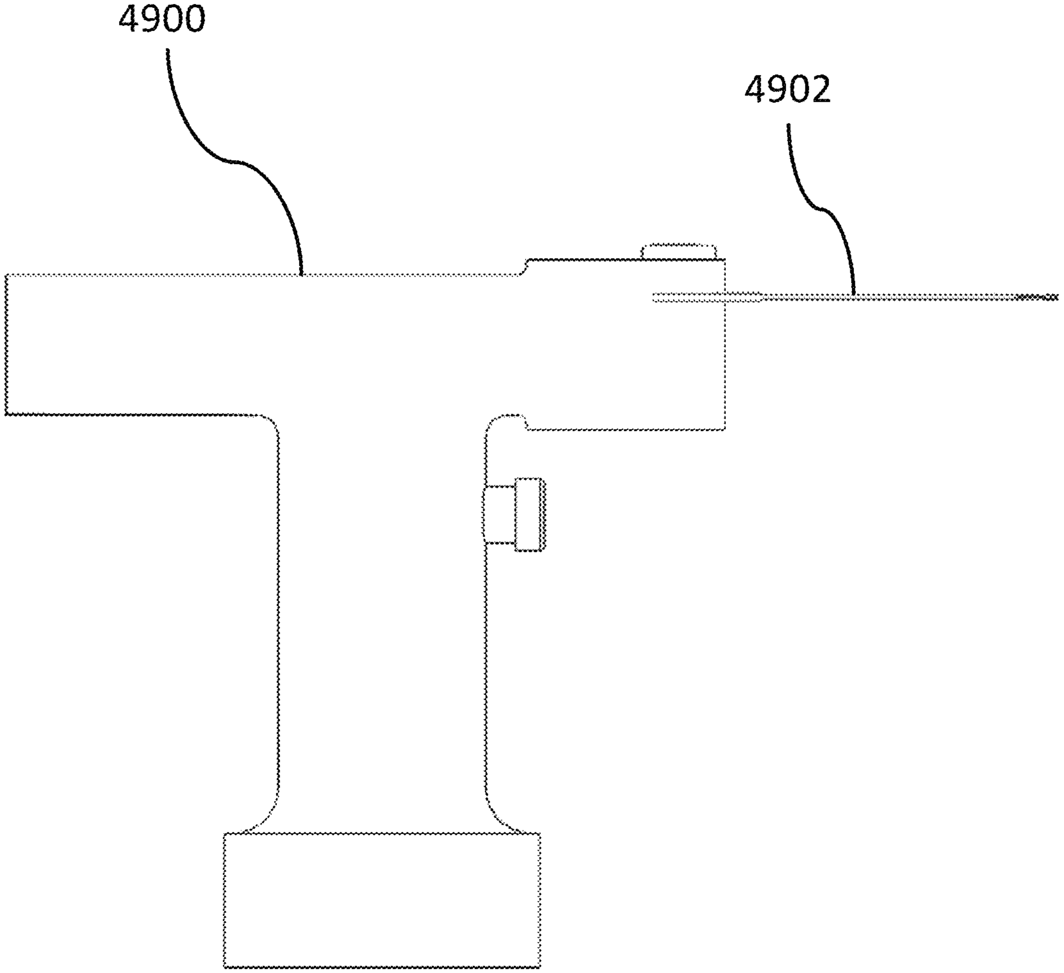
Figure 53A:
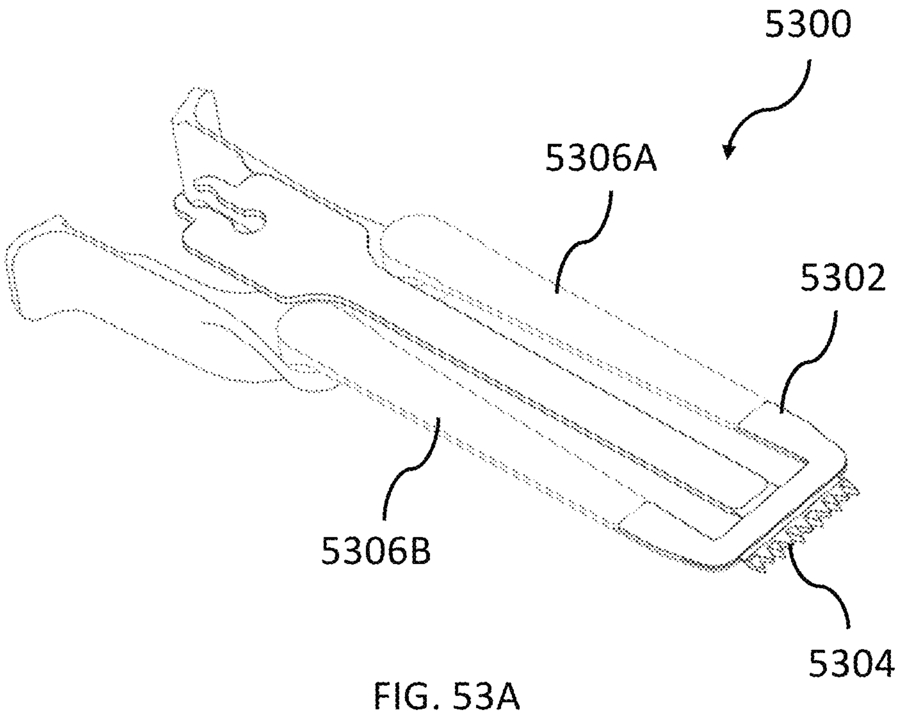
Figure 53B:
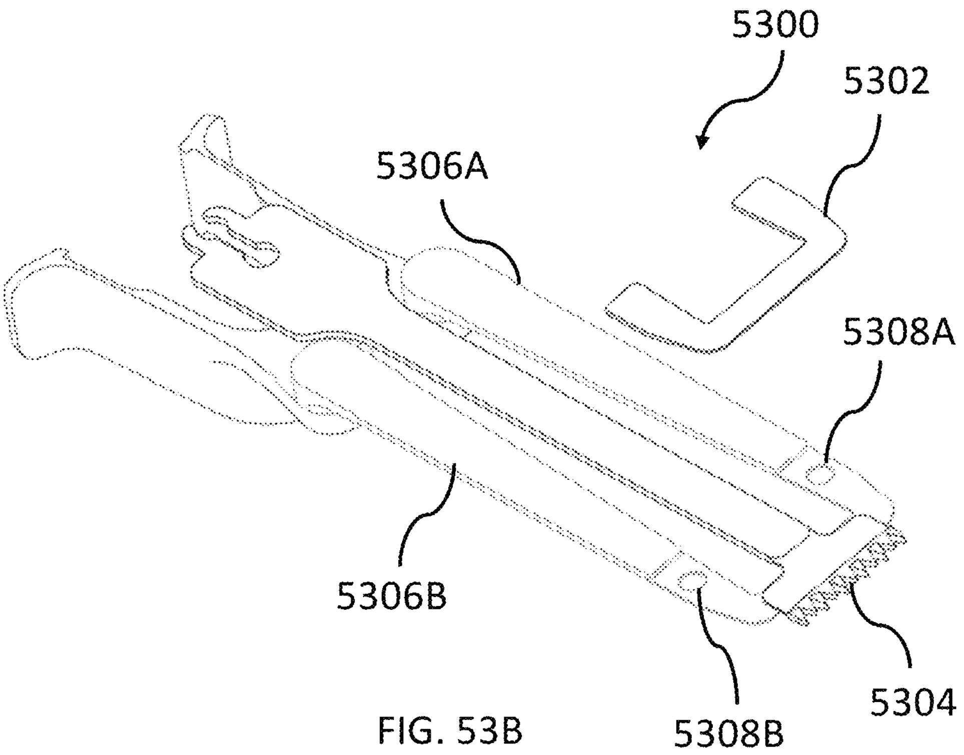
Figure 54A:
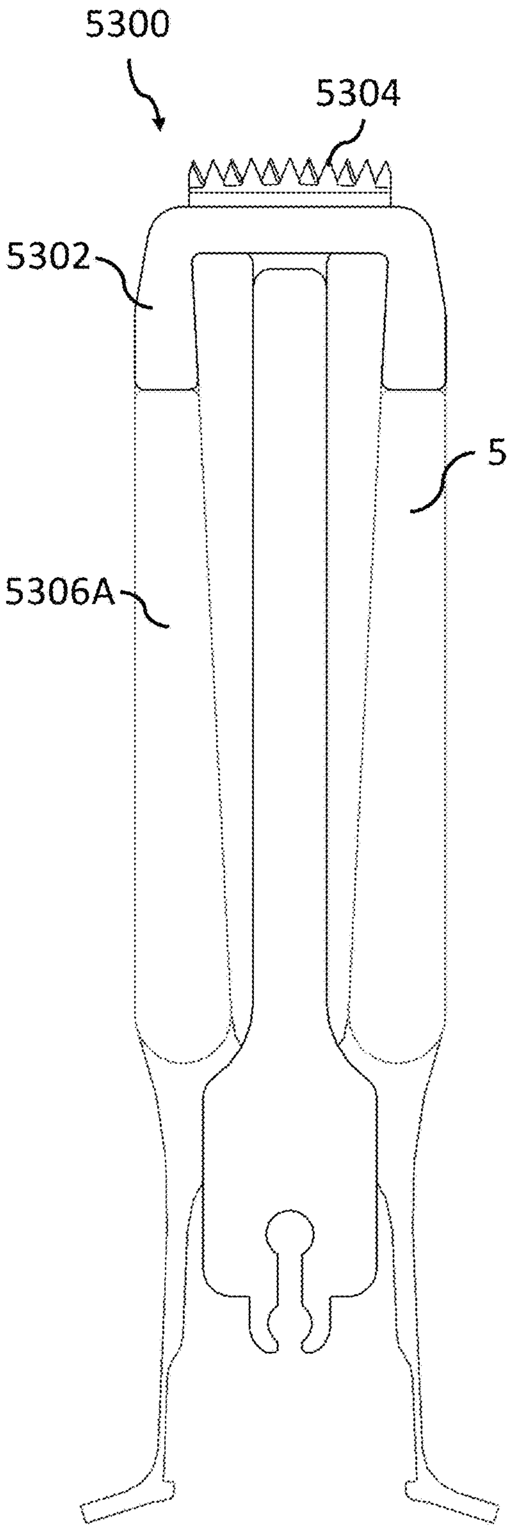
Figure 54B:
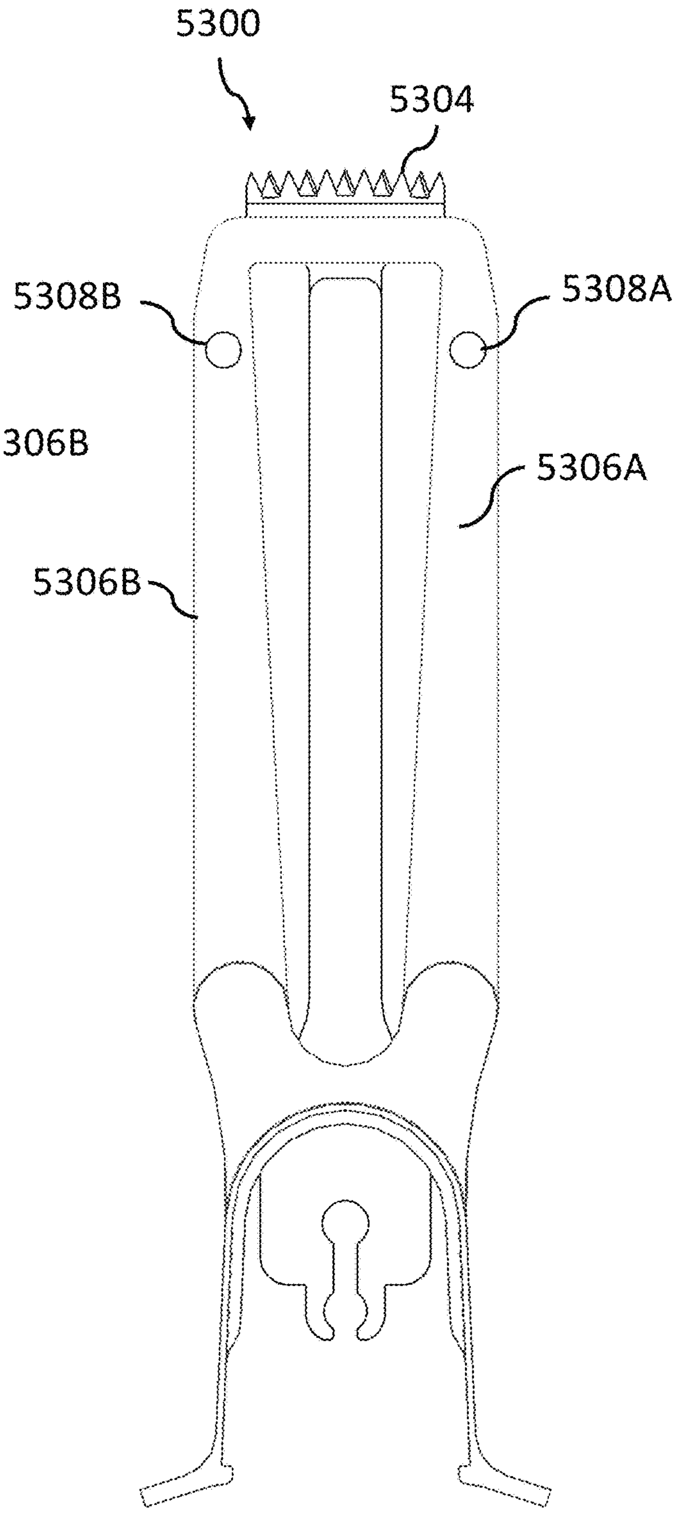
Figure 55A:
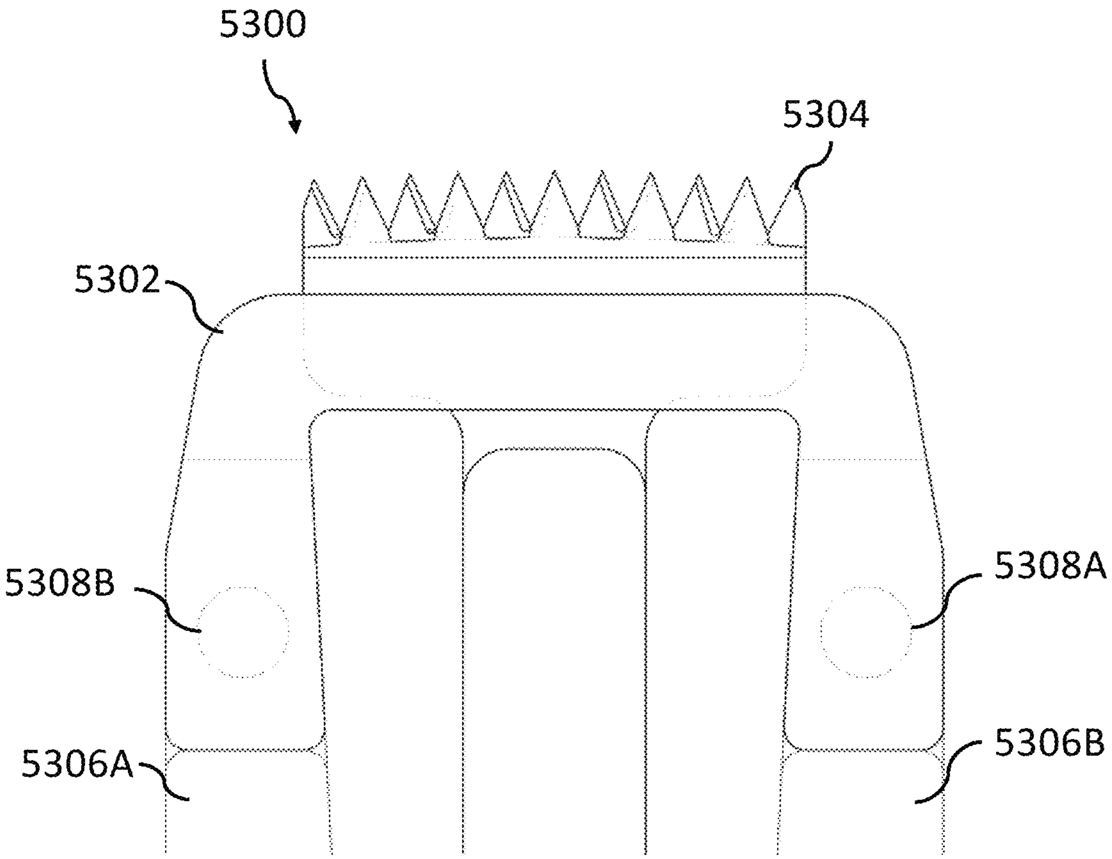
Figure 55B:
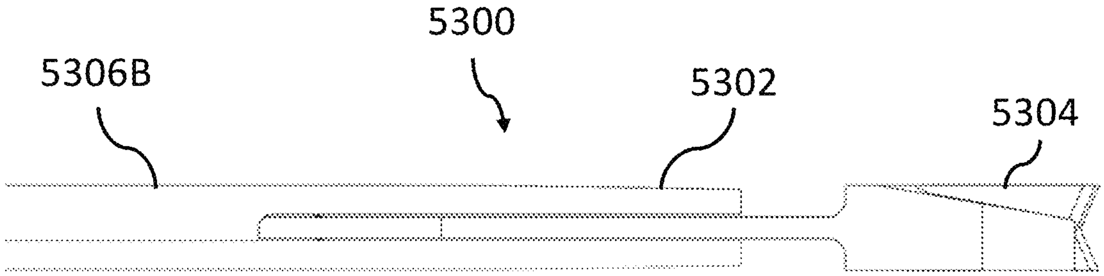
Figure 56A:
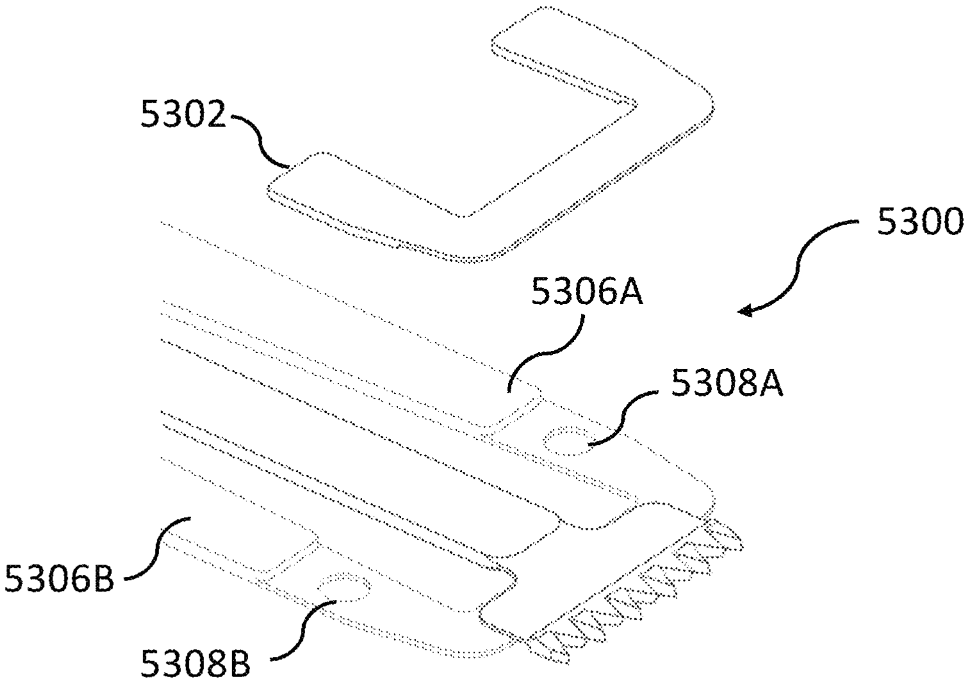
Figure 56B:
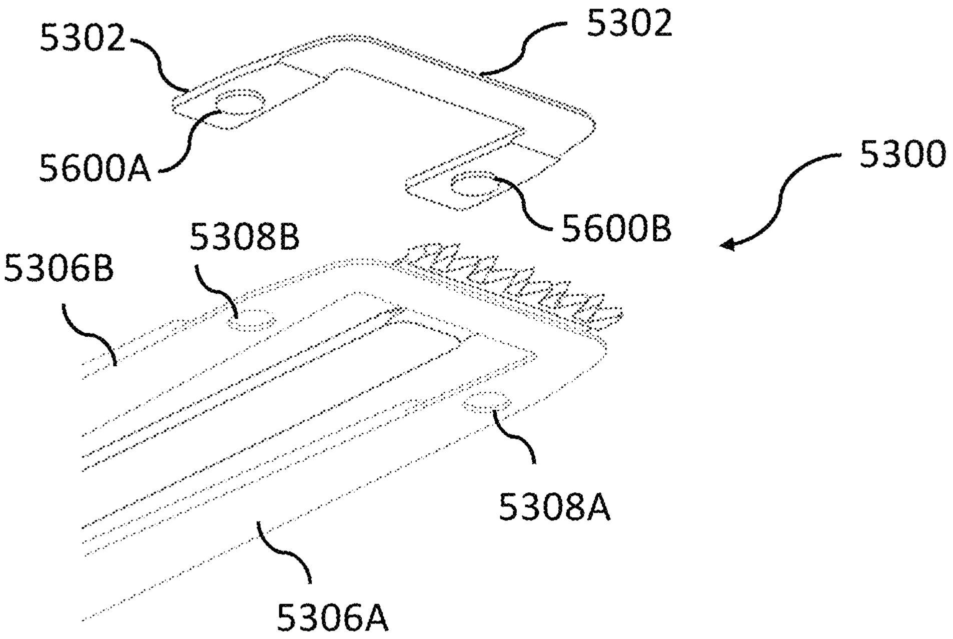
Figure 57A:
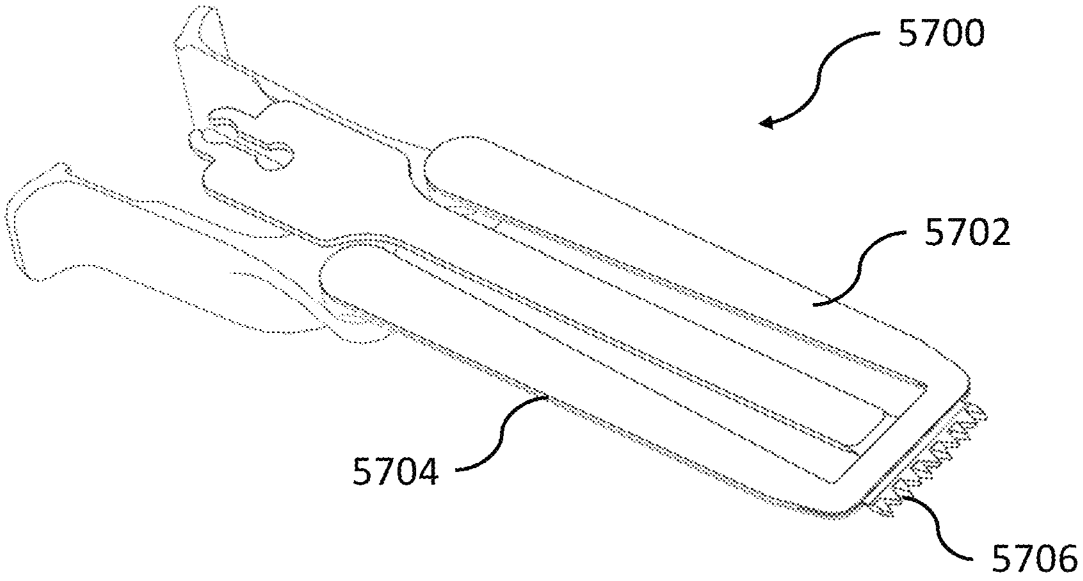
Figure 57B:
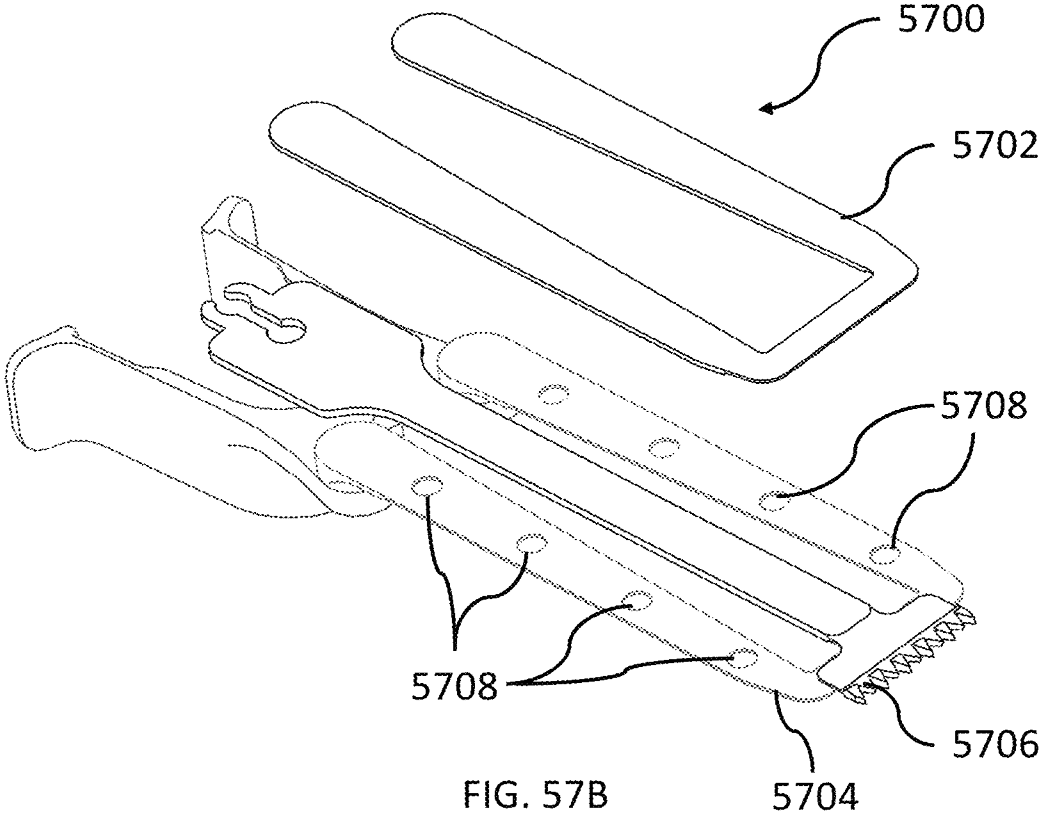
Figure 58A:
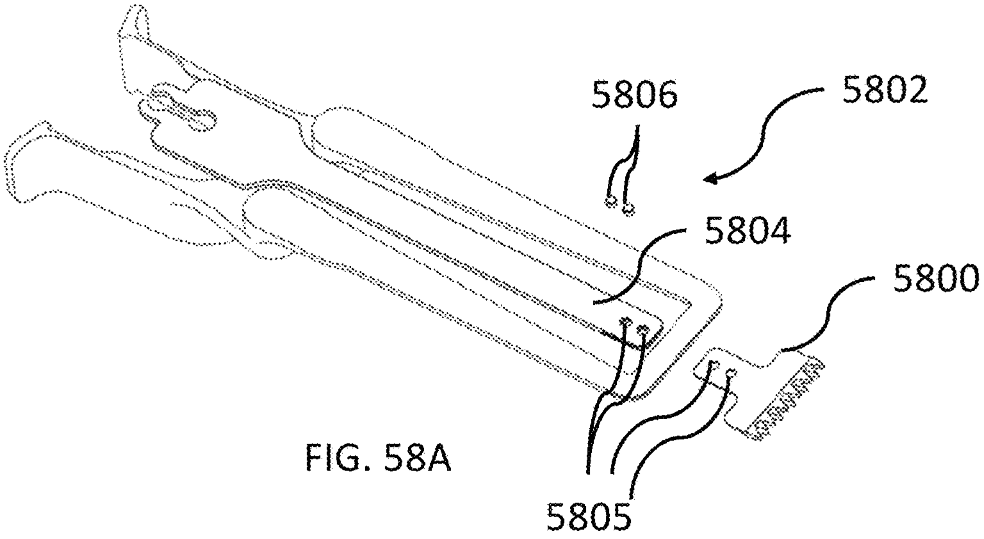
Figure 58B:
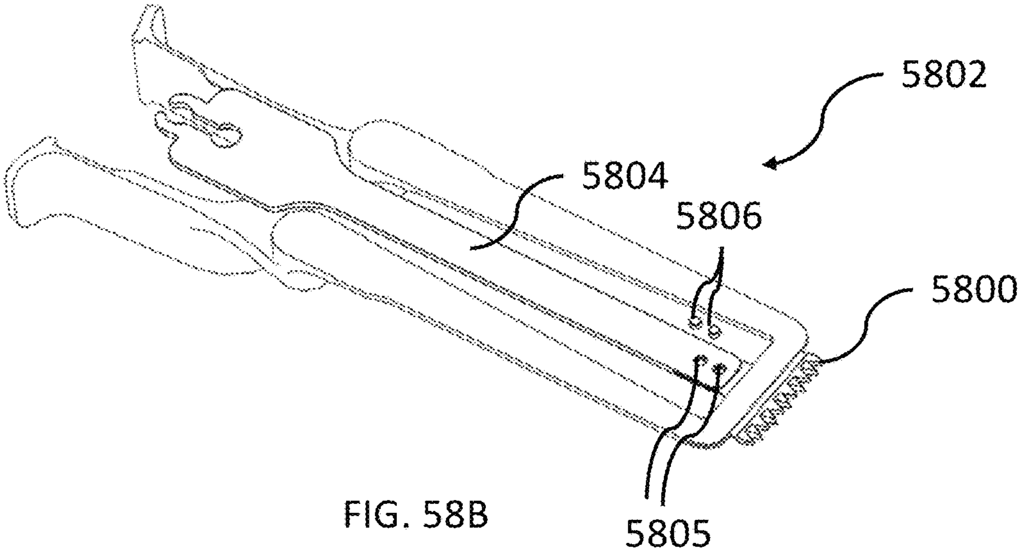
Figure 58C:
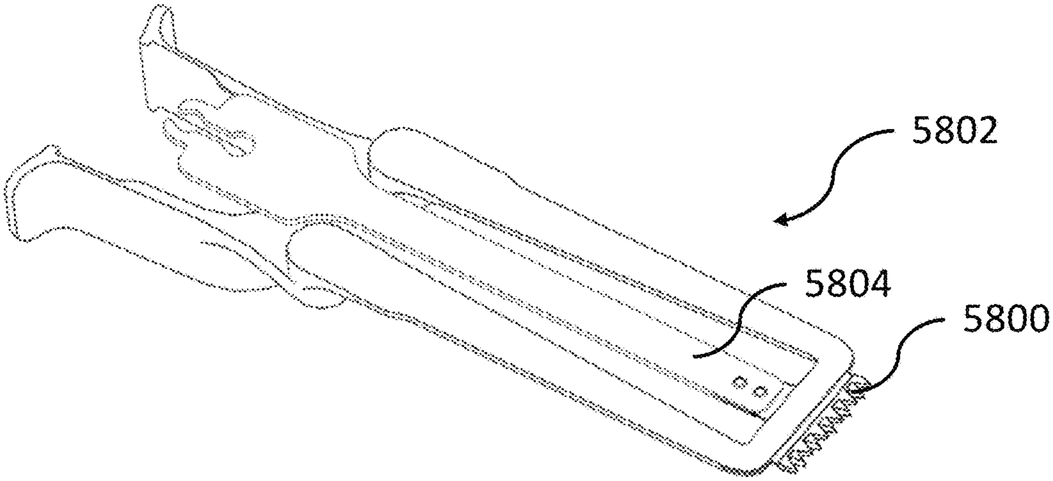
Figure 59A:
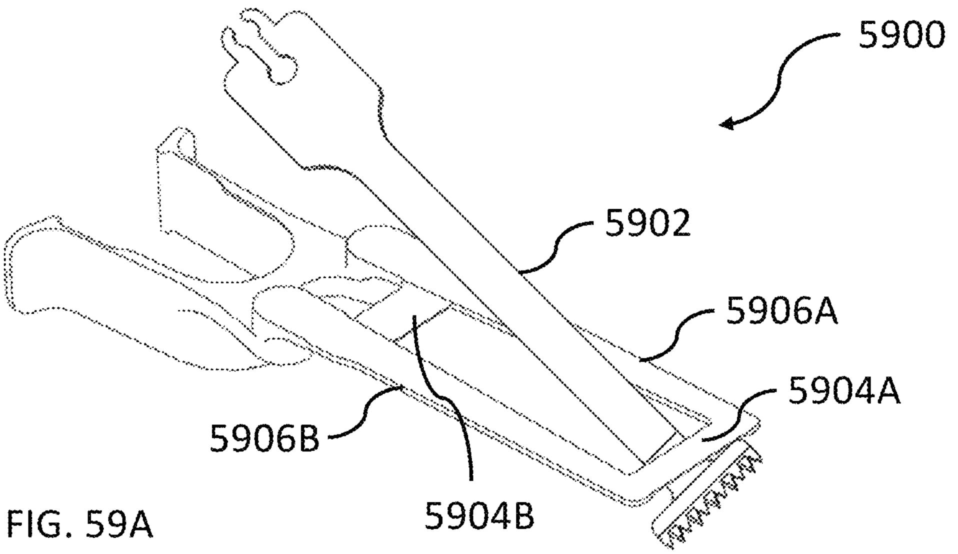
Figure 59B:
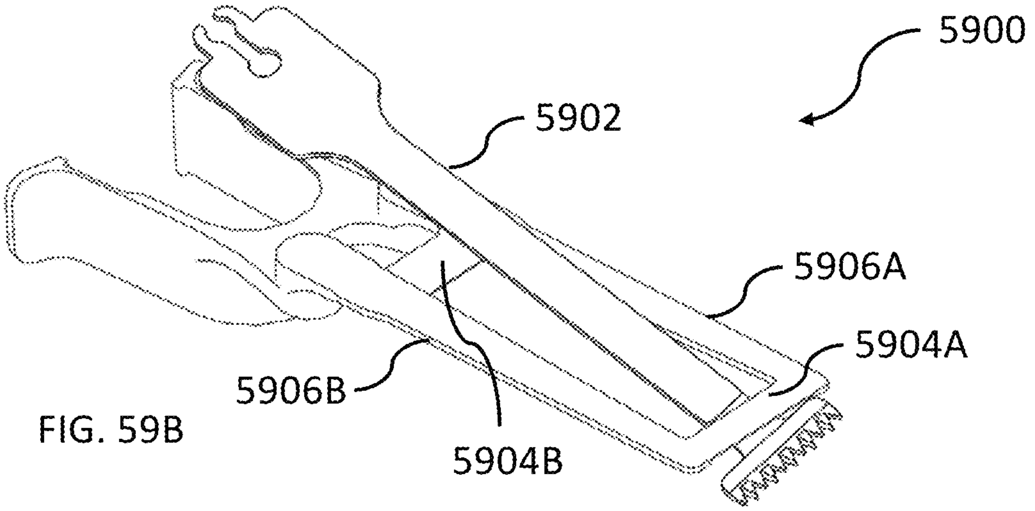
Figure 59C:
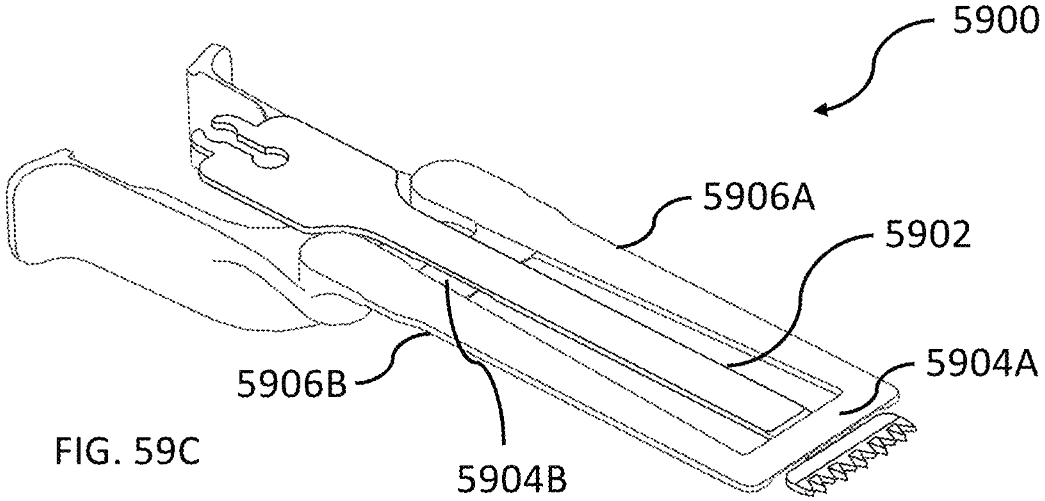
Figure 60A:
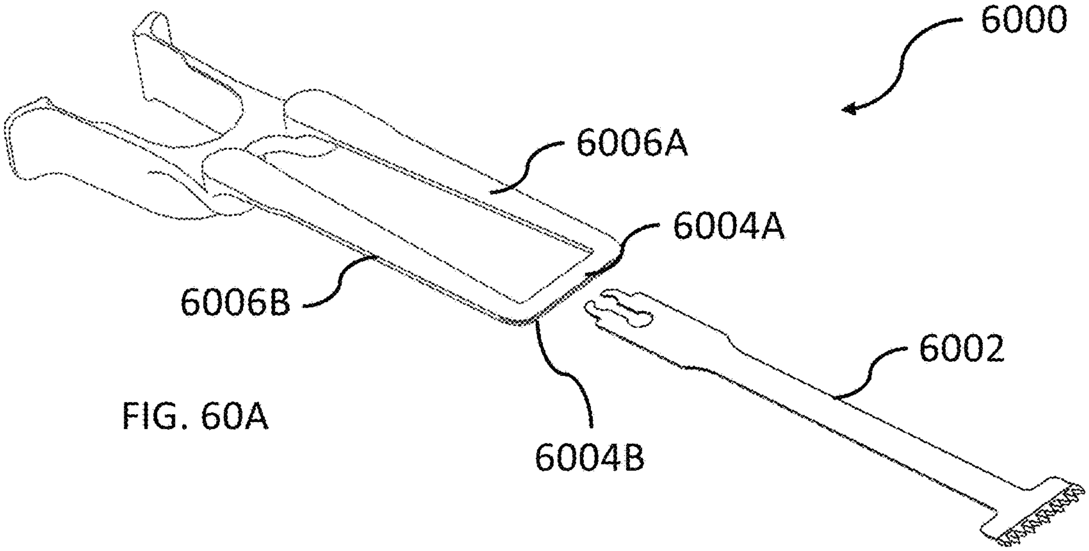
Figure 60B:
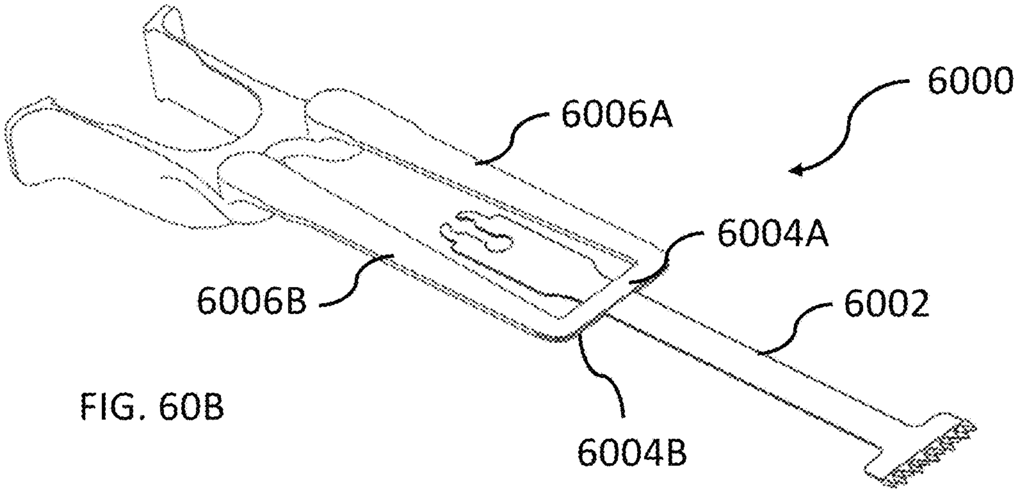
Figure 60C:
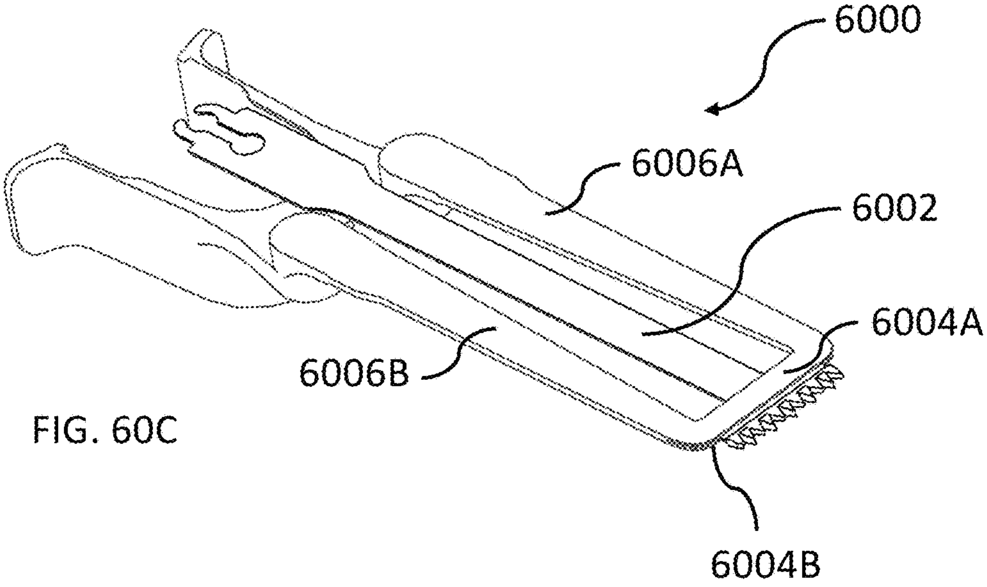
Figure 61:
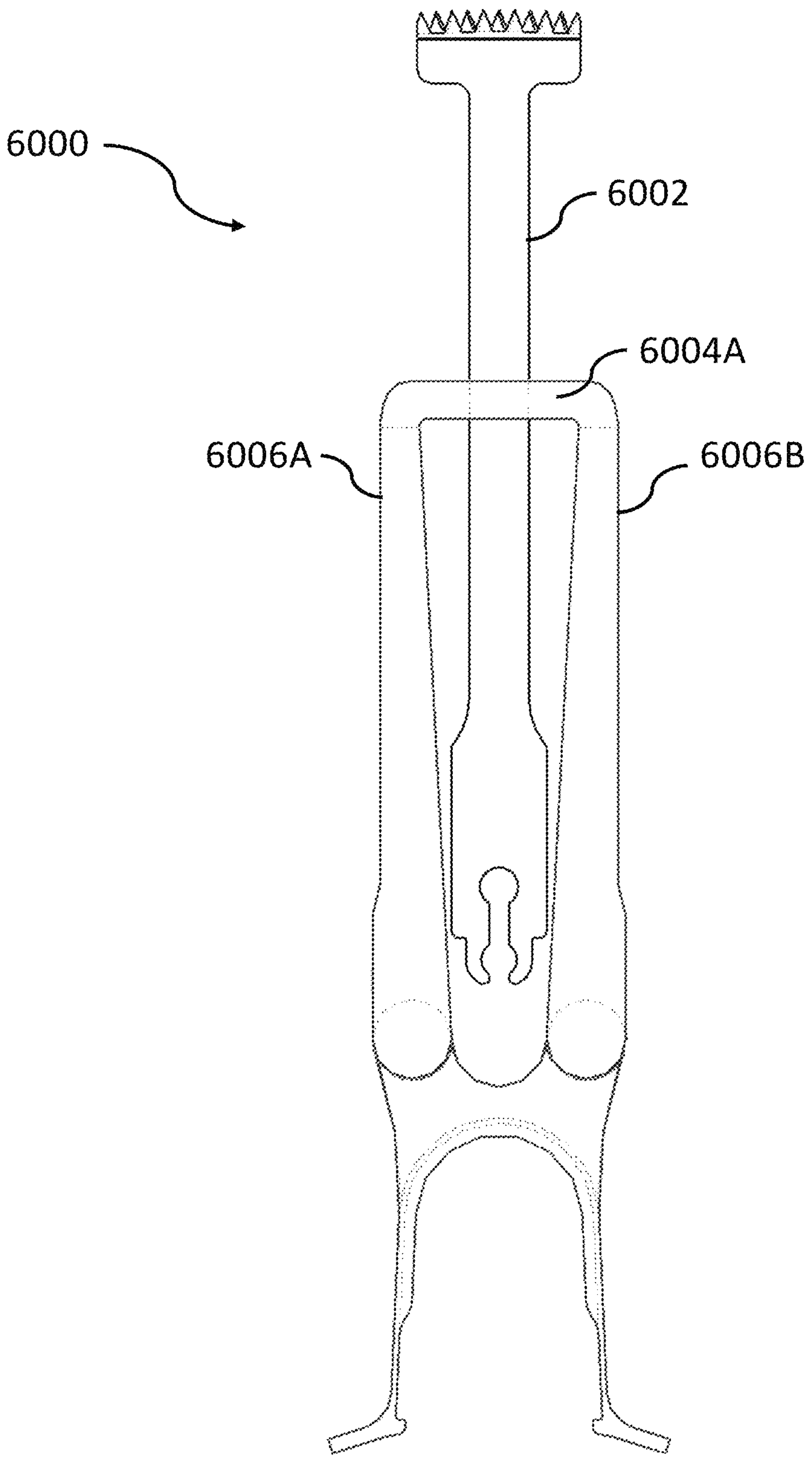
Figure 66A:
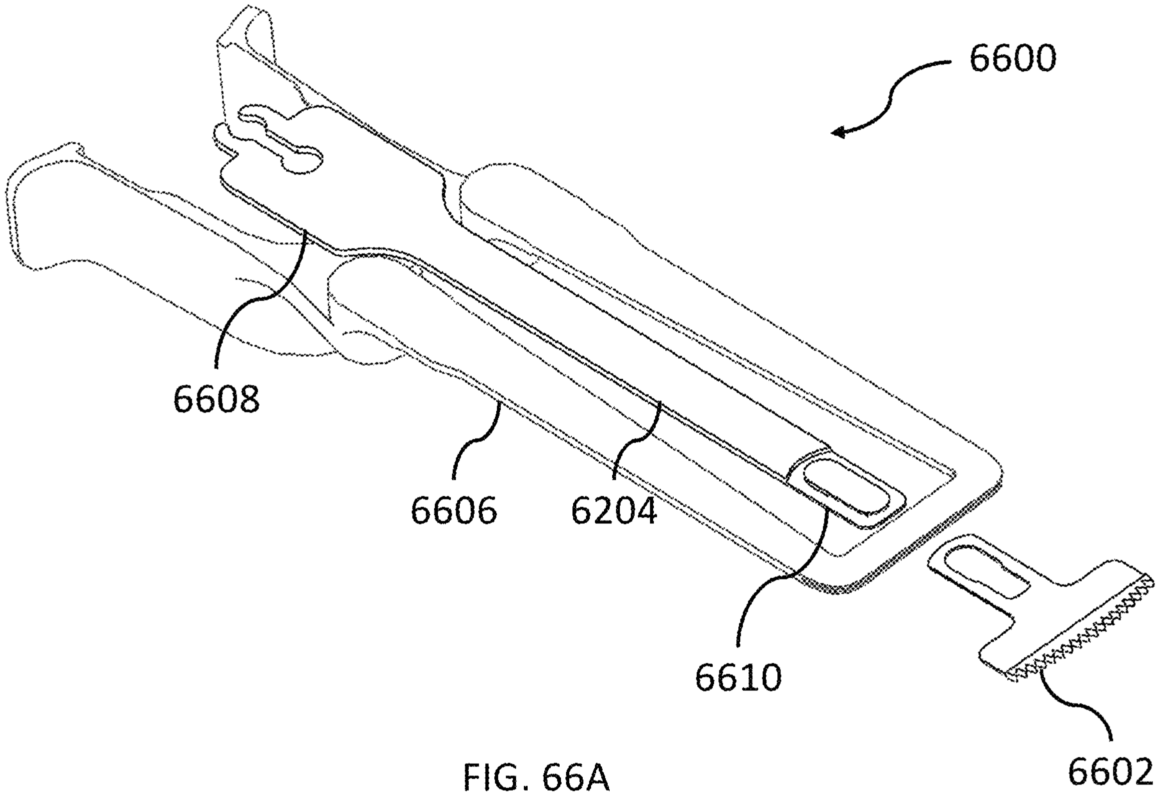
Figure 66B:
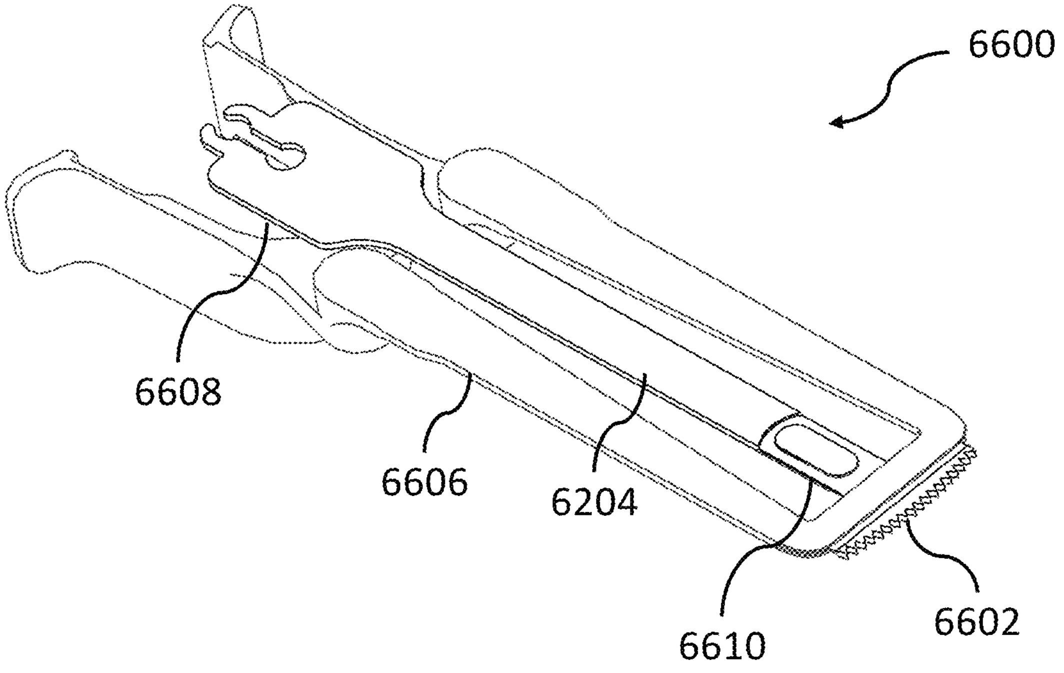
Figure 67:
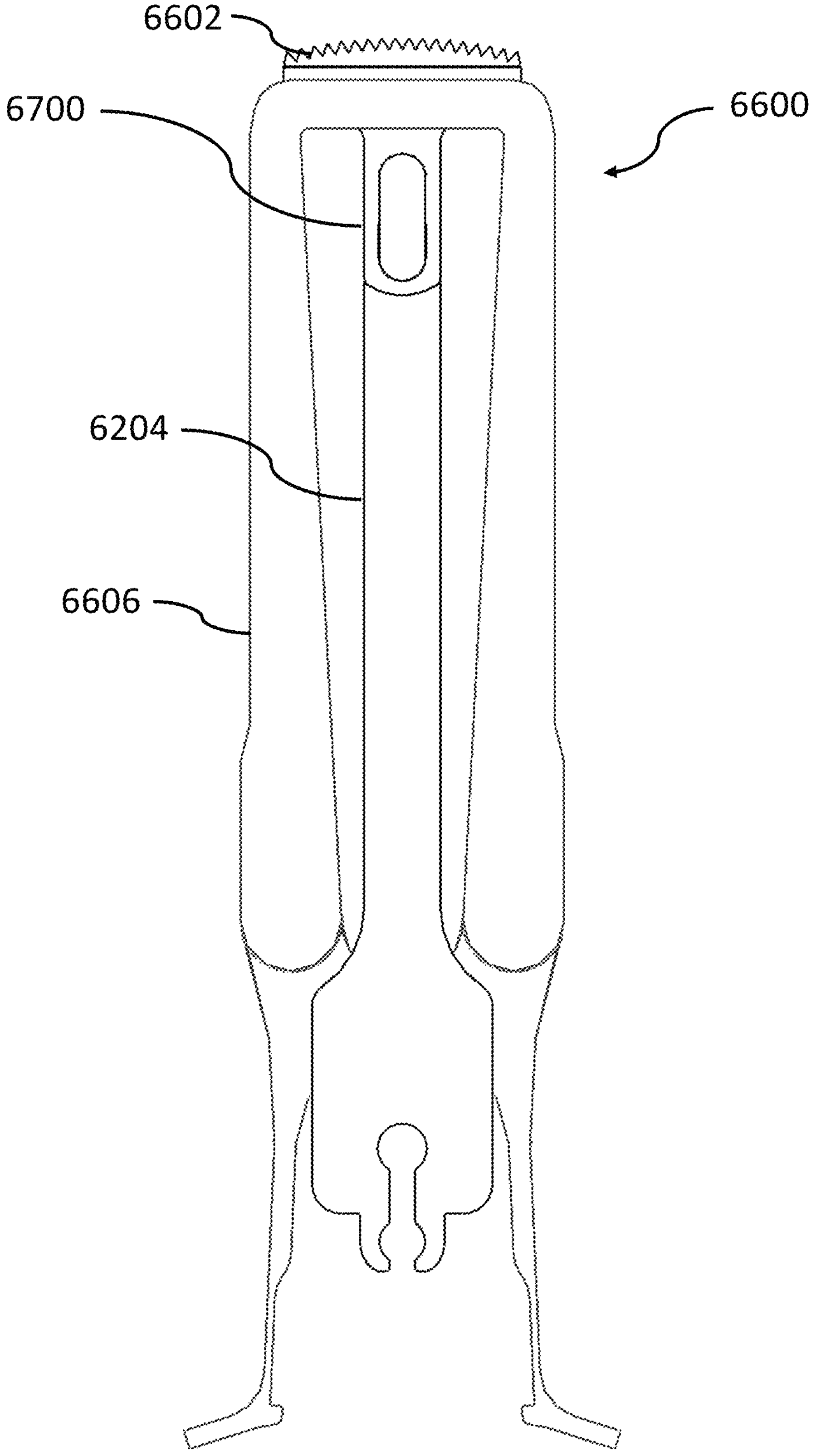
Figure 68A:
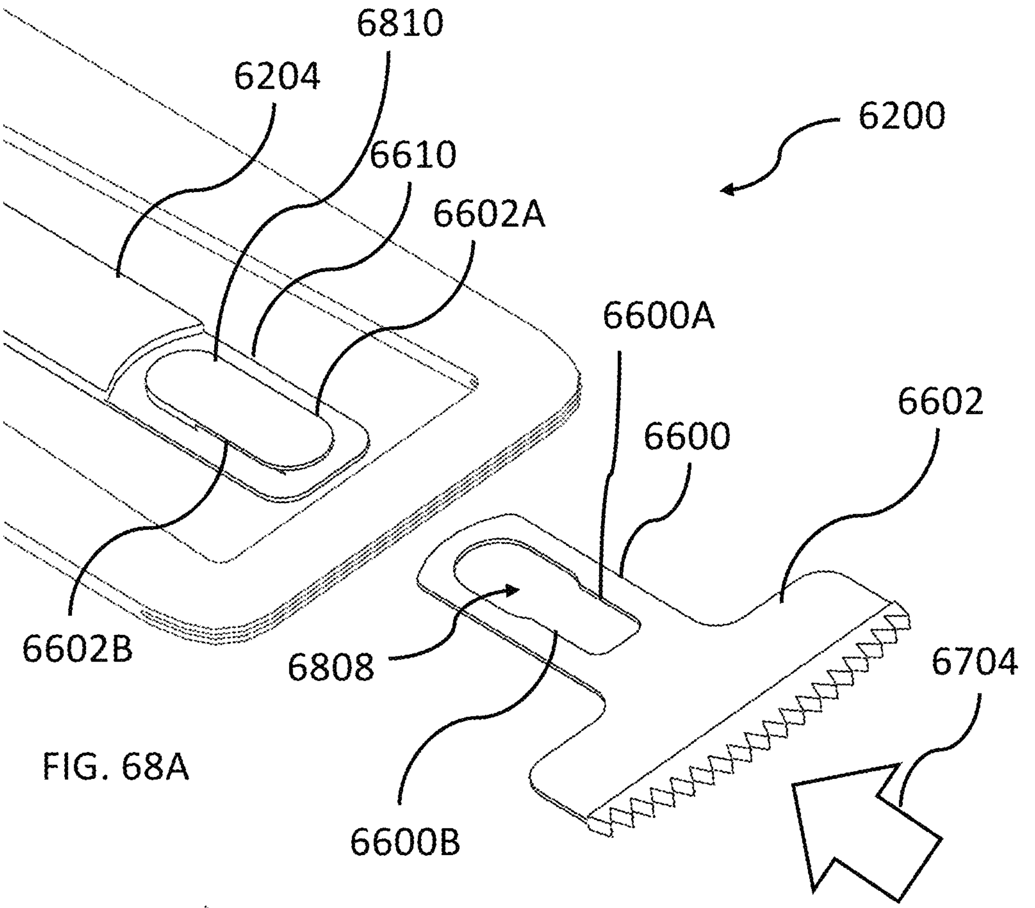
Figure 68B:
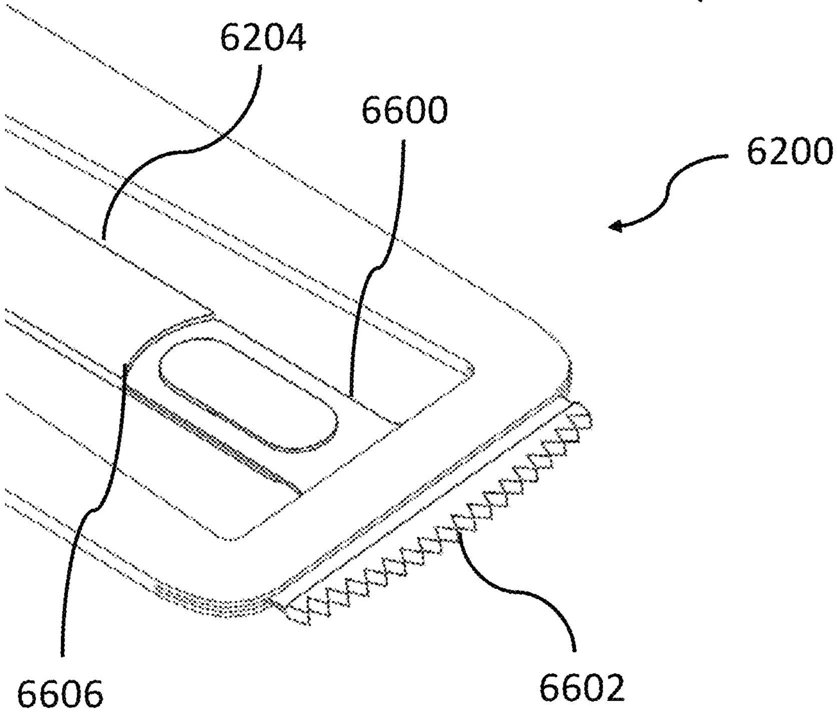
Figure 69A:
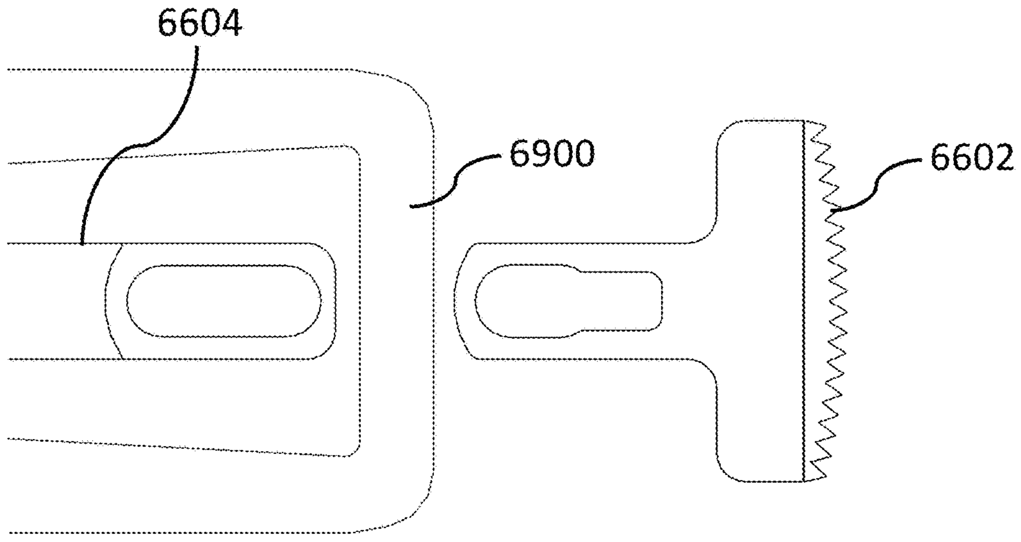
Figure 69B:
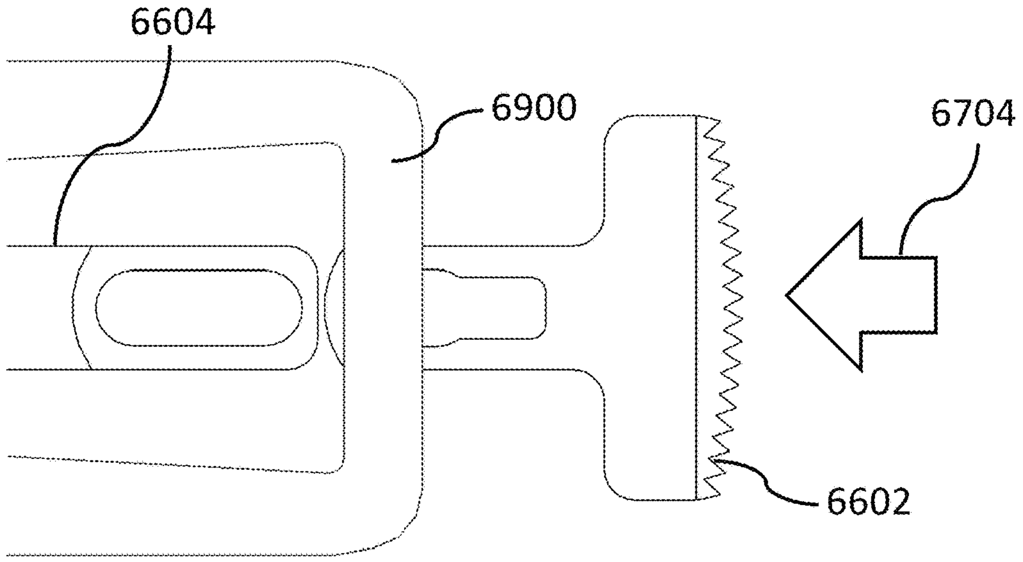
Figure 69C:
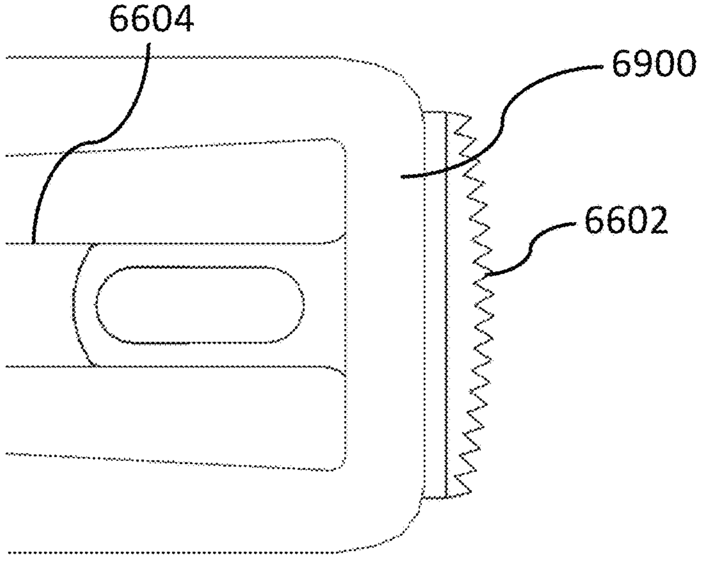
Figure 70A:
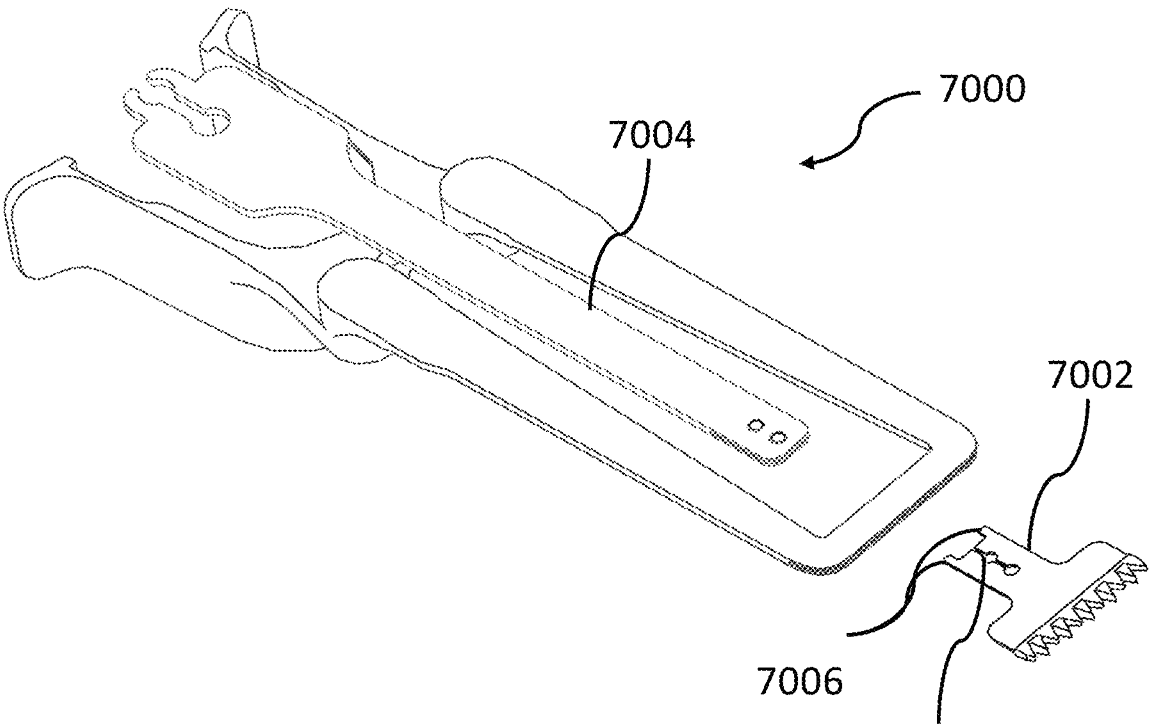
Figure 70B:
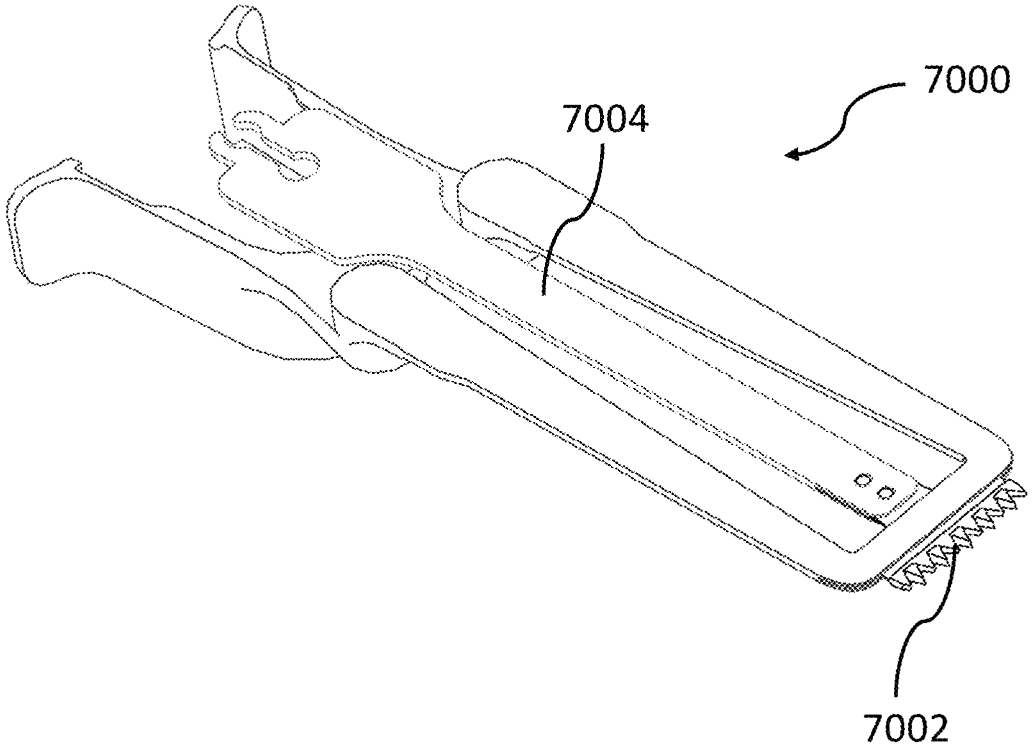
Figure 71A:
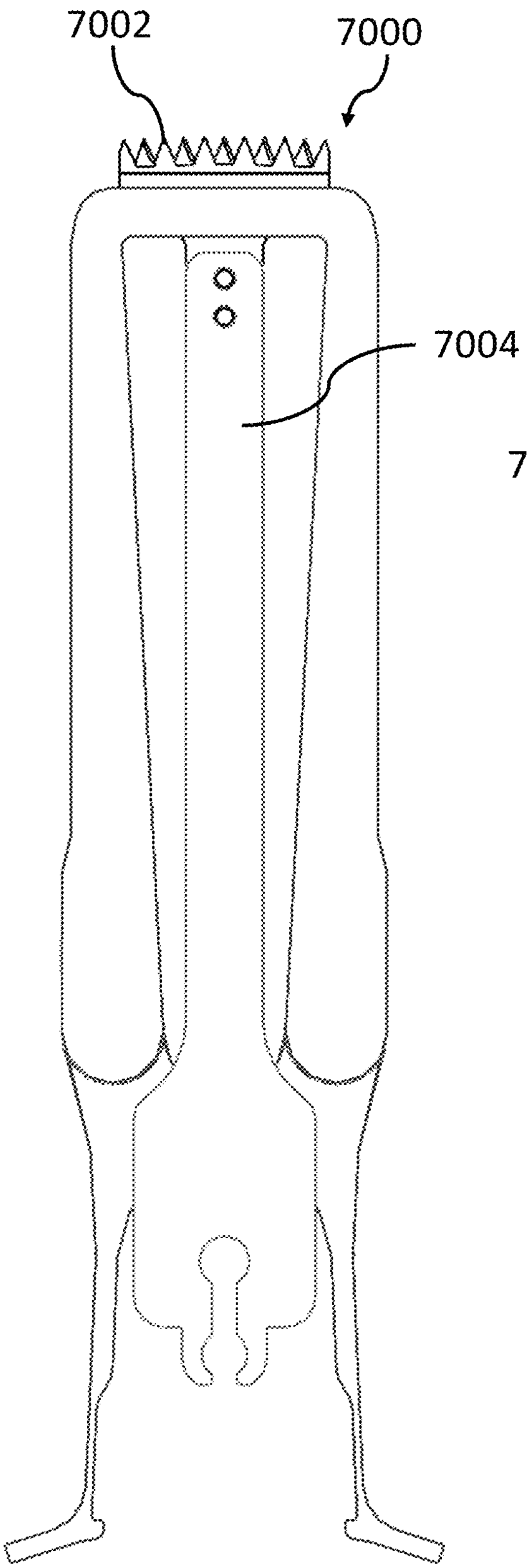
Figure 71B:
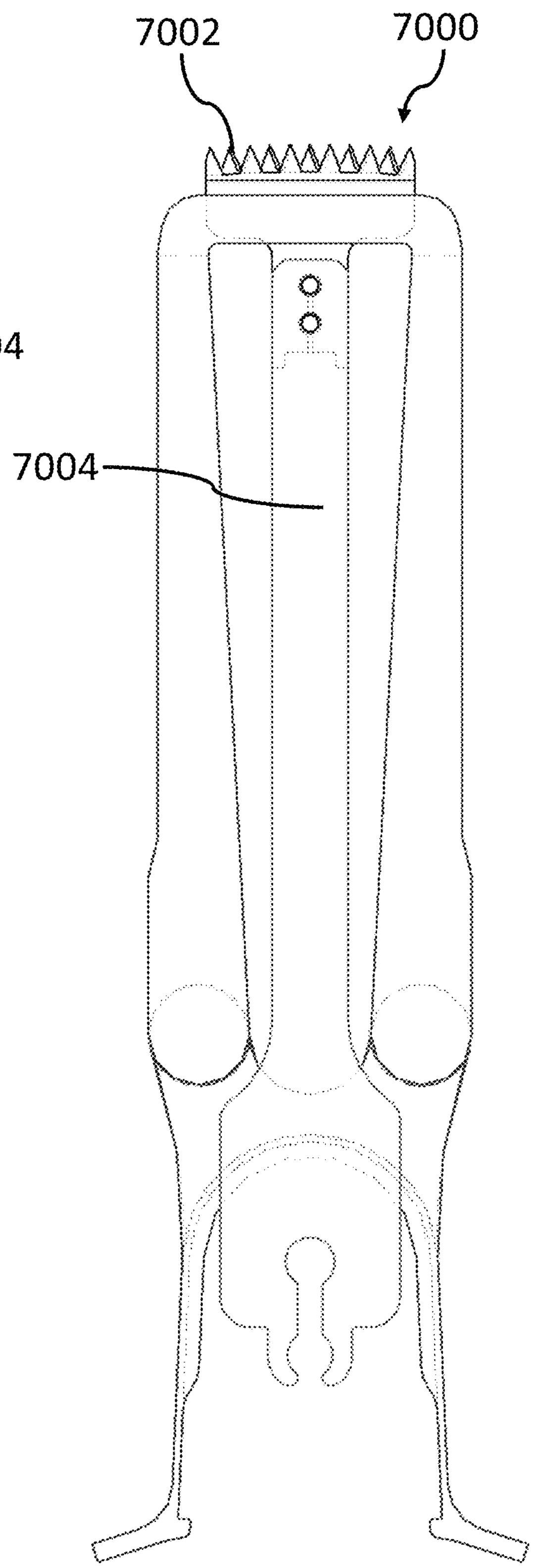
Figure 72:
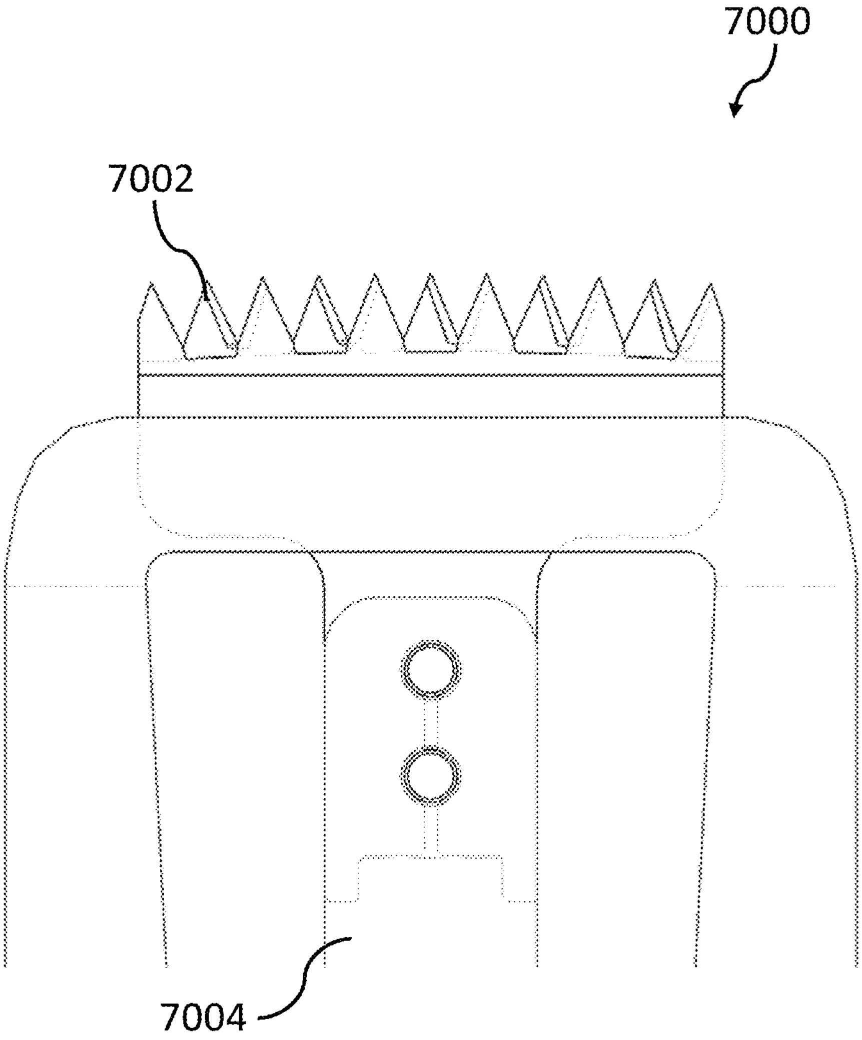
Figure 73A:
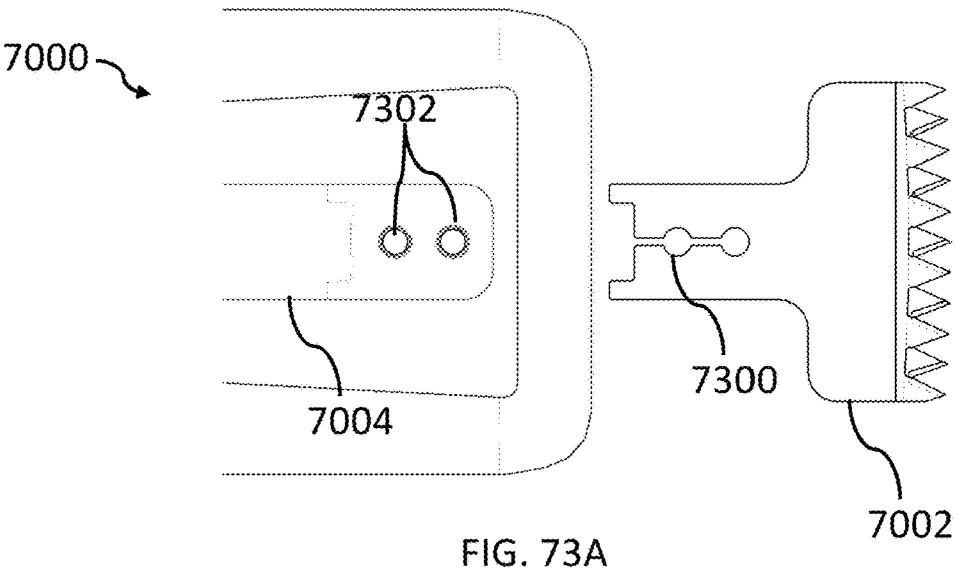
Figure 73B:
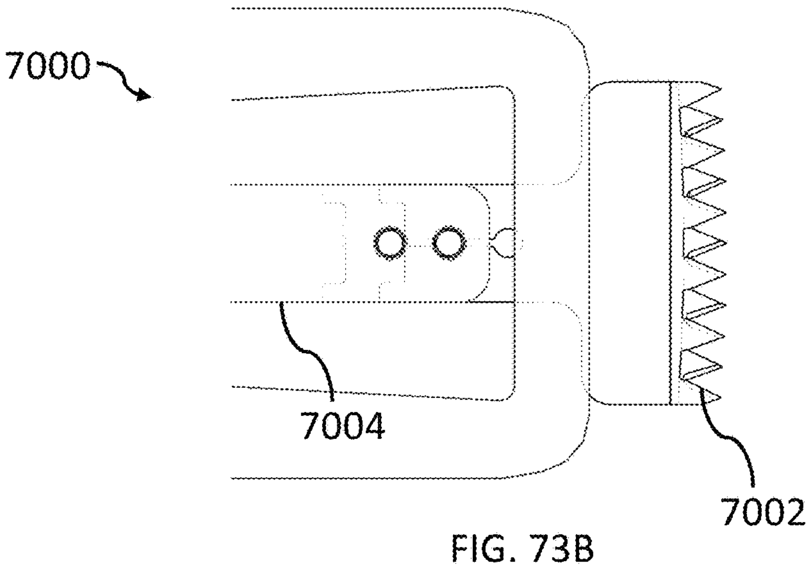
Figure 73C:
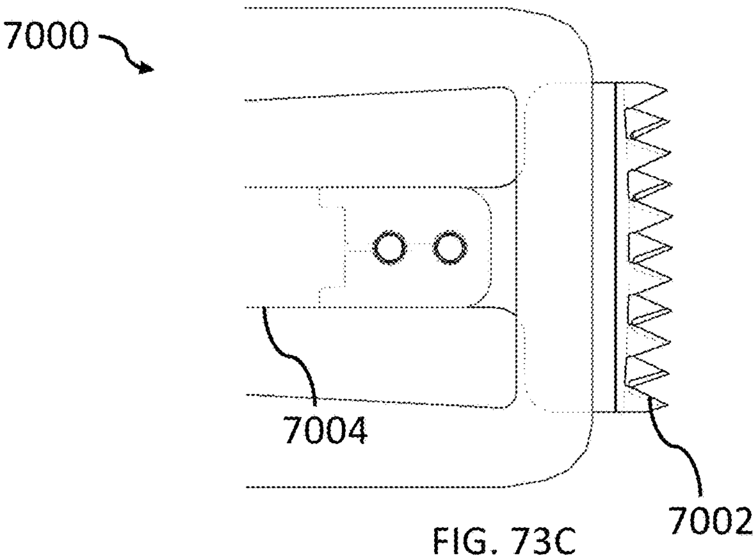
Figure 74:
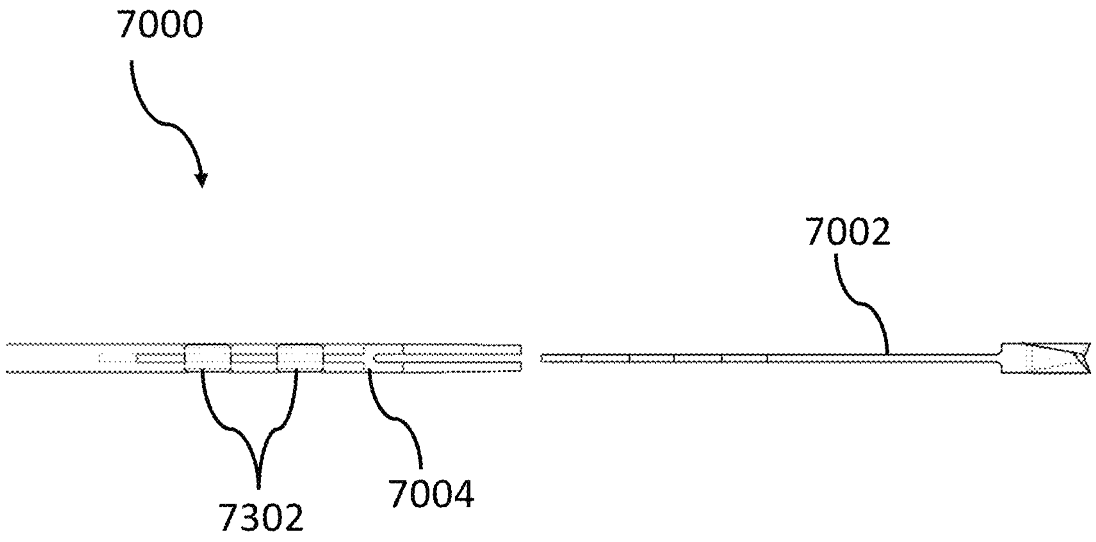
Figure 75A:
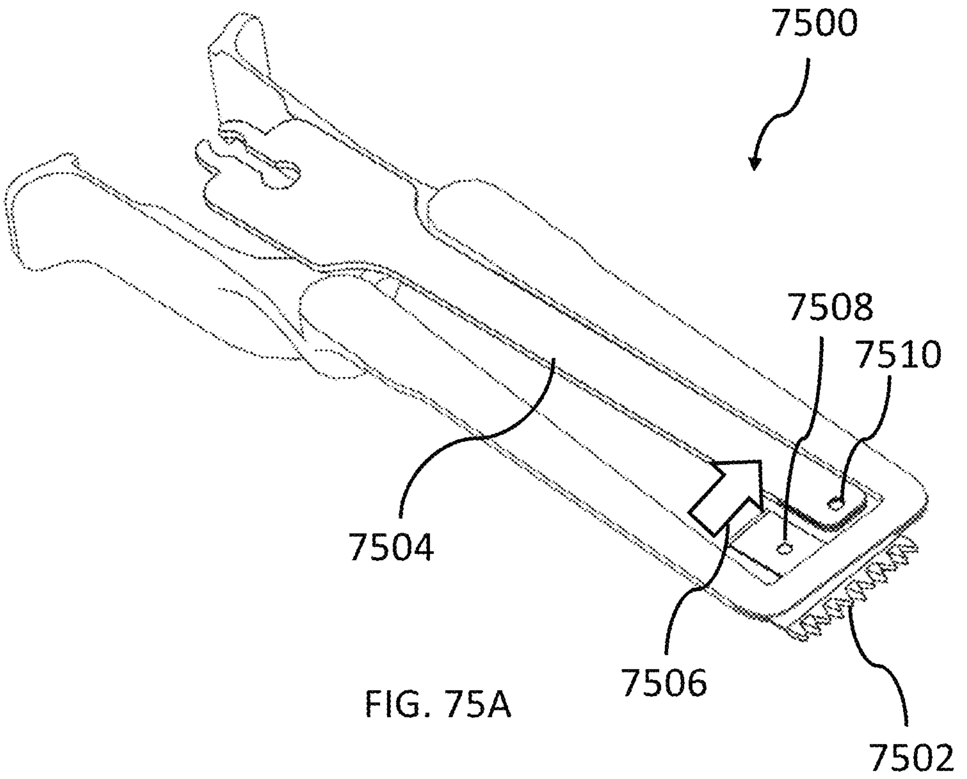
Figure 75B:
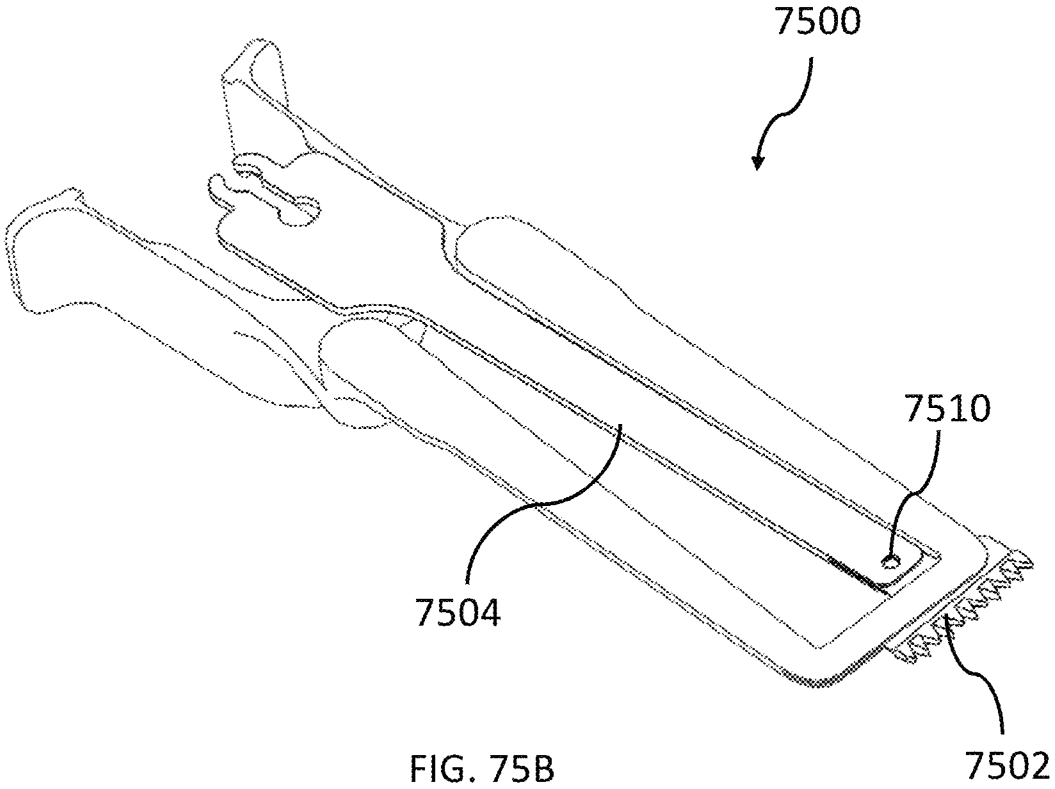
Figure 76A:
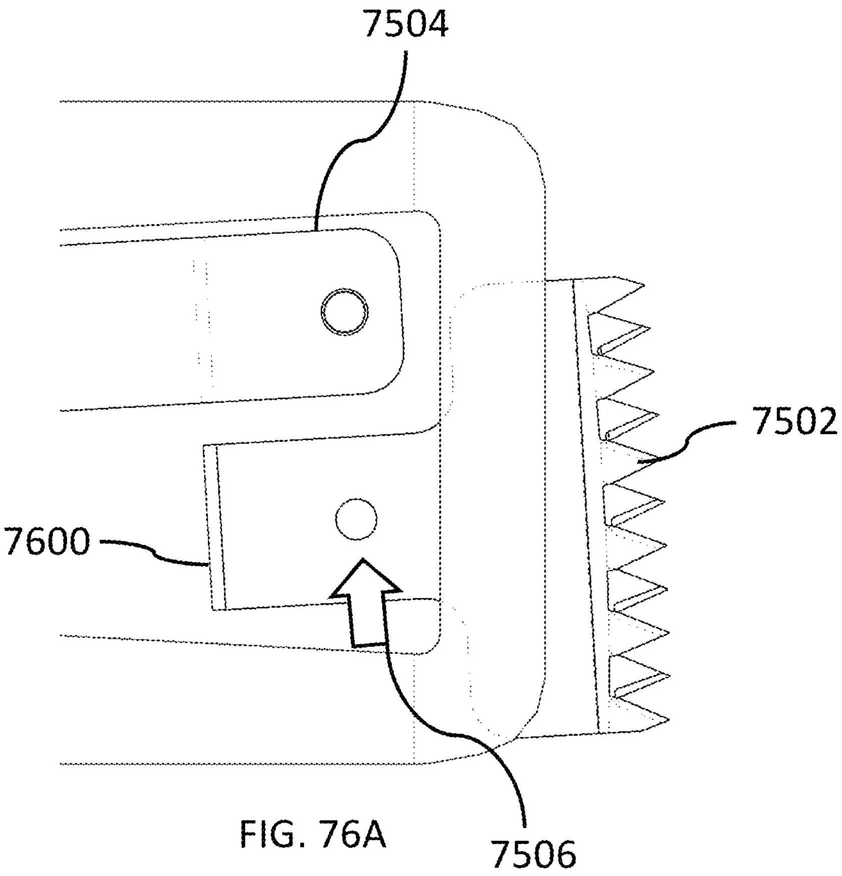
Figure 76B:
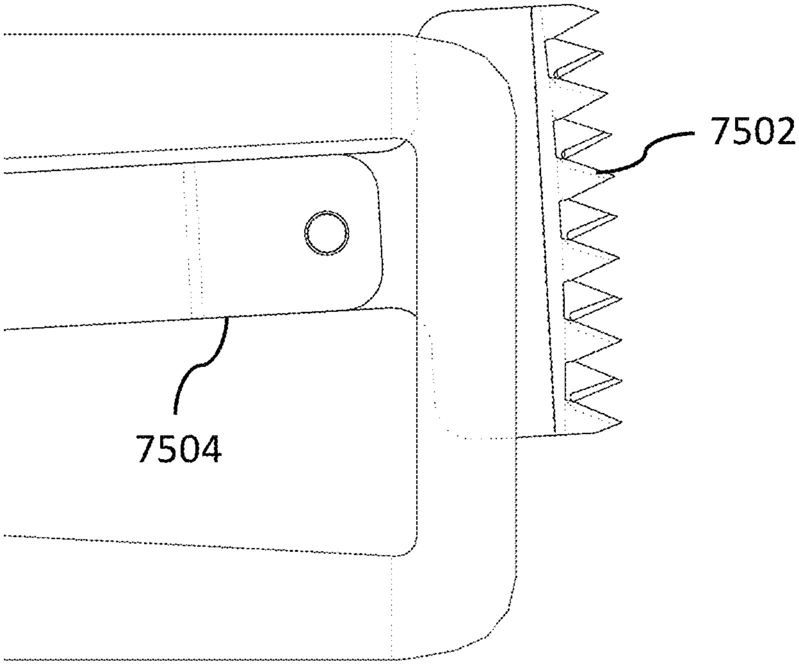
Figure 77A:
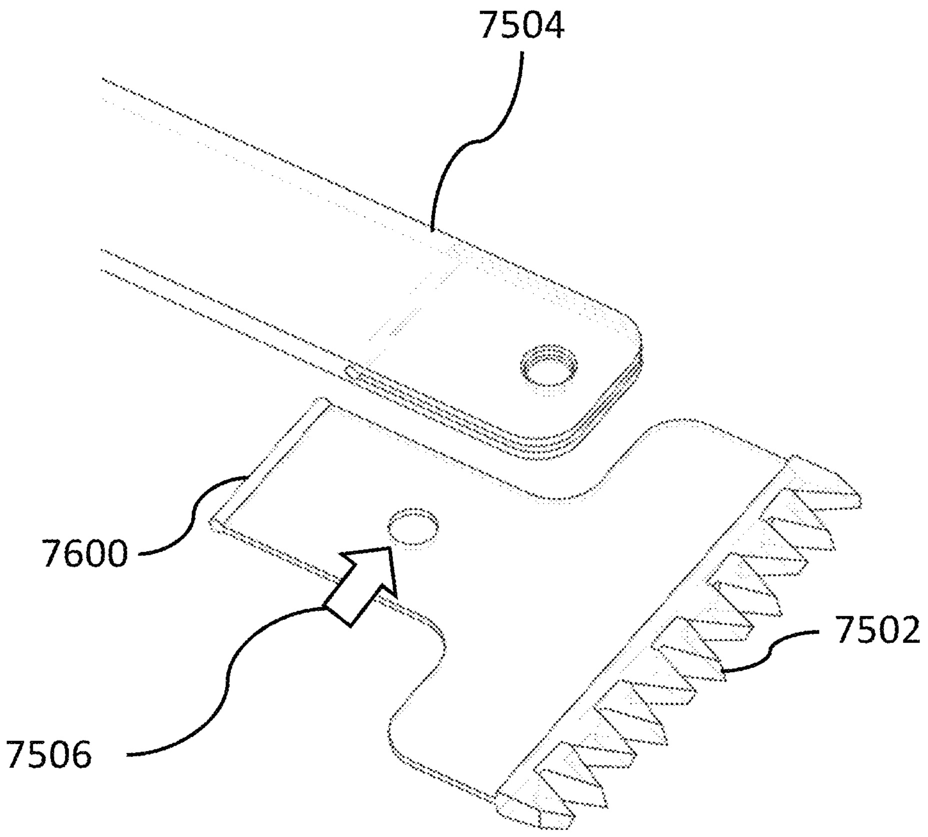
Figure 77B:
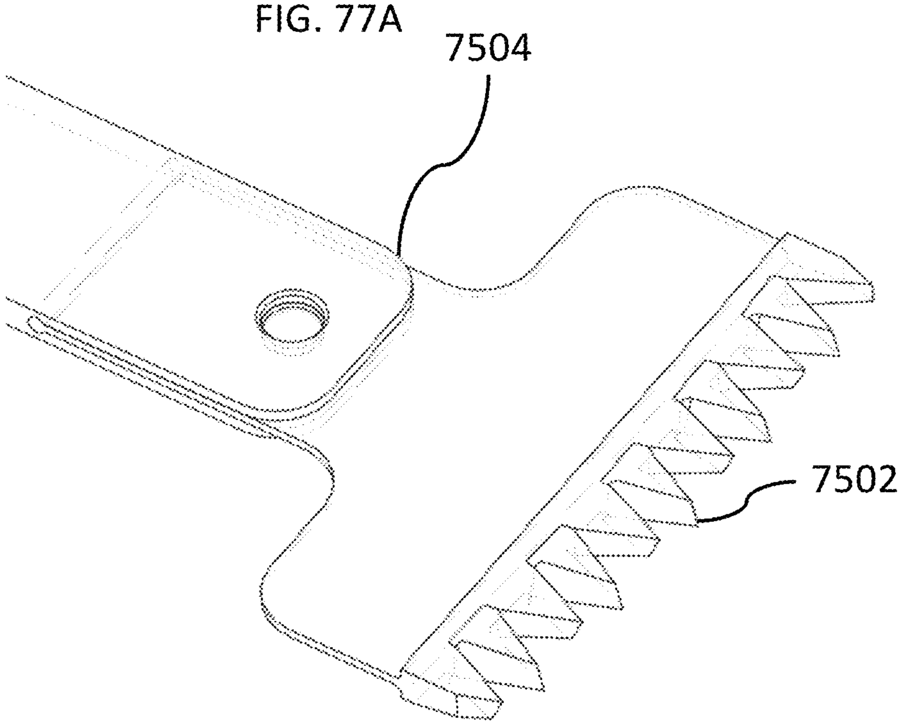
Figure 78:
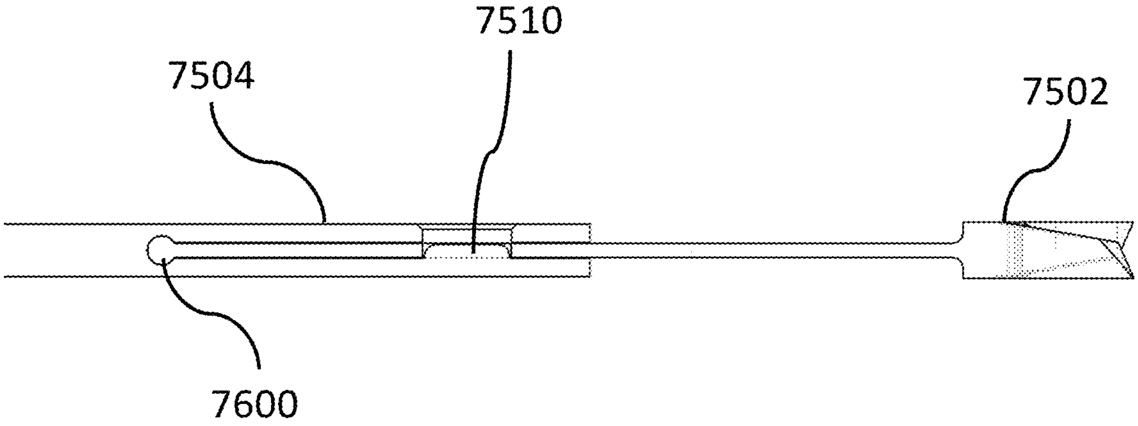
Figure 79A:
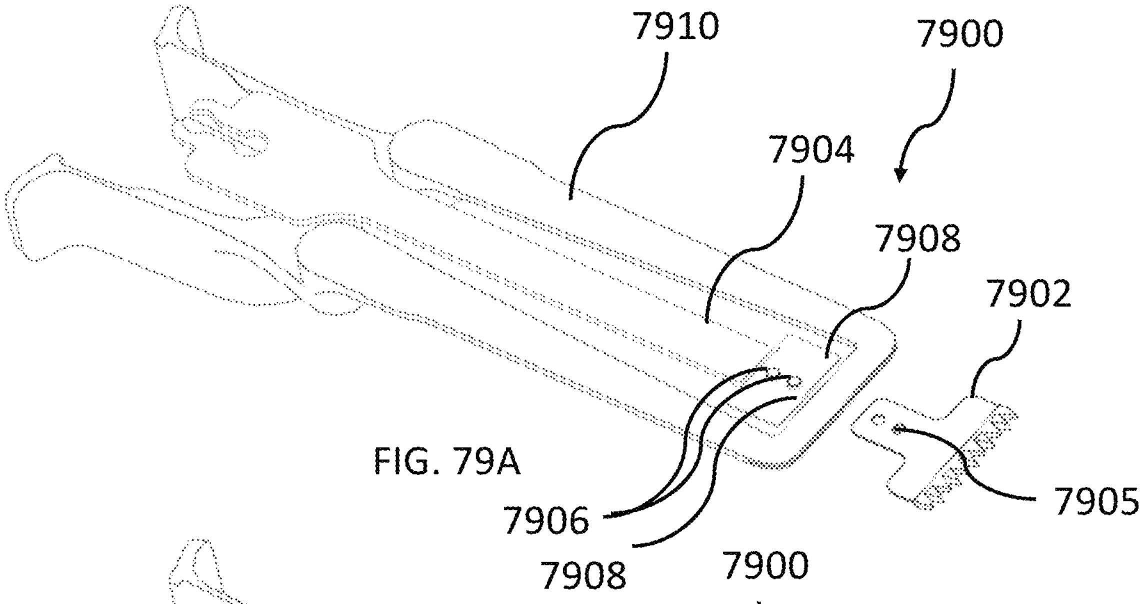
Figure 79B:
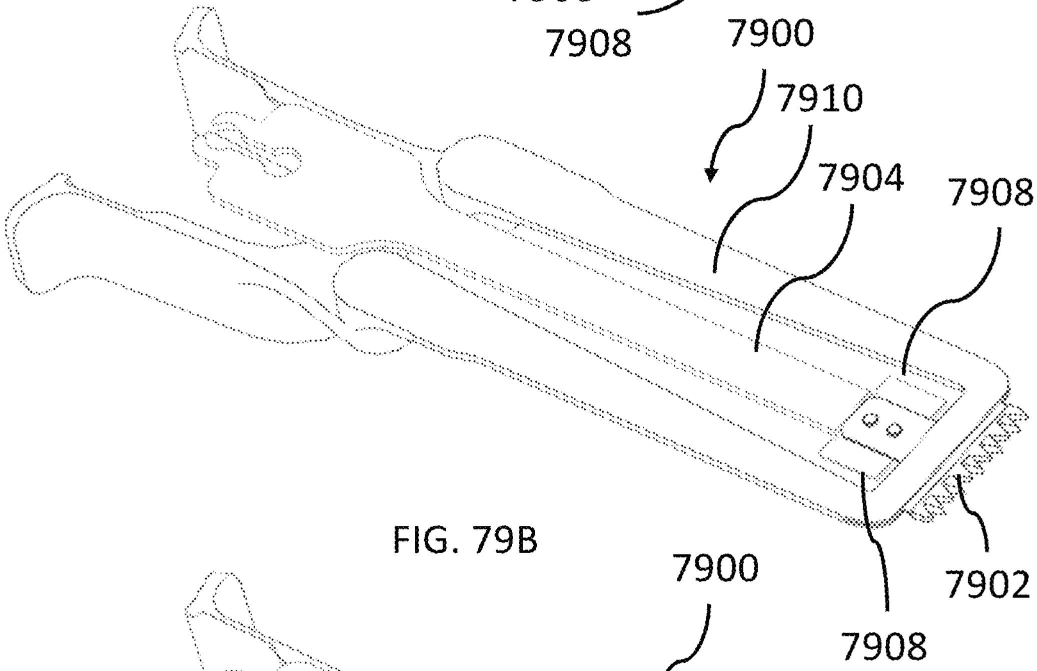
Figure 79C:
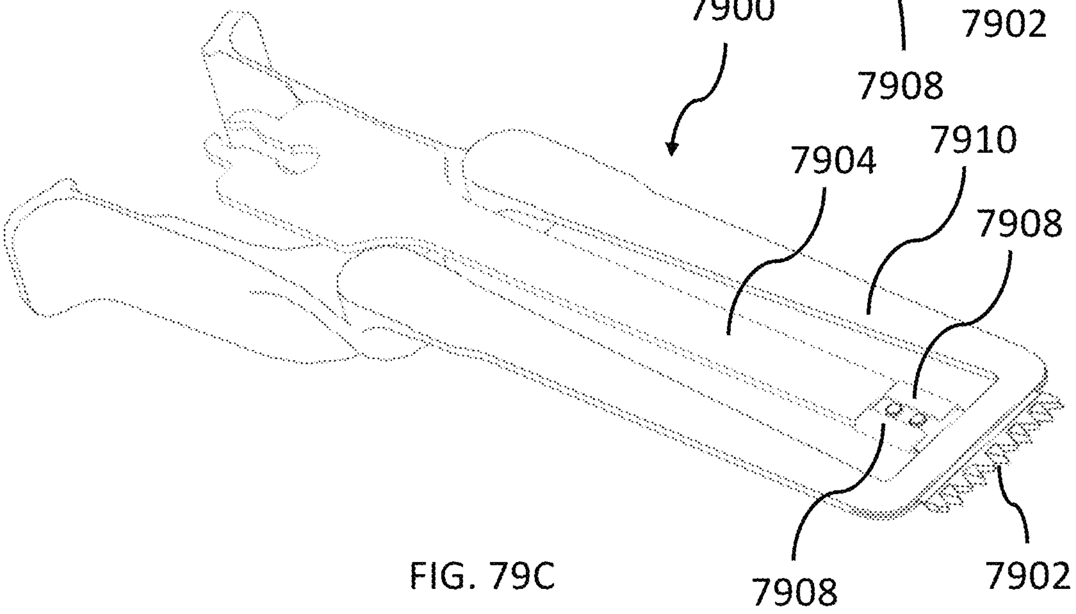
Figures 80A, 80B:
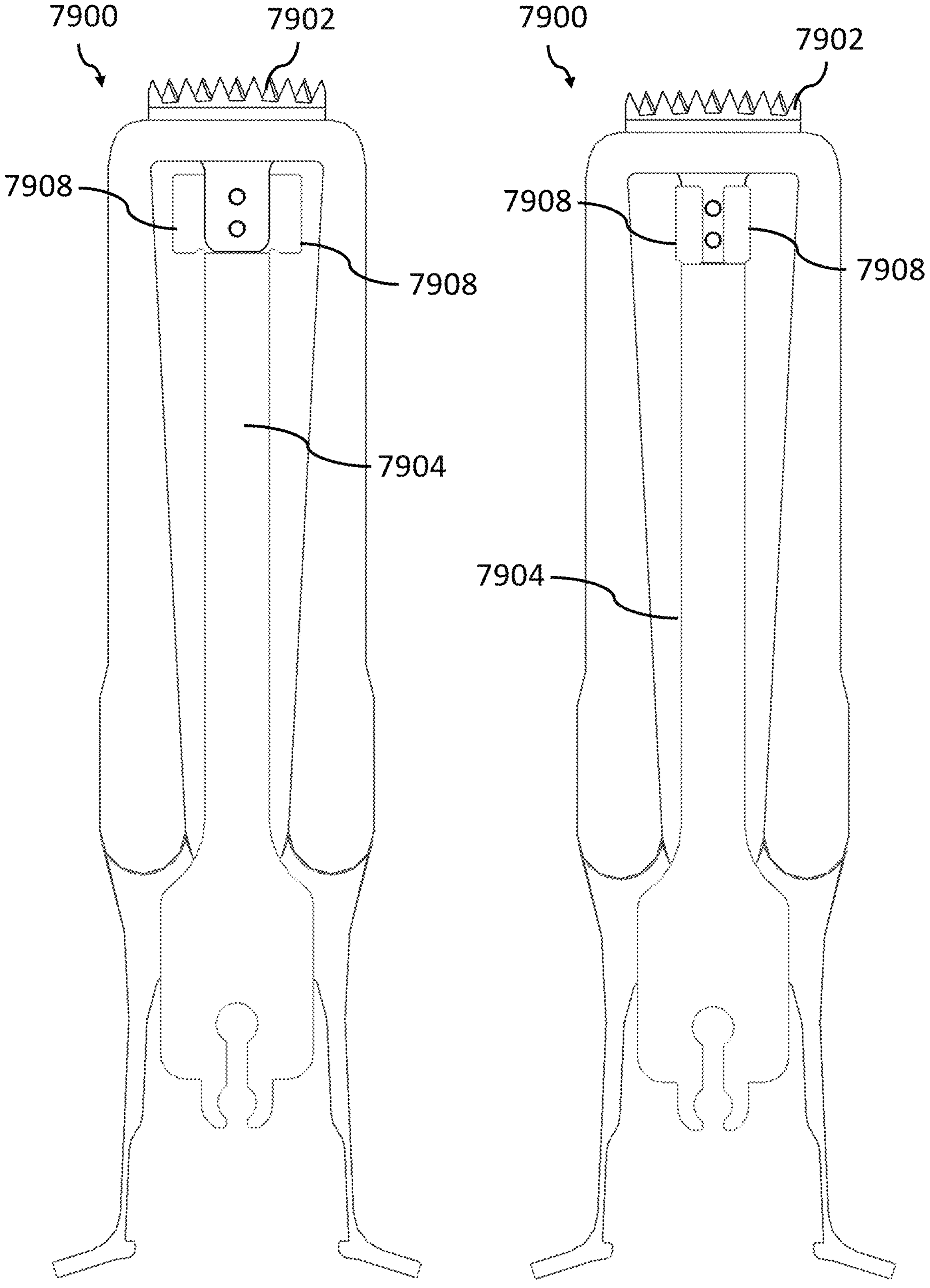
Figure 81:
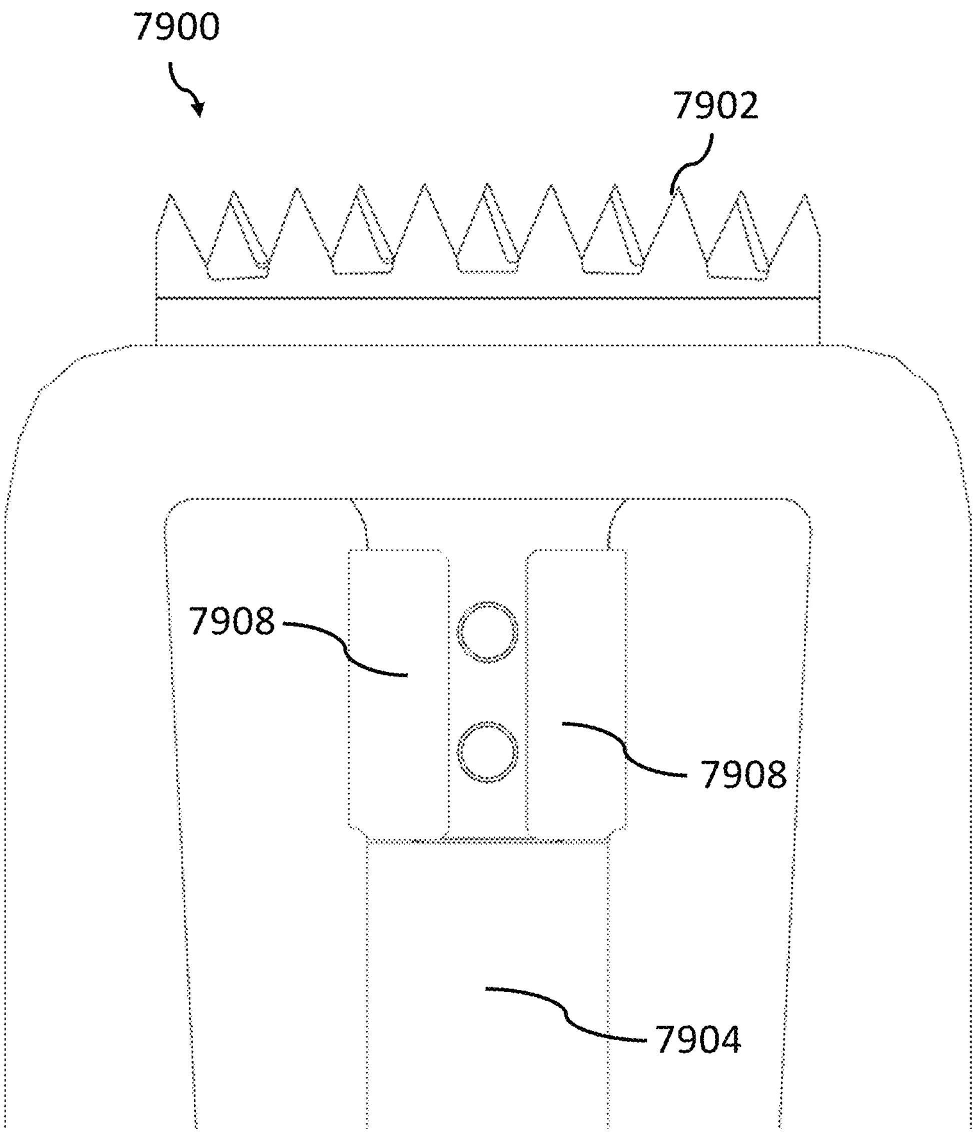
Figure 82:
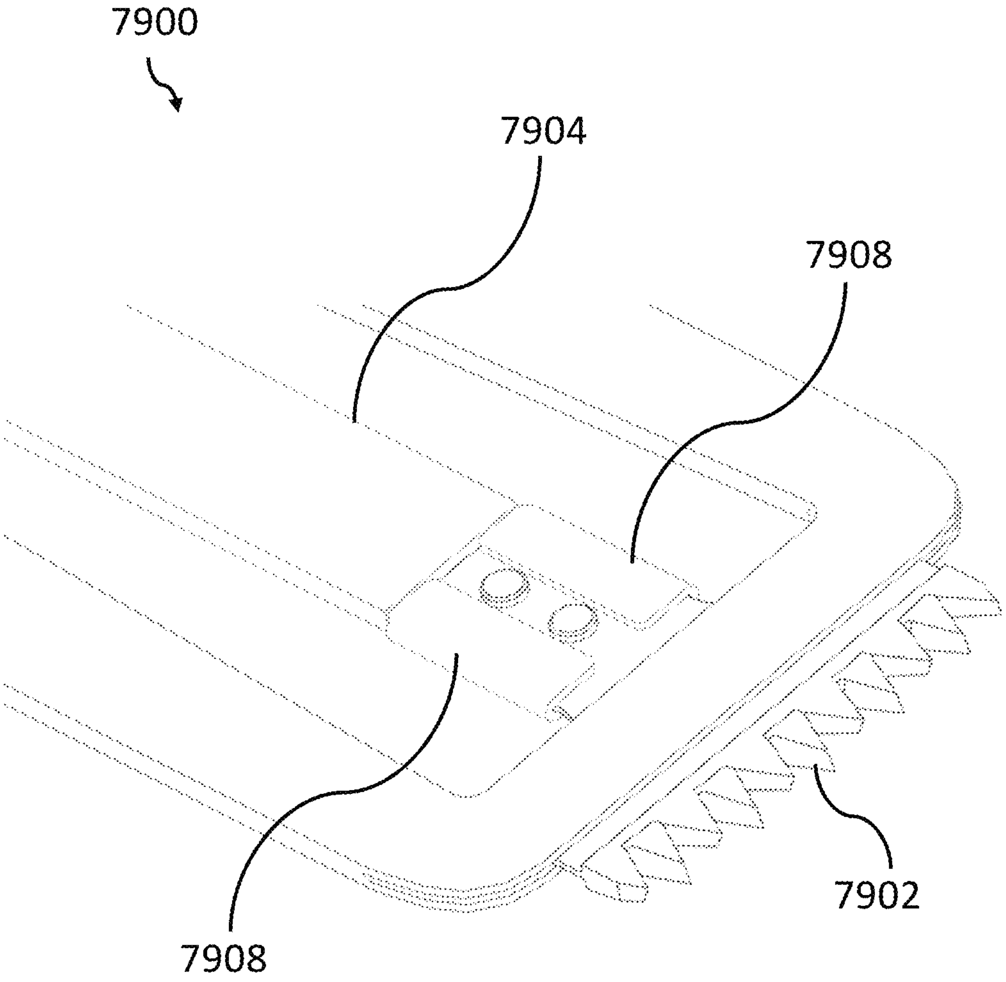
Figure 83A:
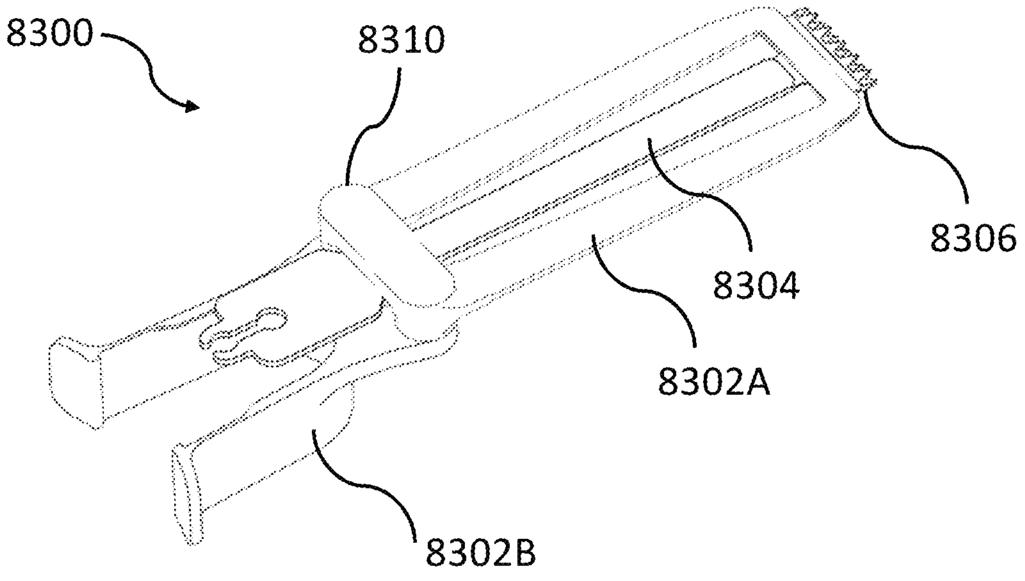
Figure 83B:
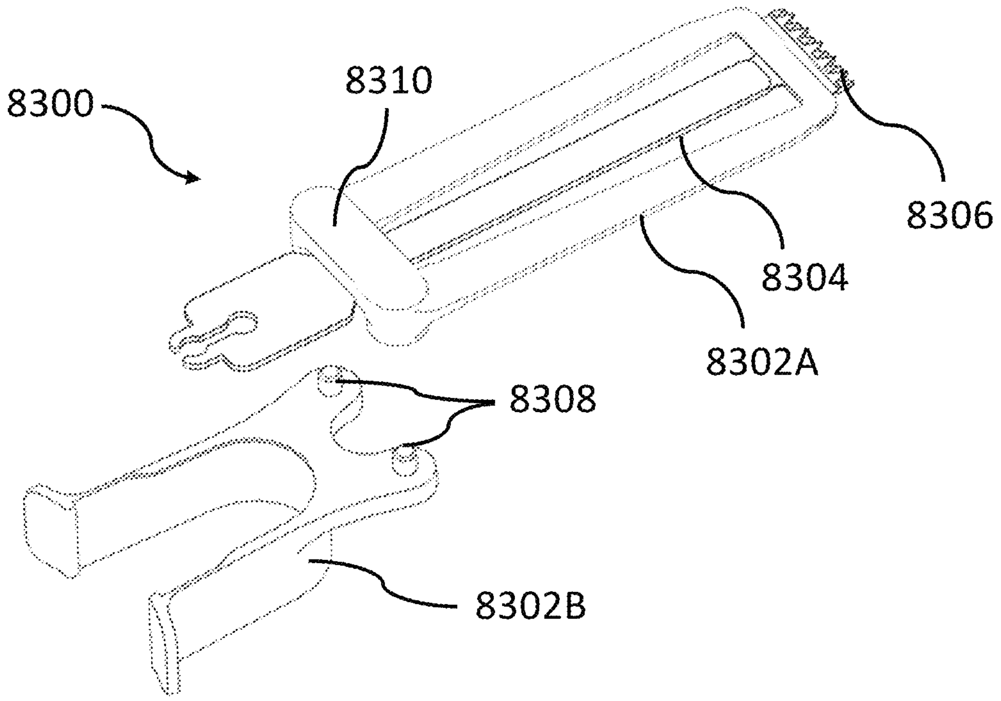
Figure 84A:
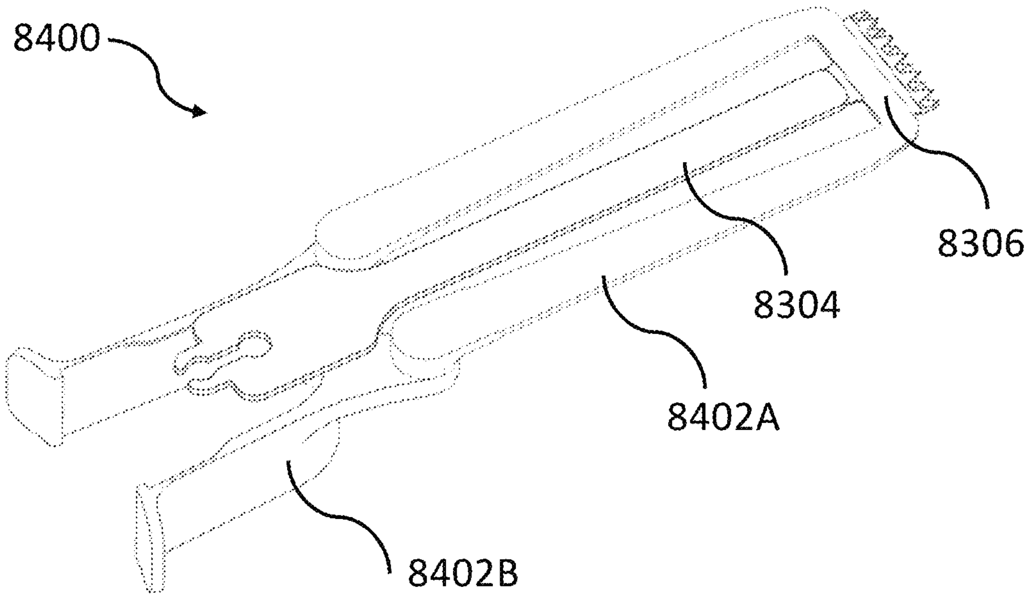
Figure 84B:
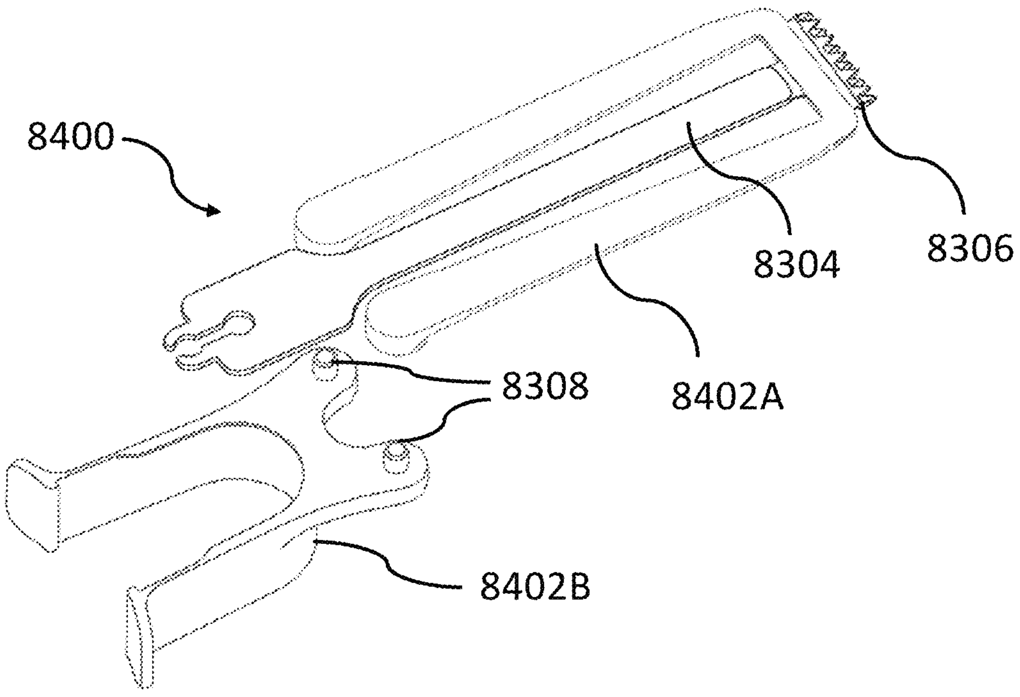
Figure 85:
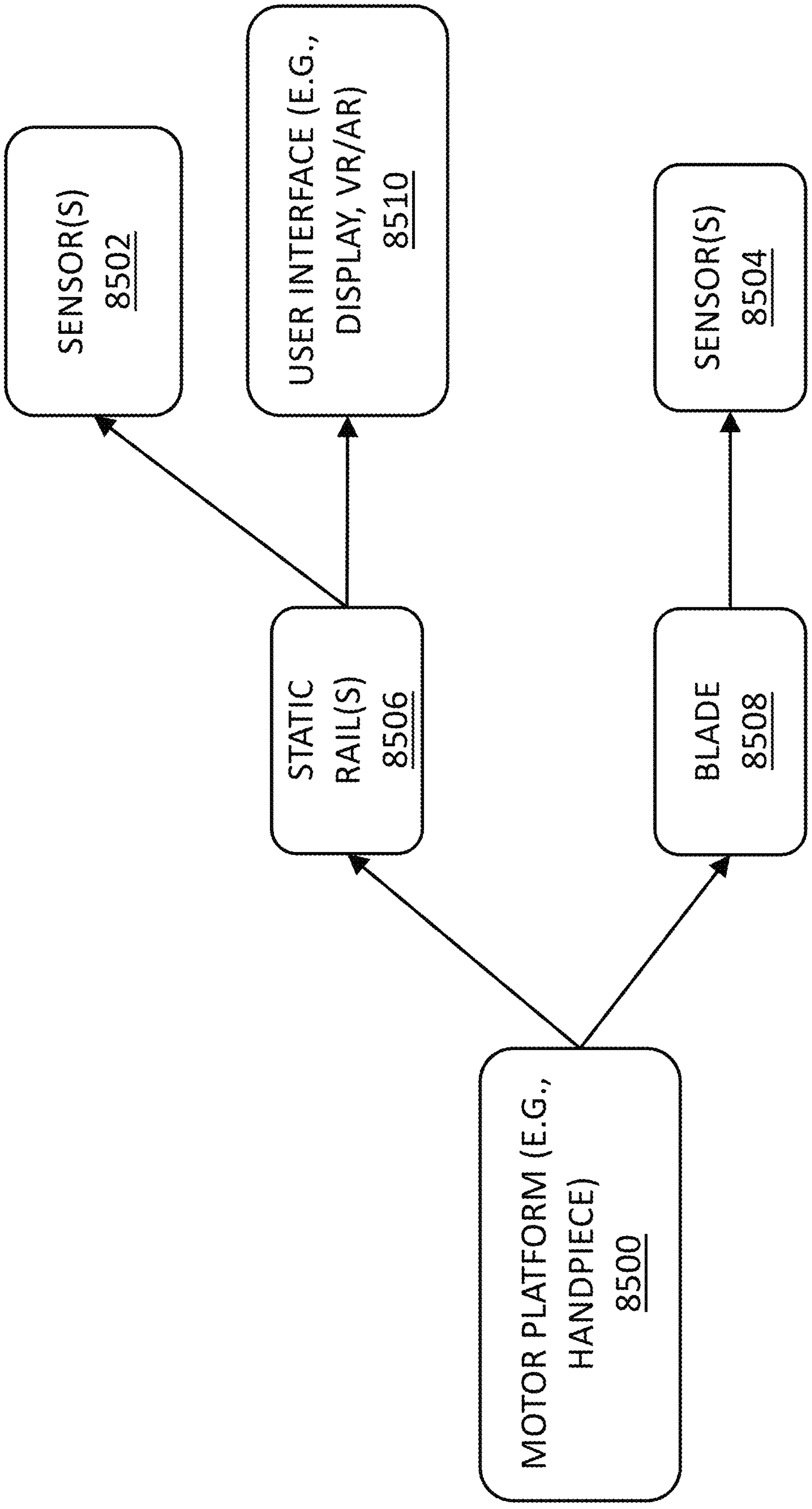
Figure 86A:
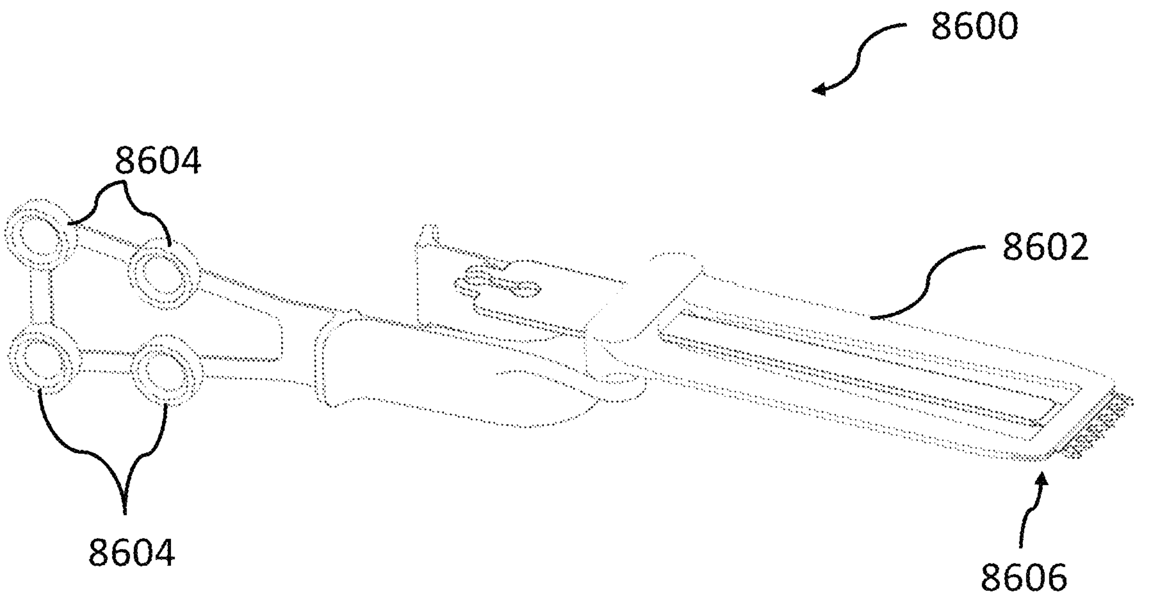
Figure 86B:
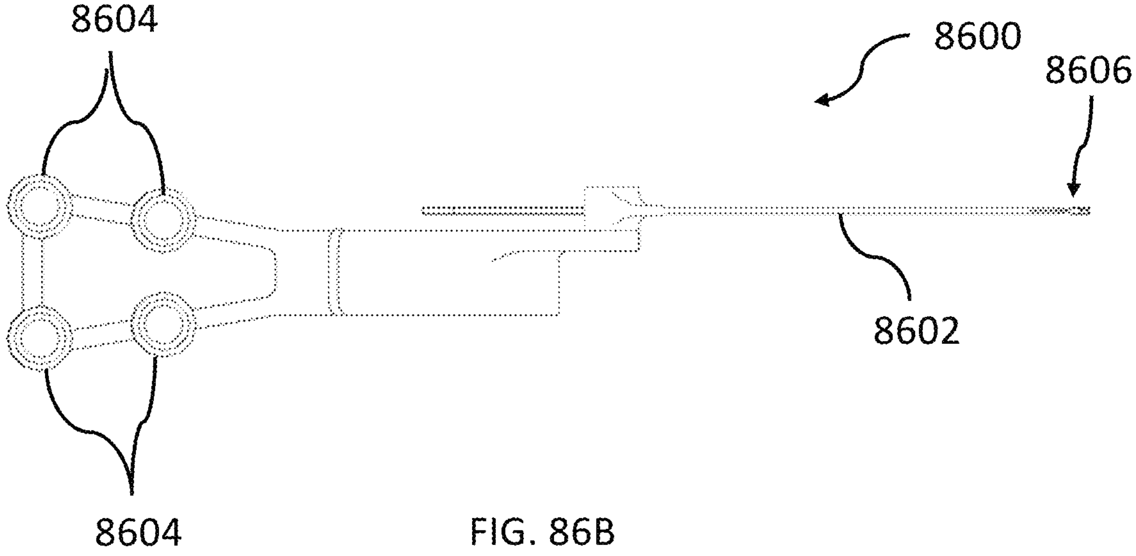
Figure 87A:
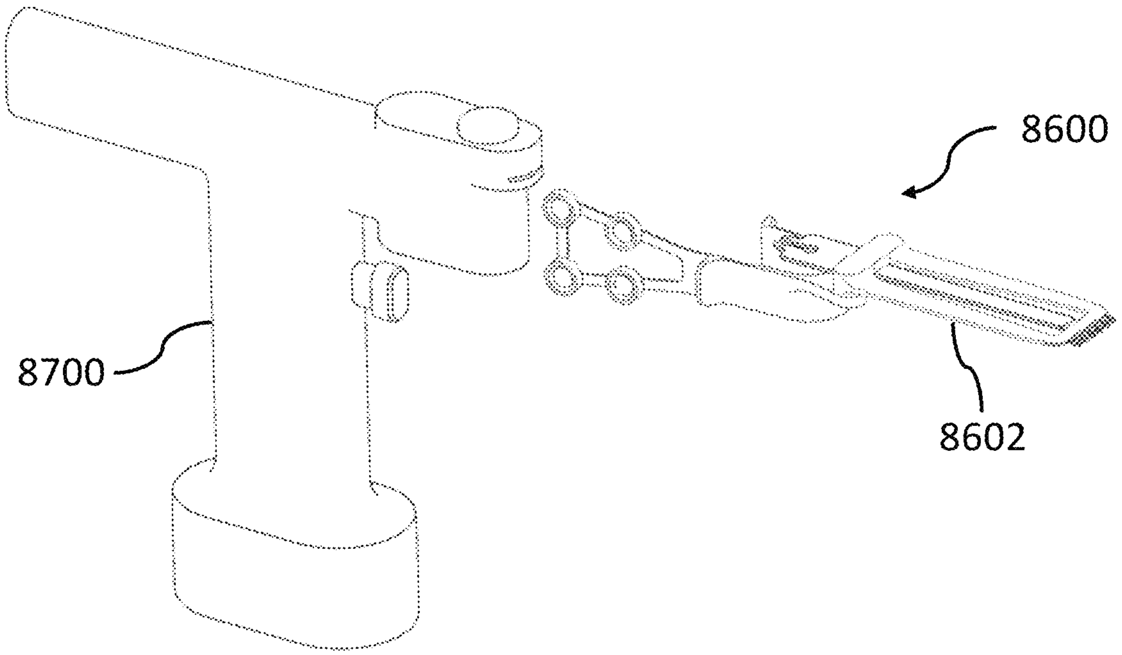
Figure 87B:
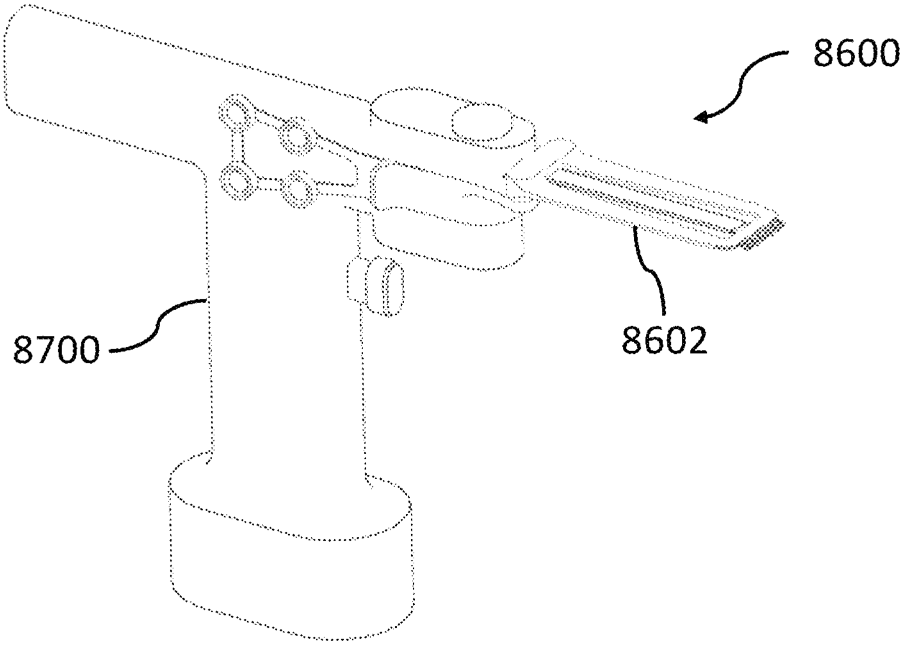
Figure 88:
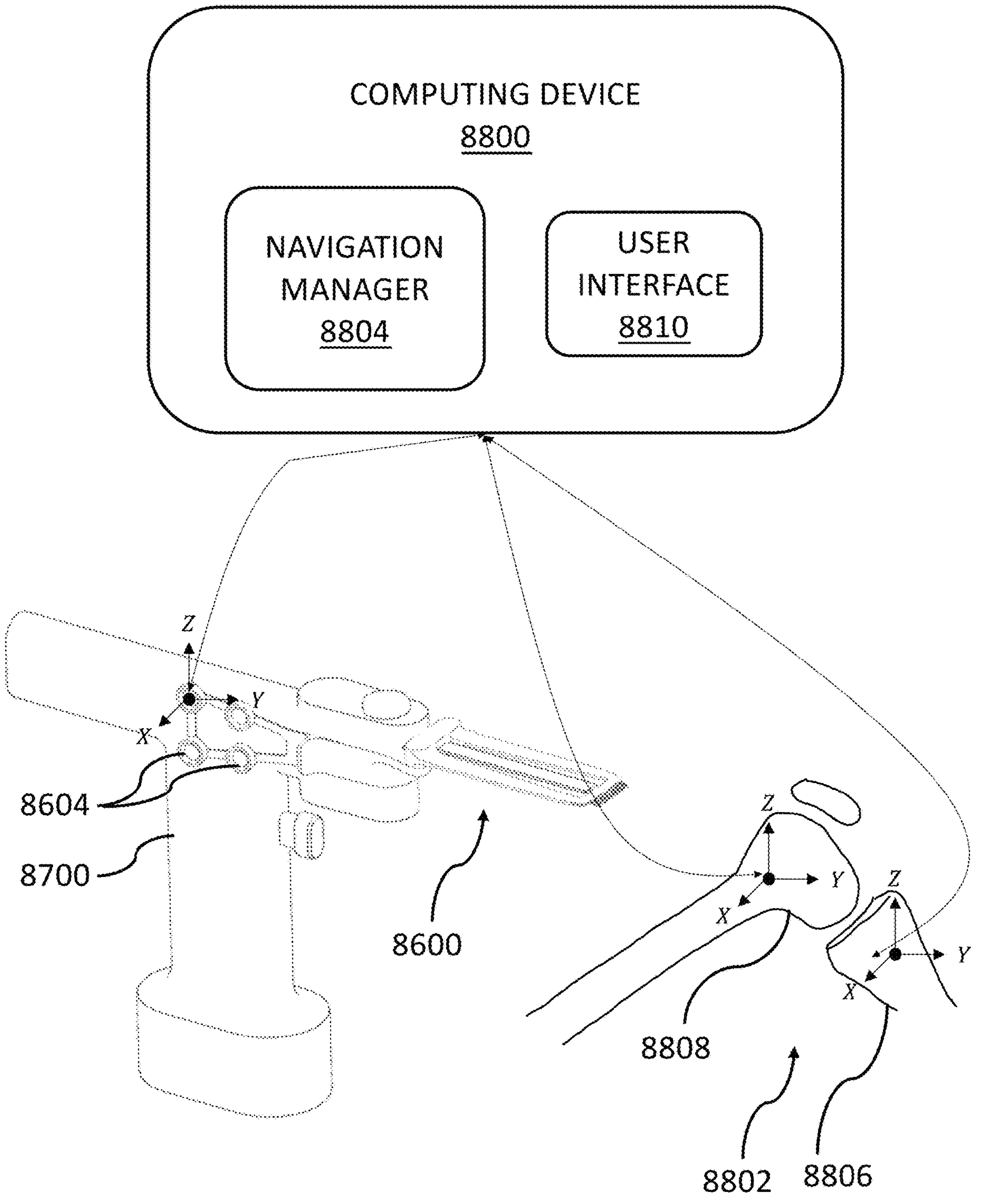
Figure 89:
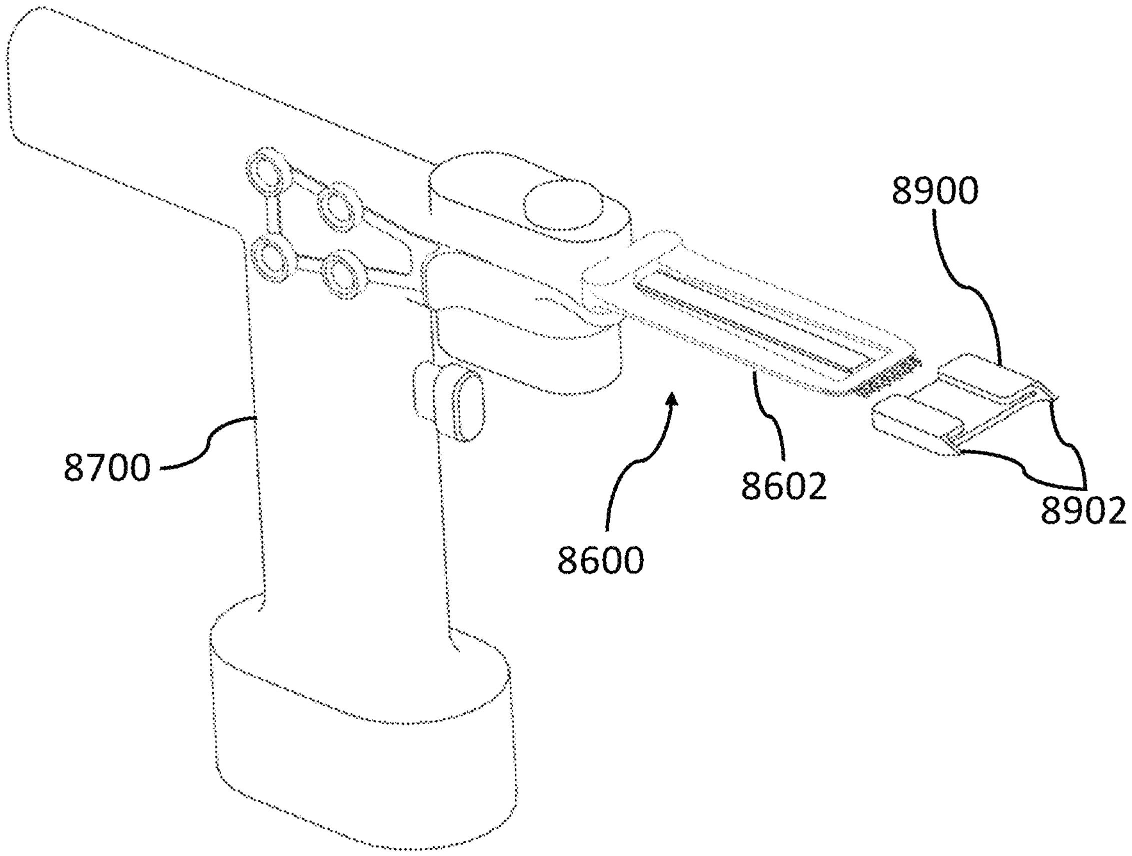
Figures 90A, 90B, 90C:
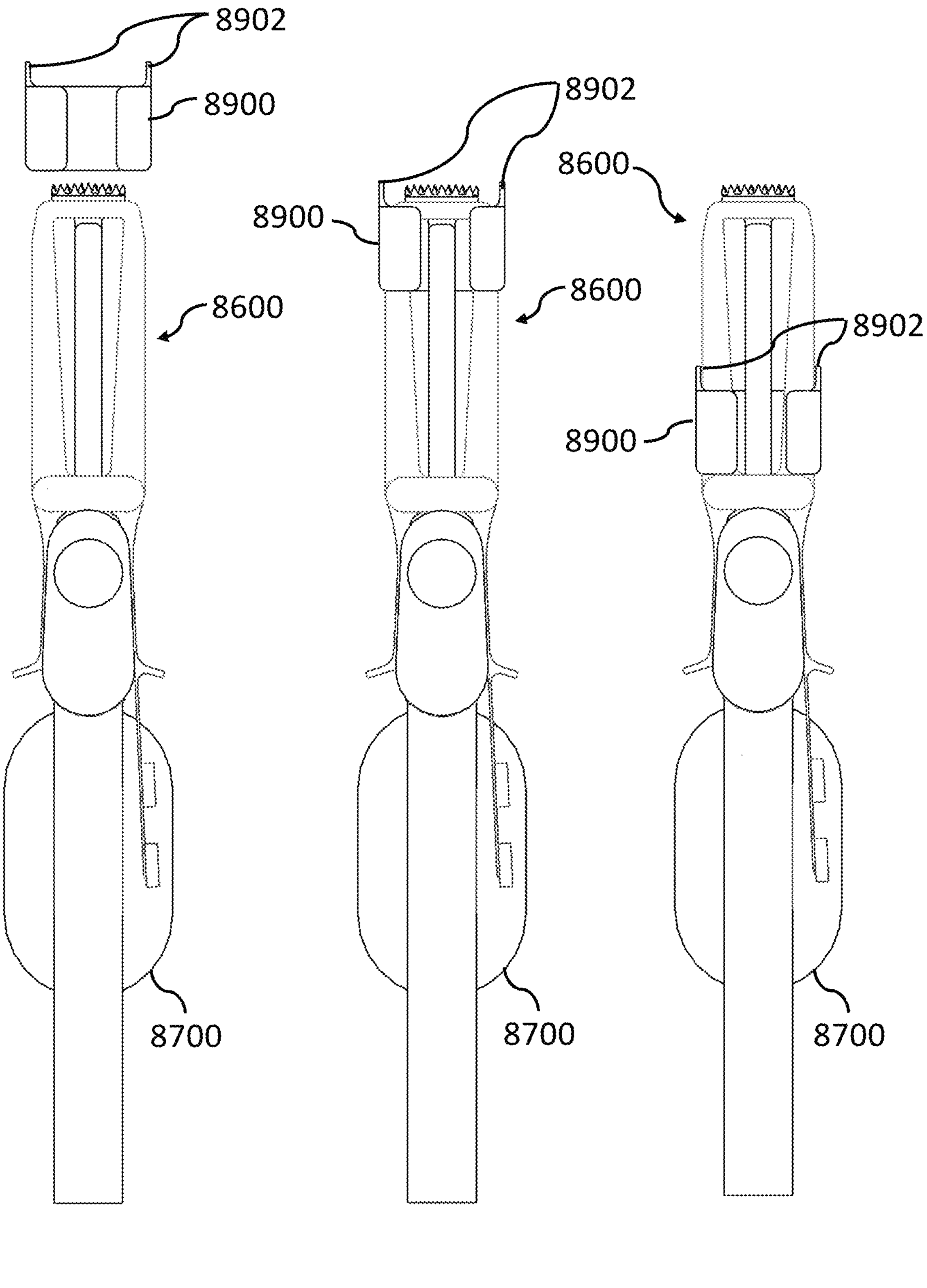
Figure 91A:
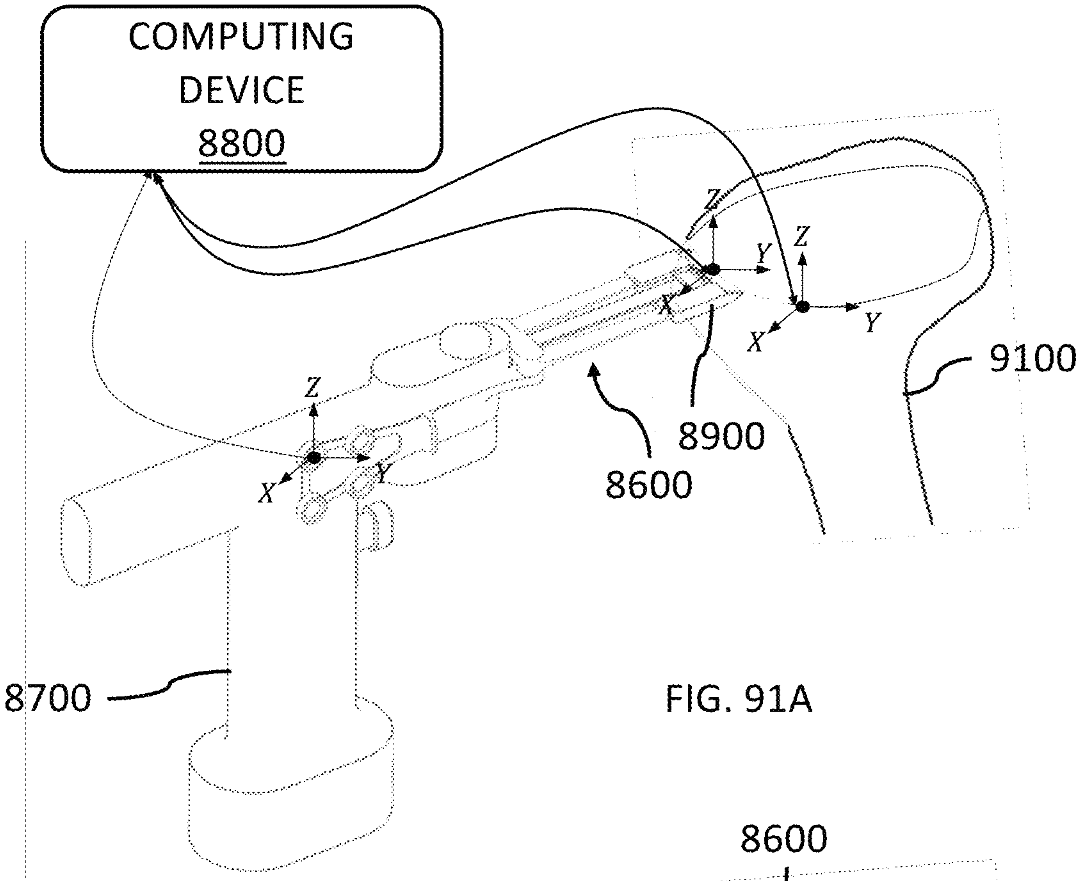
Figure 91B:
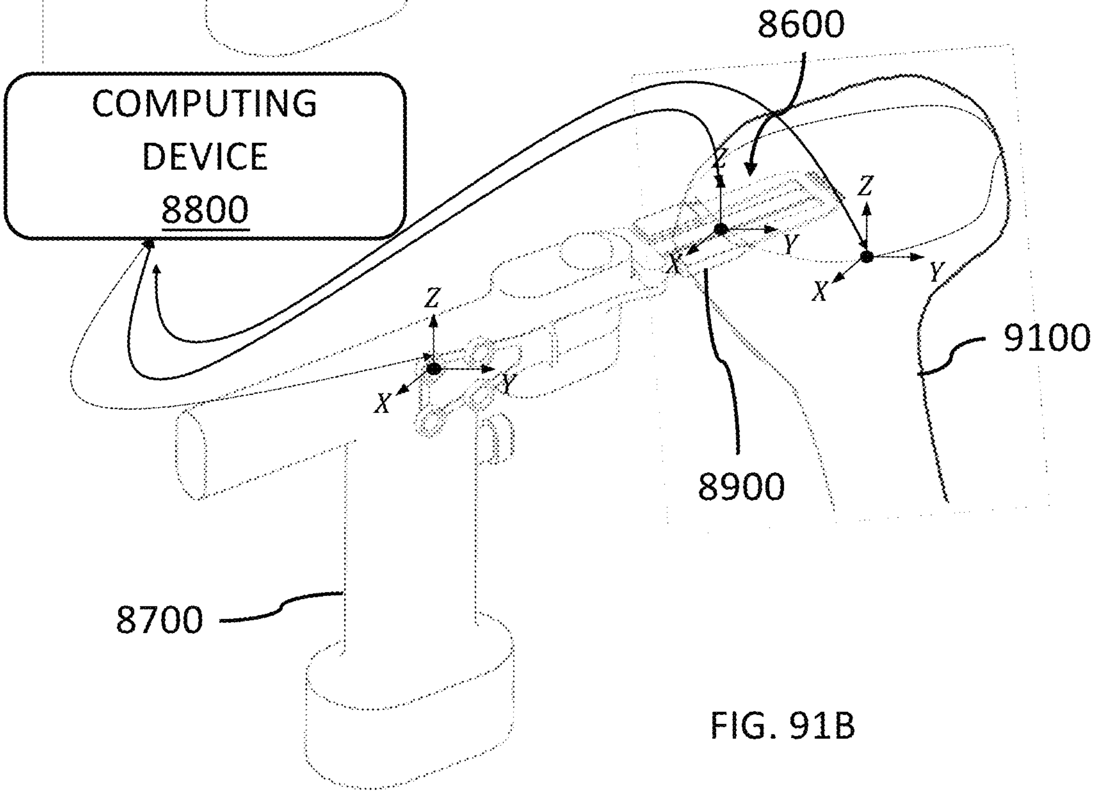
Figure 92A:
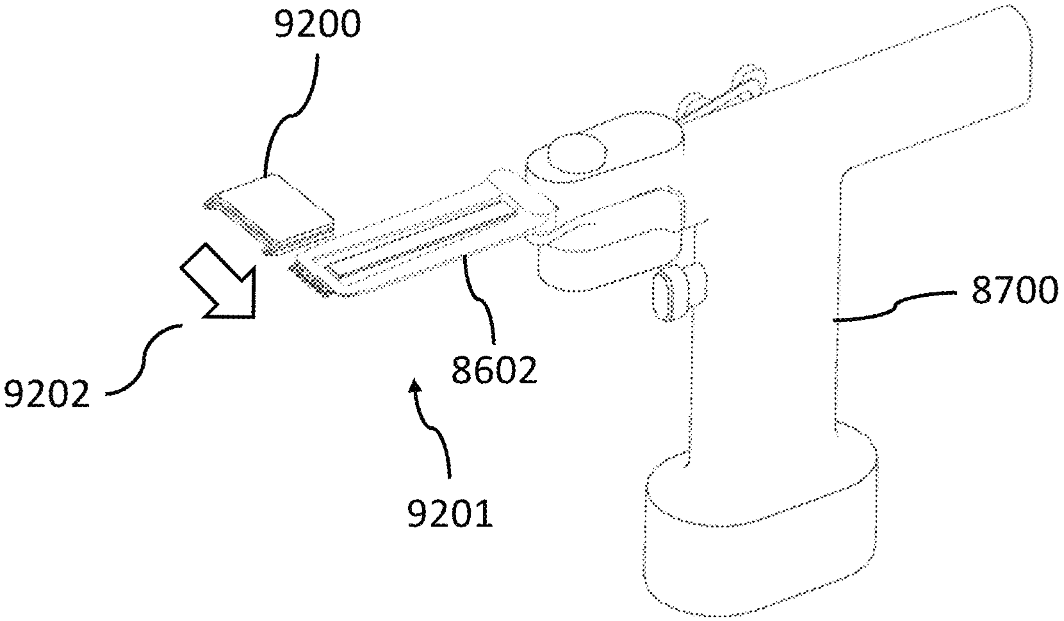
Figure 92B:
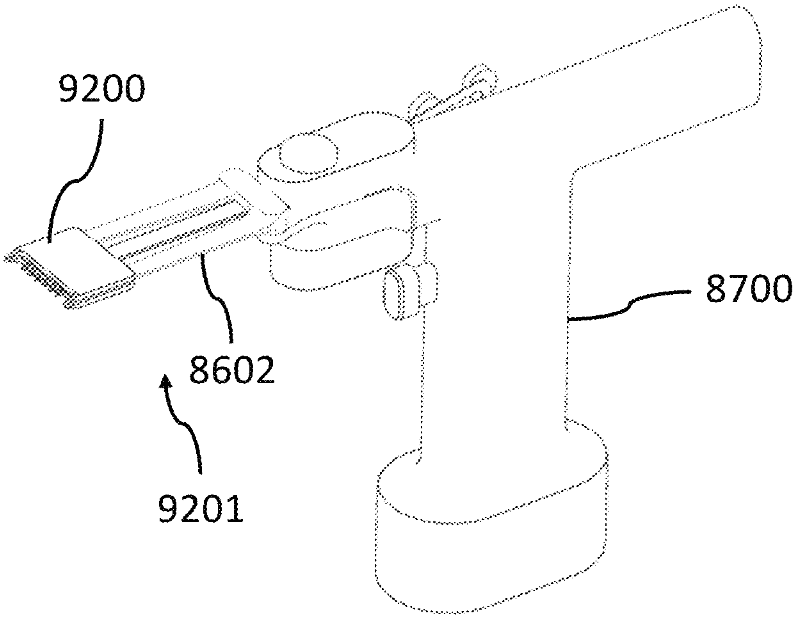
Figure 93:
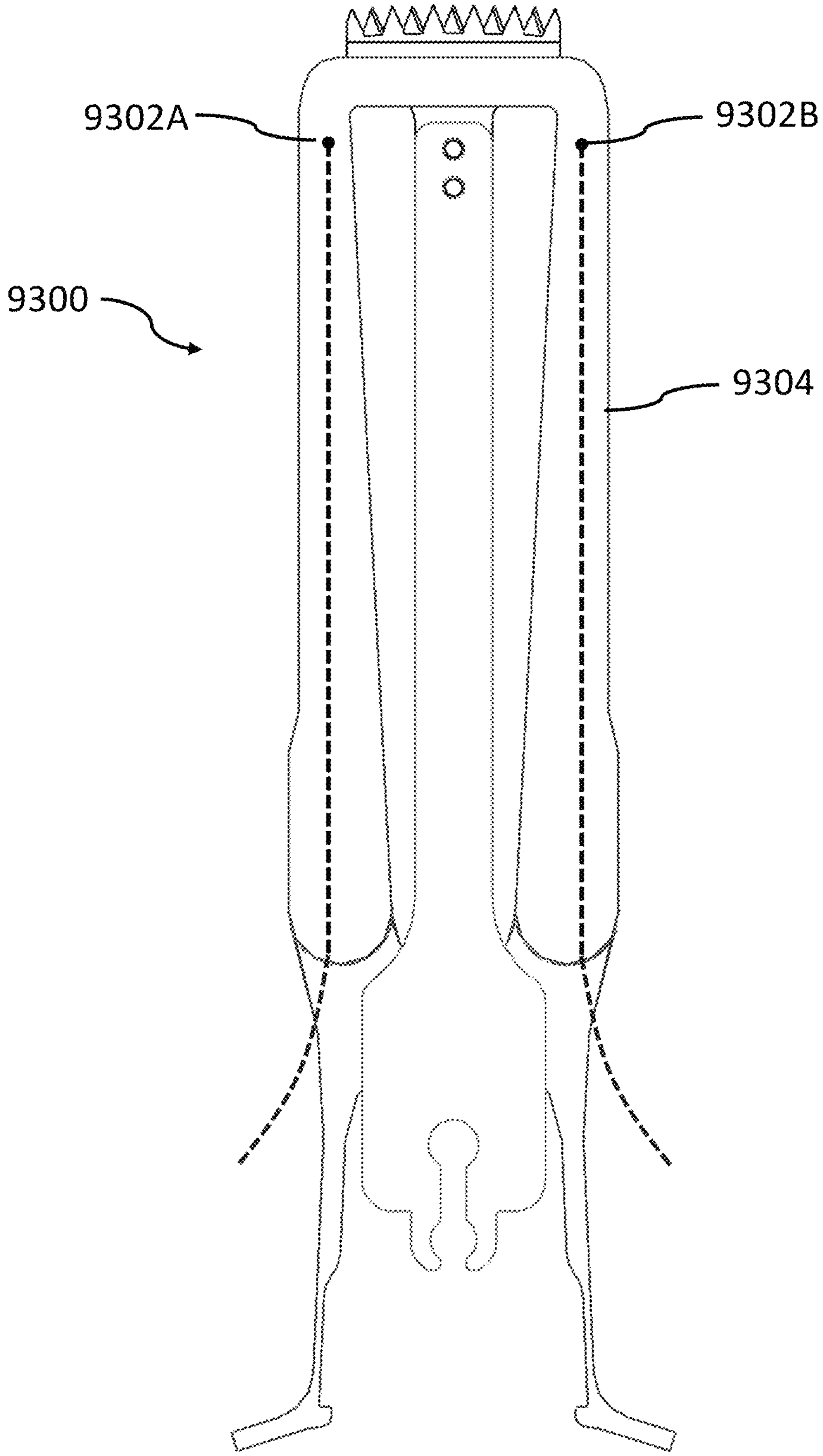
Figure 94:
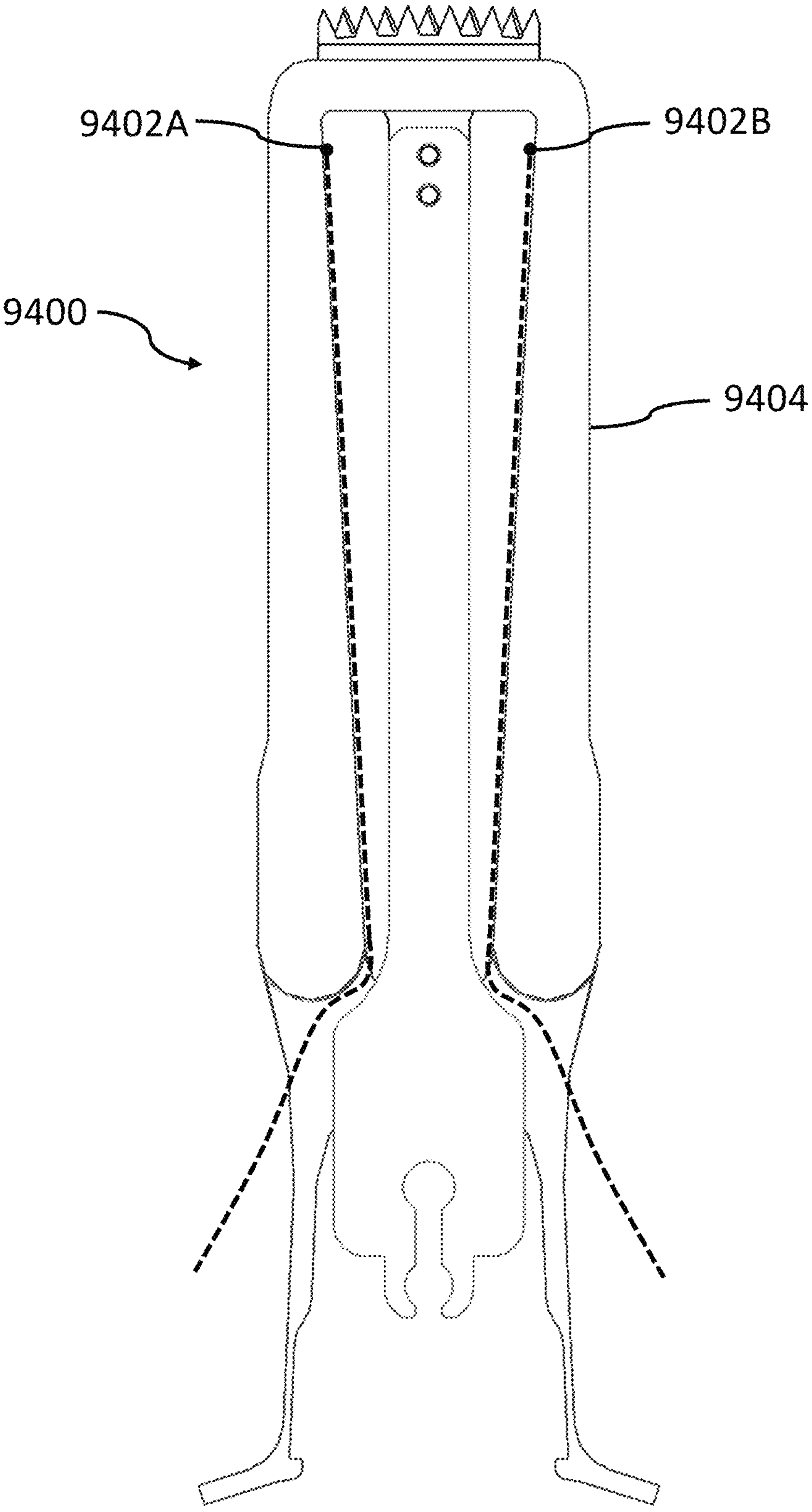
Figure 95:
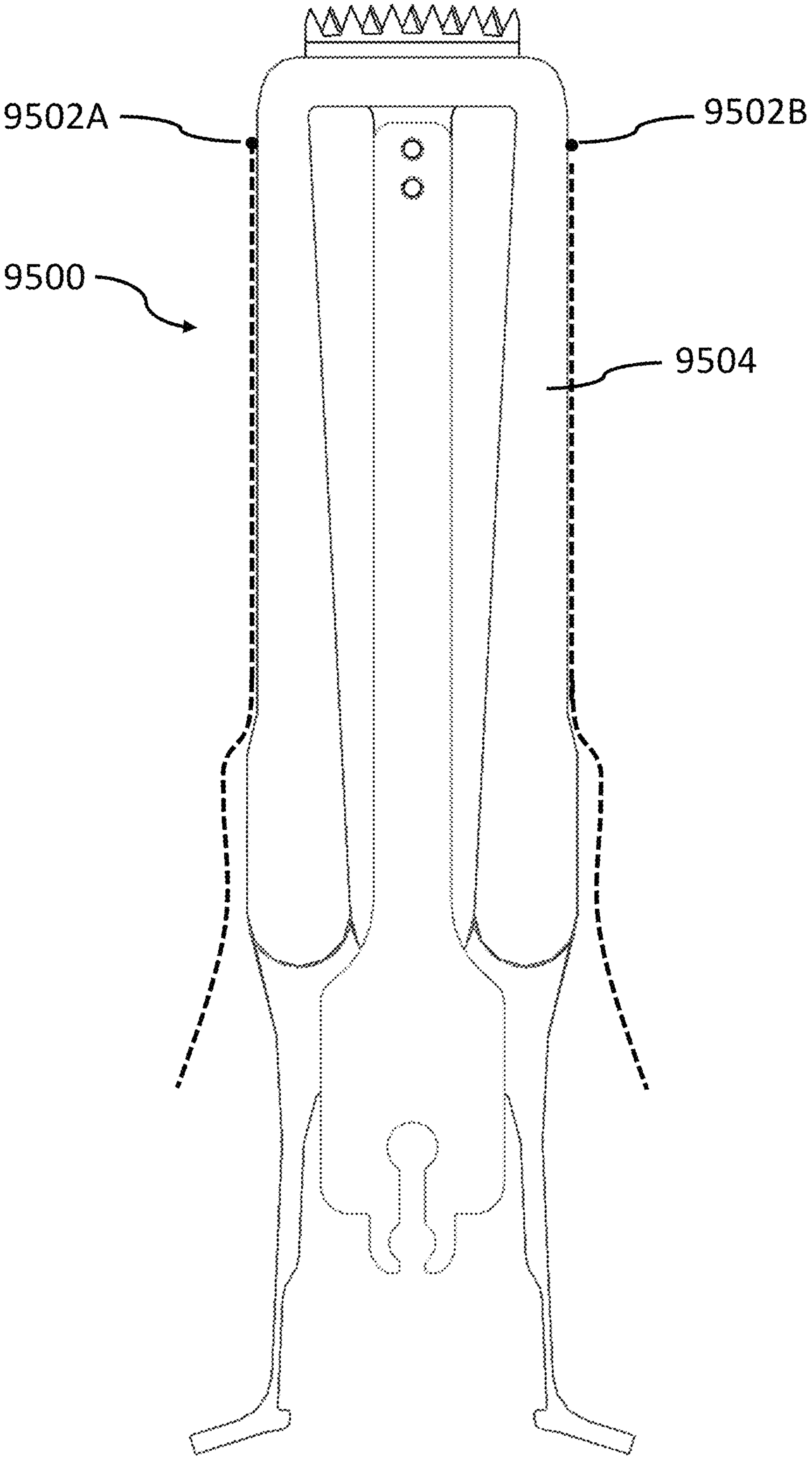
Figure 96:
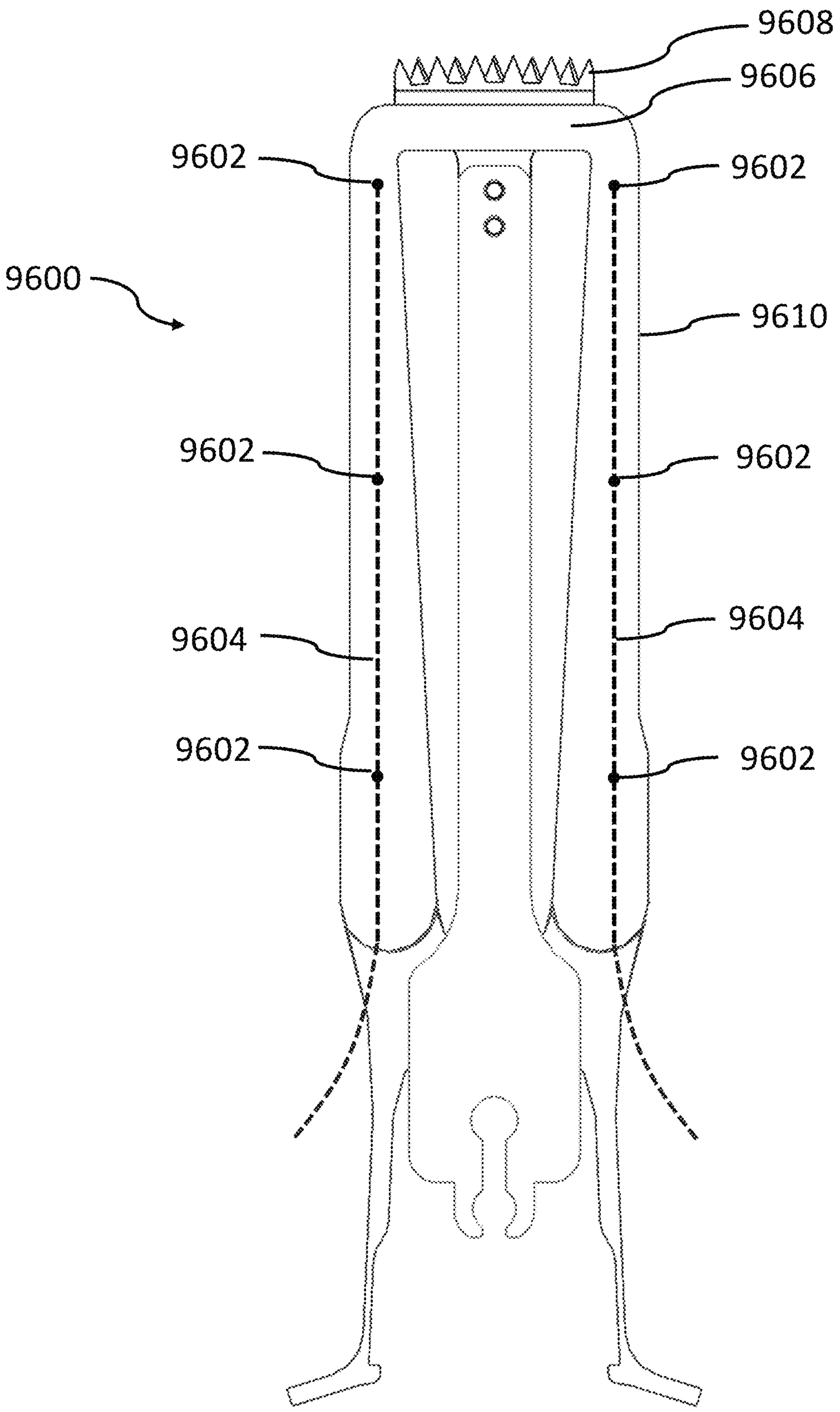
Figure 97:
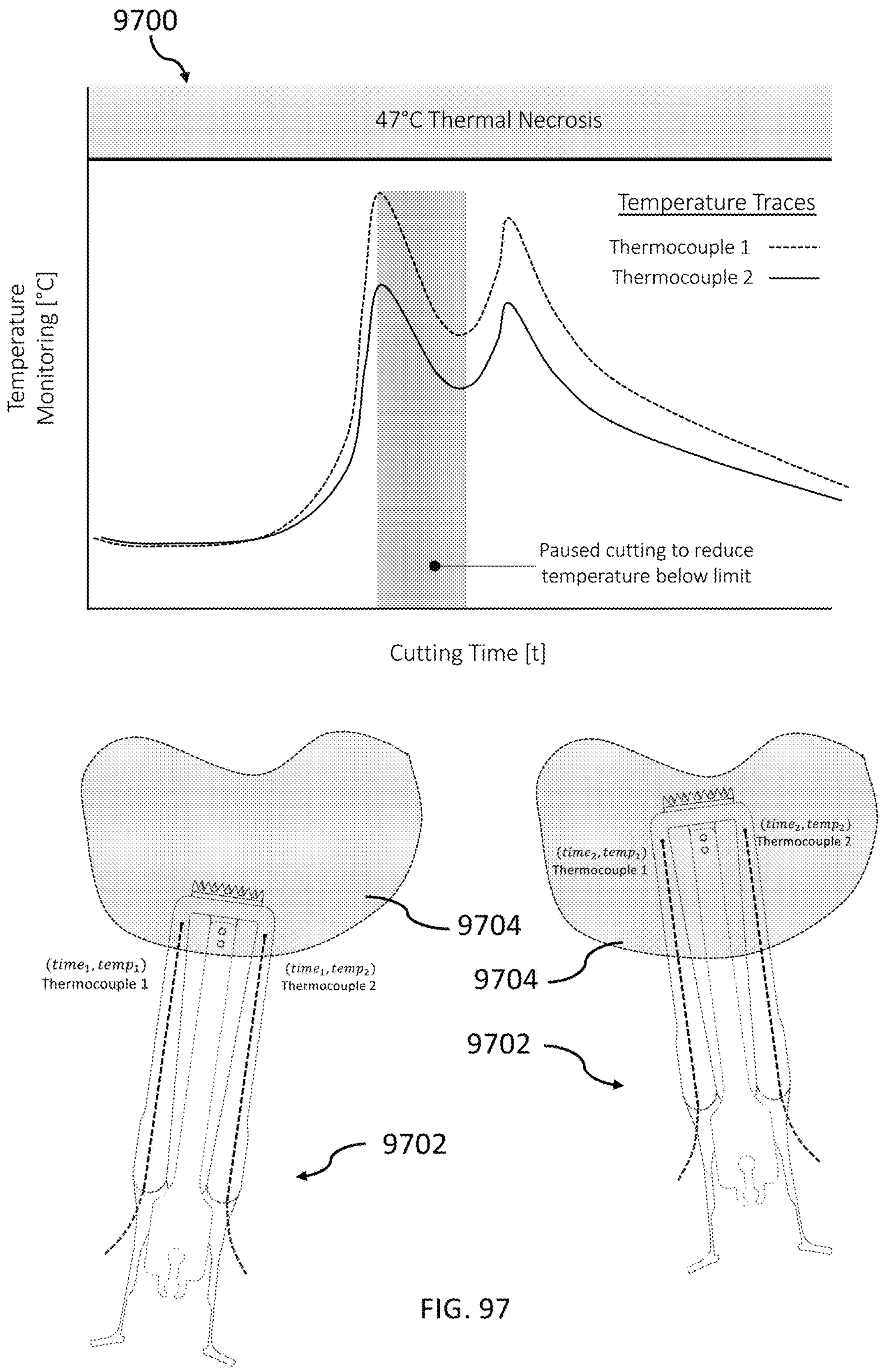
Figure 98:
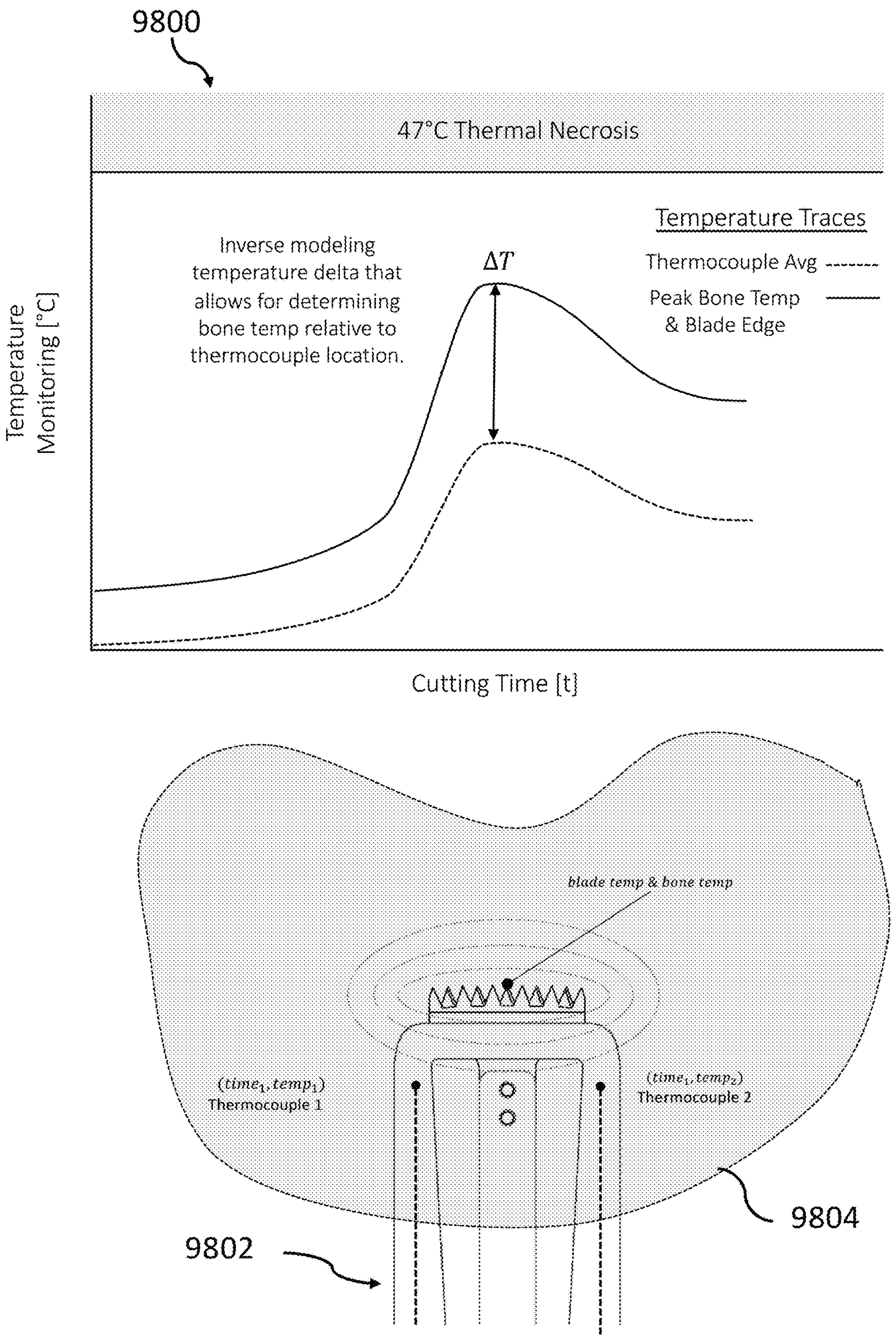
Figure 99:
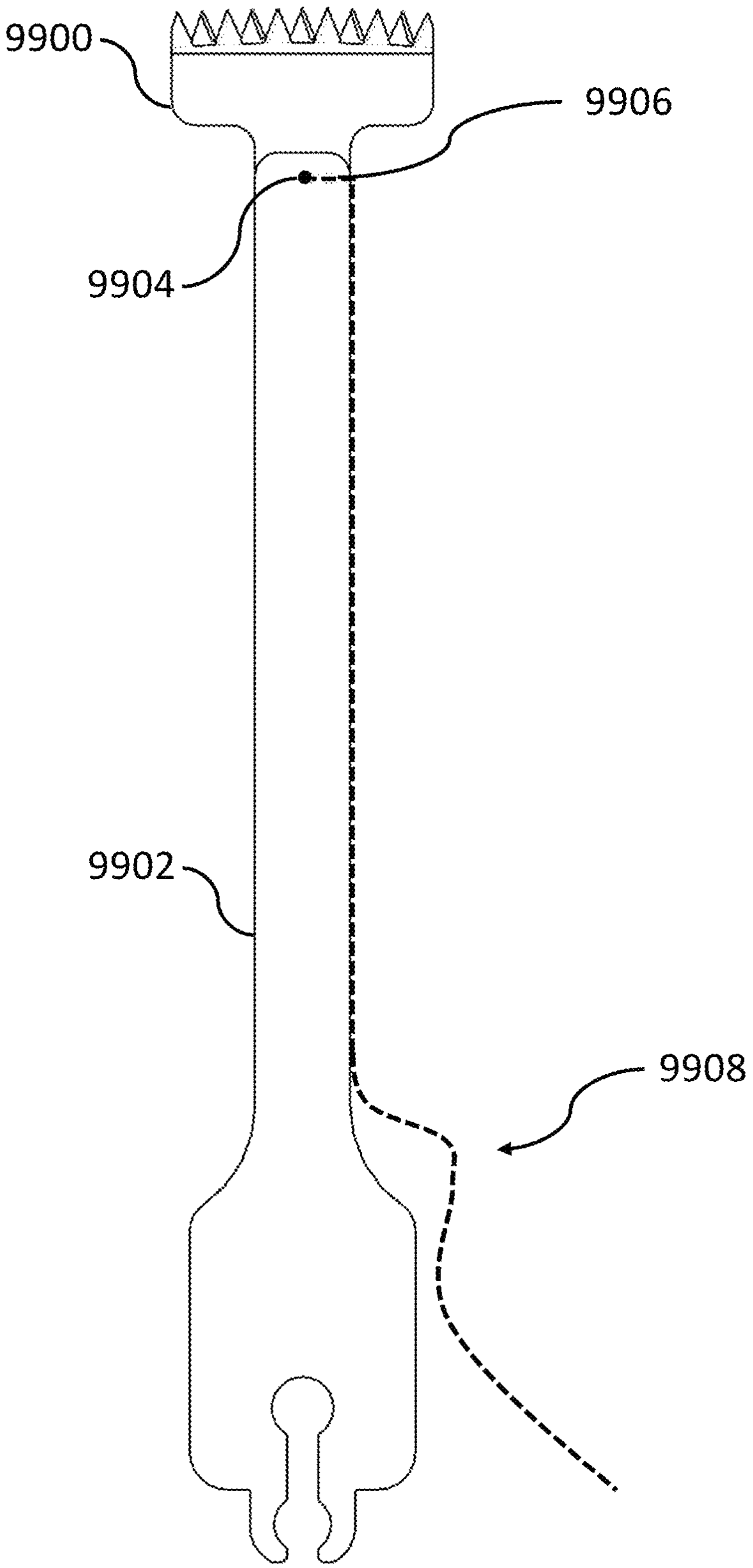
Figure 100:
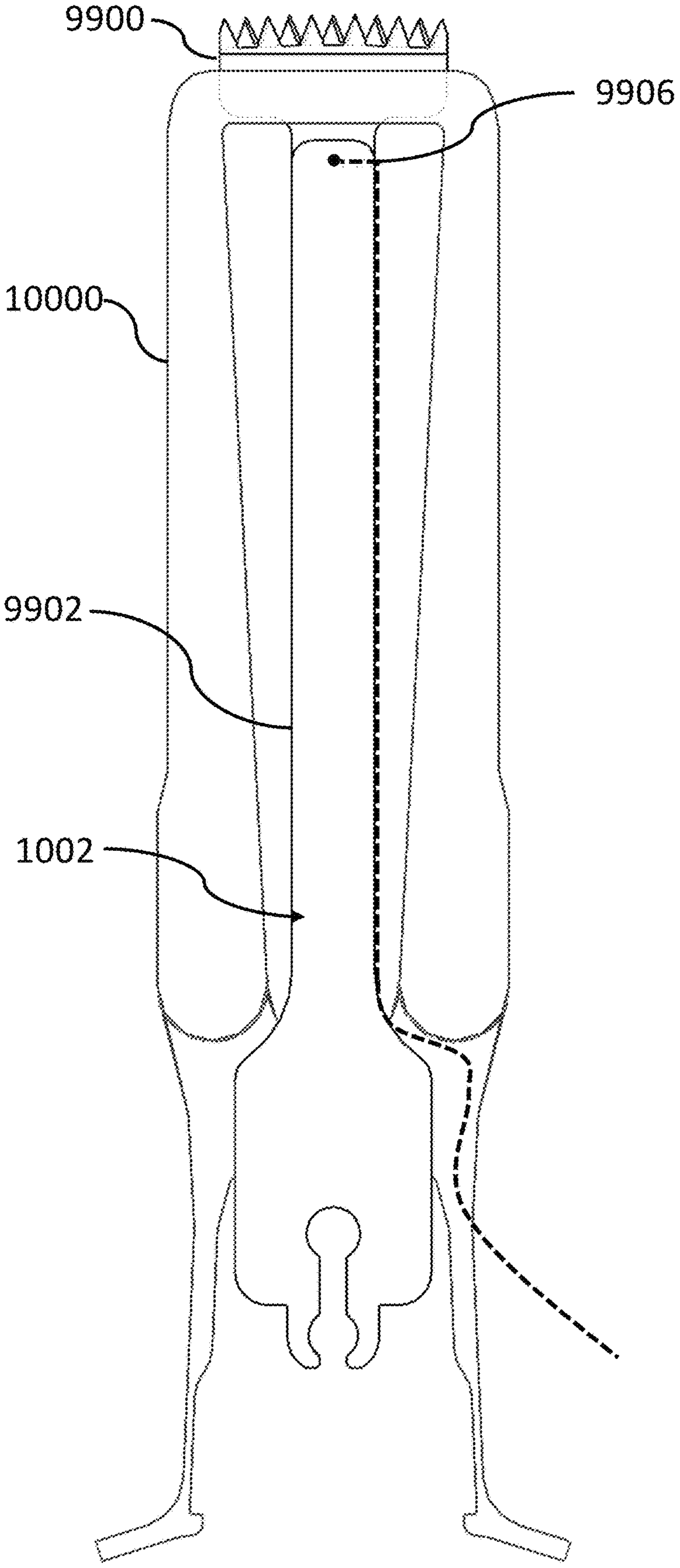
Figure 101:
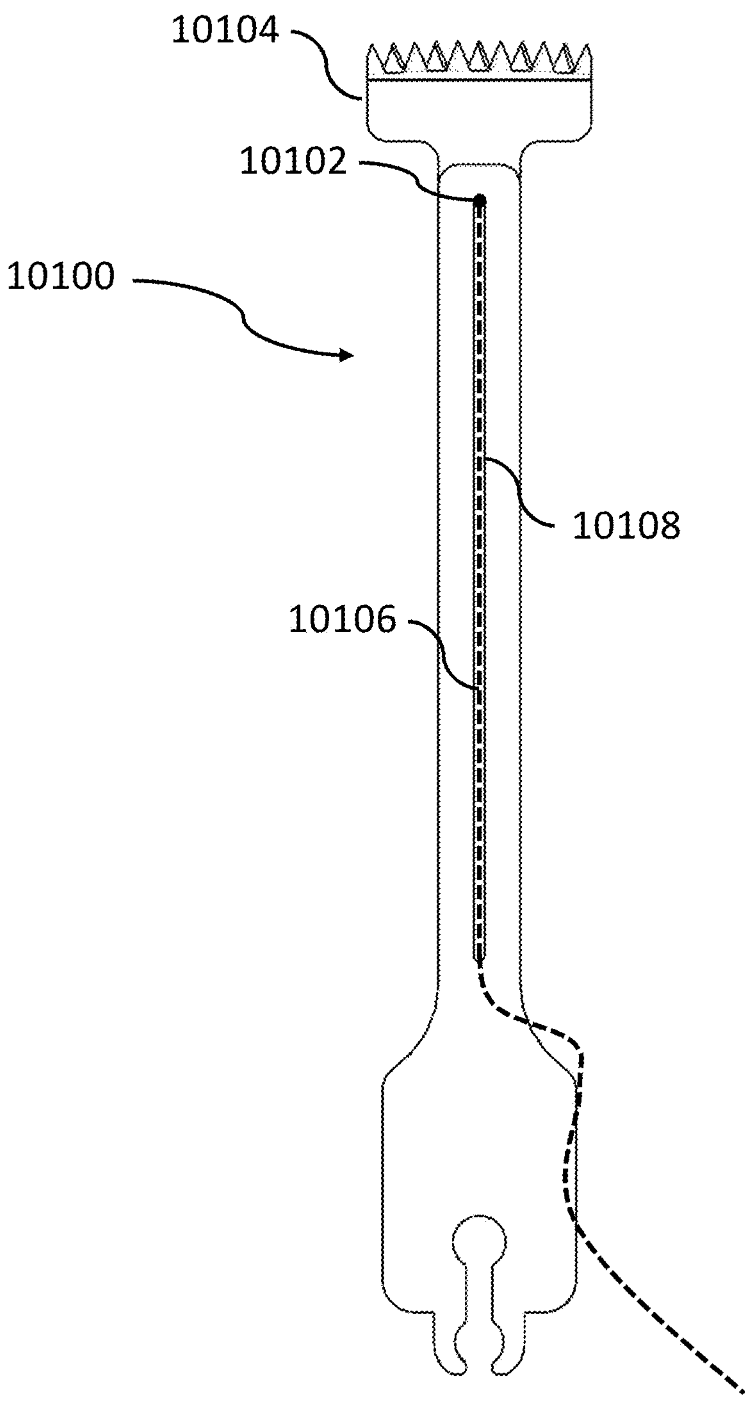
Figure 102:
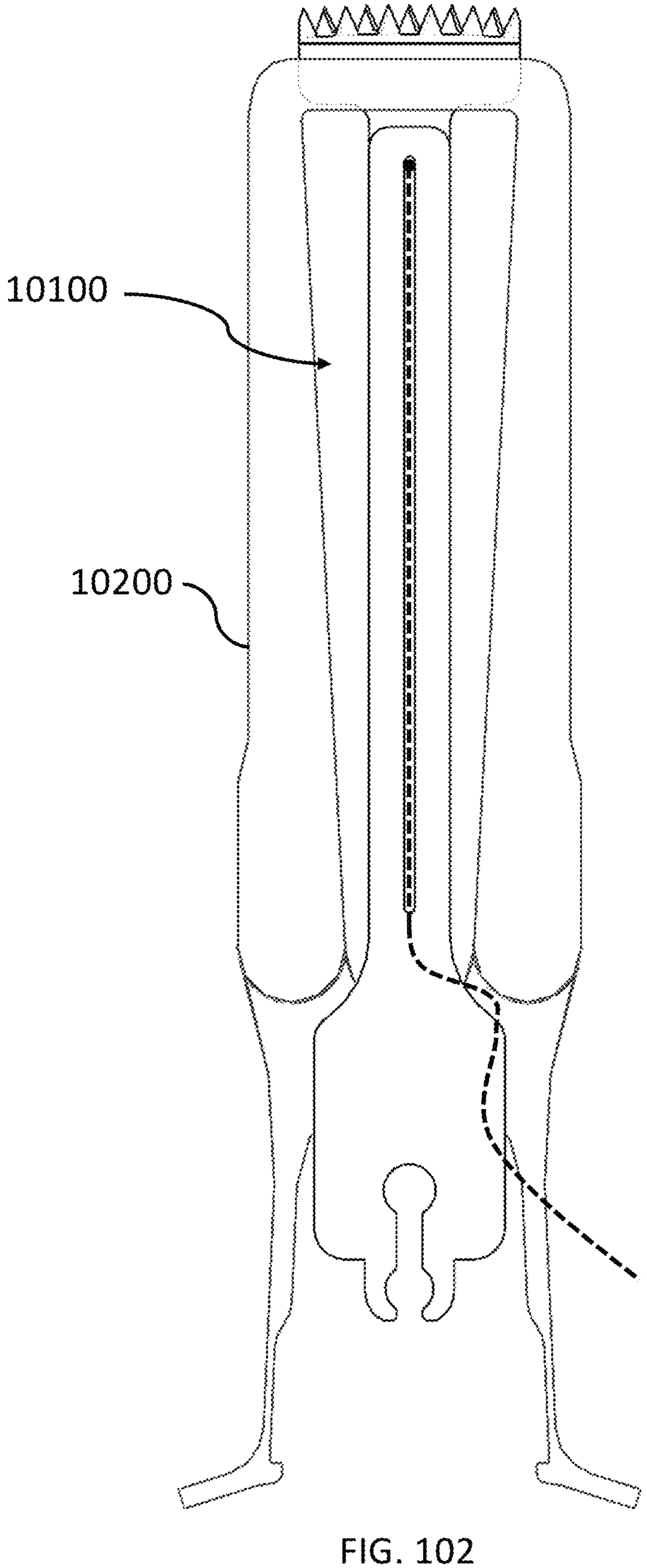
Figure 103:
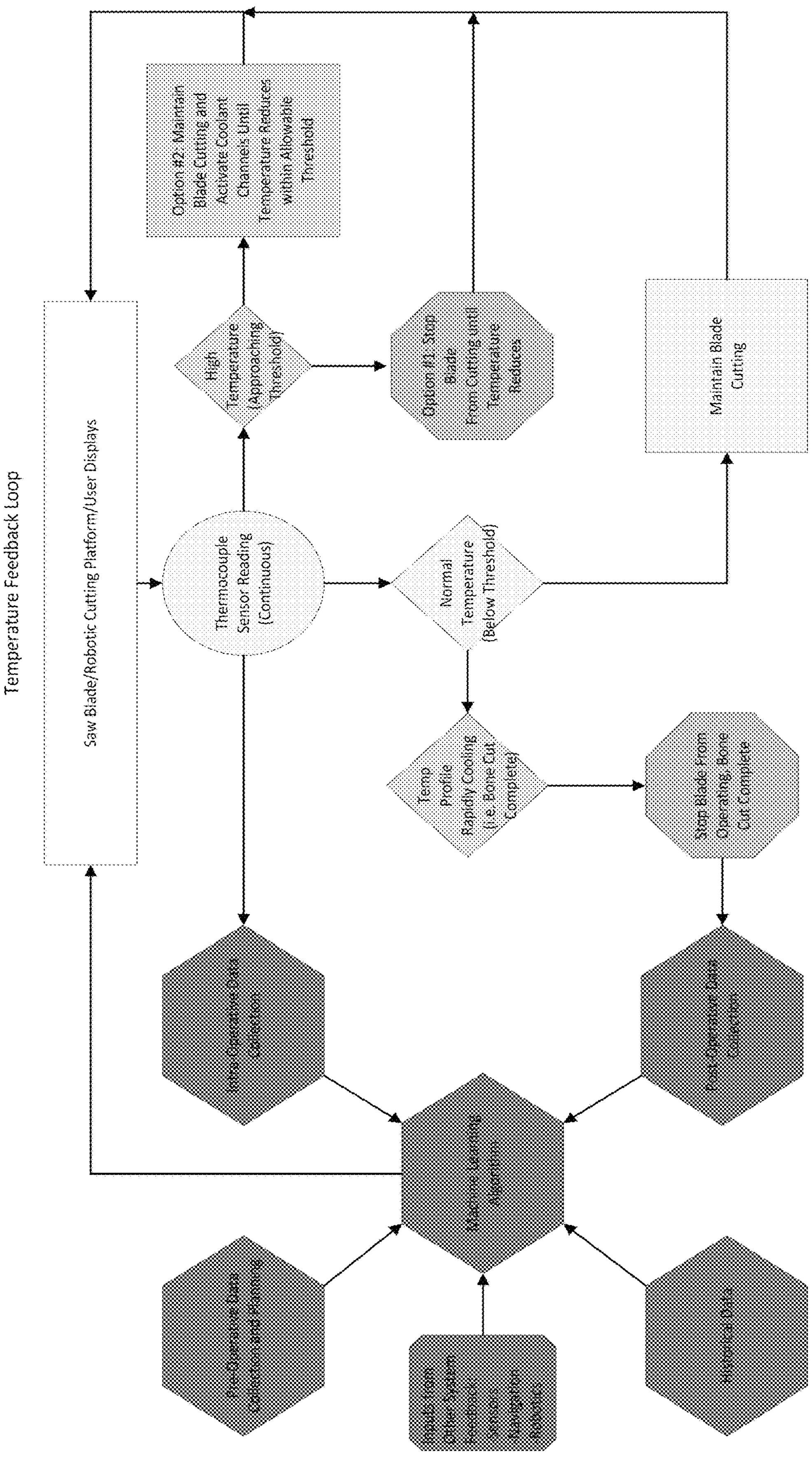
Figure 104:
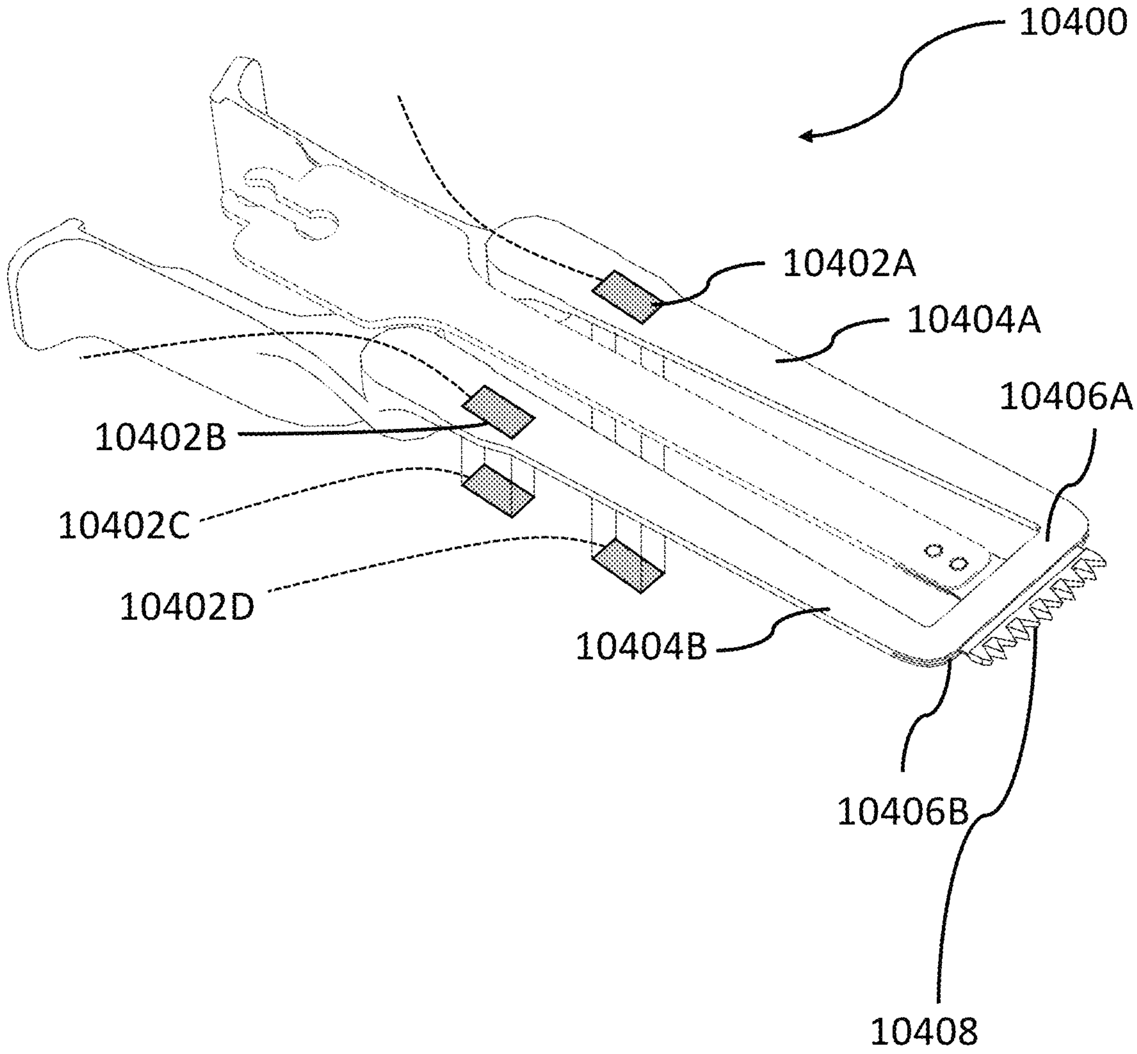
Figure 105:
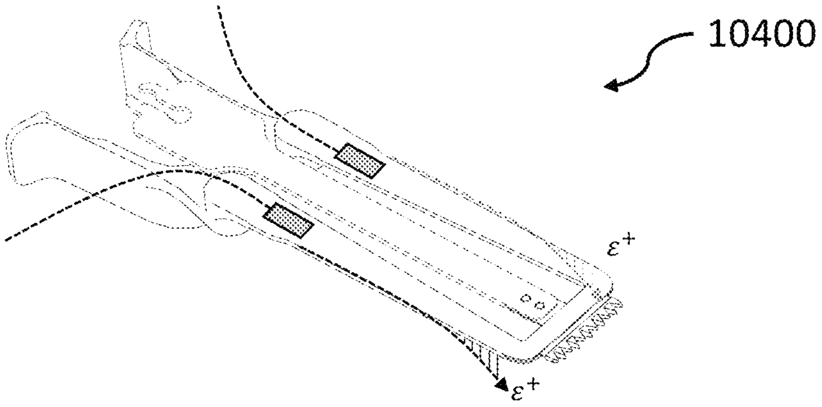
Figure 105:
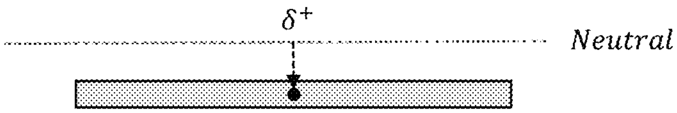
Figure 105:
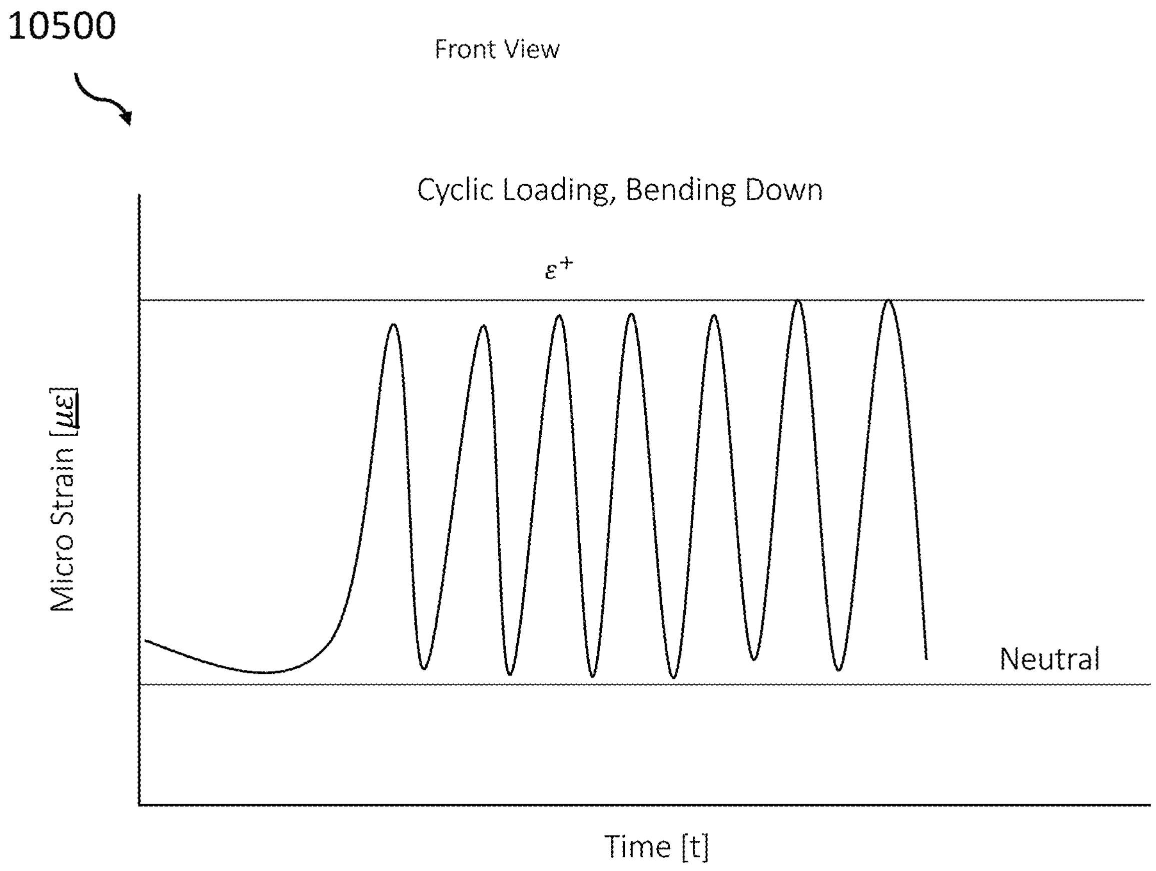
Figure 106:
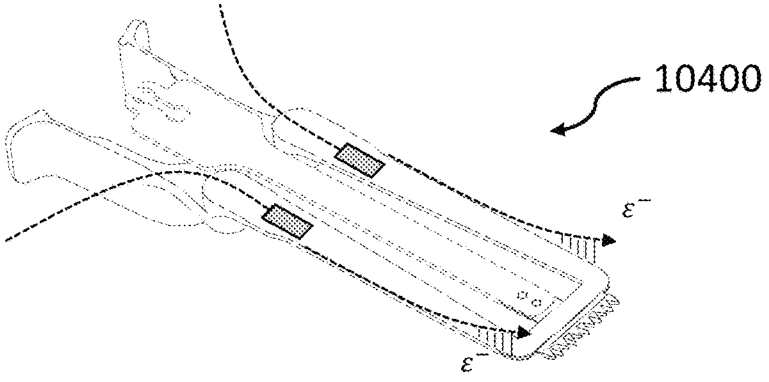
Figure 106:
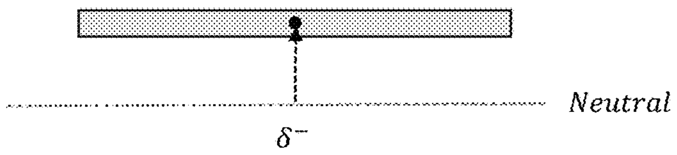
Figure 106:
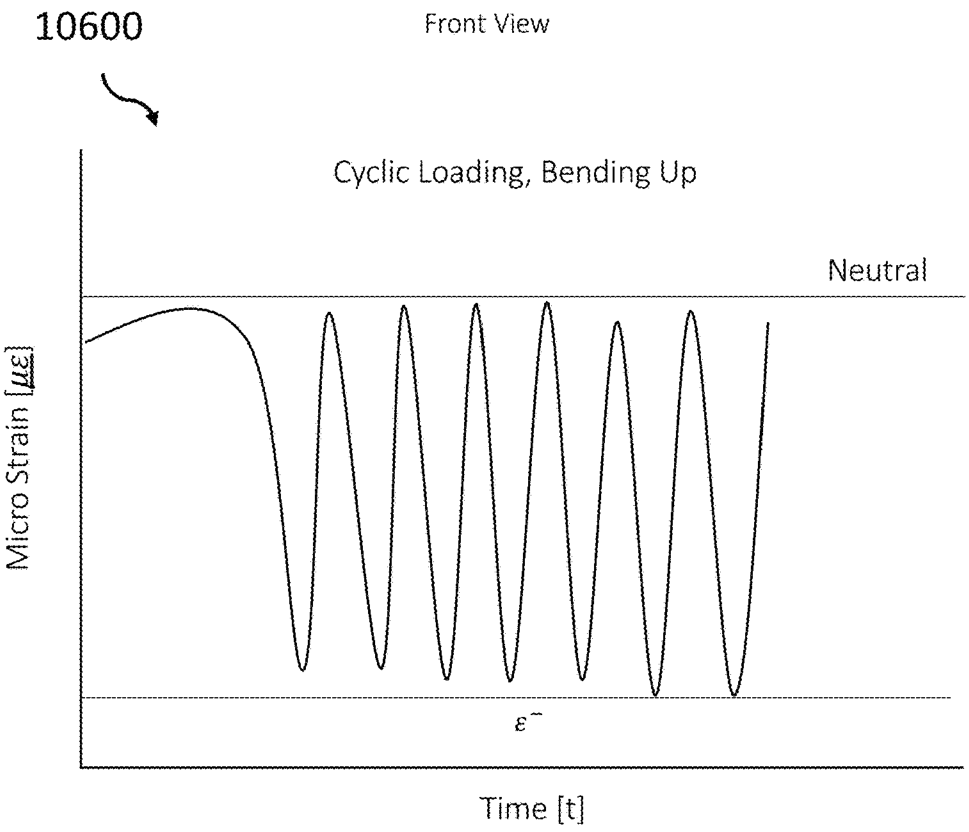
Figure 107:
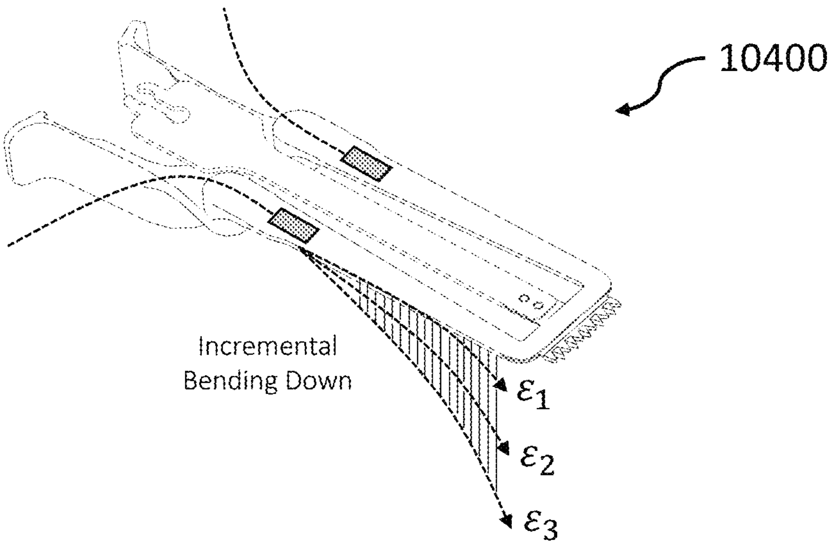
Figure 107:
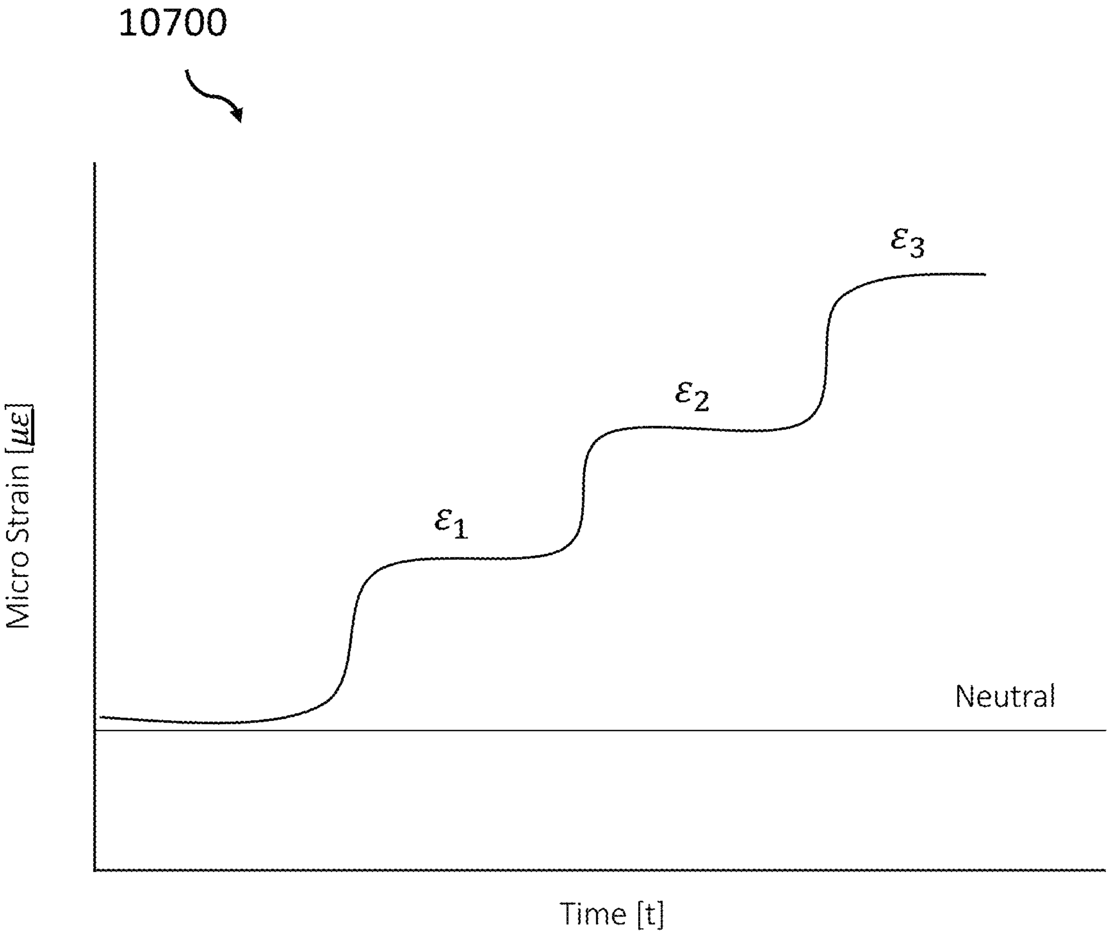
Figure 108:
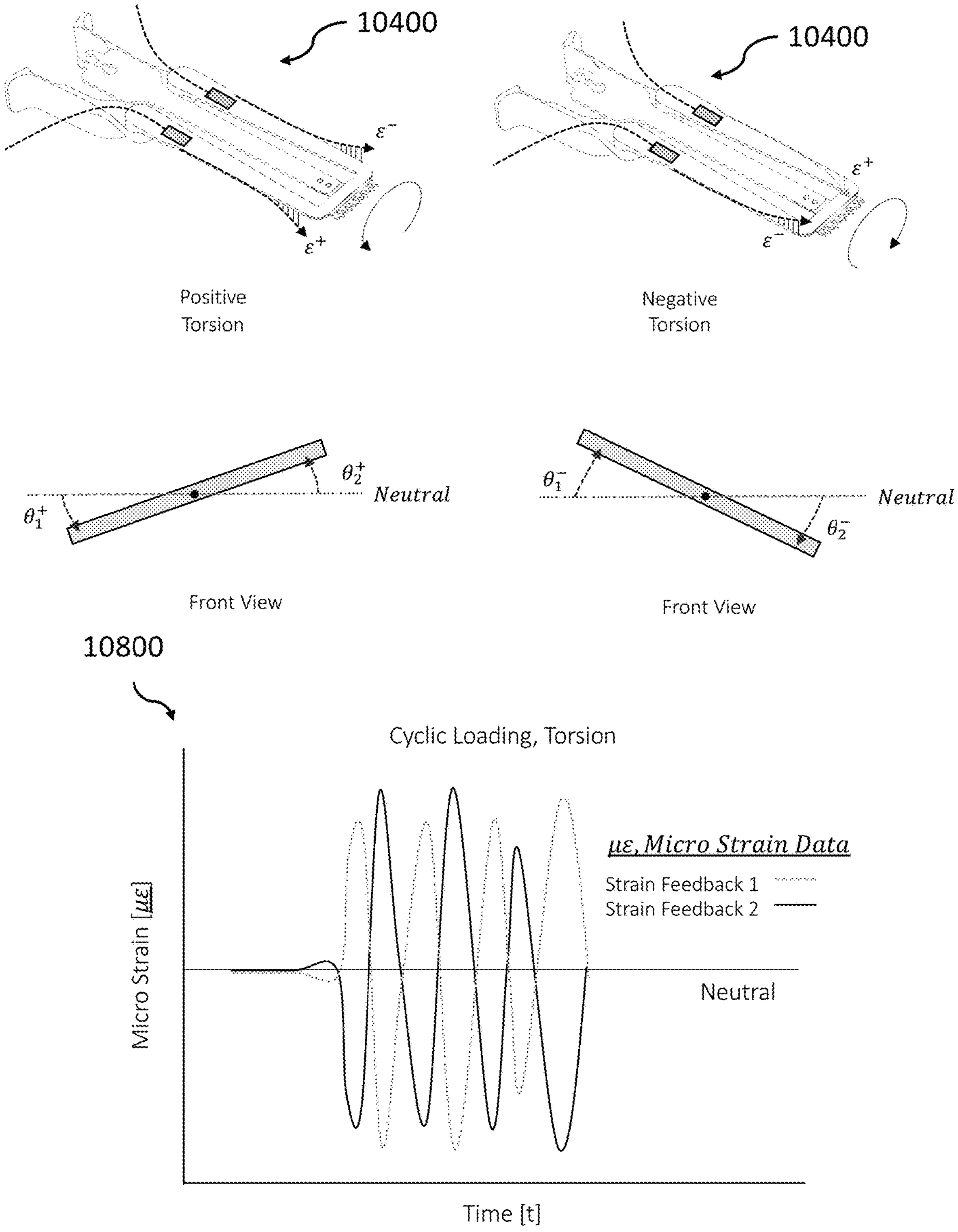
Figure 109:
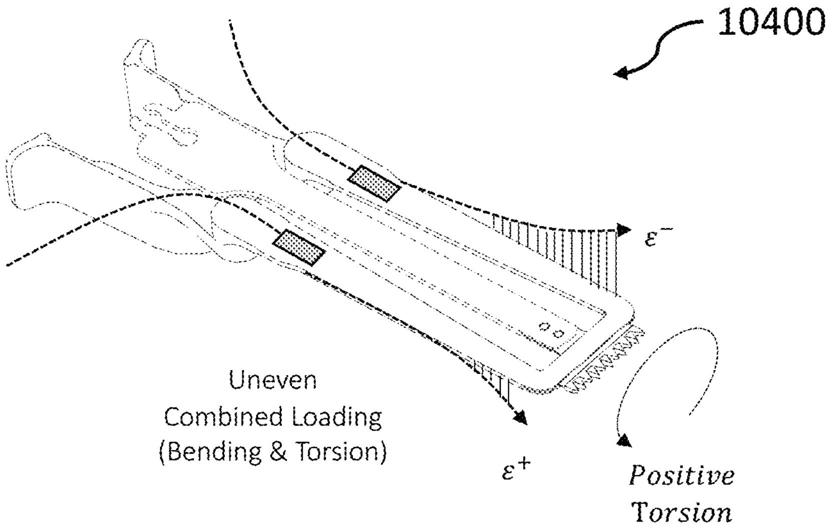
Figure 109:
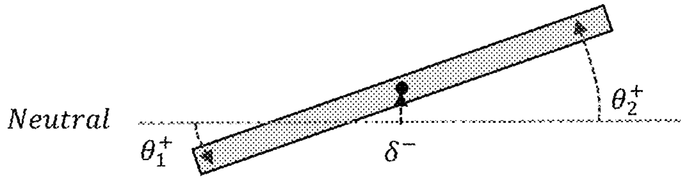
Figure 110:
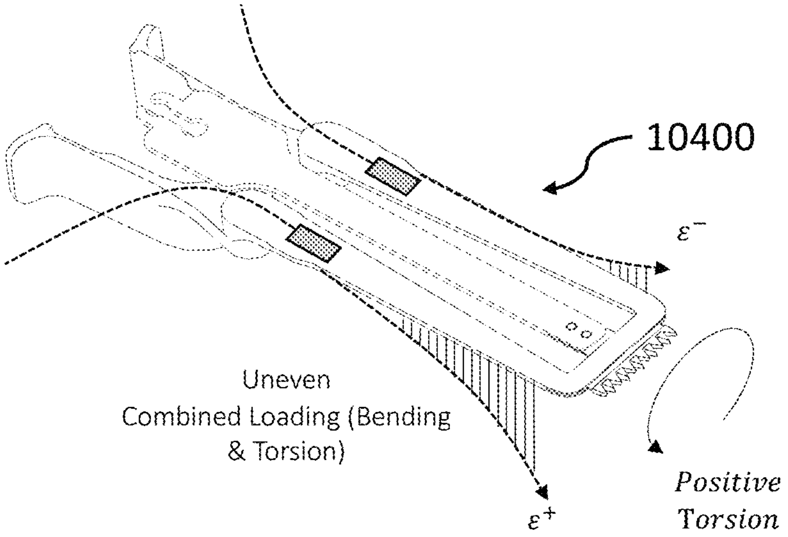
Figure 110:
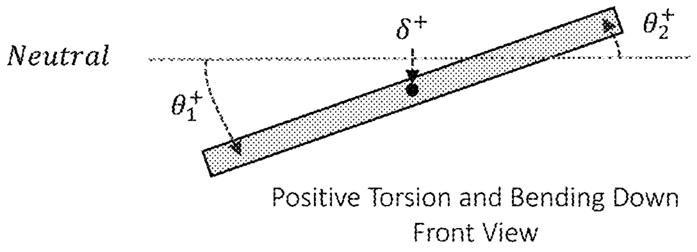
Figure 111:
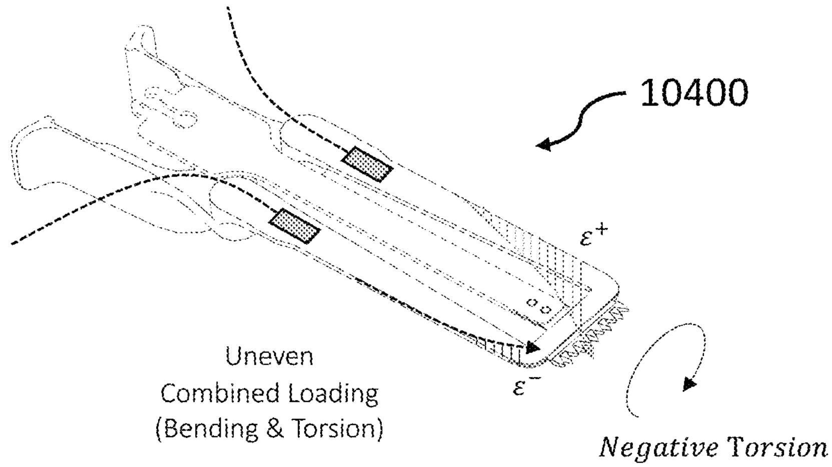
Figure 111:
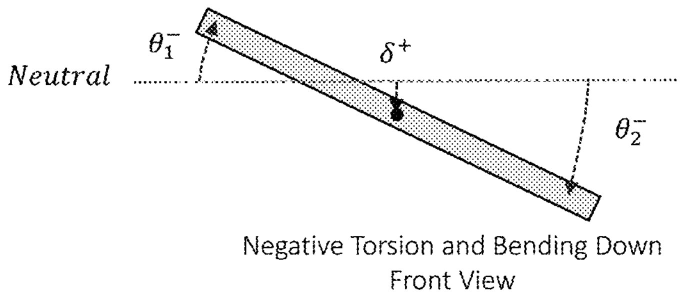
Figure 112:
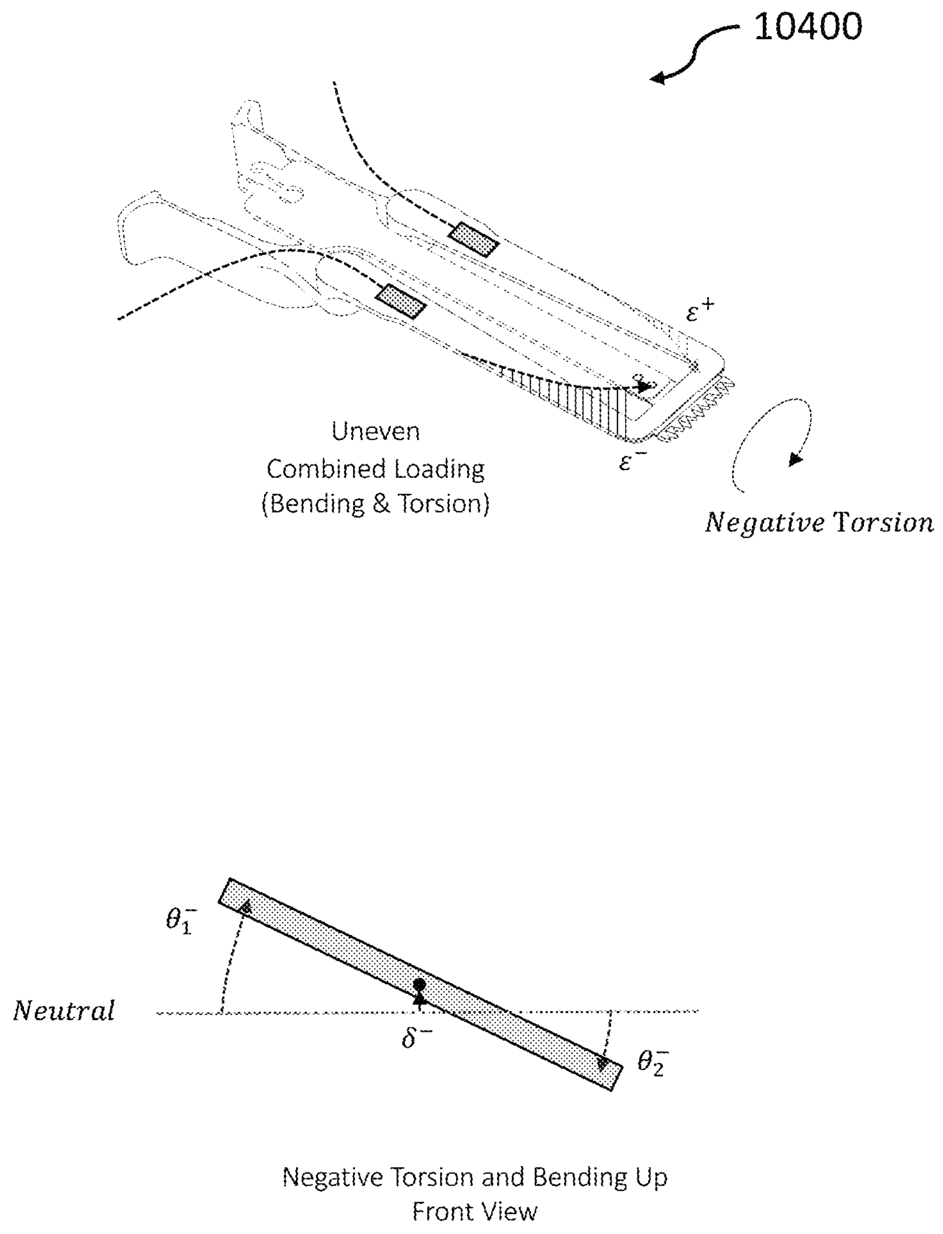
Figure 113:
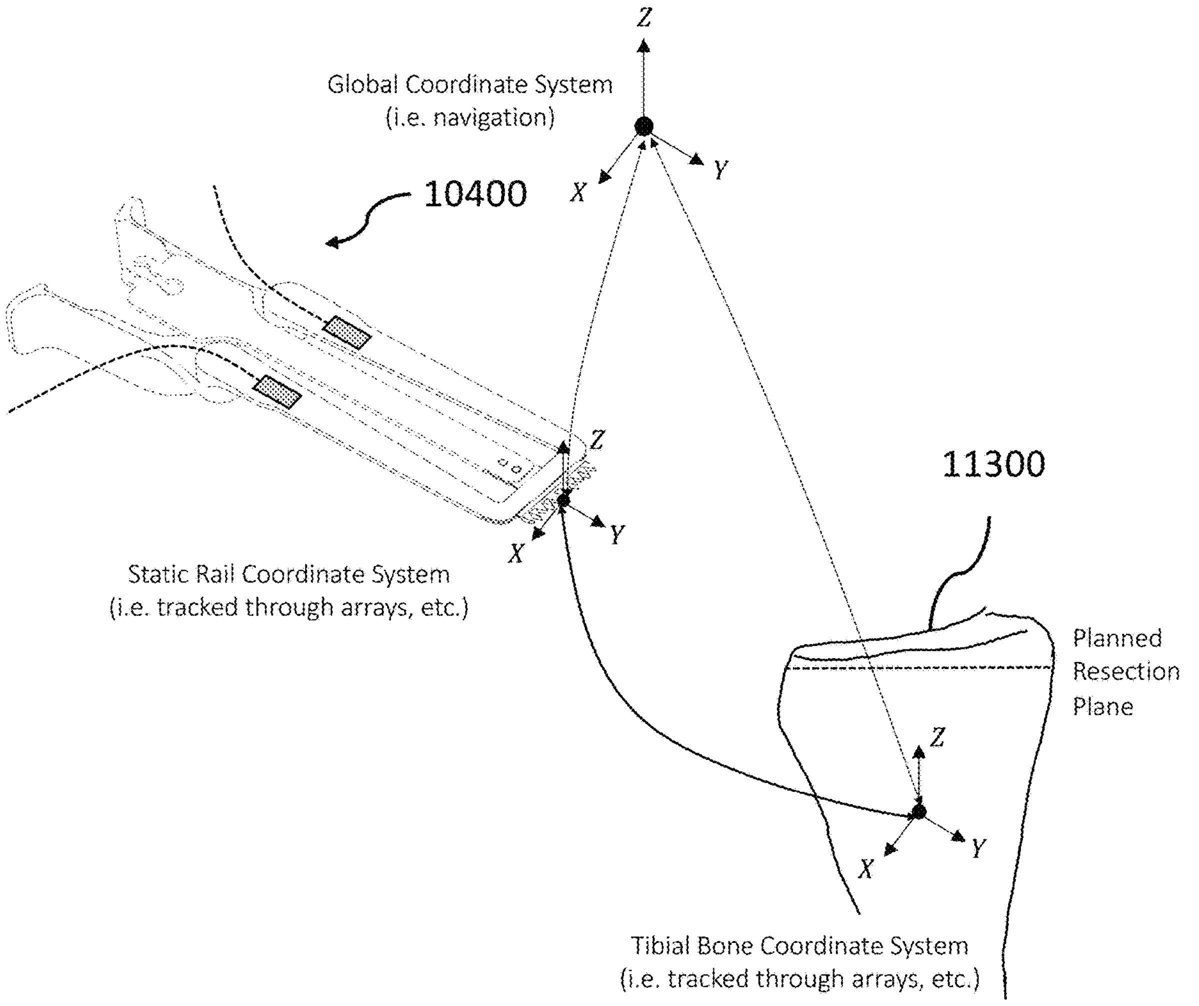
Figure 114:
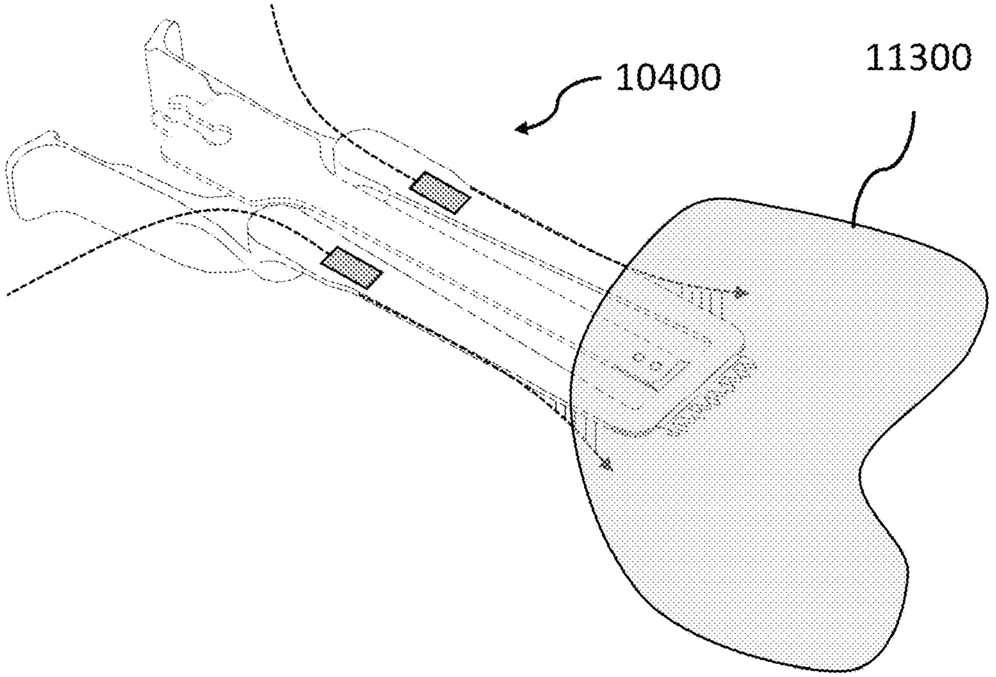
Figure 114:
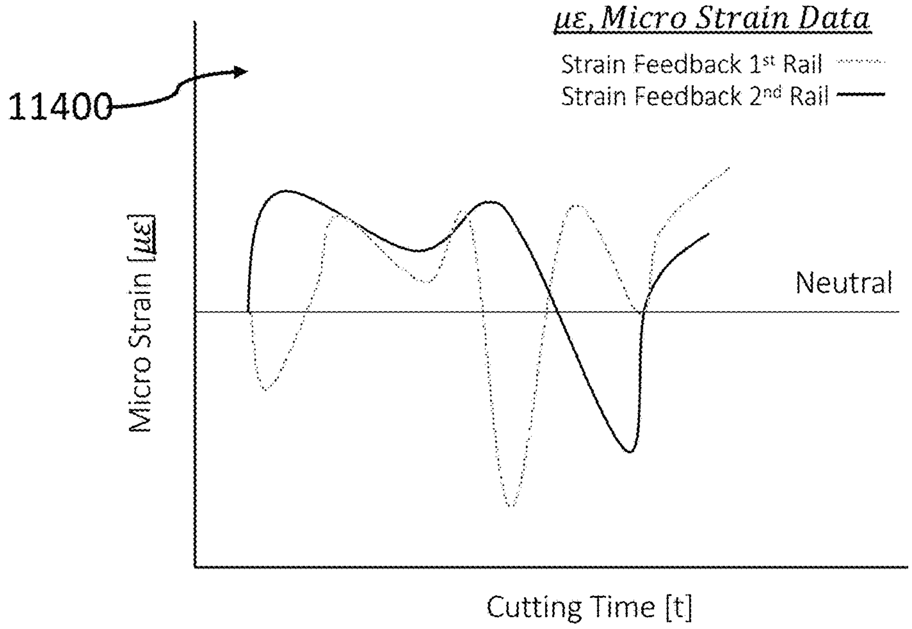
Figure 115:
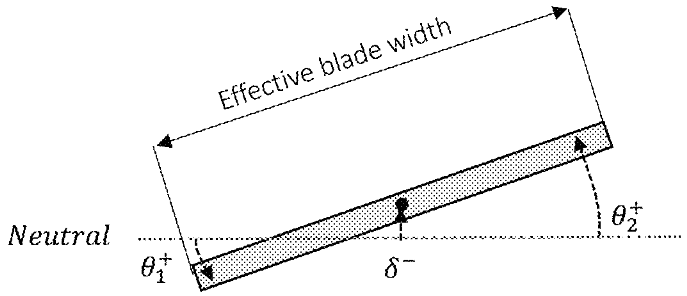
Figure 115:
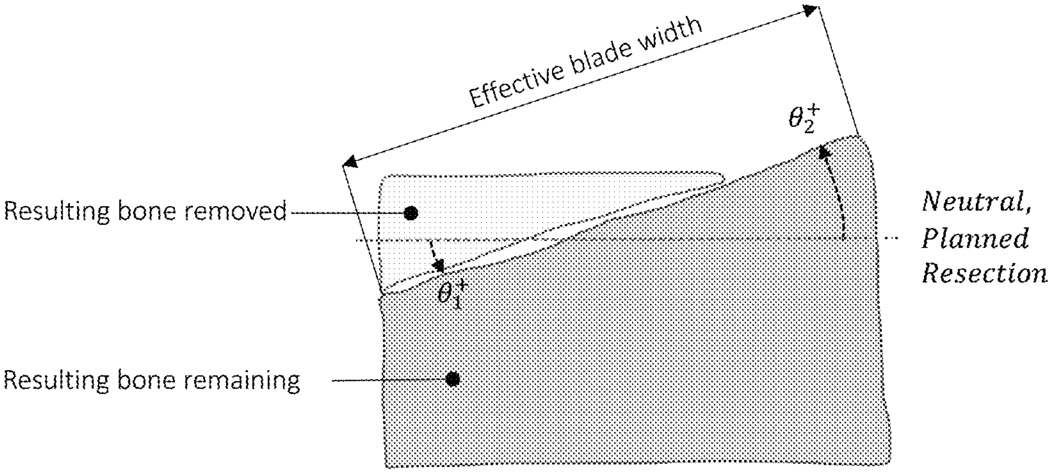
Figure 116:
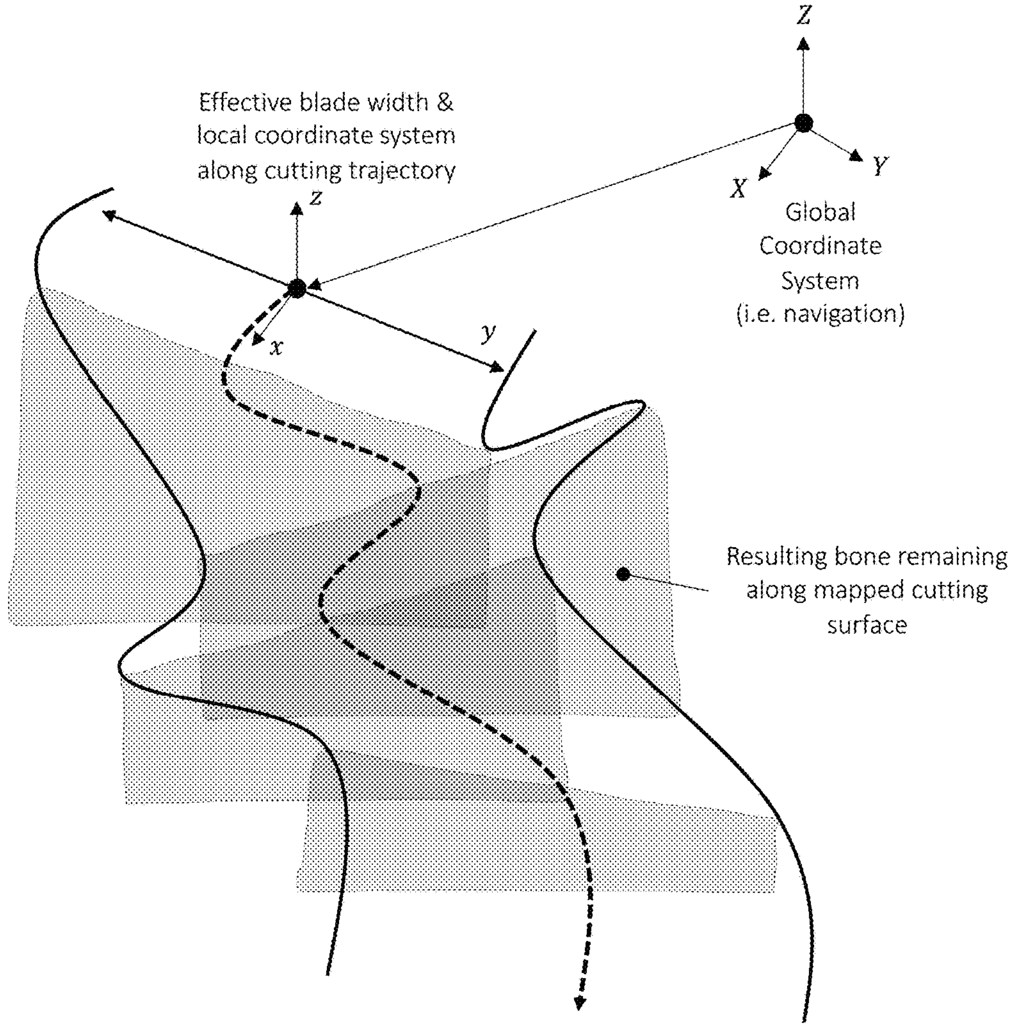
Figure 117:
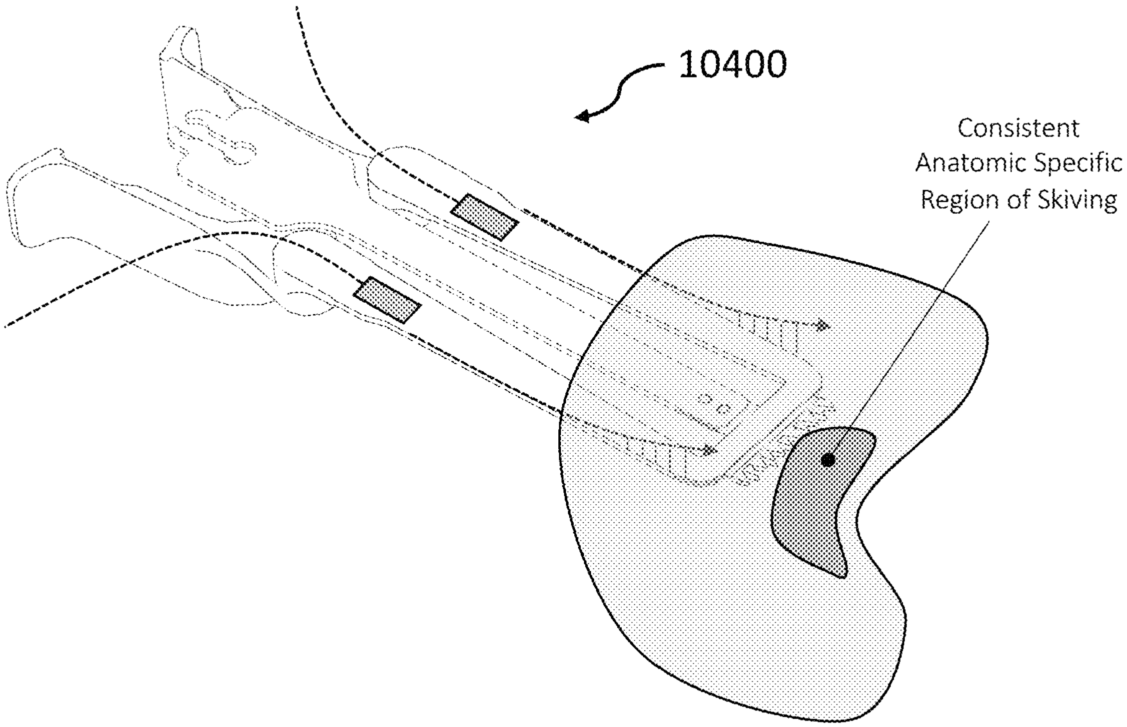
Figure 118:
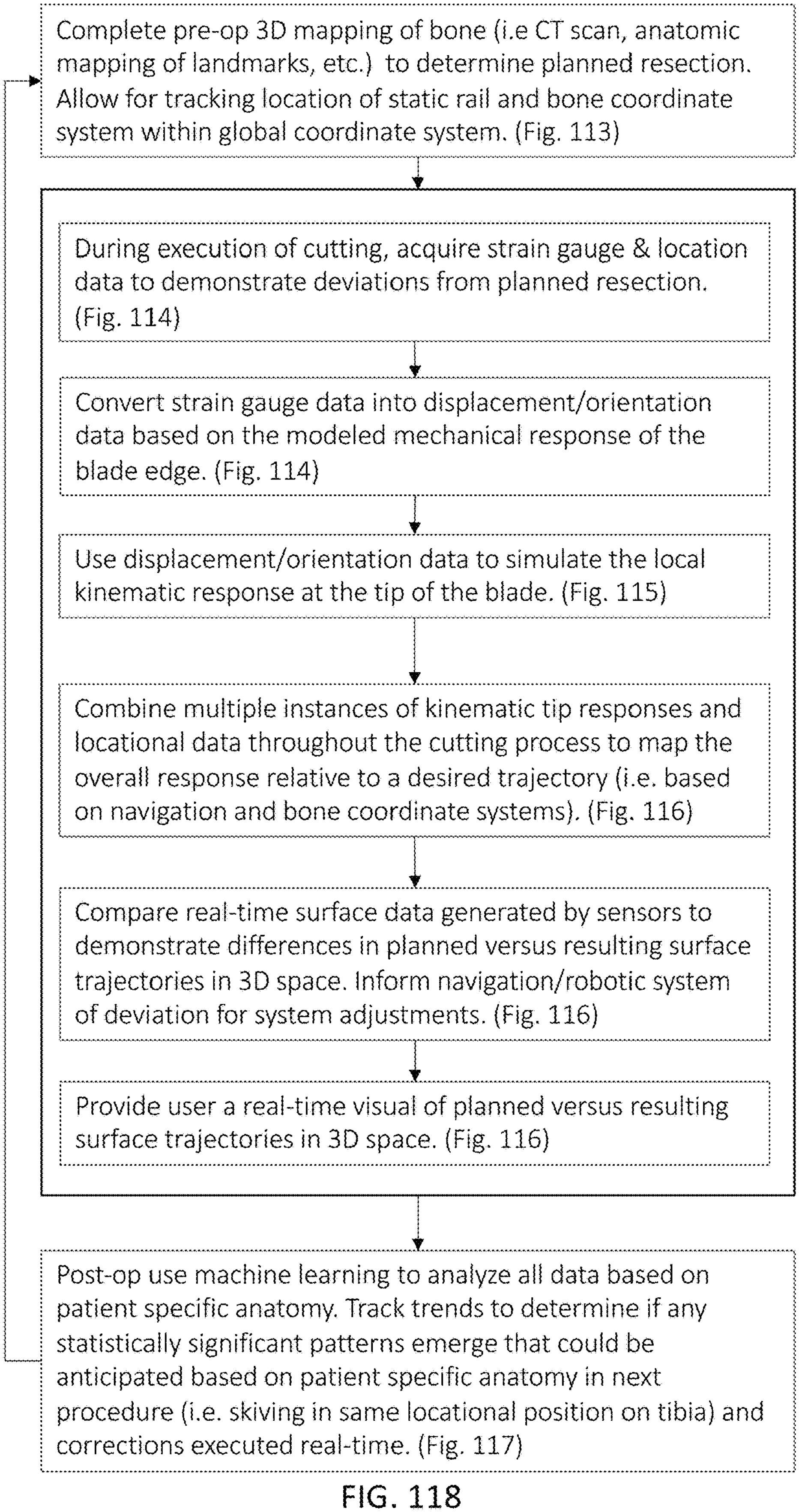
Figure 119:
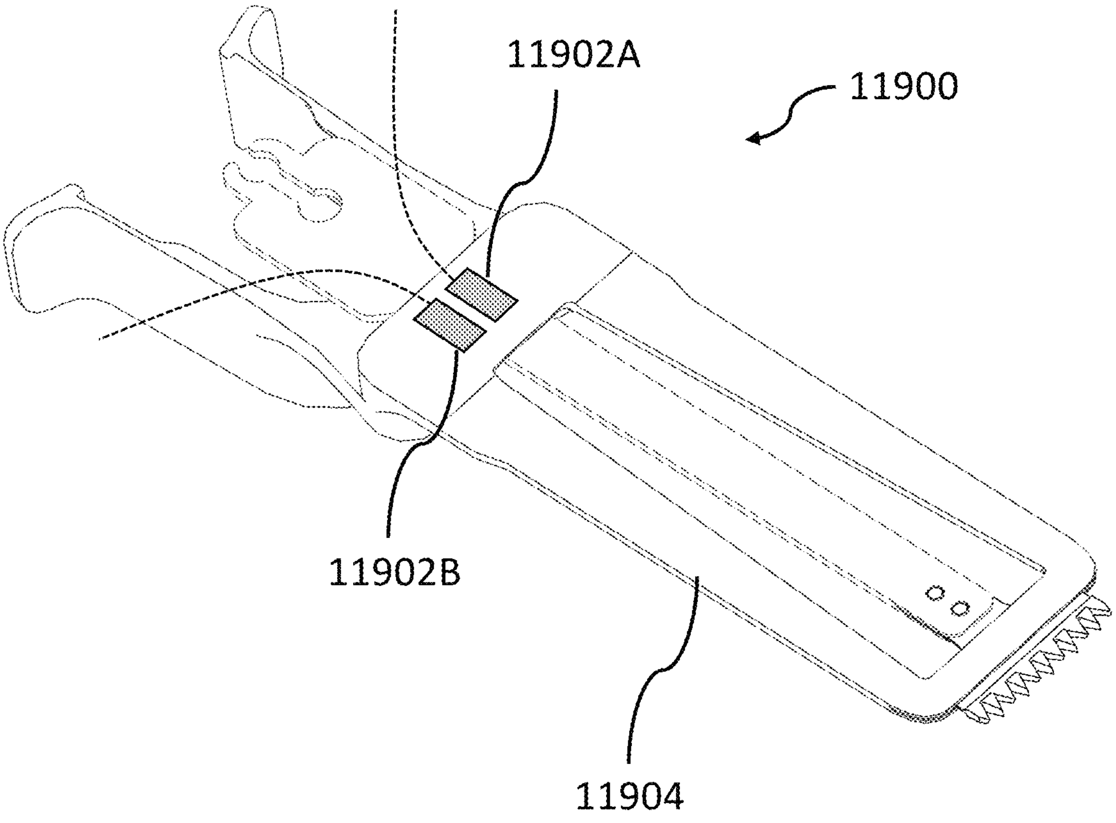
Figure 120:
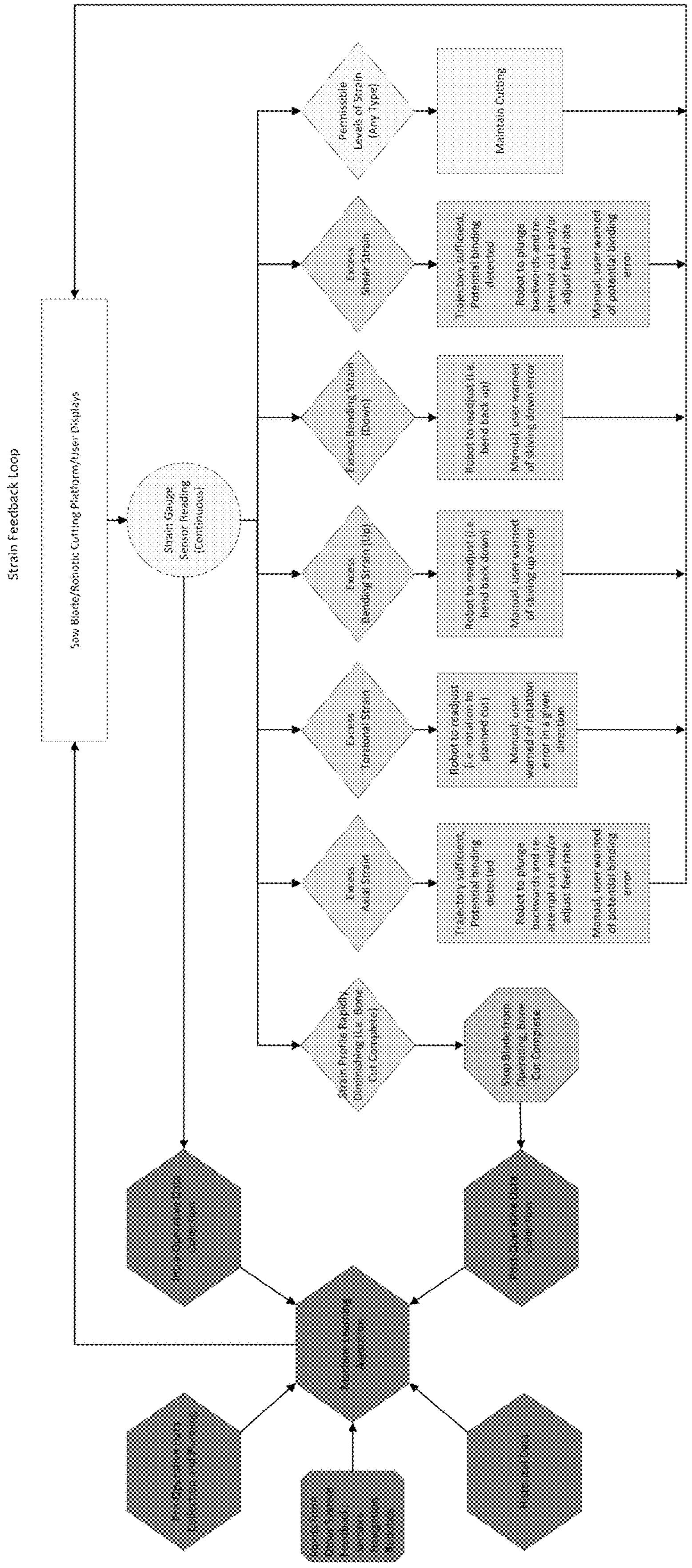
Figure 121:
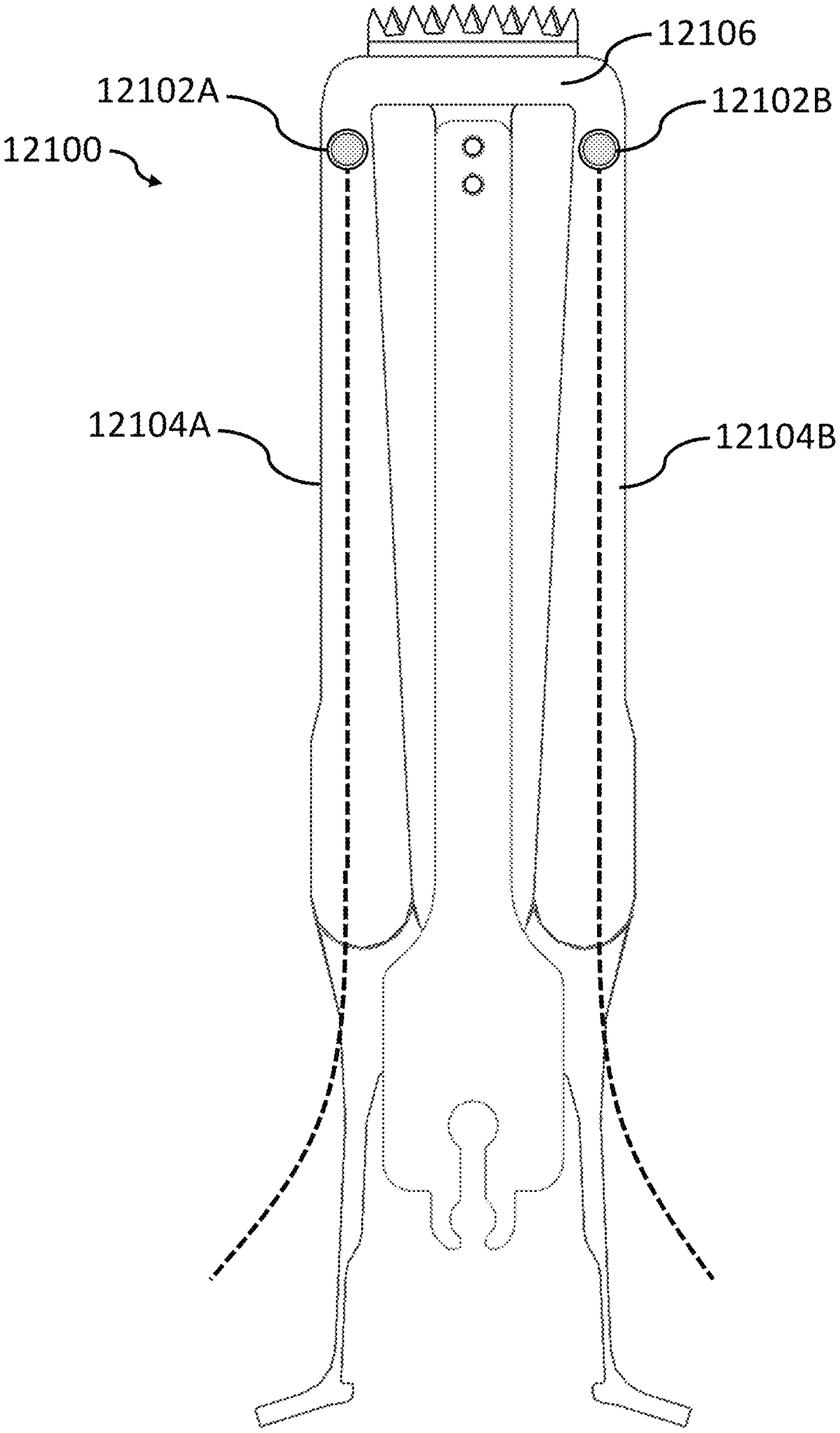
Figure 122:
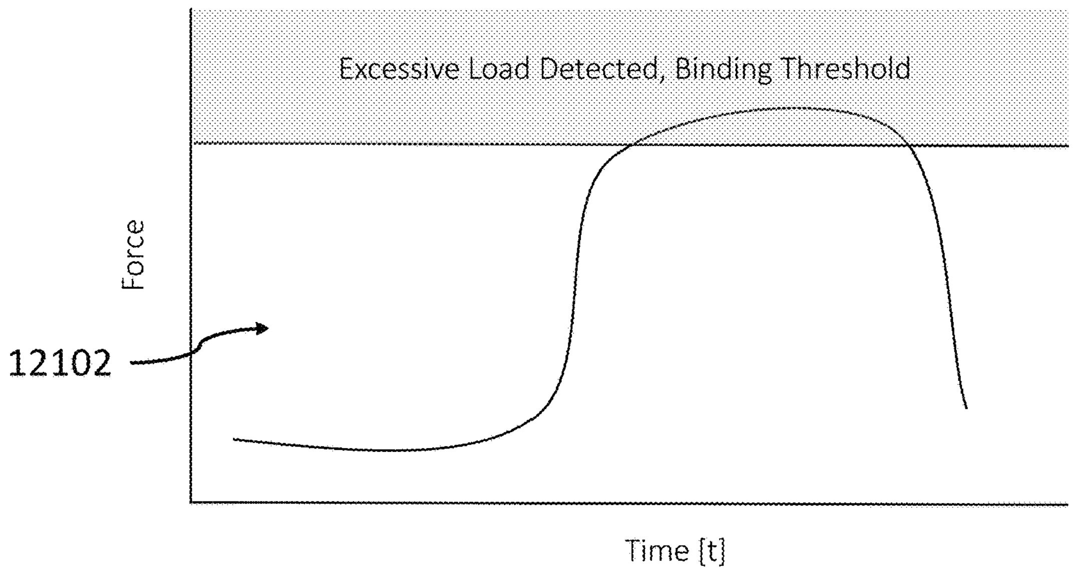
Figure 122:
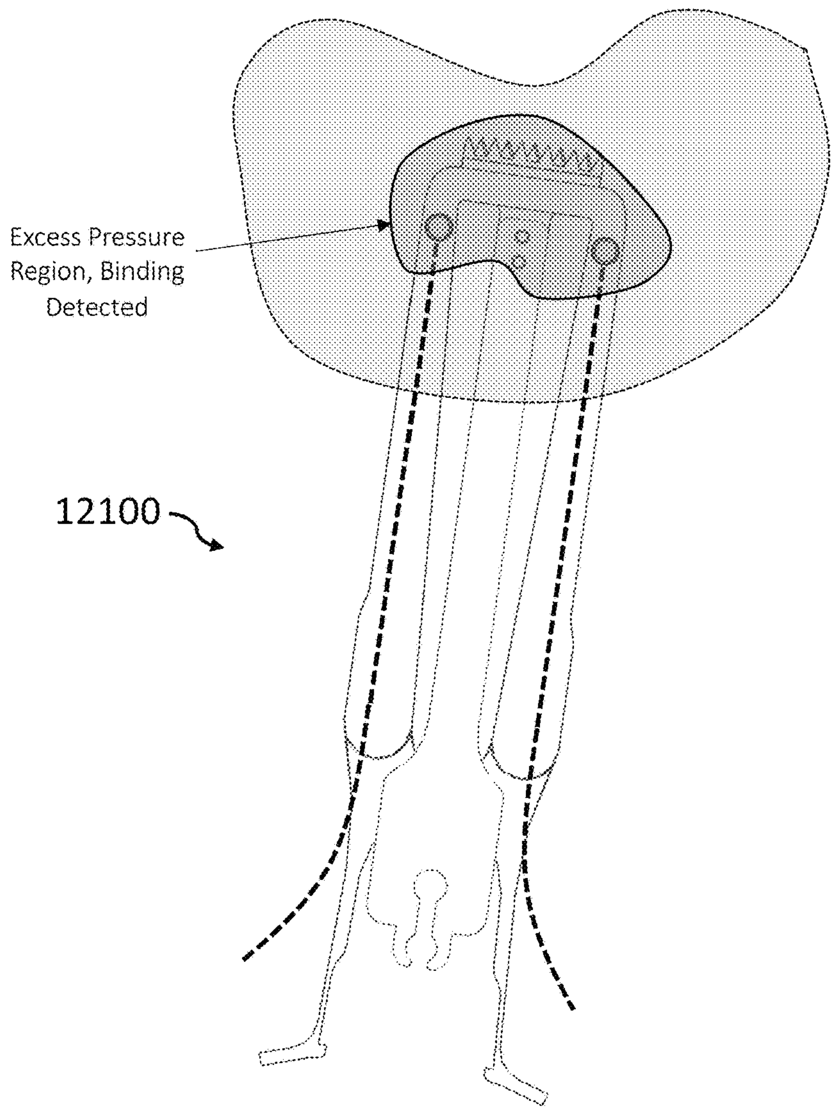
Figure 123:
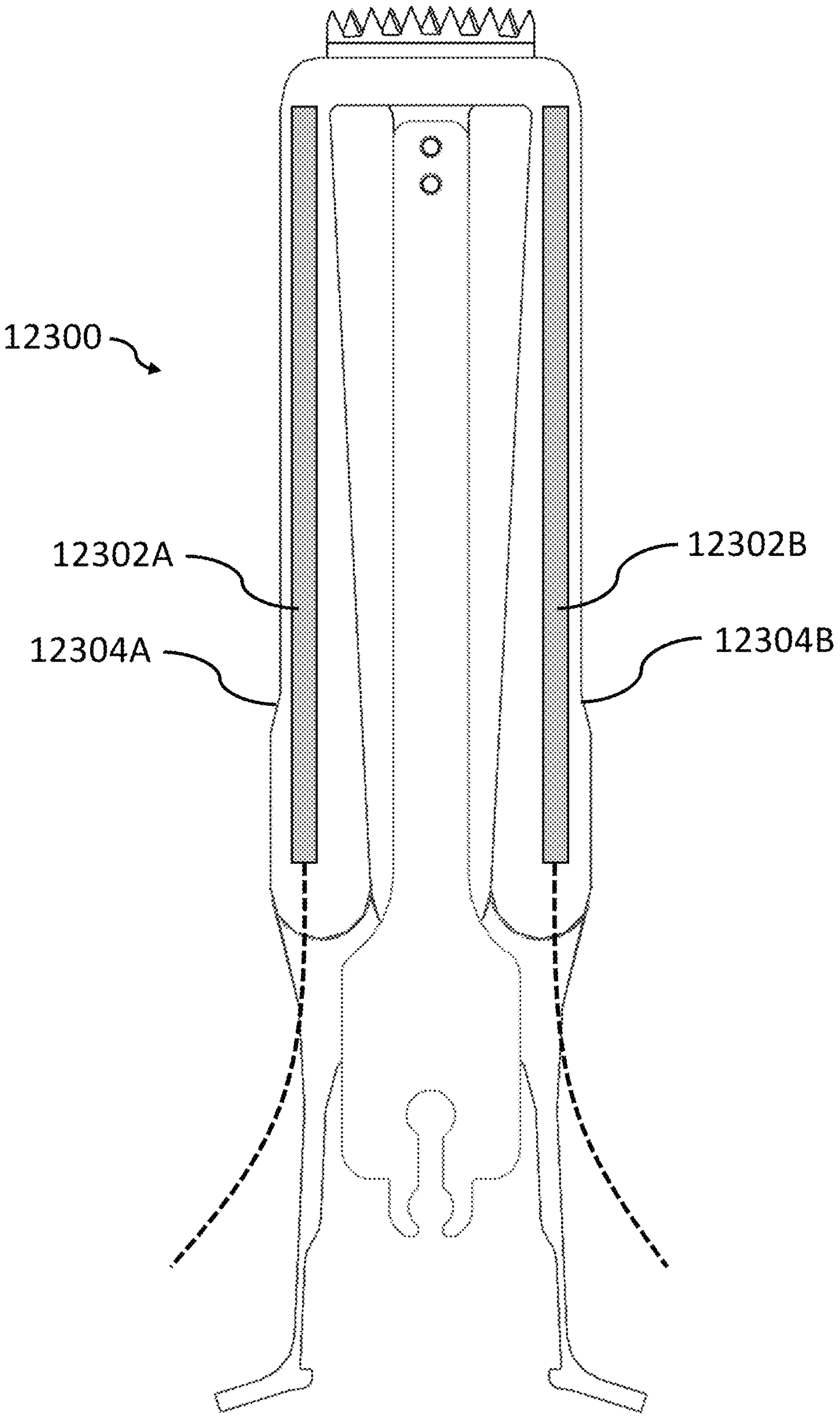
Figure 124:
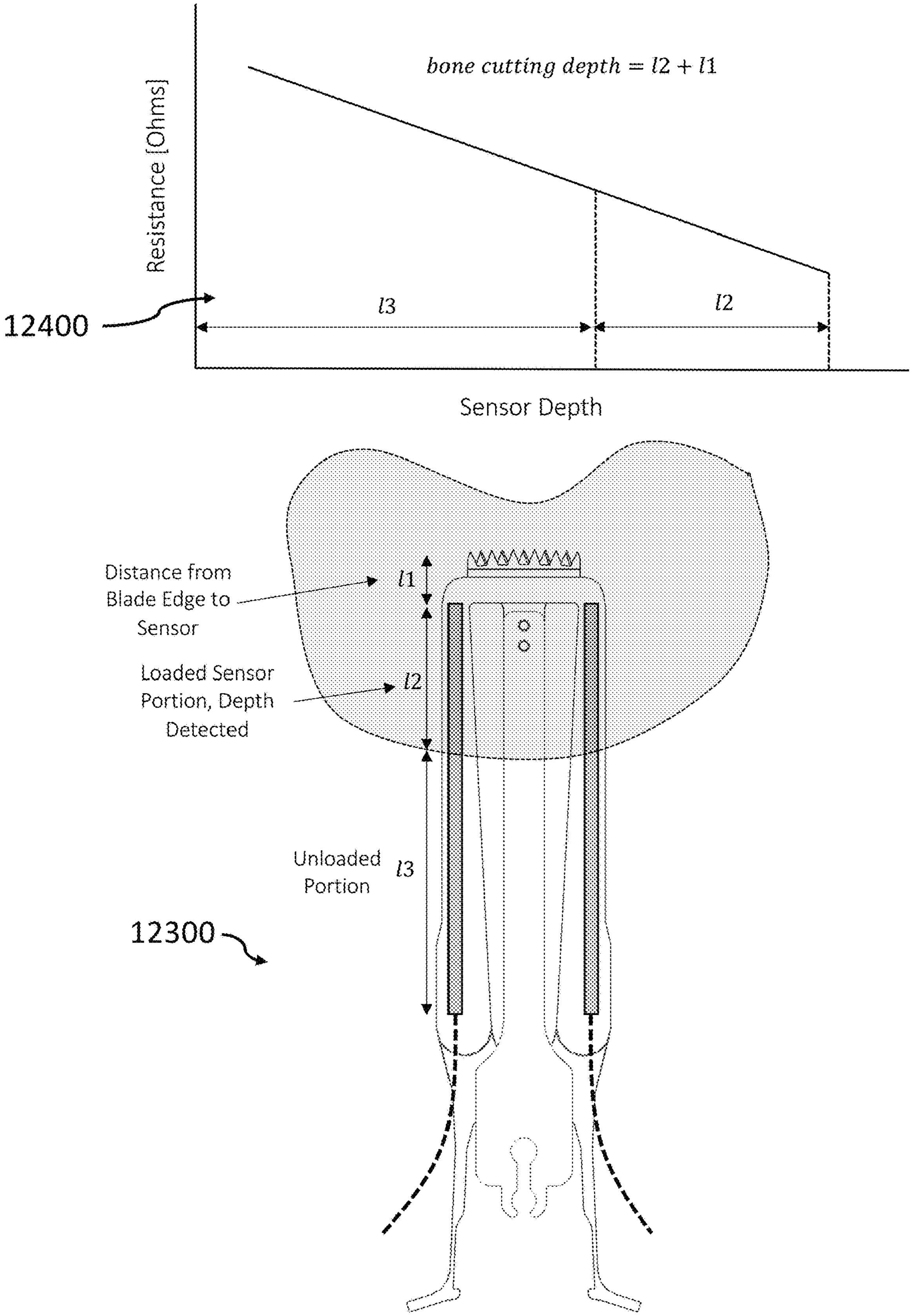
Figure 125:
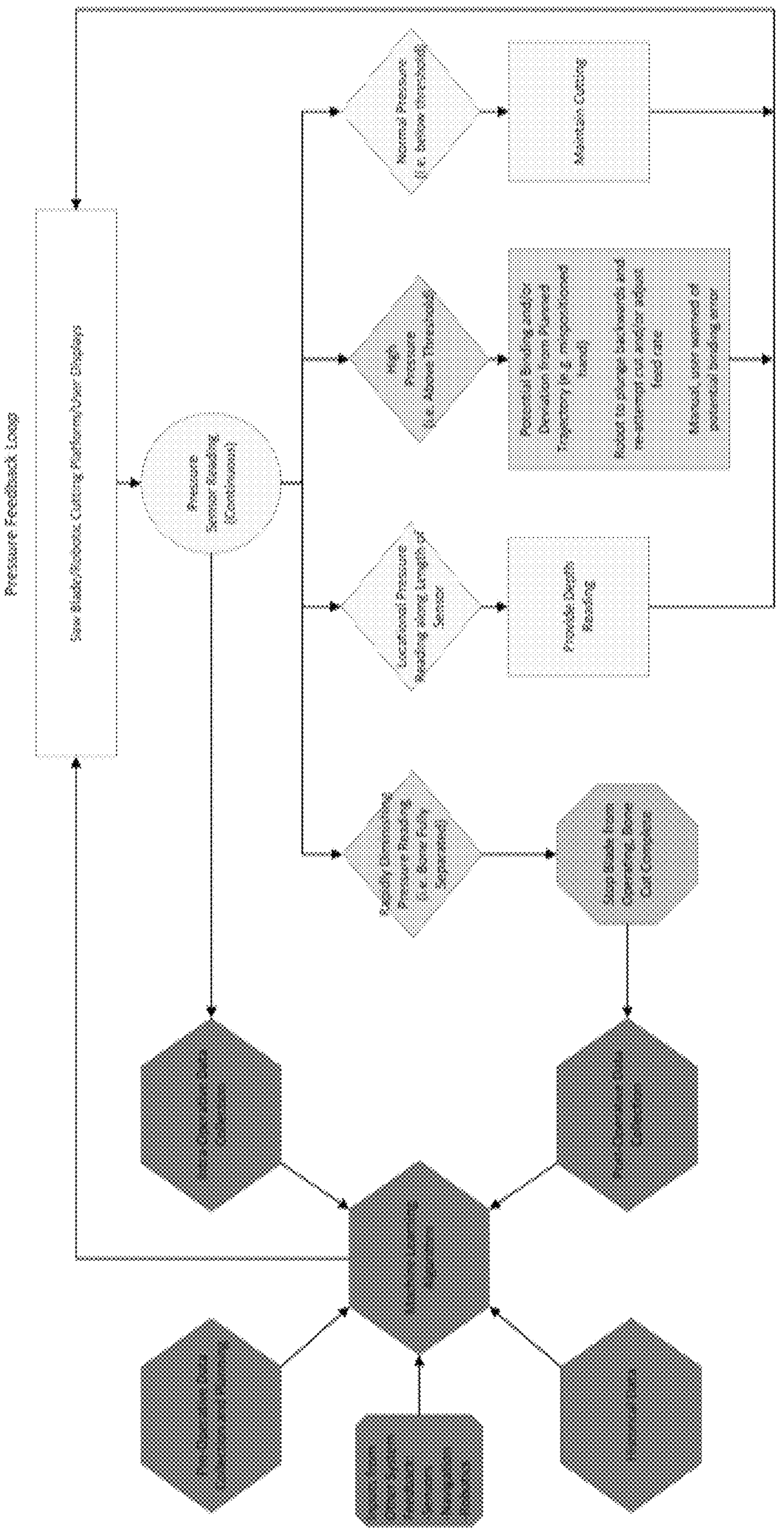
Figure 126:
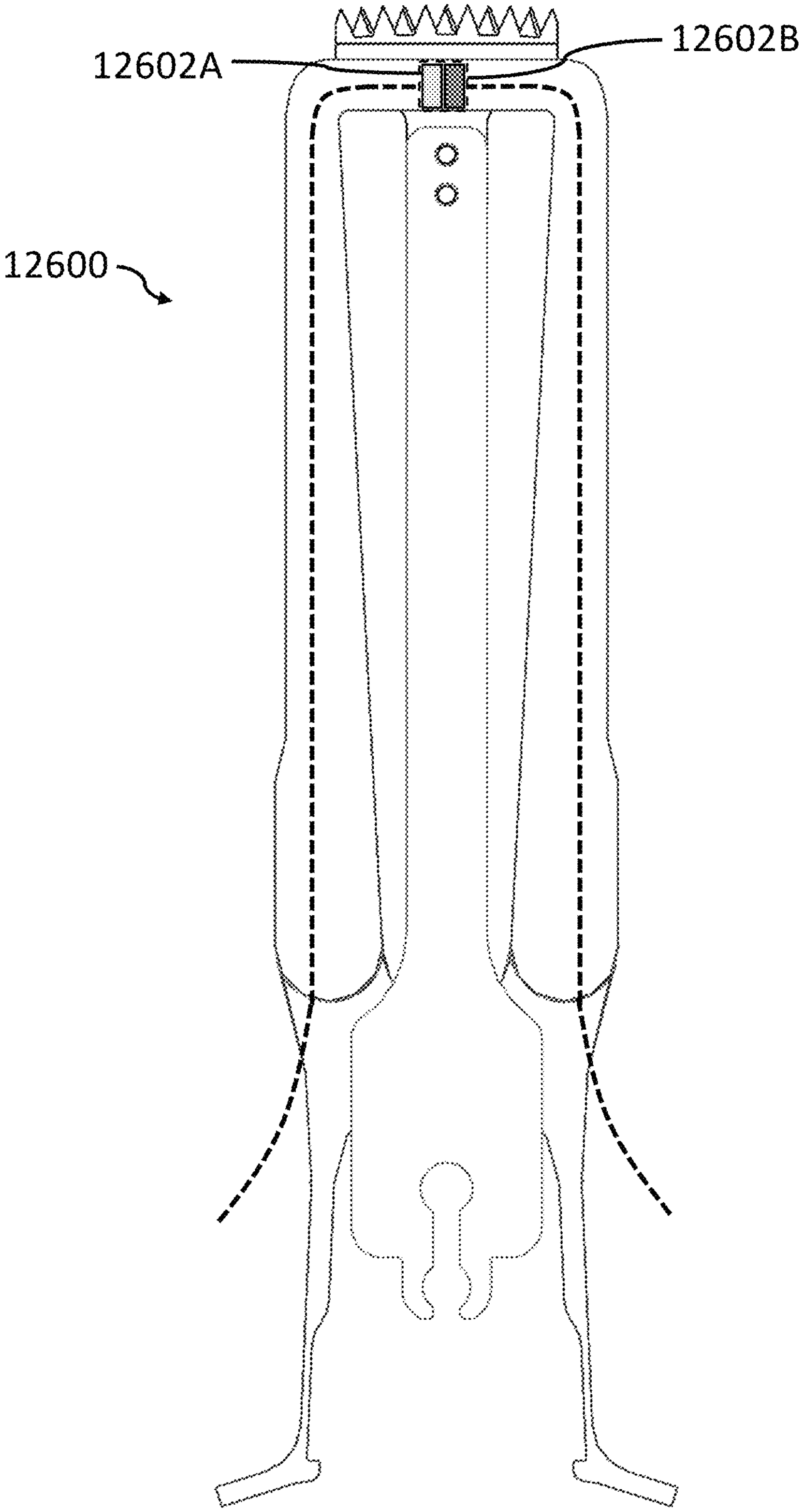
Figure 127:
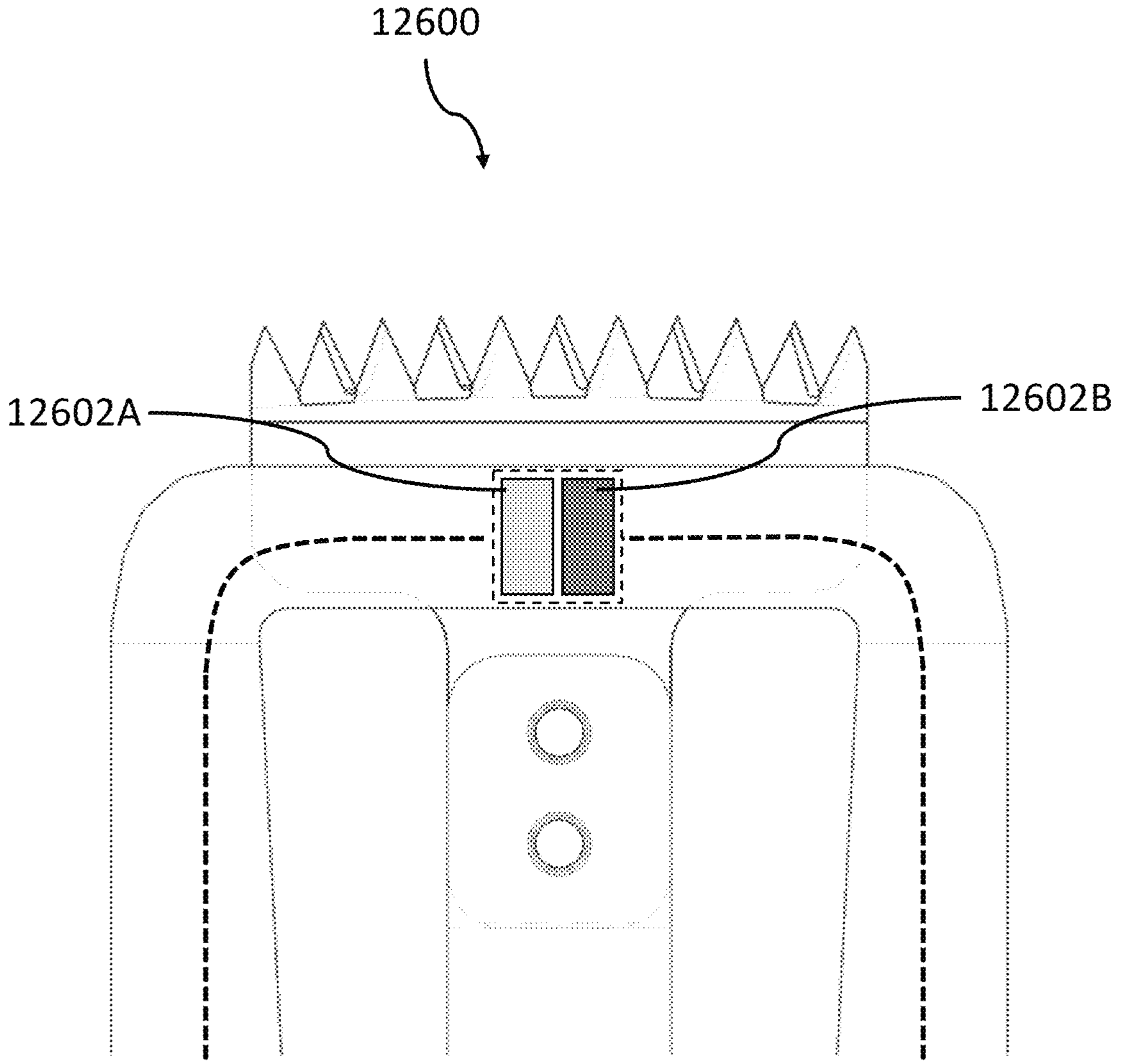
Figure 128:
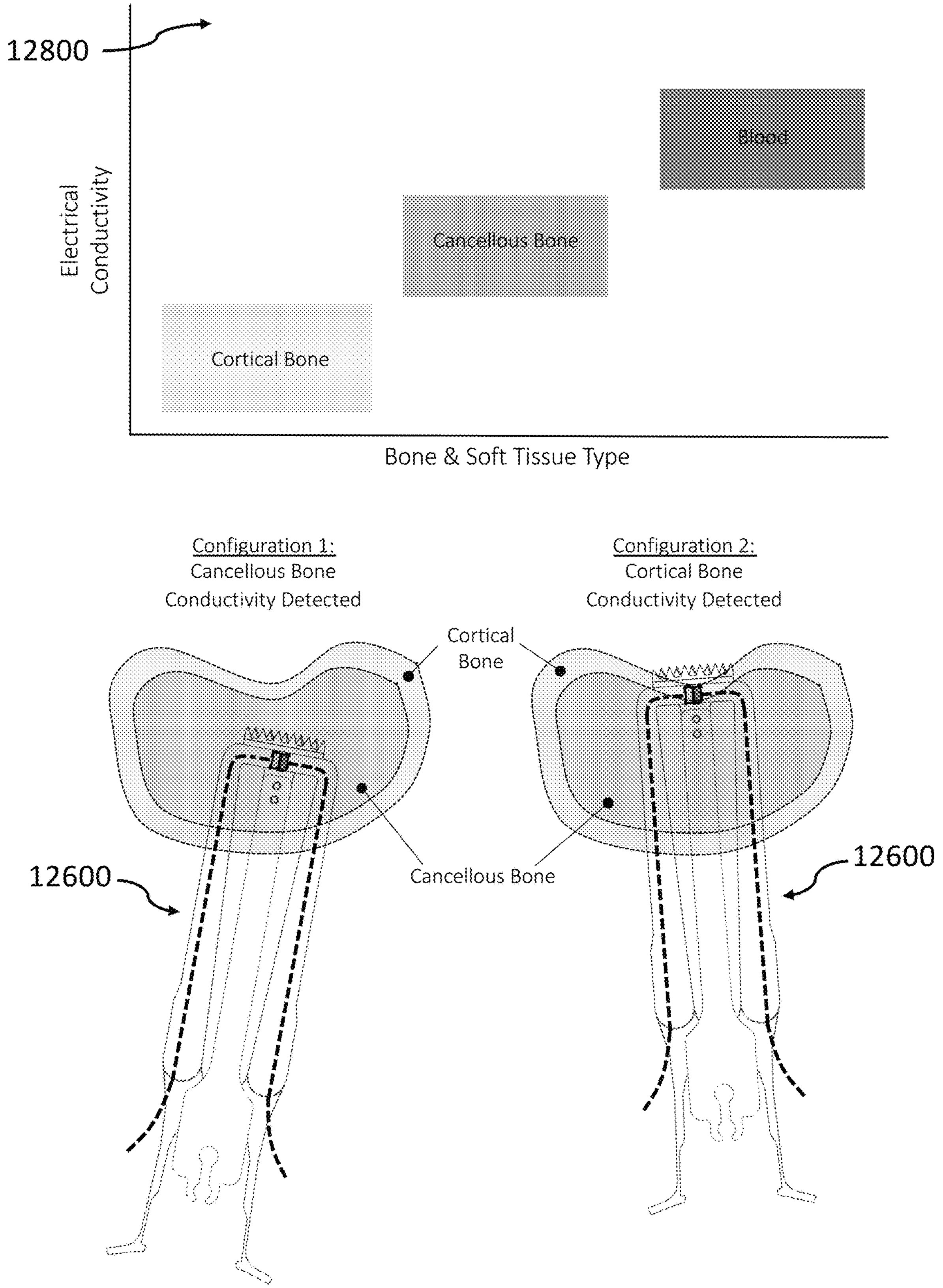
Figure 129:
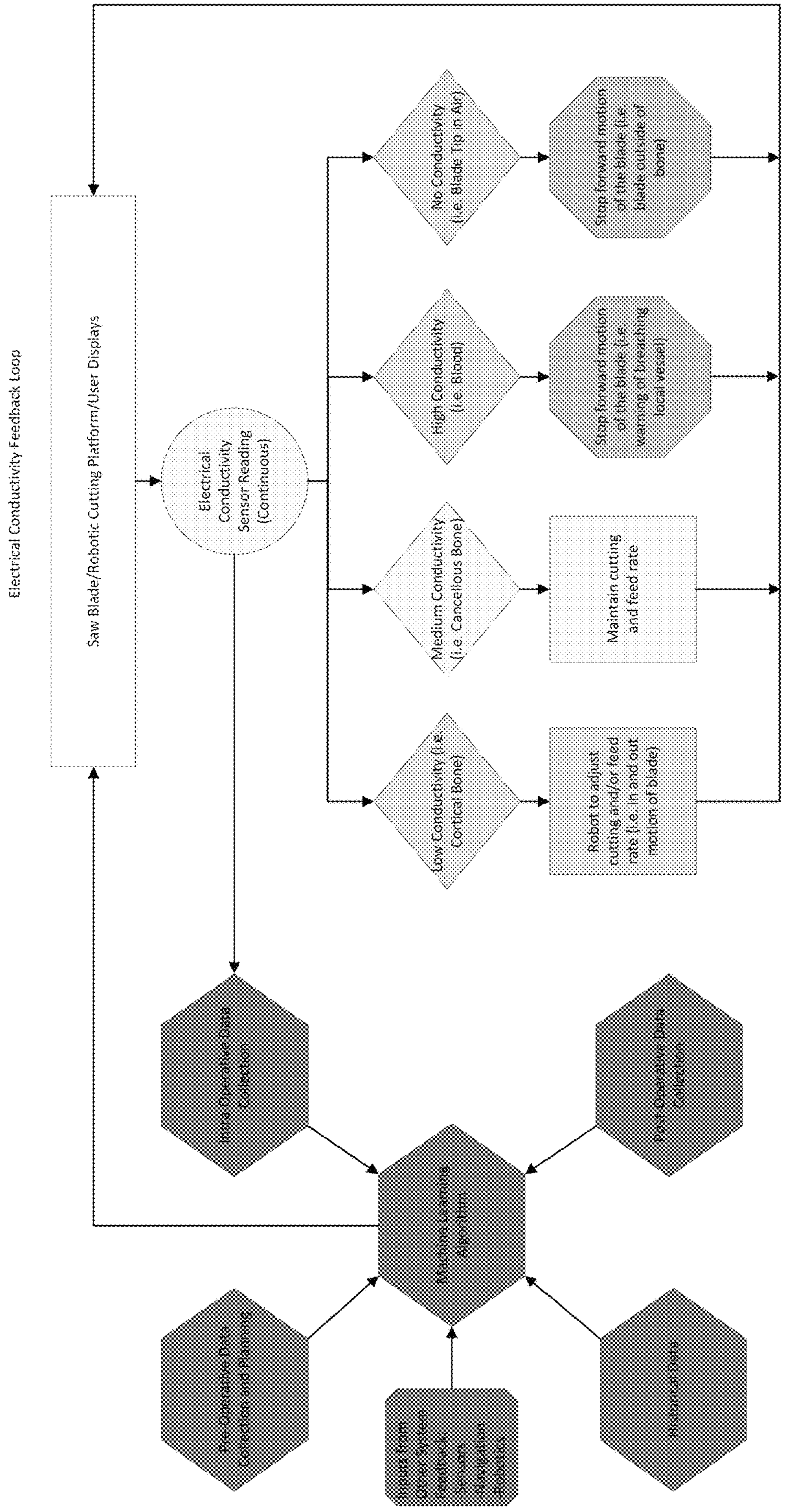
Figure 130:
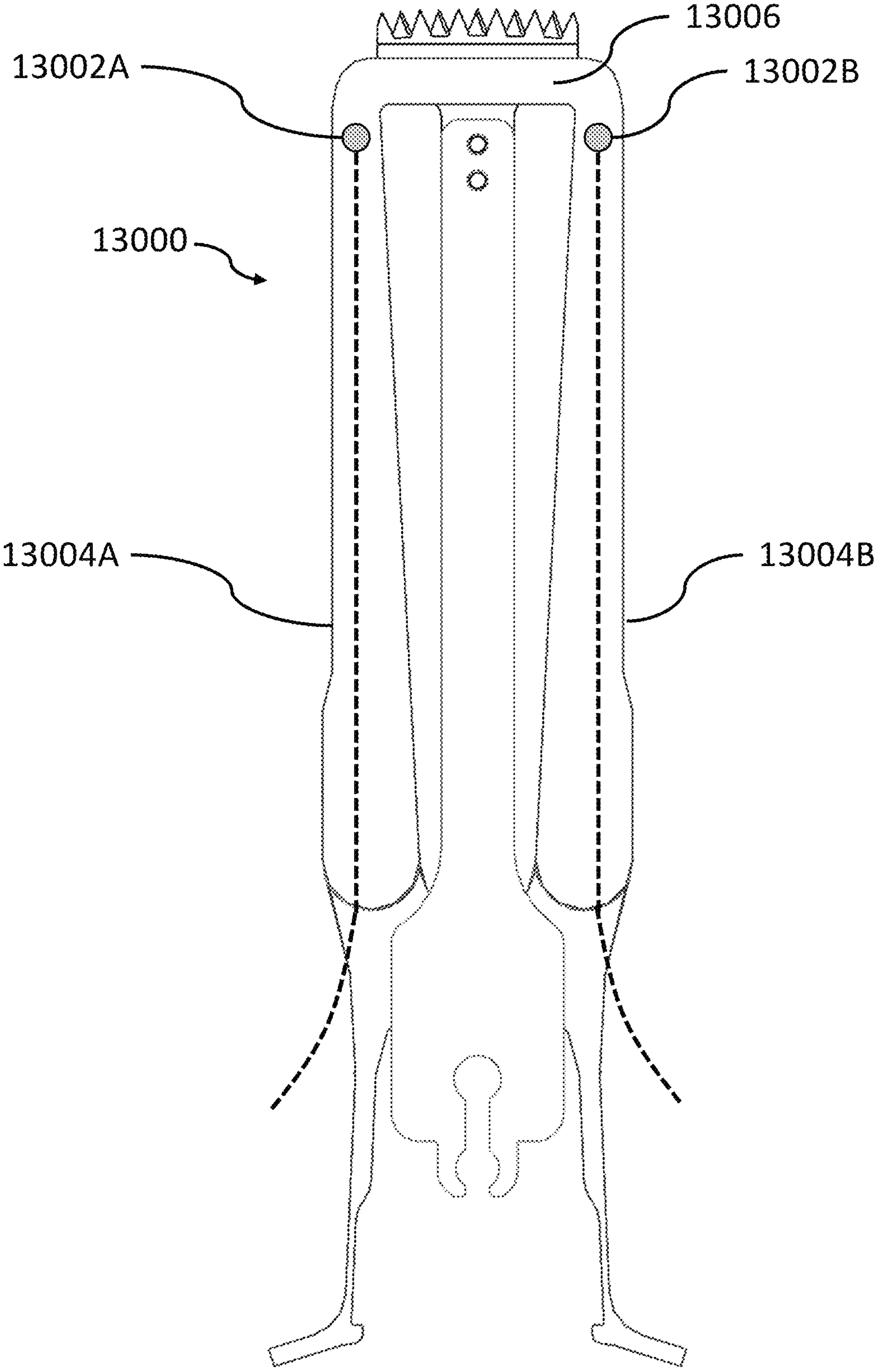
Figure 131:
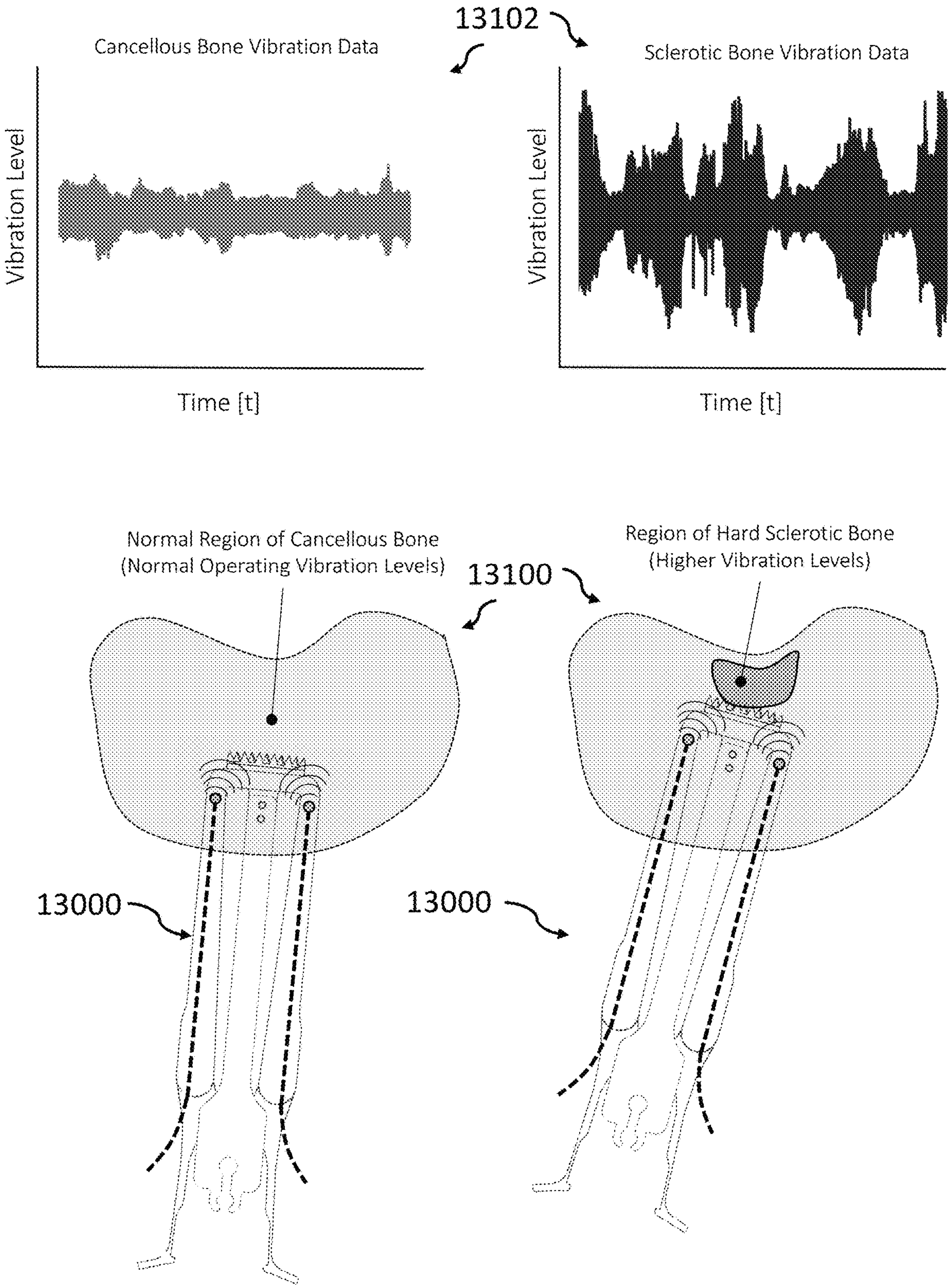
Figure 132:
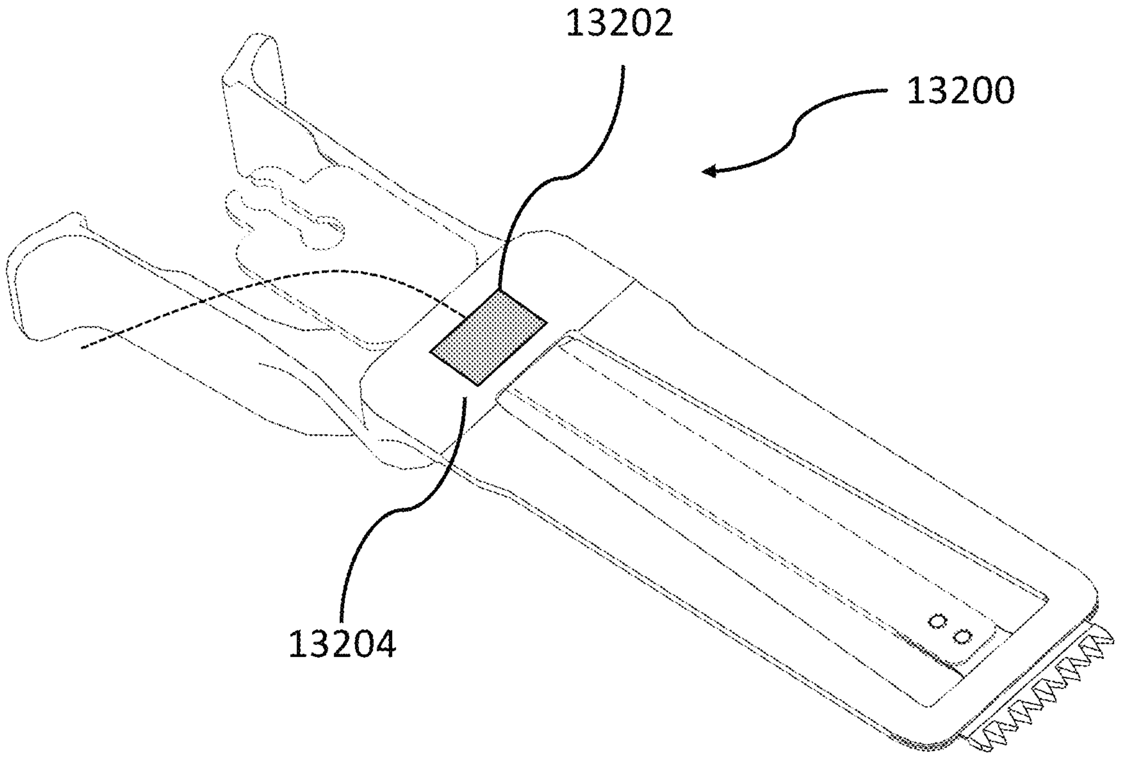
Figure 133:
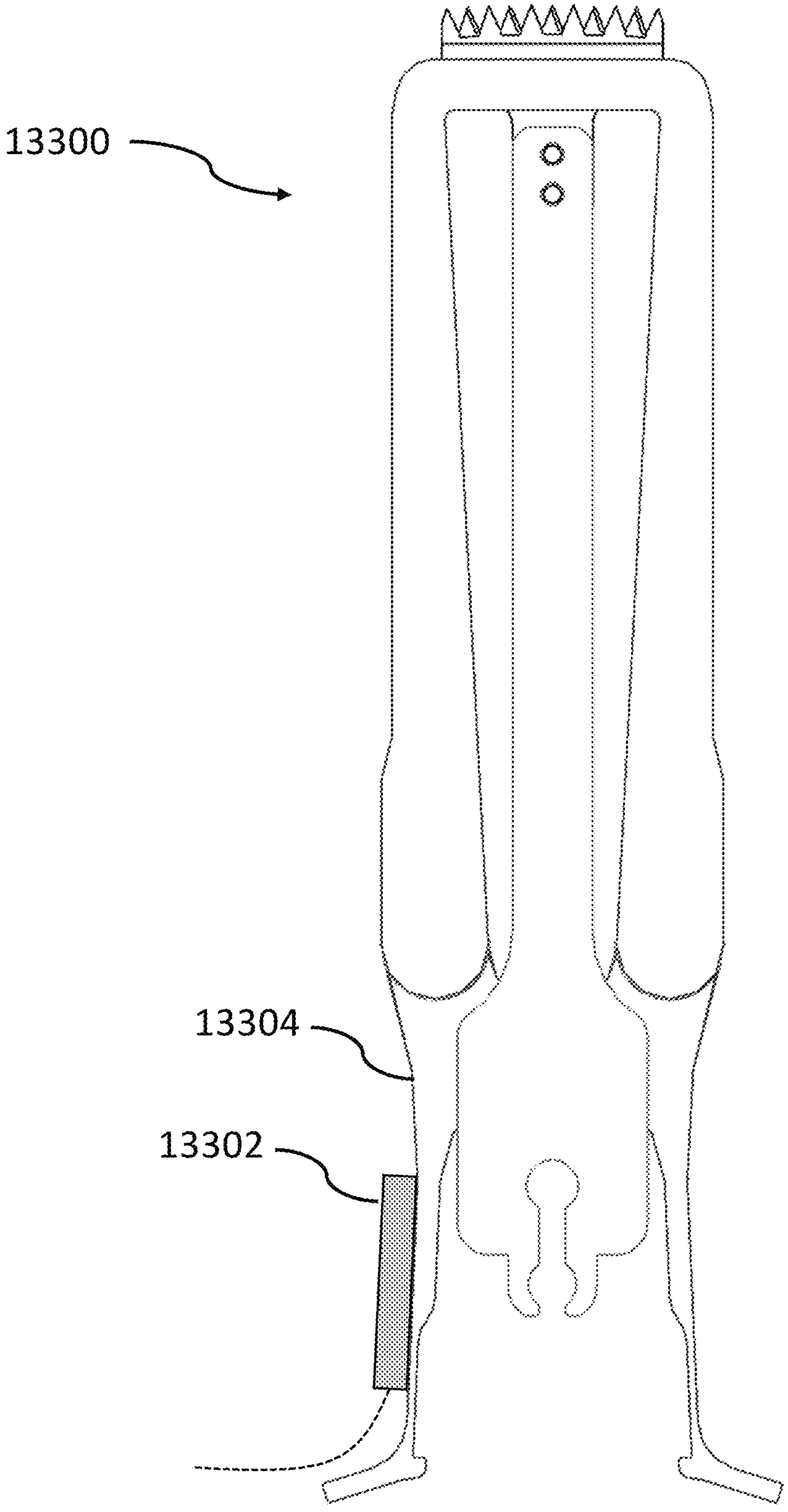
Figure 134:
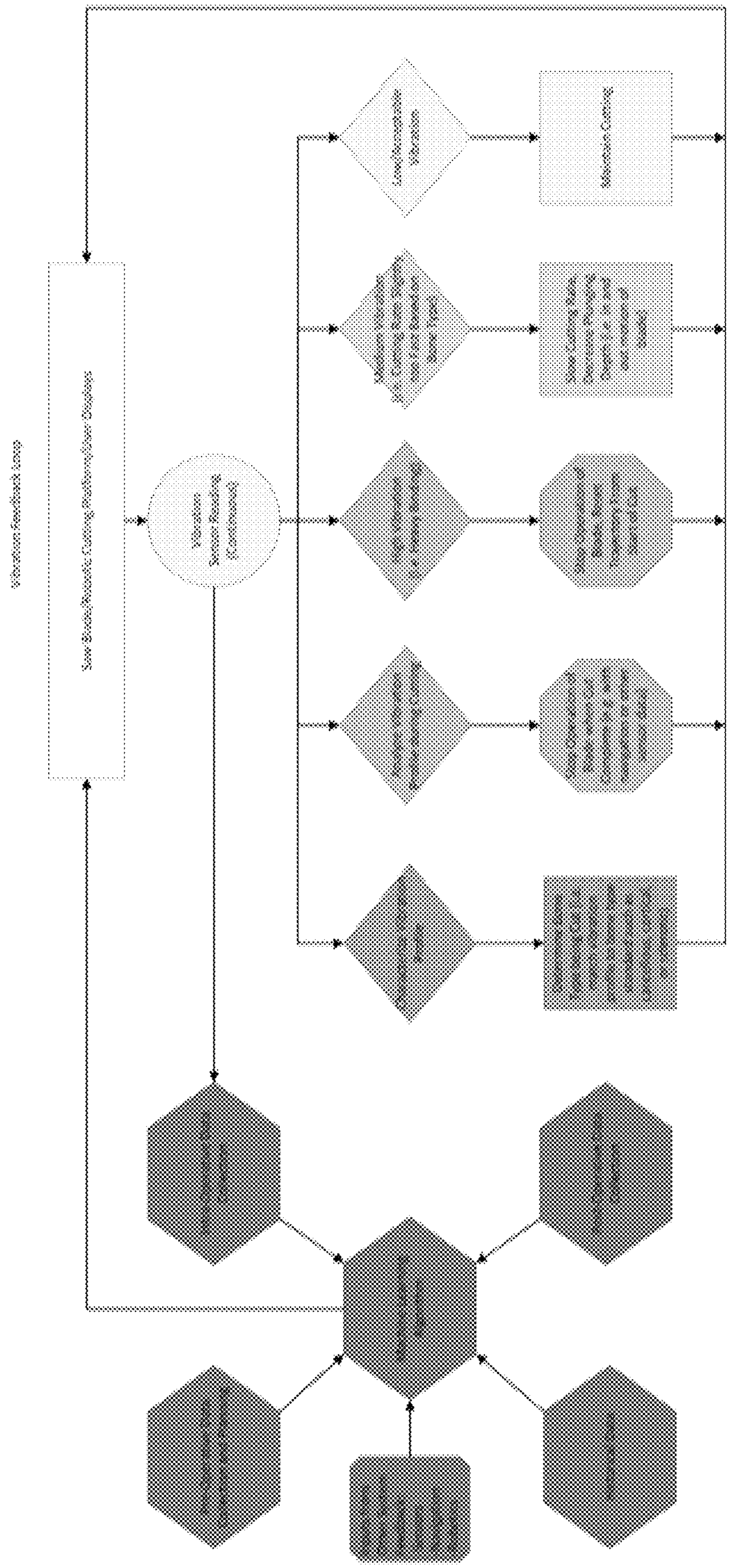
Figure 135:
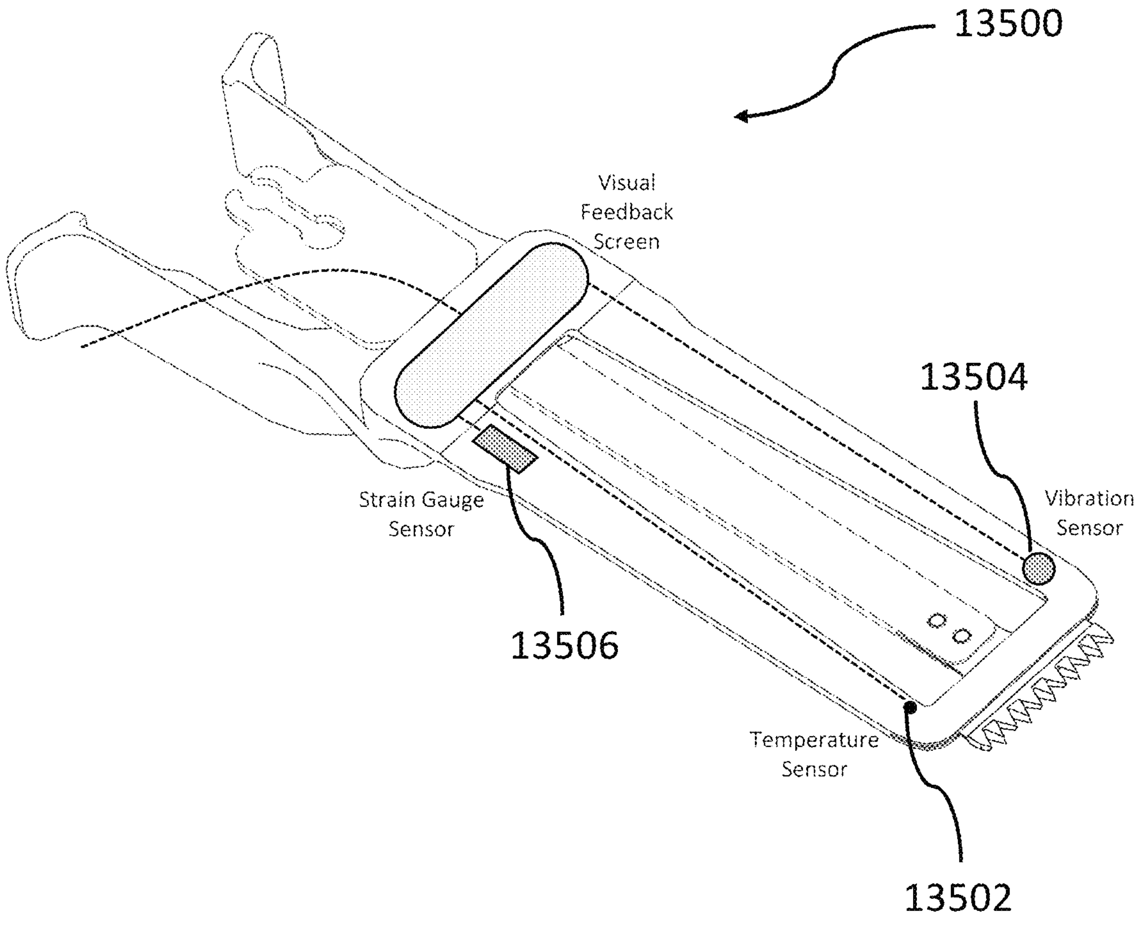
Figure 136:
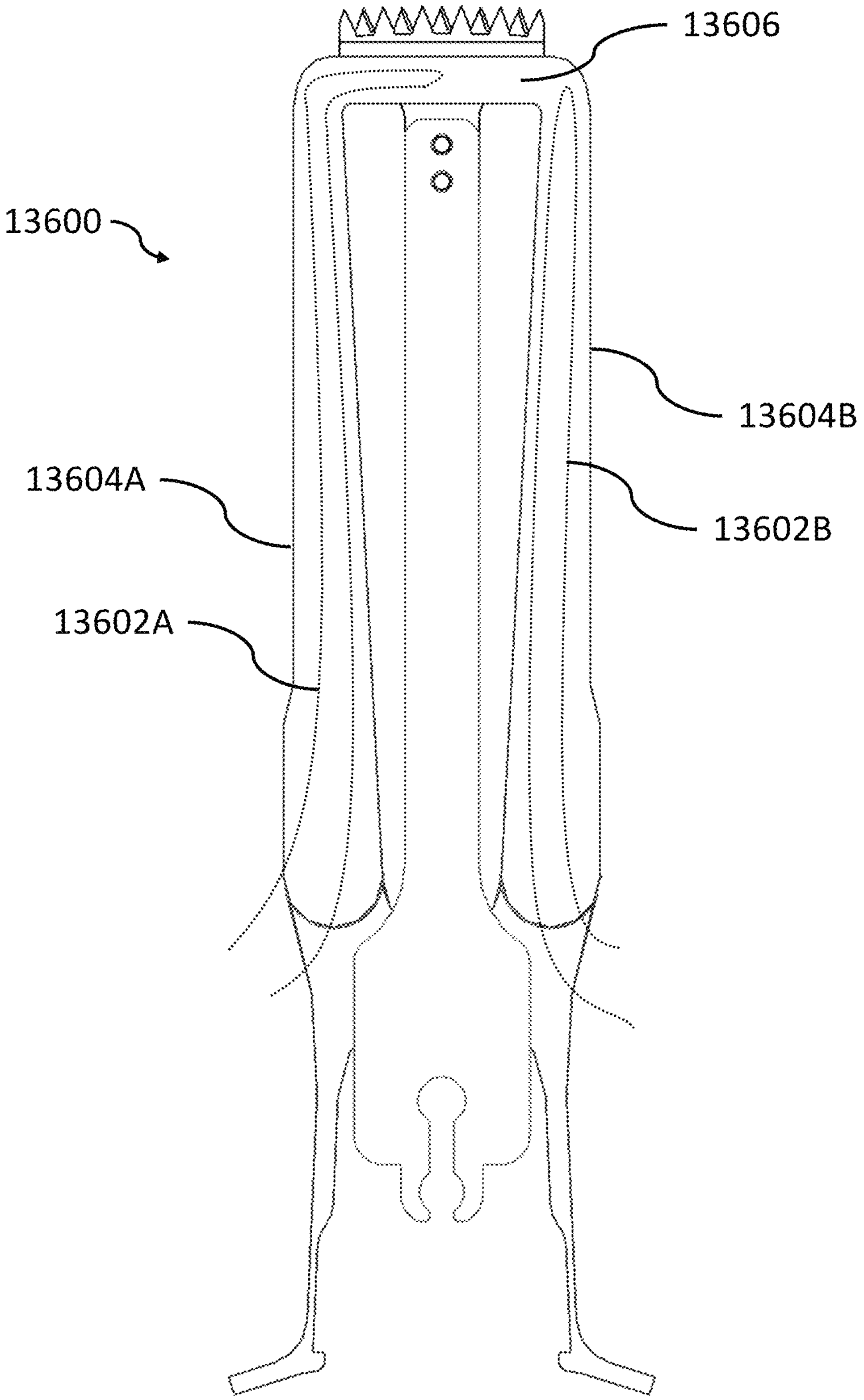
Figure 137:
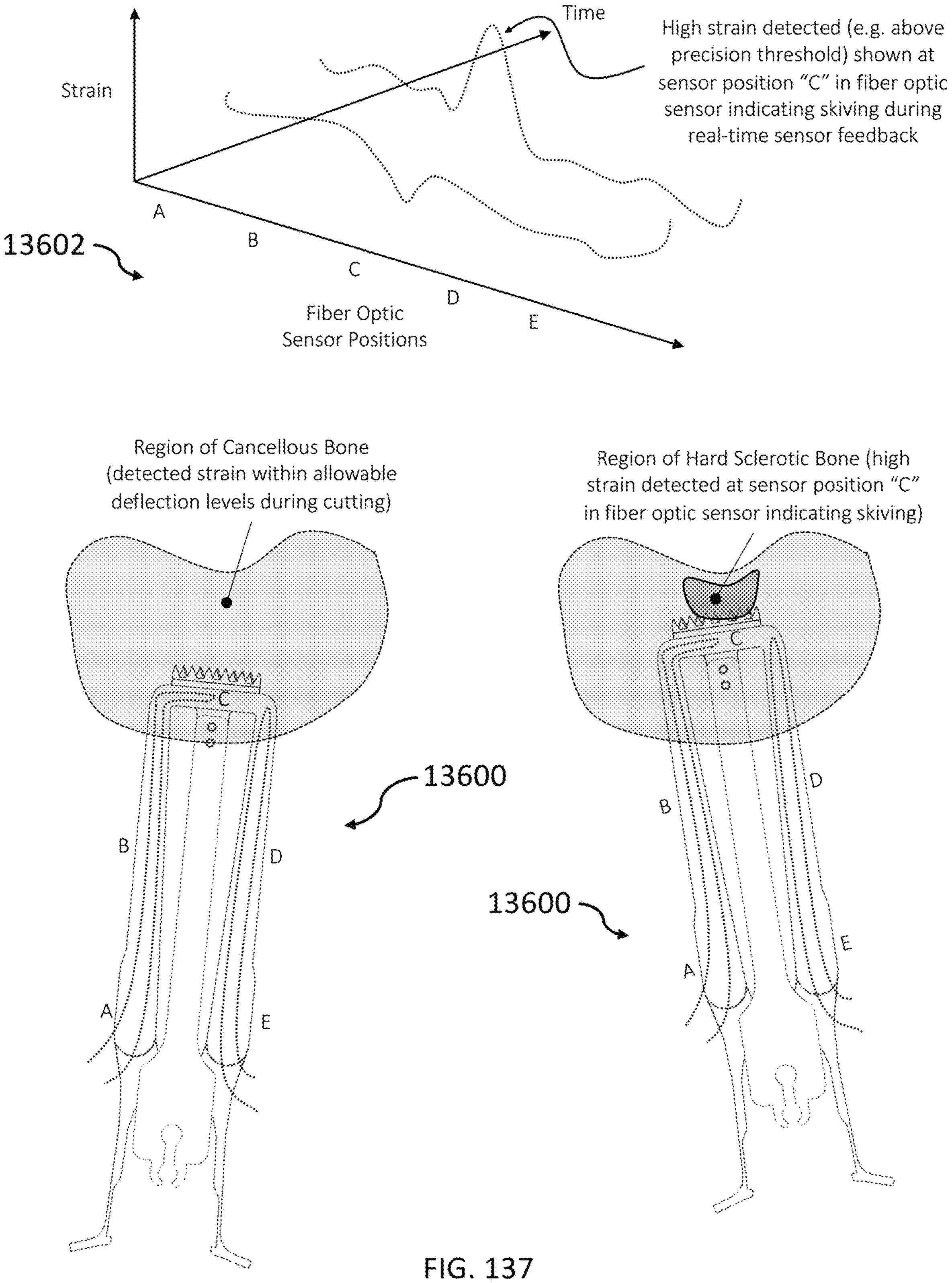
Figure 138:
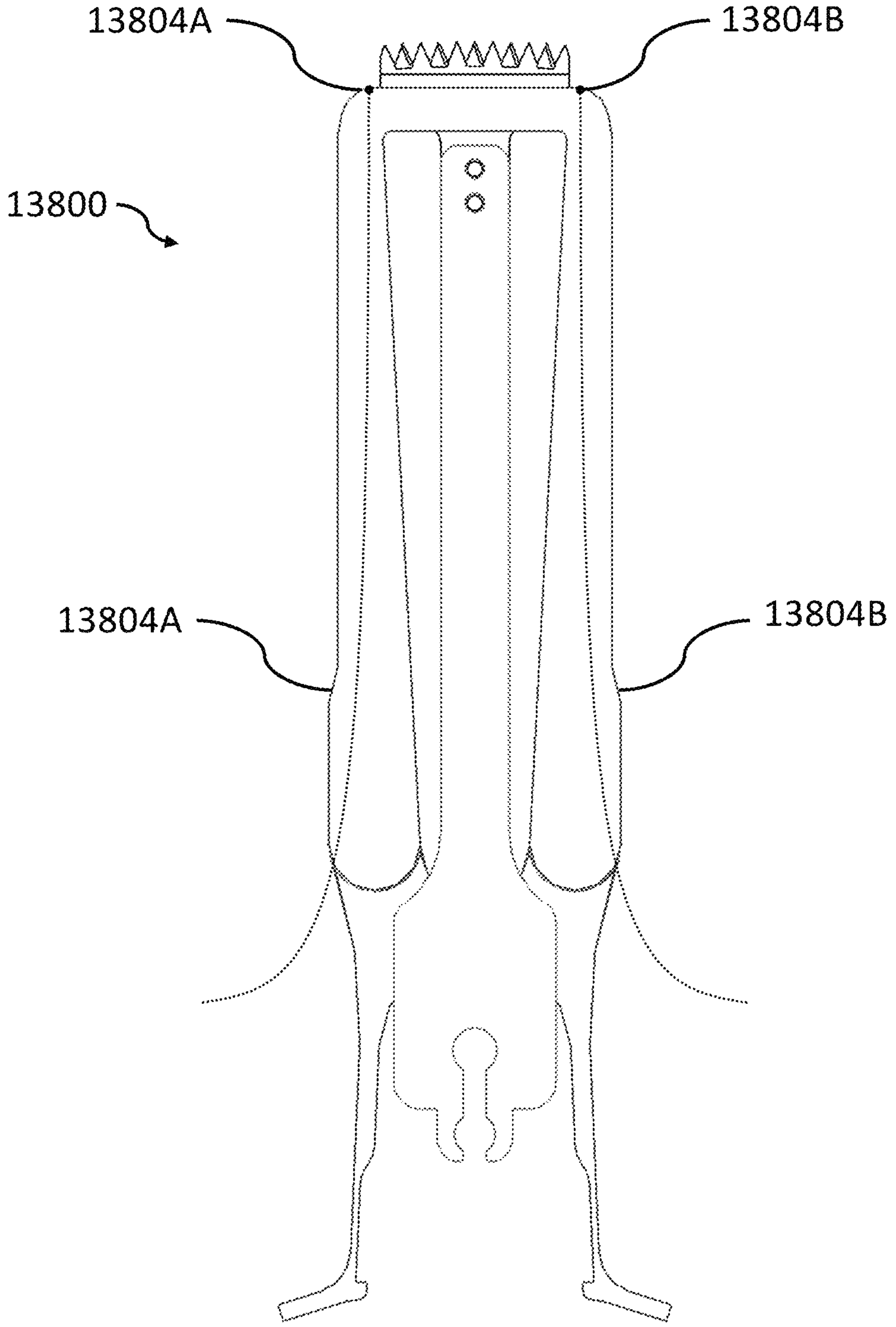
Figure 139:
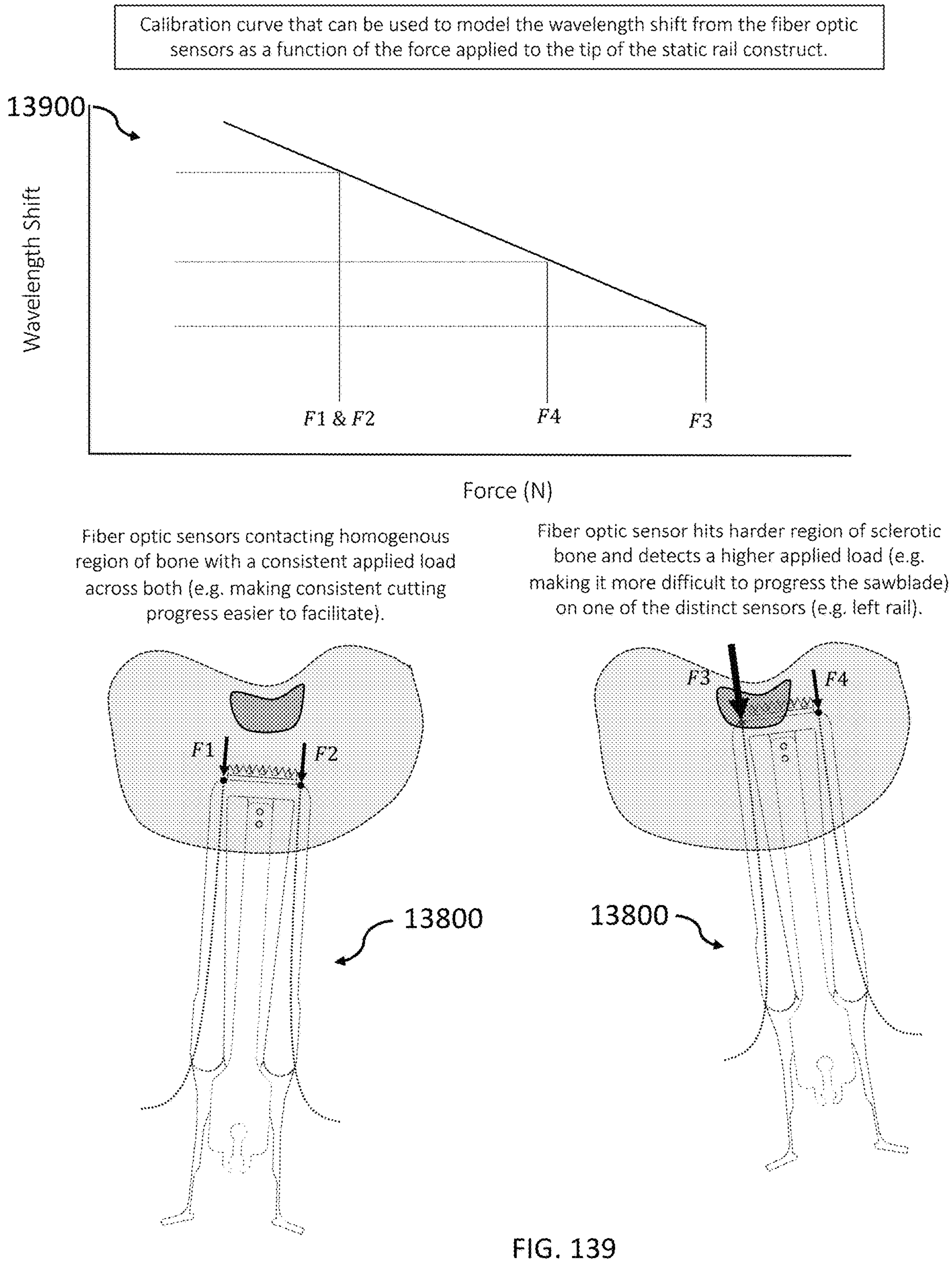
Figure 140:
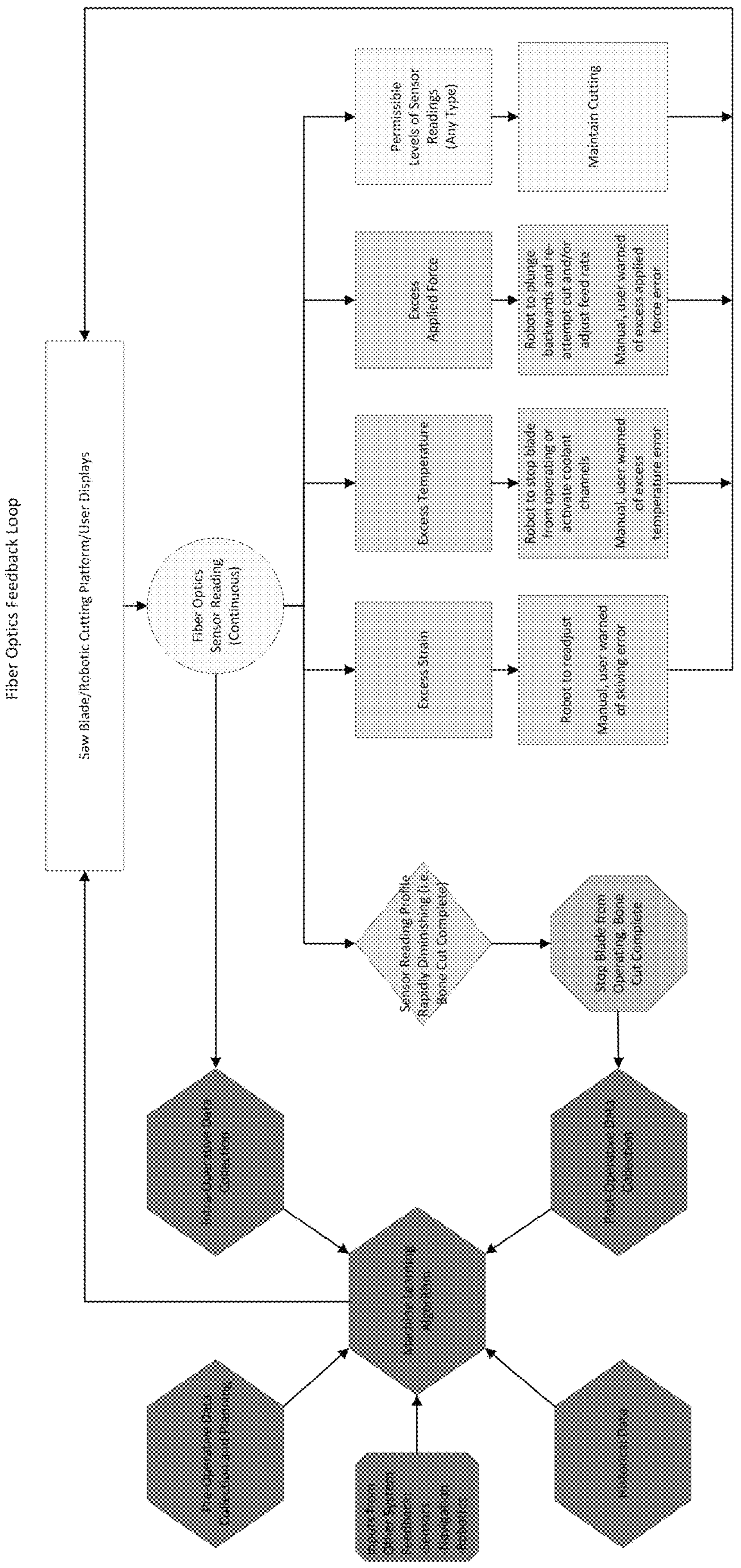
Figure 141:
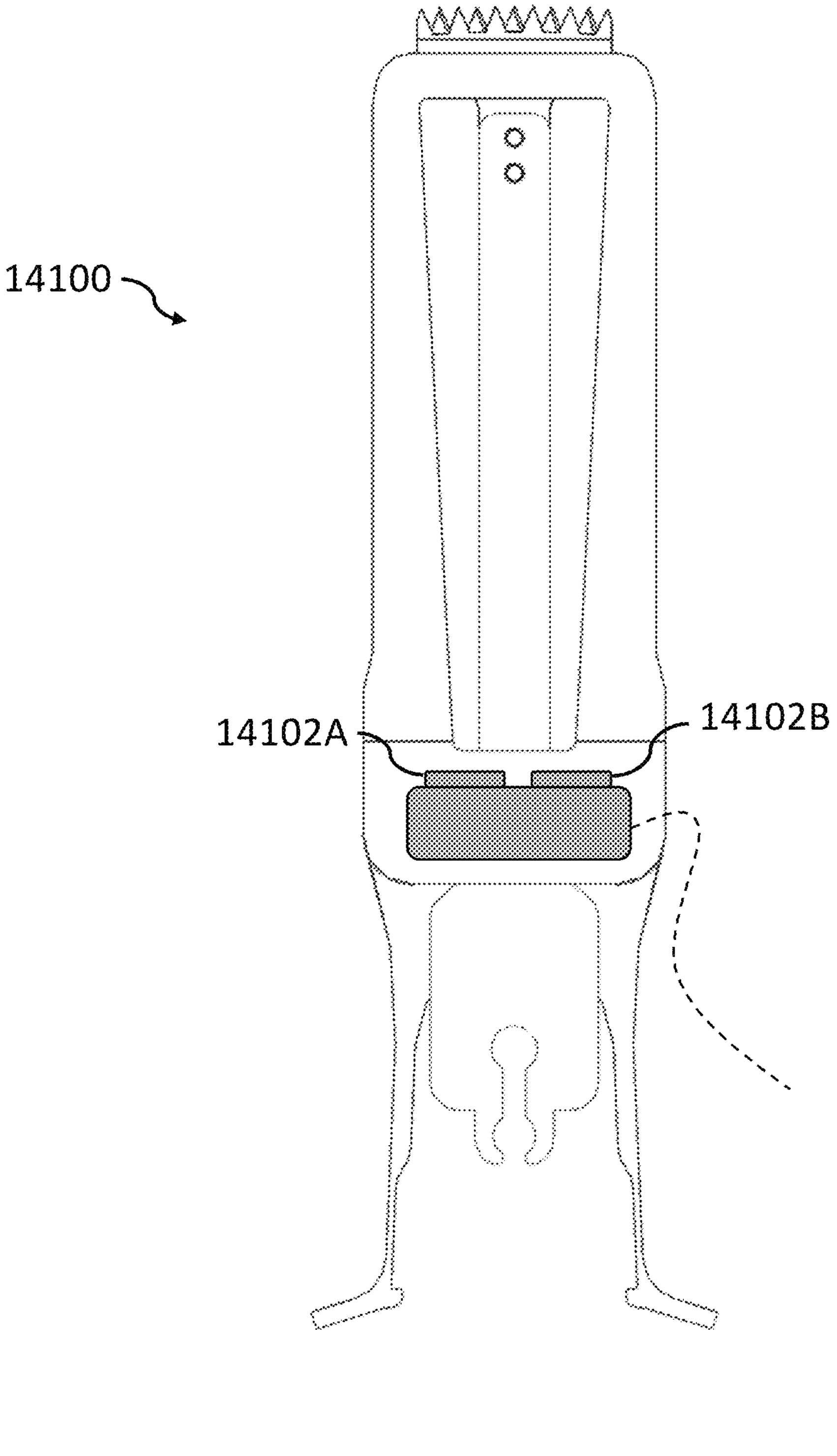
Figure 142A:
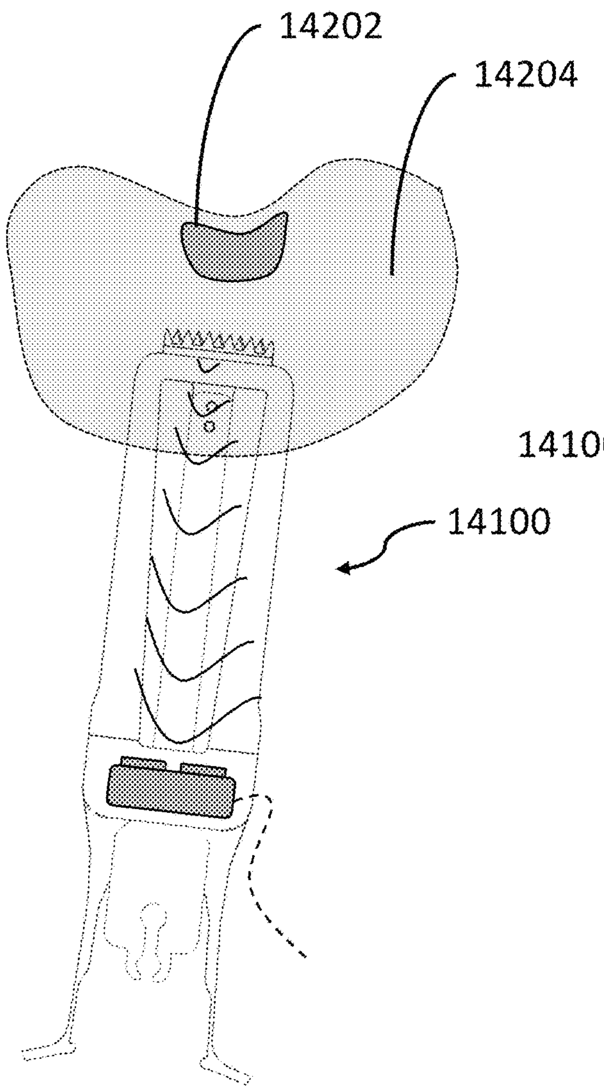
Figure 142B:
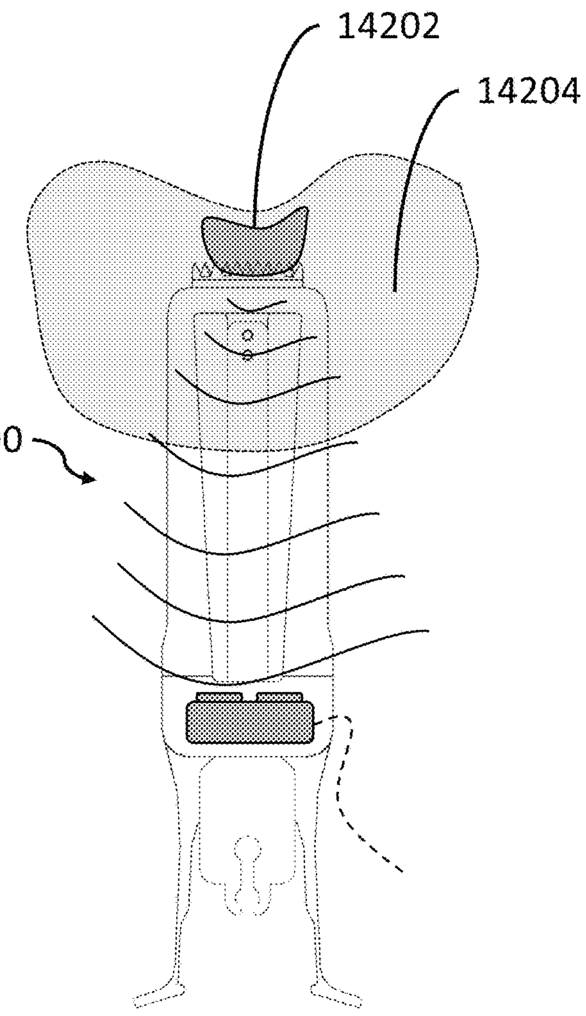
Figure 143A:
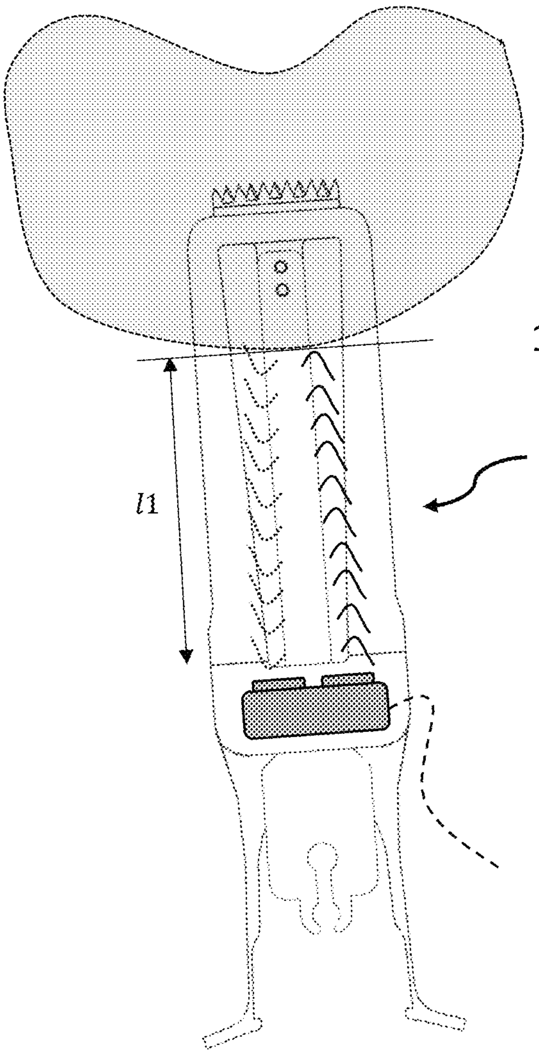
Figure 143B:
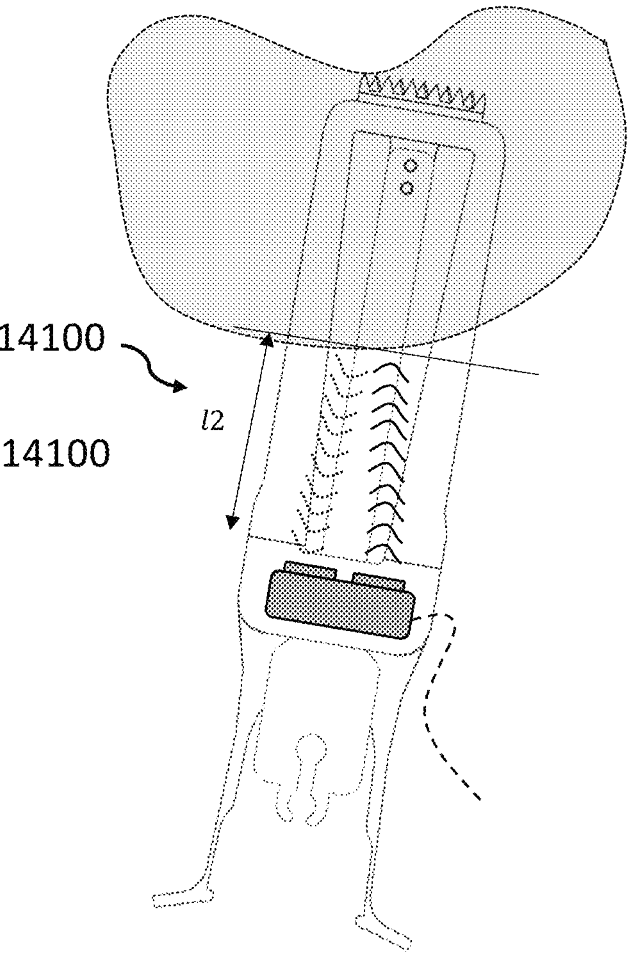
Figure 144:
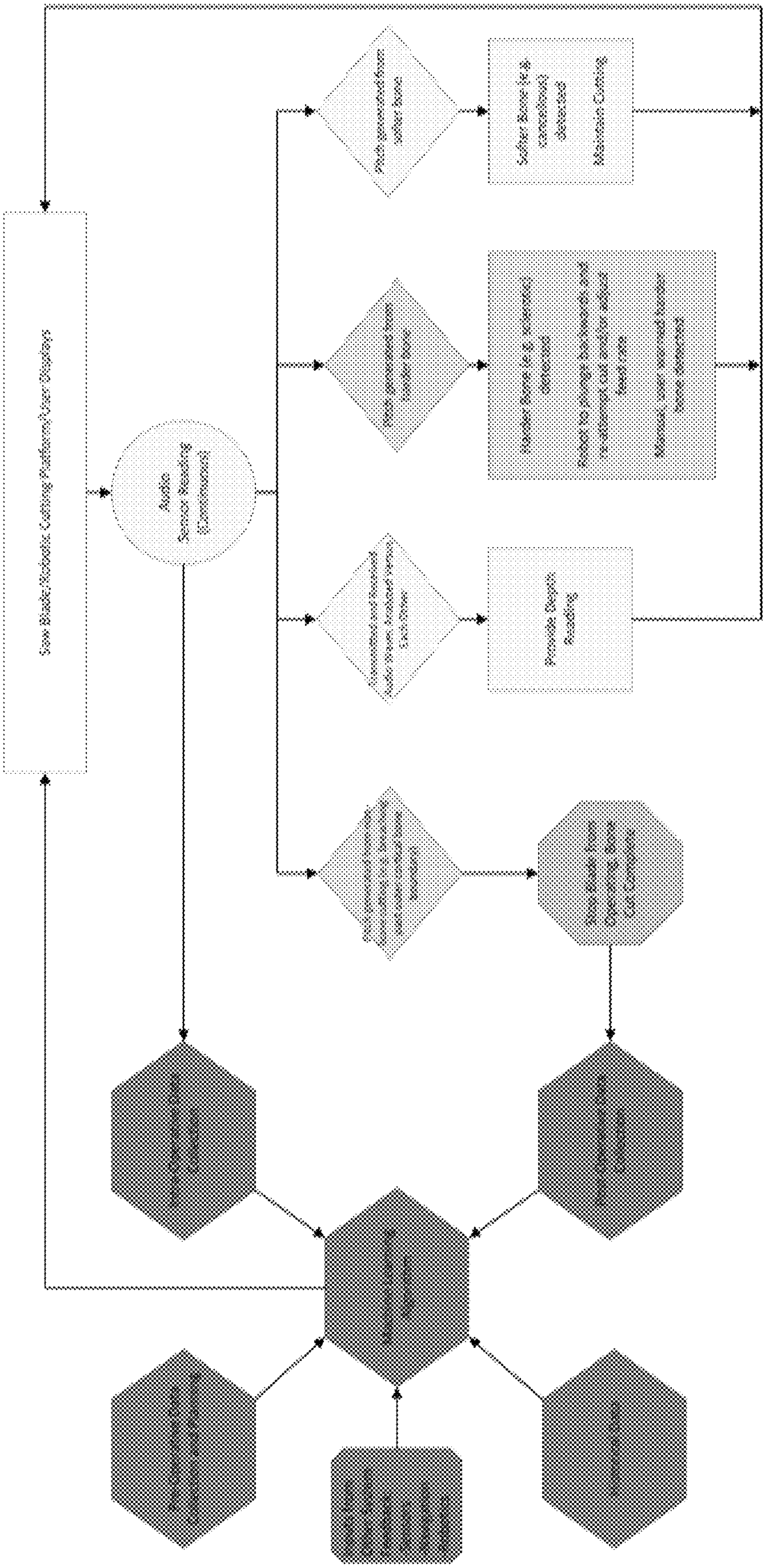
Figure 145:
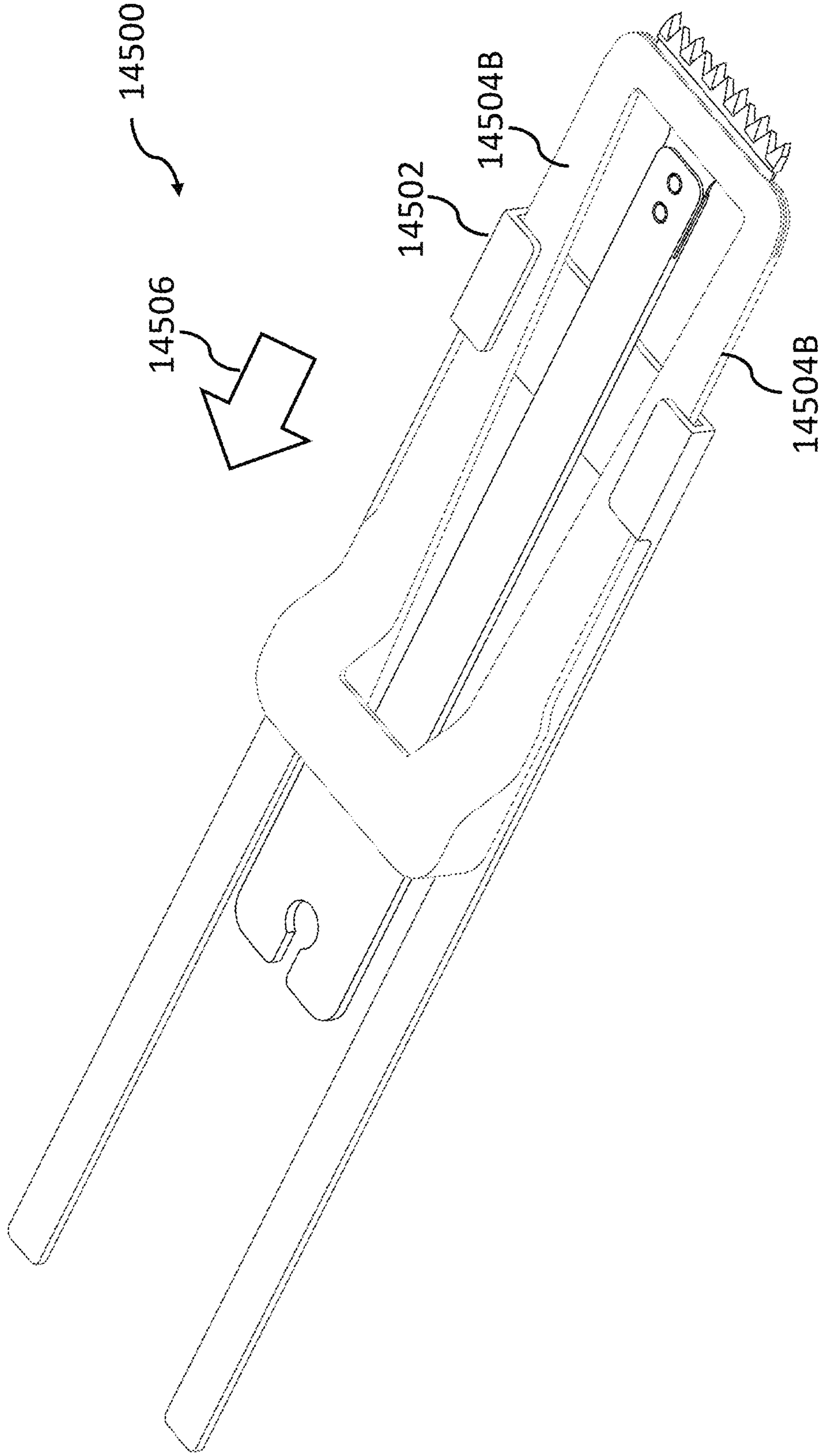
Figure 146A:
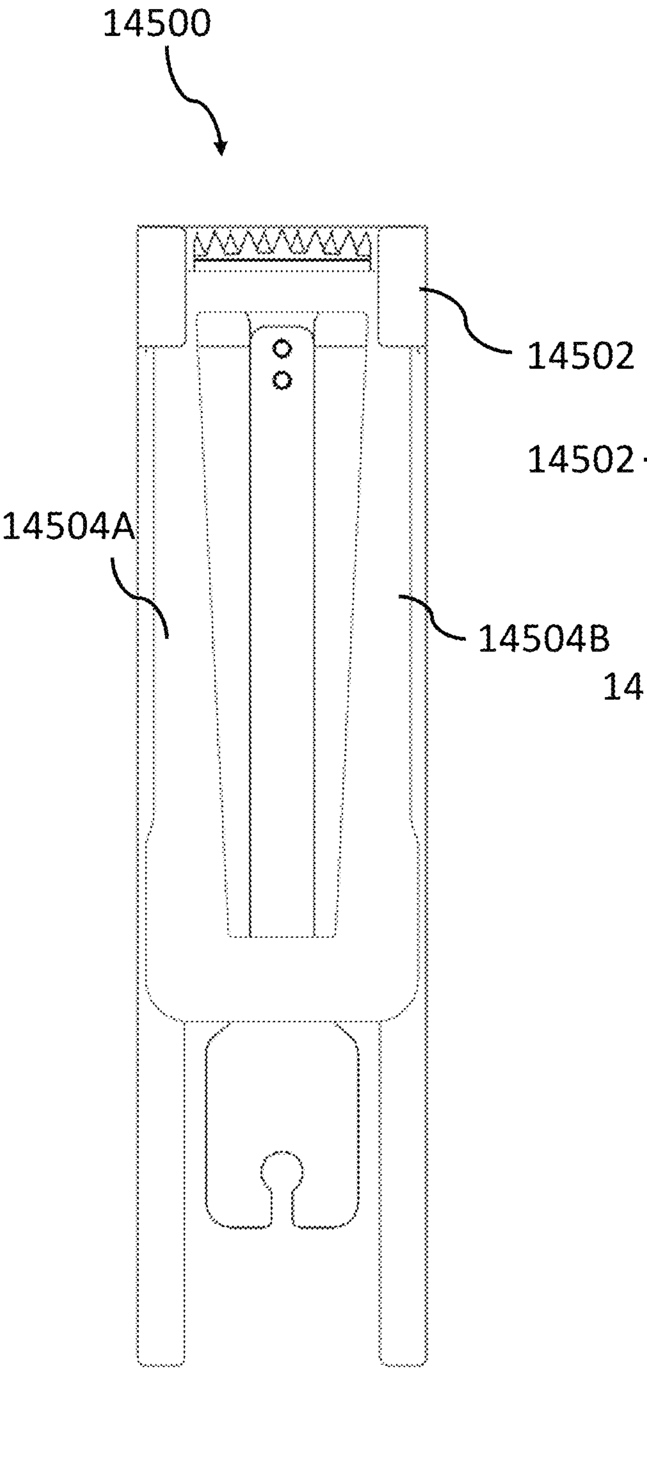
Figure 146B:
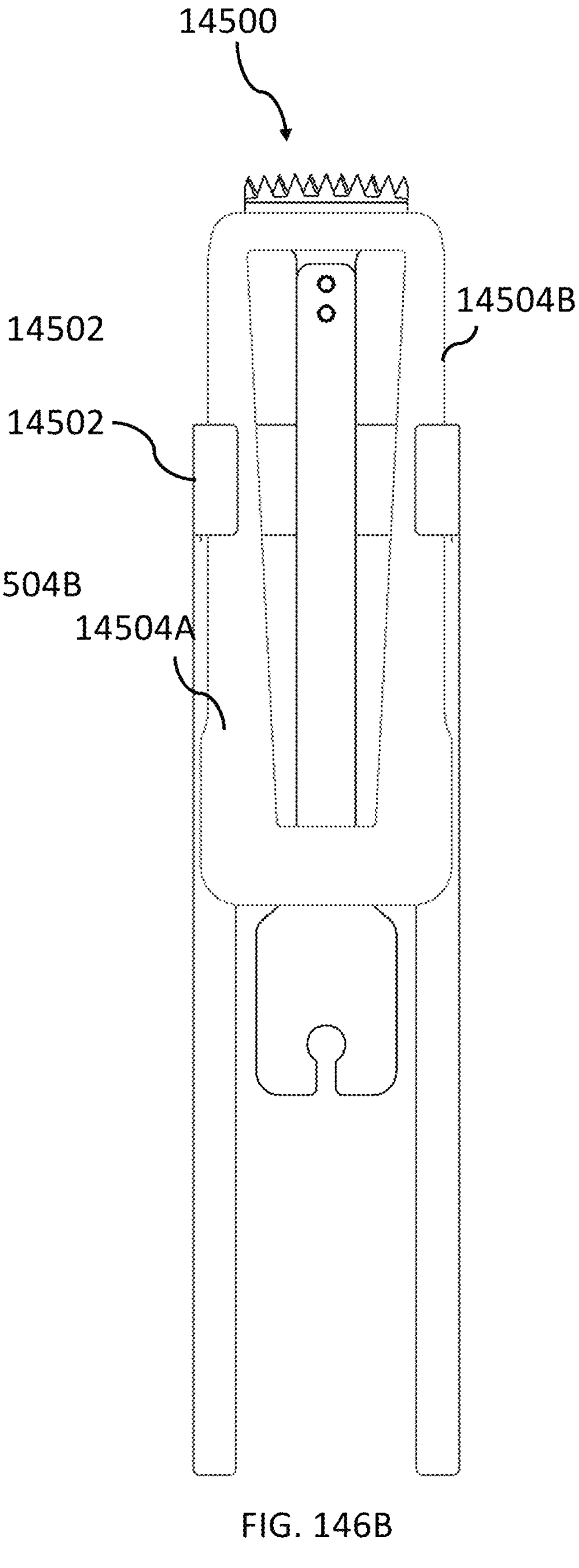
Figure 147:
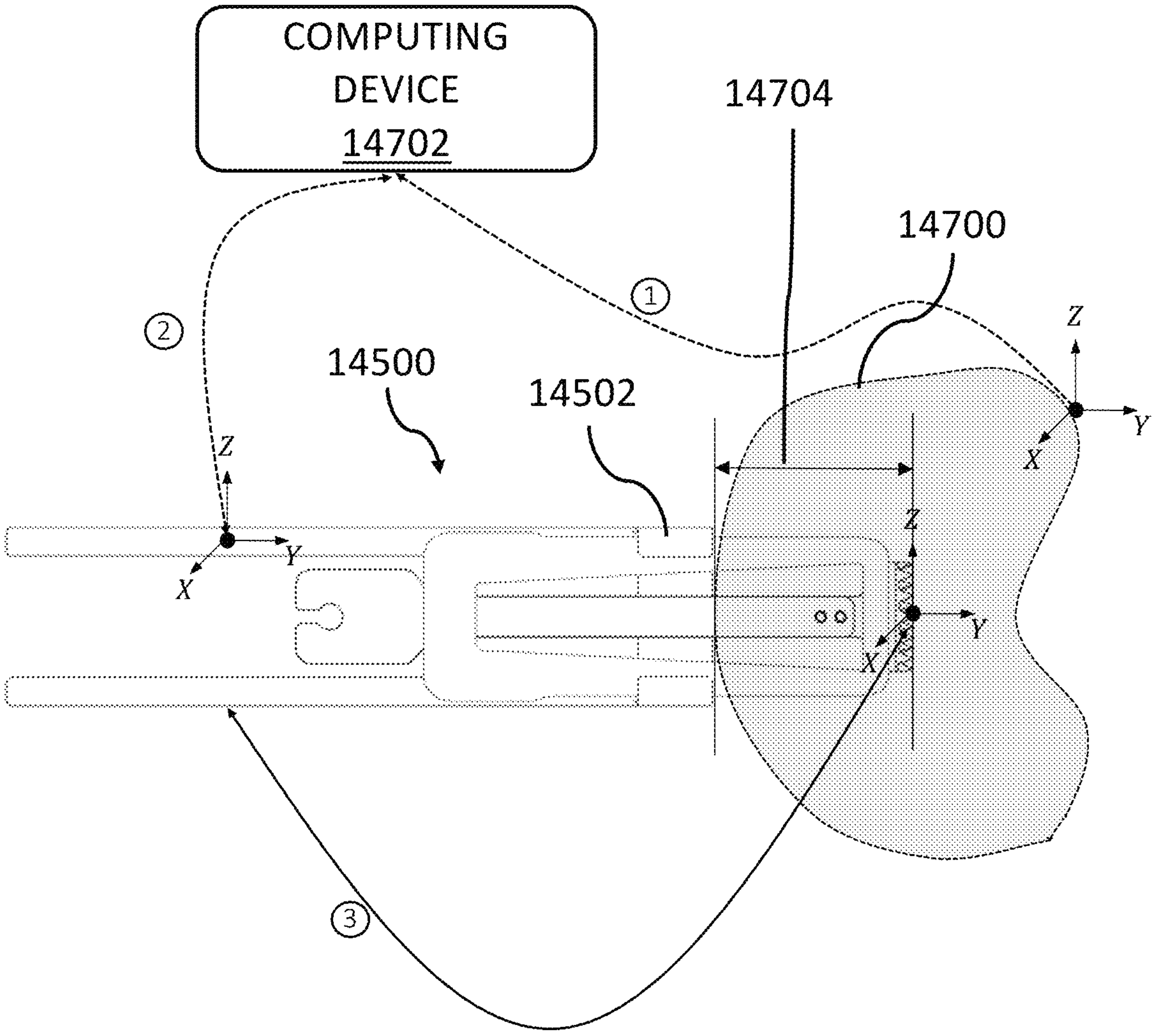
Figure 148A:
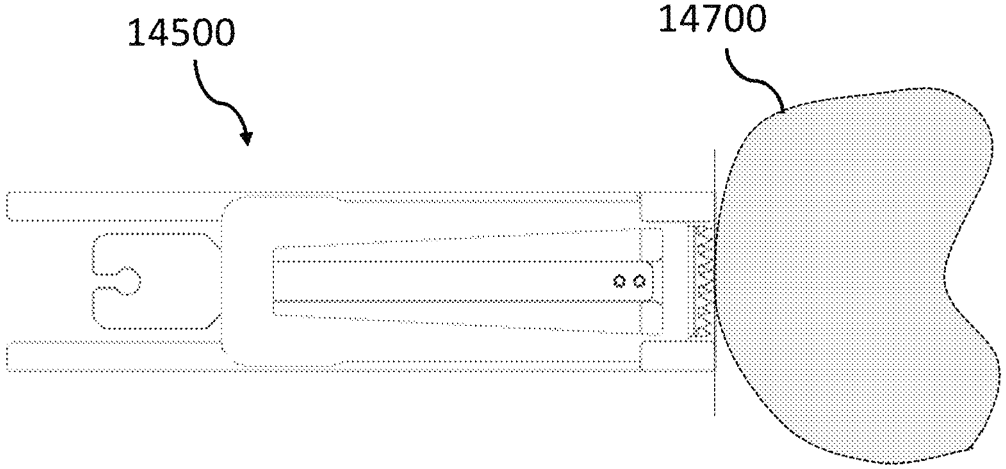
Figure 148B:
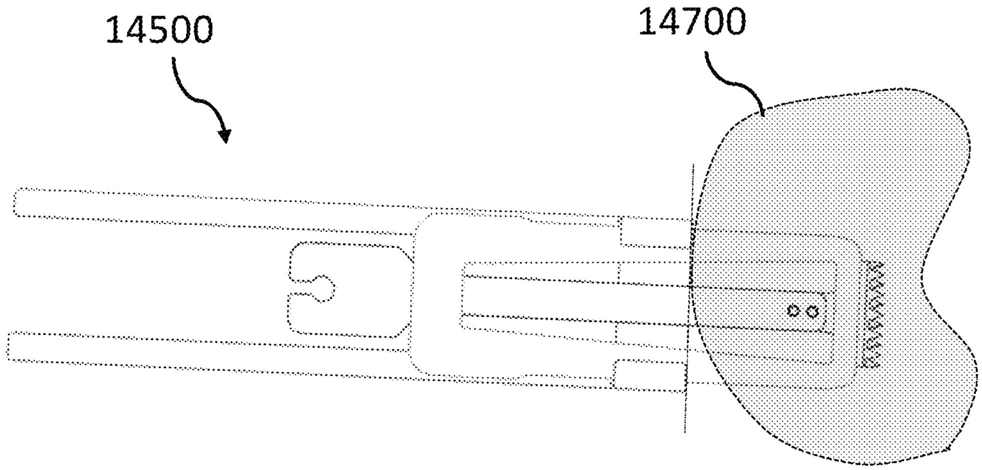
Figure 148C:
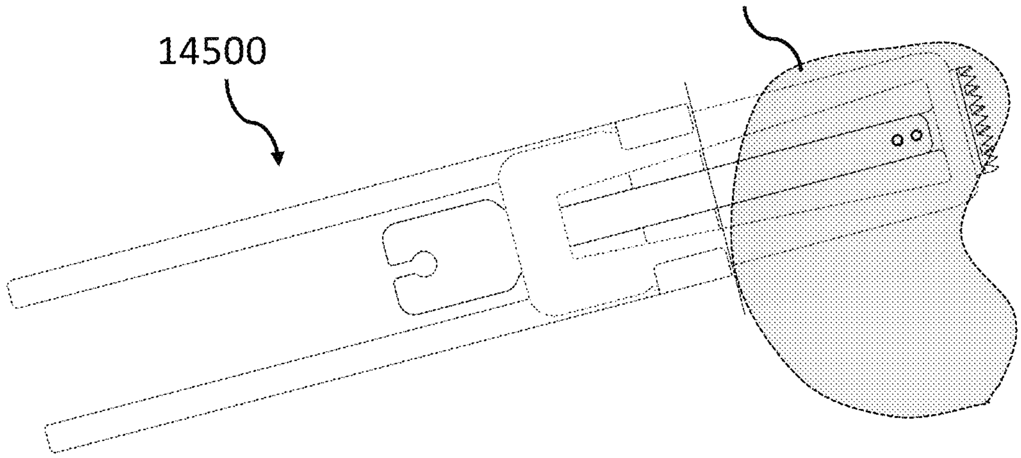
Figure 149:
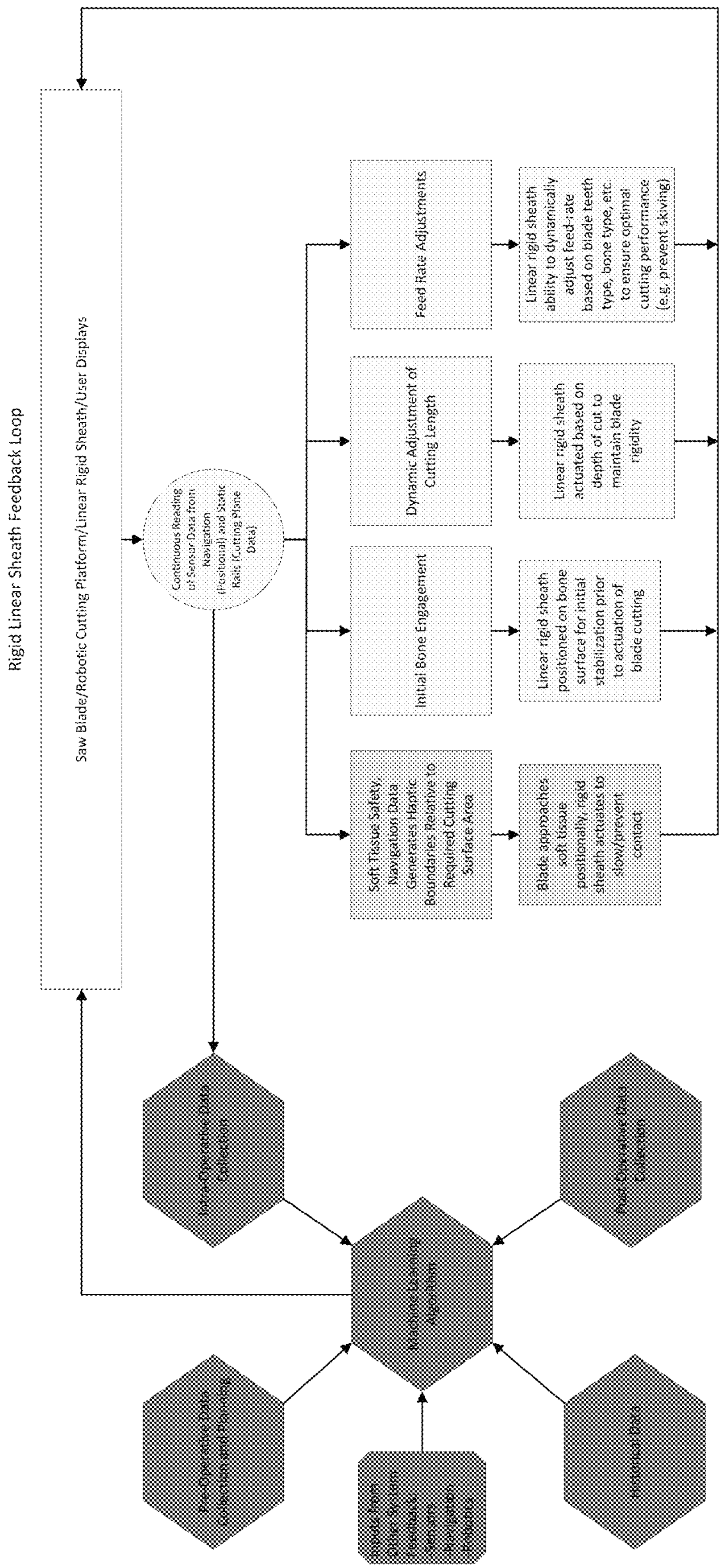
Figure 150:
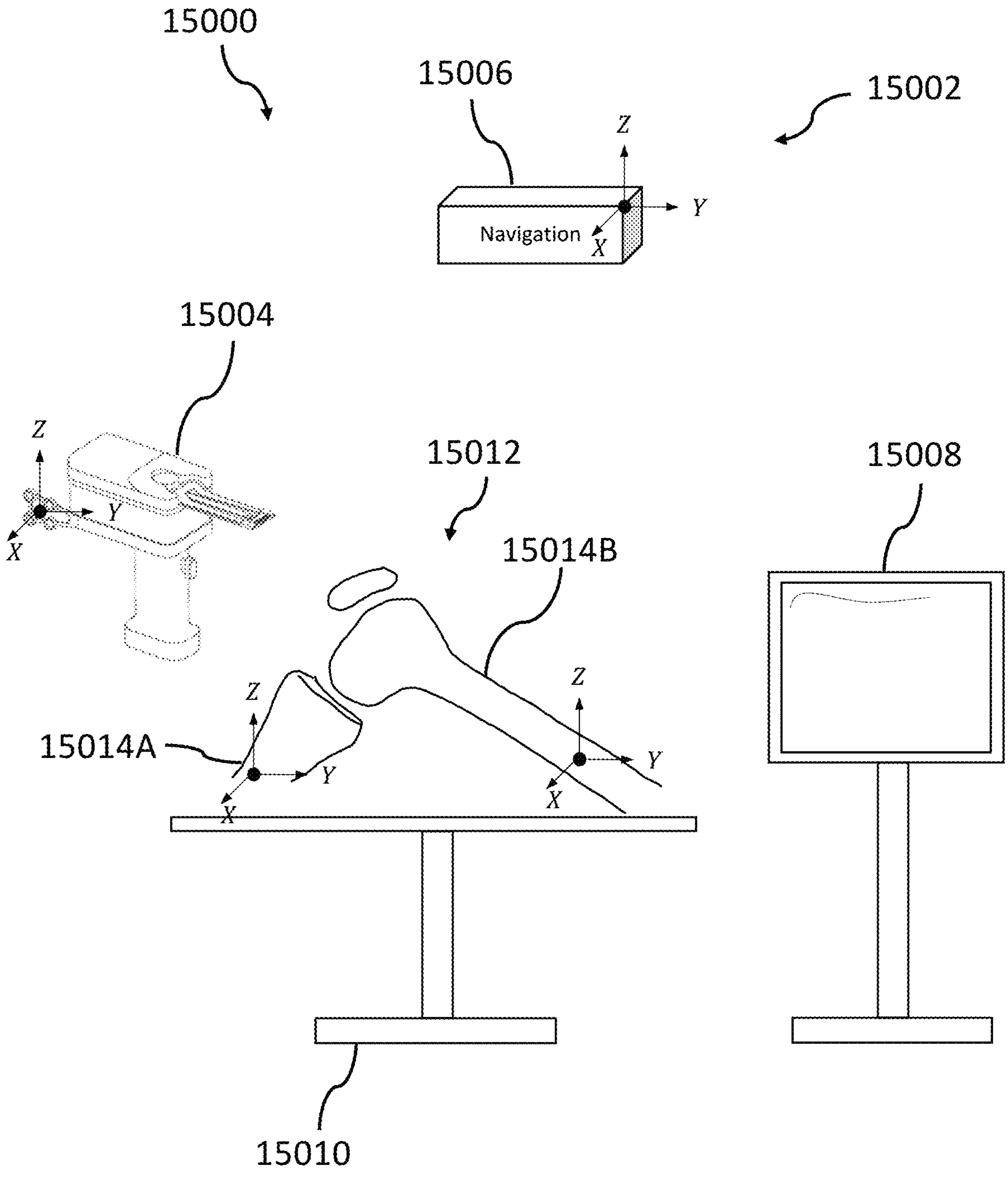
Figure 151:
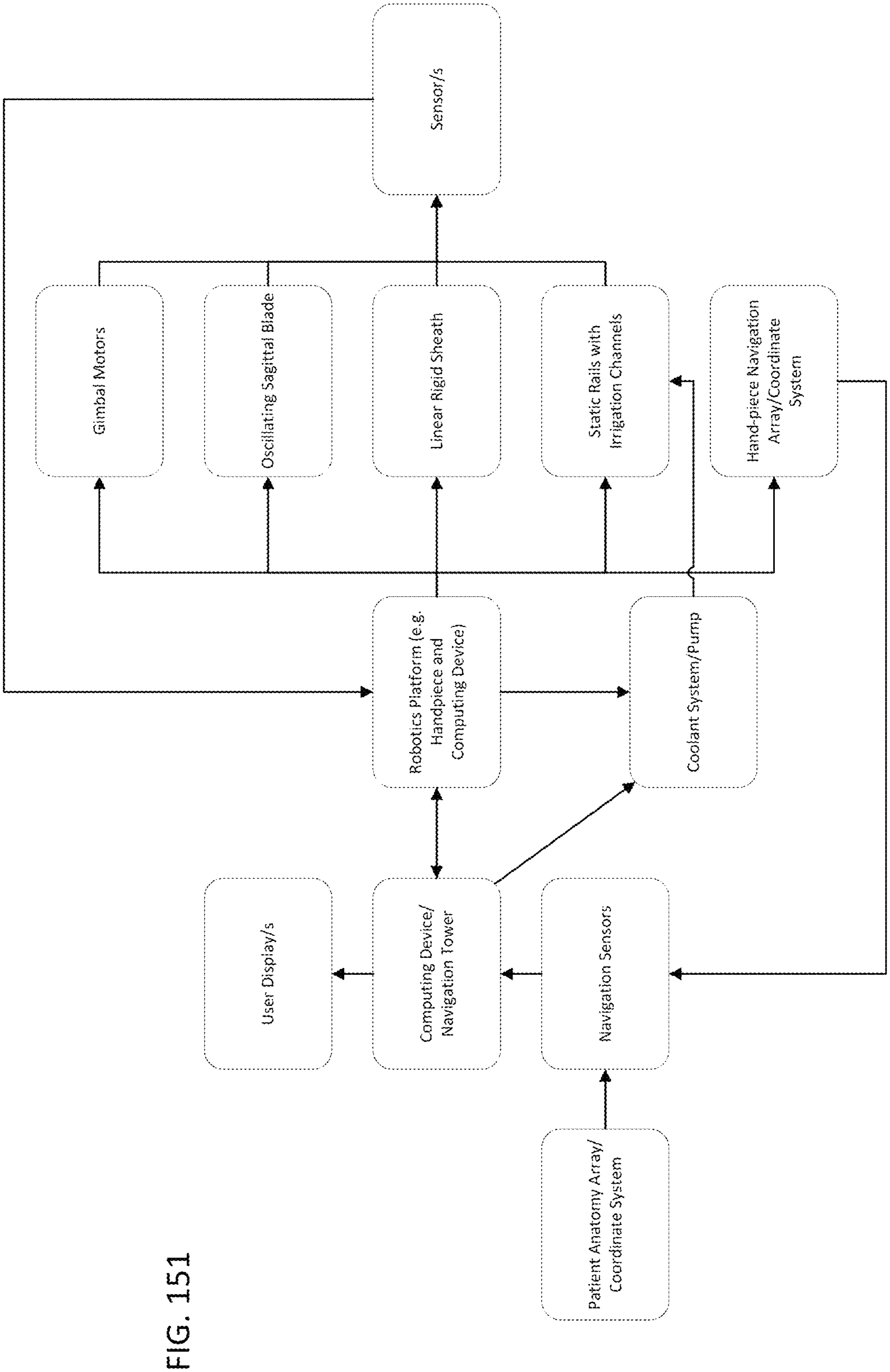
Figure 152:
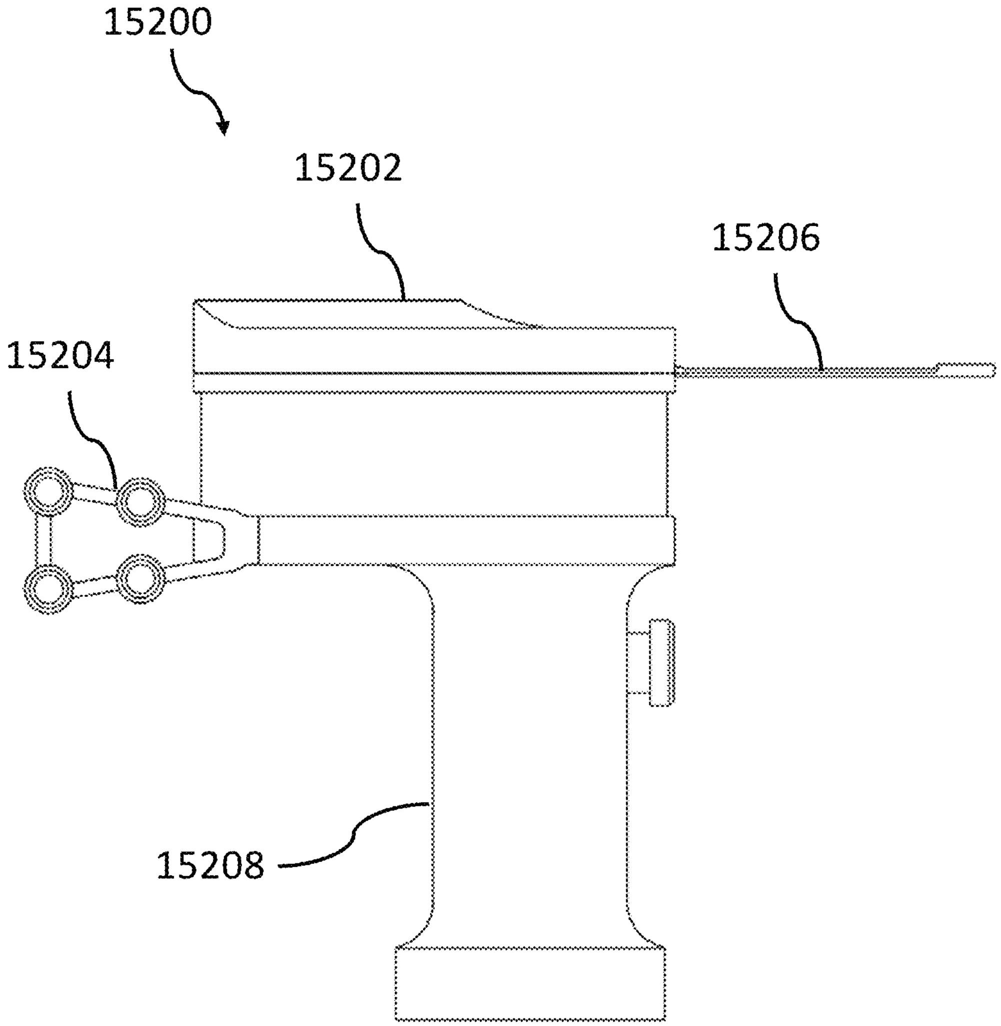
Figure 153:
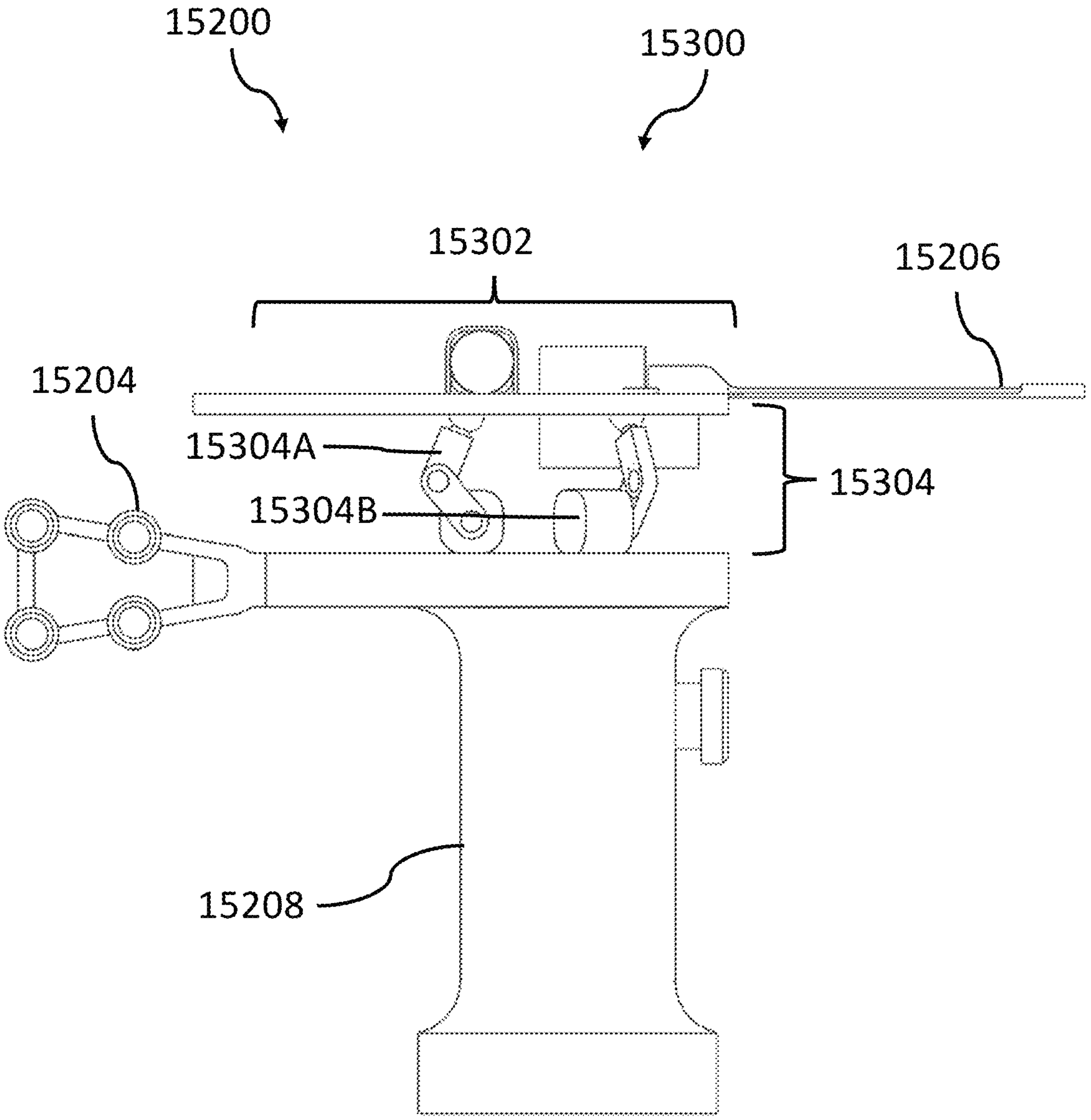
Figure 154:
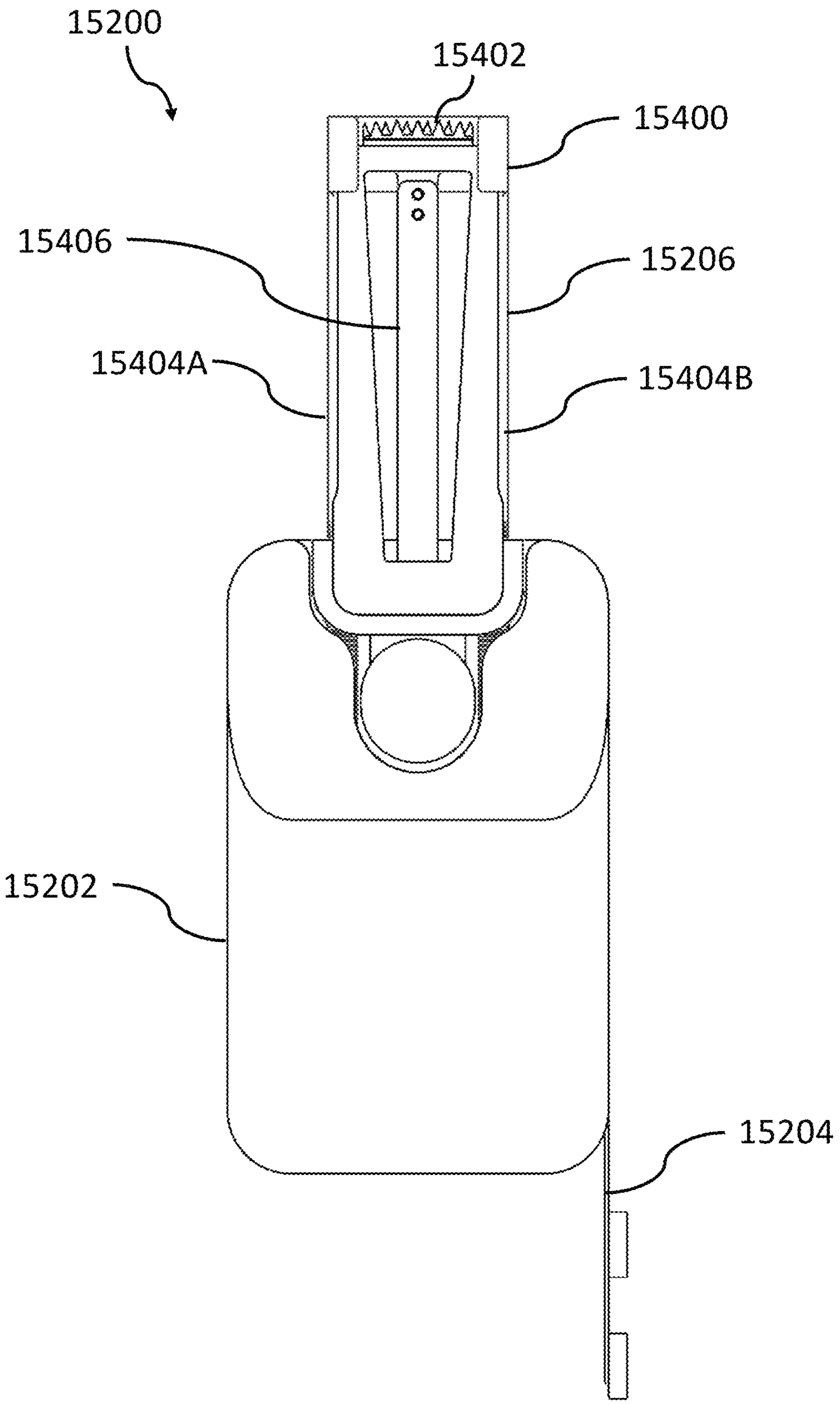
Figure 155:
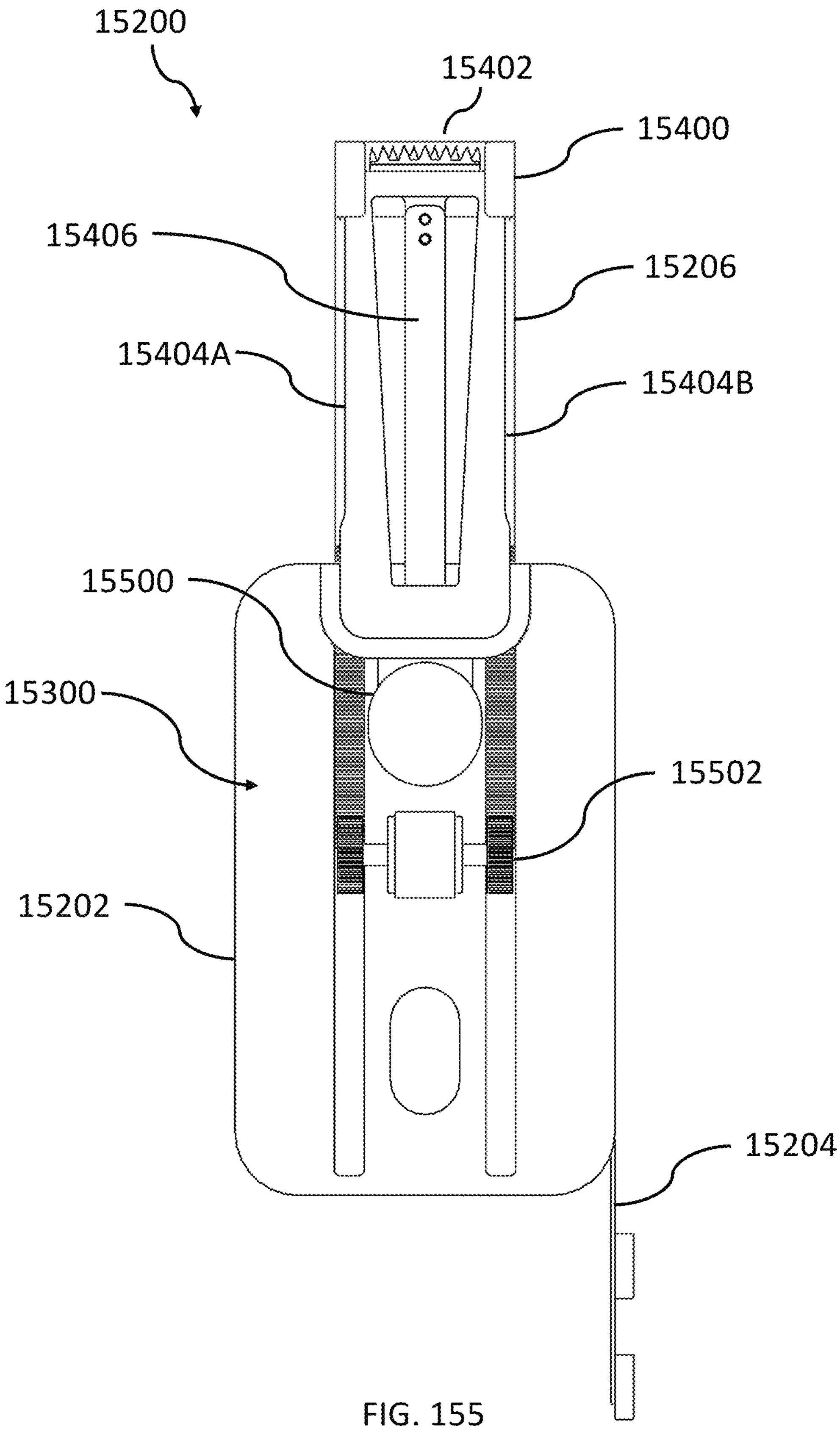
Figure 156:
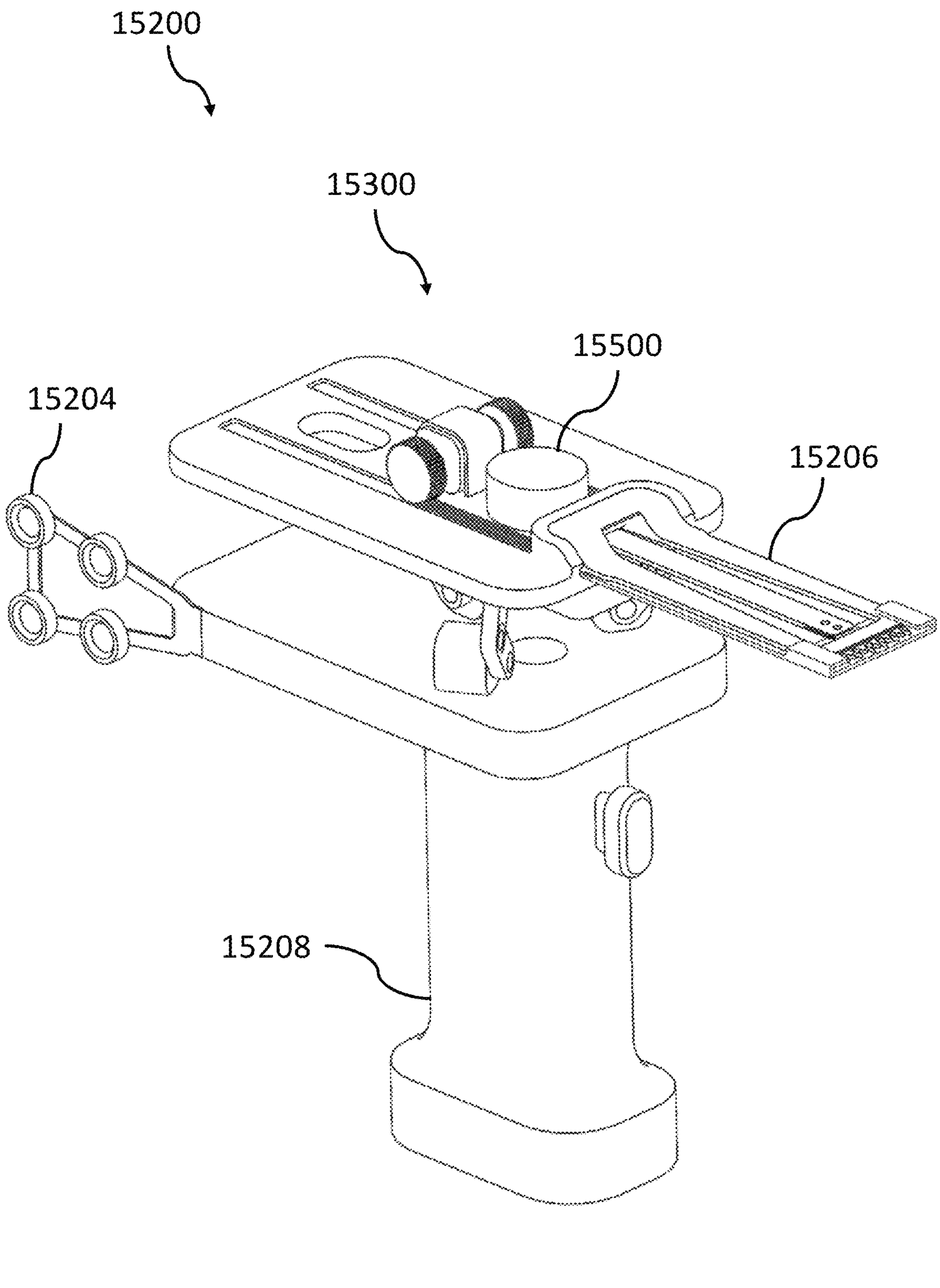
Figure 157:
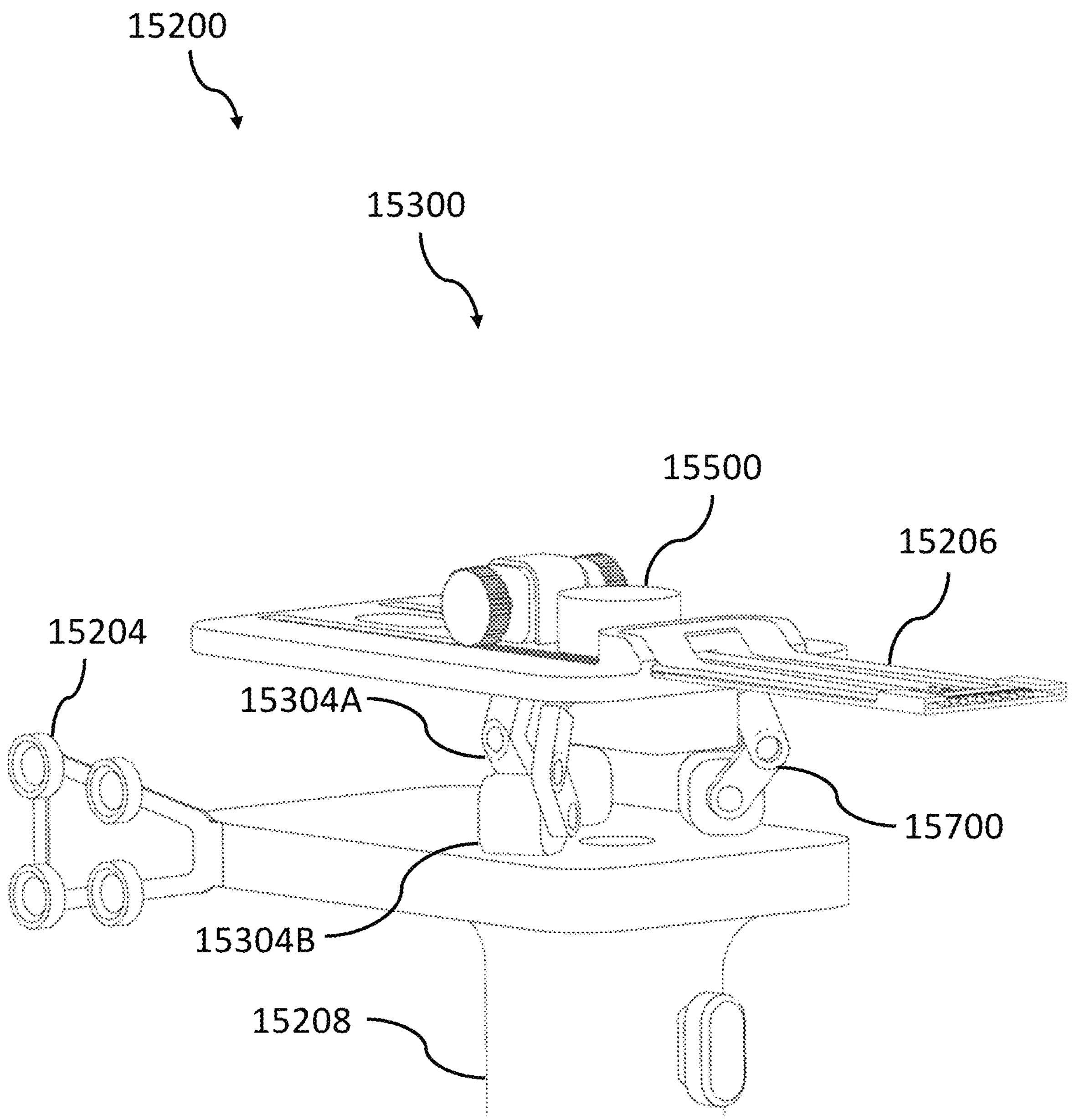
Figure 158:
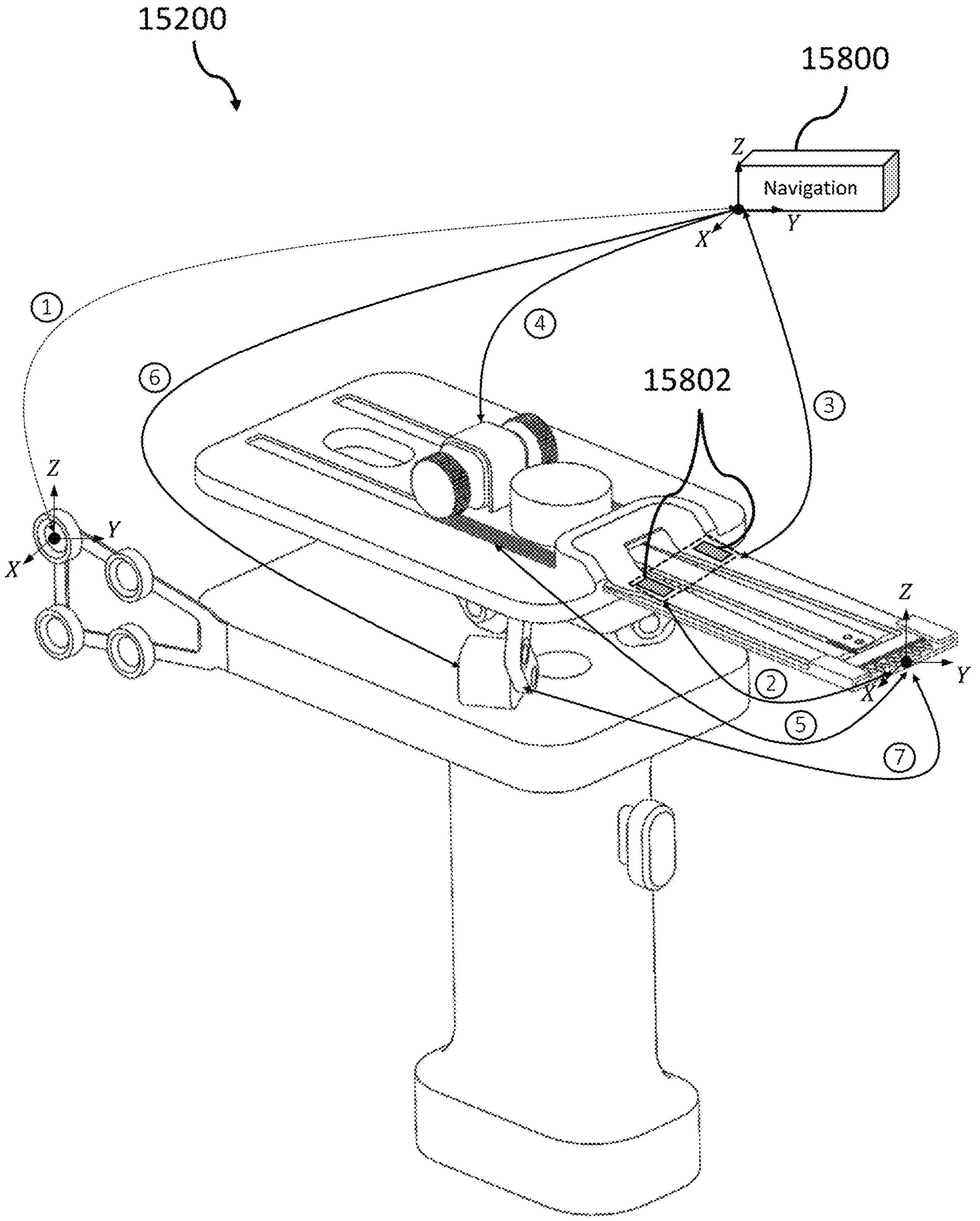
Figure 159A:
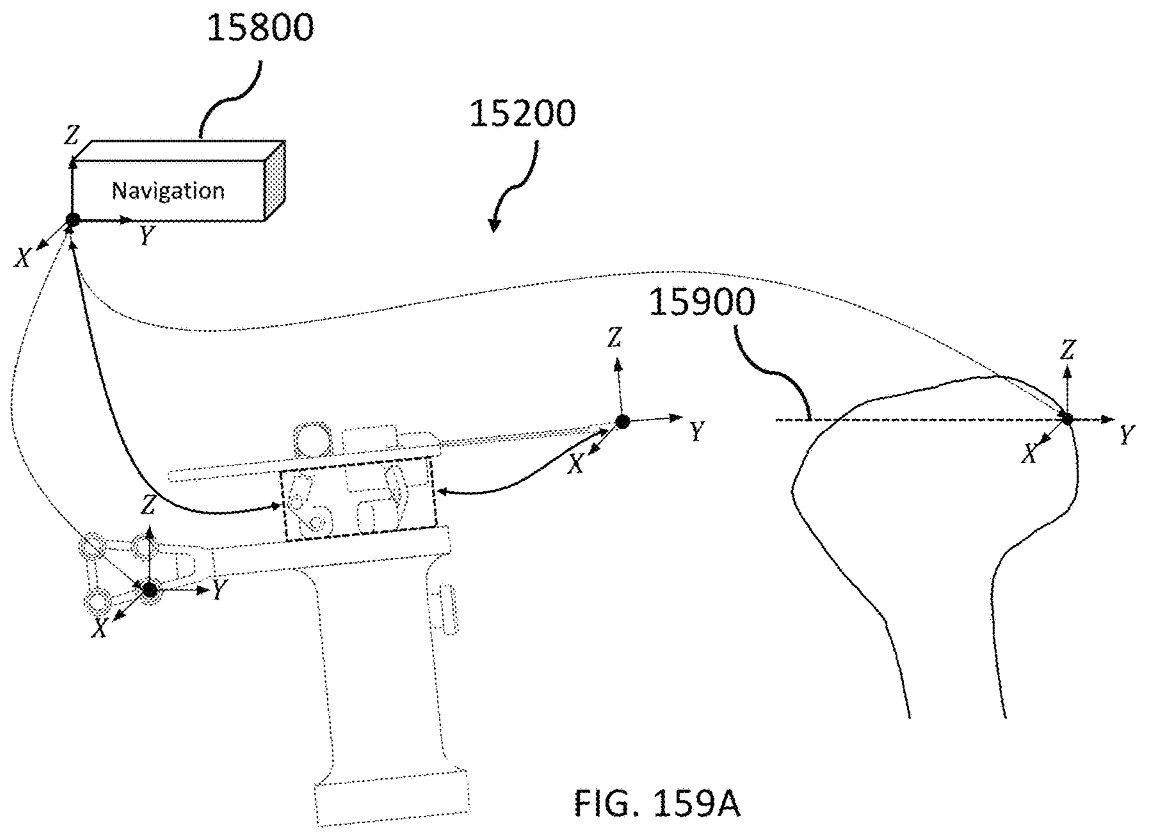
Figure 159B:
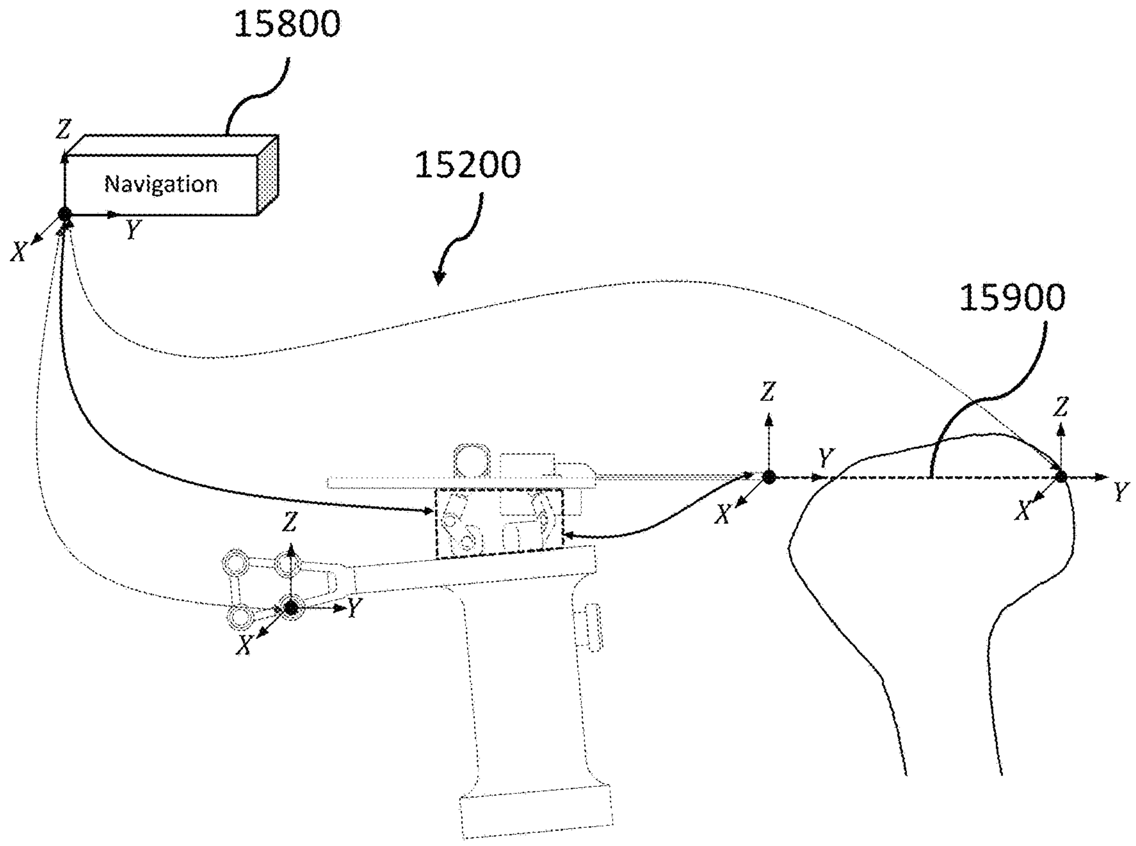
Figure 160A:
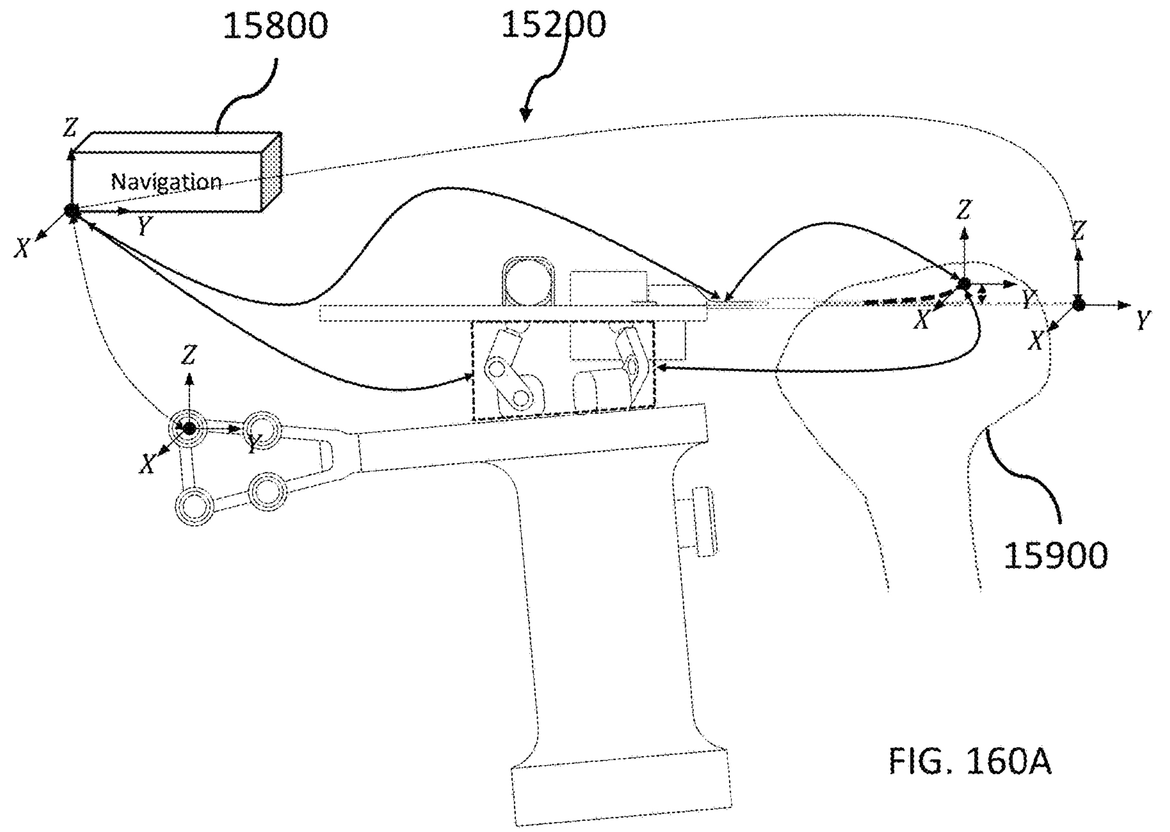
Figure 160B:
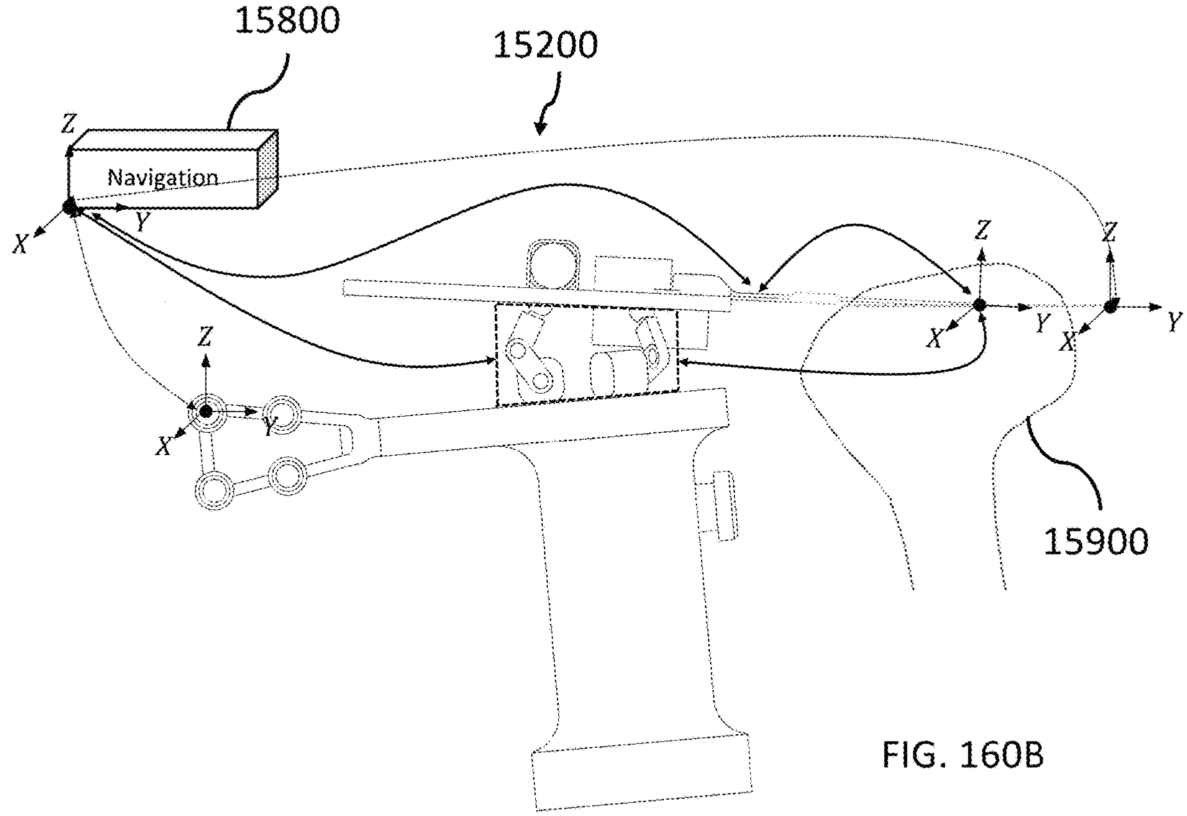
Figure 161A:
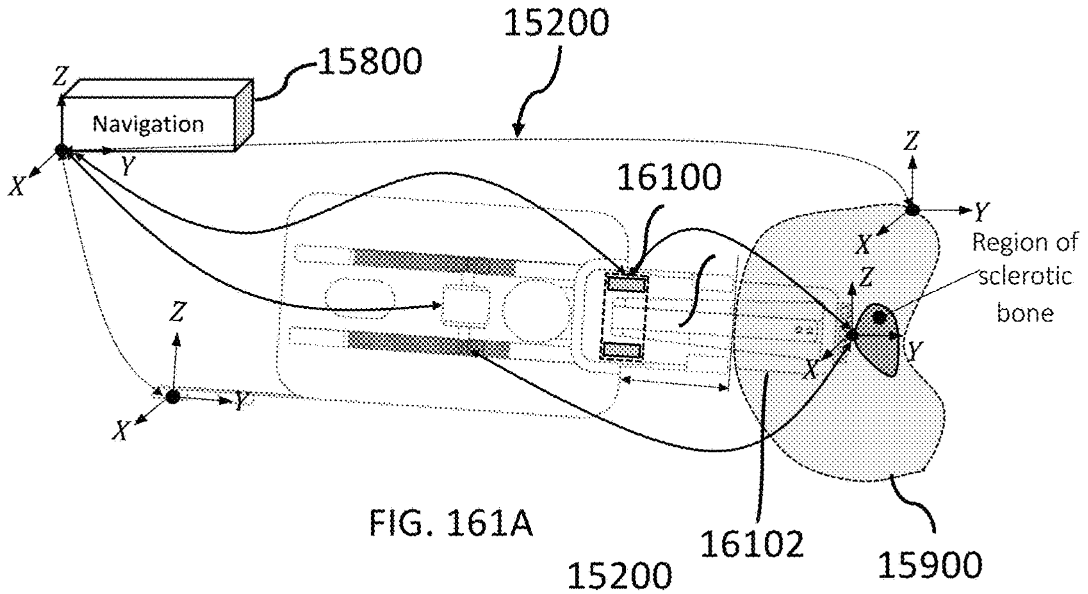
Figure 161B:
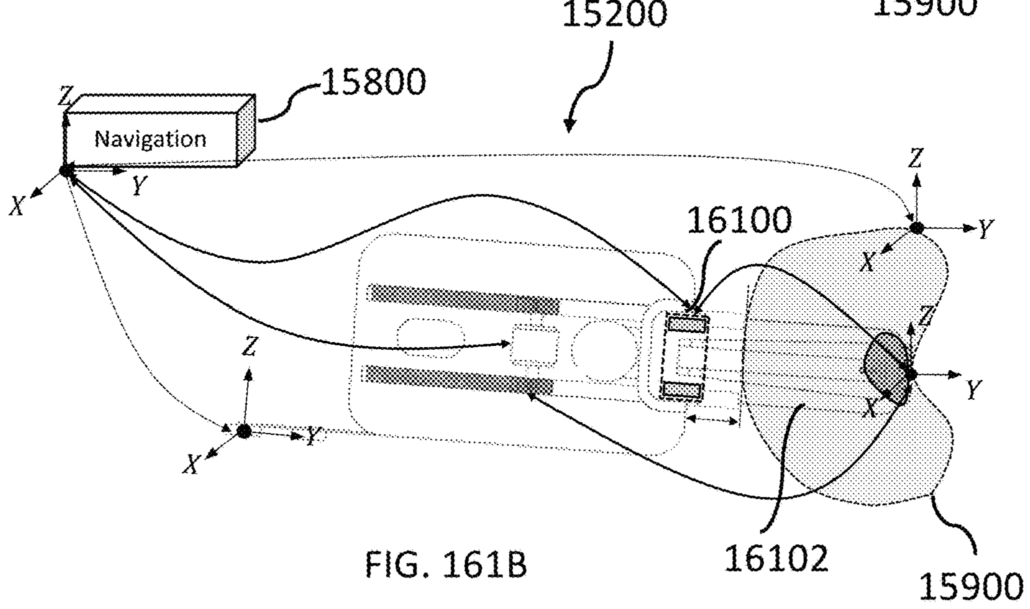
Figure 161C:
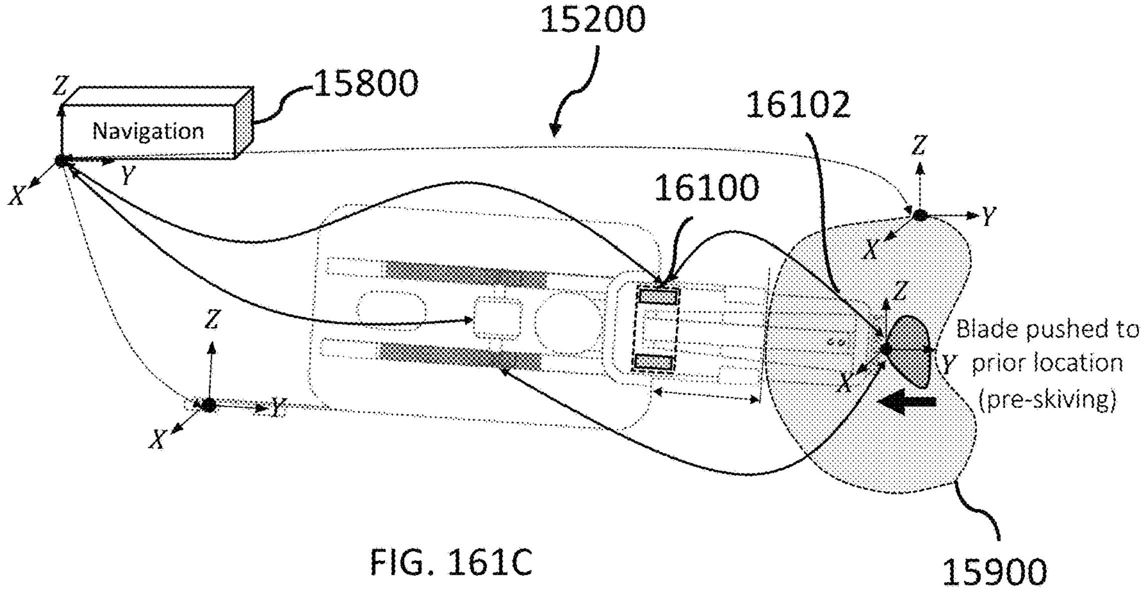
Figure 162A:
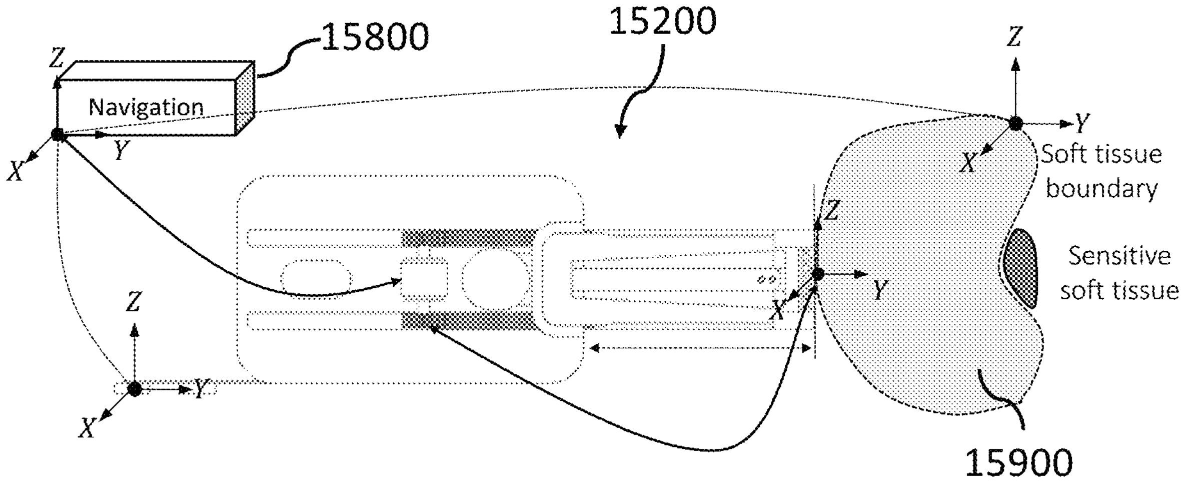
Figure 162B:
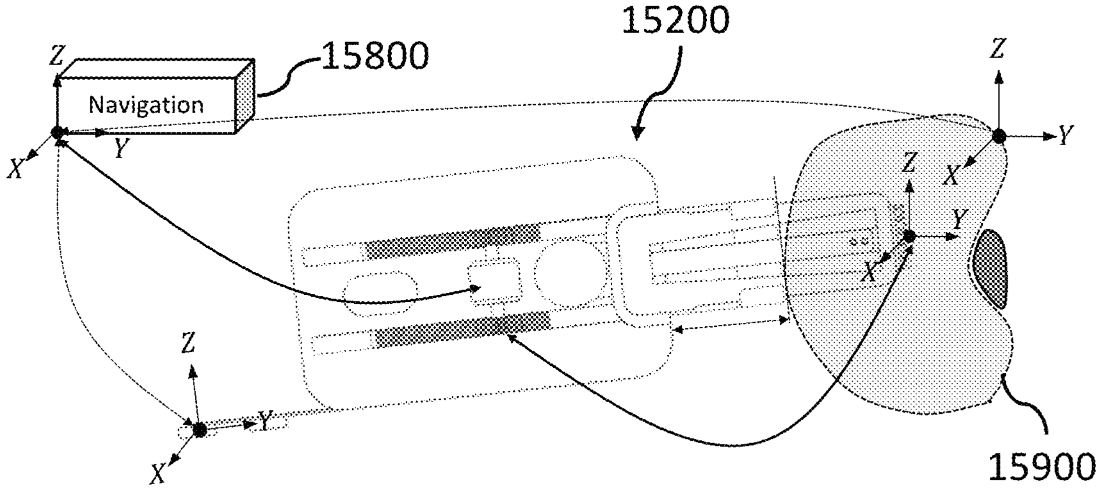
Figure 162C:
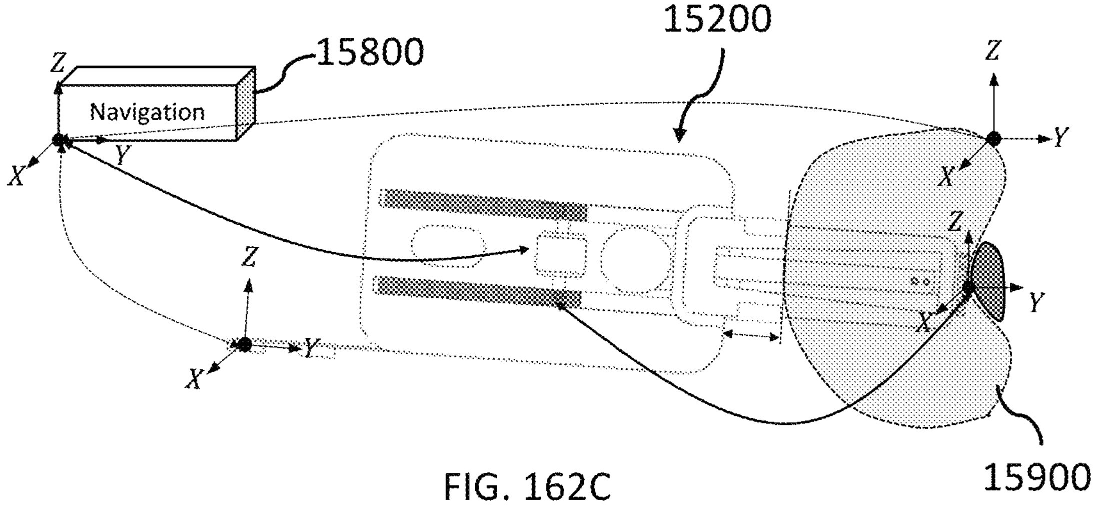
Figure 163A:
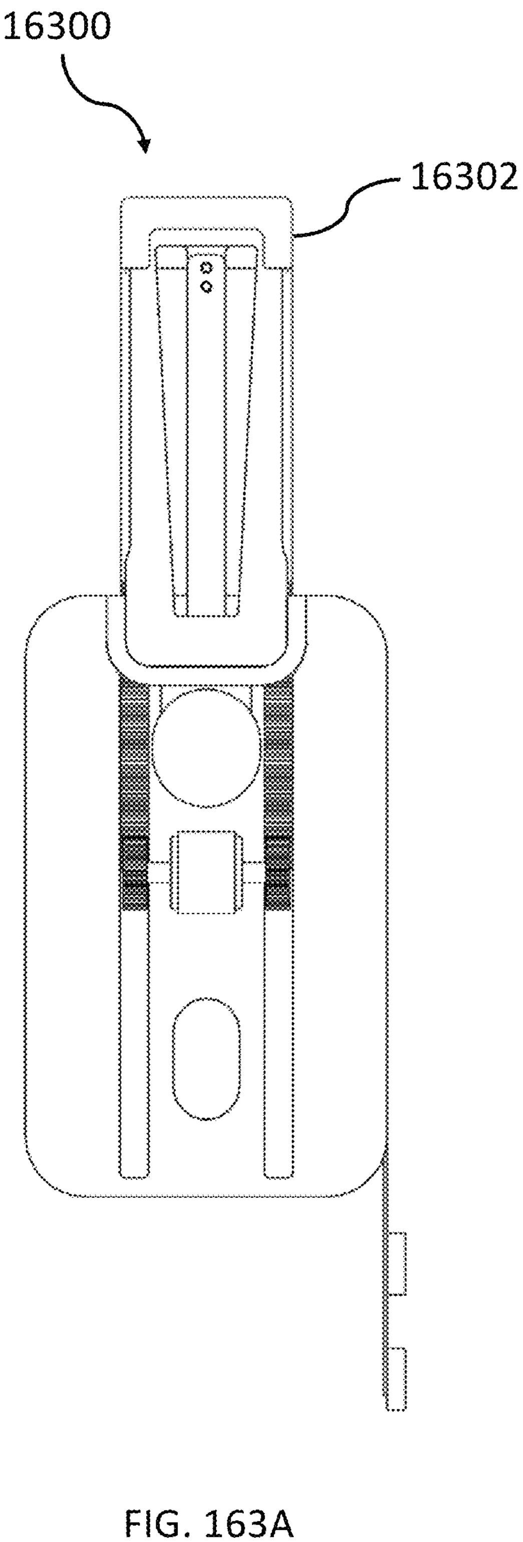
Figure 163B:
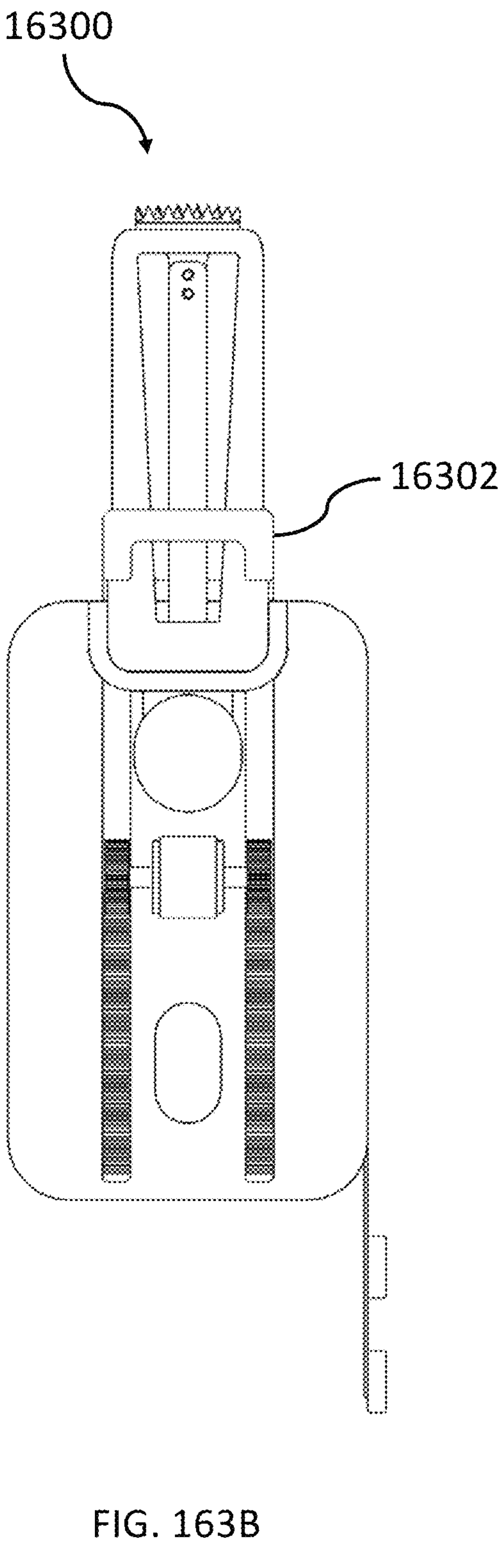
Figure 164A:
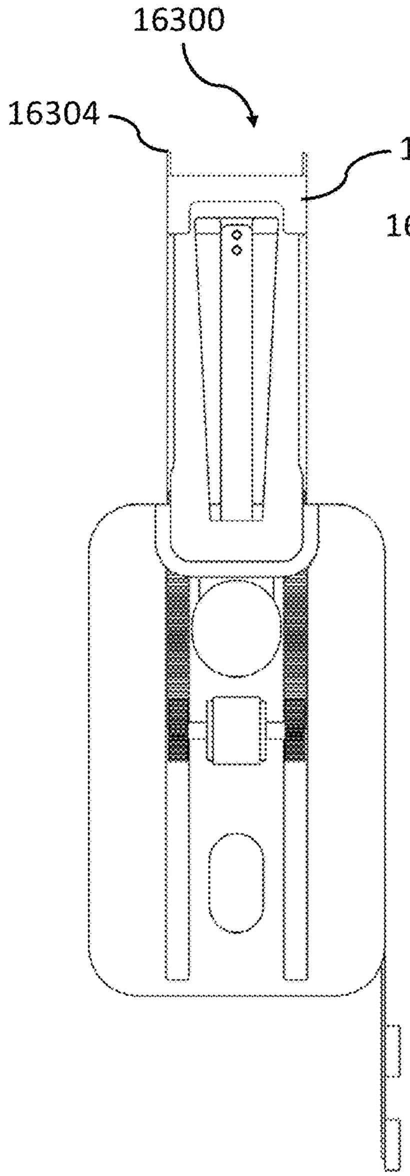
Figure 164B:
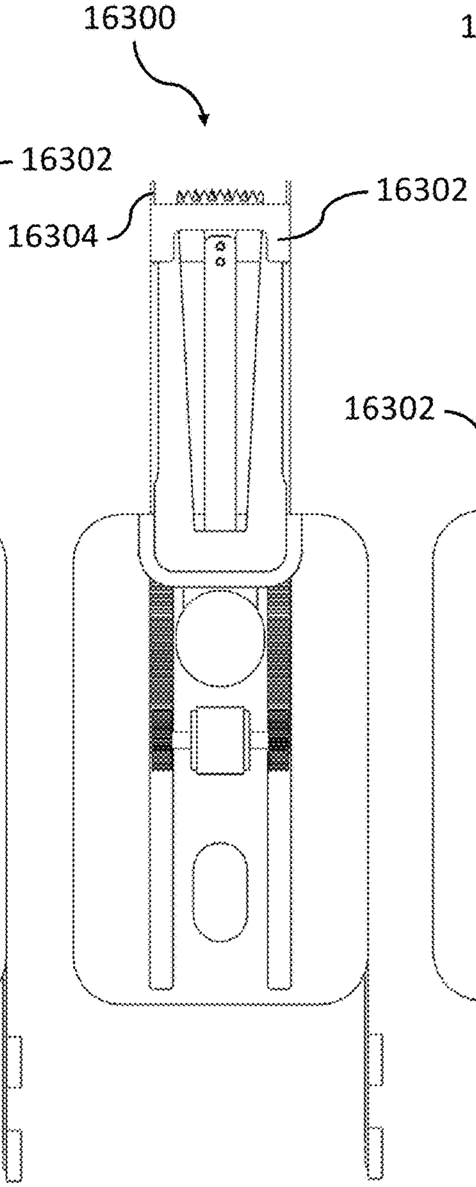
Figure 164C:
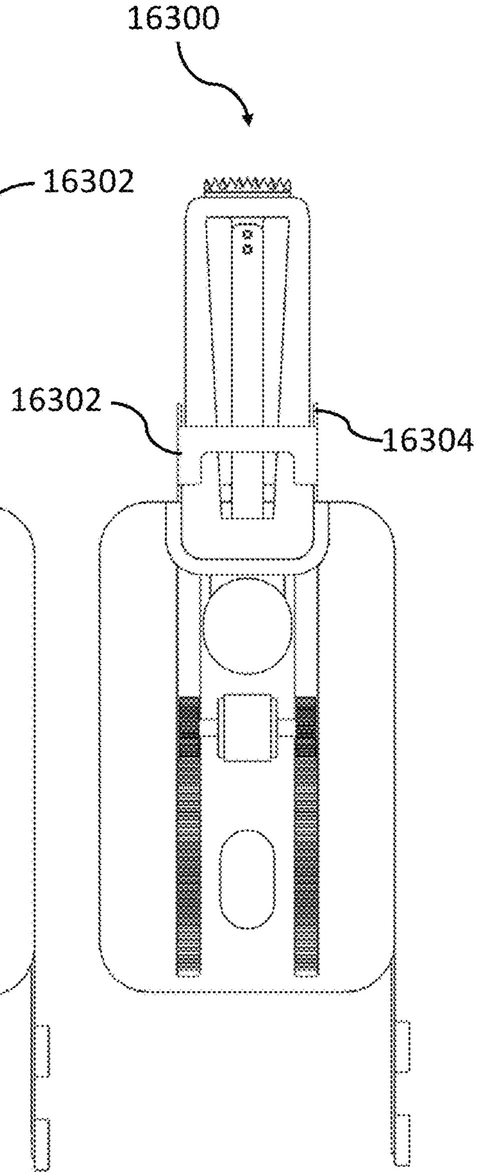
Figure 165:
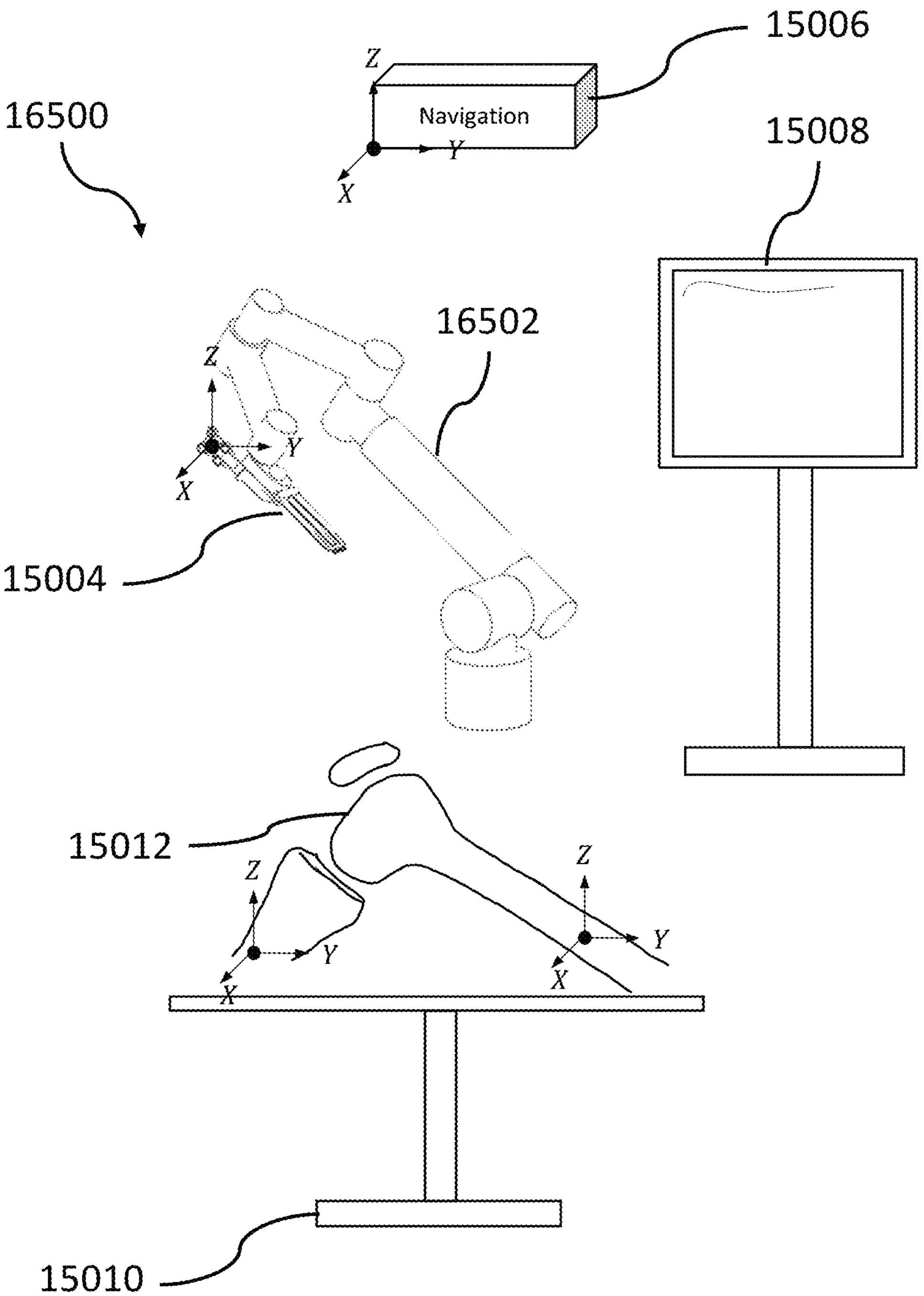
Figure 166:
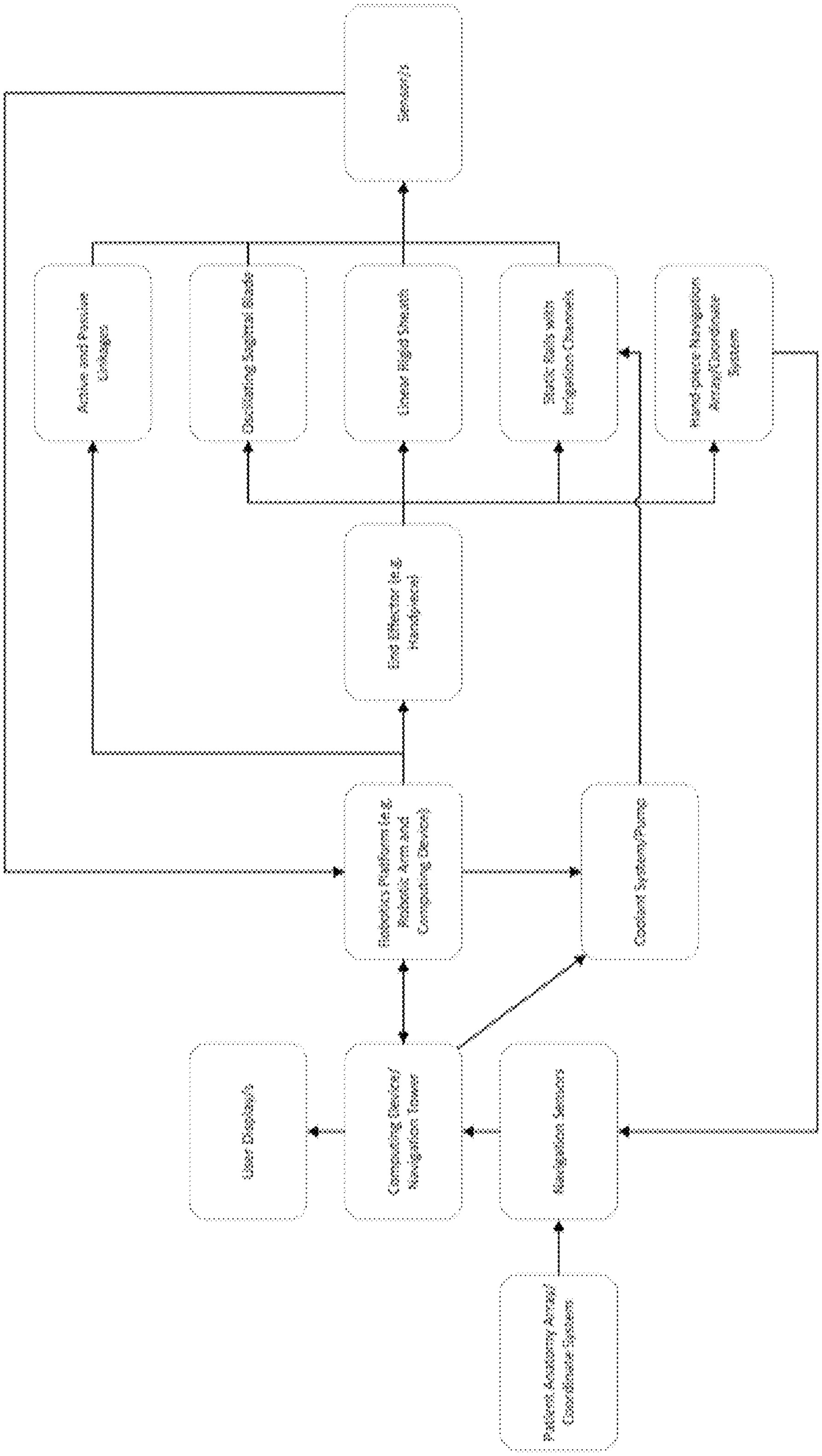
Figure 167:
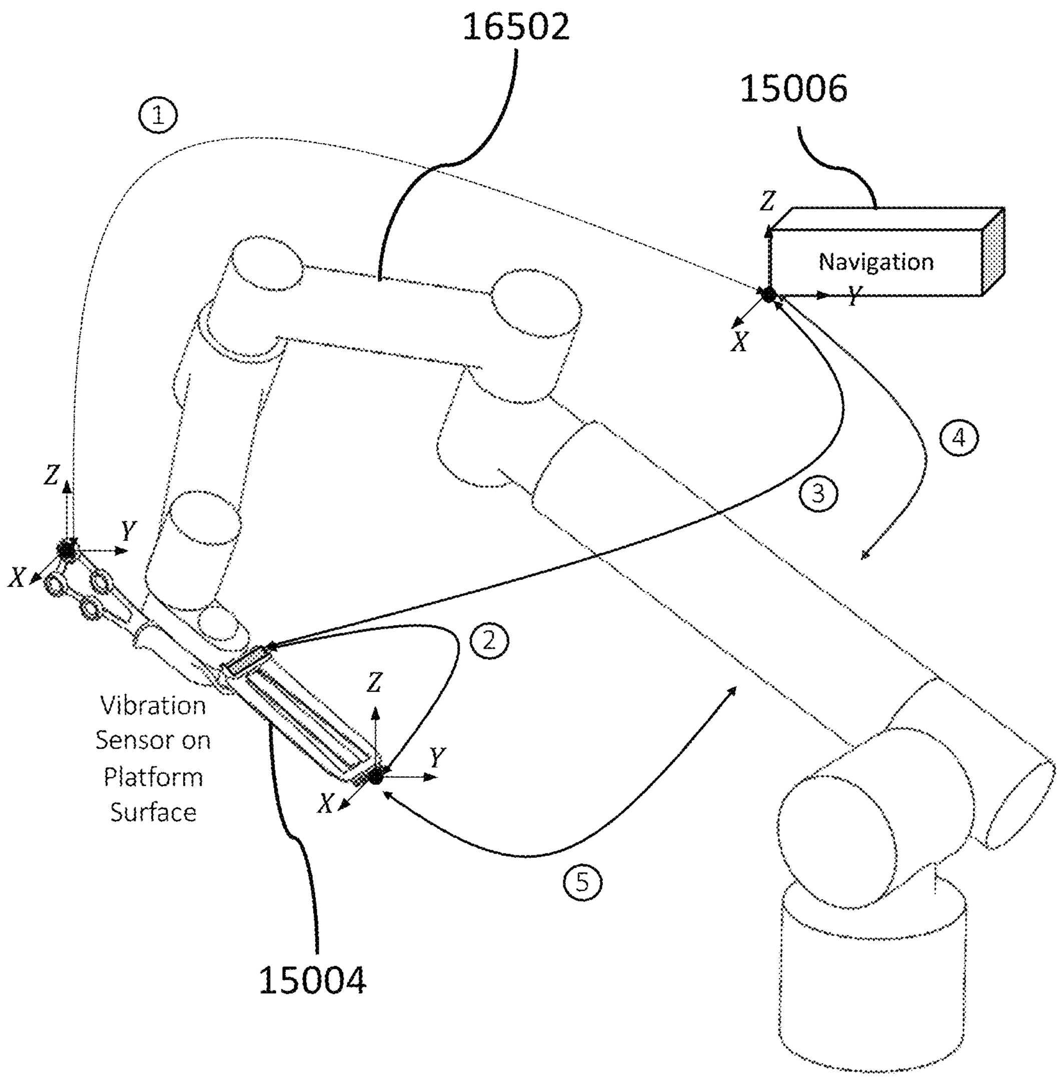
Figure 168A:
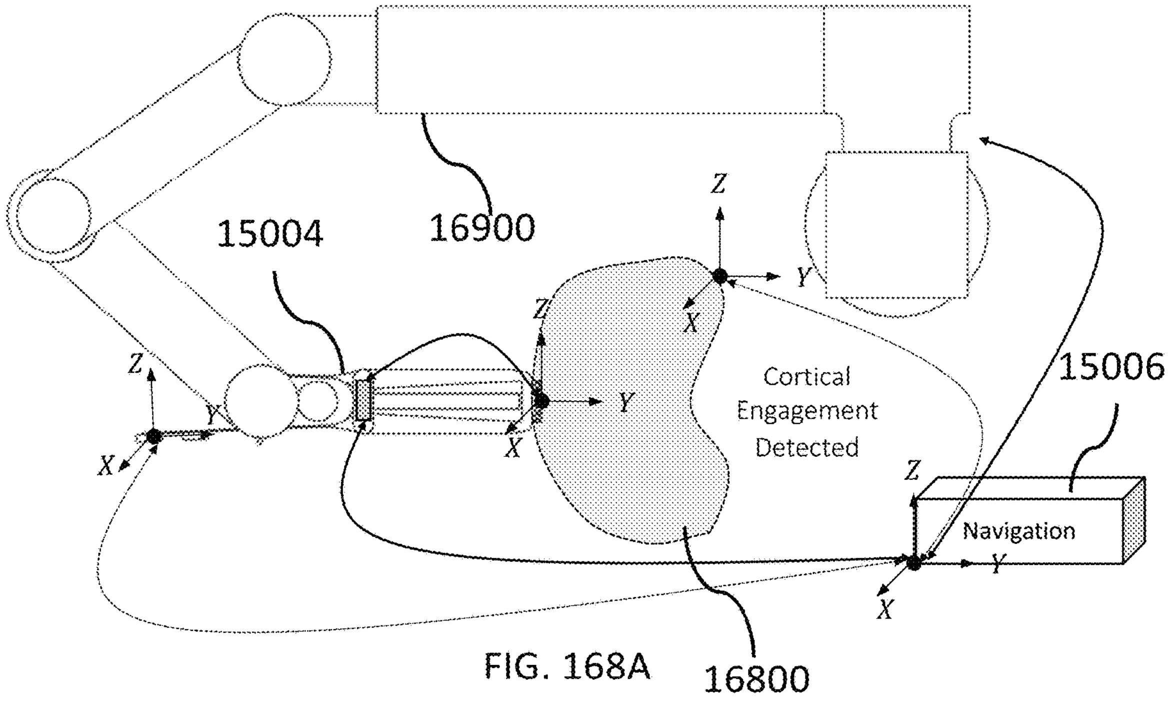
Figure 168B:
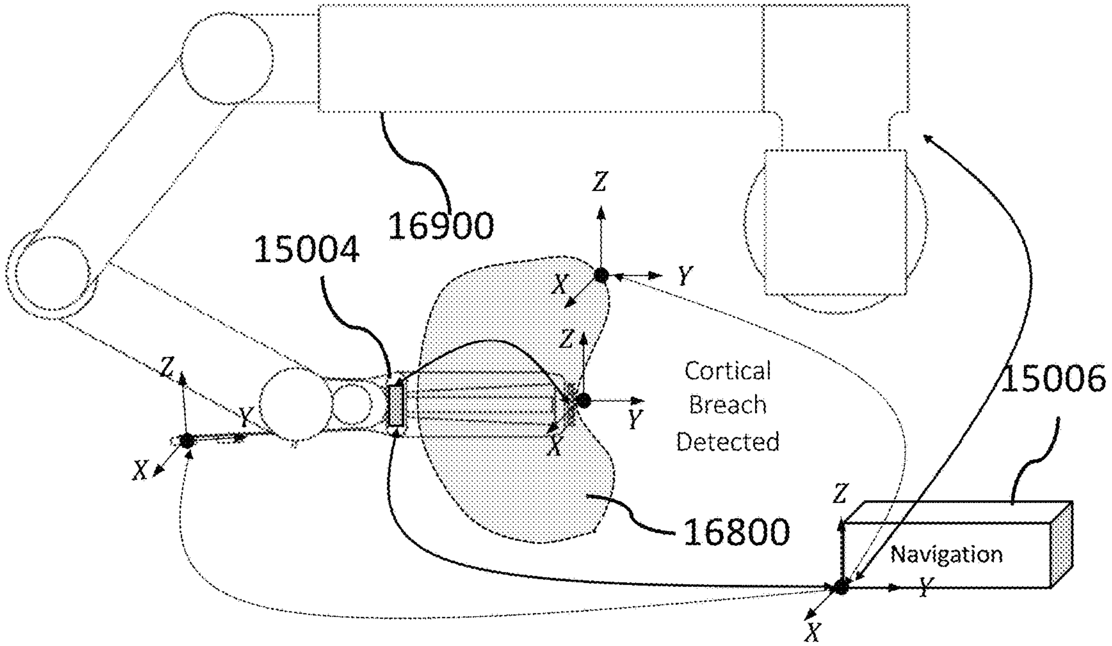
Figure 169:
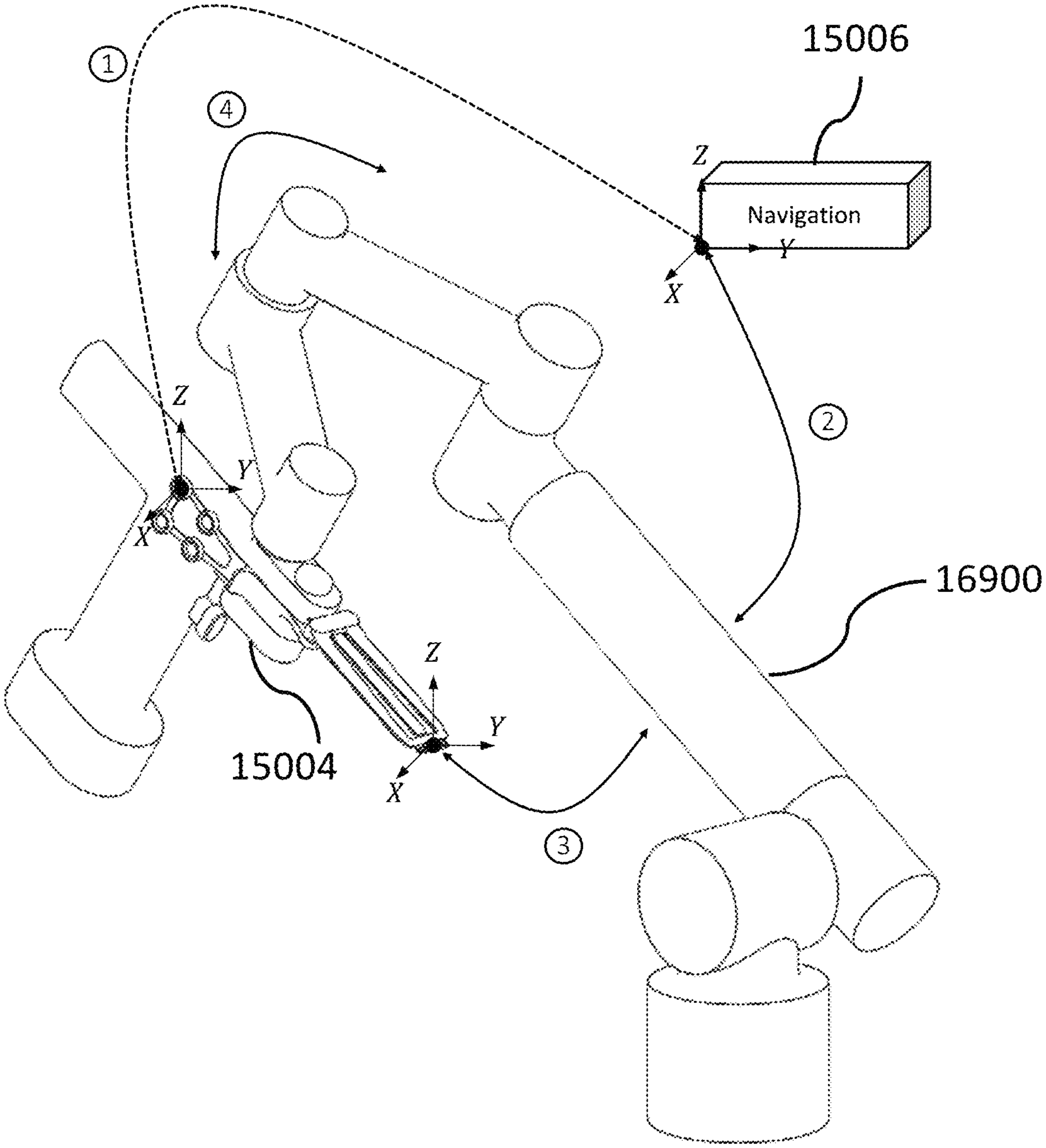
Figure 170:
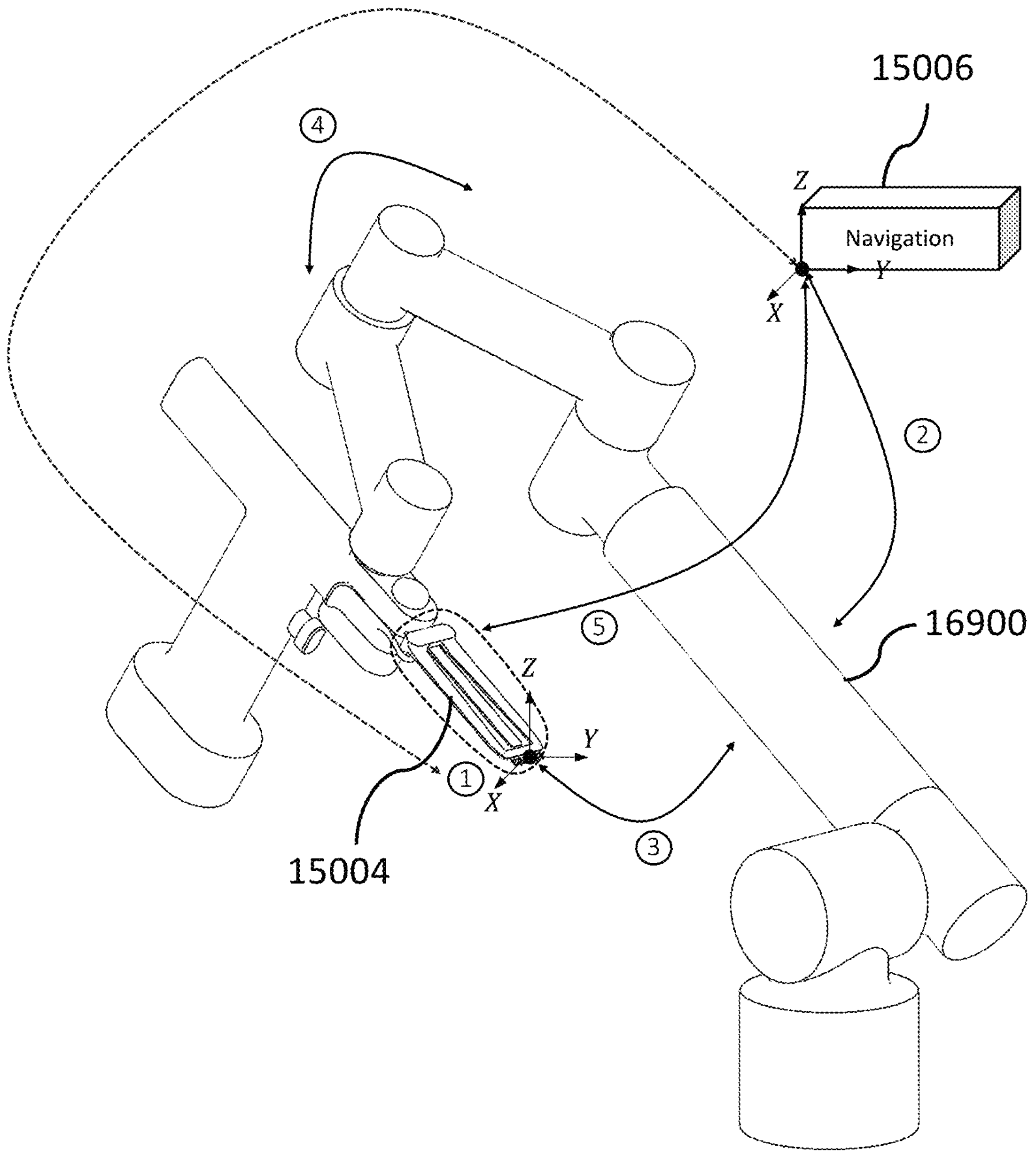
Figure 171:
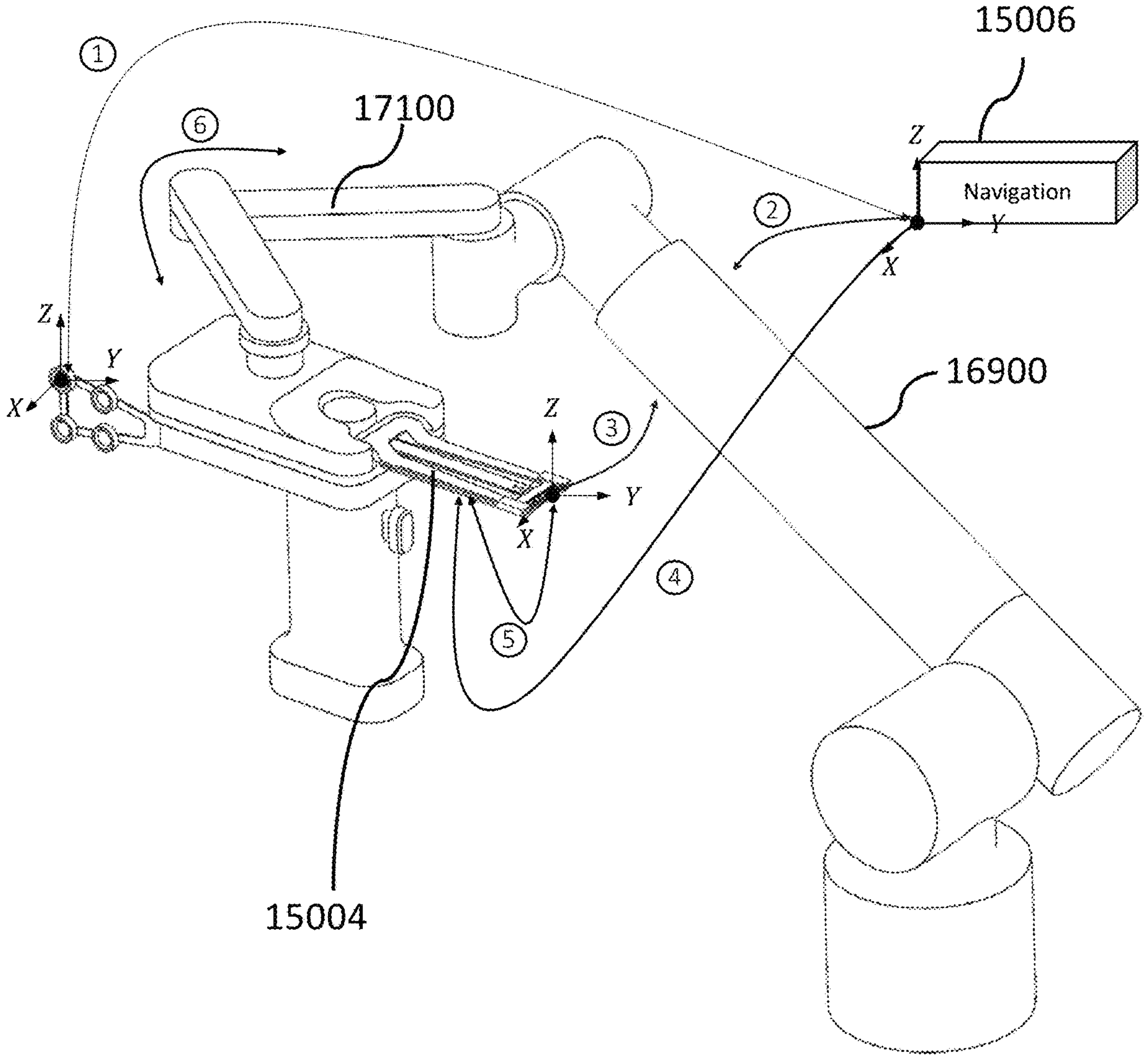
Figure 172A:
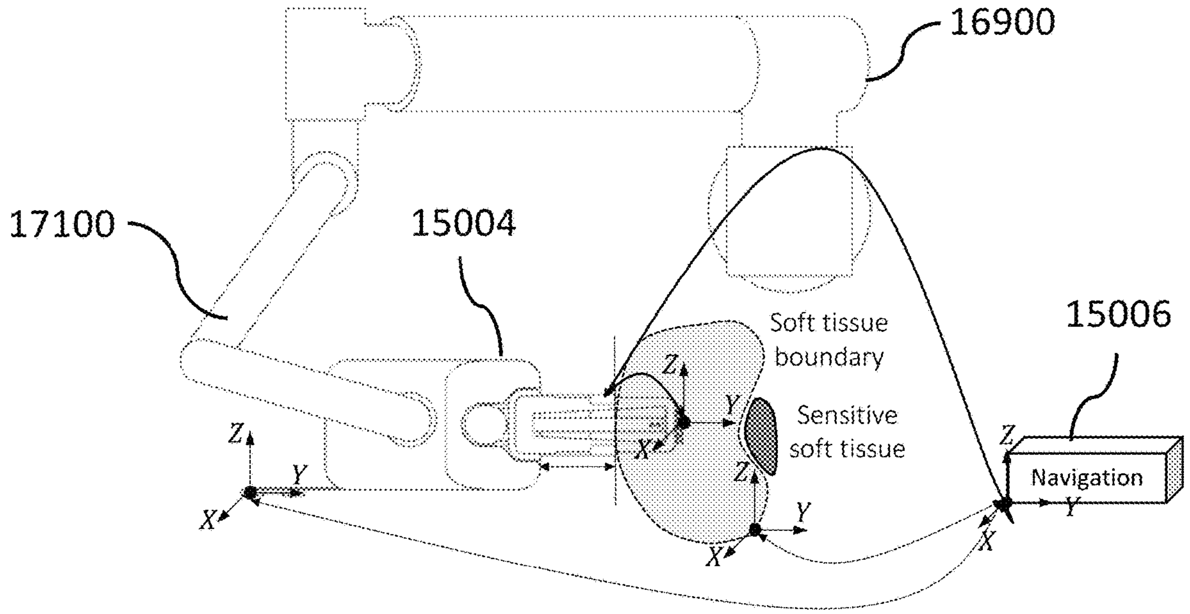
Figure 172B:
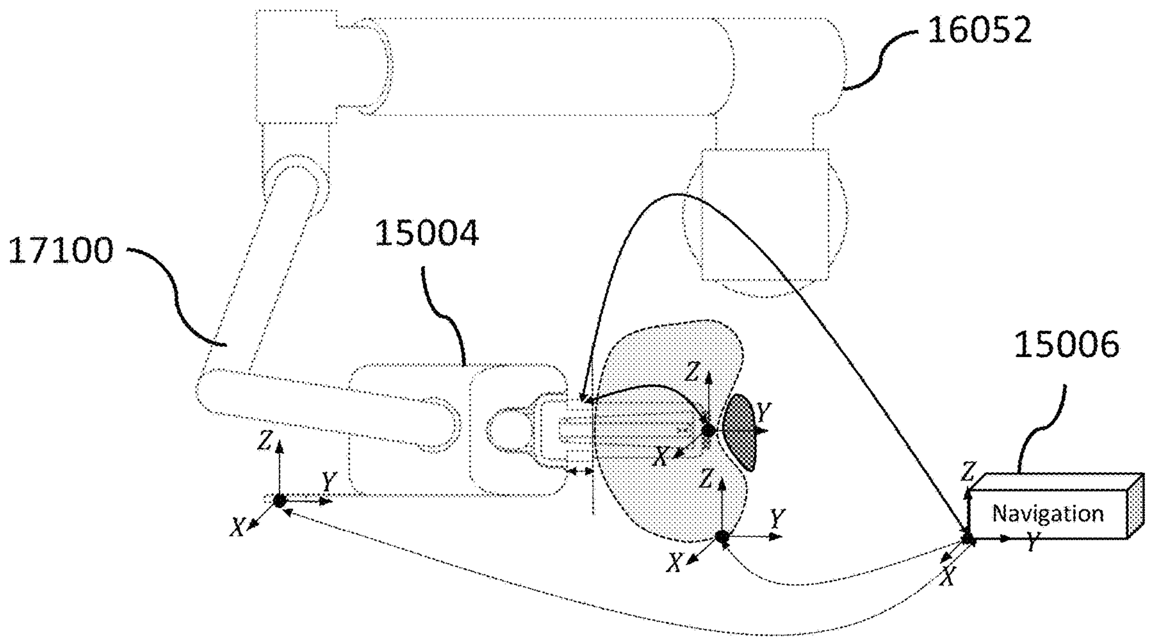
Figure 173:
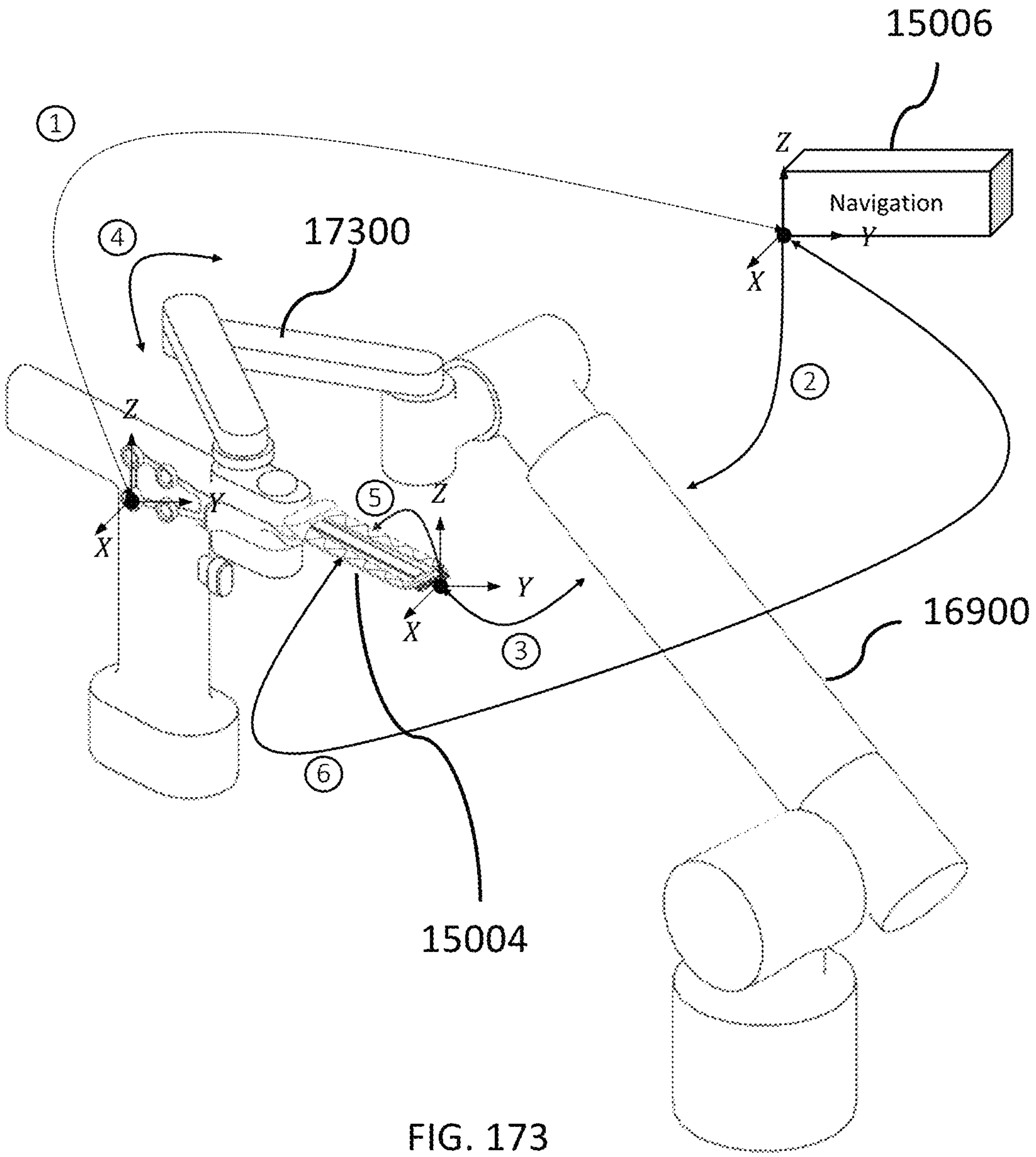
Figure 174A:
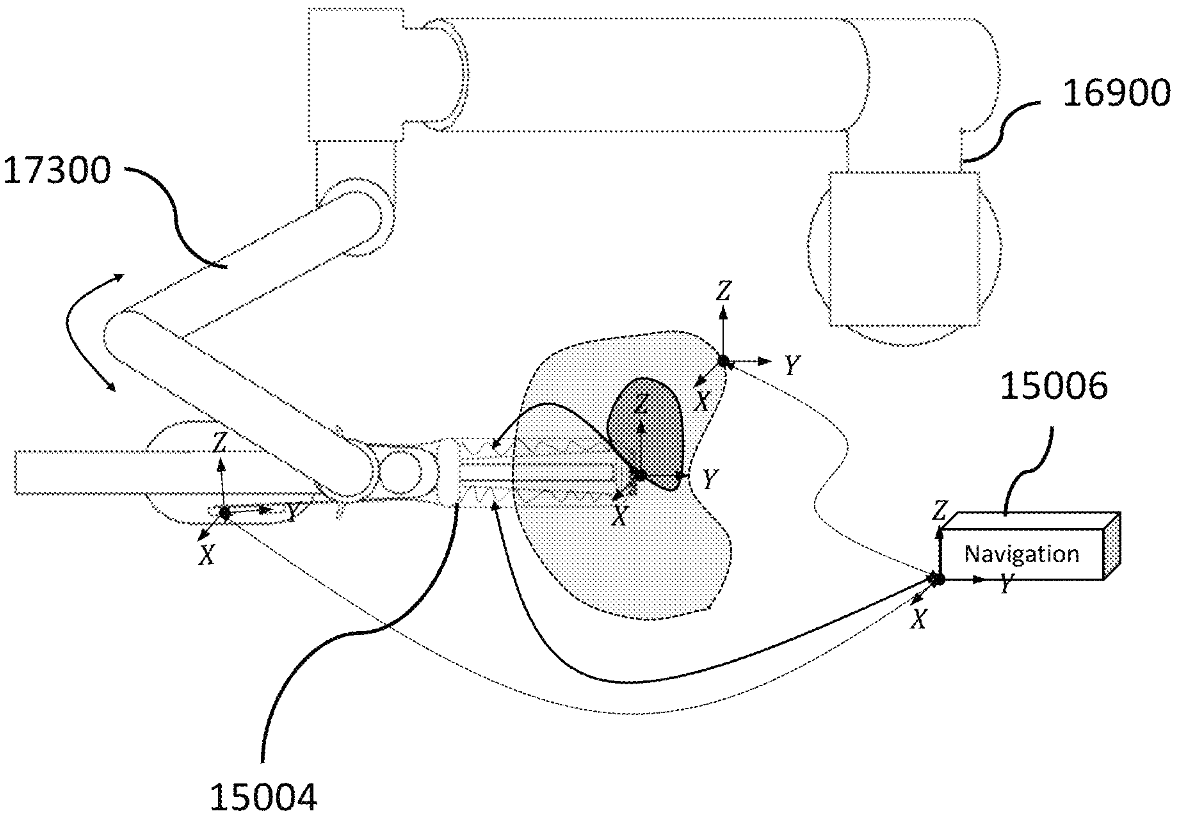
Figure 174B:
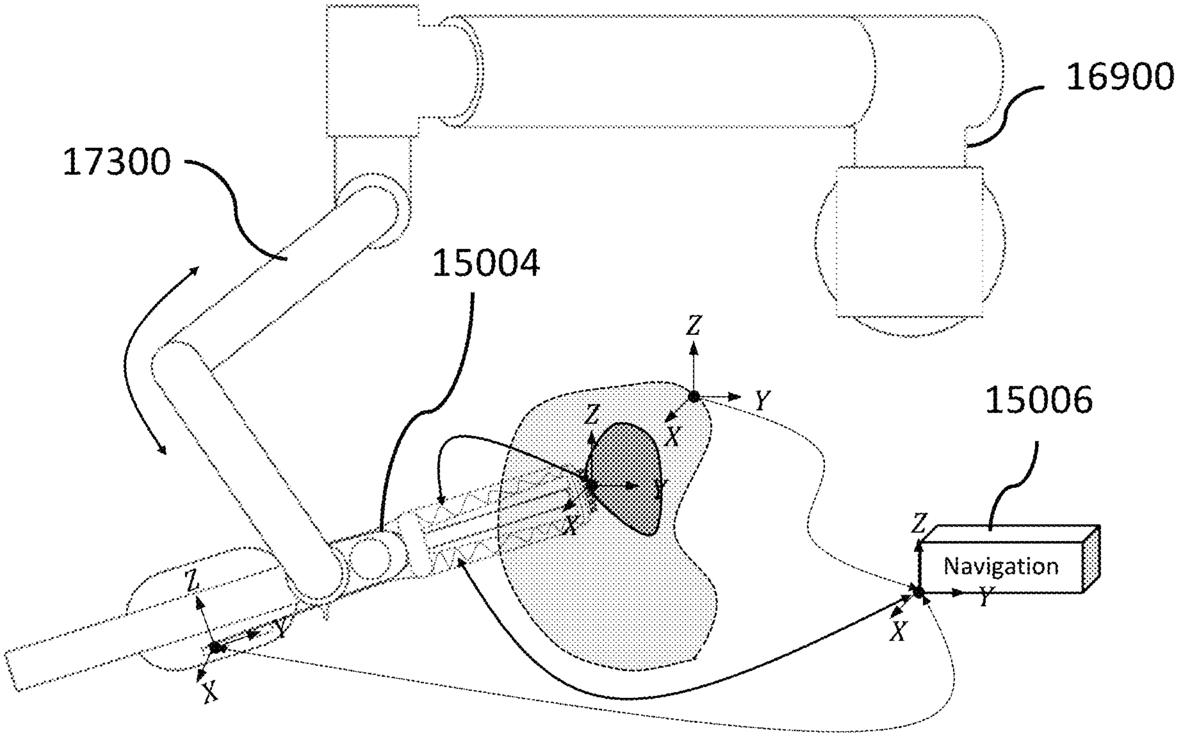
Figure 175:
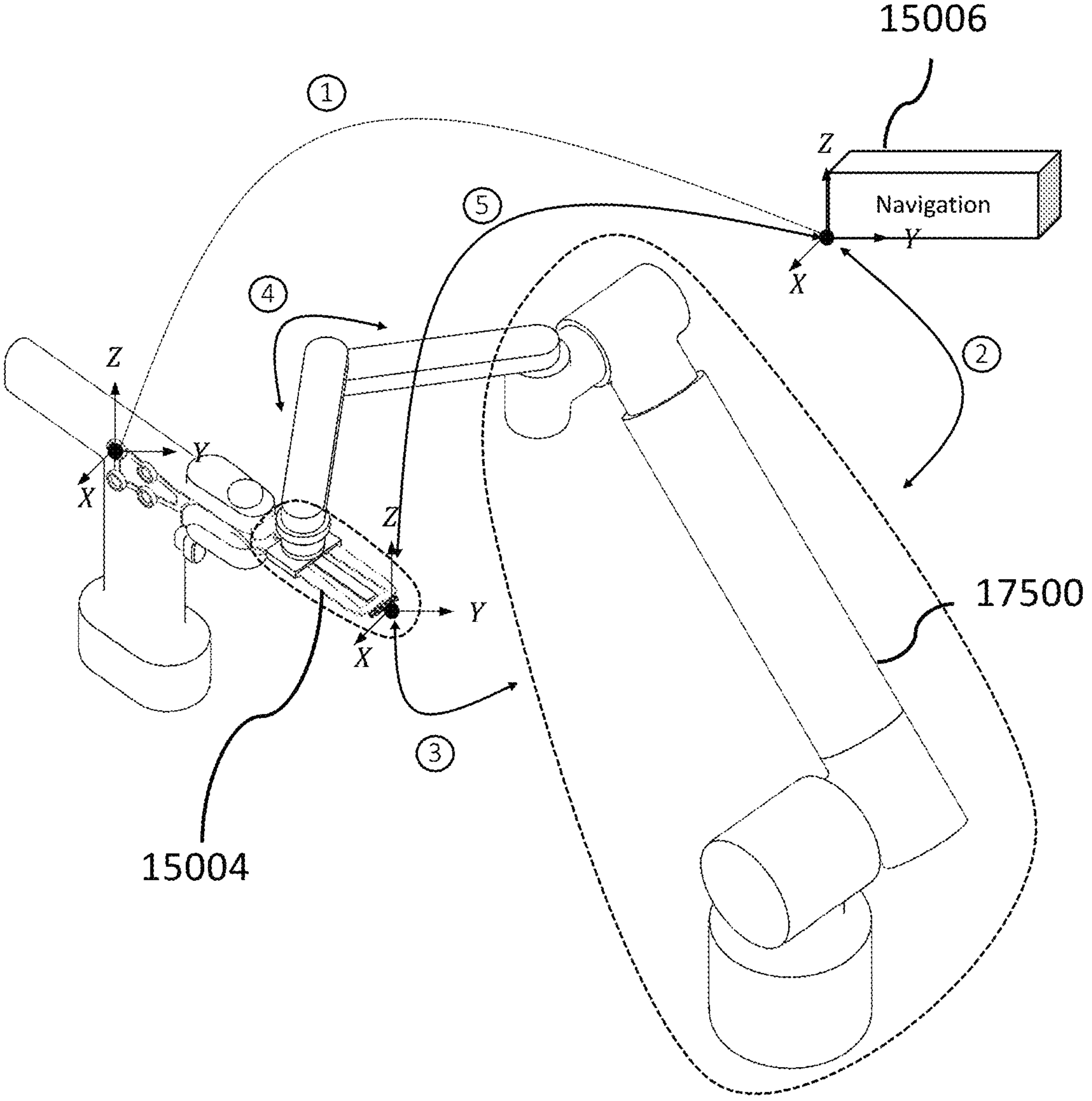
Figure 176A:
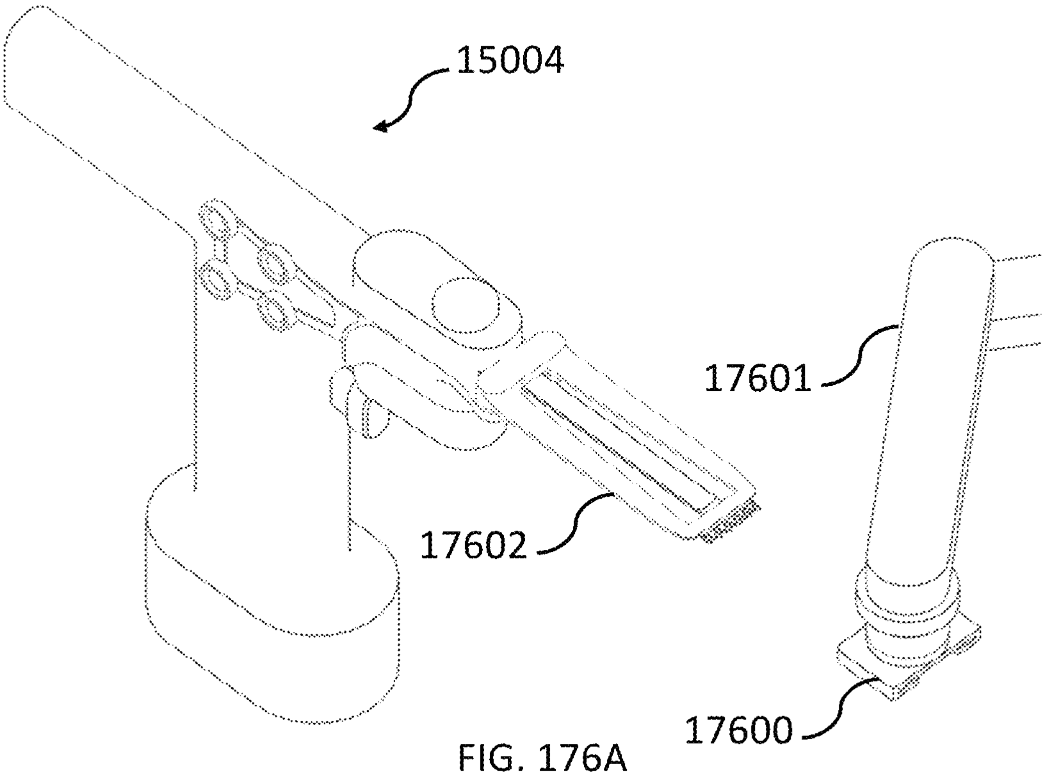
Figure 176B:
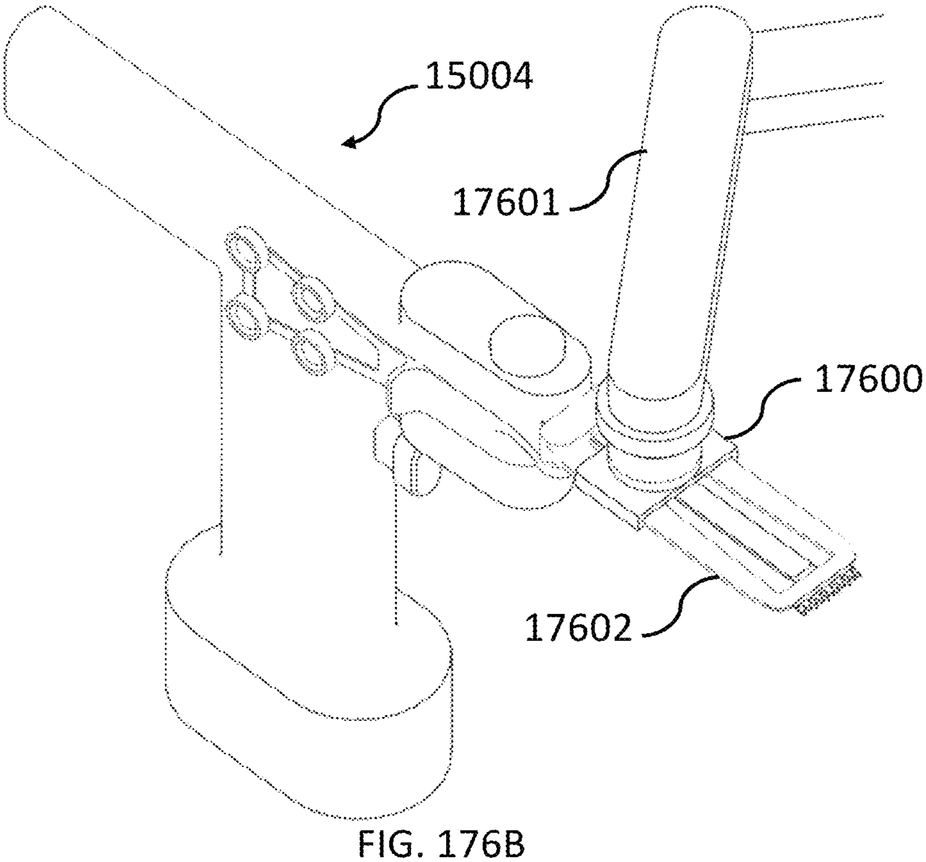
Figure 177:
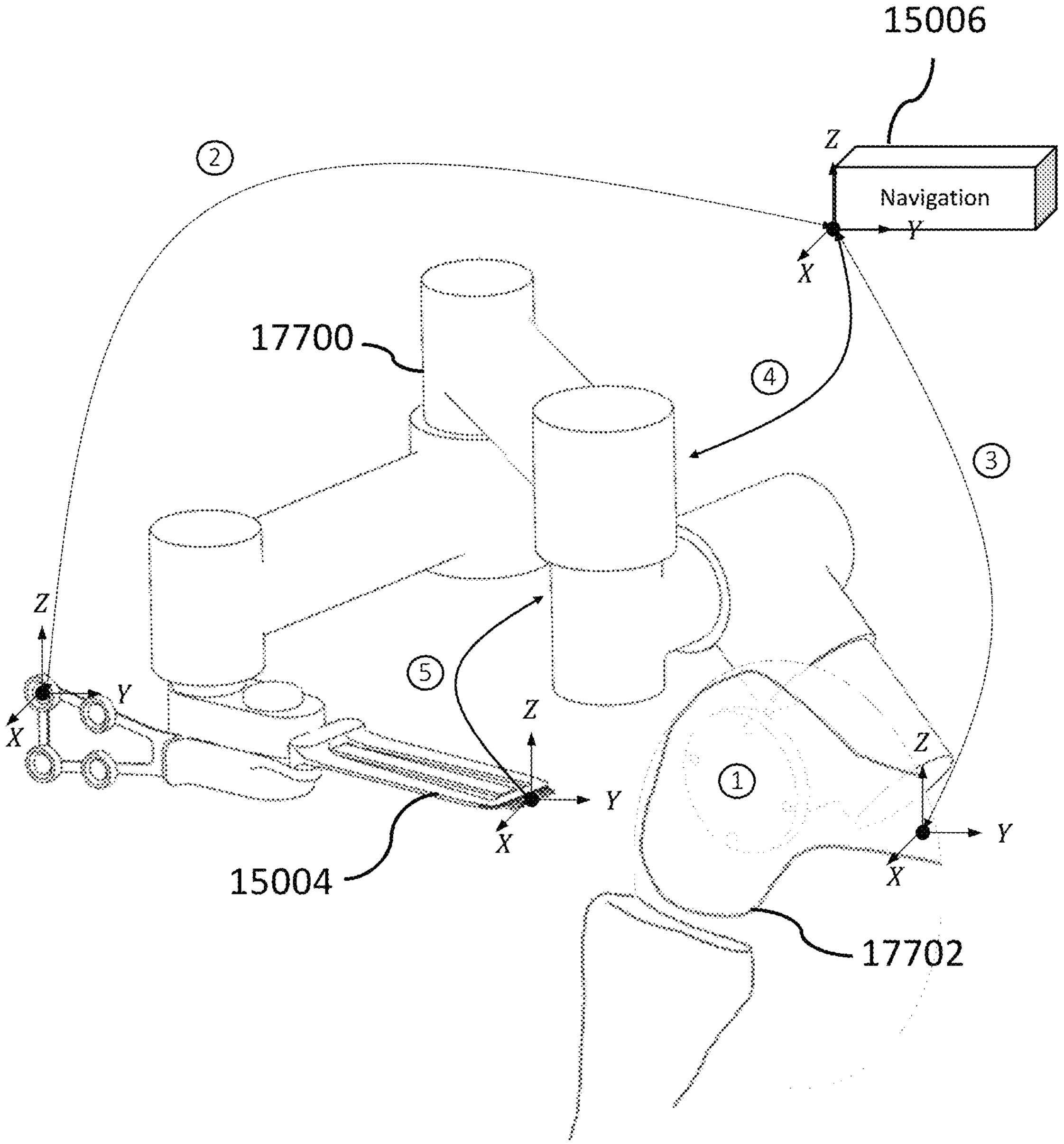
Figure 178:
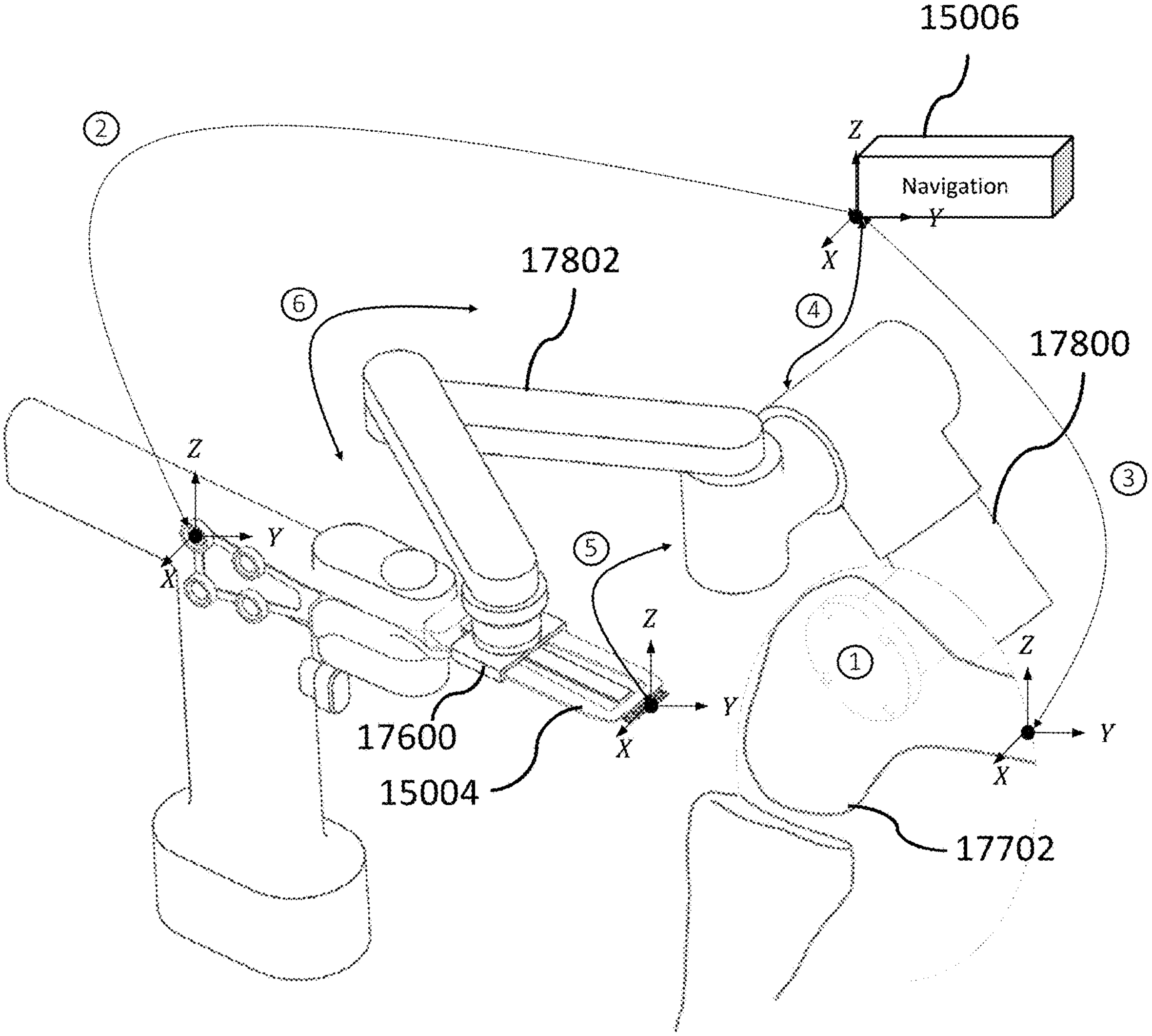
Figure 179:
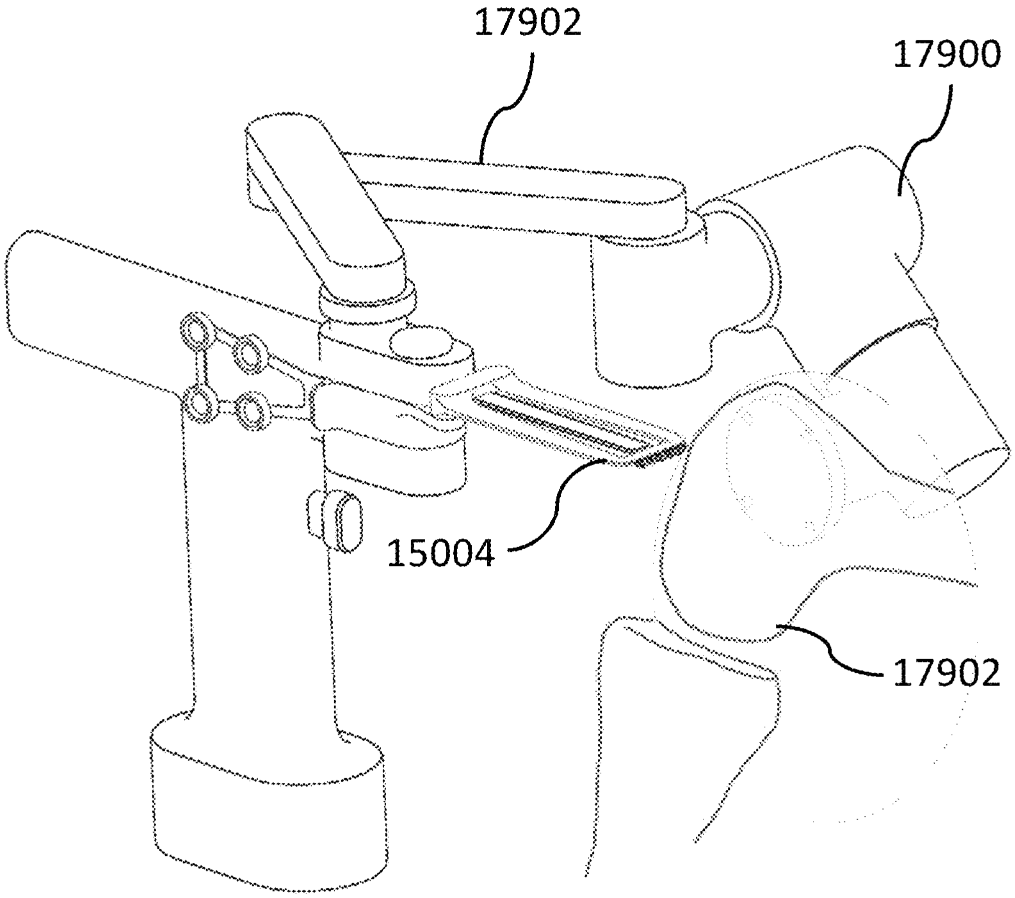
Figure 180A:
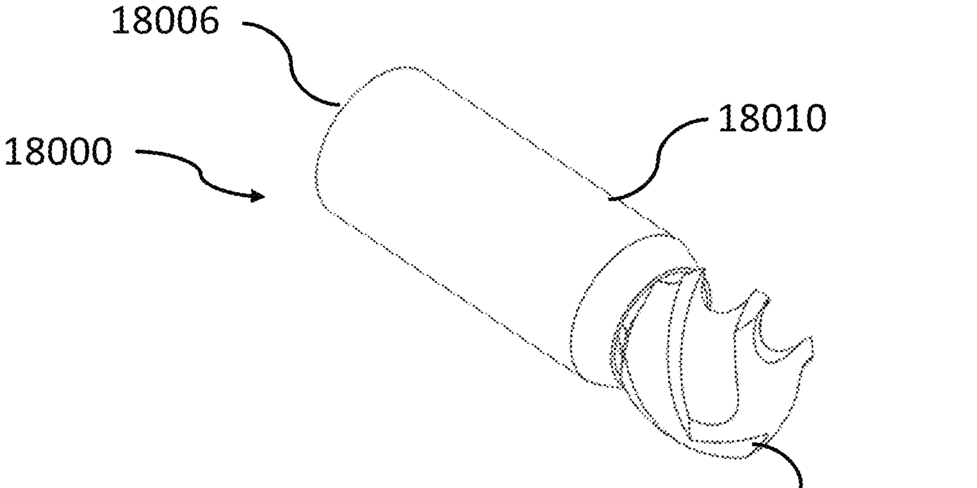
Figure 180B:
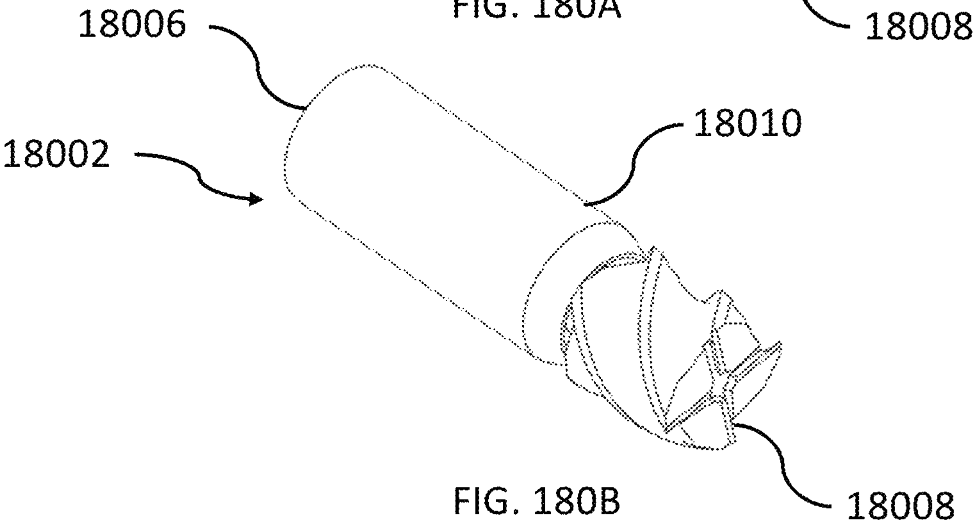
Figure 180C:
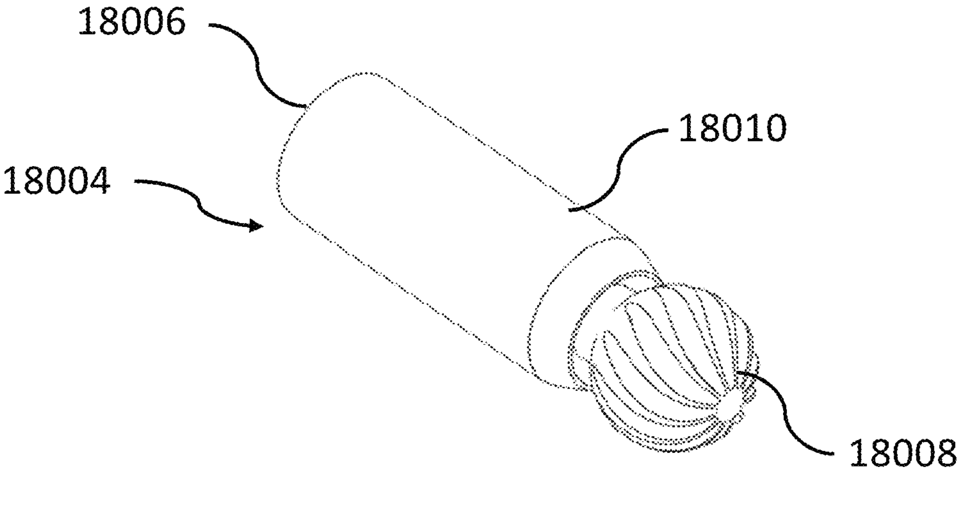
Figure 181A:
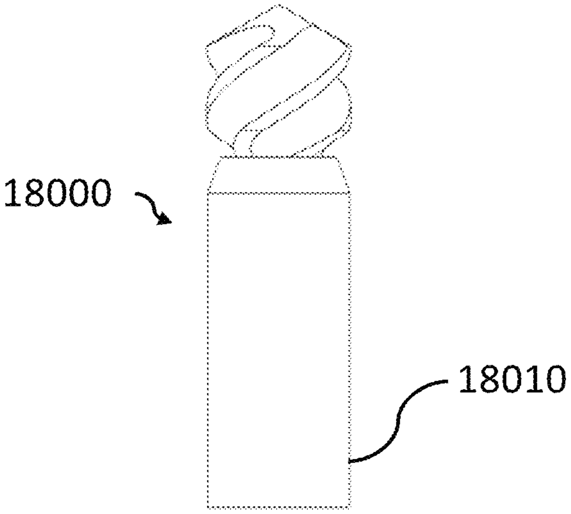
Figure 181B:
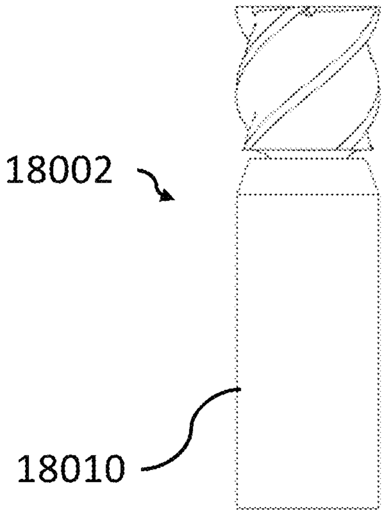
Figure 181C:
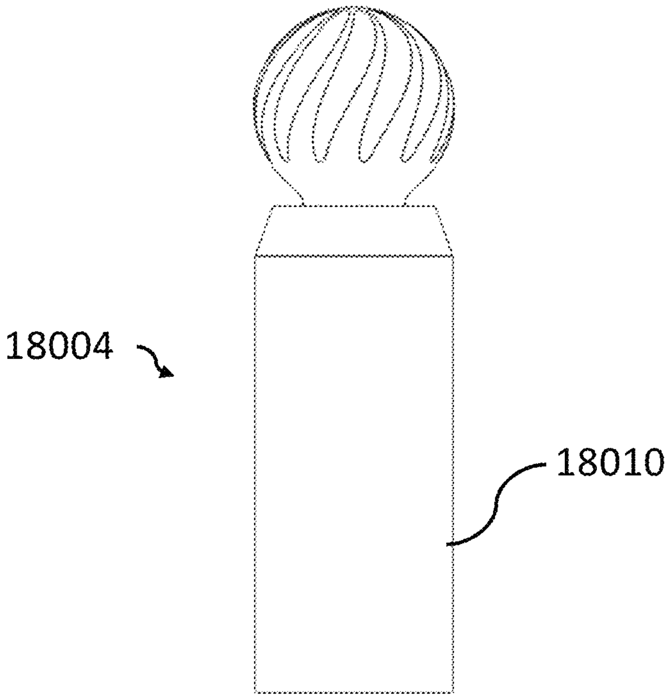
Figure 182A:
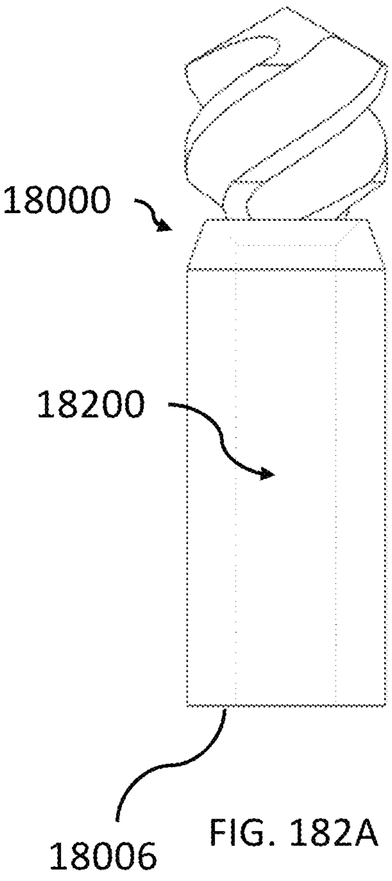
Figure 182B:
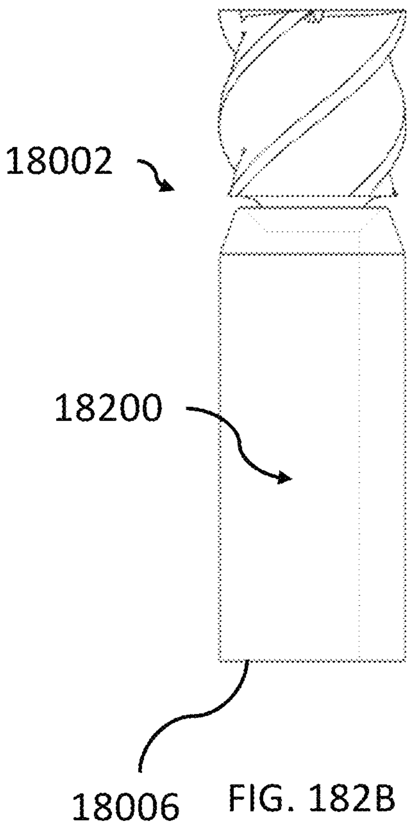
Figure 182C:
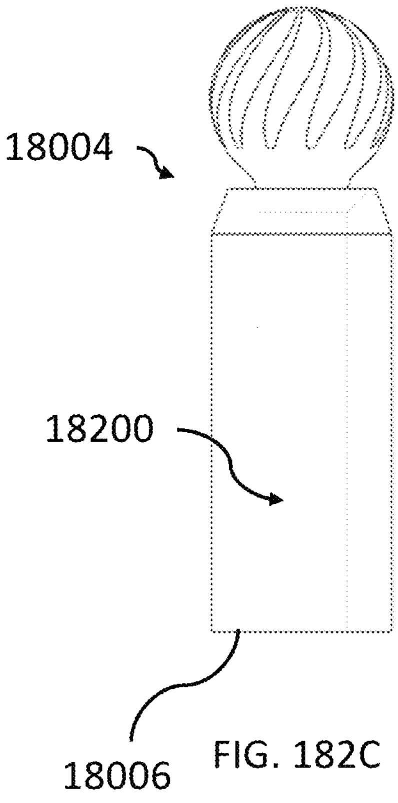
Figure 183A:
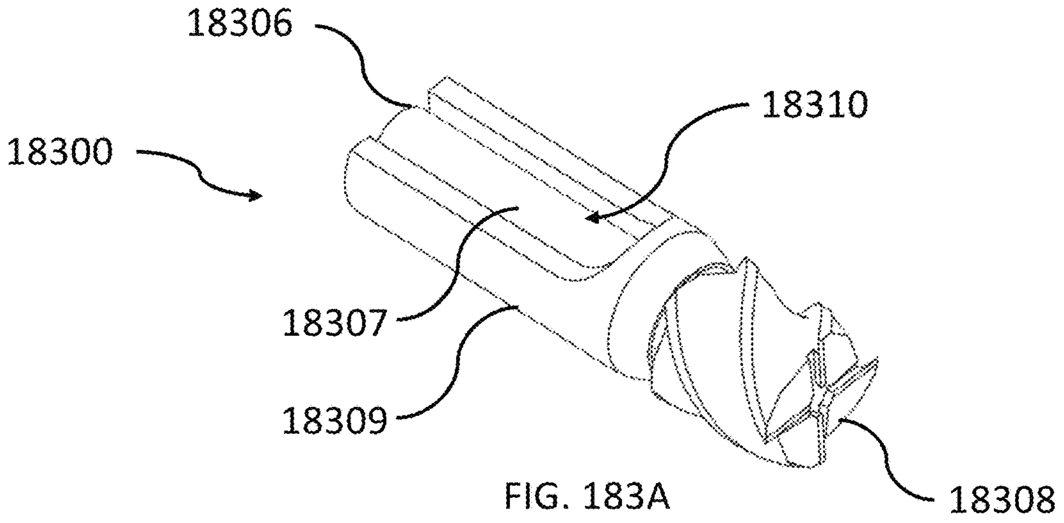
Figure 183B:
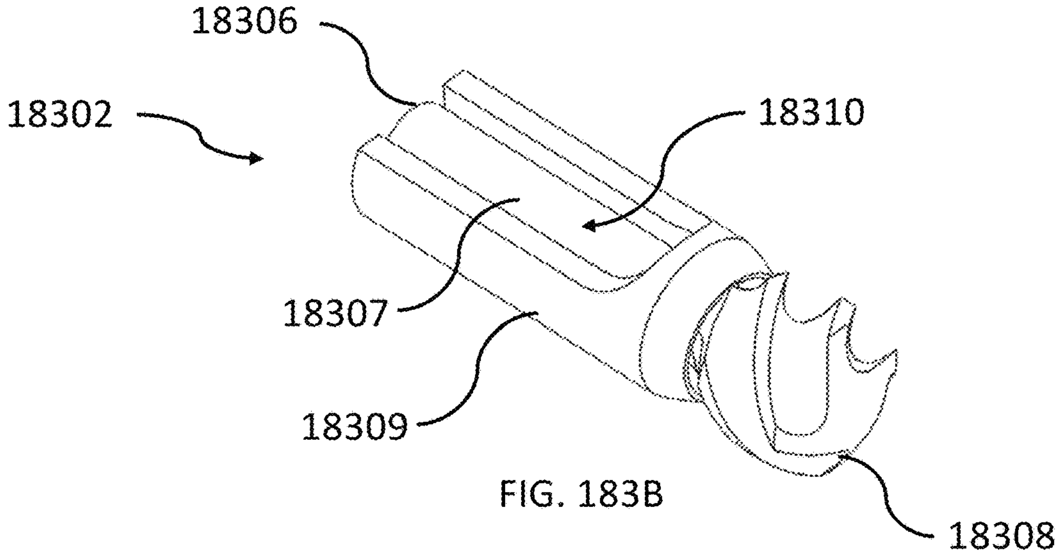
Figure 183C:
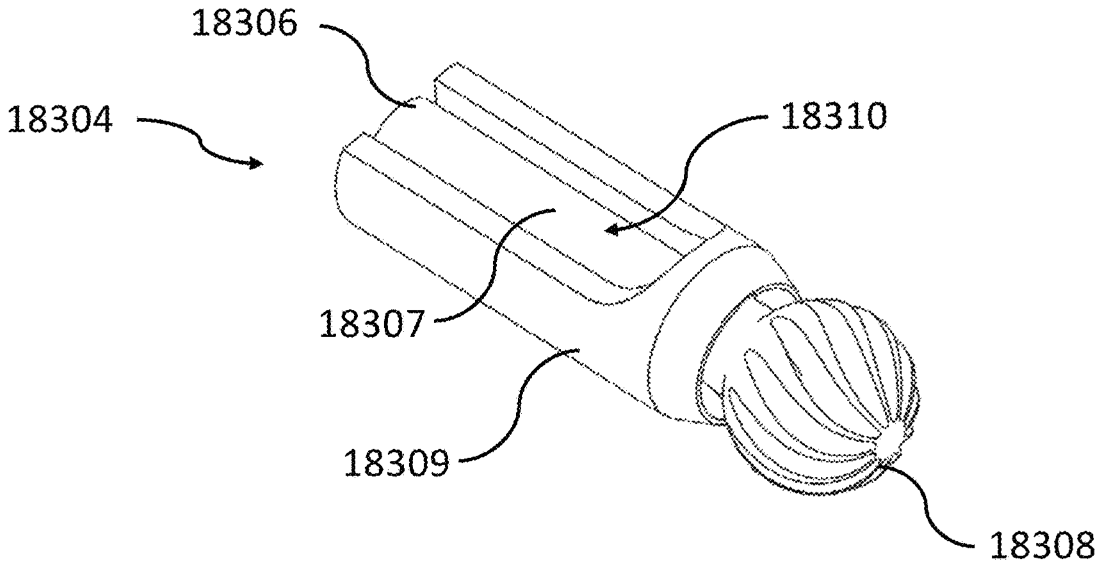
Figure 184A:
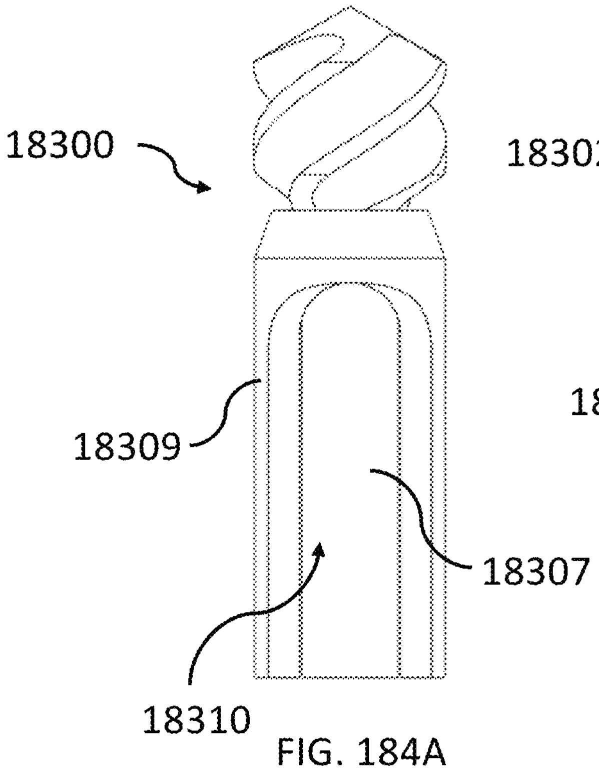
Figure 184B:
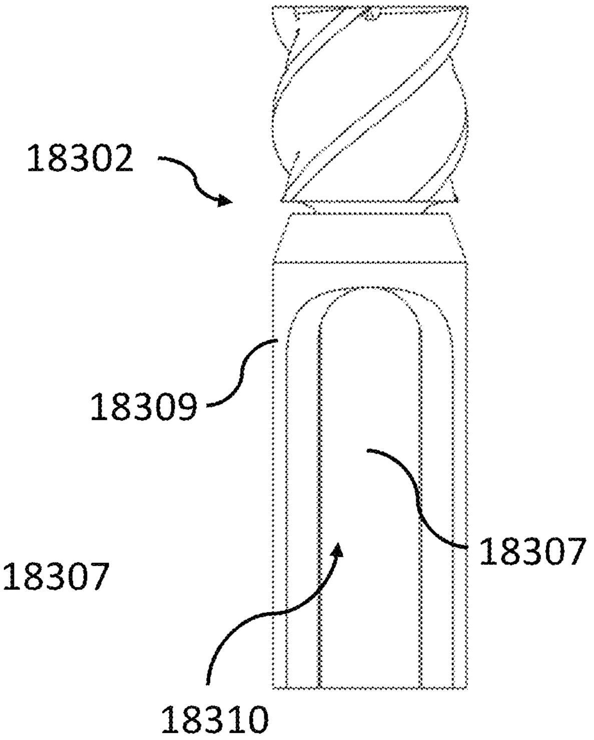
Figure 184C:
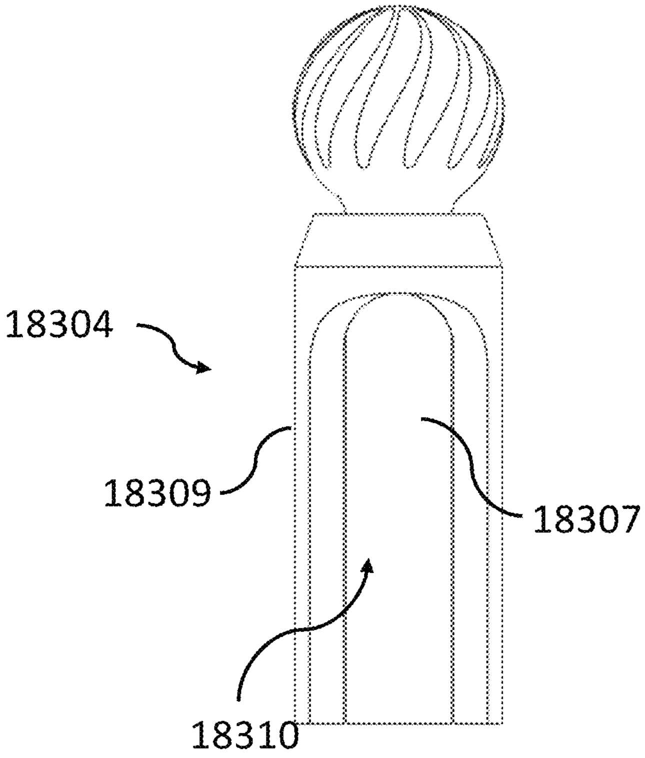
Figure 185:
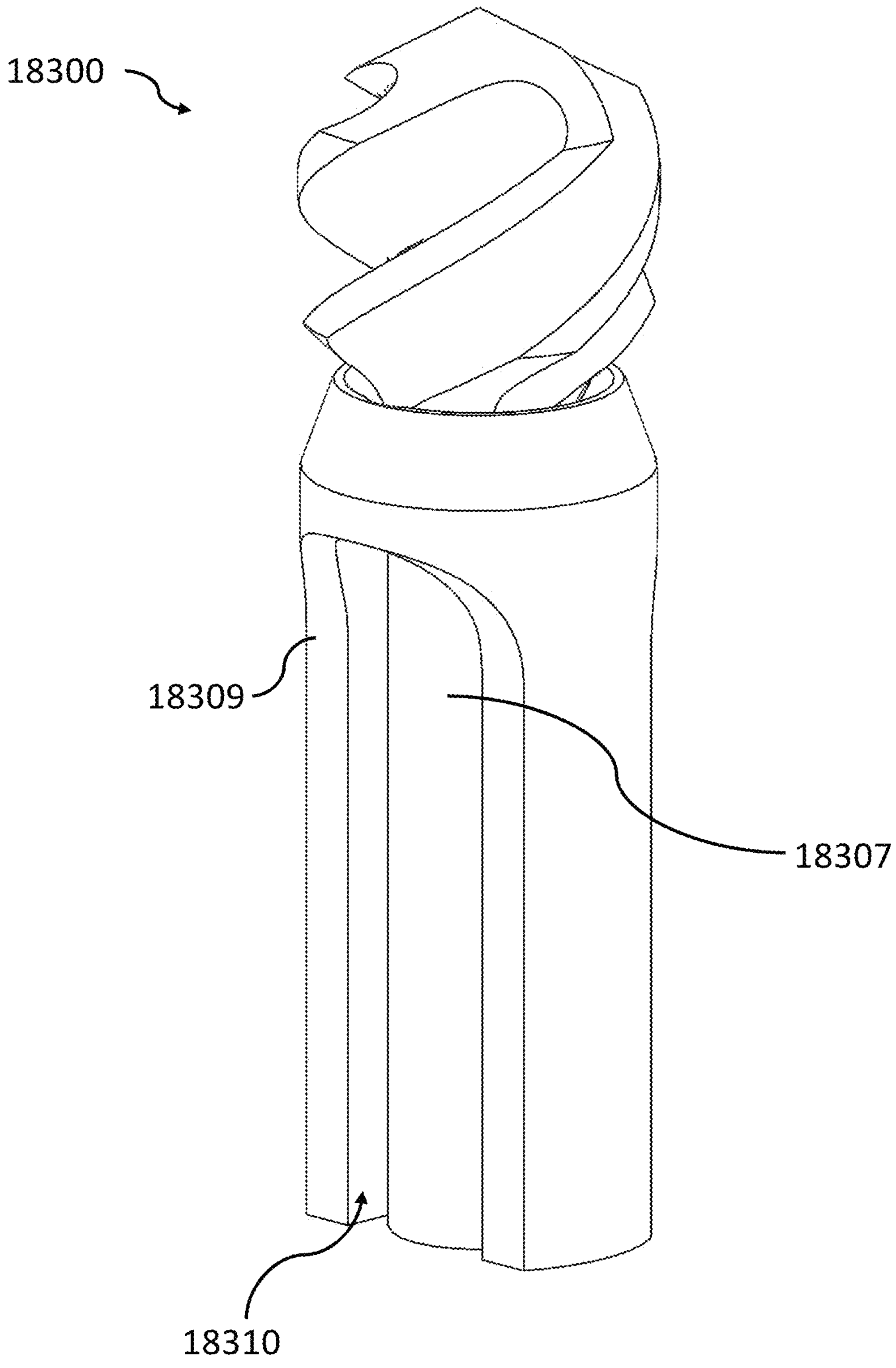
Figure 186:
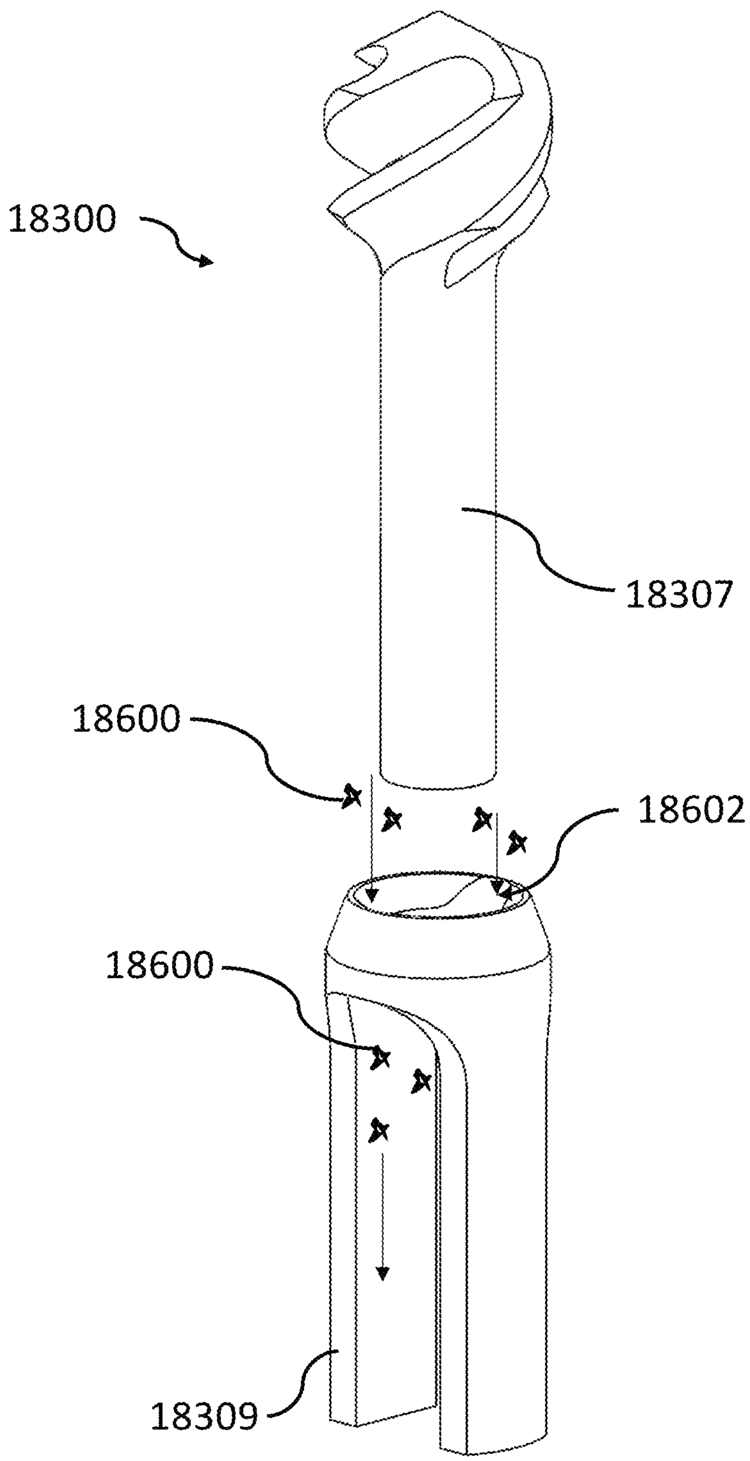
Figure 187:
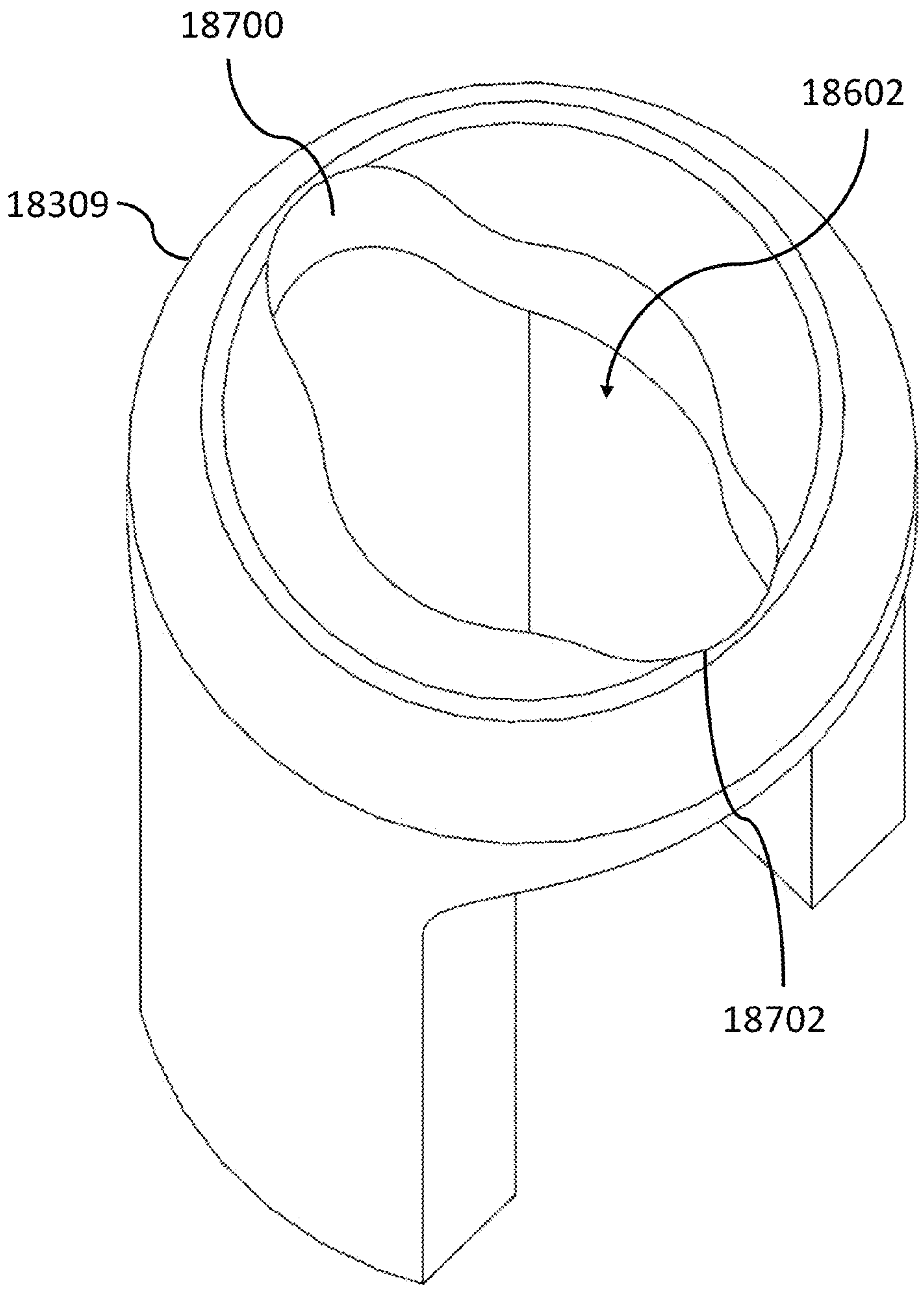
Figures 188A, 188B, 188C:
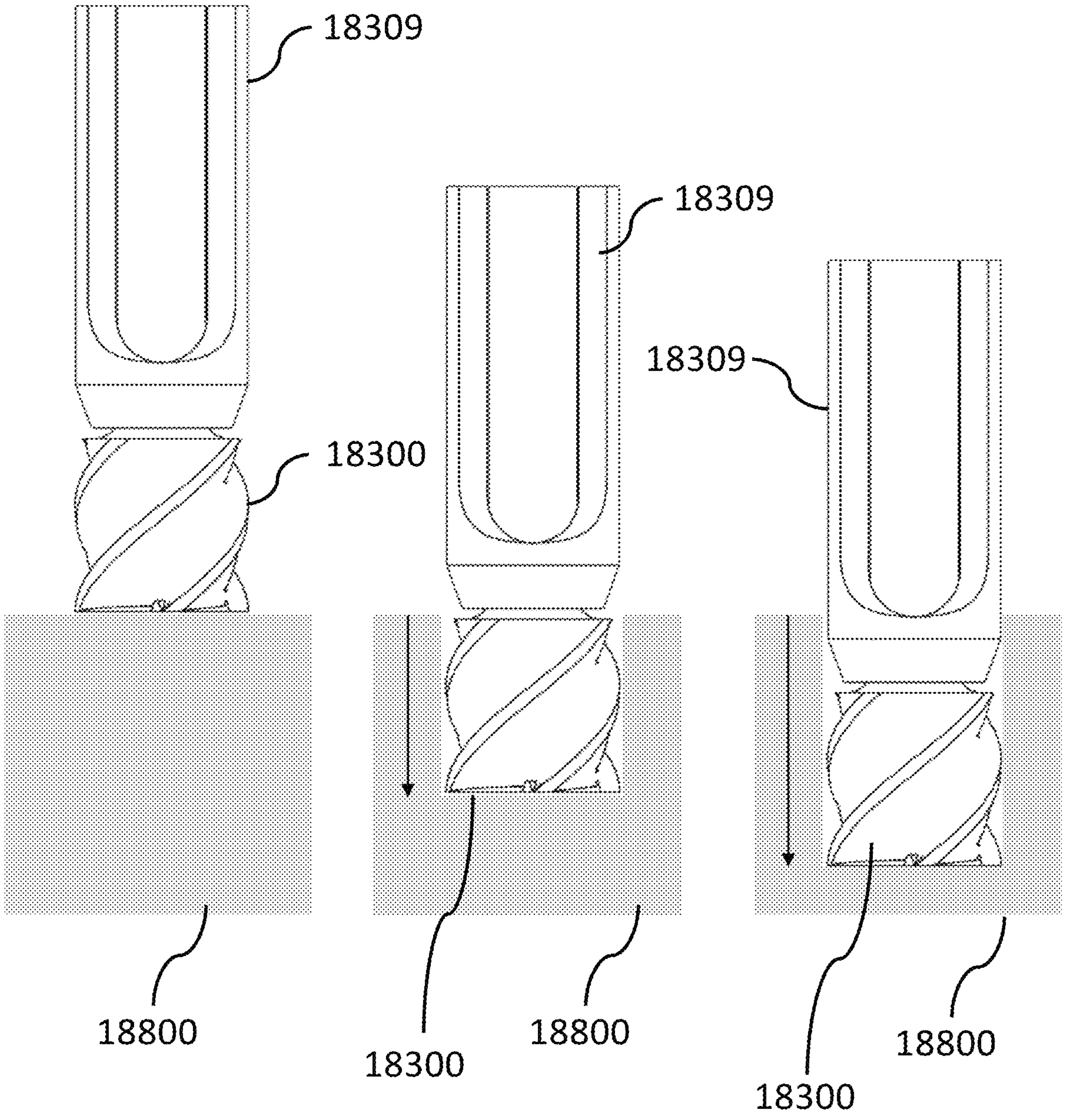
Figure 189A:
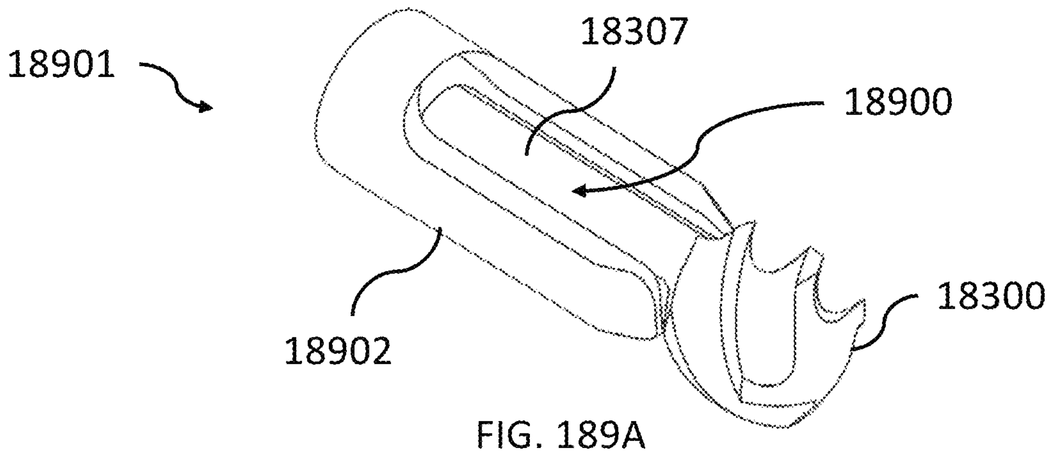
Figure 189B:
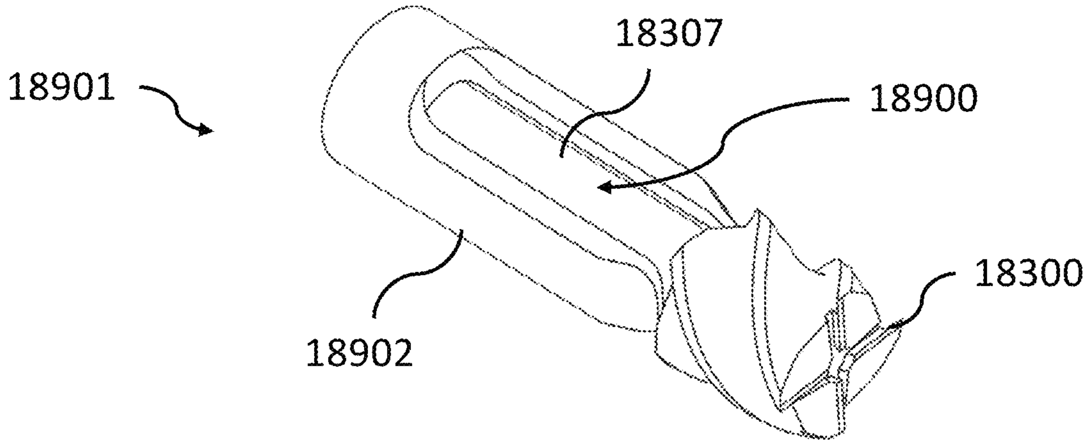
Figure 189C:
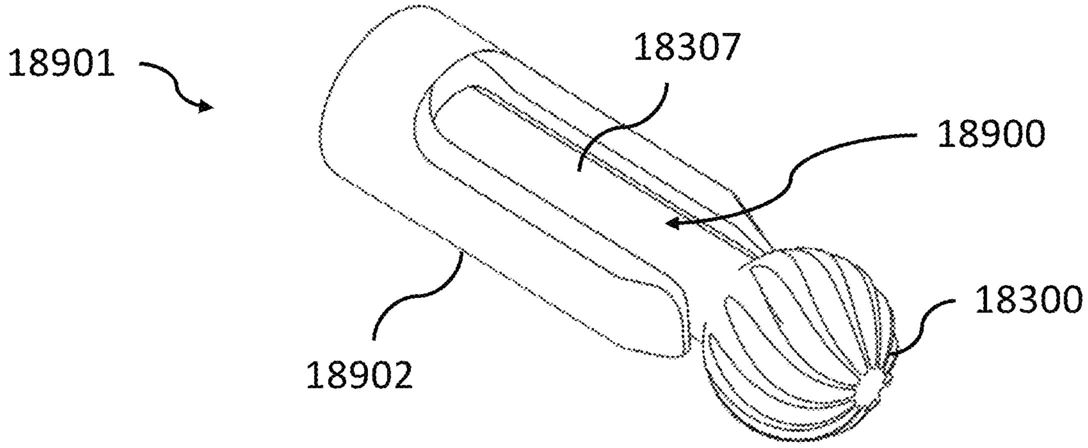
Figure 190A:
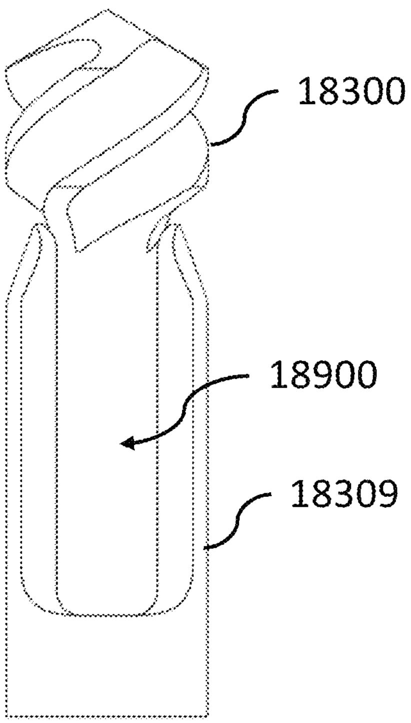
Figure 190B:
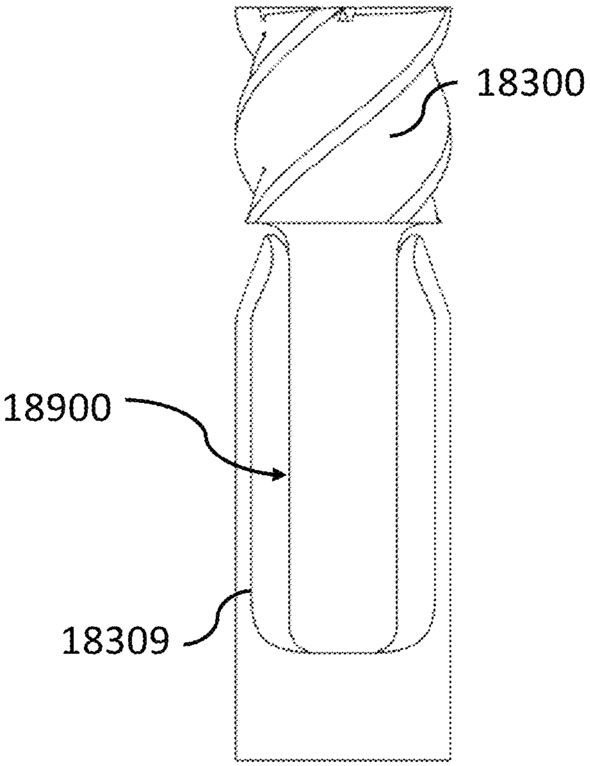
Figure 190C:
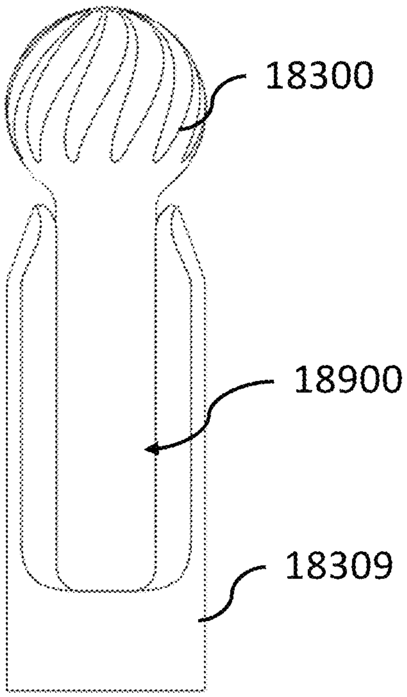
Figure 191:
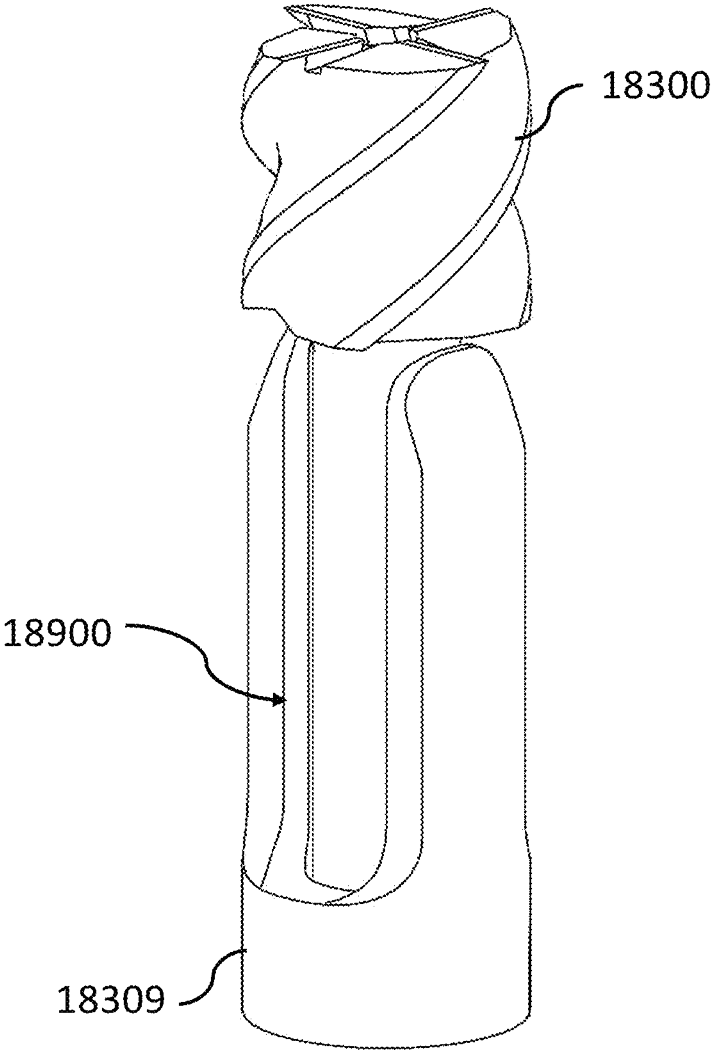
Figure 192:
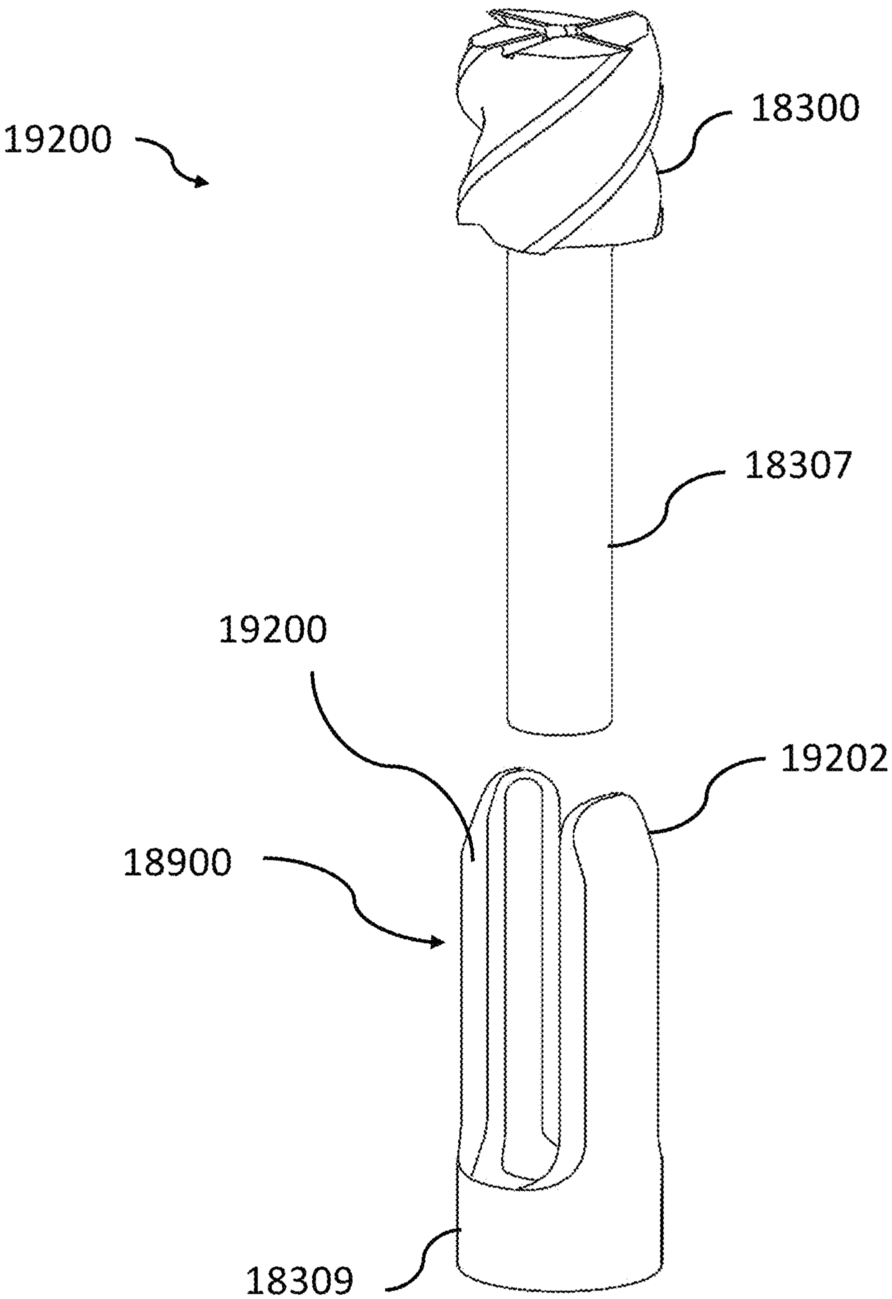
Figure 193:
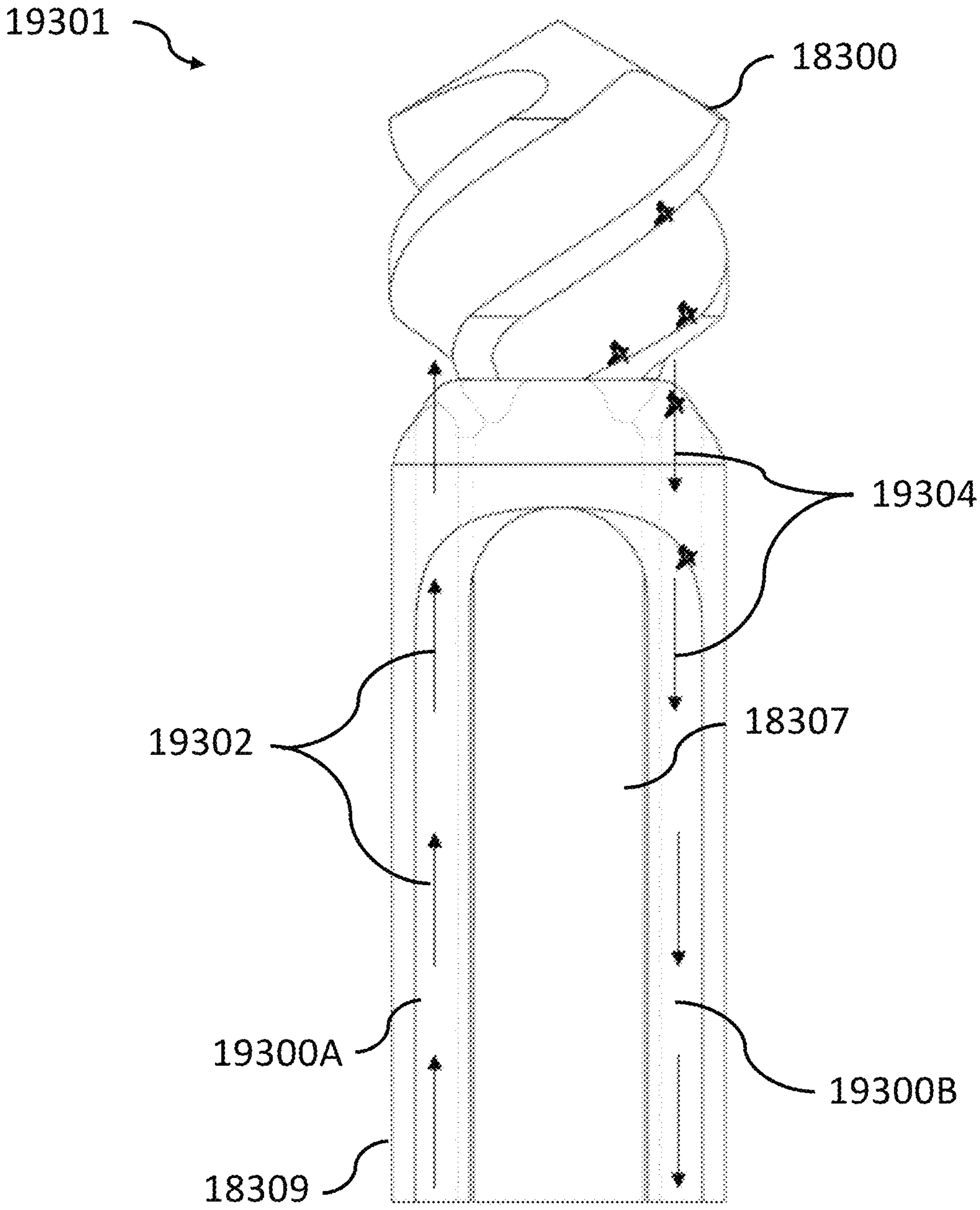
Figure 194A:
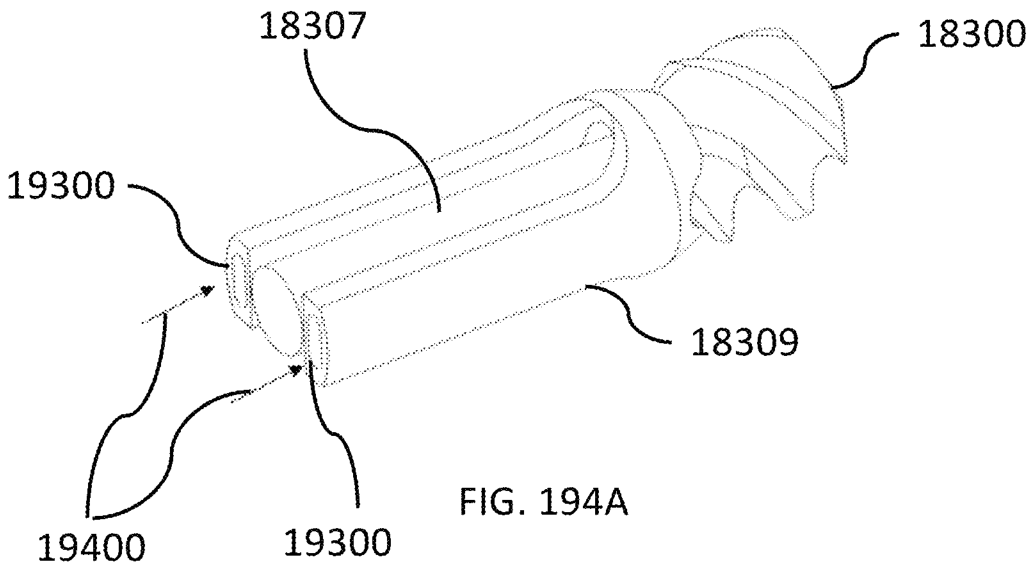
Figure 194B:
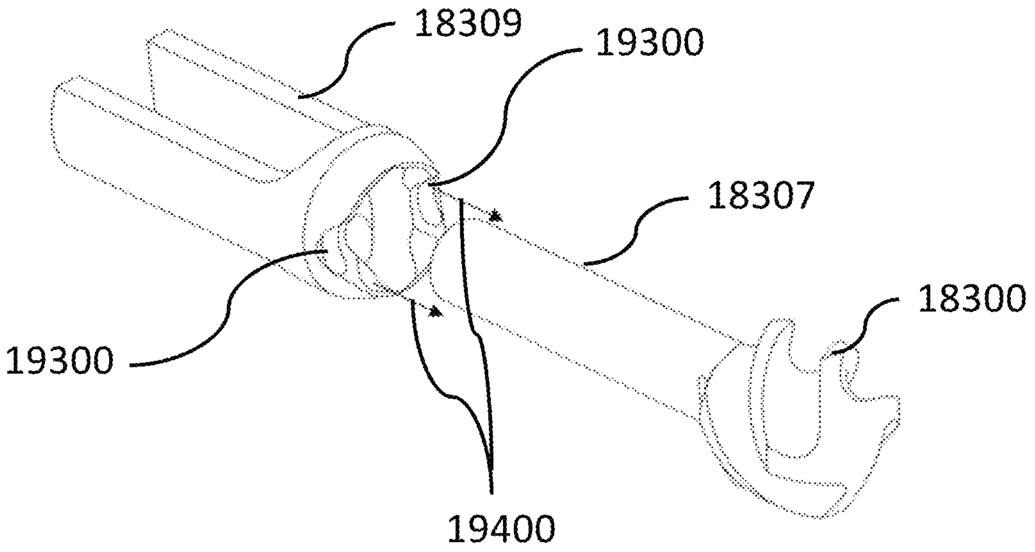
Figure 195:
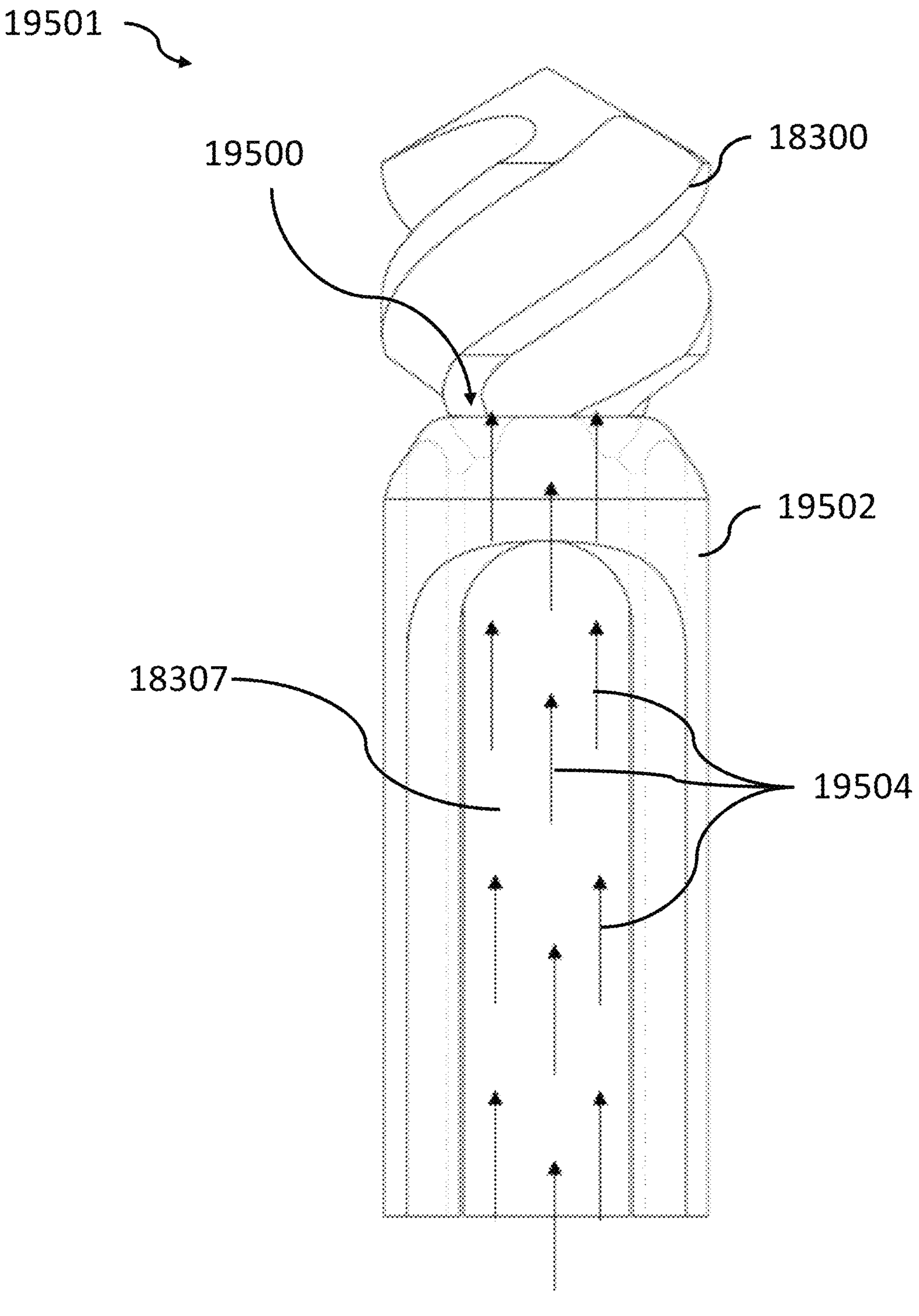
Figure 196:
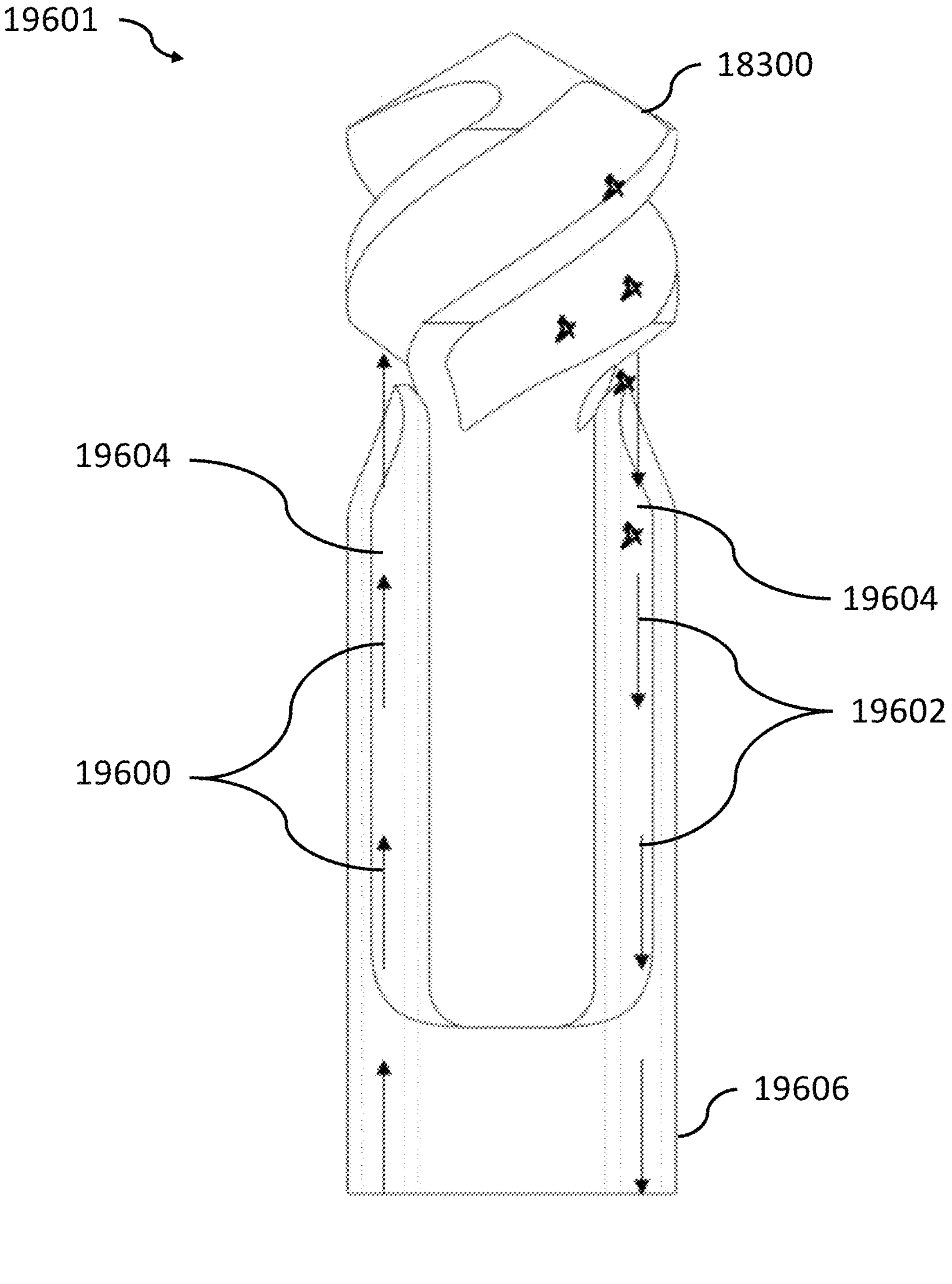
Figure 197A:
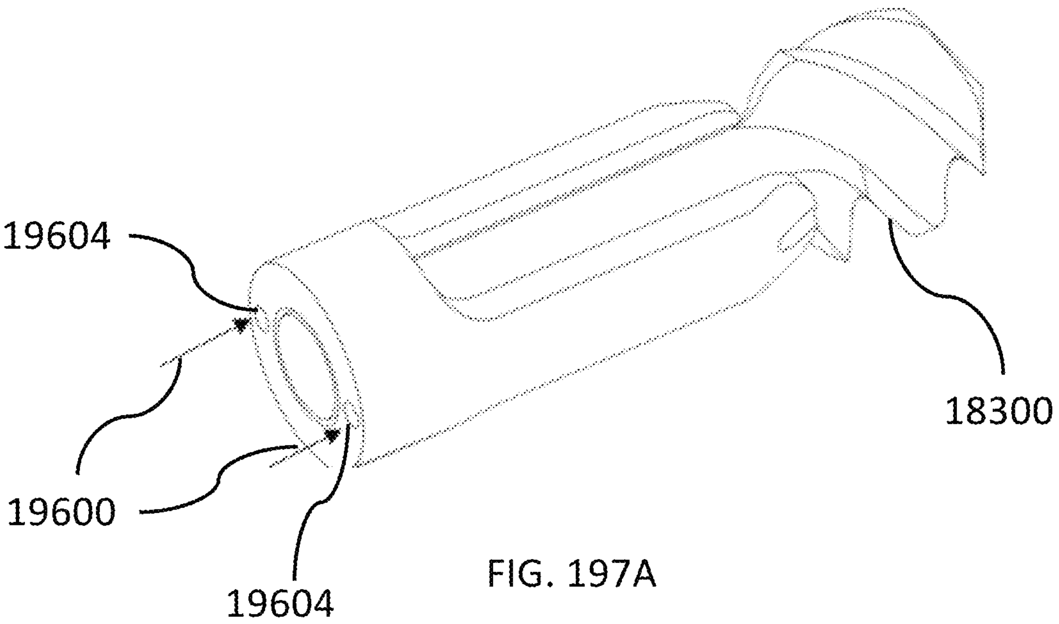
Figure 197B:
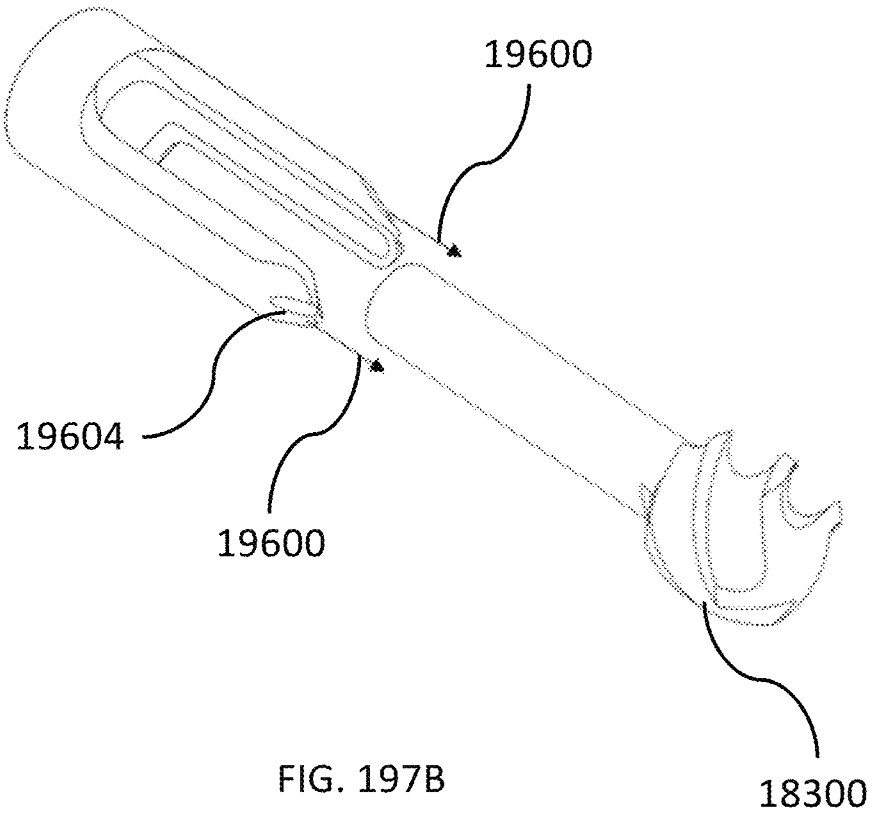
Figure 198A:
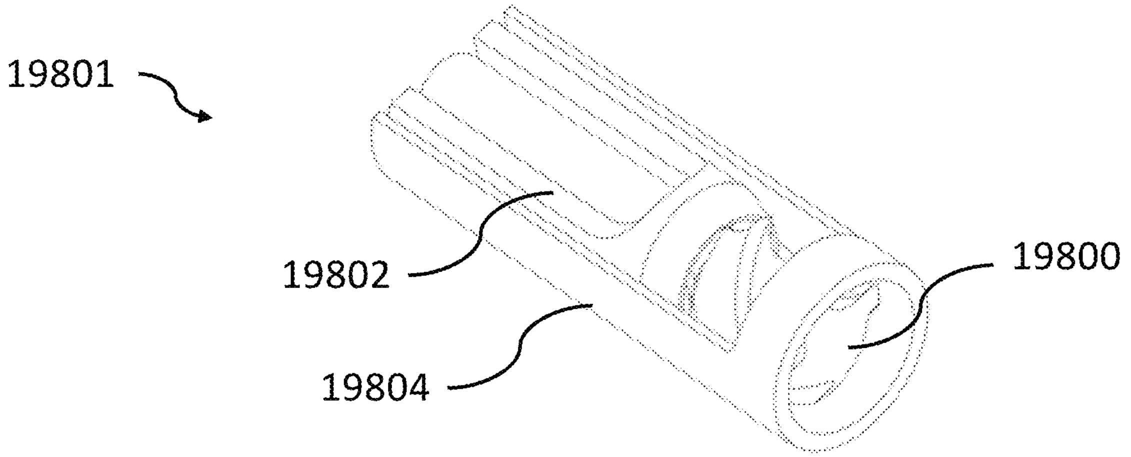
Figure 198B:
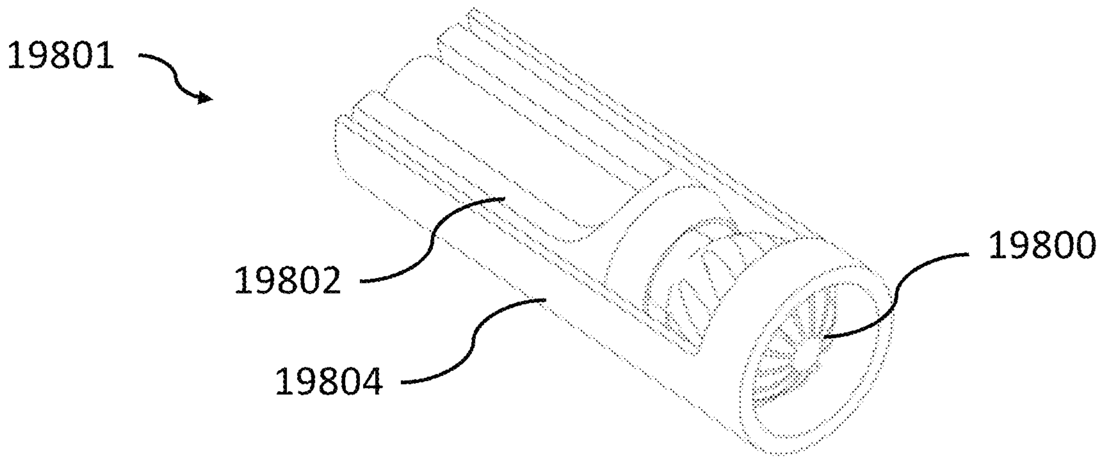
Figure 198C:
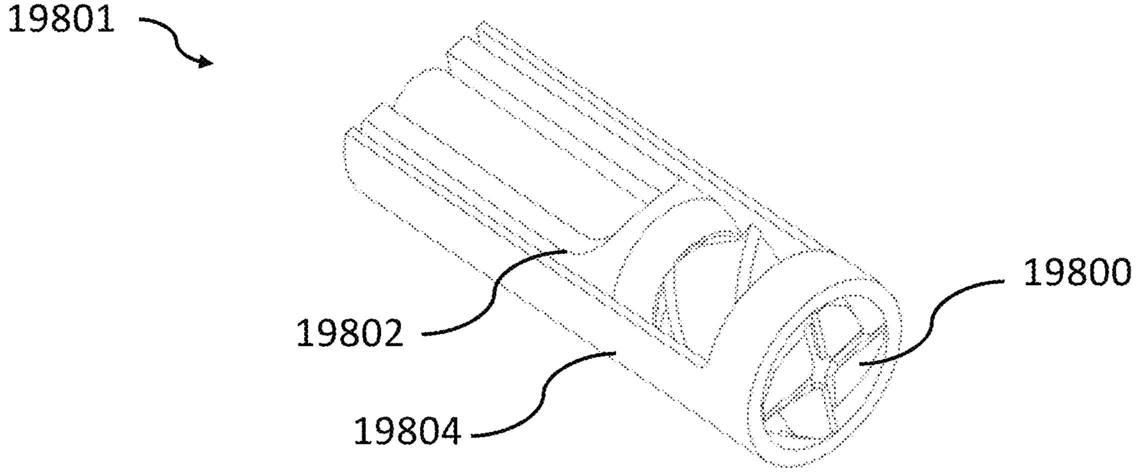
Figure 199A:
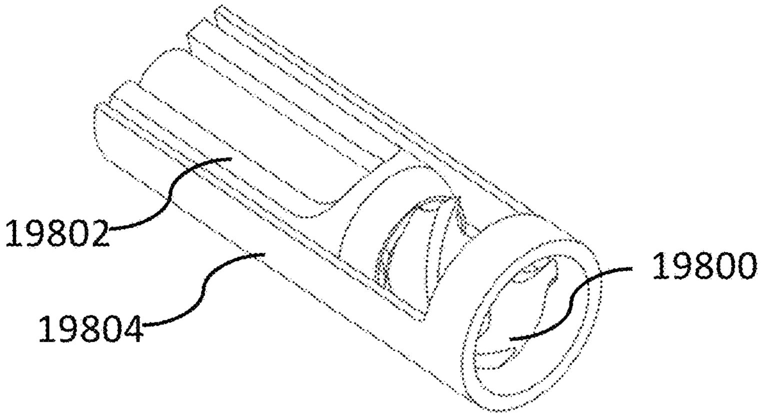
Figure 199B:
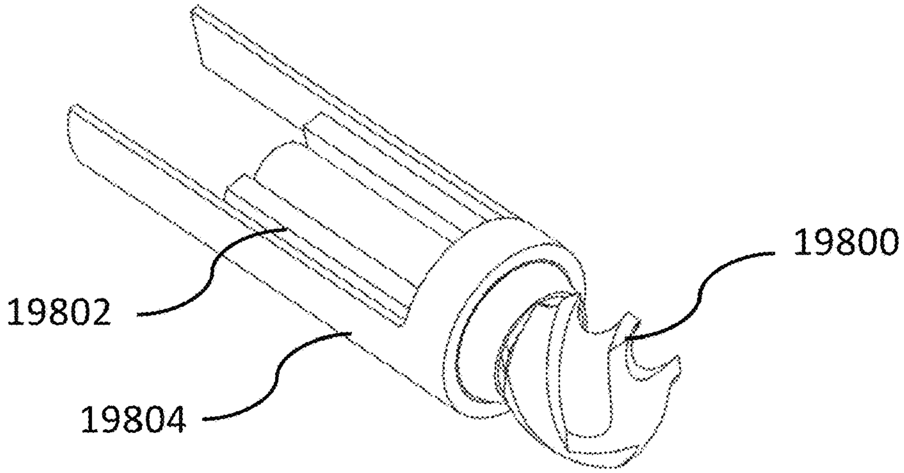
Figure 199C:
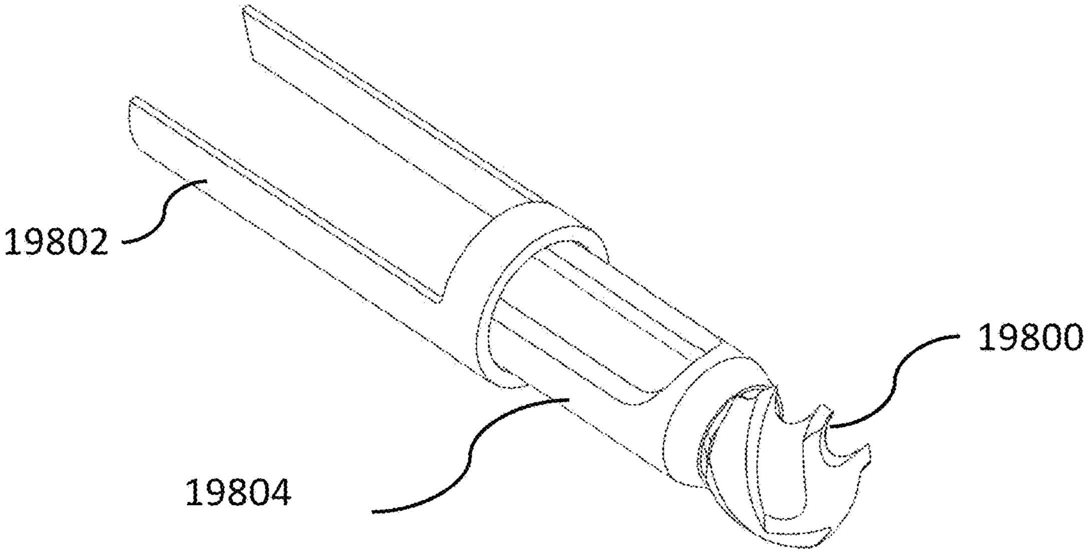
Figure 200A:
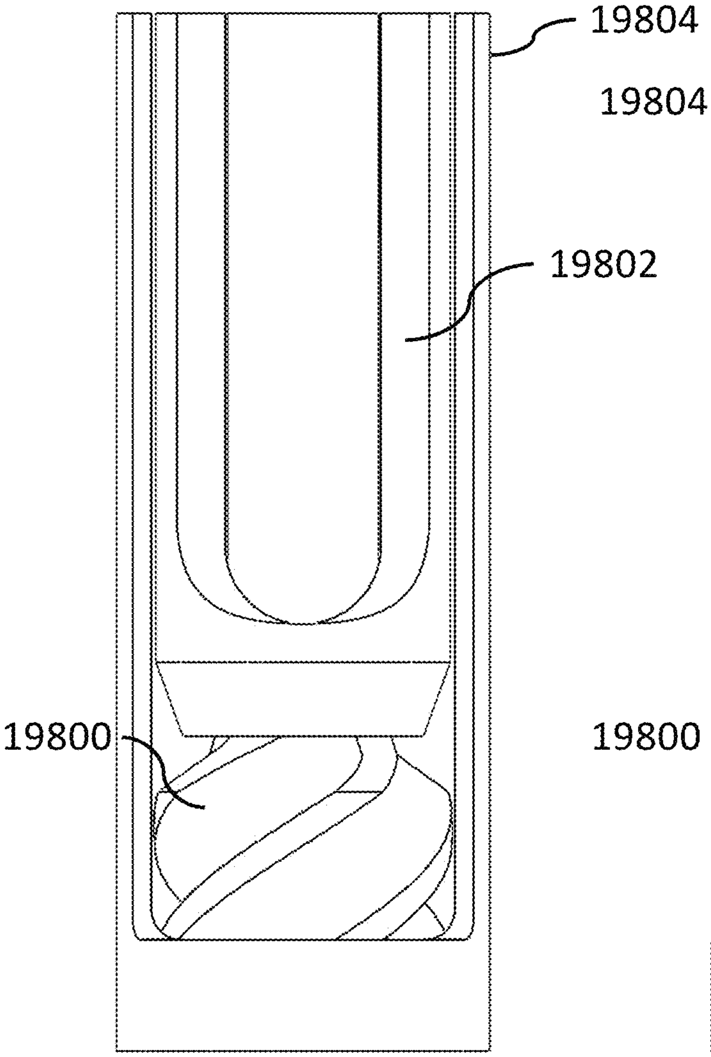
Figure 200B:
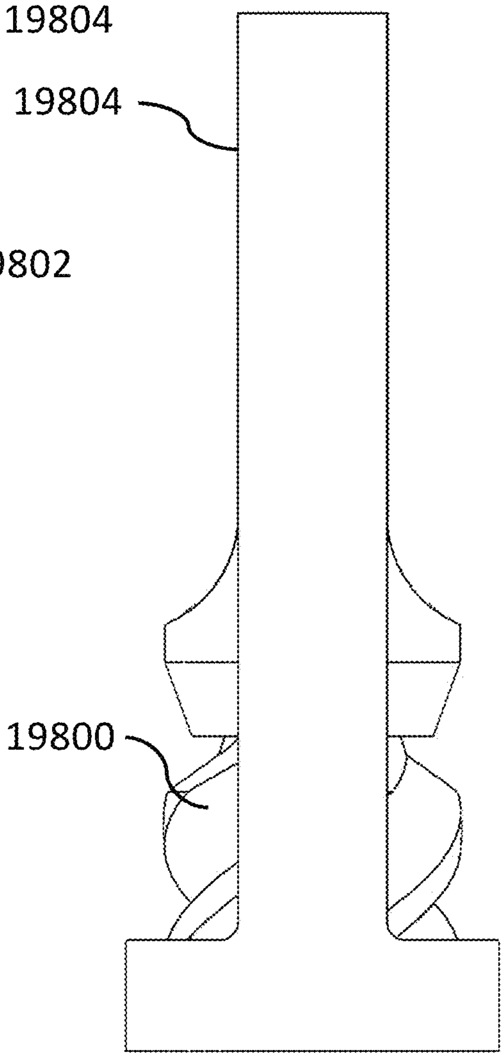
Figures 201A, 201B, 201C:
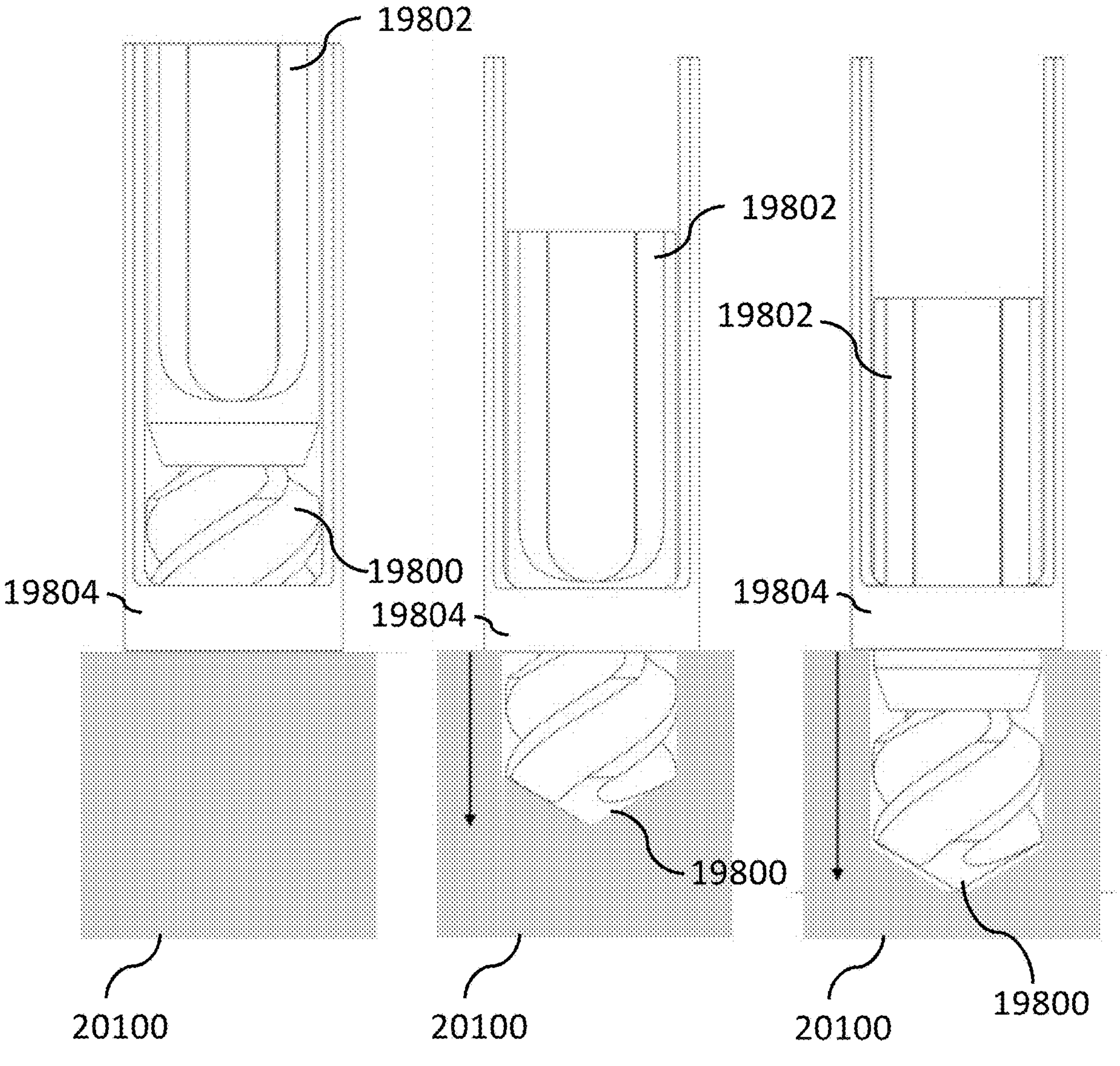
Figure 202:
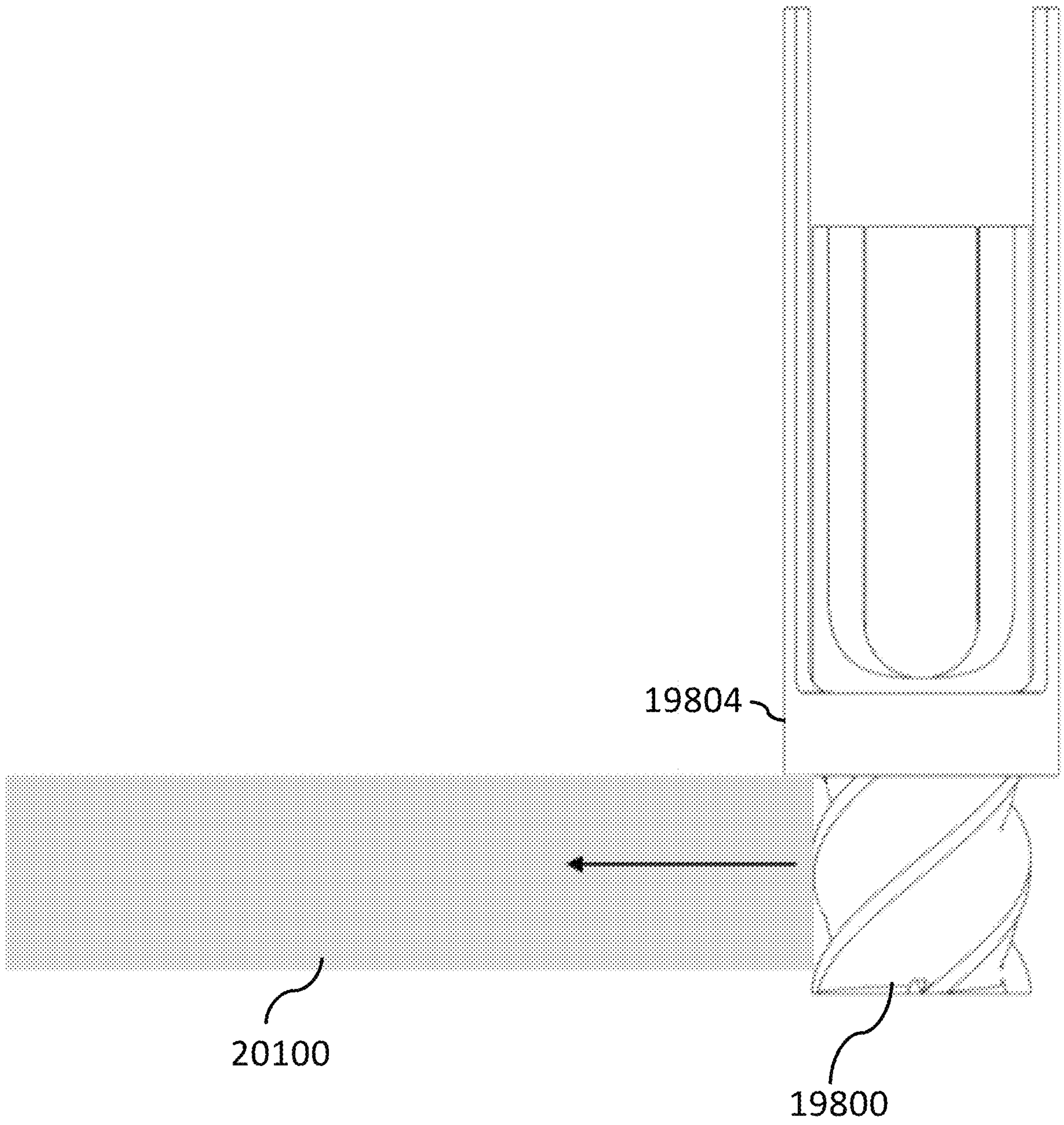
Figure 203A:
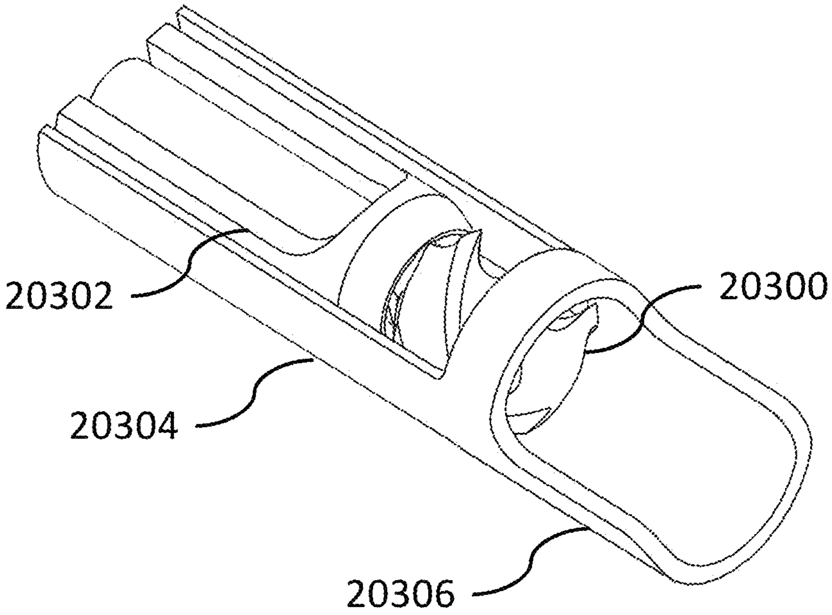
Figure 203B:
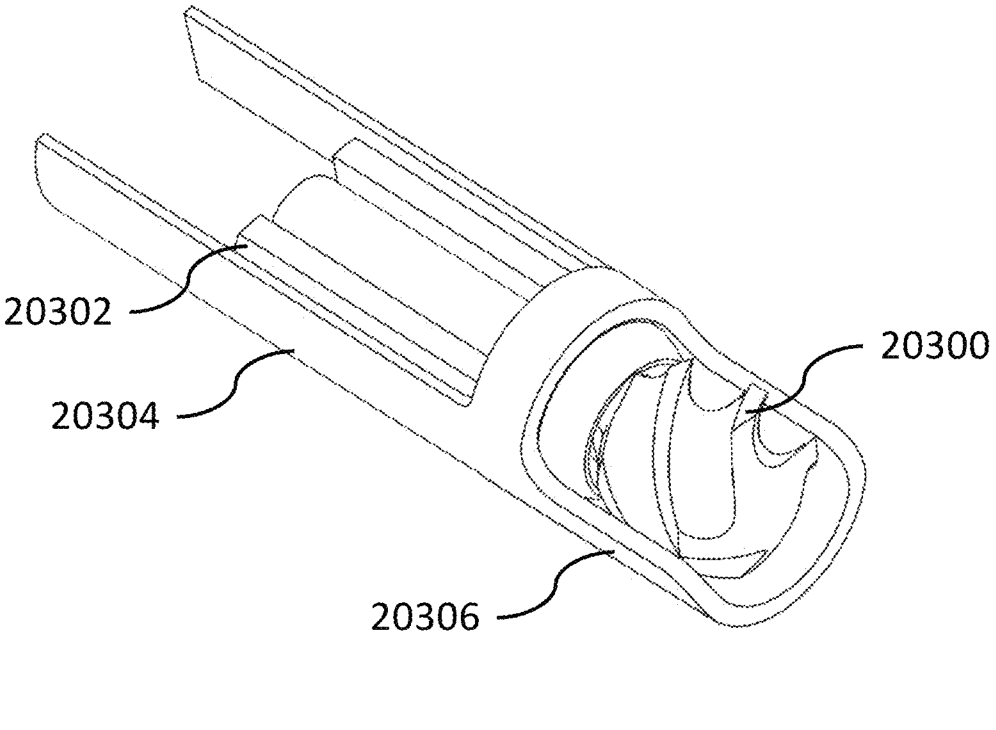
Figure 204A:
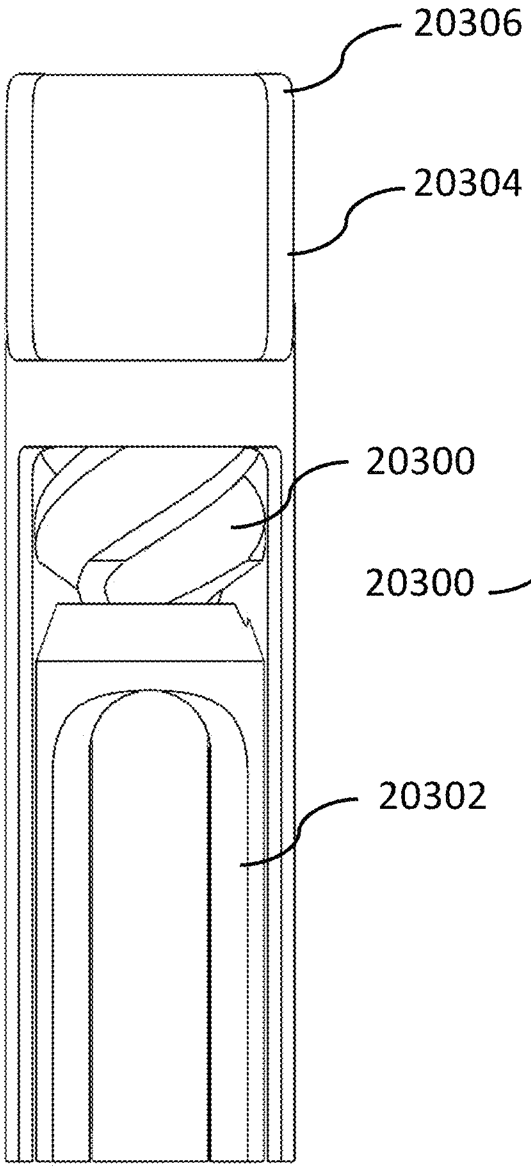
Figure 204B:
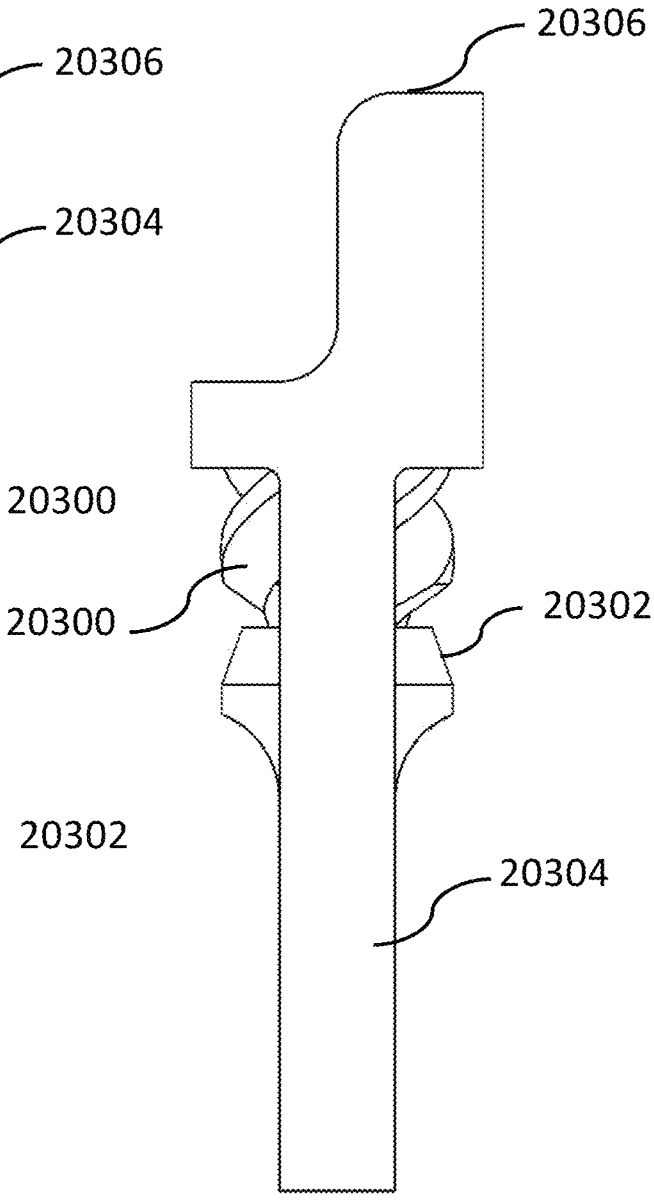
Figure 205:
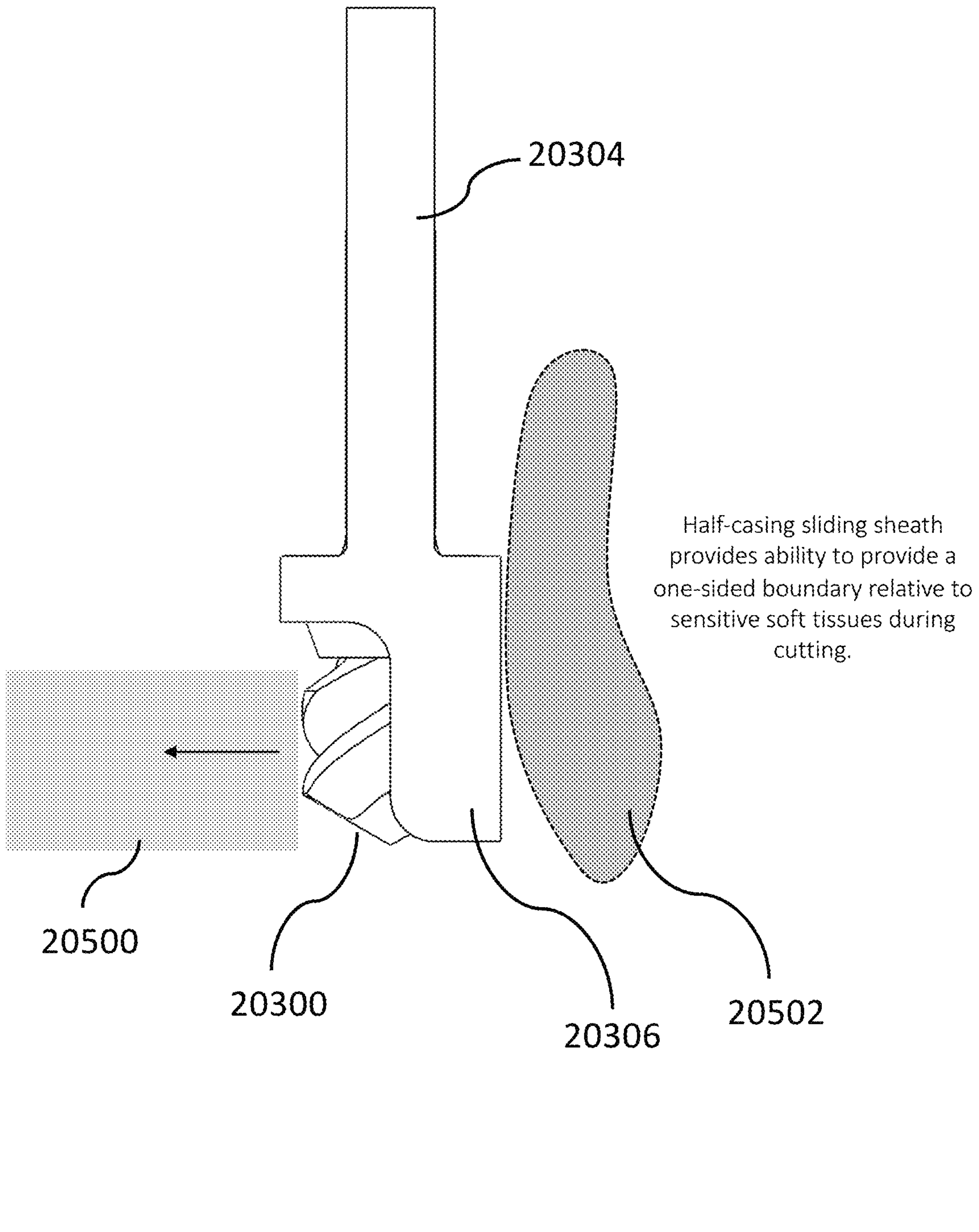
Figure 206A:
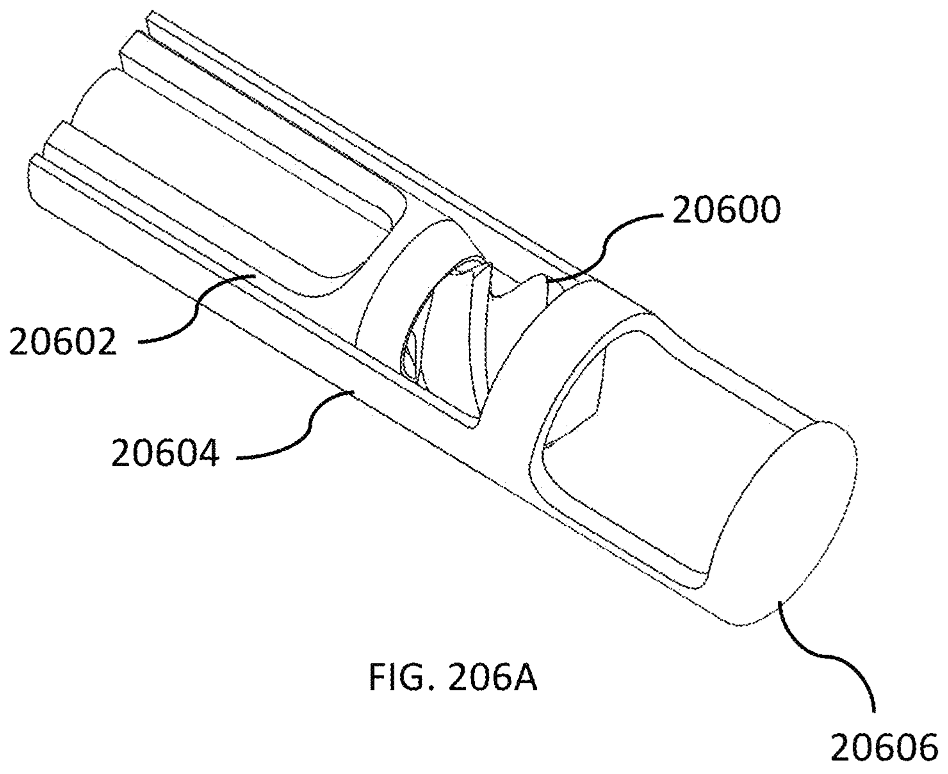
Figure 206B:
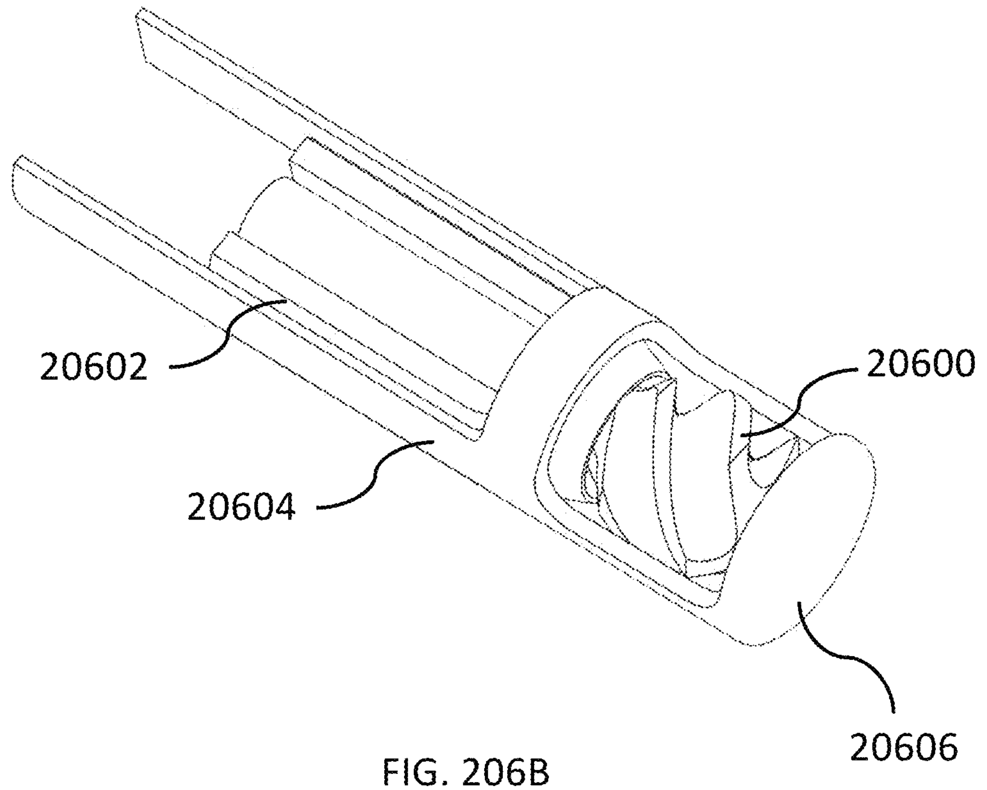
Figure 206C:
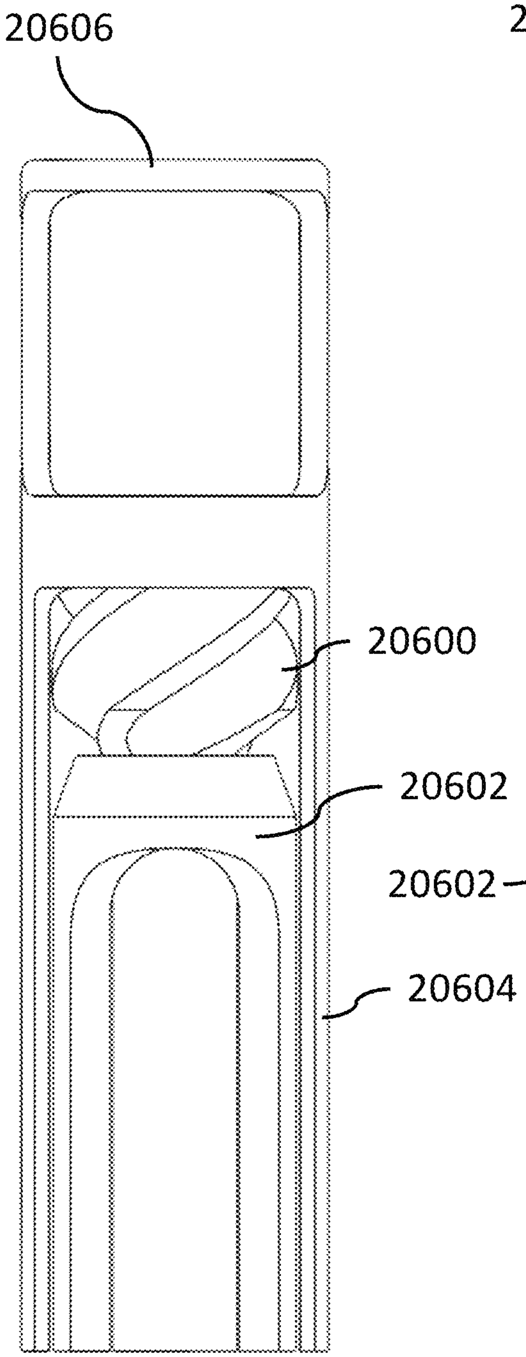
Figure 206D:
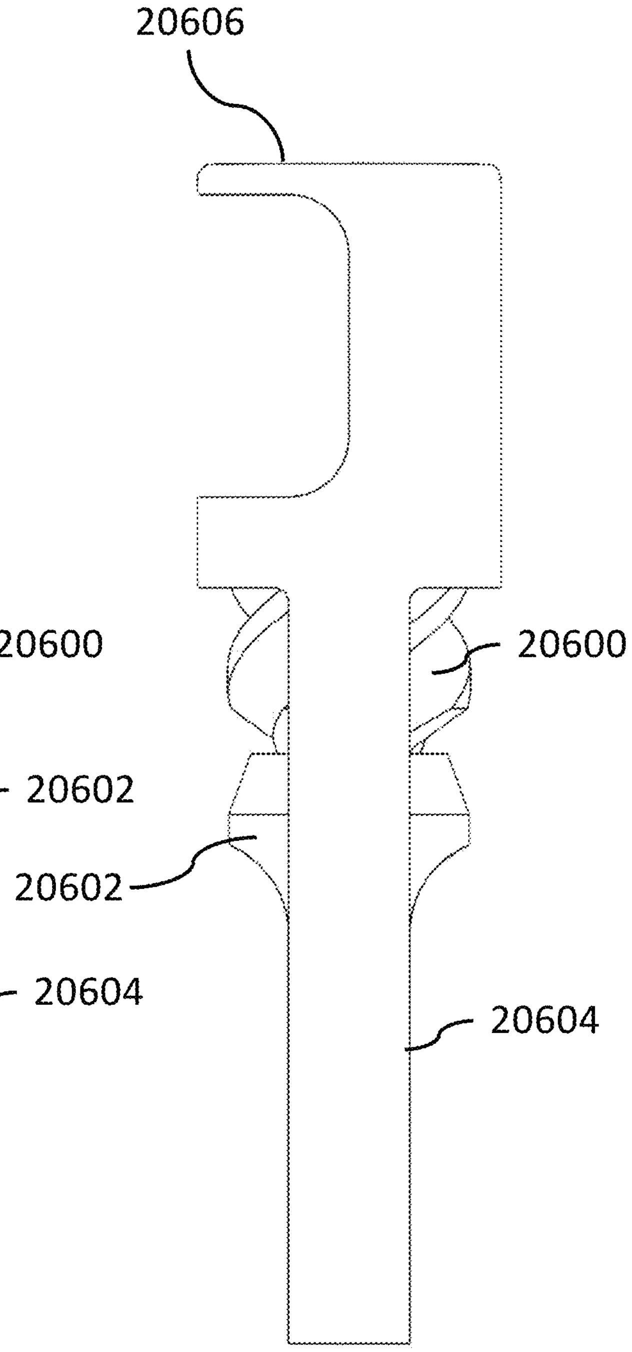
Figure 207A:
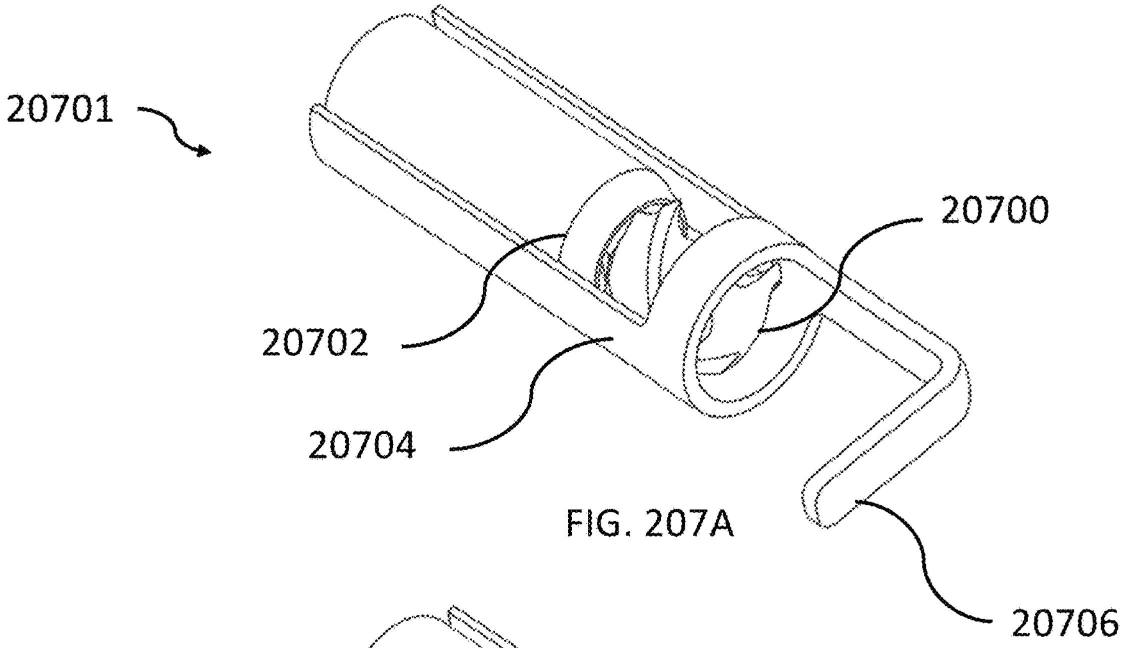
Figure 207B:
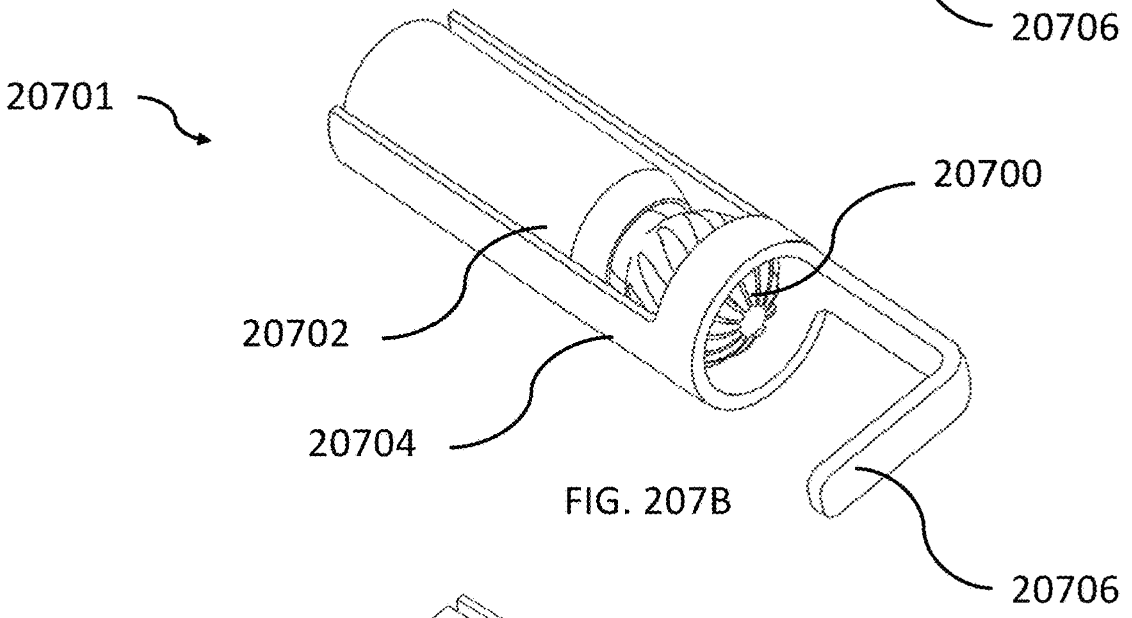
Figure 207C:
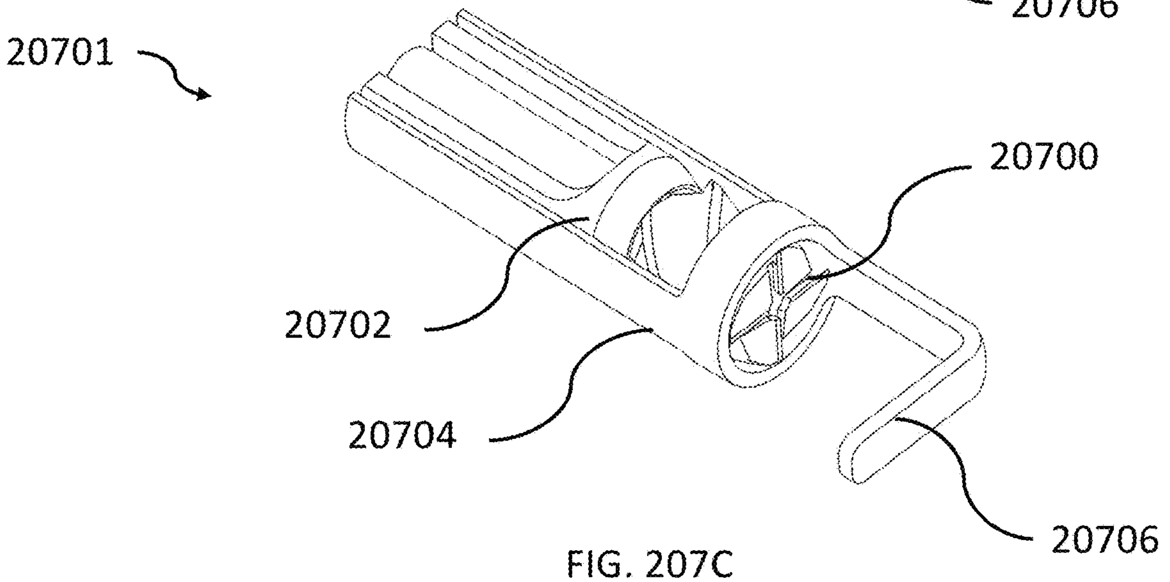
Figure 208A:
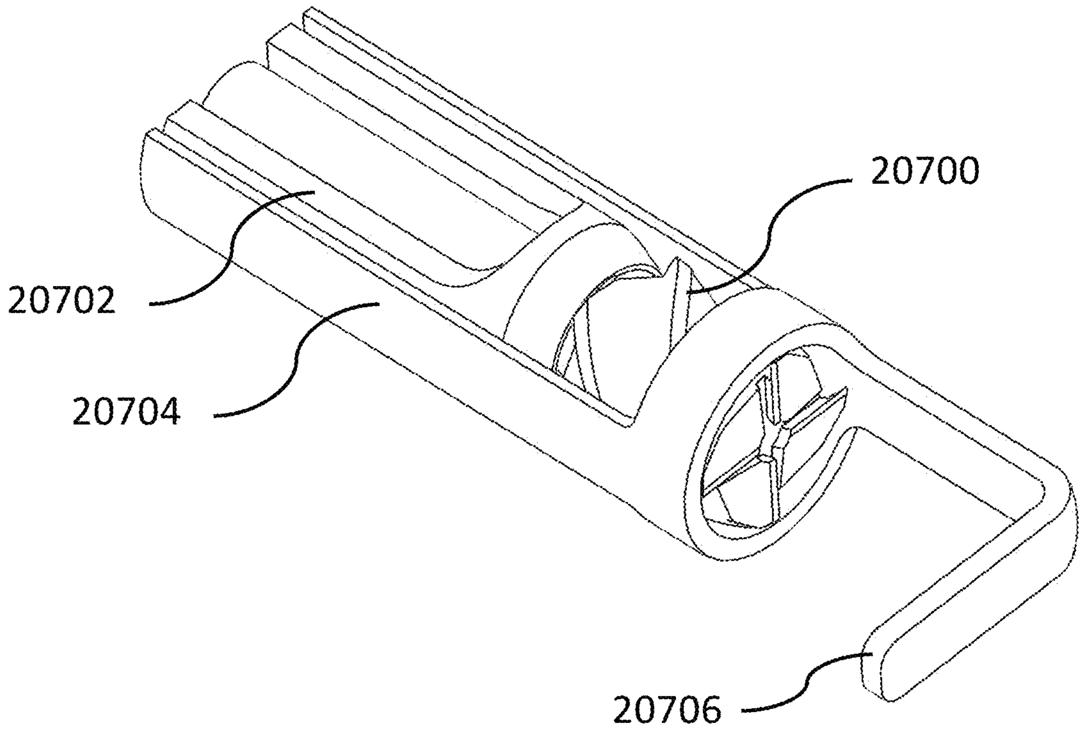
Figure 208B:
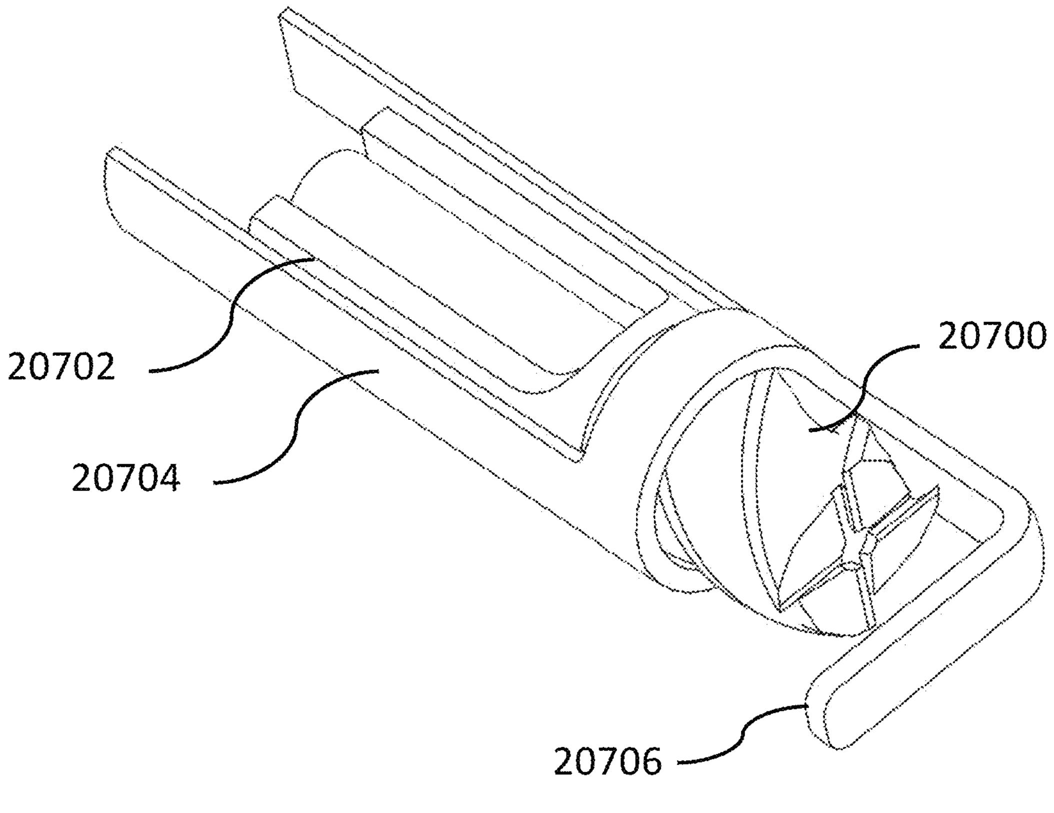
Figure 209A:
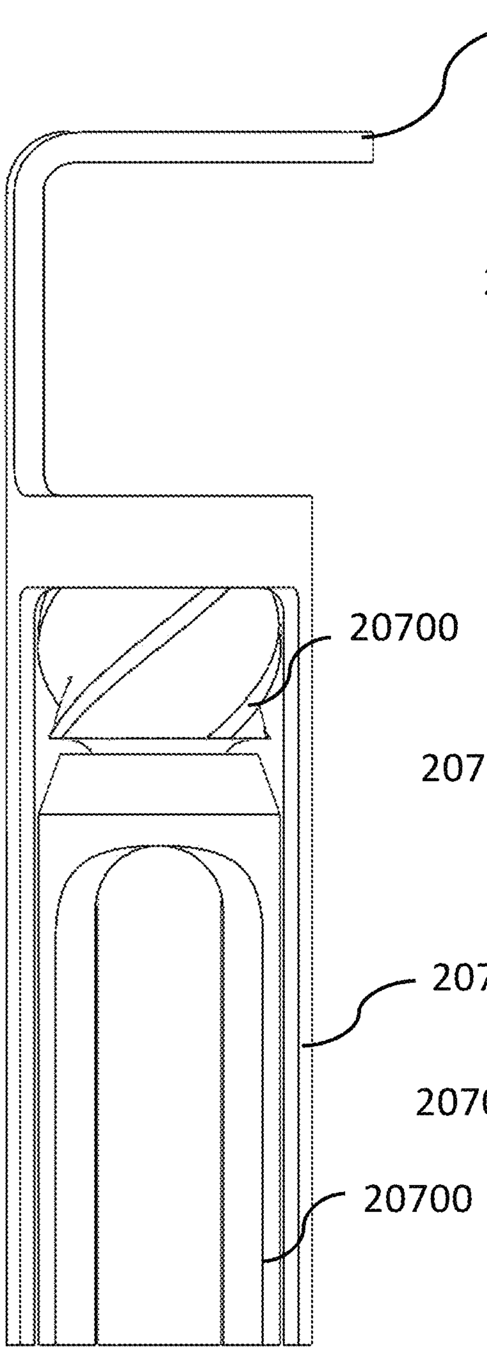
Figure 209B:
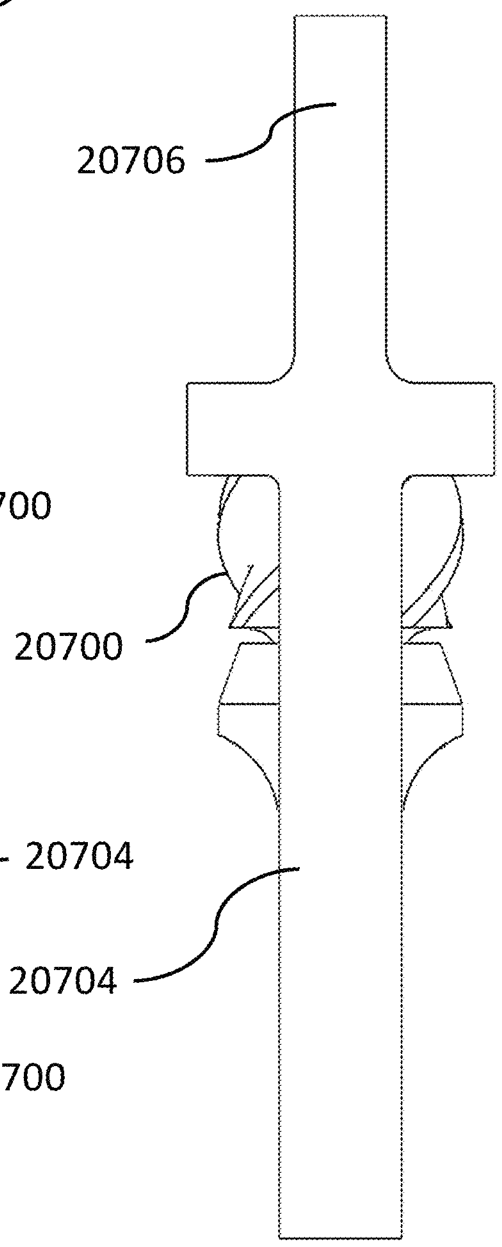
Figure 210A:
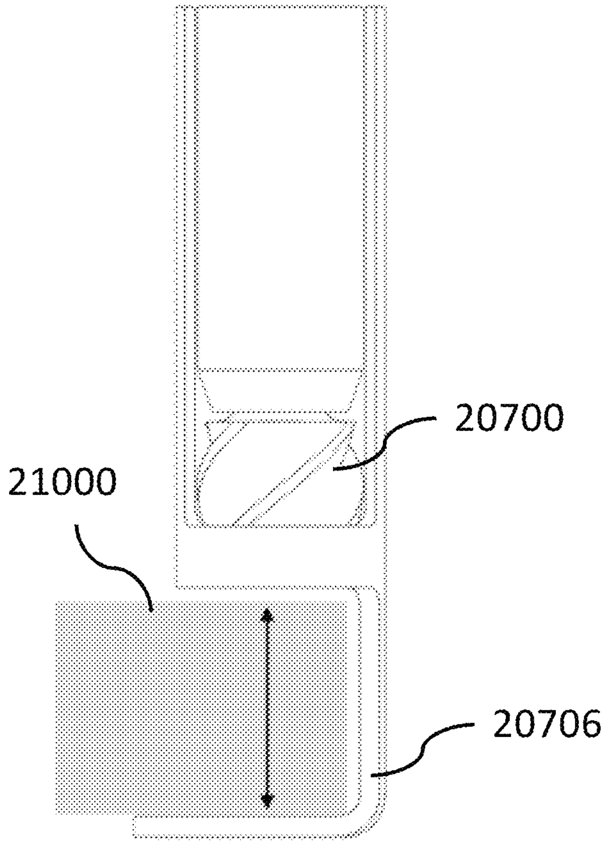
Figure 210B:
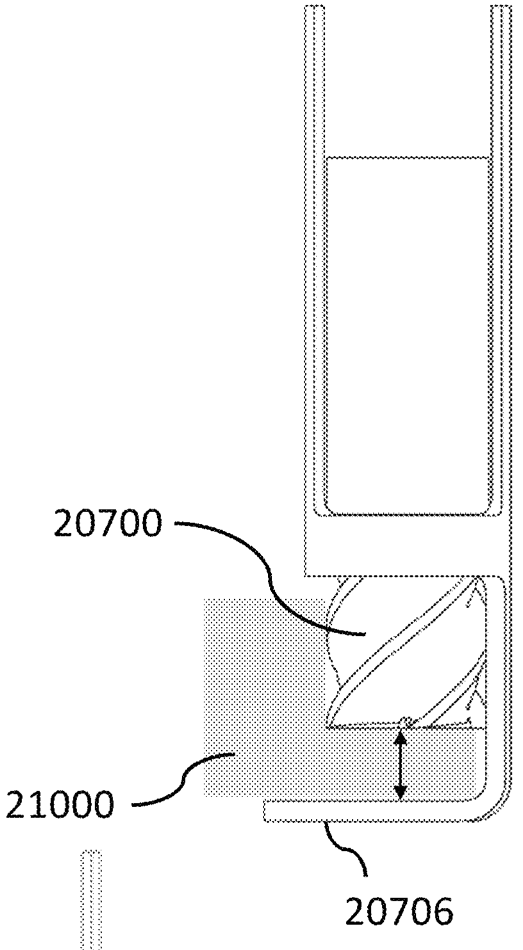
Figure 210C:
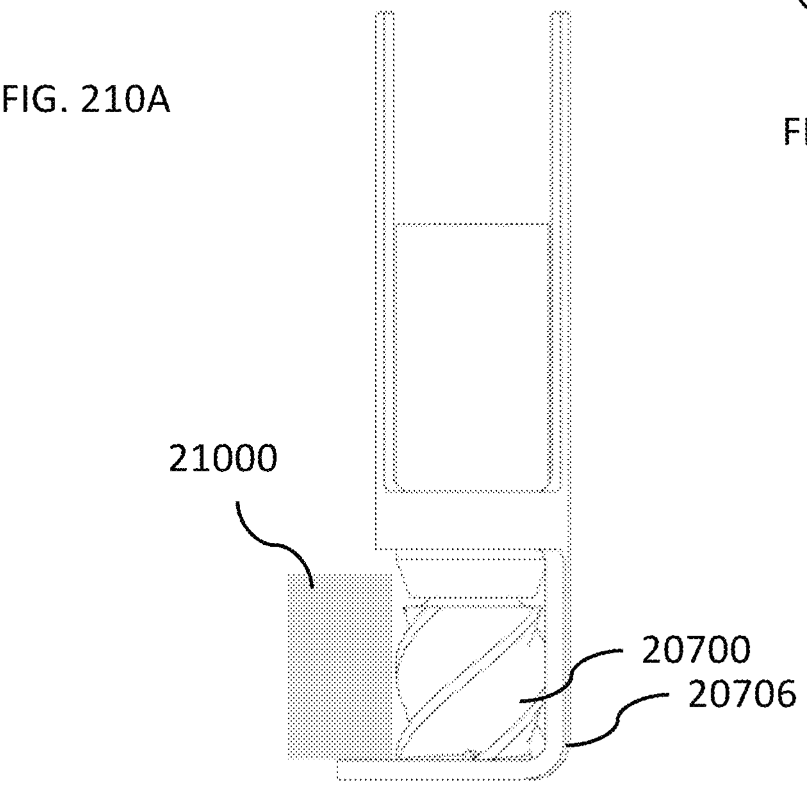
Figure 211:
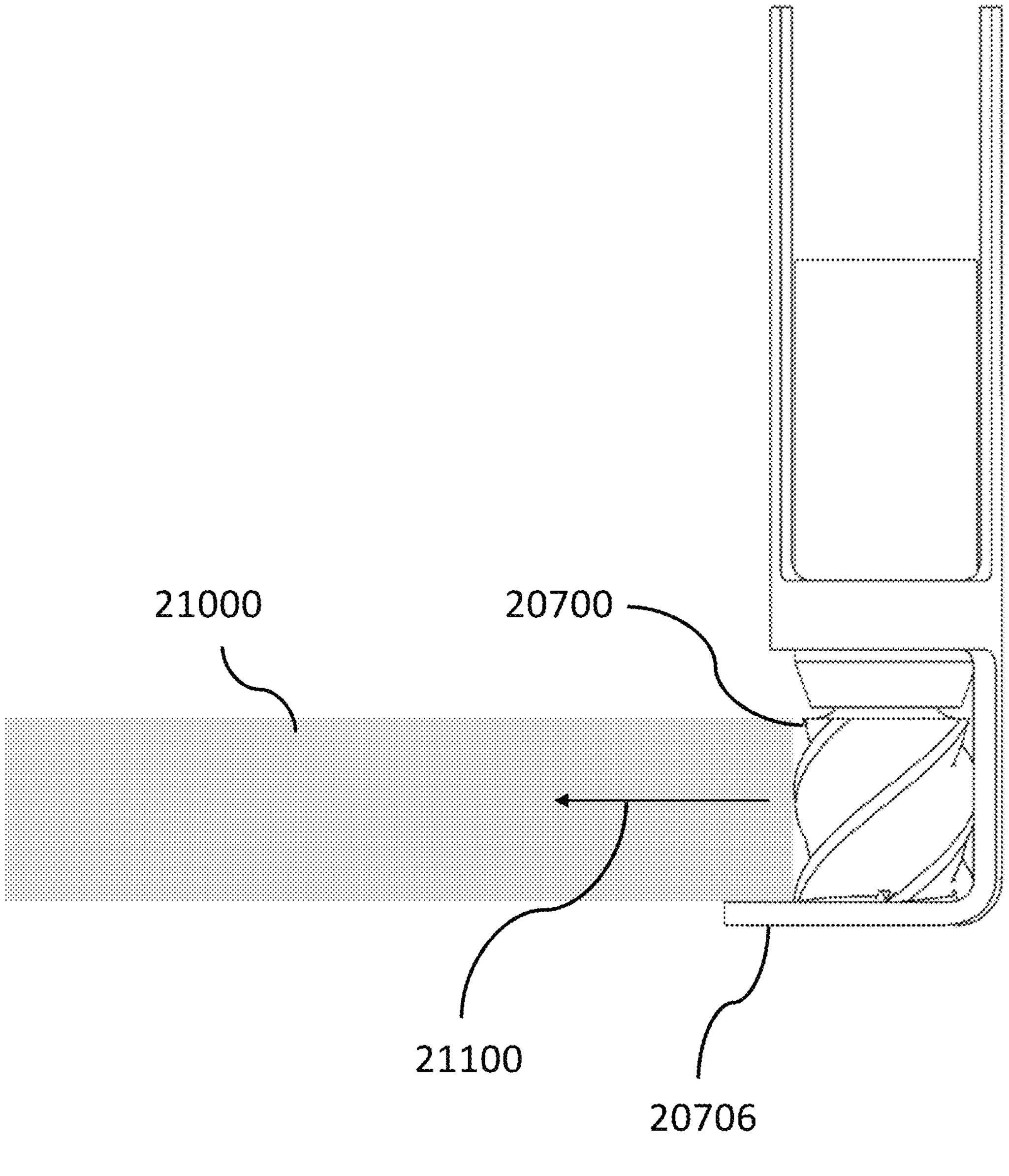
Figure 212:
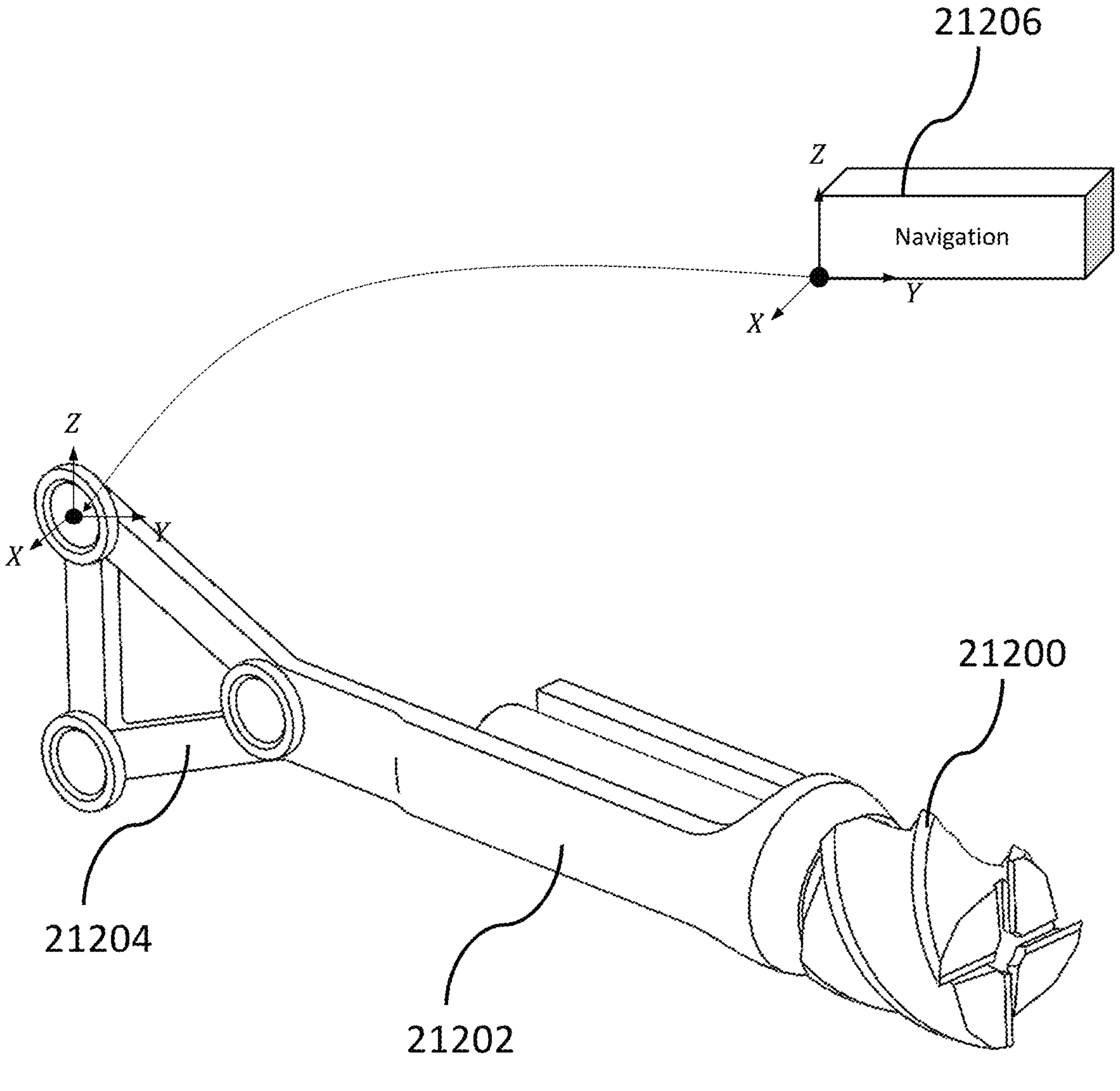
Figure 213A:
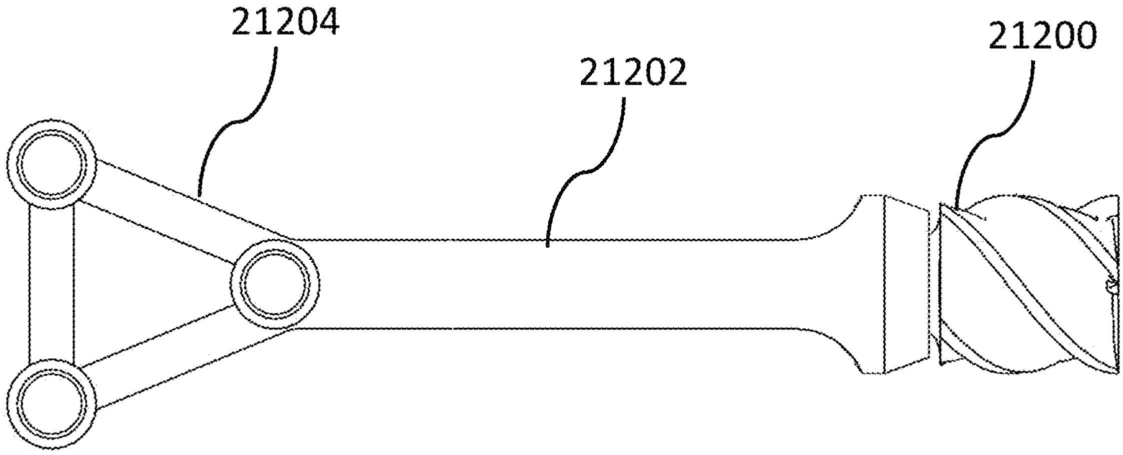
Figure 213B:
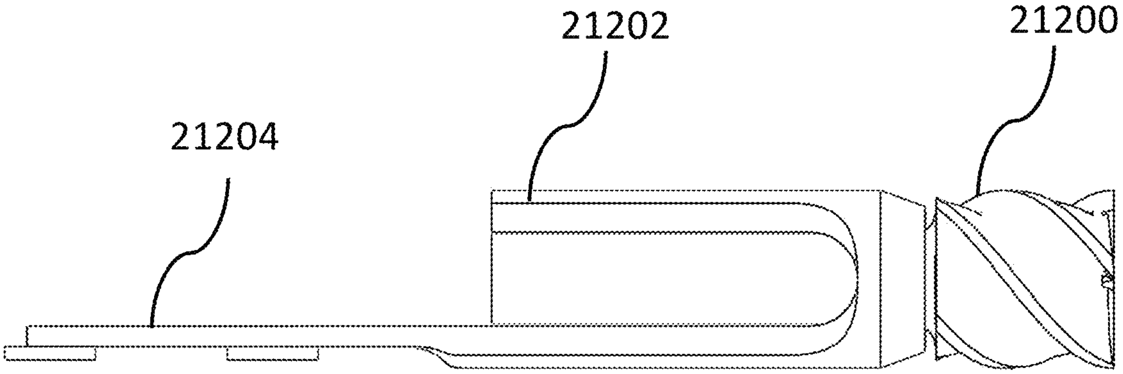
Figure 214A:
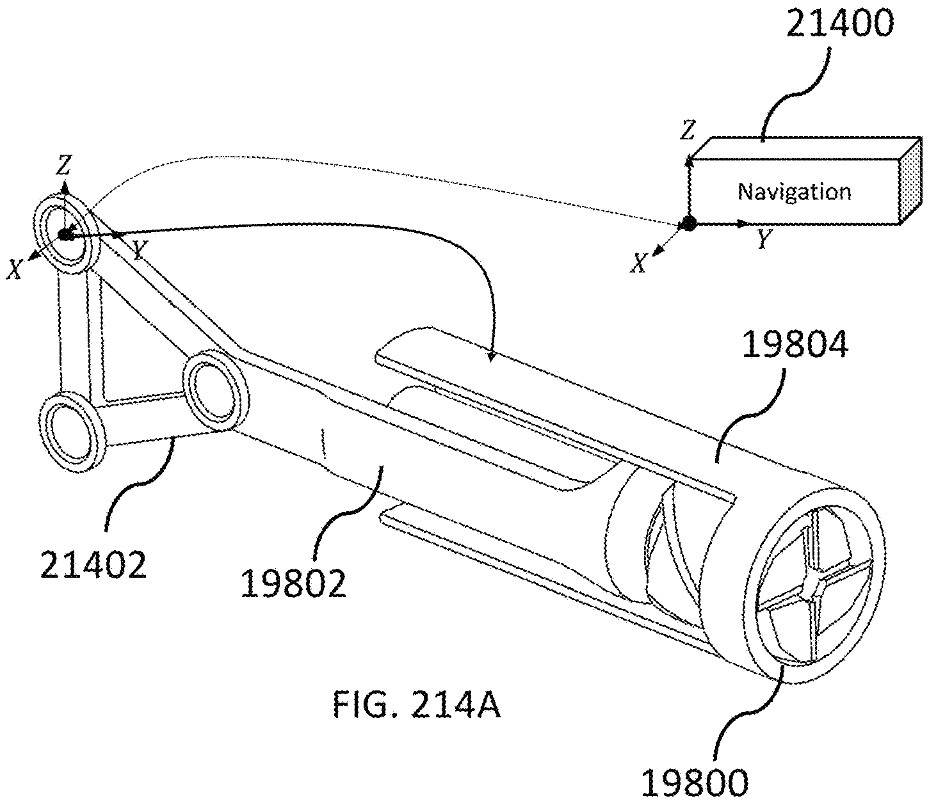
Figure 214B:
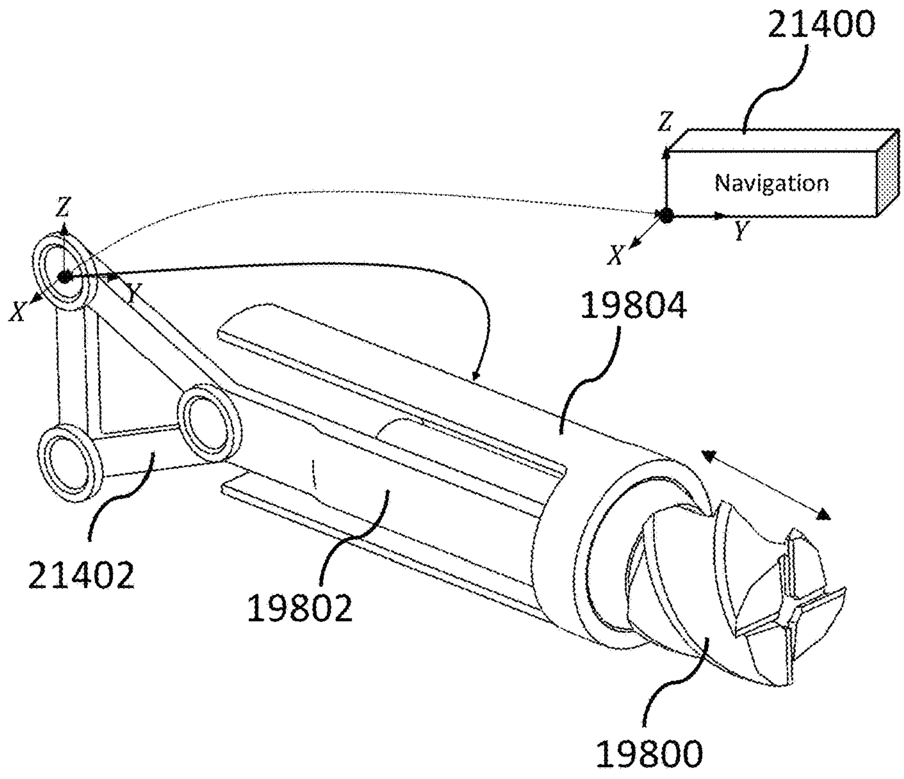
Figure 215A:
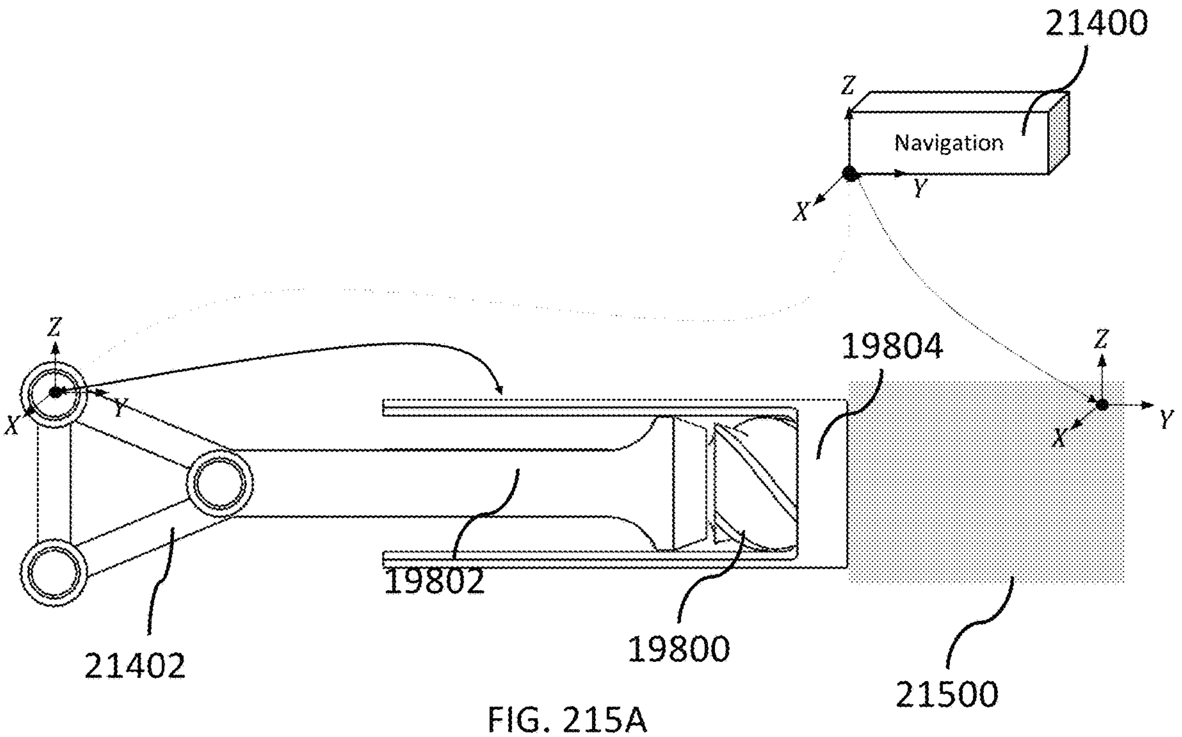
Figure 215B:
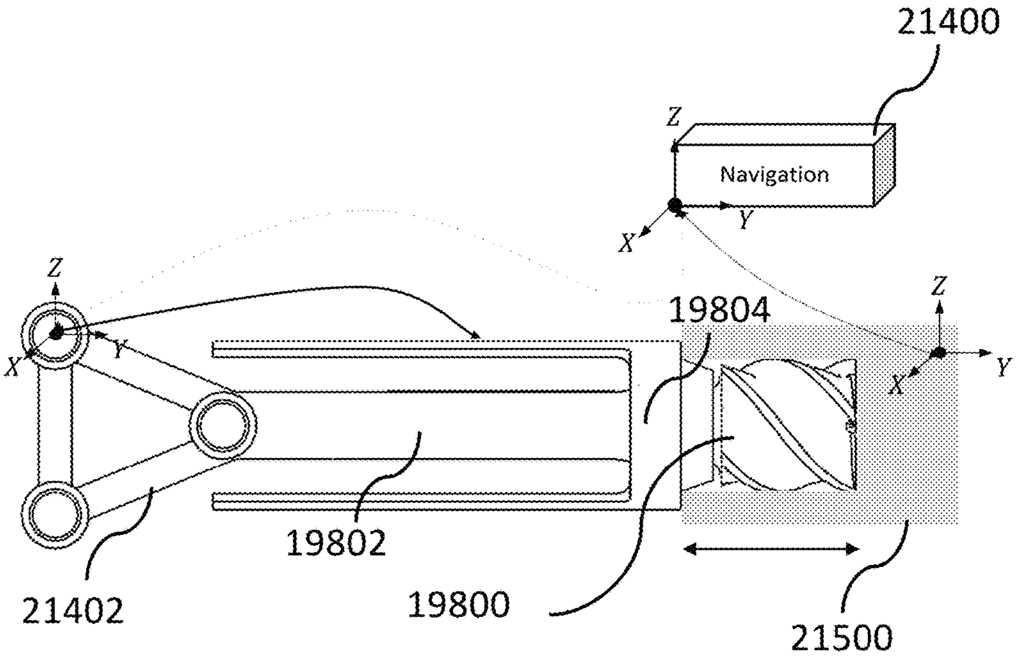
Figure 216:
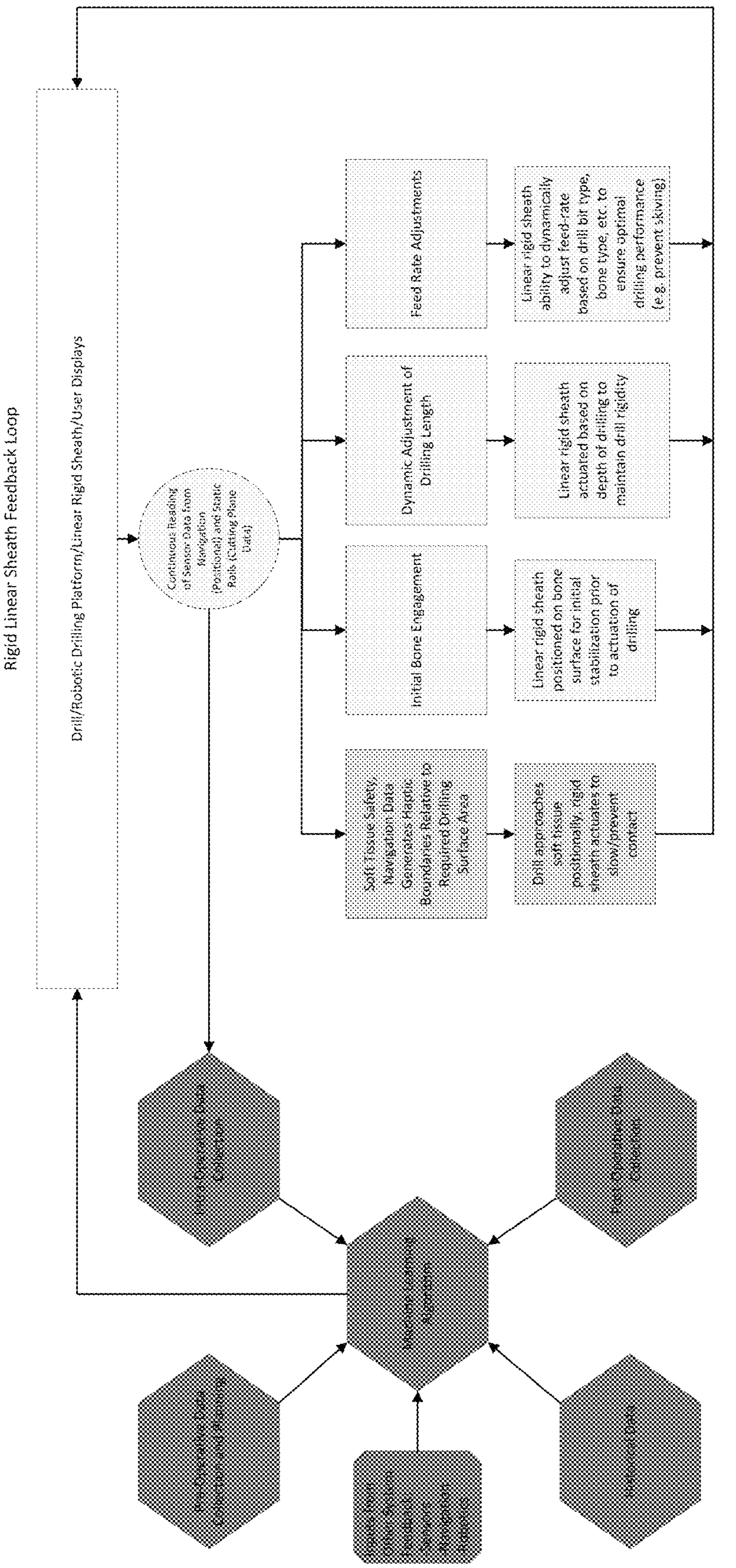
Figure 217:
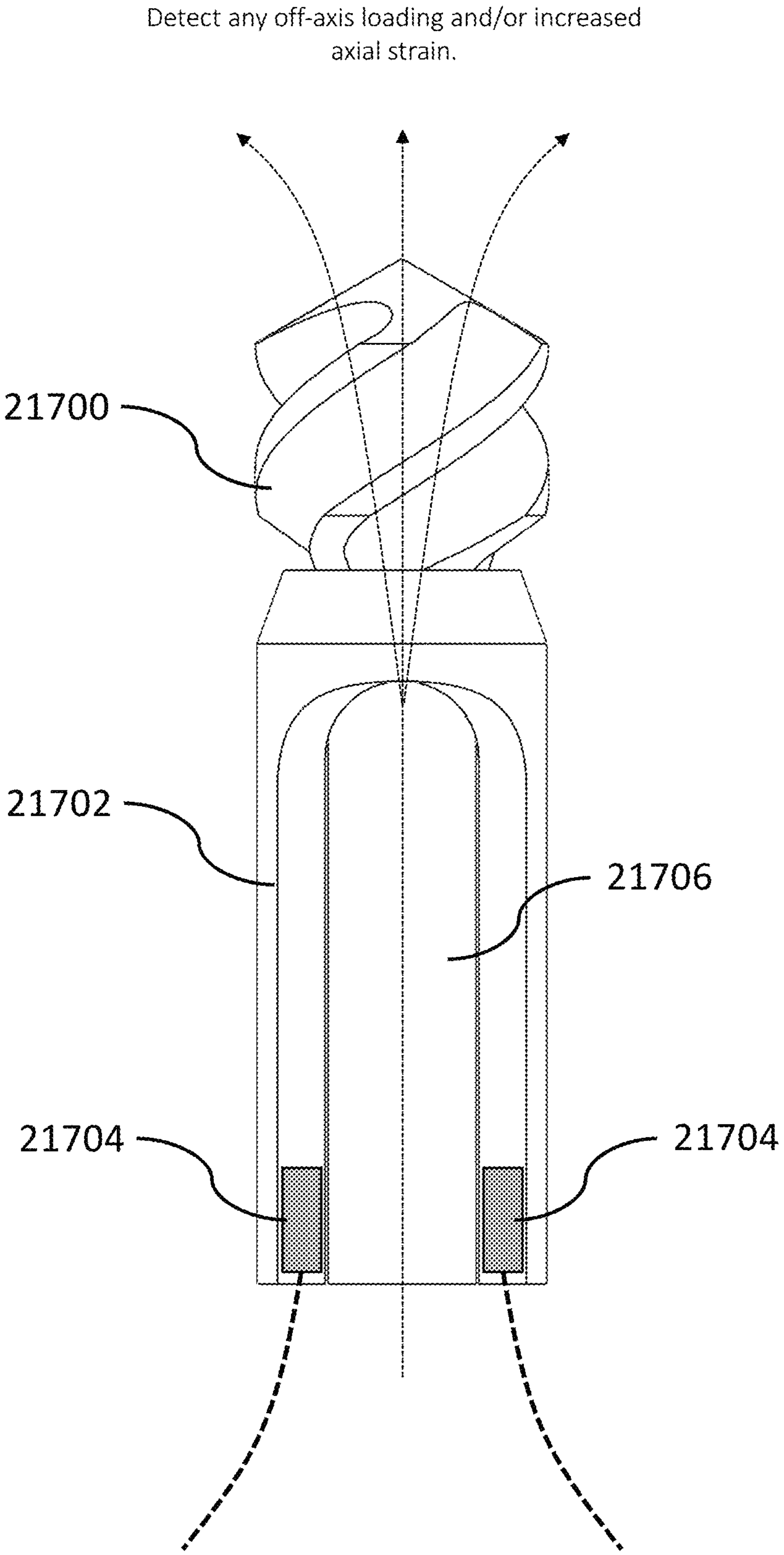
Figure 218A:
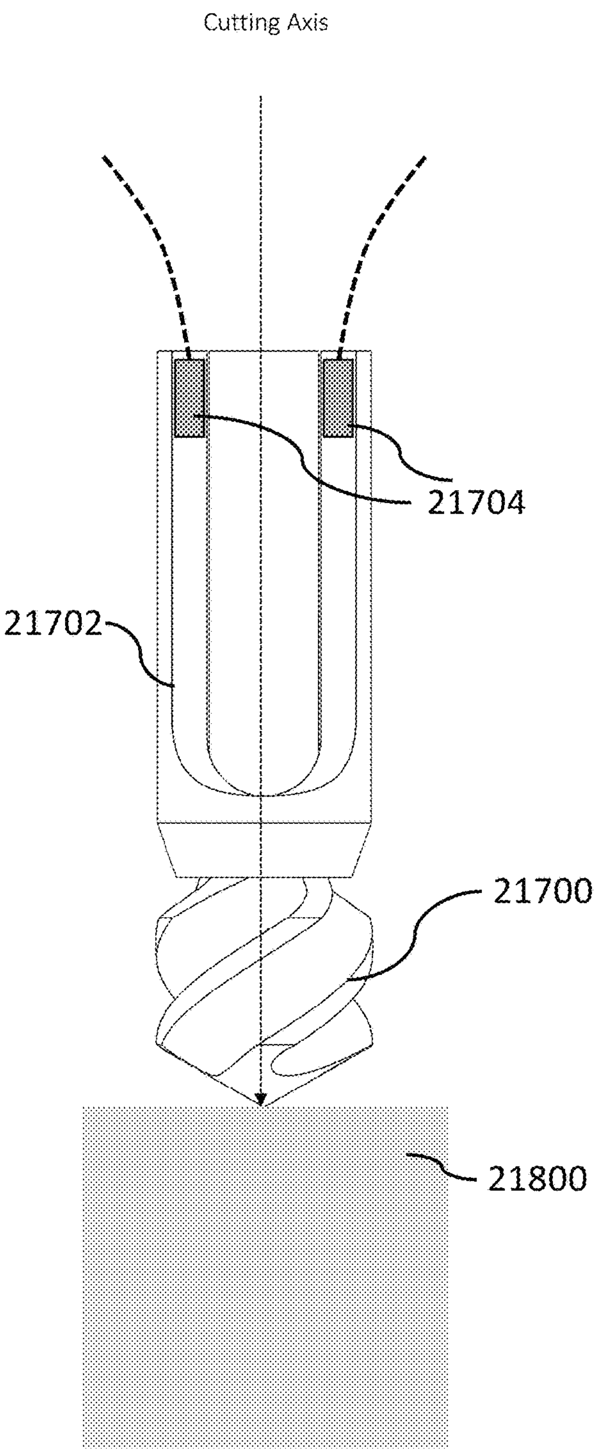
Figure 218B:
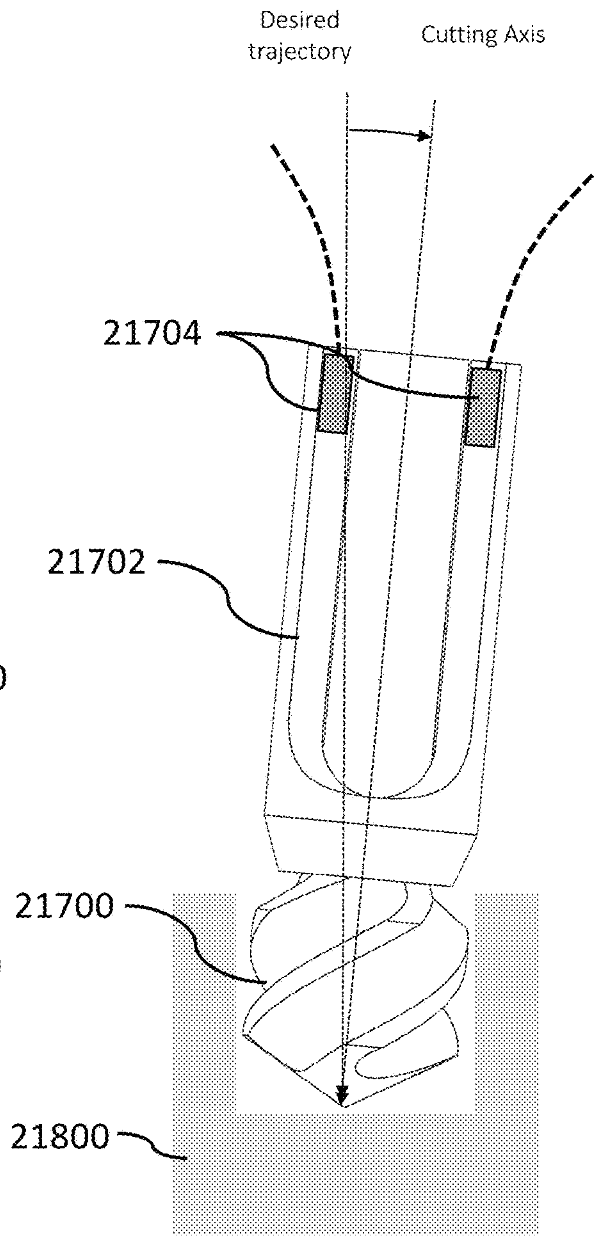
Figure 219:
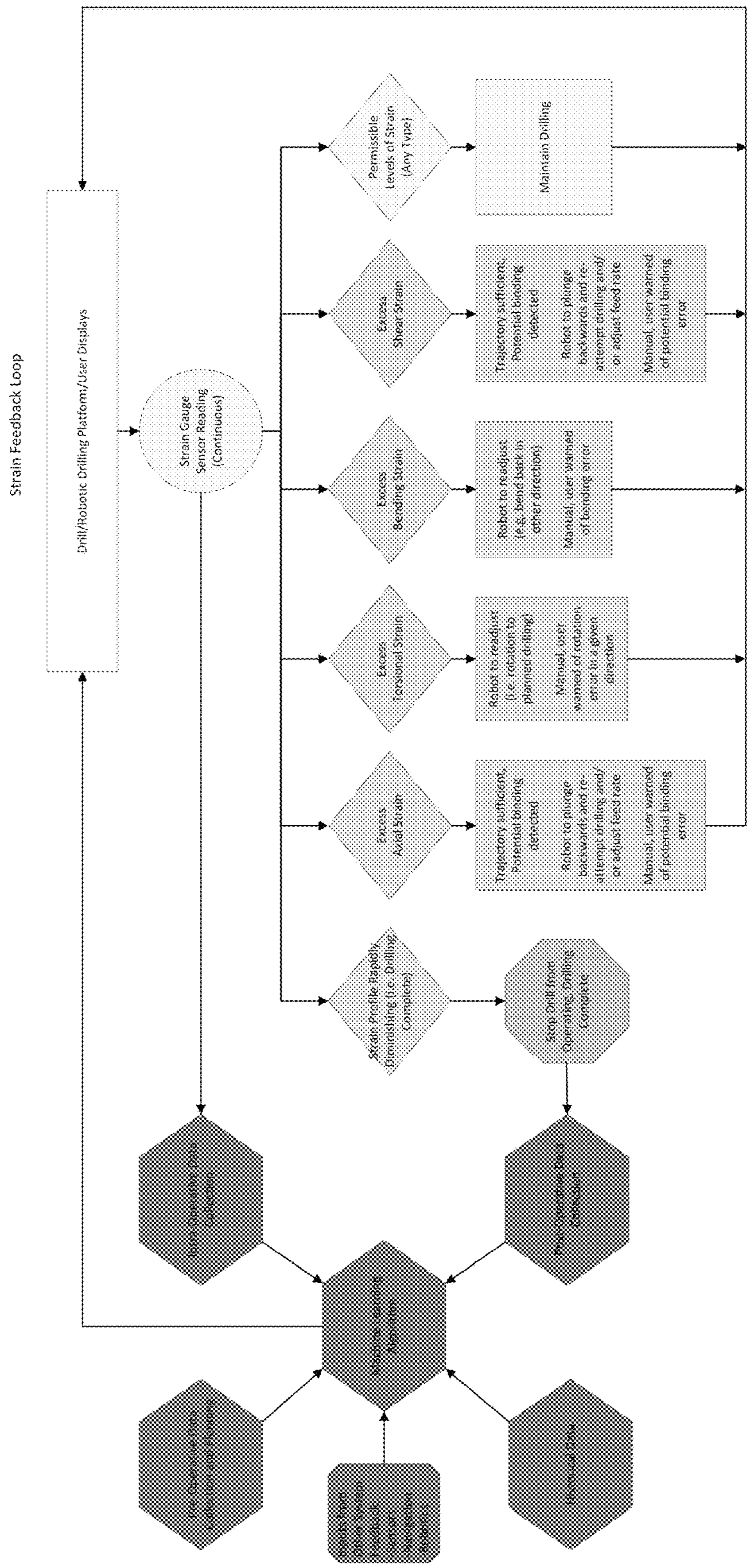
Figure 220:
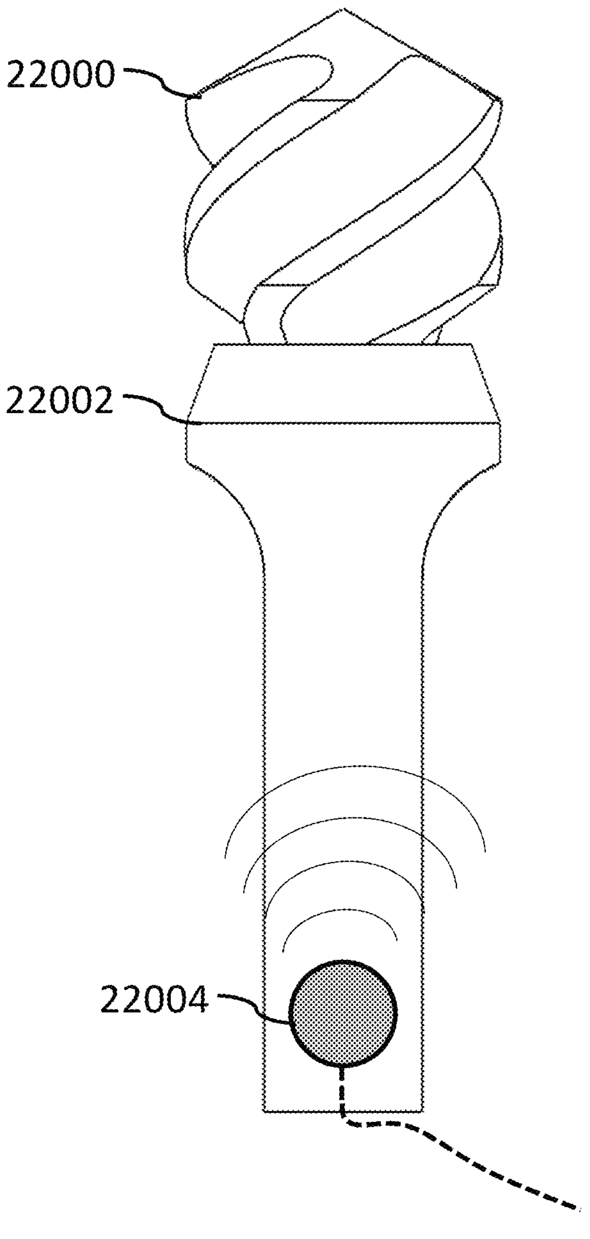
Figures 221A, 221B, 221C:
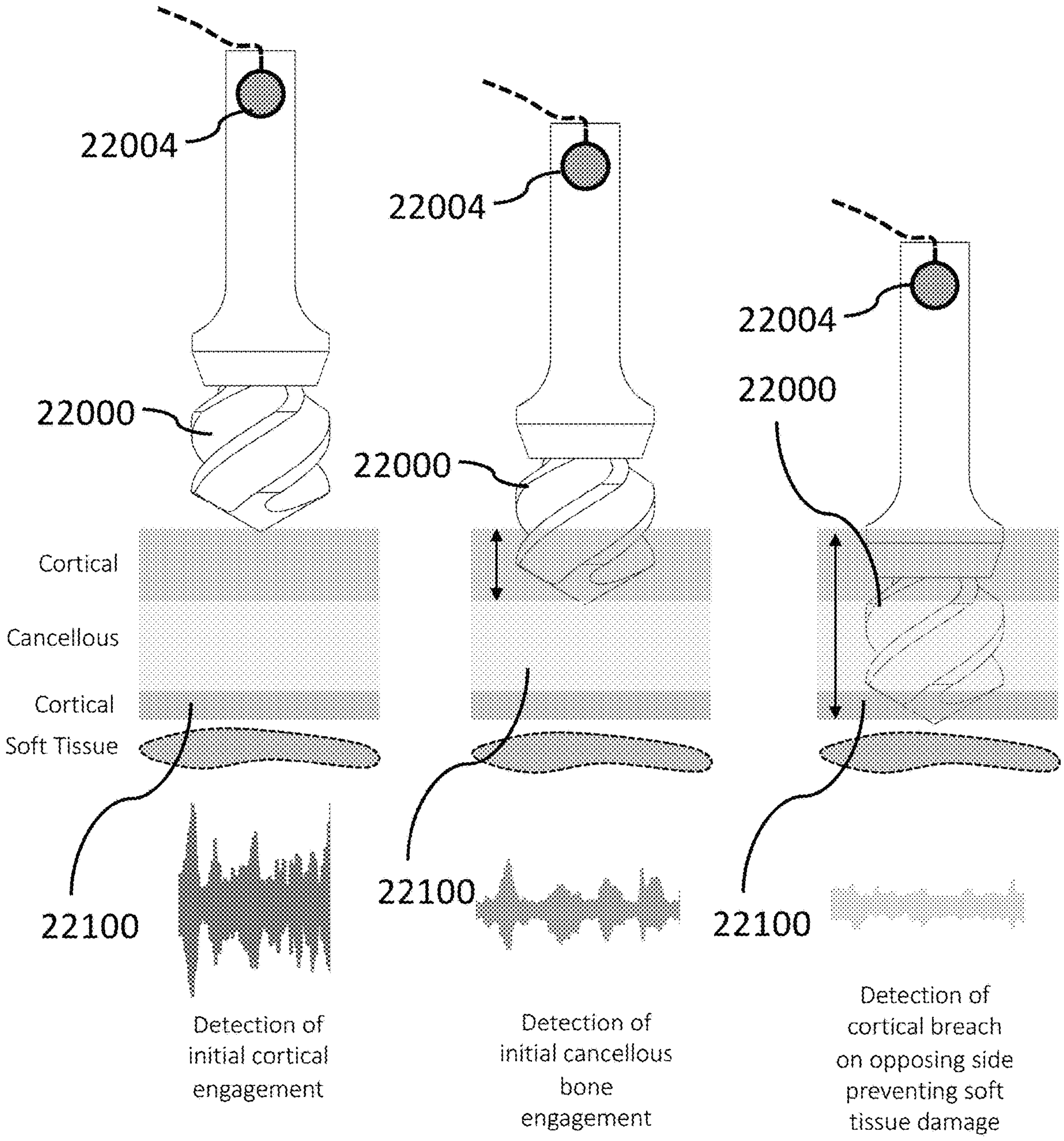
Figure 222:
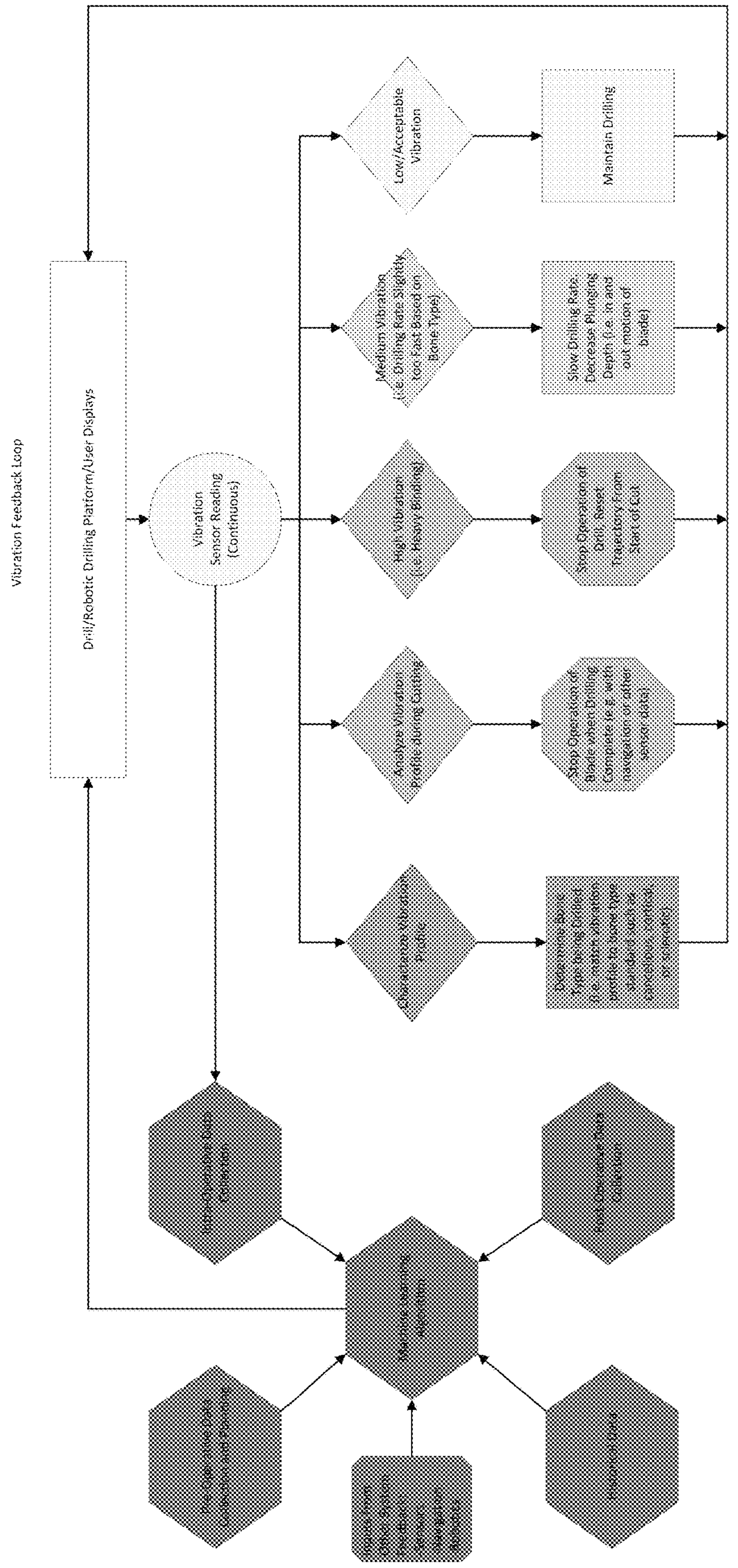
Figure 223:
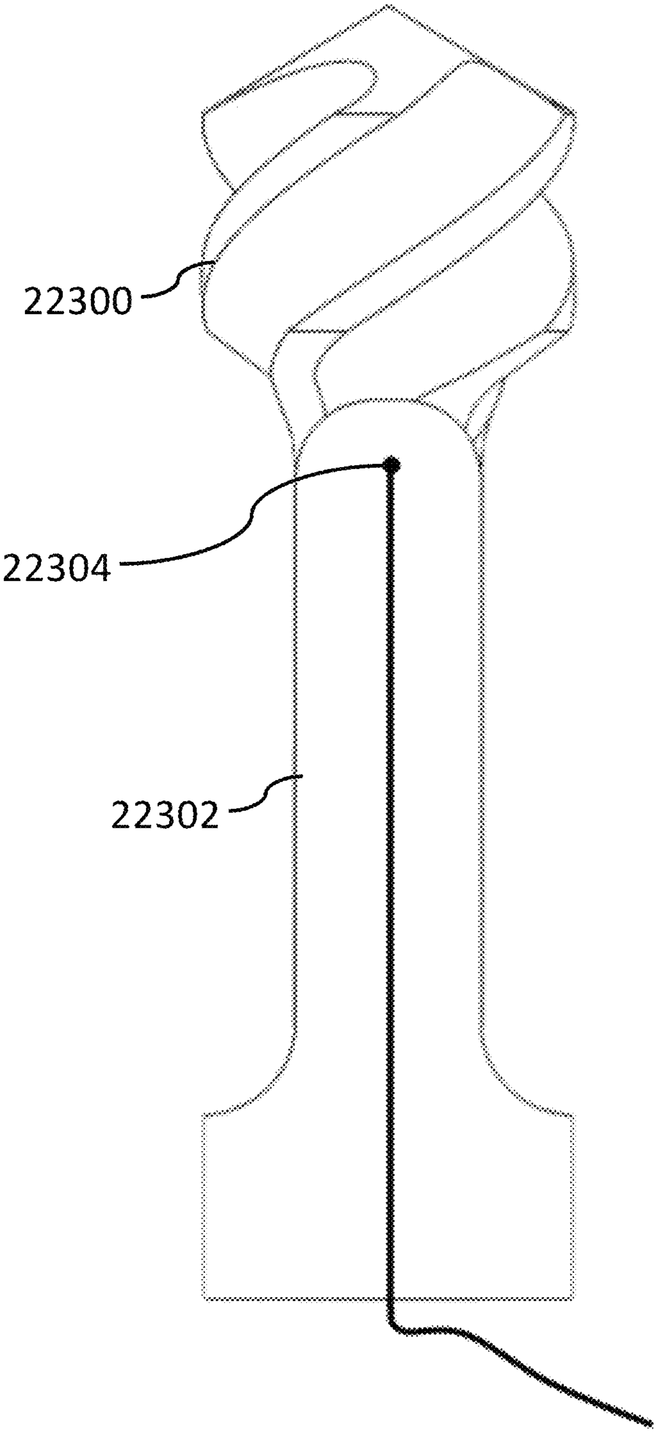
Figure 224:
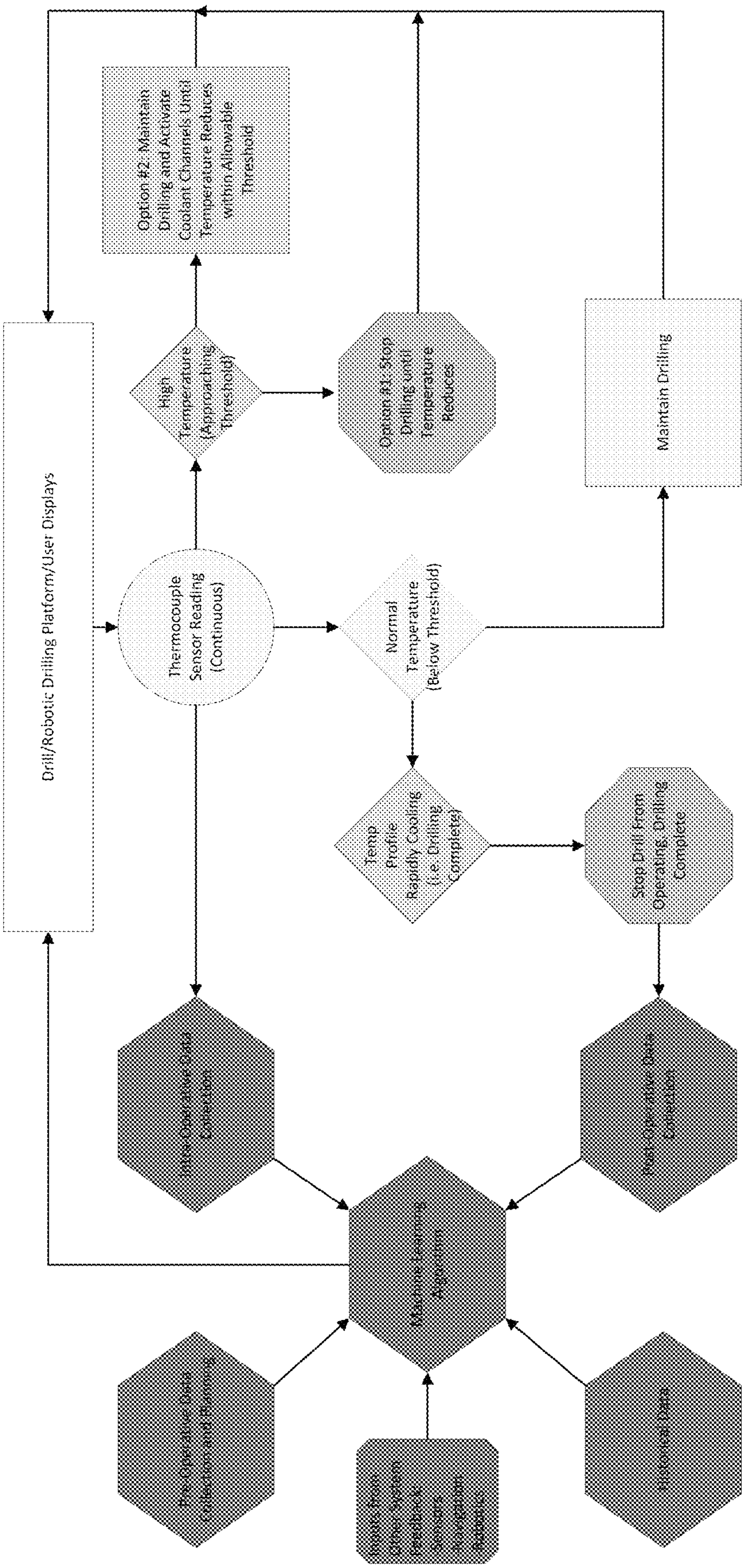

Having thus described the presently disclosed subject matter in general terms, reference will now be made to the accompanying Drawings, which are not necessarily drawn to scale, and wherein:

FIGS. 1-3 are different views of a cutting device having a static casing with rails and struts in accordance with embodiments of the present disclosure;

FIGS. 4A-4C are cross-sectional, side views of cutting device shown in FIGS. 1-3 and their working body and static rail in accordance with embodiments of the present disclosure;

FIG. 5 is a top view of the cutting device shown in FIGS. 1-3, 4A, and 4B;

FIG. 6 is another top view of the cutting device shown in FIGS. 1-5 but with shadow lines indicating the extended tabs of the captured blade within the struts;

FIG. 7 is another top view of the cutting device shown in FIG. 6 in close up;

FIG. 8 is a top view of a cutting device similar to the cutting device shown in FIGS. 1-6 but with shadow lines indicating debris reliefs within the cutting edge of the blade to allow for debris to translate from the leading cutting edge through the rigid struts (bottom not shown) into the open-air gap;

FIGS. 9A and 9B are top views of the cutting device shown in FIGS. 1-6 at the left-most and right-most extents, respectively, of movement side-to-side of the blade working body and cutting blade edge;

FIGS. 10A and 10B show close-up views of the cutting device shown in FIGS. 9A and 9B, respectively;

FIGS. 11A-11E are side views of the cutting device positioned at different steps for cutting material in accordance with embodiments of the present disclosure;

FIG. 12 is a perspective view of another cutting device in accordance with embodiments of the present disclosure;

FIG. 13 is a top view of the cutting device shown in FIG. 12;

FIG. 14 is a perspective view of a cutting device with a single-entry irrigation port in accordance with embodiments of the present disclosure;

FIG. 15 is a top view of the cutting device shown in FIG. 14;

FIG. 16 is another top view of the cutting device shown in FIGS. 14 and 15 but with shadow lines indicating the interior channels for conveying fluid from ports to outlets;

FIG. 17 is a close-up, side view of the cutting device shown in FIGS. 14-16;

FIG. 18 is a perspective view of a cutting device having two ports for entry or exit of fluid conveyed in rails in accordance with embodiments of the present disclosure;

FIG. 19 is a top view of the cutting device shown in FIG. 18;

FIG. 20 is another top view of the cutting device shown in FIGS. 18 and 19 but with shadow lines indicating the interior channels for conveying fluid from ports to outlets;

FIG. 21 is a close-up, top view of the cutting device shown in FIGS. 18-20;

FIG. 22 is another close-up, top view of the cutting device shown in FIG. 18 but with shadow lines indicating a different mode of operation for receiving fluid through apertures and into its channels;

FIG. 23 is a close-up, side view of the cutting device shown in FIGS. 18-20 with shadow lines indicating the interior channels;

FIG. 24 is a top view of another cutting device having external irrigation channels in accordance with embodiments of the present disclosure;

FIG. 25 is a top view of the cutting device shown in FIG. 24 except with fluid being received at ends in an aspiration mode in accordance with embodiments of the present disclosure;

FIG. 26 is a close-up, top view of the cutting device shown in FIG. 25 in the aspiration mode where debris is being pulled into ends due to fluid flow;

FIGS. 27-30 are views of another cutting device with a strut supporting a neck portion of a cutting blade in accordance with embodiments of the present disclosure;

FIGS. 31-35B are views of another cutting device with a strut supporting a neck portion of a cutting blade in accordance with embodiments of the present disclosure;

FIGS. 32A and 32B is a top view and a bottom view of the cutting device shown in FIG. 31;

FIG. 33 is a close-up, top view of the cutting device shown in FIG. 31 but with shadow lines indicating the strut supporting the neck portion;

FIGS. 34A and 34B are a side view and a close-up, side view of the cutting device shown in FIG. 31;

FIGS. 35A and 35B are top views of the cutting device shown in FIGS. 31-34B at the left-most and right-most extents, respectively, of movement side-to-side of the cutting blade;

FIG. 36 is a perspective view of another cutting device in accordance with embodiments of the present disclosure;

FIG. 37A shows a top view of the cutting device shown in FIG. 36;

FIG. 37B shows a bottom view of the cutting device shown in FIG. 36 with shadow lines to indicate internal features and/or hidden geometry;

FIG. 38 is a top view of a cutting device in accordance with embodiments of the present disclosure;

FIG. 39 is a top view of the cutting device with shadow lines to show internal features and/or hidden geometry;

FIG. 40 is a close-up, top view of the cutting device shown in FIG. 38 with shadow lines to show internal features and/or hidden geometry;

FIG. 41A is a top view of the cutting device shown in FIG. 38 showing the blade at the extent of its range of movement to the left and with shadow lines to show internal features;

FIG. 41B is a top view of the cutting device shown in FIG. 38 showing the blade at the extent of its range of movement to the right and with shadow lines to show internal features;

FIG. 42 is a close-up, perspective view of the cutting device shown in FIG. 38 with the blade at the extent of its range of movement to the left;

FIG. 43 is a top view of another cutting device similar to the cutting device of FIG. 38 except without the partial struts;

FIGS. 44A-44C are side views of different embodiments of a cutting device similar to the cutting device shown in FIG. 43;

FIG. 45 is a perspective view of the cutting device shown in FIG. 1 attached to a handpiece in accordance with embodiments of the present disclosure;

FIG. 46 is a perspective view of the cutting device and handpiece shown in FIG. 45 but with the cutting device detached from the handpiece;

FIGS. 47 and 48A-B are a top view and a close-up, side view of the cutting device and handpiece, with the cutting device attached to handpiece;

FIG. 49 is a perspective view of another handpiece attached to an in-line cutting device;

FIG. 50 is a perspective view of the handpiece attached to a manually-detachable in-line cutting device;

FIGS. 51 and 52 are a top view and a side view, respectively, of the handpiece and cutting device shown in FIGS. 49 and 50;

FIGS. 53A and 53B are top perspective views of a modular cutting device in accordance with embodiments of the present disclosure;

FIGS. 54A and 54B are a top view and a bottom view, respectively, of FIG. 53A with the cutting device and the strut/rail portion being attached;

FIG. 55A is a close-up, top view of the distal end of the cutting device shown in FIG. 54A with shadow lines to show internal and/or hidden features;

FIG. 55B is a close-up, side view of the distal end of the cutting device shown in FIG. 54A;

FIGS. 56A and 56B are a close-up, top perspective view and a close-up, bottom perspective view, respectively, of the cutting device shown in FIG. 54A with the strut/rail portion being detached;

FIGS. 57A and 57B are perspective views of another modular cutting device in accordance with embodiments of the present disclosure;

FIGS. 58A-58C are different steps for attaching a cutting blade to its cutting device in accordance with embodiments of the present disclosure;

FIGS. 59A, 59B, and 59C are perspective views of another cutting device in accordance with embodiments of the present disclosure demonstrating assembly of the blade within the construct;

FIGS. 60A, 60B, and 60C are perspective views of another cutting device in accordance with embodiments of the present disclosure demonstrating assembly of the blade within the construct;

FIG. 61 is a top view of the cutting device with partial insertion of the working blade body;

FIGS. 62A-65 are views of cutting device with a modular support component for its working body in accordance with embodiments of the present disclosure;

FIGS. 66A and 66B are top perspective views of a cutting system in accordance with embodiments of the present disclosure demonstrating assembly of the cutting blade to the cutting device;

FIG. 67 is a top view of the cutting system shown in FIGS. 66A and 66B;

FIGS. 68A and 68B are zoomed-in, top perspective views of the cutting device shown in FIGS. 66A and 66B of the cutting blade being detached from the attachment end of the working body and attached to the attachment end of the working body;

FIGS. 69A-69C are tops views of the cutting system shown in FIGS. 66A and 66B, depicting various steps for attaching the cutting blade to the working body;

FIGS. 70A and 70B are top perspective views of another cutting system in accordance with embodiments of the present disclosure demonstrating assembly of the blade within the construct;

FIGS. 71A and 71B are top views of the cutting system shown in FIGS. 70A and 70B;

FIG. 72 illustrates a close-up, top view of the cutting system shown in FIGS. 70A and 70B with shadow lines to depict interior features and/or hidden geometry;

FIGS. 73A-73C are top views of the cutting system shown in FIGS. 70A and 70B at different steps for attaching the cutting blade to the working body;

FIG. 74 is a cross-sectional, side view of the cutting system shown in FIGS. 70A and 70B with the cutting blade being detached;

FIGS. 75A and 75B are perspective views of a cutting device with a detachable cutting blade in accordance with embodiments of the present disclosure;

FIGS. 76A and 76B are close-up, top views that correspond to the positions shown in FIGS. 75A and 75B, respectively;

FIGS. 77A and 77B are close-up, perspective views that correspond to the positions shown in FIGS. 76A and 76B, respectively (without the static component rails shown);

FIG. 78 is a cross-sectional, side view of the cutting device shown in FIGS. 77A and 77B where the protrusion is locked into place;

FIGS. 79A-79C are top perspective views of a cutting system at different steps for attaching the cutting blade to a working body in accordance with embodiments of the present disclosure;

FIGS. 80A and 80B are top views of the cutting system shown in FIGS. 79B-79C with the flaps in an open position and closed position, respectively;

FIGS. 81 and 82 are a close-up, top view and a close-up, perspective view, respectively, of the cutting system shown in FIG. 79C with the flaps in the closed position;

FIGS. 83A and 83B are perspective views of a cutting system with a modular static casing having upper and lower components in an attached positioned and a detached position, respectively, in accordance with embodiments of the present disclosure;

FIGS. 84A and 84B are perspective views of another cutting system with a modular static casing having upper and lower components in an attached position and a detached position, respectively, in accordance with embodiments of the present disclosure;

FIG. 85 is a flow diagram of overall sensor control and feedback methods for implementation by a cutting system in accordance with embodiments of the present disclosure;

FIGS. 86A and 86B are a perspective view and a side view, respectively, of a cutting system having navigation rails and functionalities for guiding cutting in accordance with embodiments of the present disclosure;

FIGS. 87A and 87B are perspective views of the cutting system shown in FIGS. 86A and 86B in a detached position and an attached position, respectively, with respect to a power handpiece/handle in accordance with embodiments of the present disclosure;

FIG. 88 is a perspective view of the cutting system attached to the handle (as shown in FIG. 87B) and also depicts operative connection to a computing device for controlling navigation and orientation with respect to material to be cut;

FIG. 89 is a perspective view of the cutting device and handle of FIG. 88 with a manual, sliding stabilizer sheath in accordance with embodiments of the present disclosure;

FIGS. 90A-90C are top views of the cutting device and handle shown in FIG. 89 with the stabilizer sheath with fixation feature at different positions;

FIGS. 91A and 91B are views of the cutting device, handle, and stabilizer sheath shown in FIG. 89 in use for cutting bone;

FIGS. 92A and 92B are perspective views of the cutting device and the handle shown in FIG. 89 with a different stabilizer sheath that assembles with the static rail through a slot on the side of the stabilizer sheath rather than from the distal end of the static rail in accordance with embodiments of the present disclosure;

FIG. 93 is a top view of a cutting device with temperature sensors attached to a left side and right side, respectively, of a static rail in accordance with embodiments of the present disclosure;

FIG. 94 is a top view of a cutting device with temperature sensors attached to a left side and right side, respectively, of a static rail in accordance with embodiments of the present disclosure;

FIG. 95 is a top view of a cutting device with temperature sensors attached to a left side and right side, respectively, of a static rail in accordance with embodiments of the present disclosure;

FIG. 96 is a top view of a cutting device being configured with multiple temperature sensors attached to a left side and right side, respectively, for integrated in-plane temperature feedback in accordance with embodiments of the present disclosure;

FIG. 97 is a graph showing temperature readings and top views of a cutting device shown in FIG. 93 cutting into bone;

FIG. 98 is a graph showing temperature readings and top views of a cutting device shown in FIG. 93 cutting into bone;

FIG. 99 is a top view of a cutting blade with working body having an integrated temperature sensor being connected by conductive wire via a side port;

FIG. 100 is a top view of the cutting blade and working body of FIG. 99 along with a static casing;

FIG. 101 is a top view of another cutting device having an integrated temperature sensor located near a blade edge in accordance with embodiments of the present disclosure;

FIG. 102 is a view of the cutting device of FIG. 101 along with a static casing;

FIG. 103 is a flow diagram of a temperature feedback loop in accordance with embodiments of the present disclosure;

FIG. 104 is a perspective view of a cutting device having strain sensors for in-plane trajectory feedback in accordance with embodiments of the present disclosure;

FIG. 105 is a perspective view of the cutting device shown in FIG. 104 and a front view and graph depicting micro strain measurements obtained by the cutting device's strain sensors in a cyclic loading bending down loading condition;

FIG. 106 is a perspective view of the cutting device shown in FIG. 104 and a front view and graph depicting micro strain measurements obtained by the cutting device's strain sensors in a cyclic loading bending up loading condition;

FIG. 107 is a perspective view of the cutting device shown in FIG. 104 and a graph depicting micro strain measurements obtained by the cutting device's strain sensors in an incremental bending down loading condition;

FIG. 108 are perspective views of the cutting device shown in FIG. 104 and front views and a graph depicting micro strain measurements obtained by the cutting device's strain sensors in a cyclic loading torsion loading condition;

FIG. 109 are perspective views of the cutting device shown in FIG. 104 in a positive torsion and bending up loading condition;

FIG. 110 are perspective and front views of the cutting device shown in FIG. 104 in a positive torsion and bending up loading condition;

FIG. 111 are perspective and front views of the cutting device shown in FIG. 104 in a negative torsion and bending down loading condition;

FIG. 112 are perspective and front views of the cutting device shown in FIG. 104 in a negative torsion and bending up loading condition;

FIG. 113 is a perspective view of the cutting device shown in FIG. 104 depicting tracking the location of the static rail and bone coordinate system within a global coordinate system through communication with a navigation/computing system;

FIG. 114 is a perspective view of the cutting device shown in FIG. 104 and a graph showing real-time sensor data used to generate the kinematics of the blade edge;

FIG. 115 is a front view of a blade edge of the cutting device shown in FIG. 114 and a front view of a bone cutting section;

FIG. 116 is a diagram showing a 3D surface trajectory relative to planned cutting trajectory;

FIG. 117 is a perspective view of a cutting device that uses post-op, analysis data from many data sets to determine trends in cutting error and help make real-time corrections in future applications;

FIG. 118 is a flow diagram of an example method of cutting device control in accordance with embodiments of the present disclosure shown in FIGS. 113-117;

FIG. 119 illustrates a perspective view of a cutting device having strain sensors attached to a strut in accordance with embodiments of the present disclosure;

FIG. 120 is a flow diagram of strain sensor feedback loop in accordance with embodiments of the present disclosure;

FIG. 121 is a top view of a cutting device having pressure sensors for integrated, in-plane binding feedback in accordance with embodiments of the present disclosure;

FIG. 122 is a top view of the cutting device shown in FIG. 121 cutting into bone and a graph showing excessive load detected and a binding threshold;

FIG. 123 is a top view of a cutting device with a pair of flexible, linear potentiometers that extend along a length of a static rail;

FIG. 124 is a top view of the cutting device shown in FIG. 123 cutting into bone and a graph showing detected bone cutting depth;

FIG. 125 is a flow diagram of a pressure feedback loop in accordance with embodiments of the present disclosure;

FIGS. 126 and 127 are a top view and a close-up, top view, respectively, of another cutting device having electrical conductivity sensors for integrated in-plane feedback for tissue characterization in accordance with embodiments of the present disclosure;

FIG. 128 illustrates the cutting device shown in FIG. 126 cutting into bone along with a graph showing detection of different bone and soft tissue types;

FIG. 129 is a flow diagram of an electrical conductivity feedback loop in accordance with embodiments of the present disclosure;

FIG. 130 is a top view of a cutting device having vibration sensors for integrated in-plane vibration detection in accordance with embodiments of the present disclosure;

FIG. 131 shows the cutting device shown in FIG. 130 cutting into bone along of graphs with cancellous bone vibration data and sclerotic bone vibration data;

FIG. 132 is a perspective view of a cutting device having a vibration sensor attached to a strut in accordance with embodiments of the present disclosure;

FIG. 133 is a top view of a cutting device having a vibration sensor positioned on a base of the static component;

FIG. 134 is a flow diagram of a vibration feedback loop in accordance with embodiments of the present disclosure;

FIG. 135 is a perspective view of a cutting device with multiple integrated sensors and a dedicated visual feedback screen on the device in accordance with embodiments of the present disclosure;

FIG. 136 is a top view of a cutting device having optical fibers for providing sensor readings in accordance with embodiments of the present disclosure;

FIG. 137 shows the cutting device of FIG. 136 cutting into bone and a graph showing detection of high strain;

FIG. 138 is a top view of another cutting device with fiber optic sensors extending to a distal end of static rails in accordance with embodiments of the present disclosure;

FIG. 139 shows the cutting device of FIG. 138 cutting into bone and a graph showing a calibration curve for measuring applied load;

FIG. 140 is a flow diagram of a fiber optics feedback loop in accordance with embodiments of the present disclosure;

FIG. 141 is a top view of a cutting device having audio sensors for integrated in-plane feedback for tissue characterization in accordance with embodiments of the present disclosure;

FIGS. 142A and 142B are top perspective views of the cutting device of FIG. 141 being used for bone type detection;

FIGS. 143A and 143B are top perspective views of the cutting device of FIG. 141 being used for depth detection;

FIG. 144 is a flow diagram of an audio sensors feedback loop in accordance with embodiments of the present disclosure;

FIG. 145 is a perspective view of a cutting device having a sliding rigid, linear sheath on its rails in accordance with embodiments of the present disclosure;

FIGS. 146A and 146B are different top views of the cutting device shown in FIG. 145 at various positions in accordance with embodiments of the present disclosure;

FIG. 147 is a top view of the cutting device shown in FIG. 145 cutting into bone with the working surface depth being informed by a computing device in accordance with embodiments of the present disclosure;

FIGS. 148A-148C are different top views of various positions of a cutting device of FIG. 145 when cutting into bone in accordance with embodiments of the present disclosure;

FIG. 149 is a flow diagram of a rigid linear sheath feedback loop in accordance with embodiments of the present disclosure;

FIG. 150 is a diagram of an operational environment for a system including a handheld cutting device and navigation system in accordance with embodiments of the present disclosure;

FIG. 151 is a block diagram of an example cutting system in accordance with embodiments of the present disclosure;

FIG. 152 is a side view of a handheld cutting system in accordance with embodiments of the present disclosure;

FIG. 153 is a side view of the cutting system with the housing removed so that its internal components can be seen;

FIG. 154 is a top view of the cutting device shown in FIG. 152;

FIG. 155 is a top view of the cutting device shown in FIG. 153;

FIG. 156 is a perspective view of the cutting device shown in FIG. 153;

FIG. 157 is another perspective view of the cutting device shown in FIG. 153 such that the third actuator is visible;

FIG. 158 is the same perspective view of the cutting device shown in FIG. 156 with a navigation/computing system being operatively connected thereto;

FIGS. 159A and 159B are side views of the cutting device shown in FIG. 158 during operation for cutting bone in accordance with embodiments of the present disclosure;

FIGS. 160A and 160B are side views of example steps that can be implemented by the cutting device shown in FIGS. 159A and 159B when cutting into bone and skiving is detected;

FIGS. 161A-161C are top views of other example steps that can be implemented by the cutting device shown in FIGS. 159A and 159B during skiving when using the communication channels established between the navigation/computational system, the strain sensors, and the dynamically driven linear rigid sheath;

FIGS. 162A-162C are example steps that can be implemented by the cutting device shown in FIGS. 159A and 159B when soft tissue is detected;

FIGS. 163A and 163B are top views of a cutting device depicting a fully captured, rigid, linear sheath mechanism in accordance with embodiments of the present disclosure;

FIGS. 164A-164C are top views of a cutting device with its stabilizer sheath mechanism at different positions in accordance with embodiments of the present disclosure;

FIG. 165 is a diagram of an operational environment for a system including a fully autonomous robot with attached cutting device and connected to a navigation system in accordance with embodiments of the present disclosure;

FIG. 166 is a flow diagram of a robotic platform and cutting end effector system in accordance with embodiments of the present disclosure;

FIG. 167 is a perspective view of the fully autonomous robot configuration shown in FIG. 165 and communication of the various components of the configuration with each other in accordance with embodiments of the present disclosure;

FIGS. 168A and 168B are top views of the fully autonomous robot configuration shown in FIG. 167 when cutting into bone and detecting cortical engagement and breach, respectively;

FIG. 169 is a perspective view of a semi-autonomous robot configuration controlling the cutting device, which is driven through the use of a manually manipulated handpiece, and communication of the various components of the configuration with each other in accordance with embodiments of the present disclosure;

FIG. 170 is a perspective view of the semi-autonomous robot configuration shown in FIG. 169 with additional communication of the cutting device with the navigation system;

FIG. 171 is a perspective view of a semi-autonomous robot configuration with passive planar linkages controlling the cutting device and communication of the various components of the configuration with each other in accordance with embodiments of the present disclosure;

FIGS. 172A and 172B are top views of a semi-autonomous robot configuration shown in FIG. 171 when cutting into bone and detecting soft tissue;

FIG. 173 is a perspective view of a semi-autonomous robot configuration with passive planar linkages controlling the cutting device and communication of the various components of the configuration with each other in accordance with embodiments of the present disclosure;

FIGS. 174A and 174B are top views of the semi-autonomous robot configuration shown in FIG. 173 when cutting into bone and detecting skiving and/or hard tissue;

FIG. 175 is a perspective view of a passive mechanical positioning arm configuration and communication of the various components of the configuration with each other that can lock any of the DOF available as needed to set position and trajectory controlling the cutting device in accordance with embodiments of the present disclosure;

FIGS. 176A and 176B are perspective views of a modular attachment of the cutting device that leverages the static rail mechanism for attachment to the passive mechanical positioning arm using a modular attachment sheath in accordance with embodiments of the present disclosure;

FIG. 177 is a perspective view of a fully autonomous micro-robot arm configuration with passive planar linkages attached to bone and being operably connected to and controlling the cutting device to cut into bone in accordance with embodiments of the present disclosure;

FIG. 178 is a perspective view of a semi-autonomous micro-robot arm configuration with passive planar linkages attached to bone and being operably connected to and controlling the cutting device to cut into bone similar to FIGS. 176A and 176B as well as communication of the various components of the configuration with each other in accordance with embodiments of the present disclosure;

FIG. 179 is a perspective view of a semi-autonomous micro robot arm configuration with passive planar linkages attached to bone and being operably connected to and controlling movement of the cutting device to cut into bone in accordance with embodiments of the present disclosure;

FIGS. 180A-180C are perspective views of a drill bit, end mill, and burr, respectively, (collectively known as drill bits) for use with a medical rotary drill/robotically driven arm in accordance with embodiments of the present disclosure;

FIGS. 181A-181C are front views of the drill bits shown in FIGS. 180A-180C, respectively;

FIGS. 182A-182C are other front views of the drill bits shown in FIGS. 180A-180C, respectively, with shadow lines to show interior features;

FIGS. 183A-183C are perspective views of drill bits with an opening in the static casing/sheath proximal to the captured tip for debris relief for use with a medical rotary drill/robotically driven arm in accordance with embodiments of the present disclosure;

FIGS. 184A-184C are front views of the drill bits shown in FIGS. 183A-183C, respectively;

FIG. 185 is a perspective view of the drill bit shown in FIG. 183A;

FIG. 186 is another perspective view of the drill bit shown in FIG. 183A with the drill bit being spaced apart from its sheath in order to depict the traversal path of debris through an opening of the static casing/sheath;

FIG. 187 is a top perspective view of the sheath shown in FIG. 186;

FIGS. 188A-188C are side views of the drill bit shown in FIG. 183A drilling into material in accordance with embodiments of the present disclosure;

FIGS. 189A-189C are perspective views of drill bits having cut-away sections that extend a length of static casing/sheath from the distal end;

FIGS. 190A-190C are front views of the drill bits of FIGS. 189A-189C, respectively;

FIG. 191 is a perspective view of the drill bit shown in FIG. 190B;

FIG. 192 is another perspective view of the drill bit shown in FIG. 190B including the drill bit being spaced apart from its static casing/sheath;

FIG. 193 is a side view of a drill bit with shadow lines to show internal features for depicting the traversal of fluids, debris, or particles through internal channels in accordance with embodiments of the present disclosure;

FIGS. 194A and 194B show opposing, perspective end views of the drill bit for depicting the traversal of fluid into and out of the internal channels to the distal end of the drill bit;

FIG. 195 is a side view of a drill bit for depicting the traversal of fluid, etc. along the shaft and through one or more openings defined by the static casing/sheath;

FIG. 196 is a side view of a drill bit with arrows for depicting the flow of fluid and debris within internal channels in accordance with embodiments of the present disclosure;

FIGS. 197A and 197B show opposing, perspective end views of the drill bit for depicting the traversal of fluid into and out of the internal channels to the distal end of the drill bit;

FIGS. 198A-198C are perspective views of drill bits that are each assembled with a static casing/sheath, and a sliding sheath in accordance with embodiments of the present disclosure;

FIGS. 199A-199C are perspective views of the drill bit shown in FIG. 198A with the sliding sheath at different positions with respect to the drill bit and static casing/sheath;

FIGS. 200A and 200B show a side view and front view, respectively, of the drills bit, static sheath, and sliding sheath shown in FIG. 198A;

FIGS. 201A-201C are side views of the drill bit shown in FIG. 198A drilling into material in accordance with embodiments of the present disclosure;

FIG. 202 is a side view of the drill bit side shown in FIG. 198C drilling sideways into material in accordance with embodiments of the present disclosure;

FIGS. 203A and 203B are perspective views of a drill bit assembled with a static sheath and sliding sheath in accordance with embodiments of the present disclosure;

FIGS. 204A and 204B show a front view and a side view, respectively, of the drill bit assembled with the static sheath and sliding sheath with partial opening at the distal end at various positions in the position shown in FIG. 203A;

FIG. 205 is a front view of the drill bit shown in FIGS. 203A and 203B drilling into bone or other material while the shield portion is protecting a sensitive soft tissue on the other side;

FIGS. 206A and 206B are perspective views of a drill bit assembled with a static sheath and sliding sheath having a partial end cap in accordance with embodiments of the present disclosure;

FIGS. 206C and 206D are a side view and a front view, respectively, of the drill bit shown in FIG. 206A;

FIGS. 207A-207C are perspective views of drill bits assembled with a static sheath and sliding sheath having a hook/end cap feature in accordance with embodiments of the present disclosure;

FIGS. 208A and 208B are perspective views of the drill bit shown in FIG. 207C in various positions;

FIGS. 209A and 209B are a side view and a front view, respectively, of the drill bit shown in FIG. 207C in various positions;

FIGS. 210A-210C are side views of the drill bit shown in FIGS. 208A-209B at different depths of drilling into a material;

FIG. 211 is a side view of the drill bit shown in FIG. 207C being moved in the direction of arrow for side drilling into material;

FIG. 212 is a system for navigation of a drill bit due to linkage of its static sheath to a navigation array in accordance with embodiments of the present disclosure;

FIGS. 213A and 213B are a side view and a top view, respectively, of the system shown in FIG. 212;

FIGS. 214A and 214B are perspective views of a drill bit with sliding sheath at various positions in communication with a navigation system in accordance with embodiments of the present disclosure;

FIGS. 215A and 215B are top views of the drill bit of FIGS. 214A and 214B drilling into the material in accordance with embodiments of the present disclosure;

FIG. 216 is a flow diagram of a rigid linear sheath feedback loop for a drilling device similar to those shown in FIGS. 198-215 in accordance with embodiments of the present disclosure;

FIG. 217 is a side view of a drill bit and its static casing/sheath with strain sensors attached thereto in accordance with embodiments of the present disclosure;

FIGS. 218A and 218B show the drill bit of FIG. 217 at different positions with off-axis loading being detected in accordance with embodiments of the present disclosure;

FIG. 219 is a flow diagram of a strain sensor feedback loop for a drilling device similar to those shown in FIGS. 217 and 218 in accordance with embodiments of the present disclosure;

FIG. 220 is a side view of a drill bit with its static casing/sheath and an attached vibration sensor in accordance with embodiments of the present disclosure;

FIGS. 221A-221C are side views showing the drill bit of FIG. 220 at different stages of drilling into a material having layers of varying densities and detection in accordance with embodiments of the present disclosure;

FIG. 222 is a flow diagram of a vibration sensor feedback loops for a drilling device similar to those shown in FIGS. 220 and 221 in accordance with embodiments of the present disclosure;

FIG. 223 is a side view of a drill bit with its static casing/sheath and an attached temperature sensor in accordance with embodiments of the present disclosure; and FIG. 224 is a flow diagram of a temperature sensor feedback loop for a drilling device similar to that shown in FIG. 223 in accordance with embodiments of the present disclosure.

SUMMARY

The presently disclosed subject matter relates to medical cutting devices having static components, working blade bodies, rails, struts, channels for fluid and gas flow, and hand-piece and robotic arm attachment capabilities. According to an aspect, a cutting device includes a working blade body being configured for operable connection to a source of movement. The cutting device also includes a static component being configured for operable connection to the source of movement. The static component comprises at least one rail, wherein the at least one rail extends substantially the same length as the working blade body.

According to another aspect, a cutting device includes a working blade body being configured for operable connection to a source of movement. The cutting device also includes a static component configured for operable connection to the source of fluid or gas and/or aspiration source. The static component defines at least one channel that extends between a port and an opening at a distal end of the static component for delivering fluid from the source of fluid via the at least one channel and out of the opening and/or removing fluid via the at least one channel through the opening and out towards the aspiration source.

According to another aspect, a cutting device includes a working blade body being configured for operable connection to a source of movement. The cutting devices also includes a static component configured for operable connection to the source of movement. The static component attaches offset from the working blade body relative to the attachment with the source of movement. Further, the cutting device includes a hand-piece or robotic arm being attached to the static component.

According to another aspect, a cutting device includes a working blade body being configured for operable connection to a source of movement. The cutting device also includes a static component configured for operable connection to the source of movement. The static component attaches in-line with the working blade body relative to the attachment with the source of movement. Further, the cutting device includes a hand-piece or robotic arm being attached to the static component.

According to another aspect, a method includes providing a cutting device. The cutting device includes a working blade body being configured for operable connection to a source of movement. Further, the cutting device includes a static component being configured for operable connection to the source of movement. The static component comprises at least one rail, wherein the at least one rail extends substantially the same length as the working blade body. The method includes using the cutting device for cutting into an object.

According to another aspect, a method includes providing a cutting devices. The cutting device includes a working blade body being configured for operable connection to a source of movement. The cutting device also includes a static component being configured for operable connection to the source of fluid or gas and/or aspiration source, the static component defines at least one channel that extends between a port and an opening at a distal end of the static component for delivering fluid from the source of fluid via the at least one channel and out of the opening and/or removing fluid via the at least one channel through the opening and out towards the aspiration source. Further, the method includes using the cutting device for cutting into an object.

According to another aspect, a method includes providing a cutting devices. The cutting device includes a working blade body being configured for operable connection to a source of movement. The cutting device also includes a static component being configured for operable connection to the source of movement. The static component attaches offset from the working blade body relative to the attachment with the source of movement. Further, the cutting device includes a hand-piece or robotic arm being attached to the static component. The method includes using the cutting device for cutting into an object.

According to another aspect, a method includes providing a cutting device. The cutting device includes a working blade body being configured for operable connection to a source of movement. Further, the cutting device includes a static component being configured for operable connection to the source of movement. The static component attaches in-line with the working blade body relative to the attachment with the source of movement. Further, the cutting device includes a hand-piece or robotic arm being attached to the static component. The method also includes using the cutting device for cutting into an object.

DETAILED DESCRIPTION

The following detailed description is made with reference to the figures. Exemplary embodiments are described to illustrate the disclosure, not to limit its scope, which is defined by the claims. Those of ordinary knowledge in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary knowledge in the art to which this disclosure belongs.

As referred to herein, the term "cutting device" or "cutting system" can be used interchangeably and can be any suitable component or system that is movable for cutting into or generally transforming a material (e.g. bone). Typical surgical procedures include cutting hard tissue (bone), soft tissue, or the like. The cutting device can include a blade that operates through large or small (e.g. vibrations) mechanical motion. The motion can be in a specific direction(s). For example, the cutting device can be moved in an oscillating manner, flexing, bending, rotating, torsionally, longitudinally, and the like. The cutting device can be driven and/or interact with a variety of systems including cutting guides, manual handpieces, handheld robots robotic arms, micro robots, robotic cutting guides secured locally to bone, and the like. They can also interact with many other systems like coolant pumps, navigation systems, AR/VR systems, and the like to provide output functionality and/or feedback to the user and/or robotically driven systems. In some examples, the surgical procedure involves completing operations related to knee surgery, hip surgery, shoulder surgery, spine surgery, or ankle surgery. These procedures may involve removing tissue to be replaced by surgical implants, such as knee implants, hip implants, shoulder implants, spine implants, or ankle implants. The surgical procedures may be any other type of procedure requiring the use of a cutting instrument to execute transforming a material.

As referred to herein, the term "drill device" or "drill system" can be used interchangeably and can be any suitable component (e.g., drill bit) or system being movable for drilling into or generally transforming a material (e.g. bone). Typical surgical procedures include drilling into hard tissue (bone), soft tissue, or the like.

In some applications, there is a need to detect sensor data such as temperature, strain, pressure, sound, vibration, or any combination thereof in real time at the working surface of the blade and/or adjacent to the cutting blade. The present disclosure provides device that position a wide variety of sensors, including but not limited to, temperature sensors, pressure sensors, strain sensors, acoustic sensors, vibration sensors, electrical conductivity sensors, fiber optic sensors, and/or any combination of a required sensing modality, in and around the cutting plane and bone-blade interface. This provides important temperature, strain, pressure, sound, and/or vibration measurements in-situ on a cutting device. This sensor data generated locally as a part of the cutting devices operation may be used for providing critical feedback to users completing surgical procedures and control outputs for robotically enabled systems. For example, the sensor data may provide the ability to communication with any system within the surgical environment that supports the cutting process of the procedure, including but not limited to, supporting real-time haptics, controlling robotic outputs, and/or enabling autonomous cutting applications. The sensor data from the surgical procedures may also be stored in external systems like data wells to support the analysis of historical data for machine learning and predictive analytics with respect to surgical planning, robotic controls, and the like. The sensor data gathered as a part of the cutting device and the techniques disclosed herein may be used to perform other procedures surgical or non-surgical, and may be used in industrial applications or other applications where data communicated from a cutting device informs a robotic system.

It is noted that embodiments of the present disclosure are described as producing or having oscillatory saw blade movement, drilling, or any other suitable source for motion. It is noted that in the alternative the movement may be any suitable type of movement produced by any suitable source (e.g., such as an ultrasonic transducer driving the blade through piezoelectric elements and smaller vibrations). Further, cutting may be applied to any suitable material or technical field. Suitable mechanical sources could include anything from piezoceramics, electro-mechanical motors, user generated hand motion, etc. However, it is important to note that all types of mechanisms can produce equivalent types of movements. These may include, but are not limited to, axial motion, bending motion, torsional motion, flexural motion, etc. It is also feasible that the source of mechanical motion can combine all of these modes of motion to create more complex movements. Regardless of the motion and/or the manner in which it is produced, there would be a resultant motion at the end of the functional device/blade edge. This motion would, under the claims of this patent, be captured within the bounds of the static casing which function to share load, decouple motion, and prevent heat transfer to the functional working surfaces. Examples include oscillating/sagittal/reciprocating medical bone cutting saws, medical rotary drills, medical rotary burs, construction hammer drills, construction rotary hammer, wood cutting axes, construction oscillating multi-tools, oscillating medical cast saws, cutting saws, etc. The principles of the claims presented in this patent could be applied to all of these devices with equivalently realized benefits.

FIGS. 1-3 illustrate different views of a cutting device 100 having a static casing with rails and struts in accordance with embodiments of the present disclosure. Referring initially to FIG. 1, the figure illustrates a perspective view of a cutting device 100 having a static casing with rails 102A, 102B and struts 104A, 104B in accordance with embodiments of the present disclosure. The struts 104A, 104B are positioned near a blade edge 106 of a working body 103. In this example, rails 102A, 102B extend close to the blade cutting edge 106. Top and bottom struts 104A, 104B are situated at the end of the static rails 102A, 102B and capture the blade above and below so that the blade cutting edge 106 sits in a slot with just the teeth of the cutting edge sticking out/protruding.

The struts 104A, 104B hold the static rails 102A, 102B rigidly together and help to maintain the trajectory of the cutting edge during cutting (i.e. prevent the leading edge of the blade from migrating away from the trajectory of the cutting plane).

The rails 102A, 102B have an extended cutout, generally designated 108, from the struts moving towards the rear attachment point of the rails with the handpiece so that the blades can be easily assembled after the rails are installed. The cutout 108 may be any suitable size and shape to help with the goals of allowing for: blade assembly; reducing working surface contact of the blade with the adjacent bone; allowing for free flow of debris; reducing metal-on-metal contact of the blade with the static rail construct; and preventing transfer of heat to adjacent bone (i.e. air gap insulates/prevents frictional sliding interactions).

The articulation surface between the moving blade/static rails/struts is minimized to optimize the ability of the mechanism to operate freely without generating excessive wear. Coatings and/or dry lubricants can be used to help with frictional properties at this interface, but since this is also positioned at the leading edge of the device natural lubricants exposed during the cutting process (i.e. synovial fluid) may help as well.

Although not shown in the figure, the working body 103 and the static casing (with rails 102A, 102B and struts 104A, 104B) can be operatively connected to a housing and a handle as will be understood by those of knowledge in the art. For example, a transducer or motor may be attached to the working body 103 for producing a desired mechanical motion with the blade cutting edge 106 (e.g. oscillating motion). It is noted that in this example the cutting device 100 is described as being an oscillating saw blade, but it may alternatively be of any other suitable type (e.g. such as an ultrasonic transducer driving the blade through piezoelectric elements and smaller vibrations). The oscillating motor, which may be suitably powered to produce motion through the working surface of the blade to its blade edge, can be operatively attached to an end 119 of the working body 103 that is closest to the housing. Oscillatory motion produced by the transducer/motor can propagate along a main body of the working body towards an end 121 of the working body 103 that opposes the end 119 of the blade working body 103 that is attached to the oscillatory transducer/motor. The end 121 of the working body 103 is shown as being attached to the cutting blade 106 so that the cutting blade 106 moves due to the oscillatory motion. It is noted that any other suitable motion may be produced alternative to mechanical oscillations such as those produced by traditional bone saws (e.g. such as those produced by ultrasonic cutting devices that use smaller scale vibrations). One of knowledge in the art can envision the attachment end 119 being of any suitable configuration/hub connection with the mechanical driver to produce the desired motion.

The cutting edge of the cutting blade 106 can be a blade tip configured to cut, ablate, abrade or otherwise transform, for example, bone or other tissue. The cutting edge can define at least one blade edge. In this example, the blade edge 106 has serrations for cutting, ablating, abrading, or otherwise transforming bone or other tissue. In the alternative, the blade edge 106 is a continuous, planar arc, and sharpened along its entirety for cutting, ablating, abrading, or otherwise transforming bone or other tissue.

The support structure (i.e. rails 102A, 102B and struts 104A, 104B) may be made of a material suitable for biomedical applications, such as ceramic, titanium, stainless steel, PEEK, PE, PTFE, or the like. The outer surface of the support structure 6606 may be coated with a lubricant, such as a solid film or a fluid film, and/or any other insulative material (e.g. titanium nitride, chromium coatings, etc.). The working body 103 and the cutting blade 106 may be made of a material suitable for biomedical applications, such as titanium, stainless steel or the like. In embodiments, a lubrication film may cover the working body 103 and the cutting blade 106 and may be made of a solid film lubricant, or other suitable lubricant and/or coating (i.e. titanium nitride). Further, for example, support structure may be coated with a lubrication film and/or coating, such lubrication film/coating being a solid film lubricant/coating suitable for the application (i.e. titanium nitride). The support structure, the working body 103, and the cutting blade 106 may be coated with the lubrication film.

FIGS. 4A-4C illustrate cross-sectional, side views of cutting blades 400 and their working body 402 and static rail 404 in accordance with embodiments of the present disclosure. FIG. 4A shows the static rail 404 with a tapered tip 406 that is sub-flush to the cutting blade 400 to allow for smoother transition of the static rail into the cutting plane. One of knowledge in the art can envision other types of features to allow for this transition from the bone translating over the cutting end onto the static rail features (e.g. break edge at the tip and/or scaling the thickness of the cutting edge 400 to allow for more clearance). The static rail 404 can be either flush or sub-flush to the cutting blade 400 in terms of thickness. The clinical benefit of having the rails be flush & sub-flush surfaces is that it provides significant rigidity for cut plane alignment as soon as the bone translates over the cutting edge 400. FIG. 4B shows a cross-sectional side view without the static rails of the attachment of the cutting blade 400 within the working body slot 408 of the working body 402. FIG. 4C shows a cross-sectional, side view of the entire construct with cutting blade 400, working body 402, static rail 404, static rail tapered tip 406, and working body slot 408. The working body 402 can be either flush or sub-flush to the static rail 404. One knowledgeable in the art could also envision a combination of flush & sub-flush surfaces and features along the static rails 404. The clinical benefit of these flush & sub-flush surfaces is that they allow for reduced surface friction interactions and can thus reduce wear debris and/or heat generation. For example, when cutting through a cutting guide, the rapidly oscillating surface of the blade can come in contact with the cutting guide and cause significant wear debris and heat generation on both the blade and the cutting guide surface itself. A sub-flush blade surface relative to the static rails reduces this contact and the deleterious effects. It also allows the sub-flush blade surface to more freely oscillate since the rails take on a load supporting role.

FIG. 5 illustrates a top view of the cutting device 100 shown in FIGS. 1-3. Referring to FIG. 5, an arrow 500 shows generally the location of a slot defined by the static rails/struts 102A, 102B, 104A (and strut 104B, not shown in FIG. 5) around the blade edge 106 and how it is open around the front and sides. The general dimensions (e.g. length, width, thickness, etc.) of these can be scaled/adjusted to meet the needs of the blade/procedure such as to maintain mobility and fit within a cutting guide.

FIG. 6 illustrates another top view of the cutting device 100 shown in FIGS. 1-3 and 5. Referring to FIG. 6, this figure includes broken lines to show interior features. FIG. 7 illustrates another top view of the cutting device 100 in close up. Extended tabs 107 on the cutting blade 106 within the slot can maintain trajectory/precision of the cutting edge during cutting. The extended tabs 107 can be positioned substantially close to the base of the captured slot feature 110A and 110B to increase engagement/strength versus other blades on the market. For example, when the blade cuts through a harder material the extended tabs minimize skiving by reducing the amount the blade can deflect within the slot. It also allows the distance between the distal end of the slot and the cutting edge to be closer together and thus reducing the tip deflection of the blade during cutting (e.g. through immediate load sharing with the static components just behind the leading edge of the blade).

FIG. 8 illustrates a top view of a cutting device similar to the cutting device shown in FIGS. 1-3, 5, and 6 but with debris reliefs 800 within the cutting edge of the blade 106 to allow for debris to translate from the leading cutting edge through the rigid struts 104A (bottom not shown) into the open-air gap 108. The debris reliefs 800 may be defined channels within the working blade body. The debris reliefs 800, in this embodiment, are apertures that extend through the blade but may alternatively be any suitable shape, size, or feature of the blade for providing pathways for debris to traverse away from the blade edge 106.

FIGS. 9A and 9B illustrate top views of the cutting device 100 shown in FIGS. 1-3, 5, and 6 at the left-most and right-most extents, respectively, of movement side-to-side of the blade working body 103 and cutting blade edge 106. Lateral clearance reliefs 114A and 114B provide extra mobility for the cutting system within the cutting plane when in bone and/or cutting guide. Lateral clearance reliefs 114A and 114B can be adjusted to allow for more or less mobility based on the application. Generally more clearance (i.e. narrower overall width or less rail material) results in more mobility. Lateral clearance reliefs are defined by the cutting edge 106 excursion, which is defined as the cutting plane created by the furthest cutting edge 106 left (FIG. 9A) and right (FIG. 9B) during cutting edge oscillation, and the base static rails width 112A and 112B is defined to be within the excursion. An exception when base static rails 112A and 112B can be wider than the cutting edge excursion, is in applications where the base static rails do not need to translate into the cutting plane created by the cutting blade excursion as may be the case in a very long cutting system (e.g. the final portion of the rails would reside within the capture of a cutting guide). Lateral clearance reliefs 114A and 114B are contained within the width of the base static rails width 112A and 112B. There may be cutting applications when lateral clearance reliefs 114 A and 114B may not be needed at all, where robotic arms drive the cutting device without the need for use with guides (e.g. less mobility required). Furthermore, since they are relatively motionless, the static rails 102A and 102B provide a surface that a user can manually hold for greater tip control (e.g. holding the end of the rails closer to the cutting end provides more control over the blade on the part of the user). Finally, the static rails 102A and 102B provide a clinical benefit in the form of preventing the rapidly oscillating working body 103 from contacting the inner surfaces of manual cutting guides. Therefore, the outer edges of the static rails (e.g. lateral clearance reliefs 114A and 114B and base static rail width 112A and 112B) can directly contact the inner surfaces of cutting guides. This lack of guide kicking improves the stability of the guide (e.g. prevents dislodging of pinned connections) and translates to more precise cuts.

FIGS. 10A and 10B show close-up views of the cutting device 100 shown in FIGS. 9A and 9B, respectively. The width of the working blade body is defined by edges 118A and 118B, which are contained within the static rails inner edges 116A and 116B, at its furthest excursion left (FIG. 10A) and right (FIG. 10B) during oscillation of the working blade body. These static rail inner edges 116A and 116B can also be calibrated based on cutting application and can be set based on the need for more or less excursion. They can also allow for narrower/wider rails and working blade body geometry based on the strength requirements of the cutting application.

Figure 11A:
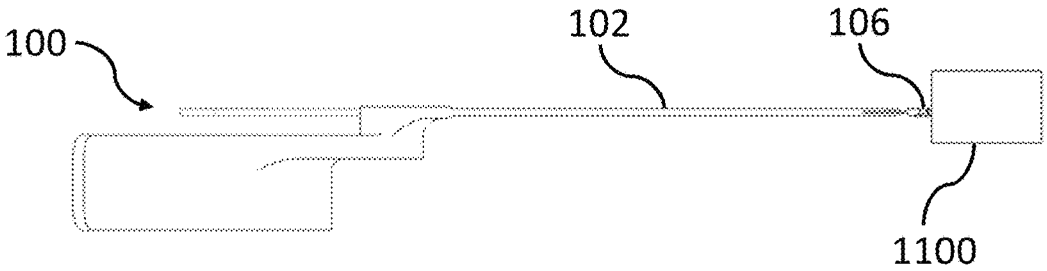
Figure 11B:
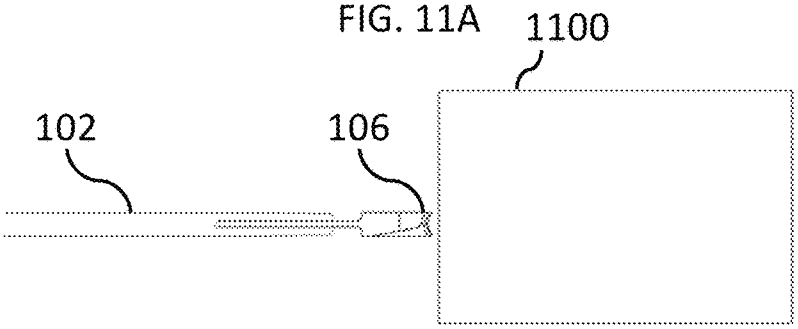
Figure 11C:
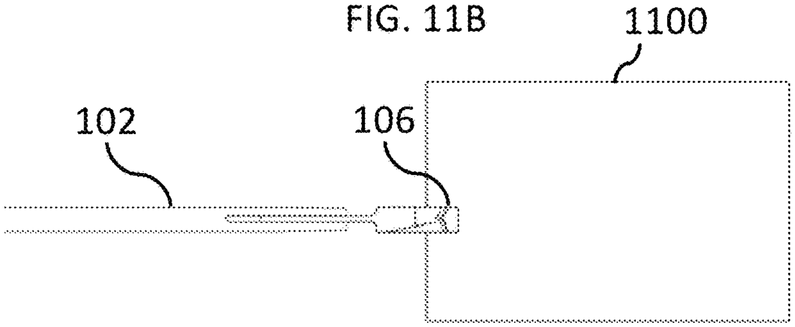
Figure 11D:
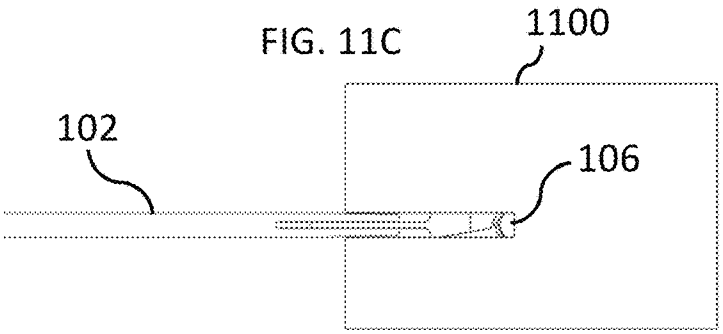
Figure 11E:
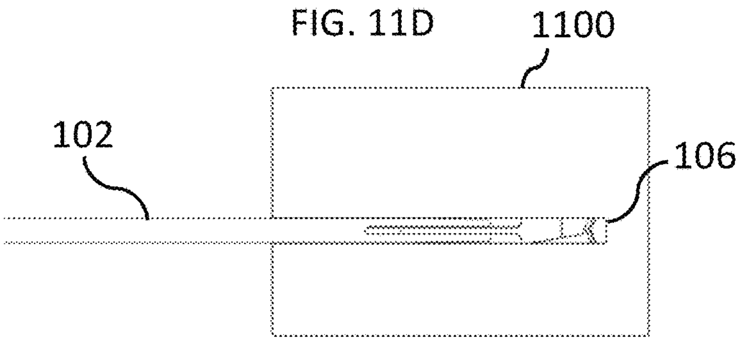

FIGS. 11A-11E are side views of the cutting device 100 positioned at different steps for cutting material 1100 in accordance with embodiments of the present disclosure. Referring to FIG. 11A, this figure shows the blade edge 106 near the material 1100, which may be bone in an example. FIGS. 11B-11E show close-ups of the blade edge 106 and material 1100. Particularly, FIG. 11B is a close-up view of the view shown in FIG. 11A. FIG. 11C shows the blade edge 106 having cut and inserted into material 1100, which represents initial scoring of the planar cut prior to insertion of the static rails 102 for stability/alignment. FIG. 11D shows the blade edge 106 having cut further into material 1100, where the static rails 102 have been engaged within the cutting plane to allow for load sharing with the blade edge 106. FIG. 11E shows the blade edge 106 having cut deeper than the depiction shown in FIG. 11D. One knowledgeable in the art can envision various flush and sub-flush configurations of the static rails 102 with respect to the blade edge 106.

FIG. 12 illustrates a perspective view of another cutting device 1200 in accordance with embodiments of the present disclosure. Referring to FIG. 12, this cutting device 1200 is similar to the cutting device 100 of FIG. 1, but a rear top strut 1202 extends across a top of a working body 103. The rear top strut 1202 provides rigidity to the overall cutting system. In one version, the strut is thicker than the working surface of the static rails 102A and 102B and does not require any cutouts in the working blade body 103 (i.e. there is clearance between rear top strut 1202 and working blade body 103). It does not translate into the cut directly since the blade edge 1204 is lower in thickness than the rear top strut 1202 even though the static rails 102A and 102B is lower in thickness than the blade edge 1204. In another version, the rear top strut 1202 is lower in thickness than the blade edge 1204 and can translate into the cut directly. It is noted that in some embodiments, various sensors as described herein can be positioned on the strut 1202. FIG. 13 is a top view of the cutting device 1200 shown in FIG. 12. Finally, this rear top strut 1202 is shown on top of the rails, but can also be across the bottom and/or be placed on both sides if desired based on the application.

FIG. 14 illustrates a perspective view of a cutting device 1400 with a single-entry irrigation port 1402 in accordance with embodiments of the present disclosure. The cutting device 1400 is similar to the cutting device 1200 except with the inclusion of the port 1402 and corresponding interior channels to the rails 102A and 102B (not shown) that exit at the cutting end 1204. FIG. 15 illustrates a top view of the cutting device 1400 shown in FIG. 14. During operation, fluid can enter via port 1402 and exits at 2 outlets, generally indicated by reference numbers 1404A, 1404B near the cutting blade 1204. One knowledgeable in the art can envision that these channels could exit at any other location within the geometric constraints of the static rails.

Now turning to FIG. 16, this figure illustrates another top view of the cutting device 1400 shown in FIGS. 14 and 15. Also, this figure shows shadow lines of interior channels 1600 that are used for conveying fluid from the port 1402 to outlets 1404A, 1404B.

FIG. 17 illustrates a close-up, side view of the cutting device 1400 shown in FIGS. 14-16. Referring to FIG. 17, this view shows a close up of port 1402 and channels 1600 shown in shadow lines.

FIG. 18 illustrates a perspective view of a cutting device 1800 having two ports 1802A, 1802B for entry or exit of fluid conveyed in rails 1804A, 1804B, respectively, in accordance with embodiments of the present disclosure. Referring to FIG. 18, fluid can be delivered to both ports 1802A and 1802B for conveyance along respective interior channels to exit at outlets generally indicated by arrows 1806A and 1806B, respectively. The fluid can exit in a direction generally forward of the cutting device 1800 near blade edge 1808 for irrigating an area near blade edge 1808. Otherwise, the cutting device 1800 is similar to the cutting device 1400 of FIG. 14.

FIG. 19 illustrates a top view of the cutting device 1800 shown in FIG. 18. FIG. 20 illustrates another top view of the cutting device 1800 but with shadow lines indicating the interior channels 2000 for conveying fluid from ports 1802A, 1802B to outlets 1806A, 1806B, respectively. FIG. 21 illustrates a close-up, top view of the cutting device 1800 shown in FIGS. 18-20. Referring to FIG. 21, arrows 2100 generally indicate the direction of flow of fluid within channels and out outlets 1806A, 1806B during operation. A clinical benefit to having fluid directly delivered to the cutting end is that it allows for more efficient removal of any bone debris at the cutting edge, by providing focused pressurized fluid to flush the area. This also creates a cooling effect for temperature management of the area. This can support a better surface finish and more accurate cutting when compared to cutting without fluid or using a different method of debris removal. It can also provide an opportunity to maintain the sharpness/life of the cutting end (e.g. coolant to help prevent dulling). One knowledgeable in the art can envision different types of fluid (e.g. saline) being used and that they can additionally contain therapeutics such as antibiotics or biologics to stimulate bone growth, prevent infection, etc.

FIG. 22 illustrates another top view of the cutting device 1800 shown in FIG. 18 but in a different mode of operation for receiving fluid through apertures and into its channels. Referring to FIG. 22, this mode of operation is an aspiration mode for pulling in fluid and/or other material near the blade edge 1808. Arrows 2200 generally indicate the direction of flow of fluid into and through channels during operation in the aspiration mode. Aspiration can have the benefit of helping with debris removal and removing heat to help manage temperature at the cutting site. These applications can help with surface finish, cutting accuracy, and helping to maintain visualization if excess coolant/fluid is used based on the application. FIG. 23 illustrates a close-up, side view of the cutting device 1800 with shadow lines indicating the interior channels 2000.

FIG. 24 is a top view of another cutting device 2400 having external irrigation channels 2402A, 2402B in accordance with embodiments of the present disclosure. Referring to FIG. 24, fluid can enter at ends 2404A, 2404B, and exit at ends 2406A, 2406B near blade edge 2408. One knowledgeable in the art can envision having a single port of entry for the fluid that leads to separate external irrigation channels.

FIG. 25 illustrates a top view of the cutting device 2400 shown in FIG. 24 except with fluid being received at ends 2406A, 2406B in an aspiration mode in accordance with embodiments of the present disclosure. Referring to FIG. 25, the direction arrows show the direction of flow of the received fluid to and out of ends 2404A, 2404B. It is noted that although one irrigation channel (i.e., channels 2402A, 2402B) per rail is shown in this example, it should be appreciated that more than one channel may be suitably attached to each rail. FIG. 26 illustrates a close-up, top view of the cutting device shown in FIG. 25 in the aspiration mode where debris 2600 is being pulled into ends 2406A, 2406B due to fluid flow. One knowledgeable in the art can envision having a single port for receiving the aspirated fluid based on the application.

Figure 27:
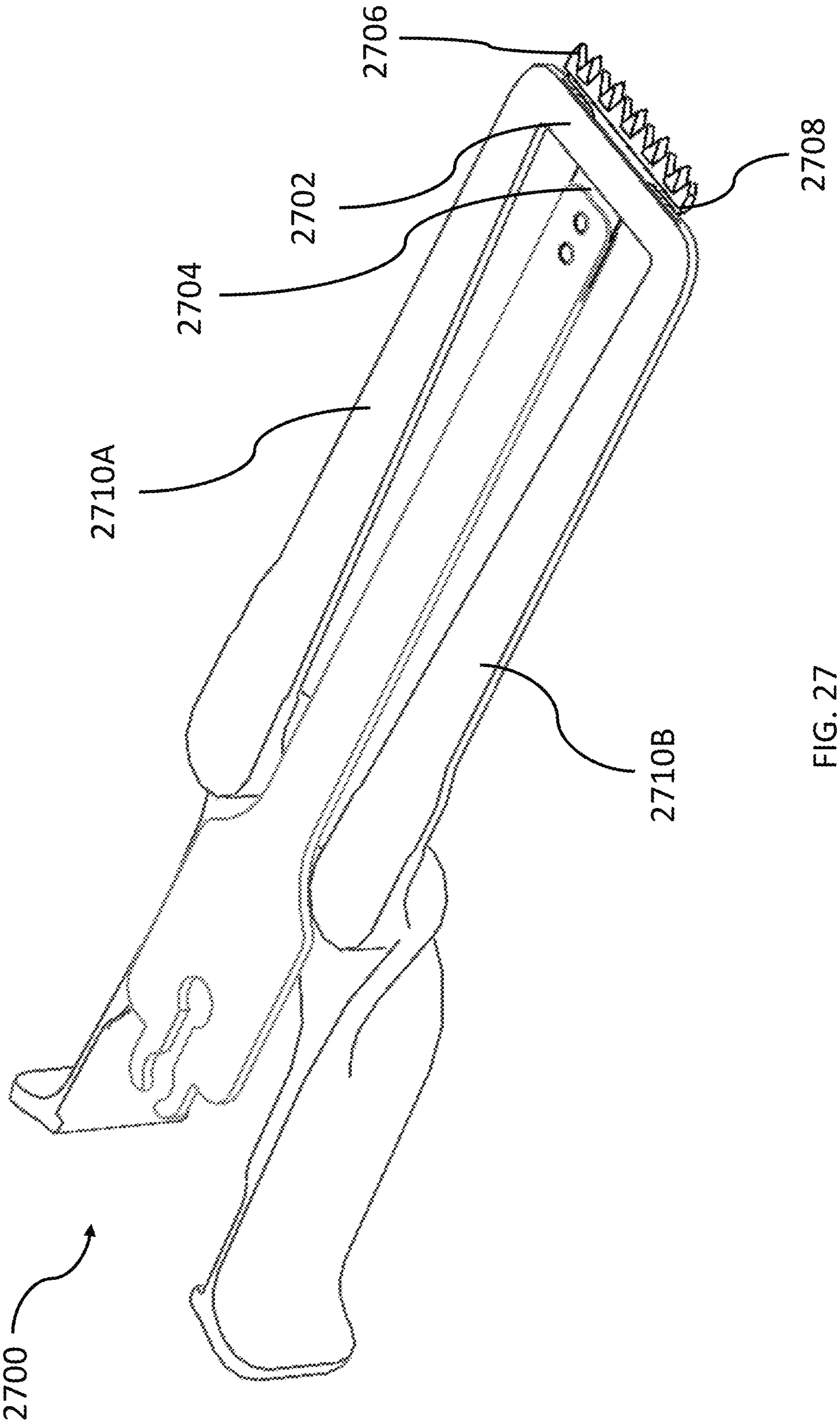

FIGS. 27-30 illustrate views of another cutting device 2700 with a strut 2702 supporting a neck portion 2704 of a cutting blade 2706 in accordance with embodiments of the present disclosure. The cutting device 2700 is similar to the cutting device 100 shown in FIG. 1 except that the strut 2702 supports the neck portion 2704 of a narrower body 2708 of the cutting blade 2706. Referring to FIG. 27, the cutting device 2700 has rails 2710A, 2710B attached to strut 2702. This represents a slightly different method of capturing the blade edge through the use of an opening (e.g. versus the slot style with extended blade tabs previously shown). Therefore, it provides an opportunity to allow for slightly different types of blade configurations that still allow for a precision captured interaction between the static components and the oscillating blade. One knowledgeable in the art can envision this may allow for debris to more easily flow from the cutting end 2706 through the strut 2702 and into the open cavity on the other side. Clinically this may benefit certain cutting procedures based on the specific application.

Figure 28:
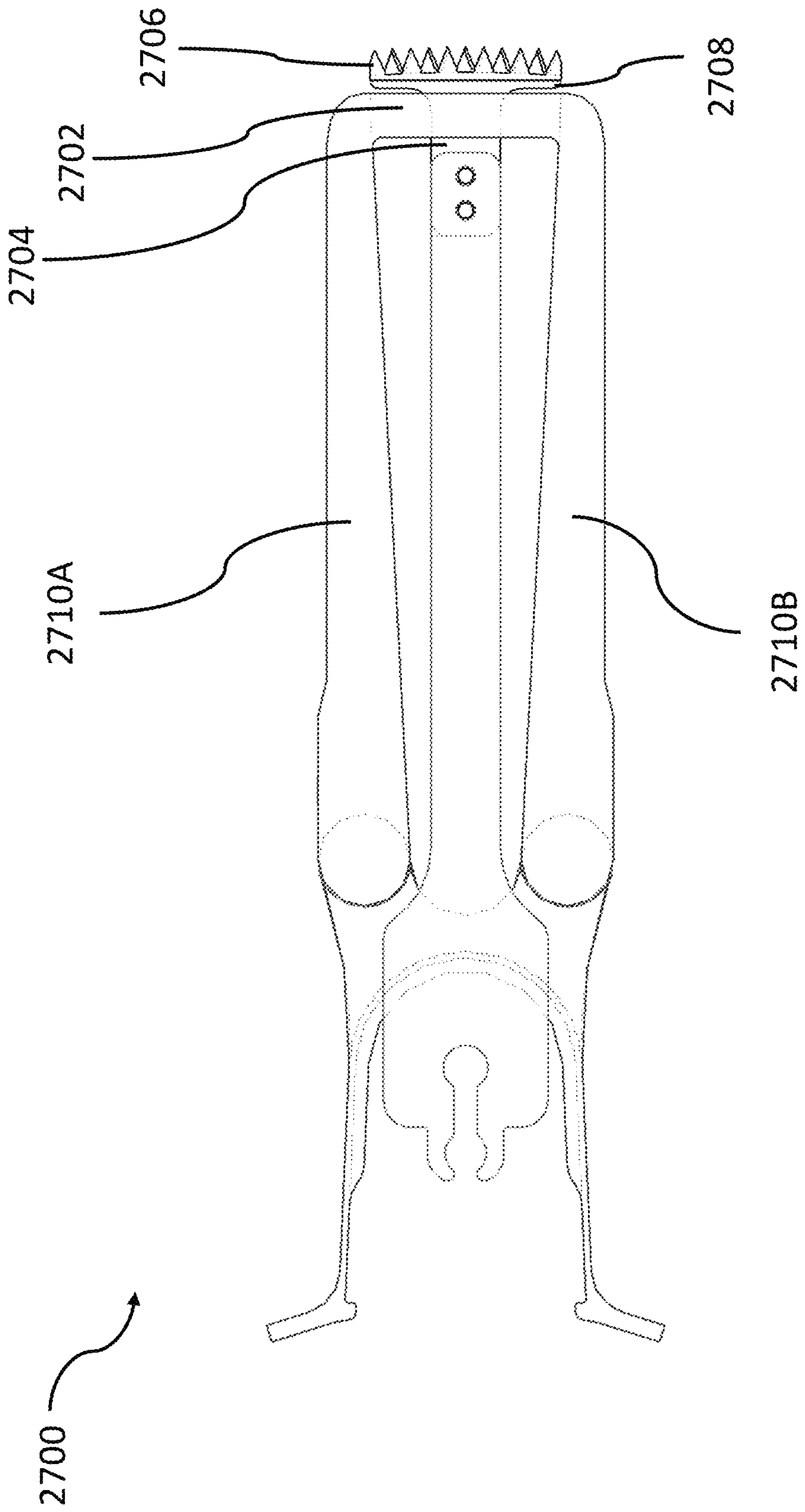
Figure 29:
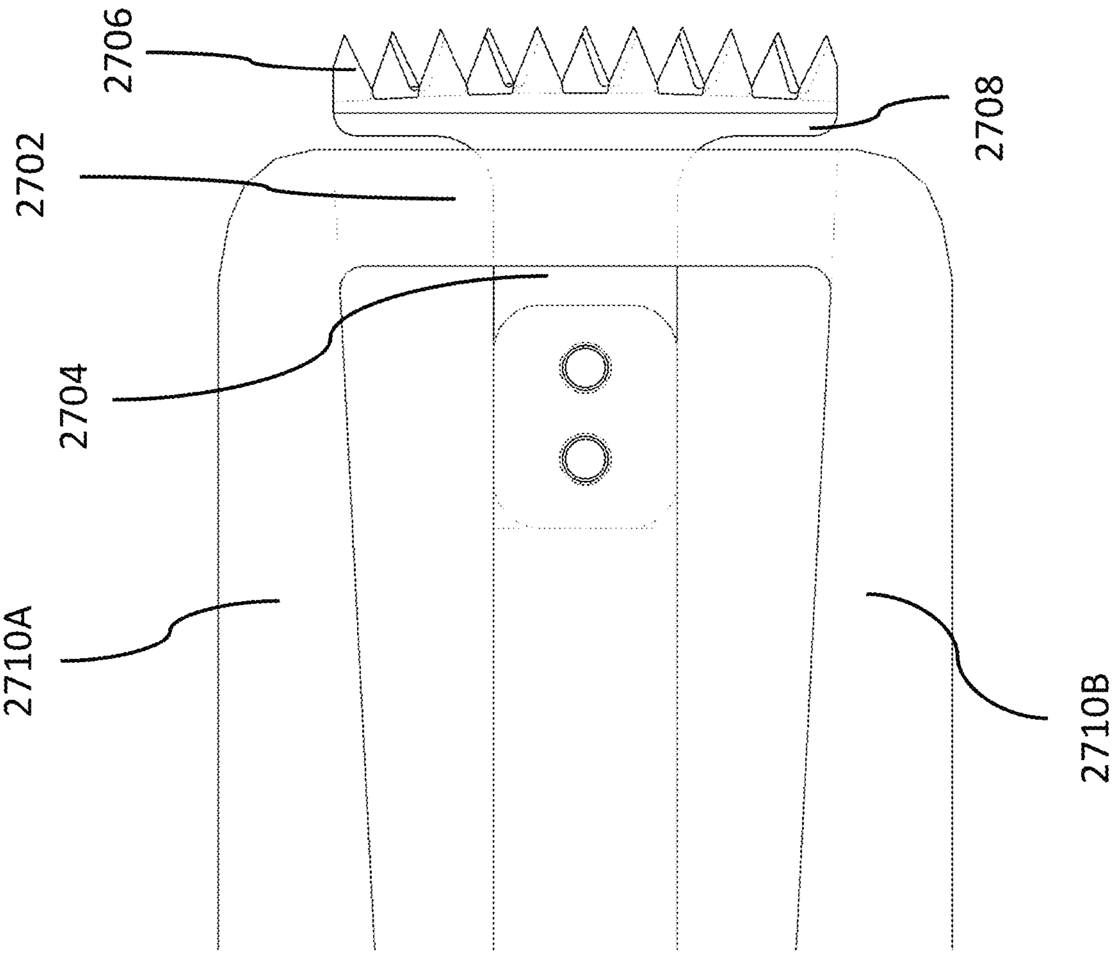
Figure 30:
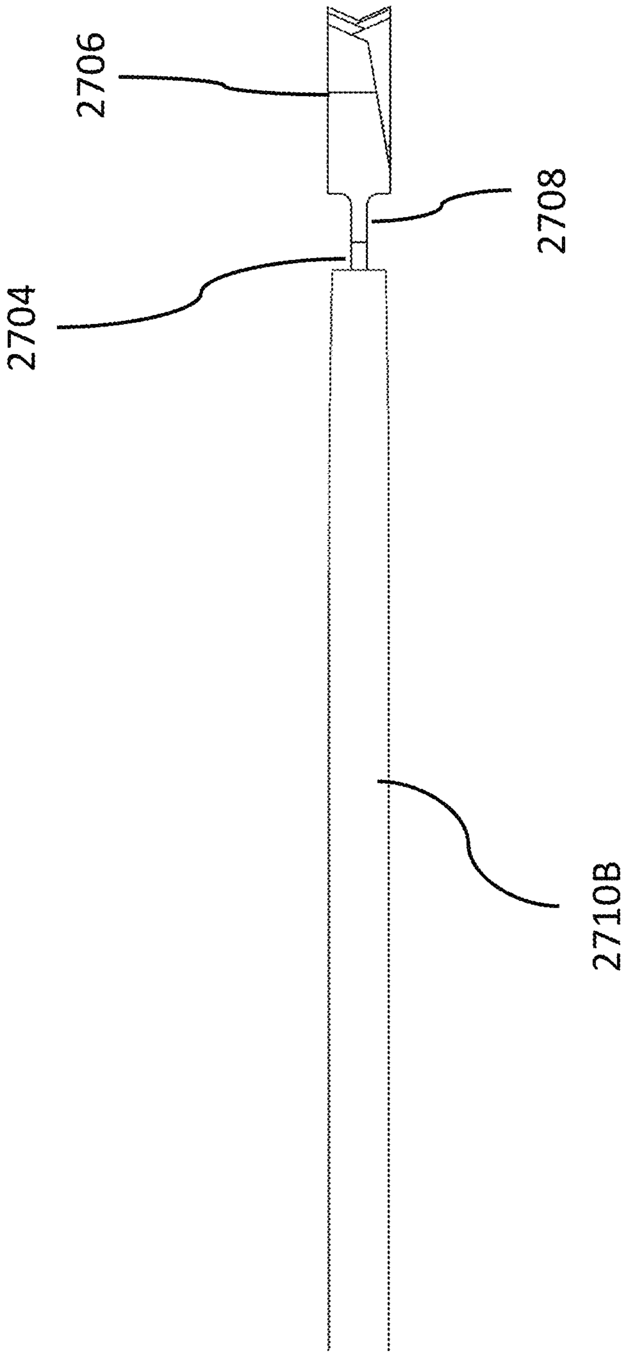

FIG. 28 illustrates a top view of the cutting device 2700 shown in FIG. 27. FIG. 29 illustrates a close-up, top view of the cutting device 2700 shown in FIG. 27. FIG. 30 illustrates a close-up, side view of the cutting device 2700 shown in FIG. 27.

FIGS. 31-35B illustrate views of another cutting device 3100 with a strut 3102 supporting a neck portion 3104 of a cutting blade 3106 in accordance with embodiments of the present disclosure. The cutting device 3100 is similar to the cutting device 2700 shown in FIG. 27 with the neck of the portion supported. However, one knowledgeable in the art could envision the strut 3102 supporting extended tabs similar to the device shown in FIG. 6 just on one side (e.g. rather than captured with struts on both sides). Referring to FIG. 31, the cutting device 3100 has rails 3110A, 31101B attached to strut 3102 for supporting the cutting blade's 3106 body 3108 via neck portion 3104. The strut 3102 can be located either on top or bottom of the cutting blade neck portion 3104. The clinical benefit of the strut at the blades leading edge is that it can be configured such that it prevents skiving (e.g. if skiving up is more common the strut could be placed in such a way to resist this motion and maintain a more precise cut).

FIGS. 32A and 32B illustrate a top view and a bottom view, respectively, of the cutting device 3100 shown in FIG. 31. A rear strut 3112 proximal to front strut 3102 provides further support to the cutting blade 3106 and is offset/opposite top or bottom from the front strut 3102 to allow for a single monolithic piece cutting blade 3106. Both struts 3102 and 3112 are beneficial for preventing skiving. Struts 3102 and 3112 may be flipped and/or placed in any number of configurations that make sense to the procedure (e.g. location of the struts along the working surface could be adjusted as well). Although two struts are shown in this embodiment, it should be noted that any suitable number of struts may be provided. In addition, struts may be longer or shorter than shown in these figures. This design can stabilize both sides of the working blade body. Further, embodiment design can prevent independent motion of each rail (i.e. if one rail was in cutting plane and the other outside the cut). It is also noted that this design can provide the user with a further surface to stabilize the blade for tactile feel on the bottom. FIG. 33 illustrates a close-up, top view of the cutting device 3100. FIGS. 34A and 34B illustrates a side view and a close-up, side view, respectively, of the cutting device 3100.

FIGS. 35A and 35B illustrate top views of the cutting device 3100 shown in FIGS. 31-34B at the left-most and right-most extents, respectively, of movement side-to-side of the cutting blade 3106.

FIG. 36 illustrates a perspective view of another cutting device 3600 in accordance with embodiments of the present disclosure. Referring to FIG. 36, the cutting device 3600 includes a cutting blade 3602 and rails 3604A, 3604B. The cutting device 3600 also include an upper strut 3606 and a lower strut 3608 each attached to rails 3604A, 3604B. It is noted that the lower strut 3608 extends a substantial length of the rails 3604A, 3604B. FIG. 37A shows a top view of the cutting device 3600. FIG. 37B shows a bottom view of the cutting device 3600 with shadow lines to indicate internal features and/or hidden geometry.

FIG. 38 illustrates a top view of a cutting device 3800 in accordance with embodiments of the present disclosure. Referring to FIG. 38, it can be seen that this embodiment does not include full struts, but rather just partial struts 3804A and 3804B extending from the side rails 3802A and 3802B for supporting the blade 3806 on either side (struts on the bottom view that capture the other side of the blade are not visible).

While this design does not have full struts, the partial struts 3804A and 3804B capture the cutting edge within a slot to provide added precision. This also allows for application of sensor technology near the cutting edge. FIG. 39 illustrates a top view of the cutting device 3800 with shadow lines to show internal features and/or hidden geometry. FIG. 40 illustrates a close-up, top view of the cutting device 3800 with shadow lines to show internal features and/or hidden geometry.

FIG. 41A illustrates a top view of the cutting device 3800 showing the blade 3806 at the extent of its range of movement to the left and with shadow lines to show internal features. FIG. 41B illustrates a top view of the cutting device 3800 showing the blade 3806 at the extent of its range of movement to the right and with shadow lines to show internal features. FIG. 42 is a close-up, perspective view of the cutting device 3800 with the blade 3806 at the extent of its range of movement to the left. In this view it is possible to see one of the bottom partial struts 3804C that captures the other side of the blade. At its full extent, the blade 3806 always remains captured within the partial struts. Although the partial struts do not span across and fully capture the blade they still provide a mechanism to couple the static rails 3802A and 3802B with the blade edge for increased stability and blade control. The clinical benefit of the partial struts is that there is a large region between the partial struts that allow for migration of cutting debris backwards. It also allows for capturing both sides of the blade without having a completely closed opening (e.g. the partial struts may allow for easier assembly of a monolithic cutting blade components through the centralized opening).

FIG. 43 illustrates a top view of another cutting device 4300 similar to the cutting device 3800 of FIG. 38 except without the partial struts 3804A and 3804B. Referring to FIG. 43, the cutting device 4300 includes rails 4302A, 4302B, and a cutting blade 4304. This means that the cutting blade 4304 can be a single monolithic piece construction without any cutouts in the thickness for fit with the rails 4302A and 4302B while also gaining the benefit of having the static rails for stabilizing the device within the cutting plane. This increases overall cutting blade strength and rigidity which could have certain clinical benefits based on the application.

FIGS. 44A-44C illustrate side views of different embodiments of a cutting device 4400 similar to the cutting device 4300 shown in FIG. 43. The cutting devices 4400 each include rails 4402 and cutting blade 4404. The cutting devices 4400 have static rails 4402, cutting blade 4404, and blade neck portions 4406 of different thicknesses in the vertical direction. These different thicknesses can allow for the static rails 4402 and blade neck portions 4406 to be flush or sub-flush with respect to each other and to the blade 4404. Sub-flush configurations can allow for easier translation of the static rails 4402 and blade neck portions 4406 into the cutting plane. One knowledgeable in the art in the art could also envision a combination of flush & sub-flush surfaces and features along the static rails 4402.

FIG. 45 illustrates a perspective view of the cutting device 100 shown in FIG. 1 attached to a handpiece 4500 in accordance with embodiments of the present disclosure. Referring to FIG. 45, this figure shows the offset nature of the cutting device 100 static rail components away from the attachment to the source of movement (e.g. oscillating mechanism coupling) on the handpiece. Offset attachment allows for separate, universal, modular attachment to any viable handpiece (i.e. not constrained to a single handpiece type) and/or end effector attachment (e.g. robotic arm, not shown in image). One knowledgeable in the art can envision that modifying the fit of the offset attachment to meet the needs of other power systems may be necessary (i.e. where the blade attachment maintains the systems current fit, but the rails attachment could be adjusted to work with other devices). This includes locating/indexing surfaces or features to set the offset attachment height relative to the blade engagement (e.g. lip feature that attaches relative to the housing of the source of movement) and to set the offset attachment depth relative to the working surface length (e.g. cylindrical surface feature on attachment sits flush to the housing of the source of movement). This could also include a locking feature to ensure secure attachment of the cutting device 100 to the handpiece 4500 during operation, but still allows for removal when not operating. Taken together the locating/indexing surfaces or features and locking mechanisms allow for the cutting device 100 to stay secure during operation under a variety of loading conditions (e.g. plunging in or out of the bone, bending, flexing, tension, compression, rotation/torsional, etc.). One knowledgeable in the art can envision the offset attachment being made of multiple components and/or assembly of components if needed (e.g. versus the single snap attachment shown).

FIG. 46 illustrates a perspective view of the cutting device 100 and handpiece 4500 shown in FIG. 45 but with the cutting device 100 detached from the handpiece 4500. Referring to FIG. 46, this shows that the cutting device 100 can be removed or attached as needed.

FIGS. 47 and 48A-B illustrate a top view and a side view, respectively, of the cutting device 100 and handpiece 4500, with the cutting device 100 attached to handpiece 4500. FIGS. 48A and 48B illustrates a side view and a close-up, side view, respectively, of the cutting device 100 and handpiece 4500, with the cutting device 100 attached to handpiece 4500. As can be seen in FIGS. 48A and 48B, the cutting device 100 generally operates within a plane connected to the source of movement and the attachment of the cutting device 100 to the handpiece 4500 is at a point outside of this plane.

Current embodiment demonstrates an offset attachment that is a snap fit around the blade attachment area of the handpiece and provides indexing features to set height and blade working depth. Various complementary and/or separate attachment methods are possible such as a set screw, magnetic, adhesive, articulating/mating design feature on the attachment with the handpiece.

FIG. 49 illustrates a perspective view of another handpiece 4900 attached to a cutting device 4902. In this example, the cutting device 4902 is similar to the cutting device 100 shown in FIG. 1 except that rails 4904A, 4904B are rigidly attached in-plane to the handpiece 4900 source of movement. This is an example of the in-line assembly of the rails 4904A, 4904B being rigidly attached for permitting a shortened overall length of the assembly for ease of manufacturing and assembly as well as added stiffness of the cutting device. One knowledgeable in the art can envision that the in-line attachment can be used with all previous embodiments shown with the offset attachment. One knowledgeable in the art can also envision that modifying the fit of the in-line attachment to meet the needs of various power systems may be necessary (i.e. where the blade attachment maintains the systems current fit, but the rails attachment could be adjusted to work with other devices). This includes locating/indexing surfaces or features (e.g. cutouts, pinned engagements, slots, tracks, etc.) that are lateral/parallel to the blade engagement outside or inside of the source of movement and to set in-line locking depth relative to the blade engagement. This could also include a locking feature to ensure secure attachment of the cutting device 4902 to the handpiece 4900 during operation, but still allows for removal when not operating. Taken together the locating/indexing surfaces or features and locking mechanisms allow for the cutting device 4902 to stay secure during operation under a variety of loading conditions (e.g. plunging in or out of the bone, bending, flexing, tension, compression, rotation/torsional, etc.)

FIG. 50 illustrates a perspective view of the handpiece 4900 attached to a manually-detachable cutting device 4902. In this example, the cutting device 4902 is shown with cutting device 4902 detached. FIGS. 51 and 52 illustrates a top view and a side view, respectively, of the handpiece 4900 and cutting device 4902 shown in FIG. 50.

FIGS. 53A and 53B illustrates top perspective views of a modular cutting device 5300 in accordance with embodiments of the present disclosure. The cutting device 5300 is modular as it includes a separate attachable strut/rail portion 5302 at its end near cutting blade 5304. FIG. 53A shows the cutting device with the strut/rail portion 5302 attached to ends of rails 5306A and 5306B. FIG. 53B shows the cutting device with the strut/rail portion 5302 detached from the rest of the cutting device 5300. In embodiments, the strut/rail portion 5302 is attachable via a pair of pins that securely fit (e.g. whether via press-fit, snap fit, magnetic engagement, etc.) into apertures 5308A and 5308B defined at the ends of rails 5306A and 5306B. The underside of the strut/rail portion 5302 can include corresponding protrusions (not shown in FIGS. 53A and 53B) for fitting into the apertures 5308A and 5308B when in the attached position shown in FIG. 53A.

It is noted that alternative to the method of attachment described with respect to FIGS. 53A and 53B, the strut/rail portion 5302 can otherwise be suitably attached to sustain loading under operation. For example, the strut/rail portion 5302 may be attached by snap fit, magnets, or a slotted mechanism (e.g. with a rail and track and/or keyhole style feature). During operation the attachment would be under compression from surrounding material being cut (e.g. bone) and that would help maintain the secure attachment. One of knowledge in the art could envision the secure attachment being made reversible to allow for reuse (e.g. blade could be disposable and the modular rail and its corresponding strut/rail portion 5302 sterilizable for multiple uses).

FIGS. 54A and 54B illustrate a top view and a bottom view, respectively, of FIG. 53A with the cutting device 5300 and the strut/rail portion 5302 being attached. FIG. 55A illustrates a close-up, top view of the cutting device 5300 distal end with shadow lines to show internal and/or hidden features. FIG. 55B illustrates a close-up, side view of the cutting device 5300 distal end.

FIGS. 56A and 56B illustrate a close-up, top perspective view and a close-up, bottom perspective view, respectively, of the cutting device 5300 with the strut/rail portion 5302 being detached. Referring to FIG. 56B, protrusions 5600A and 5600B are shown for fitting into apertures 5308A and 5308B.

FIGS. 57A and 57B illustrate perspective views of another modular cutting device 5700 in accordance with embodiments of the present disclosure. This embodiment is similar to the one shown in FIGS. 53-56B, however, the modular portion extends substantially further down the surfaces of the rails. In these embodiments, the cutting device 5700 includes an upper rail portion 5702 and a lower rail portion 5704. The upper rail portion 5702 is attachable to and detachable from the lower rail portion 5704. FIG. 57A shows the upper rail portion 5702 attached to the lower rail portion 5704. FIG. 57B shows the upper rail portion 5702 detached from the lower rail portion 5704. When attached, the upper rail portion 5702 can partially enclose a cutting blade 5706.

The upper rail portion 5702 can attach to the lower rail portion 5704 by any suitable mechanism, such as magnets, press-fit, welding, set screws, adhesive, articulating/mating features, etc. In this example, the lower rail portion 5704 includes multiple apertures 5708 that extend its length on both sides for receiving corresponding apertures (not shown) on the upper rail portion 5702 for attachment. This is similar to the example of attachment shown and described with respect to cutting device 5300 shown in FIGS. 53-56B.

FIGS. 58A-58C illustrate different steps for attaching a cutting blade 5800 to its cutting device 5802 in accordance with embodiments of the present disclosure. Referring initially to FIG. 58A, the cutting blade 5800 is shown as being apart from the cutting device prior to its attachment in the subsequent steps. The cutting blade 5800 and an end of the working body 5804 defines apertures 5805 that can be aligned for receiving pins 5806 to affix the cutting blade 5800 to the working body 5804. Once the cutting blade 5800 is in its operational position as shown in FIG. 58B, the pins 5806 can be suitably inserted for securely attaching (e.g. press-fit or welding) the cutting blade 5800 to the working body 5804 as shown in FIG. 58C so that it survives any loading conditions during operation.

FIGS. 59A, 59B, and 59C illustrate perspective views of another cutting device 5900 in accordance with embodiments of the present disclosure. The cutting system 5900 is similar to the cutting system 3100 shown in FIGS. 32A and 32B. Referring to FIG. 59A, this figure shows a step in assembly in which a monolithic working blade body 5902 is "threaded" in between the two offset struts 5904A and 5904B (one captures the top side and the other the bottom side of the working blade body 5902). FIG. 59B depicts a step after the step shown in FIG. 59A where the working body 5902 is placed farther between struts 5904A and 5904B. FIG. 59C shows the fully assembled cutting system. The functional benefit of this embodiment is that the top side strut at the distal end of the cutting system 5900 prevents skiving up during operation while allowing for easy assembly by maintaining monolithic working blade body 5902 and static rail components 5906A and 5906B. This also allows for having distinct components that would provide the option of making the blades disposable and the static rail components reusable (e.g. autoclave the components for use with another sterile blade in subsequent surgeries).

FIGS. 60A, 60B, and 60C illustrate perspective views of another cutting device 6000 in accordance with embodiments of the present disclosure. Referring to FIG. 60A, this figure shows a step in assembly in which a working blade body 6002 is "threaded" in between the two distal-positioned struts 6004A and 6004B (one captures the top side and the other the bottom side of the working blade body 6002). Rails 6006A and 6006B are connected to struts 6004A and 6004B at their respective ends. FIG. 60A shows an initial step with the working blade body 6002 apart from the rest of the cutting device 6000, FIG. 60B shows partial insertion, and FIG. 60C shows an operating position with the working blade body 6002 fully inserted. FIG. 61 illustrates a top view of the cutting device 6000 with partial insertion of the working blade body 6002. This assembly method allows for reusable applications (i.e. reusable rails 6006A and 6006B) and/or swapping out blades 6002 during a procedure. One knowledgeable in the art can envision the working blade body 6002 having any type of attachment coupling to the source of movement and/or the cutout in the rails accommodating different sizes.

Figure 62A:
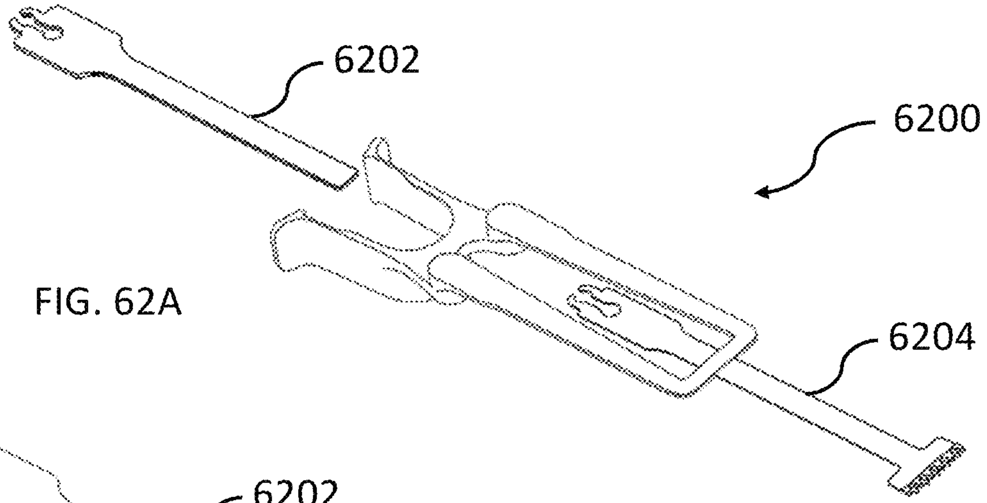
Figure 62B:
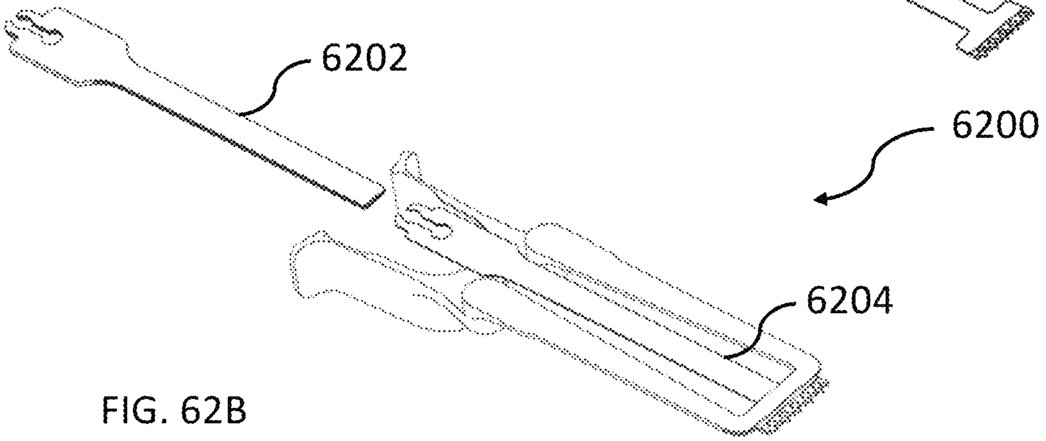
Figure 62C:
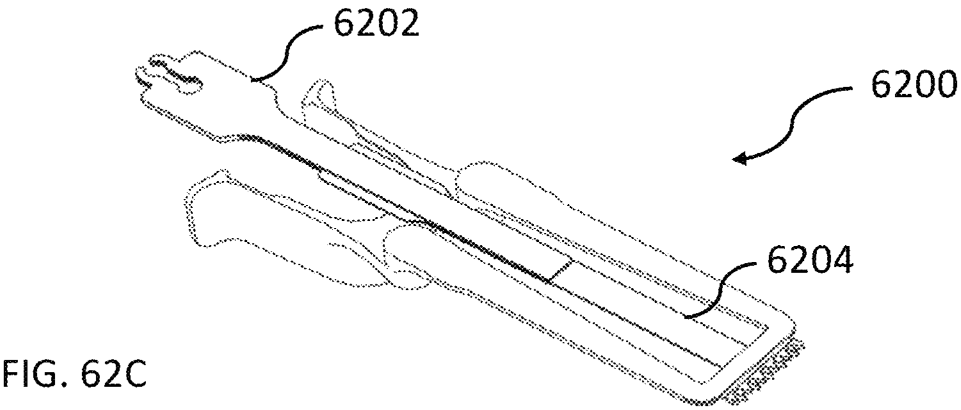
Figure 62D:
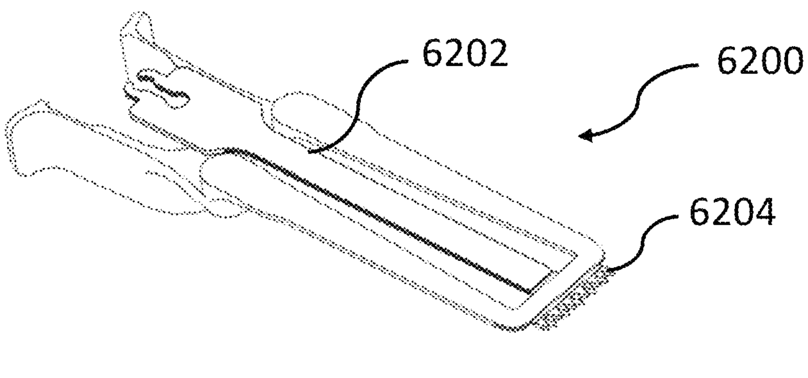

FIGS. 62A-65 illustrates views of cutting device 6200 with an extension 6202 for its working body 6204 in accordance with embodiments of the present disclosure. Referring to FIG. 62A, this figure depicts a perspective view of the cutting device 6200 unassembled with the extension 6202 being apart from the working body 6204. FIG. 62B shows the working body 6204 moved closer to the extension 6202 for attachment together. FIG. 62C shows the working body 6204 being attached to the extension 6202. This attachment can be made by any suitable mechanism (e.g. magnetic, adhesive, press-fit, set screws, welding, or articulating/mating features) and provides additional rigidity to the working body 6204 during operation to reduce blade deflection during operation and increase cutting accuracy. FIG. 62D shows the working body 6204 fully attached to the extension 6202 in an operational position.

Figure 63:
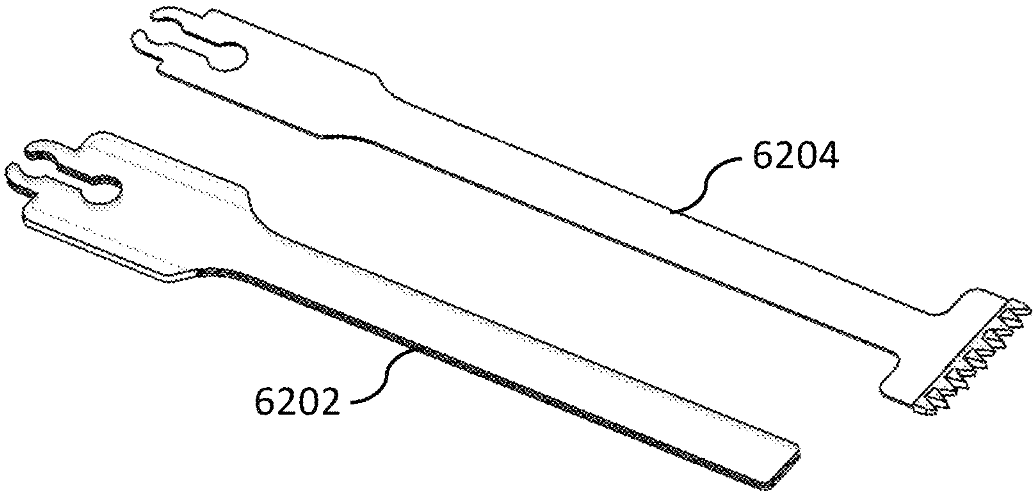

FIG. 63 illustrates a perspective view of the working body 6204 and the extension 6202 side-by-side. This figure includes shadow lines to show where the working body 6204 attaches to the extension 6202.

Figure 64A:
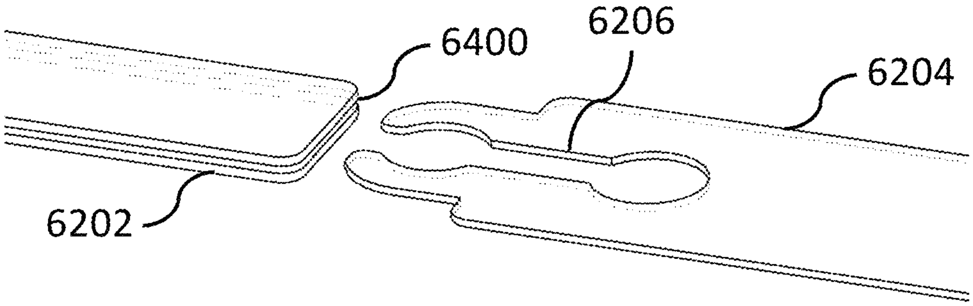
Figure 64B:
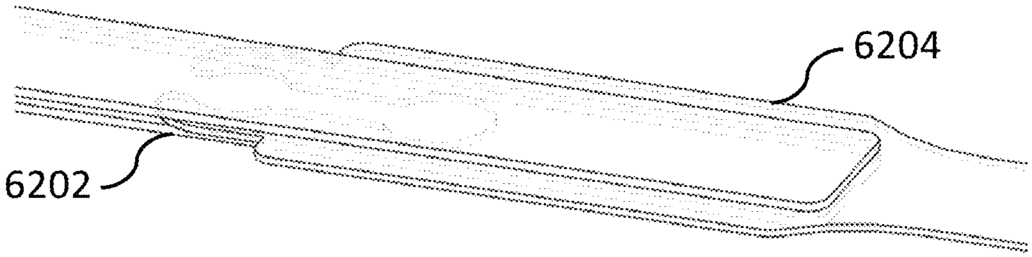

FIGS. 64A-64D illustrate close-up views of the working body 6204 and the extension 6202 with shadow lines to show internal features and/or hidden geometry. FIG. 64A shows an opening 6400 at an end of the extension 6202 for insertion of the working body 6204. This mechanism provides for a "clip" attachment of the working body 6204 to the extension 6202. FIG. 64B shows the working body 6204 "clipped" onto the extension 6202 for attachment.

Figure 64C:
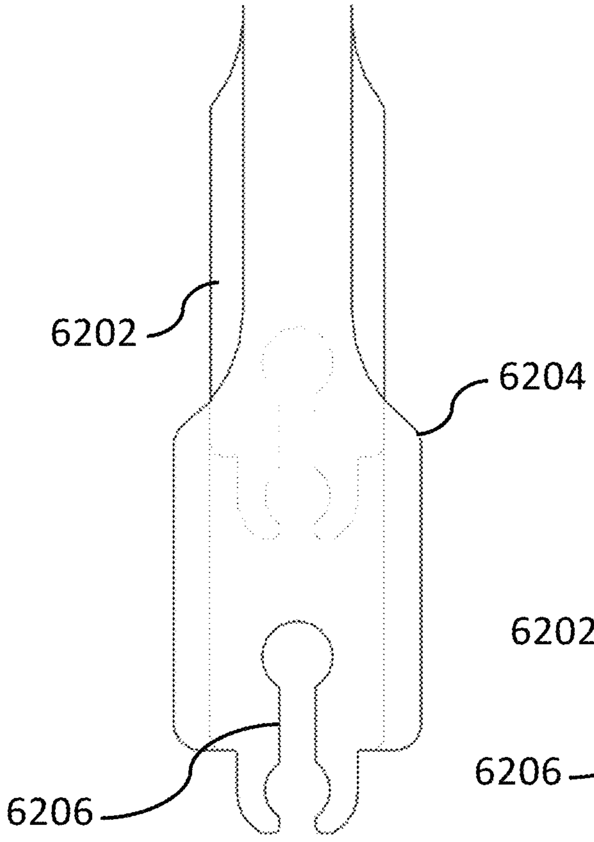
Figure 64D:
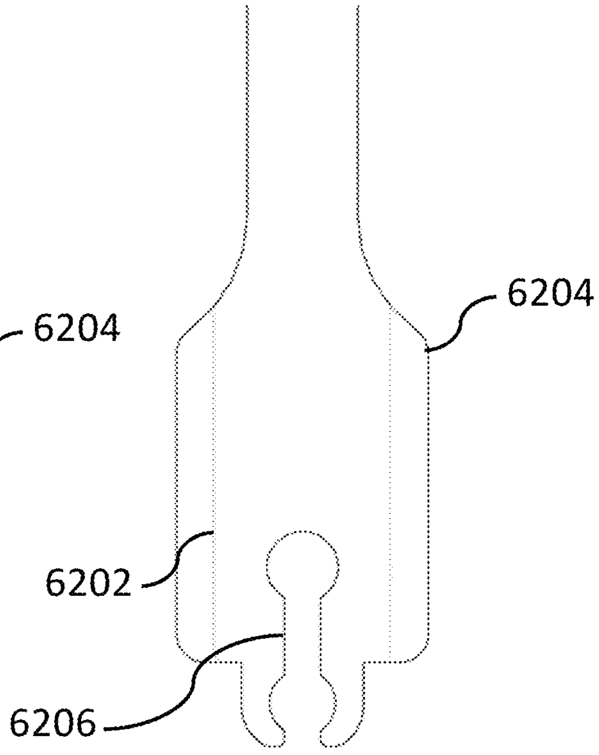
Figure 65:
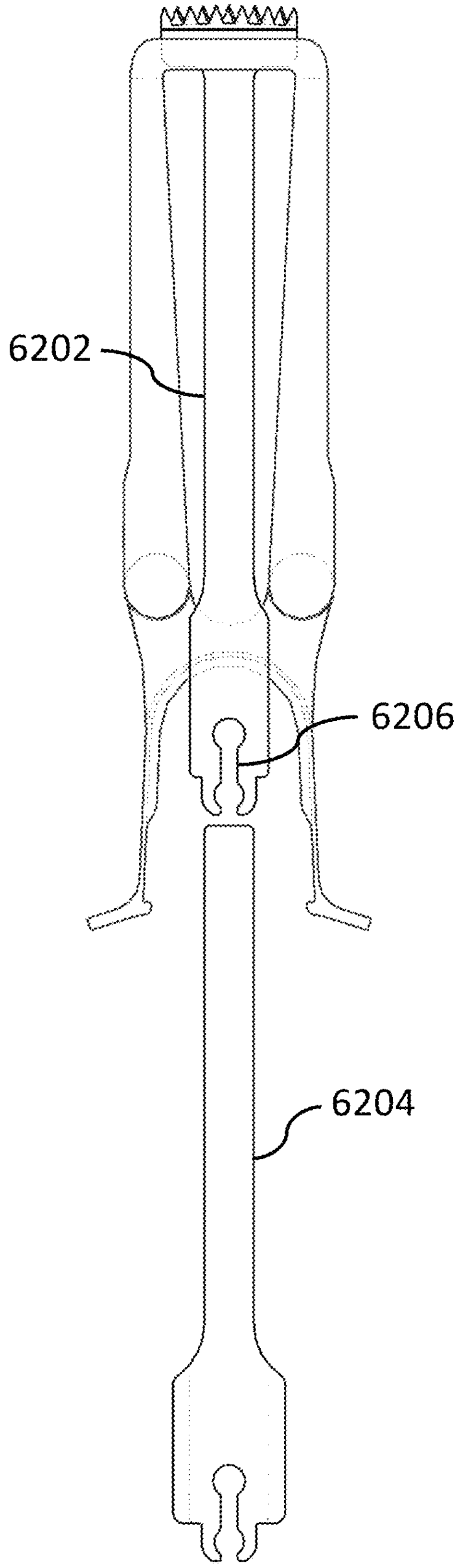

FIGS. 64C and 64D show top views of the working body 6204 being attached to the extension 6202. Particularly, FIG. 64C shows the components being separated, and FIG. 64D shows them in an attached position. In the attached position, the coupling 6206 for the extension 6202 aligns with the coupling feature on the working body 6204. This allows for translating the motion at the source of movement (e.g. oscillating motor mechanism) to both members of the modular assembly. One knowledgeable in the art can envision that this coupling could be made of any size and/or shape to create the desired attachment/motion. It is also feasible for just the extension 6202 to have the coupling adaptor to the source of movement, whereas the working body 6204 would only have to rigidly attach to the extension itself (e.g. one could envision having the same working body but different extension components for attachment to various devices). FIG. 65 illustrates a top view with the working body 6204 being apart from the extension 6202. One knowledgeable in the art could envision the extension 6202 being any size and/or length to meet the needs of the application.

FIGS. 66A and 66B illustrate top perspective views of a cutting system 6600 in accordance with embodiments of the present disclosure. Referring to FIGS. 66A and 66B, the system 6600 includes a cutting blade 6602, a working body 6204, and a support structure (also a "static casing" in this example) 6606. FIG. 66A shows the cutting blade 6602 being detached from the working body 6204. FIG. 66B shows the cutting blade 6602 being attached to the working body 6204. The benefits of a modular blade system would allow for potentially having a reusable working body 6204 that attaches with a cutting blade 6602. There are currently no blades on the market have been able to achieve this modularity and/or functionality with a more premium blade offering that can withstand the strength requirements and cost implications inherent to the design. This is would also allow for meeting a wide variety of surgeon preferences since blades of various geometries could be attached seamlessly based on procedure type (i.e. different teeth geometries could be offered).

FIG. 67 illustrates a top view of the cutting system 6600 shown in FIGS. 66A and 66B. Referring to FIG. 67, the cutting blade 6602 includes attachment end 6700 for attachment to the end of the working body 6204. The attachment end 6700 is configured to be removably attachable to the end of the working body 6204.

FIGS. 68A and 68B illustrate zoomed-in, top perspective views of the cutting blade 6602 being detached from the attachment end 6610 of the working body 6204 and attached to the attachment end 6610 of the working body 6204, respectively. Referring to FIG. 68A, the attachment end 6600 of the cutting blade 6602 defines rails 6600A and 6600B for fitting to corresponding rails 6602A and 6602B, respectively, defined by the attachment end 6610 of the working body 6204. With rails 6600A and 6600B being aligned with rails 6602A and 6602B, respectively, as shown in FIG. 68A, the cutting blade 6602 can be moved generally in the direction indicated by arrow 6704 (e.g. through the opening created by the struts that capture the cutting blade) for attaching the cutting blade 6602 to the working body 6204. FIG. 68B shows the attachment position for cutting blade 6602 where its end meets an abutment or stop portion 6606 of the attachment end 6610.

With reference to FIG. 68A, the cutting blade 6602 defines an aperture 6808 positioned adjacent and between rails 6600A and 6600B. Further, attachment end 6610 defines a raised feature 6810 positioned adjacent to and between its rails 6602A and 6602B. Feature 6810 is substantially equivalent in height to working body 6204. As shown in FIG. 68B, the raised feature 6810 fits within the aperture 6808 to secure the cutting blade 6602 to the attachment end 6610. It is noted that a portion of the attachment end 6600 flexes over the raised feature 6810 while rails 6600A and 6600B track within rails 6602A and 6602B. Once in the attached position as shown in FIG. 68B, the flexible portion lowers such that it provides a locking function together with the raised feature 6810. The functional benefit of this attachment is that it provides a permanent resilient means of securing the blade 6602 to the working body 6204 during the cutting operation, but can be removed afterwards (e.g. to allow for attachment of new cutting blades while allowing for reuse of the rails component).

FIGS. 69A-69C illustrate tops views depicting various steps for attaching the cutting blade 6602 to the working body 6604. At FIG. 69A, the cutting blade 6602 is apart from the working body 6604. At FIG. 69B, the cutting blade 102 has been moved closer to the working body 6604 through the front strut 6900 in the direction of arrow 6704. At FIG. 69C, the cutting blade 6602 is aligned with the tracks, flexed into place, and attached to the working body 6604.

FIGS. 70A and 70B illustrate top perspective views of another cutting system 7000 in accordance with embodiments of the present disclosure. Referring to FIG. 70A, this figure shows a cutting blade 7002 that is detached from a working body 7004. The cutting system 7000 shown in FIGS. 70A and 70B has an attachment mechanism similar to the attachment mechanism described with respect to FIGS. 58A-58C except for protrusions 7006 (shown in FIG. 70A) that enhance stability of the attachment and the slot 7300 that allows for snap attachment of the cutting blade 7002 to the working body 7004. FIG. 70B depicts the cutting blade 7002 attached to the working body 7004. The functional benefit of this attachment is that it provides a permanent resilient means of securing the blade 7002 to the working body 7004, but can be removed afterwards (e.g. to allow for attachment of new cutting blades while allowing for reuse of the rails component).

FIGS. 71A and 71B illustrate top views of the cutting system 7000 shown in FIGS. 70A and 70B. FIG. 71B is different than FIG. 71A in that it includes shadow lines to depict interior features and/or hidden geometry. FIG. 72 illustrates a close-up, top view of the cutting system 7000 with shadow lines to depict interior features and/or hidden geometry.

FIGS. 73A-73C illustrate top views of the cutting system 7000 at different steps for attaching the cutting blade 7002 to the working body 7004. As described herein, the cutting blade 7002 includes a slot 7300 for fitting to protrusions 7302 (e.g. pinned joints) for securely attaching the cutting blade 7002. FIG. 74 illustrates a cross-sectional, side view of the cutting system 7000 with the cutting blade 7002 being detached.

FIGS. 75A and 75B illustrate perspective views of a cutting device 7500 with a detachable cutting blade 7502 in accordance with embodiments of the present disclosure. Referring to FIG. 75A, the cutting blade 7502 is shown as being detached from an end of a working body 7504. To attach the cutting blade 7502, it can be moved in the direction of arrow 7506 (i.e. from the side) to the position shown in FIG. 75B, where a protrusion 7510 of the working body 7504 can fit into an aperture 7508 of the cutting blade 7502. The functional benefit of this attachment is that it provides a permanent resilient means of securing the blade 7502 to the working body 7504, but can be removed afterwards (e.g. to allow for attachment of new cutting blades while allowing for reuse of the rails component).

FIGS. 76A and 76B are close-up, top views that correspond to the positions shown in FIGS. 75A and 75B, respectively. Referring to FIG. 76A, a ridge-shape feature 7600 is defined in the attachment end of cutting blade 7502 for fitting to an interior portion of working body 7504 for enhancing stability. Also, this feature facilitates moving the cutting blade 7502 in the direction of arrow 7506 into place as shown in FIG. 76A. FIG. 76B shows the assembled cutting blade 7502 and working body 7504. FIGS. 77A and 77B are close-up, perspective views that correspond to the positions shown in FIGS. 76A and 76B, respectively (without the static component rails shown). FIG. 78 is a cross-sectional, side view of the cutting device 7500 where the protrusion 7510 is locked into place. One knowledgeable in the art can envision the sideways attachment of these components being done in a number of ways that allow for lateral tracking (e.g. using some keyed alignment feature) and any other geometry of fixation similar to the protrusion. Most loading on a cutting system is experienced as an axial load from the cutting blade 7502 leading edge. Therefore, it represents a very stable connection that provides permanent resilience, but can be removed afterwards (e.g. to allow for attachment of new cutting blades while allowing for reuse of the rails component).

FIGS. 79A-79C illustrate top perspective views of a cutting system 7900 at different steps for attaching the cutting blade 7902 to a working body 7904 in accordance with embodiments of the present disclosure. As described herein, the cutting blade 7902 can include apertures 7905 for fitting to protrusions 7906 of the working body 7904. The cutting system 7900 also includes bendable flaps 7908 at the distal end of the working body 7904 for securely attaching the cutting blade 7902. FIG. 79A shows the cutting blade 7902 apart from the working body 7904. FIG. 79B shows the cutting blade 7902 in the attached position without the bendable flaps 7908 wrapped around the cutting blade 7902. FIG. 79C shows the cutting blade 7902 in the attached position with the bendable flaps 7908 wrapped around the cutting blade 7902. When assembled, the bendable flaps 7908 would be flush/sub-flush to the static rails 7910 on the device and in turn the thickness of the cutting blade 7902 edge. This would ensure that the assembly of the the cutting end 7902 and the working body 7904 would not interfere with the functionality of the device (e.g. prevent the device from binding on an assembly junction that is thicker than the blades leading edge). The functional benefit of this attachment is that it provides a permanent resilient means of securing the blade 7902 to the working body 7904 but can be removed afterwards (e.g. to allow for attachment of new cutting blades while allowing for reuse of the rails component). One knowledgeable in the art can envision that the assembly could include protrusions/apertures and bendable flaps of of any size, shape, and number to meet the needs of the cutting application.

FIGS. 80A and 80B are top views of the cutting system 7900 shown in FIGS. 79B-79C with the flaps 7908 in an open position and closed position, respectively. FIGS. 81 and 82 illustrate a close-up, top view and a close-up, perspective view of the flaps 7908 in the closed position.

FIGS. 83A and 83B illustrate perspective views of a cutting system 8300 with a modular static casing having upper and lower components 8302A and 8302B, respectively, in an attached positioned and a detached position, respectively, in accordance with embodiments of the present disclosure. Referring to FIG. 83A, a working body 8304 and its cutting blade 8306 are situated within the upper component 8302A. Turning to FIG. 83B, the lower component 8302B includes two protrusions 8308 for fitting to apertures (not shown) on the underside of the upper component 8302A. Also, the cutting system 8300 includes a rear strut 8310 for stabilization and compatibility with sensor placement and/or coolant channels. The functional benefit of this assembly is that it provides a detachable resilient means of securing the lower component 8302B to the upper component 8302A (e.g. whether through press-fit, snap-fit, etc.). This can allow for modular handpiece attachment to various power systems on the market (i.e. by modifying lower component 8302B) and helps with manufacturing by making the upper component 8302A the same regardless of the lower component 8302B required.

FIGS. 84A and 84B illustrate perspective views of another cutting system 8400 with a modular static casing having upper and lower components 8402A and 8402B, respectively, in an attached position and a detached position, respectively, in accordance with embodiments of the present disclosure. The cutting system 8400 is similar to the cutting system 8300 shown in FIGS. 83A and 83B except that it does not include the strut 8310.

FIG. 85 illustrates a flow diagram of overall sensor control and feedback methods for implementation by a cutting system in accordance with embodiments of the present disclosure. In a cutting system utilizing this method, one or more sensors may be operably attached to a static casing (e.g., rails and/or struts), cutting blade, and/or working body of a cutting system or device. Example sensors include, but are not limited to, temperature sensors, strain sensors, vibration sensors, pressure sensors, electrical conductivity sensors, and the like. The sensors may be applied to a cutting system of any suitable type of mechanism for cutting. As described in further detail herein, the sensors can be placed along a rigid member (e.g., struts and/or rails) surrounding the blade mechanism (e.g., cutting blade) for use in determining real-time in cutting plane properties such as, but not limited to, deflection of the blade, temperature, and/or other properties. The benefit of this design is that the rigid member provides a stable platform for consistent and reliable sensor readings while being connected to and located near the blade mechanism where cutting is occurring.

Referring to FIG. 85, block 8500 is representative of functionalities of a motor platform of the cutting system (which can include but is not limited to manual handpieces, robotic arms, passive positioning arms, etc.). For example, block 8500 may represent the functionalities of a handpiece for operating a cutting device as described herein. Controls may include starting, stopping, or adjusting the speed of the motor based on signals received from one or more of the sensors. Sensors 8502 and 8504 may be operatively attached to one or more static rails 8506 and/or a blade 8508, respectively. Sensors 8502 and 8504 can detect temperature, strain, vibration, pressure, electrical conductivity, and/or other conditions at their respective placements, and communicate signals representative of the conditions to a controller (e.g., suitable hardware, software, and/or firmware) at a computing device for implementing functionalities and/or providing feedback to an operator at a user interface 8510. At the user interface 8510, the feedback information may be presented to the operator via a screen, virtual reality (VR) or augmented reality (AR) interface.

FIGS. 86A and 86B illustrate a perspective view and a side view, respectively, of a cutting system 8600 having navigation rails and functionalities for guiding cutting in accordance with embodiments of the present disclosure. Referring to FIGS. 86A and 86B, this system 8600 allows for cutting without a traditional fixed cutting guide through the use of navigation data (e.g. provided by pre-op scans such as CT or anatomical landmarks registered intra-operatively) to locate the desired cutting plane and/or trajectory relative to the anatomy. Navigational features 8604 (e.g. using passive optical navigation markers and/or active infrared light emitting markers) can be rigidly attached to the static rail 8602 and/or surrounding construct to provide a coordinate system for the hand-held device relative to the anatomy. The navigational features 8604 can also be used to track position of the cutting end 8606 and/or any other geometric features present as a part of the cutting device 8600 (e.g. the position of all geometric features are known relative to the navigation array coordinate system to inform its location in space. The system 8600 can also visually inform an operator on soft tissue safety boundaries through a dedicated user interface that is provided to the operator through navigational feedback. An example benefit of having the navigational features 8604 directly attached to the cutting system 8600, is that it can transform any manual handpiece into a navigationally driven device since not all power systems on the market have navigation capabilities. That can allow for completing any type of manual cut with just navigation where appropriate (e.g. removing a bone tumor based on a calculated margin, completing rough proximal tibial cuts, completing long bone osteotomies along a given trajectory, completing augment cuts for revision knee procedures, etc.). The ability of the tracker array to be rigidly attached/integrated to the cutting system construct allows for more precise and relatively localized data of the blade itself since an array attached to the handpiece at a relatively further location away from the cutting end would increase errors due to any motion between modular junctions.

FIGS. 87A and 87B illustrate perspective views of the cutting system 8600 shown in FIGS. 86A and 86B in a detached position and an attached position, respectively, with respect to a power handpiece/handle 8700 in accordance with embodiments of the present disclosure. The handpiece/handle 8700 may contain one or more of drive mechanism, power, and controls.

FIG. 88 illustrates a perspective view of the cutting system 8600 attached to the handle 8700 (as shown in FIG. 87B) and also depicts operative connection to a computing device 8800 for controlling navigation and orientation with respect to material 8802 to be cut (e.g. bones of a knee 8806 and 8808). Referring to FIG. 88, a computing device 8800 includes a navigation manager 8804 that is functional with the navigational features 8604 for determining a position and orientation of the cutting device 8600 with respect to the material 8802 to be cut.

As depicted in FIG. 88, the navigation manager 8804 can track the orientation of the cutting device 8600 via navigational features 8604. Also, the navigation manager 8804 can track the orientation and position of bones 8806 and 8808 through the use of navigation data (e.g. aligning the navigation features on the bone with a provided pre-op CT scan and/or through the use of anatomical landmarks registered intra-operatively). The orientation and positioning of the cutting device 8600 and bones 8806, 8808 can be tracked within, for example, a Cartesian coordinate system maintained by the navigation manager 8804. In this example, the navigation manager 8804 can track the X-, Y-, Z-coordinates of each of the cutting device 8600 and bones 8806, 8808. The navigation manager 8804 can be implemented by suitable hardware, software, and/or firmware (e.g. memory and one or more processors). Further, the computing device 8800 can include a user interface 8810 for providing positioning information to the operator and/or real-time feedback. This user interface could include an AR/VR head set that could allow for directly overlaying the cutting device within the cutting plane during use and/or simulating its geometry for increased visual feedback (e.g. blade is unable to be seen when inside a cut and AR could virtually generate a visual of its location in 3D space using the navigation data).

FIG. 89 illustrates a perspective view of the cutting device 8600 and handle 8700 of FIG. 88 with a manual, sliding stabilizer sheath 8900 in accordance with embodiments of the present disclosure. Referring to FIG. 89, the sheath 8900 is shaped and sized to slide over the static rail 8602. The stabilizer sheath 8900 represents an integrated guide that can slide along the surface of the cutting device 8600. It represents a method in which a user can stabilize the entire cutting device 8600 on the surface of the adjacent bone through the use of fixation features 8902 (e.g. spikes at the end of the sliding sheath that contact the adjacent bone) for providing a more stable means of scoring and engaging the bone. Further, the sliding stabilizer 8900 provides additional stiffness for the static rail construct based on having the sheath shorten the effective length of the device.

FIGS. 90A-90C illustrate top views of the cutting device 8600 and handle 8700 with the stabilizer sheath 8900 with fixation feature 8902 at different positions. Particularly, FIG. 90A shows the stabilizer sheath 8900 apart from the cutting device 8600, FIG. 90B shows the stabilizer sheath 8900 positioned on the cutting device 8600 at its end, and FIG. 90C shows the stabilizer sheath 8900 positioned at a proximal end of the cutting device 8600.

FIGS. 91A and 91B illustrates views of the cutting device 8600, handle 8700, and stabilizer sheath 8900 in use for cutting bone 9100. Referring to FIG. 91A, this figure shows the stabilizer sheath 8900 initially engaging the bone 9100 during a cutting operation aligned with a desired cutting plane as informed by the computing device 8800. FIG. 91B shows the cutting device 8600 having cut deeper into the bone 9100 such that the stabilizer sheath 8900 is pushed to the proximal end of the cutting device 8600. Computing device 8800 and its navigation manager (not shown for ease of illustration) are monitoring the cutting operation including the positioning and orientation of the cutting device 8600, the stabilizer sheath 8900, and the bone 9100 where the cut is being made.

FIGS. 92A and 92B illustrate perspective views of the cutting device 9201 and the handle 8700 with a different stabilizer sheath 9200 that assembles with the static rail 8602 through a slot on the side of the stabilizer sheath 9200 rather than from the distal end of the static rail 8602 in accordance with embodiments of the present disclosure. This sliding engagement 9202 from the side of the static rail construct removes the need for attaching the component from the distal end. Referring to FIG. 92A, this figure shows the stabilizer sheath 9200 being spaced apart from the static rail 8602. FIG. 92B shows the stabilizer sheath 9200 being attached to the distal end of the static rail 8602. The stabilizer sheath 9200 can be a rigid, sliding component that can complete the initial scoring of bone to help align a manually navigated handpiece and allows for taking it off mid-cut so that the full working surface becomes available throughout the cutting process (i.e. once initial scoring process complete).

FIG. 93 illustrates a top view of a cutting device 9300 with temperature sensors 9302A and 9302B attached to a left side and right side, respectively, of a static rail 9304 in accordance with embodiments of the present disclosure. Referring to FIG. 93, the temperature sensors 9302A and 9302B can measure temperatures at their respective locations and output signals to a computing device for processing in accordance with embodiments of the present disclosure. The temperature sensors 9302A and 9302B can be positioned on the top or bottom surfaces of the static rail 9304 to allow for monitoring temperatures on adjacent surfaces of the cutting plane. They can also sit inside cutouts designed to allow the sensors to sit flush/sub-flush with the surfaces of the static rail 9304 to protect them through the use of the cutting device 9300. It is important to note, temperature sensors can be of any relevant size and type (e.g. thermocouples, thermistors, resistance temperature detectors, semiconductor based sensors, etc.) to meet the needs of the application/geometric constraints.

FIG. 94 illustrates a top view of a cutting device 9400 with temperature sensors 9402A and 9402B attached to a left side and right side, respectively, of a static rail 9404 in accordance with embodiments of the present disclosure. The embodiment of FIG. 94 is similar to the embodiment of FIG. 93 except that the temperature sensors 9402A and 9402B are positioned on an inside surface of the static rail 9404 mechanism.

FIG. 95 illustrates a top view of a cutting device 9500 with temperature sensors 9502A and 9502B attached to a left side and right side, respectively, of a static rail 9504 in accordance with embodiments of the present disclosure. The embodiment of FIG. 95 is similar to the embodiment of FIG. 93 except that the temperature sensors 9502A and 9502B are positioned on an outside surface of the static rail 9504.

FIG. 96 illustrates a top view of a cutting device 9600 being configured with temperature sensors 9602 for integrated in-plane temperature feedback in accordance with embodiments of the present disclosure. The device 9600 includes temperature sensors 9602 for in-plane temperature feedback as described herein. Temperature sensors 9602 can detect temperature local to its respective position, such as the temperature of the area of the static rails 9610 where it is attached. In this example, temperature sensors 9602 are connected by wire 9604 to a computing device or other hardware (not shown for ease of illustration) for receiving and processing the temperature detected by each sensor 9602. This embodiment can be utilized to obtain real-time, in-plane temperature measurements at multiple locations along the surface of the static rails 9610 while cutting bone to monitor and if needed take action to ensure the integrity of the adjacent bone.

With continuing reference to FIG. 96, this embodiment provides a platform in which temperature sensors 9602 can be applied to the working surface of the device. Since rigid static rails 9610 can remain relatively motionless to the rapidly oscillating blade, the integrity of any sensors 9602 placed on the surfaces can remain intact and provide repeatable/reliable results tied to the location of the cutting device 9600, which may not be feasible if they were to be placed directly on the blades surface which rapidly oscillates back and forth during operation. This embodiment provides the additional benefit that temperature sensors 9602 can be placed directly on the rigid strut 9606 (itself a part of the static rails 9610), which translates across the working blade body 9608. This may provide a more accurate reading closer to the edge of the blade. The feedback provided by temperature sensors 9602 can be used to inform an operator to stop cutting, to output an active coolant, and/or be combined into a robotic platform that leverages the data to carry out the cutting procedure in a safer and more efficient manner. The computing device can integrate with a manual, standalone device, handpiece, and/or robotic platform. Also, it is noted that temperature sensors can be suitably attached to any portion of a static casing or elsewhere for acquiring temperature readings.

FIG. 97 illustrates a graph 9700 showing temperature readings and top views of a cutting device 9702 cutting into bone 9704. Referring to FIG. 97, the cutting device has temperature sensors, and the graph 9700 shows the measured temperature over time for the 2 sensors with a region set at 47 degrees Celsius that the sensor system functions to remain below. Further, the shaded part of the graph 9700 shows the time period when cutting was paused to reduce the temperature below a limit for the bone 9704. One other means of lowering temperature in this region may be accomplished using coolant based on the sensor feedback.

FIG. 98 illustrates a graph 9800 showing temperature readings and top views of a cutting device 9802 cutting into bone 9804. Referring to FIG. 98, the cutting device has temperature sensors, and the graph 9800 shows the measured temperatures over time for the 2 sensors with a region set at 47 degrees Celsius that the sensor system functions to remain below. Turning to the graph 9800, it shows the ability to leverage the real-time data from both temperature sensors to inverse model the temperature of the cutting devices leading edge. Specifically, this allows for taking data from sensors on the static rails and correlating it to the temperature of the bone at the cutting edge.

FIG. 99 illustrates a top view of a cutting blade 9900 with working body 9902 having a sensor (e.g. temperature sensor) 9904 being connected by conductive wire via a side port 9906. Referring to FIG. 99, a flexible area of the wire may be located at a portion of its length indicated by arrow 9908.

FIG. 100 illustrates a top view of the cutting blade 9900 and working body 9902 of FIG. 99 along with a static casing 10000. Referring to FIG. 100, the working body 9902 can include a low-profile, thermocouple insertion that rides along one of the outer side edges of the blade edge and is connected through a side port 9906. The thermocouple sensor itself can sit encased within the blade working body 9902 and its respective wiring can be flush/sub-flush to the thickness of the moving working body 9902 to protect it from rubbing on adjacent bone surfaces. The thermocouple can also be molded into place with a flexible material that also conducts heat to protect from vibration due to cutting.

With continuing reference to FIG. 100, the embodiment version can use any suitable assembly method. However, there is an option to place the initial wiring along the rails themselves to have the rail be the platform for the sensors technology (along with any others required, e.g. strain gauges, etc.). One of knowledgeable in the art can envision the thermocouple lead wires originating from a hardware pack (e.g. that provides power, data acquisition, and communicates with other computing devices through blue tooth low energy signals) on the static rails themselves as opposed to having to be integrated into the corresponding power handpiece directly allowing for more modularity with various handpieces. This type of configuration can be applied across all sensor types and can be combined with other sensors depending on the desired detection needs of the procedure/system.

FIG. 101 illustrates a top view of another cutting device 10100 having an integrated temperature sensor 10102 located near a blade edge 10104 in accordance with embodiments of the present disclosure. Referring to FIG. 101, this embodiment can include a modular or preassembled thermocouple unit 10106 that snaps into place within a slot central 10108 to the blade (within its working surface geometry). The unit 10106 can be covered to make it encased, but may be below the profile of the surface of the blade to protect it from excess vibration and/or damage. FIG. 102 illustrates the cutting device 10100 of FIG. 101 along with a static casing 10200.

FIG. 103 illustrates a flow diagram of a temperature feedback loop in accordance with embodiments of the present disclosure. Referring to FIG. 103, this figure depicts example control steps implemented by a computing device based on measurements obtained by one or more temperature sensors, such as temperature sensors 9302A and 9302B shown in FIG. 93. Temperature measurements can be received by the computing device and used to determine whether threshold levels are met. The computing device can implement one or more actions based on whether threshold levels are met. The computing system can also leverage machine learning based on patterns recognized from the data (e.g. pre-operative, intra-operative, post-operative, historical data) to provide more actions based on the real-time sensor data. The data generated by the sensors can be more broadly used to communicate with any type of system (e.g. robotic arms, micro-robotic guides, hand-held robotics, AR/VR headset, etc.) to provide feedback and output functionality. One knowledgeable in the art can envision the temperature sensors providing location specific visuals of real-time bone temperatures (e.g. contour plot, heat map, etc.) using an AR/VR overlay locked on the specific anatomic region of interaction/cutting plane to visually demonstrate temperature gradients on the patient bone (e.g. VR/AR visual temperature overlays using a contour map, heat map, etc. on top of a proximal tibial cut that was executed).

FIG. 104 is a perspective view of a cutting device 10400 having strain sensors 10402A-10402D for in-plane trajectory feedback in accordance with embodiments of the present disclosure. Referring to FIG. 104, static rail 10404A and 10404B provide a platform on which sensors 10402A-10402D, such as strain gauges, can be applied to the working surface of the device 10400. For example, the sensors

10402A-10402D may be placed on the top and/or bottom surfaces of the rails. Since struts 10406A and 10406B and the surfaces of the rails themselves 10404A and 10404B contribute to the overall static casing being relatively motionless with respect to the rapidly oscillating blade 10408, the integrity of sensors 10402A-10402D placed on the surface can remain intact and provide repeatable/reliable results, which may not be feasible if they were to be placed directly on the blade's surface, which rapidly oscillates back and forth during operation. Struts 10406A and 10406B are also critical in that they provide a mechanism in which the rapidly oscillating saw blade is precisely captured between its surfaces. This precision capture mechanism is critical to coupling the two independent structures (i.e. the static rails and oscillating blade) and providing a means of mechanically translating the deflection/loading conditions of the tip of the blade back to the sensors themselves. If this coupling did not exist, there would not be a strong correlation between the strain data generated by the sensors 10402A-10402D and the true motion of the blade edge 10408. Therefore, without the presence of the static components and the precision captured tip, it would not be viable to collect this data using other means. Other systems with sensors housed outside of the cutting device would not have the resolution to detect the true interactions of the blade within the cutting plane (e.g. exact amount of skiving to a reasonable accuracy). Furthermore, strain sensors placed directly on a rapidly oscillating blade would have a high risk of failure due to fatigue and lack of signal quality based on heavy vibration.

The feedback provided by the strain sensors 10402A-10402D can be used to inform a user to stop/slow down cutting, adjust/correct hand position, and/or be combined into a robotic platform that leverages the data to carry out the cutting procedure in a safer/more efficient manner. Strain gauges also provide the benefit of being able to detect various loading conditions (e.g. axial, bending, shear, and torsional loading). Strain sensors 10402A-10402D can be suitably wired to hardware similar to other sensors described herein. Also, it is noted that the strain sensors can be suitably implemented on a cutting device as described herein. It is important to note, strain sensors can be any relevant size/type (linear, rosettes, shear, chain, etc.), placed in any relevant configuration/number (quarter bridge, half-bridge, full-bridge, etc.), and leverage any relevant sensing principle (e.g. resistive) on the static components to meet the needs of the application/geometric constraints. Sensors can be suitably wired to hardware similar to other sensors described herein.

The embodiment of FIG. 104 provides a solution to a need to provide real-time in-plane trajectory measurements while cutting bone to ensure optimal cutting precision/accuracy. Depending on the thickness of the sawblade used, the device's components can shift significantly outside of its intended trajectory within the cutting plane and there is no current feedback mechanism that can be applied in vivo within the cutting plane to inform the user of this concern (i.e. currently works off of surgeons "feel" rather than through a data driven mechanism/feedback). Using existing means, it is not until after the cut is complete that the surface of the cut can be evaluated (e.g. whether through trialing implant components for fit and/or validating the surface using other intra-operative tools). This inaccuracy can happen for a variety of reasons including but not limited too: (1) the user not controlling the handpiece within a consistent plane (bending the blade up-down based on hand position), (2) variations in bone type (e.g. moving from soft to hard bone within a given cut) can cause the blade to deflect within the cutting plane and shift the intended trajectory. Accuracy of the cut is critical to ensuring fit of the implant and ensuring long-term fixation (e.g. cementless implants use bone in growth requiring good surface fit of implant to bone). This embodiment makes that accuracy possible through the ability of the strain sensors mounted on the static rails to detect movement of the blade and map the kinematics of the blade edge for comparison to the intended trajectory.

FIG. 105 illustrates a perspective view of the cutting device 10400 shown in FIG. 104 and a graph 10500 depicting micro strain measurements obtained by the cutting device's 10400 strain sensors. Referring to FIG. 105, ε=strain, and δ=displacement. The graph shows an example of cyclic loading, and bending down of an end of the cutting device 10400 (e.g. moving down from its neutral position).

FIG. 106 illustrates a perspective view of the cutting device 10400 shown in FIG. 104 and a graph 10600 depicting micro strain measurements obtained by the cutting device's 10400 strain sensors. Referring to FIG. 106, ε=strain, and δ=displacement. The graph shows an example of cyclic loading, and bending up of an end of the cutting device 10400 (e.g. moving up from its neutral position).

FIG. 107 illustrates a perspective view of the cutting device 10400 shown in FIG. 104 and a graph 10700 depicting micro strain measurements obtained by the cutting device's 10400 strain sensors. Referring to FIG. 107, the graph shows an example of cyclic loading, and the incremental bending down of an end of the cutting device 10400.

FIG. 108 illustrates a perspective view of the cutting device 10400 shown in FIG. 104 and a graph 10800 depicting micro strain measurements obtained by the cutting device's 10400 strain sensors. Referring to FIG. 108, 0=angle. The graph shows an example of cyclic loading and torsion at an end of the cutting device 10400. This demonstrates the ability of the sensors to detect how each static rail surface is moving independently of one another and provides a resultant motion of the blade edge itself.

FIG. 109 illustrates a perspective view of the cutting device 10400 shown in FIG. 104 depicting micro strain measurements obtained by the cutting device's 10400 strain sensors. This figure depicts an example of the strain sensors detecting uneven combined loading with positive torsion and bending up at the end of the cutting device 10400.

FIG. 110 illustrates a perspective view of the cutting device 10400 shown in FIG. 104 depicting micro strain measurements obtained by the cutting device's 10400 strain sensors. This figure depicts an example of the strain sensors detecting uneven combined loading with positive torsion and bending down at the end of the cutting device 10400.

FIG. 111 illustrates a perspective view of the cutting device 10400 shown in FIG. 104 depicting micro strain measurements obtained by the cutting device's 10400 strain sensors. This figure depicts an example of the strain sensors detecting uneven combined loading with negative torsion and bending down at the end of the cutting device 10400.

FIG. 112 illustrates a perspective view of the cutting device 10400 shown in FIG. 104 depicting micro strain measurements obtained by the cutting device's 10400 strain sensors. This figure depicts an example of the strain sensors detecting uneven combined loading with negative torsion and bending up at the end of the cutting device 10400.

FIG. 113 illustrates a perspective view of the cutting device 10400 shown in FIG. 104 depicting tracking the location of the static rail and bone coordinate system within a global coordinate system through communication with a navigation/computing system. This global coordinate system includes the tibial bone coordinate system and 3D mapping of bone 11300 (e.g. proximal tibia bone anatomy) including a planned resection. The 3D mapping may be, for example, by CT scan, which is then correlated to registered anatomic landmarks, intra-operative anatomic mapping of landmarks, and the like.

FIG. 114 illustrates a perspective view of the cutting device 10400 shown in FIG. 104 and a graph 11400 showing real-time sensor data used to generate the kinematics of the blade edge. This data is obtained by the cutting device's 10400 strain sensors while cutting through the mapped bone 11300 (e.g. proximal tibial cut). The graph shows an example of micro strain at an end of the cutting device 10400 during a cutting time.

FIG. 115 illustrates a front view of a blade edge and a front view of a bone cutting section. Referring to FIG. 115, with the data collected from the strain sensors on the cutting device, the kinematics of the blade edge can be modeled. This is completed by interpreting the strain sensor data from each of the static rails to understand what the loading conditions were at a given instance in time and layering the results together to geometrically calculate tip motion. Specifically, strain sensor data can be correlated to displacement values at the tip of the device. With a known blade width, the converted displacement data from each static rail (i.e. left and right rail) can then be used to calculate displacement and angulation of the blade tip as shown. When this data is combined in the context of a global coordinate system (e.g. in which the 3D locations of the cutting device and bone are known), the location data can be used to show relative differences in the planned resection versus how the blade is actually moving in space based on the strain sensor data. This translates to an understanding of the resulting removed bone versus the remaining bone at each instance throughout the cutting process based on the location of the cutting device combined with the tip motion. One knowledgeable in the art could envision modeling the response of the blade edge by considering the static rails a single system (e.g. using a full bridge configuration distributed across both rails) as opposed to the independent motion of the rails described.

FIG. 116 illustrates a diagram showing a 3D surface trajectory relative to planned cutting trajectory. Referring to FIG. 116, the 3D surface trajectory is generated by combining the instantaneous tip deflection data measured by the strain sensors during the cutting time within the global coordinate system (e.g. defined by the user through the pre-operative navigation plan) and relative to the planned resection. The ability to generate this data real-time provides a multitude of options for user feedback and/or actionable outputs (e.g. robotic system adjustments). For example, the system can leverage the skiving data to establish an allowable deflection threshold. If the user and/or system set the threshold to not exceed 200 microns (e.g. if they required highly accurate cuts for completing a cementless total knee procedure), then throughout the cutting process the system would leverage the strain sensor data to ensure this criteria is met whether through user feedback on specific locations that need re-cutting and/or through direct robotic compensation of measured error.

FIG. 117 illustrates a perspective view of the cutting device 10400 that uses post-op, analysis data from many data sets to determine trends in cutting error and help make real-time corrections in future applications. Data may demonstrate a pattern across multiple data sets where there is a consistent anatomic specific region of skiving. Referring to FIG. 117, the cutting devices strain sensor data communicates that over a significant number of cases the device deflects in a similar manner over the same relative region of bone (e.g. posterior portion of a proximal tibial cut). Leveraging machine learning, the system could analyze the data post-operatively to understand that there is a clear pattern in a consistent anatomic region. This pattern recognition could then provide opportunities for user feedback and/or factional outputs (e.g. robotic system adjustments). An example of this could be if the trend is for the blade to deflect up when it hits this anatomic specific region of bone, even if it is across different patients, a robotic system could make proactive micro-adjustments to push the edge of the blade downing anticipation of the measured trend to minimize any cutting error. This can improve overall system accuracy over time as procedural data is correlated to specific workflows and patient anatomy.

FIG. 118 illustrates a flow diagram of an example method of cutting device control in accordance with embodiments of the present disclosure. Other means of leveraging the strain sensor data could also be used to model various responses within the cutting system and its interactions with bone in the cutting plane. The method may be implemented by a suitable computing device such as the computing devices described herein. The method includes 3D mapping, acquisition of strain gauge and location data, and conversion of the strain gauge data into displacement/orientation data. The method also includes use of the displacement/orientation data to simulate local kinematic response at the tip of the blade.

With continuing reference to FIG. 118, the method includes combining instances of kinematic tip responses and locational data throughout the cutting process to map the overall response relative to a desired trajectory. Further, the method includes providing a user with a real-time visual of planned versus resulting surface trajectories in 3D space.

The method of FIG. 118 also include use of post-op machine learning to analyze data based on patient specific anatomy. Trends can be tracked to determine whether any statistically significant patterns emerge that may be anticipated future procedures based on patient specific anatomy.

FIG. 119 illustrates a perspective view of a cutting device 11900 having strain gauges 11902A and 11902B in accordance with embodiments of the present disclosure. Referring to FIG. 119, the strain gauges 11902A and 11902B are positioned at a proximal end of a static casing 11904 across a rigid member of the cutting device that is adjacent to the working surfaces that translate into the cut. This provides another means of generating strain sensor data that is occurring within the cutting plane without having to position the sensors directly on the cutting surface. This is made possible by the fact that the static rails 11904 are still rigidly connected to this adjacent surface to allow for measurement of strain.

FIG. 120 is a flow diagram of an example method of sensor feedback for controlling a cutting blade in accordance with embodiments of the present disclosure. Referring to FIG. 120, the flow diagram shows a trajectory feedback loop for a saw blade/robotic cutting platform/user displays. The method includes acquiring strain sensor readings and using the readings to determine whether there is strain profile rapidly diminishing (i.e. bone cut complete), excess axial strain, excess torsional strain, excess bending strain (up), excess bending strain (down), excess shear strain, and/or whether there are permissible levels of strain (of any type). The flow diagram shows example actions to implement based on these determinations. The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets, etc.) to provide feedback and output functionality. One knowledgeable in the art could envision the strain sensors working with an AR/VR headset to provide visual surface mapped feedback of real-time skiving relative to the desired trajectory as an overlay on top of the specific anatomy of interest (e.g. VR/AR visual overlay on top of proximal tibial cut that was executed showing a heat map/contour plot demonstrating high spots that need to be re-cut and where the VR/AR could provide real-time updates as the user re-passes over the higher regions of bone).

FIG. 121 illustrates a top view of a cutting device 12100 having pressure sensors 12102A and 12102B for integrated, in-plane binding feedback in accordance with embodiments of the present disclosure. Referring FIG. 121, pressure sensors 12102A and 12102B are attached to rails 12104A and 12104B, respectively, for measuring a pressure or compression on the rails. In addition or alternatively, one or more pressure sensors may be attached to a strut 12106. Since the rigid strut 12106 and rails 12104A and 12104B can remain relatively motionless to the rapidly oscillating blade, the integrity of sensors placed on the surface can remain intact and provide repeatable/reliable results, which would not be feasible if they were to be placed directly on the blade's rapidly oscillating surface.

Pressure sensors 12102A, 12102B can be attached to the struts 12106, along the rails 12104A, 12104B, and/or any other suitable component. Sensors 12102A, 12102B can be mounted along any surface (top/bottom/sides) of rails 12104A, 12104B and flush to surface of the rails. Placement of at least one pressure sensor near the device's distal end or tip can be important for real time measurements and to understand what is happening at the blade tip/cutting site. Sensors can be used to detect changes in pressure over time and can provide feedback on when a threshold pressure is reached to indicate binding or risk of binding. Reduced pressure can indicate when a cut is being completed or when breakthrough is achieved (i.e. bone progressively "fish-mouths" open at the end of the cut making it easier to complete). Different conditions can result in feedback notifications/alarms to the user. It is important to note, pressure sensors can be any relevant size to meet the needs of the application (e.g. circle pressure pad vs. long rectangular pad) and leverage any relevant sensing principle (e.g. resistive, capacitive, piezoelectric, optical, MEMs, etc.).

The use of pressure sensors 12102A and 12102B or other pressure sensors can provide a solution to quantitatively measure in-plane blade binding usually caused by pinching of the blade within the cutting plane either in the cutting block, in bone, or at the interface of the two. This is important because in-plane blade binding can cause rapid temperature increases leading to inefficient cutting. Further, the use of pressure sensors in this way provides a way to quantitatively measure when a cut is complete other than visually and to a lesser degree "feel".

FIG. 122 illustrates the cutting device 12100 and a graph 12102 showing excessive load detected and a binding threshold. The graph shows a time when the force on the pressure sensor exceeds the threshold. A user can be notified real-time when the excessive load is detected. This could also be implemented as feedback into a robotic system for specific outputs and/or corrections.

FIG. 123 illustrates a perspective view of a cutting device 12300 with a pair of flexible, linear potentiometers 12302A, 12302B that extend along a length of rails 12304A, 12304B, respectively. Referring to FIG. 123, the potentiometers 12302A, 12302B can be utilized to measure pressure for sensing depth and distance of movement of the rails 12304A, 12304B.

FIG. 124 illustrates the cutting device 12300 shown in FIG. 123 and a graph 12400 showing detected depth of the rails. The graph shows detected resistance, which can be correlated to different sensor depths. A user can be notified real-time of the detected depth data. This can also be implemented as feedback into a robotic system for specific outputs and/or corrections.

FIG. 125 illustrates a flow diagram of a pressure feedback loop in accordance with embodiments of the present disclosure. Referring to FIG. 125, this figure depicts example steps implemented by a computing device for control based on measurements obtained by one or more pressure sensors, such as pressure sensors 12102A and 12102B shown in FIG. 121. Pressure readings can be received by the computing device and used to determine whether various pressure levels are met. The computing device can implement one or more actions based on whether threshold levels are met. Also, the computing device can control a user interface to indicate a current step or completion of a step in a procedure based on pressure reading (e.g. bone cut complete). The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets etc.) to provide feedback and output functionality. One knowledgeable in the art could envision the pressure sensors working with an AR/VR headset to provide real-time feedback on potential for binding while completing cuts.

FIGS. 126 and 127 illustrate a top view and a close-up, top view, respectively, of another cutting device 12600 having electrical conductivity sensors 12602A and 12602B (e.g. such as electrodes that pass a voltage through them and measure the resistance between a given medium of material) for integrated in-plane feedback for tissue characterization in accordance with embodiments of the present disclosure. Referring to FIGS. 126 and 127, sensors 12602A and 12602B can be used for sending an electrical signal at the leading edge of the blade to determine differences in conductivity of the surrounding tissue. The signal received at sensors 12602A and 12602B can be used to detect differences in bone/tissue type along the leading edge of the device 12600 during cutting. This can be used to change the pace at which a cut is complete. If it is known that, for example, a harder segment of bone is approaching the user and/or robotic platform can change its parameters to better meet the situation. If the device 12600 was approaching a soft tissue boundary, the user can be notified and the platform can again change its approach. These electrical conductivity sensors may be placed in a region that contacts the adjacent bone on the surfaces of the device 12600 that touch either side of the cutting plane and/or any other orientation that helps detect tissue in a given direction. It is important to note, electrical conductivity sensors can be any relevant size to meet the needs of the application, placed on any surface of the static components, and leverage any relevant sensing principle (e.g. contacting, inductive, etc.).

FIG. 128 illustrates the cutting device 12600 shown in FIGS. 126 and 127 along with a graph 12800 showing detection of different bone and soft tissue types. The cutting device 12600 is shown on the left side with its end within cancellous bone. In the right side, the cutting device 12600 is shown with its end within cortical bone.

FIG. 129 illustrates a flow diagram of a bone type/tissue sensing feedback loop in accordance with embodiments of the present disclosure. Referring to FIG. 129, this figure depicts example steps implemented by a computing device for control (e.g. control of the cutting device) based on readings obtained by one or more electrical conductivity sensors, such as electrical conductivity sensors 12602A and 12602B shown in FIGS. 126 and 127. Electrical conductivity data can be received by the computing device and used to determine whether various levels of conductivity are met. The computing device can implement one or more actions based on whether threshold levels are met. Also, the computing device can control a user interface to indicate a current step or completion of a step in a procedure based on an impedance reading (e.g. low impedance can indicate bone cut is complete). The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets etc.) to provide feedback and output functionality. One knowledgeable in the art could envision the electrical conductivity sensors working with an AR/VR headset to provide visual feedback of the bone type being cut through overlayed on the specific anatomic region of interest.

FIG. 130 illustrates a top view of a cutting device 13000 having vibration sensors 13002A and 13002B for integrated in-plane vibration detection in accordance with embodiments of the present disclosure. Referring to FIG. 130, vibration sensors 13002A and 13002B may be attached at any suitable location on rails 13004A, 13004B, struts 13006, and/or any other component of the device 13000. Placing vibration sensors in the cutting plane can detect how the cutting device 13000 is reacting throughout the cutting process (e.g. based on bone type, feed-rate, etc.). This feedback can be provided to a user or robotic platform to, for example, pause cutting in the case of excessive binding. Vibration sensor data could also be leveraged to detect differences in bone type (e.g. if a robotic system were plunging into bone at a constant rate, the vibration profile would be specific to the region of bone/type of bone rather than variable/independent cutting parameters that would come as a result of being driven manually by a user) and/or be used to optimize cutting parameters based on patient specific anatomy (e.g. cutting sclerotic bone would require different feed-rate/cutting parameters than cancellous bone to provide the most accurate/precise cut). It is important to note, vibration sensors can be any relevant size to meet the needs of the application and leverage any relevant sensing principle (e.g. piezoelectric, capacitive, accelerometer, gyroscope, eddy-current, strain gauge, wired, wireless, etc.).

It would not be possible to gather viable vibration data without the presence of the rails and the precision captured tip. Since the rigid strut 13006 and rails 13004A and 13004B can remain relatively motionless with respect to the rapidly oscillating blade, the integrity of sensors placed on the surface can remain intact and provide repeatable/reliable results, which would not be feasible if they were to be placed directly on the blade's rapidly oscillating surface. Furthermore, the static components are still coupled to the motion of the rapidly oscillating saw blade through the captured tip/rails, so when certain vibration profiles are experienced at the blades leading edge during cutting (e.g. interacting with hard bone), the vibration is passed through this junction to the sensors on the static components. The static components represent a rigid construct made of a material that allows for a viable vibration signal to be detected (e.g. not made of a material that would attenuate the amplitude of the signal). As this design separates the cutting operation of the blade and the load sharing capabilities of the static components, it thus creates a lower moment of inertia for the blade and reducing the baseline vibration of the device (e.g. static components represent a significant amount of mass that is no longer a part of the rapidly oscillating blade). Therefore, the presence of the static components provides a higher resolution of detection of what is occurring in the cutting plane (e.g. placing vibration sensors on a blade would just show heavy vibration of the system itself versus providing insight into the performance of the cutting device as it translates through various materials). Placing sensors further back (e.g. on a handpiece and/or robotic arm) would not provide sufficiently localized information since the signal would be dampened and/or unclear.

FIG. 131 illustrates the cutting device 13000 shown in FIG. 130 along with graphs 13102 with cancellous bone vibration data and sclerotic bone vibration data. Particularly, the graphs 13102 show the data acquired as the cutting device 13000 cuts into bone 13100. The acquired data can be used to detect difference in bone/tissue types. This data can also be used to optimize cutting performance (e.g. feed-rate, plunging technique, etc.) for manual and robotic systems.

FIG. 132 illustrates a perspective view of a cutting device 13200 having a vibration sensor 13202 (e.g. accelerometer, piezoelectric sensor, piezoresistive sensor, etc.) attached to a strut 13204 in accordance with embodiments of the present disclosure. Referring to FIG. 132, the strut 13204 is positioned at a proximal end, but it should be appreciated that the sensor 13202 can be placed on a strut at the distal end or other suitable location. The vibration sensor 13202 can detect vibration since it is still rigidly attached to the static rail construct and provides for detection of cutting parameters and bone type based on specific vibration profiles.

FIG. 133 illustrates a top view of a cutting device 13300 having a vibration sensor 13302 positioned on a base of rail 13304. The vibration sensor 13302 can detect vibration since it is still rigidly attached to the static rail construct and provides for detection of cutting parameters and bone type based on specific vibration profiles.

FIG. 134 illustrates a flow diagram of an example method of a vibration feedback loop in accordance with embodiments of the present disclosure. The method may, for example, be implemented by the cutting device 13300 with the vibration sensors 13002A, 13002B shown in FIG. 130. Referring to FIG. 134, the flow diagram shows a vibration feedback loop for a saw blade/robotic cutting platform/user displays. The method includes acquiring vibration sensor readings and using the readings to determine whether there are certain levels of vibration, to analyze vibration profiles during cutting, and characterize the vibration profiles of the material. The vibration sensor data provides a means of introducing safety measures during the procedure (e.g. to prevent hitting critical soft tissues when a cortical breach is detected), to help characterize bone type during cutting, and help optimize cutting performance. The flow diagram shows example actions to implement based on these determinations. The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets, etc.) to provide feedback and output functionality. One knowledgeable in the art could envision the vibration sensors working with an AR/VR headset to provide visual feedback of the desired cutting technique (e.g. adjusting feed-rate) overlayed on the specific anatomic region of interest.

FIG. 135 illustrates a perspective view of a cutting device 13500 with multiple integrated sensors described herein, a dedicated visual feedback screen on the device, and output functionalities in accordance with embodiments of the present disclosure. It is noted that such a device may include any number of these sensors or exclude all or any number of these sensors. The sensors may acquire readings as described herein, and the readings may be used in any suitable combination for outputting information to an operator and/or controlling a robotic system, such as system 13500 shown in FIG. 135.

With continuing reference to FIG. 135, the system 13500 provides a combination of several of the previously-described embodiments to create a "smart blade" platform that can automate osteotomy based procedures (i.e. without the need for direct user execution). The static rail rigid strut embodiment provides a platform on which sensors can easily be applied to the working surface of the device. Since the rigid strut and static rails remain relatively motionless to the rapidly oscillating blade, the integrity of any sensors placed on the surface can remain intact and provide repeatable/reliable results (i.e. which would not be feasible if they were to be placed directly on the blades surface). The system 13500 can include a temperature sensor 13502, vibration sensor 13504, and a strain gauge sensor 13506. Temperature sensors in the blade itself can be present to provide an additional data point and comparison to temperature sensors on the static rail/rigid strut platform. Further, the system 13500 can provide a visual feedback screen in accordance with embodiments of the present disclosure (e.g. demonstrate temperature readings, deflection readings, binding, or provide simple color-based feedback such as where green means a user is aligned and cutting optimally and red means the user is out of alignment or plunging the device too quickly based on the detected bone type). A platform of sensors and feedback can be useful to the surgeon regardless of whether the procedure is being completed manually or robotically and improve surgeon workflow and patient outcomes. This system can individually and collectively combine sensor inputs using various application-based algorithms to trigger blade performance outputs (e.g. motor cutoff or slowdown, coolant/therapeutic activation). The sensors can be wirelessly charged from a handpiece and/or through the use of a hardware pack. The "smart blade" can also be integrated as a required component and/or removed if needed. One knowledgeable in the art can envision these sensor technologies placed on other embodiments of the static rail or static rail rigid strut designs in accordance with embodiments of the present disclosure.

FIG. 136 illustrates a top view of a cutting device 13600 having optical fibers 13602A and 13602B for providing sensor readings in accordance with embodiments of the present disclosure. Referring to FIG. 136, the optical fibers 13602A and 13602B extend along rails 13604A and 13604B, respectively. The optical fibers 13602A and 13602B allows for a large number of sensor readings along the same fiber optic that can also provide for different types of sensors/multi-sensorial information depending on the optical parameters (e.g. temperature, strain, pressure, applied load, etc.). Further, the optical fibers allow for adding readings across the tip strut 13606 at the leading edge of the static rail. The cutting device 13600 benefits from the use of optical fibers because of the scale of the fibers themselves (i.e. they are relatively small sensors in terms of diameter and provide significant detection capabilities). Although the fibers on the cutting device 13600 are shown on the top surfaces of the rails 13604A and 13604B, they can be placed on any surface of the rails 13604A and 13604B (e.g. bottom, inner edges, outer edges, etc.) or tip strut 13606 to provide the necessary information and detection output. It is important to note, fiber optic sensors sensors can be any relevant size/type (e.g. strain based, temperature based, pressure based, multisensorial, etc.), placed in any relevant configuration and leverage any relevant sensing principle (e.g. fiber Bragg grating) on the static components.

FIG. 137 illustrates the cutting device 13600 of FIG. 136 and a graph 13602 showing detection of high strain. The graph shows fiber optic sensor positions as compared to strain over time. The cutting device 13600 is shown on the left side as having cut into a region of cancellous bone. On the right side, the cutting device 13600 is shown as cutting into a region of hard sclerotic bone. The strain data generated from the fiber optics is relatively continuous along the entire length of the wire and is unique in that it could be used to replicate the complex bending of the cutting device 13600 throughout the cutting operation by providing a means of generating 2D and 3D shape reconstruction capabilities.

FIG. 138 illustrates a top view of another cutting device 13800 with fiber optic sensors 13802A and 13802B extending to a distal end of static rails 13804A and 13804B, respectively, in accordance with embodiments. Referring to FIG. 138, the fiber optic sensors 13802A and 13802B can be configured to detect pressure or applied load. By placing them at the tips of the static rails/captured blade edge, data can be gathered to determine differences in the applied cutting load required to cut through the bone. This can help to distinguish uneven loading (e.g. which can lead to inaccurate cuts) and provide data to optimize cutting feed-rate and blade oscillation rate. It can also provide data to help re-attempt a cut over a region that was found to have uneven loading.

FIG. 139 illustrates the cutting device 13800 of FIG. 138 and a graph 13900 showing a calibration curve. Particularly, the graph 13900 shows a calibration curve that can be used to model the wavelength shift from the fiber optic sensors as a function of the force applied to the tip of the static rail construct. The cutting device 13800 is shown on the left side as having contacted a homogenous region of bone with a consistently applied load across both sensors (e.g. making consistent cutting progress easier to facilitate). On the right side, the first optic sensor hits a harder region of sclerotic bone and detects a higher applied load (e.g. making it more difficult to progress the sawblade) on one of the distinct sensors (i.e. the left rail).

FIG. 140 illustrates a flow diagram of a fiber optics feedback loop in accordance with embodiments of the present disclosure. The multi-sensorial properties of fiber optics allow them to detect a variety of interactions including strain, temperature, and pressure/applied force based on the configuration of the fibers themselves. This provides a means of combining multiple types of feedback and opportunities for outputs (e.g. whether manually and/or robotically) within a single system (e.g. one fiber optic cable rather than having multiple different types of sensors). All fiber optic signals can be received by the computing device and used to determine whether various thresholds are met to implement one or more actions (e.g. visual feedback and/or outputs to a robotic system). Also, the computing device can control a user interface to indicate a current step or completion of a step in a procedure based on a given reading (e.g. bone cut complete). The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets etc.) to provide feedback and output functionality. One knowledgeable in the art could envision the fiber optic sensors working with an AR/VR headset to provide visual surface mapped feedback of real-time skiving relative to the desired trajectory as an overlay on top of the specific anatomy of interest and provide real-time updates as the user re-passes over the higher regions of bone.

FIG. 141 illustrates a top view of a cutting device 14100 having audio sensors 14102A and 14102B for integrated in-plane feedback for tissue characterization in accordance with embodiments of the present disclosure. Referring to FIG. 141, audio sensors 14102A and 14102B can be used to detect a specific audio pitch associated with cutting different types of bone during the cutting process. For example cancellous bone has a different audio profile/pitch than cortical bone due to the difference in the density of the material. Audio sensors 14102A and 14102B can be sensitive enough to detect such differences and send the signal to a computing device or hardware for processing as described herein. Over time data gathered from thousands of cases can be used to inform the cutting process and determine real-time what type of bone is being cut through to help inform the user and/or robotic platform about activity at the blades leading edge. This may be used to help increase precision (e.g. slow down the rate of cutting to avoid skiving) and lower temperature during cutting (e.g. sense harder bone and change cutting parameters). Audio sensors shown are placed in a non-load bearing region of the static rails, but can be placed in any other reasonable region along the static rails that allows for measuring differences in the audio signal for the desired application.

Audio sensors provide a solution to the need to understand what type of tissue a saw blade is translating through during the cutting process. Bone is non-homogenous (i.e. has a spectrum between cancellous and cortical bone). Based on the type of bone it can be harder/softer. These changes can lead to differences in cutting precision and/or temperature changes based on variability of bone type (e.g. harder bone causes higher cutting temps). Finally, it can be used as a means to determine if the blade has completed cutting. It is important to note, audio sensors can be any relevant size and sensing principle (e.g. microphones, piezoelectric transducers, ultrasonic sensors, acoustic emission sensors, etc.) to meet the needs of the application.

FIGS. 142A and 142B illustrate top perspective views of the cutting device 14100 of FIG. 141 being used for bone type detection. For example referring to FIG. 142A, the cutting device 14100 is within an area 14200 of one bone type 14204, and as it cuts deeper, as shown in FIG. 142B, it encounters a different bone type at an area 14202.

FIGS. 143A and 143B illustrate top perspective views of the cutting device 14100 of FIG. 141 being used for depth detection. For example referring to FIG. 143A, the cutting device 14100 is detecting a depth l1 from the sensors to the edge of the bone, whereas in FIG. 143B, the cutting device 14100 is detecting a depth l2 from the sensors to the edge of the bone (e.g. depth of bone detected from using transmitted and received audio waves).

FIG. 144 illustrates a flow diagram of an example method of an audio sensors feedback loop in accordance with embodiments of the present disclosure. The method may be implemented by the cutting device 14100 of FIG. 141 or any other suitable device. All audio signals can be received by the computing device and used to determine whether various thresholds are met to implement one or more actions (e.g. visual feedback and/or outputs to a robotic system). Also, the computing device can control a user interface to indicate a current step or completion of a step in a procedure based on a given reading (e.g. bone cut complete). The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets etc.) to provide feedback and output functionality. One knowledgeable in the art could envision the vibration sensors working with an AR/VR headset to provide visual feedback of the desired cutting technique (e.g. adjusting feed-rate) overlayed on the specific anatomic region of interest.

FIG. 145 illustrates a perspective view of a cutting device 14500 having a rigid, linear sheath 14502 on its rails 14504A and 14504B in accordance with embodiments of the present disclosure. Referring to FIG. 145, the sheath 14502 can move in a direction indicated by arrow 14506 when it engages a material (e.g. bone or soft tissue). One knowledgeable in the art understands that the rigid linear sheath could be driven by any type of linear mechanism (e.g. gear driven by a motor that engages a track on the linear sheath surfaces). FIGS. 146A and 146B illustrate top views of the cutting device 14500 prior to engaging material and at one position when it is engaging material, respectively. It is important to note, that the linear sheath 14502 could be any relevant size/geometry to meet the needs of the cutting application as long as it allows for engaging/sliding along the surfaces of the static rail components 14504A, 14504B.

FIG. 147 illustrates a top view of the cutting device 14500 cutting into bone 14700 with the working surface depth being informed by a computing device 14702 in accordance with embodiments of the present disclosure. Referring to FIG. 147, the computing device 14702 may include a navigation manager with functionalities for tracking as disclosed herein. In this embodiment, the computing device 14700 may inform the working surface depth 14704 relative to the location of the tracked bone coordinate system. With this information the rigid, linear sheath 14502 could be allowed to passively slide until input from the computing device/navigation system require dynamic adjustments (e.g. prevent user from sliding into a certain soft tissue and/or set the feed-rate of the cutting operation). The linear sheath 14502 could also take in other types of information such as from pre-operative CT scans that could help to determine a set max depth the working surface can travel based on a given location. An example of this could be completing a craniotomy, where the pre-operative information based on patient specific information could ensure that the user does not plunge further than a given amount to prevent contact with sensitive soft tissues adjacent to the bone surface. In cases where a user would be plunging into various locations, navigation data could inform that maximum depth dynamically depending on position of the cutting device.

With continuing reference to FIG. 147, initially (Step 1), the computing device 14702 can detect a location of the bone 14700 in 3D space. At Step 2, the computing device 14702 can detect a location of the linear sliding mechanism (e.g sheath 14502) in the 3D space (e.g. using communication with an array on the handpiece). At Step 3, the linear sliding mechanism can drive and set working surface length of the blade based on information from the navigation system.

FIGS. 148A-148C illustrates different top views of various positions of a cutting device 14500 of FIG. 145 in accordance with embodiments of the present disclosure. The embodiments demonstrate how the bone 14700 may be "scored" FIG. 148A (i.e. initial cutting trajectory set) prior to fully translating into the cutting plane FIGS. 148B and 148C.

FIG. 149 shows a flow diagram for control of a cutting device (whether manual, hand-held robotic, or robotic arm system configuration) having a linear rigid sheath, and communication with sensors/navigation systems in accordance with embodiments of the present disclosure. There are multiple feedback loops that could be implemented including soft tissue safety mechanism, binding/kicking protection, initial bone engagement functionality, dynamic adjustment of blade stiffness during cutting, and real-time feedrate adjustments. All feedback could be informed by the navigation system and/or sensor data originating from the surface of the rails (e.g. deflection data generated from strain sensors on the rails) and received by the computing device to determine whether various thresholds are met to implement one or more actions (e.g. feed rate adjustments). Also, the computing device can control a user interface to indicate a current step or completion of a step in a procedure based on a given reading (e.g. bone cut complete). The computing system can also leverage machine learning based on patterns recognized from the data (e.g. pre-operative, intra-operative, post-operative, historical data) to provide more actions based on the real-time data.

FIG. 150 illustrates a diagram of an operational environment 15000 for a system 15002 including a cutting device 15004 and navigation system 15006 in accordance with embodiments of the present disclosure. Referring to FIG. 150, the system 15002 also include a display/user interface 15008 for displaying navigational information or any other relevant feedback (e.g. haptics, robotic outputs, sensor information, etc.) to an operator of the cutting device 15004 or others assisting with a procedure. One knowledgeable in the art could envision the user interface being composed of a AR/VR headset instead of a display/user interface 15008. The environment 15000 includes a table 15010 upon which a subject 15012 for a procedure can rest during a procedure. In this example, the subject 15012 is a knee of a person upon which the cutting device 15004 is being utilized. The navigation system 15006 may track the coordinates of the cutting device 15004 and portions 15014A, 15014B of the knee 15012 in accordance with embodiments of the present disclosure. Those knowledgeable in the art could envision the navigation system being used to track any relevant anatomy outside of the knee anatomy shown relative to the cutting device 15004 being utilized.

FIG. 151 is a block diagram of an example cutting system in accordance with embodiments of the present disclosure. Specifically, the cutting system described is a hand-held robotic platform that leverages a combination of a navigation system, coolant system, and localized actuators (e.g. that drive a motion platform gimbal mechanism for local handpiece DOF control and/or a rigid linear sheath that resides on the static rails for working surface depth control) that all communicate to execute the desired cutting plan. The navigation system locates the handpiece in 3D space relative to the desired cut planes and/or planned cut. The coolant system integrates with the handpiece to allow for flow of coolant into the cutting plane. All information can be seen on a desired user interface like a navigation tower with a screen. The handheld platform also benefits from local sensors on the static rail components (i.e. strain gauges) technology to help provide more feedback during the cutting process and outputs that can be implemented by the hand-held robotic platform (e.g. adjustments to any of the localized actuators to output a desired effect).

FIG. 152 is a side view of a handheld cutting system 15200 in accordance with embodiments of the present disclosure. Referring to FIG. 152, this cutting system 15200 includes a 3DOF platform+stage, linear drive mechanism for the rigid sheath, blade drive mechanism (i.e. for blade oscillating) and a static rail/blade assembly all mounted on a handpiece. The cutting system 15200 includes a housing 15202 for holding its internal components. The cutting system 15200 also includes a navigation array 15204, a cutting device 15206, and a handle 15208.

FIG. 153 illustrates a side view of the cutting system 15200 with the housing removed so that its internal components 15300 can be seen. Referring to FIG. 153, the internal components 15300 include a rigid, sheath drive mechanism and blade oscillation drive mechanism, generally designated 15302. The internal components 15300 also include a 3DOF platform and stage, generally designated 15304. Further, the handle 15208 can include various circuitry/controls and a power button.

Specifically, the 3 DOF platform 15304 can decouple the upper portion of the handle 15208 from the bottom that the user is holding. In this example, the 3 DOF platform 15304 and stage construct 15304 can be made of a combination of 3 stepper actuators with linkages that have the proper decoupling at the ends of the fixed joints (i.e. universal joints to prevent them from over-constraining). However, one knowledgeable in the art can envision that there are a variety of mechanisms that can achieve the same 3DOF result and that one could reduce the number of degrees of freedom for less complex applications. The combination of these 3 actuators allows for controlling the position of the stage within a given window of motion limited to the range of the actuators themselves. This is why the user would provide greater macro positioning of the handpiece in 3D space while the stage+platform would provide more precision stability/positioning relative to the localized desired target. This allows for incorporating stabilization of the upper portion as a user approaches a desired cutting plane with the manually held device. This decoupling is what allows for dynamic, real-time control to remove the need for items such as traditional cutting guides. The upper portion houses all of the blade mechanism components (i.e. that allow for blade oscillation), whereas the lower portion of the handle 15208 can house the electronics, control buttons, and battery components at the base. However, one knowledgeable in the art understands that the mechanisms could be assembled in any number of methods. The stage and platform in this embodiment are separated by a flexible joint/housing that allows for relative motion between the two halves. The combination of the platform and linear drive mechanism for the rigid sheath allow for direct communication with the navigation system to control a planar cut based on the planned trajectory and/or to introduce any other active robotic output/feedback desired to support the procedure.

The rigid linear sheath mechanism can be driven by a stepper motor that can, for example, allow for linear motion through a rack+pinion gear mechanism. This rigid linear sheath surrounds the static rail components and would slide linearly relative to the cutting end of the device. Incorporating the rigid linear sheath around the static rails increase the overall construct thickness and in turn its stiffness to increase precision (i.e. reduces deflection). There are a variety of ways that the desired motion could be achieved for both the rigid linear sheath and 3DOF motion platform 15304. Each of the desired motions has a variety of mechanisms that one knowledgeable in the art could incorporate in a similar manner as the ones shown.

The 3DOF platform and stage 15304 includes actuators 15304A and 15304B such that the cutting device 15206 can be positioned and oriented. A third actuator is not shown due to the side view.

FIG. 154 illustrates a top view of the cutting device 15200 shown in FIGS. 152 and 153. In this example, the cutting device 15200 includes a rigid linear sheath 15400, a blade edge 15402, rails 15404A, 15404B, navigation array 15204, and a working body 15406.

FIG. 155 illustrates a top view of the cutting device 15200 shown in FIGS. 152 and 153 with the top of housing 15202 removed so that the internal components 15300 can be seen. Referring to FIG. 155, the internal components 15300 include a blade coupling and drive mechanism 15500. They also include a gear mechanism 15502 (e.g. rack and pinon) to allow for dynamically driving/controlling the rigid linear sheath 15400. FIG. 156 illustrates a perspective view of the cutting device 15200. FIG. 157 illustrates another perspective view of the cutting device 15200 such that the third actuator 15700 that works with actuators 15304A and 15304B is visible.

FIG. 158 illustrates the same perspective view of the cutting device 15200 shown in FIG. 157 except with a navigation/computing system 15800 being operatively connected thereto. It is noted that navigation system and computing system are used interchangeably throughout. Referring to FIG. 158, one or more strain gauge sensors 15802 can provide in cutting-plane feedback about blade tip motion (i.e. skiving) and can communicate with a handpiece gimbal mechanism, the linear sheath mechanism, and the global navigation system. The navigation system 15800 can implement the steps of detecting overall location of the handpiece in 3D space (Step 1); use the strain gauge sensor(s) 15802 to detect deflection of the blade edge (Step 2); communicate strain gauge sensor(s) 15802 data to the navigation system (Step 3); inform the linear sheath on required positioning in 3D space (e.g. to set working surface length) (Step 4); use the linear sheath to set depth of the blade tip based on information from navigation (Step 5); inform the gimbal mechanism on required positioning in 3D space (Step 6); and control the gimbal to drive motion of the blade tip based on the navigation information (Step 7). The real-time data detected by the strain sensors 15802 resulting from within the cutting plane allow a means of providing feedback to the hand-held robotic actuators that previously would not exist (e.g. communication of data inside cutting plane to a navigation/computing system for more precise feedback/outputs versus data generated from sensors external to envelope of the cut/cutting device).

FIGS. 159A and 159B illustrates side views of the cutting device 15200 shown in FIG. 158 during operation for cutting bone 15900 in accordance with embodiments of the present disclosure. Referring to FIGS. 159A and 159B, these figures depict use of navigation/computational 15800 information for aligning the cutting device 15200 with a desired bone planar cut 15900. FIG. 159B depicts the cutting device 15200 as being aligned with the desired cut 15900. The initial alignment of the device to cutting plane prior to execution of cuts can be set by the manual influence of the operator and the 3DOF gimbal mechanism based on information from the navigation/computational system 15800.

FIGS. 160A and 160B illustrate example steps following the steps depicted in FIGS. 159A and 159B. Referring to FIG. 160A, this figure shows the blade edge skiving up (e.g. hitting cortical bone and deflecting upwards, which is a common occurrence in total knee bone cutting) despite correct handpiece trajectory relative to global navigation parameters provided by the overall system. Now turning to FIG. 160B, this figure shows communication from strain gauge sensors in the cutting plane to inform the handpiece and global coordinate system to correct the in-cutting plane error by implementing an equal-and-opposite motion through the gimbal system to reorient the blade edge. Although this is one means of ensuring the cutting error is corrected, one knowledgeable in the art understands that a variety of outputs may be implemented including but not limited to informing the user to re-pass over the designated area rather than an active robotic adjustment.

FIGS. 161A-161C illustrate other example steps that can be implemented by the cutting device 15200 when using the communication channels established between the navigation/computational system 15800, the strain sensors 16100, and the dynamically driven linear rigid sheath 16102. At FIG. 161A, as the blade completes the cutting process, it is allowed to progress freely (e.g. no resistance from the linear sliding sheath mechanism). At FIG. 161B, once the blade engages the region of the sclerotic bone, the strain gauge sensor(s) can then detect skiving (e.g. deflection in an upward direction). The real-time skiving detected by the strain sensors inside the cutting plane beyond a established threshold can communicate through the navigation/computational system 15800 to control the linear sliding mechanism to engage the external bone surface and push the user to the location before the skiving occurred. At FIG. 161C, once the linear sliding mechanism pushes the working surface of the blade to its previous location (i.e. based on communication with the navigation system 15800), the user can re-complete a pass over the same region to try to reduce the effect of skiving. The linear sliding sheath can also be informed by the navigation/computational system 15800 to complete the second pass at a more optimal feed rate (e.g. a slower feed rate over the harder region may allow for prevention of skiving). Visual feedback of the location of skiving can also be provided to the user (e.g. via a display).

FIGS. 162A-162C illustrate other example steps that can be implemented by the cutting device 15200. At FIG. 162A, the blade edge coordinate can understand relation to the soft tissue boundary of the bone (e.g. provided by CT scan, mapping of anatomical landmarks, etc.) based on communication with global navigation/computational system 15800. At FIG. 162B, as the blade completes the cutting process it is allowed to progress freely (e.g. no resistance from the linear sliding sheath mechanism) until it comes into proximity with the soft tissue boundary. At FIG. 162C, as the blade approaches the soft tissue boundary, the linear sliding mechanism is informed by communication with the navigation/computational system 15800 to provide a hard stop on the external surface of the bone that does not allow the user to progress deeper into the cut and prevent damage to the desired tissue (e.g. sets the working depth of the blade dynamically). The user can then continue to complete the cut after this haptic soft tissue safety boundary feedback. This is one example of a haptic boundary that could be established, but one knowledgeable in the art can envision other critical soft tissues and/or depth based haptics established throughout a procedure based on the locational and/or sensor information from the rails in the cutting plane being fed to the overall system.

FIGS. 163A and 163B illustrate top views of a cutting device 16300 depicting the fully captured, rigid, linear sheath mechanism 16302 in accordance with embodiments of the present disclosure. The fully captured tip can allow for a more rigid construct than the open-tip shown in other embodiments. The full sheath around the tip can also provide another surface that the user could actively grab on top and bottom to help stabilize the construct. It also provides slightly more tissue protection if needed. FIG. 163A shows the sheath mechanism 16302 at a distal end of the cutting device 16300, while FIG. 163B shows it having been pushed back at the proximal end. One knowledgeable in the art could envision the size of the full capture portion changing in thickness, length, and width depending on the type of interaction with bone and engagement required.

FIGS. 164A-164C show top views of the cutting device 16300 with its sheath mechanism 16302 at different positions in accordance with embodiments of the present disclosure. Referring to FIGS. 164A-164C, the cutting device 16300 shows the stabilizer tip 16304 that provides a means of providing additional stability during the initial positioning of the device relative to the cutting plane. The stabilizing tips 16304 in this embodiment are shown as relatively sharp spike components that could effectively prevent slipping when in contact with the boney surface. More or less of these stabilizing tips 16304 may be added along the rigid linear sheath along the surfaces that are in clearance from the oscillating blade teeth. These allow for using the macro positioning features of the system to contact the bone directly for a more stable approach into the bone (i.e. versus using the hand-held robotic handpiece to effectively hover in place prior to starting cutting). This can effectively set 1 DOF as a part of the initial cutting positioning process and workflow. FIG. 164A shows the sheath mechanism 16302 in a fully distal position that would allow for contacting bone (e.g. without the oscillating blade contacting bone), FIG. 164B shows the sheath mechanism 16302 having slid inward a small distance from the fully distal position (e.g. demonstrating how the blade could initially engage and score the bone surface to establish the planar alignment), and FIG. 164C shows the sheath mechanism 16302 in a fully proximal position. The sheath mechanism 16302 and cutting device can be scaled in size/length to support any cutting depth based on the application.

FIG. 165 illustrates a diagram of an operational environment 16500 for a system 16502 including a cutting device 15004 and navigation system 15006 in accordance with embodiments of the present disclosure. Referring to FIG. 165, this system 16502 is similar to the system 15002 shown in FIG. 150 except that the positioning and movement of the cutting device 15004 is controlled by a robotic arm 16504 to which the cutting device 15004 is attached. A computing device (not shown) operatively connected to the robot 16502 can receive navigational and user input information for controlling the movement of the cutting device 15004 in accordance with examples and embodiments described herein. This operating environment 16500 demonstrates one type of robotic arm, but one knowledgeable in the art can envision many other types of passive arms, semi-autonomous robotic arms, and fully autonomous robotic arms operating in the same conditions all with various degrees of freedom to accomplish the desired surgical task.

FIG. 166 shows a flow diagram of a robotic arm system in accordance with embodiments of the present disclosure. As an example, the method may be implemented by the system 16502 shown in FIG. 166. Referring to FIG. 166, specifically, the cutting system described is a robotic arm platform that leverages a combination of a navigation system, coolant system, and localized actuators that all communicate to execute the desired cutting plan. The navigation system can locate the robotic arm in 3D space relative to the desired cut planes and/or planned cut. The coolant system integrates with the handpiece to allow for flow of coolant into the cutting plane. All information can be seen on a desired user interface like a navigation tower with a screen. The robotic platform also benefits from local sensors on the static rail components (i.e. strain gauges) technology to help provide more feedback and/or output functionality to the overall robotic system during the cutting process. One knowledgeable in the art can envision for any of the robotic arm mechanisms shown in the application, any configuration/combination of robotic arm mechanisms (e.g. to drive joint rotation or translation) and articulating joint types with more or less degrees of freedom can be implemented depending on the specific surgical needs.

FIG. 167 illustrates a perspective view of the fully autonomous robot configuration 16502 shown in FIG. 165 and example operation of it for moving the cutting device 15004 in accordance with embodiments of the present disclosure. It is important to note that each of the robotic linkages can be actively driven by the system, which allows for dynamic adjustment of each of the mechanisms based on feedback/outputs (e.g. driven by sensors on the rails). Referring to FIG. 167, initially at Step 1 the navigation system 15006 detects overall location of robotic arm/cutting end effector in 3D space based on the navigation array attached to the cutting device 15004. Subsequently at Step 2, vibration and shock sensors located on the static rail surfaces of the cutting device 15004 detect bone cutting properties of the blade edge (e.g. bone type, feed-rate properties, cortical breaching, etc.) that can help inform the location data relative to bone. At Step 3, vibration and shock sensors provide information to navigation system 15006. At Step 4, navigation system 15006 can inform robotic arm system of its location in 3D space to drive blade motion/kinematics. At Step 5, the arm of the robot 16502 can drive motion of the tip based on the provided the user plan (e.g. pre-op/intra-op cutting execution plan), navigation, and any relevant sensor feedback from the static rails (e.g. changes to feed-rate, stop cutting after cortical breach, etc.). The ability of the robotic arm system to leverage real-time data from sensors on the cutting device/in the cutting plane for feedback/output functionality is unique. One knowledgeable in the art could also envision the same communication and robotic outputs being informed by any/all other sensor types originating from the cutting device 15004.

FIGS. 168A and 168B illustrate top views of the fully autonomous robot configuration 16900 controlling the cutting device 15004 to cut into bone 16800. Referring to FIG. 168A, vibration and shock sensors located on the static rails can detect initial cortical engagement, allowing the navigation system 15006 to know that the cutting process is initiated to inform robotic arm adjustments. Referring to FIG. 168B, vibration and shock sensors located on the static rails can detect breaching cortical bone, allowing the navigation system 15006 to know that the cutting boundary has been breached to provide robotic arm adjustments.

FIG. 169 is a perspective view of a semi-autonomous robot configuration 16900 controlling the cutting device 15004, which is driven through the use of a manually manipulated handpiece (e.g. which could be integral to the robotic arm and/or allow for use of any manual handpiece given a modular connection) in accordance with embodiments of the present disclosure. It is important to note that although each of the robotic linkages can be actively driven by the system, the system also allow for passive manipulation of certain linkages within certain parameters (e.g. user driving the cutting device within a given planned plane). Referring to FIG. 169, at Step 1, the navigation system 15006 can detect overall location of hand-held cutting device 15004 in 3D space which is rigidly attached to the robotic arm 16900. At Step 2, the navigation system 15006 informs robotic arm system 16900 of its location in 3D space to drive blade motion/kinematics. At Step 3, the robotic arm 16900 can find planar alignment based on the provided user plan (e.g. pre-op/intra-op cutting execution plan), navigation, and any relevant sensor feedback from the static rails (e.g. changes to feed-rate, stop cutting after cortical breach, etc.). At Step 4, the robotic arm 16900 can allow for planar motion of the cutting device 15004 based on manual user manipulation of distinct arm linkages.

FIG. 170 is a perspective view of a semi-autonomous robot 16900 controlling the cutting device 15004 in accordance with embodiments of the present disclosure. It is important to note that although each of the robotic linkages can be actively driven by the system, the system allows for passive manipulation of certain linkages within certain parameters (e.g. user driving the cutting device within a given planned plane). Referring to FIG. 170, at Step 1, a validation probe (i.e. using tracker arrays, not shown) placed on the cutting device 15004 distal end provides location of robotic arm/cutting end effector in 3D space and informs navigation system 15006 for initial positional calibration. At Step 2, the navigation system 15006 can inform and maintain positional information of the robotic arm system 16900 in 3D space through its tracked kinematics (e.g. of mechanical joints) to drive blade motion/kinematics. At Step 3, the arm of the robot 16900 can find planar alignment based on the provided user plan (e.g. pre-op/intra-op cutting execution plan), navigation, and any relevant sensor feedback from the static rails (e.g. changes to feed-rate, stop cutting after cortical breach, etc.). At Step 4, the robotic arm 16900 can allow for planar motion of the tip based on manual user manipulation. At Step 5, sensors on the static rails (e.g. strain, vibration, temperature, etc.) actively communicate with the navigation system 15006 and can inform actions related to the cutting operation (e.g. shutdown power if approaching soft tissue, inform user of temperature increases, etc.).

FIG. 171 is a perspective view of a semi-autonomous robot 16900 with passive planar linkages 17100 controlling the cutting device 15004 in accordance with embodiments of the present disclosure. It is important to note that in this case there is a hybrid combination of passive mechanical linkages, which require manual manipulation and active robotic linkages that can be actively driven by the system. Referring to FIG. 171, at Step 1, the navigation system 15006 can detect overall location of cutting device 15004 in 3D space which is rigidly connected to the robotic arm 16900 through passive planar linkages 17100. At Step 2, the navigation system 15006 can inform active robotic arm system 16900 components on required planar positioning in 3D space. At Step 3, the robotic arm 16900 can drive motion of the handpiece to the desired planar positioning based on the provided the user plan (e.g. pre-op/intra-op cutting execution plan), navigation 15006, and any relevant sensor feedback from the static rails (e.g. changes to feed-rate, stop cutting after cortical breach, etc.). At Step 4, the navigation system 15006 informs linear sheath on required positioning in 3D space during cutting process. At Step 5, the linear sheath can set depth of blade tip based on information from navigation 15006 and rail sensors during cutting process. At Step 6, the user can manually drive planar positioning of the handpiece using in-plane mechanical linkages 17100 based on robotic arm positioning.

FIGS. 172A and 172B are top views of a semi-autonomous robot 16900 with passive planar linkages 17100 controlling the cutting device 15004 in accordance with embodiments of the present disclosure. Referring initially to FIG. 172A, the blade edge coordinate system can understand the relation to the soft tissue boundary of the bone (e.g. provided by CT scan, mapping of anatomical landmarks, etc.) based on communication with global navigation system 15006. As the blade completes the cutting process it is allowed to progress freely (e.g. no resistance from the linear sliding sheath mechanism) until it comes into proximity with the soft tissue boundary. Now referring to FIG. 172B, despite the passive mechanical linkage 17100 allowing complete planar motion, as the blade approaches the soft tissue boundary, the linear sliding mechanism can provide a hard stop/haptic boundary on the outer surface of the bone that does not allow the user to progress deeper into the cut to prevent damage to the soft tissue.

FIG. 173 is a perspective view of a semi-autonomous robot 16900 with passive planar linkages 17300 controlling the cutting device 15004 in accordance with embodiments of the present disclosure. It is important to note that in this case there is a hybrid combination of passive mechanical linkages, which require manual manipulation and active robotic linkages that can be actively driven by the system. Referring to FIG. 173, at Step 1, the navigation system 15006 detects overall location of the cutting device 15004 in 3D space which is rigidly connected to the robotic arm 16900 through passive planar linkages 17300. At Step 2, the navigation system 15006 informs active robotic arm system 16900 components on required planar positioning in 3D space. At Step 3, the robotic arm 16900 can drive motion of the handpiece to the desired planar positioning based on the provided the user provided plan (i.e. pre-op/intra-op cutting execution plan), navigation 15006, and any relevant sensor feedback from the static rails (i.e. changes to feed-rate, stop cutting after cortical breach, etc.). At Step 4, a user can manually drive planar positioning of the handpiece using in-plane mechanical linkages 17300 based on robotic arm positioning. At Step 5, fiber optic sensors along the entire surface of the static rails detect real-time information regarding cutting performance of the blade related to precision (e.g. provides information on real-time blade deflection/skiving to manage precision). At Step 6, fiber optic sensors can inform the navigation system 15006 to allow for feedback to be provided back to the user/robotic system 16900 (e.g. detect skiving and re-pass over the desired region of bone) for the desired output.

FIGS. 174A and 174B are top views of the semi-autonomous robot 16900 with passive planar linkages 17300 controlling the cutting device 15004 in accordance with embodiments of the present disclosure. Referring initially to FIG. 174A, fiber optic sensors along the entire surface of the static rail members can detect uneven deflection of the cutting edge (e.g. one side loaded by harder sclerotic bone). Now turning to FIG. 174B, the fiber optic sensor can provide a real-time 2D/3D visual representation of the deformed blade geometry and demonstrates an uneven skiving up on one side of the static rails. The user can subsequently interpret the visual feedback provided by the navigation/computational system 15006 to demonstrate a different angle of attack and feed-rate to evenly cut through the harder region of bone. This represents a manner in which visual feedback can be provided a user using a robot 16900 with a passive planar linkage 17300 that is unable to actively adjust those specific DOF with the active robotic joints.

FIG. 175 is a perspective view of a passive mechanical positioning arm 17500 that can lock any of the DOF available as needed to control position and trajectory controlling the cutting device 15004 in accordance with embodiments of the present disclosure. It is important to note that in this case this embodiment represents a completely passive positioning arm that provides an ability to lock any joints to constrain motion and/or allow for planar motion with respect to the cutting device (e.g. final linkages allow for in-plane motion driven manually by a user). The cutting device 15004 is attached to a manual handpiece that can be used outside of the passive mechanical positioning arm 17500 if desired (e.g. using traditional cutting guides, but can be modularly attached to the passive arm to provide navigational and "smart-blade" capabilities/feedback). Referring to FIG. 175, at Step 1, the navigation system 15006 can detect overall location of the cutting device 15004 in 3D space which is rigidly connected to the passive mechanical arm 17500. At Step 2, the navigation system 15006 can inform the user of the desired planar positioning in 3D space relative to the tip of the blade based on the provided plan (i.e. pre-op/intra-op cutting execution plan). At Step 3, the user can leverage information from the navigation system 15006 to manually set and lock the passive mechanical arm 17500 into the required planar positioning in 3D space. At Step 4, the user can manually drive planar positioning of the handpiece using in-plane mechanical linkages to complete cutting process based on passive mechanical arm 17500 positioning informed by navigation 15006 (e.g. removes the need for pinned guides and miscellaneous instruments needed to complete a typical total knee procedure). At Step 5, sensors on the static rails (e.g. strain, vibration, temperature, etc.) actively communicate with the navigation system 15006 and can provide feedback (e.g. visual, auditory, etc.) to the user related to the cutting operation (e.g. skiving detected, inform user of temperature increases, etc.).

FIGS. 176A and 176B are perspective views of the modular attachment of the cutting device 15004 that leverages the static rail mechanism 17602 (e.g. rather than features on the handpiece) for attachment to the passive mechanical positioning arm 17601 using a modular attachment sheath 17600 in accordance with embodiments of the present disclosure. Referring initially to FIG. 176A, the modular attachment sheath 17600 is spaced apart from and attachable to static rails 17602 of the cutting device 15004. Referring to FIG. 176B, this passive positioning arm 17601 is directly attached to the static rail blade construct for increased precision of placement through the use of the modular attachment sheath 17600. In other examples, the modular attachment sheath 17600 can be attached on any other rigid surface of the rail construct (i.e. not just a sliding fit along the static rails themselves). One knowledgeable in the art could envision this modular attachment sheath 17600 that leverages the rail mechanism 17602 being used as an attachment to any source of movement (e.g. active/passive robot arms, micro-robots secured locally to the adjacent bone, etc.).

FIG. 177 is a perspective view of a fully autonomous micro-robot arm 17700 attached to bone 17702 and being operably connected to and controlling the cutting device 15004 to cut into bone 17702 in accordance with embodiments of the present disclosure. For any micro robotic arm mechanisms fixated to bone directly (as shown in the application), one knowledgeable in the art can envision implementing any configuration/combination of robotic arm mechanisms (e.g. to drive joint rotation or translation) and articulating joint types with more or less degrees of freedom depending on the specific surgical needs. It is important to note that each of the robotic linkages can be actively driven by the system, which allows for dynamic adjustment of each of the mechanisms based on feedback/outputs (e.g. driven by sensors on the rails). Referring to FIG. 177, at Step 1 the micro-robot arm 17700 can be secured with fixation (e.g. screws) locally to rigid bone stock of the desired bone 17702 (e.g. femur). At Step 2, the navigation system 15006 can detect overall location of micro-robot arm 17700 in 3D space. At Step 3, the navigation system 15006 detects overall location of bone 17702 in 3D space. At Step 4, the navigation system 15006 can inform robotic arm system 17700 of its location in 3D space to drive blade motion/kinematics. At Step 5, the fully autonomous micro-robot arm 17700 can drive motion of the tip based on the user provided plan (e.g. pre-op/intra-op cutting execution plan), navigation 15006, and any relevant sensor feedback from the static rails (e.g. changes to feed-rate, stop cutting after cortical breach, etc.). One knowledgeable in the art can envision that direct fixation of the micro-robots to the adjacent bone (e.g. versus the robotic arm embodiments that aren't directly secured) reduces the overall robotic system cutting error while still allowing for guideless cutting.

FIG. 178 is a perspective view of a semi-autonomous micro-robot arm 17800 attached to bone 17702 and being operably connected to and controlling the cutting device 15004 to cut into bone 17702 in accordance with embodiments of the present disclosure. It is important to note that in this case there is a hybrid combination of passive mechanical linkages 17802 which require manual manipulation and active robotic linkages 17800 that can be actively driven by the system. The hand-held cutting device 15004 in this embodiment demonstrates a modular sheath attachment 17600 to the surfaces of the static rails on the cutting device 15004. Referring to FIG. 177, at Step 1, the micro-robot arm 17800 is secured with fixation (e.g. screws) locally to rigid bone stock of the desired bone 17702 (e.g. femur). At Step 2, the navigation system 15006 can detect overall location of micro-robot arm 17800 in 3D space. At Step 3, the navigation system 15006 can detect overall location of bone 17702 in 3D space. At Step 4, the navigation system 15006 can inform robotic arm system 17800 of its location in 3D space. At Step 5, the micro-robot arm 17800 can drive planar positioning of the blade edge based on the user provided plan (e.g. pre-op/intra-op cutting execution plan), navigation 15006, and any relevant sensor feedback from the static rails (e.g. changes to feed-rate, stop cutting after cortical breach, etc.). At Step 6, the user can manually drive planar positioning of the handpiece using in-plane mechanical linkages based on robotic arm positioning.

FIG. 179 illustrates a perspective view of a semi-autonomous micro robot arm 17900 attached to bone 17902 and operably connected to move the cutting device 15004 for cutting the bone 17902. It is important to note that in this case there is a hybrid combination of passive mechanical linkages 17902 which require manual manipulation and active robotic linkages 17900 that can be actively driven by the system. Referring to FIG. 179, the robot arm 17900 includes passive planar linkage for manual manipulation, modular attachment to the cutting device 15004, and system communication with the location array on the cutting device 15004. The passive mechanical arm is directly attached to the cutting device 15004 which demonstrates another means of attaching to the micro robot arm 17900. One knowledgeable in the art can envision the use of sensors located on the static rail components of the cutting device 15004 for communication with the navigation and robotic systems.

FIGS. 180A-180C illustrate perspective views of a drill bit 18000, end mill 18002, and burr 18004, respectively, for use with a medical rotary drill in accordance with embodiments of the present disclosure. In this application, the term drill bits will be used generally and can refer to drill bits, end mills, burrs, drill end pieces, or rotational cutting end effectors all of which can cut using a different rotational modality (e.g. side cutting versus end cutting). Drill bits can scale to any desired diameter and length based on the desired application. Referring to FIGS. 180A-180C, each drill bit 18000, 18002, and 18004 includes an end 18006 for attachment to and turning by a rotary drill mechanism (not shown, but can include manual handpieces, hand-held robotics, or any viable end effector) and robotic end effectors with various DOF (degrees of freedom) control that can be scaled depending on the application (e.g. passive positioning arm, semi-autonomous robotic arms, autonomous robotic arms, etc.). An opposing end 18008 can engage and transform (e.g. drill into) bone, soft tissue, or other material (e.g. whether through end-cutting and/or side cutting edges). FIGS. 181A-181C illustrate front views of the drill bits 18000, 18002, and 18004, respectively. Each drill bit 18000, 18002, and 18004 can have a static casing/sheath 18010 within which a shaft (not visible, internal feature) is turned.

These drill bits 18000, 18002, and 18004 can operate with a static casing 18010 as disclosed herein. These drill bits are unique in that the static casing 18010 follows the end effector axially into the cutting site based on its unique geometry to be flush/sub-flush to the cutting end of the drill bit. Other "sheaths" do not translate into the cutting axis (e.g. they simply sit on the outer adjacent surface more so as a guide mechanism, rather than the support mechanism provided by the static casing described throughout). Drill bits 18000, 18002, and 18004 can be attached to any suitable type of mechanism that provides rotational motion and in combination with any type of passive or active systems (e.g. robotic arms, hand-held robotics, etc.). The static casing can be rigidly attached to the housing of that mechanism to provide a static surface (mechanisms and housing not shown). Each of the embodiments static casing/sheath 18010 can be scaled in length, diameter, and/or size depending on the application. It is important to note that the static casing/sheaths 18010 provide a means of decoupling the motion of the rapidly rotating drill bit end from the adjacent surfaces (e.g. bone) within the cutting axis. They also provide a means of stabilizing the drill bit cutting end and corresponding working surface to ensure axial alignment.

Further, the static casing/sheath 18010 can have a tapered engagement behind the drill bit end for ease of entry. One knowledgeable in the art can envision other types of features to allow for the ability of the static casing/sheath 18010 to seamlessly translate into the cutting site (e.g., break edge at the tip and/or scaling the thickness of the opposing end 18008 to allow for more clearance).

FIGS. 182A-182C illustrate other front views of the drill bits 18000, 18002, and 18004, respectively, with shadow lines to show interior features. Particularly, an aperture at ends 18006 opens to an interior space, generally designated 18200, for each drill bit 18000, 18002, and 18004.

FIGS. 183A-183C illustrate perspective views of drill bits 18300, 18302, and 18304, respectively, for use with a medical rotary drill/robotically driven arm in accordance with embodiments of the present disclosure. Referring to FIGS. 183A-183C, each drill bit 18300, 18302, and 18304 includes an end 18306 for attachment to and turning by a rotary drill/robotically driven arm (not shown). An opposing end 18308 can engage and transform (e.g. drill into) bone, soft tissue, or other material material (e.g. whether through end-cutting and/or side cutting edges). Each drill bit 18300, 18302, and 18304 can have a shaft 18307 that is rotatable within a sheath 18309.

With continuing reference to FIGS. 183A-183C, each drill bit 18300, 18302, and 18304 defines a cut-away section present on the static casing/sheath 18309 component, generally indicated 18310, along its shaft. This feature adds increased debris relief within the cutting site while still providing a precision captured tip for increased axial stability. One knowledgeable in the art could envision any number of cutouts with a given size/shape to meet the needs of the cutting application. The cutouts could also run the entire length of the working shaft of the drill such that debris could migrate entirely out of the cutting axis. In the embodiments of FIGS. 183A-183C, a surface of the shaft 18307 is exposed due to the cut-away section 18310. The drill bits 18300, 18302, and 18304 can be attached to any type of mechanism that provides rotational motion and the static casing/sheath 18309 can be rigidly attached to the housing of that mechanism to provide a static surface (mechanisms and housing not shown). FIGS. 184A-184C illustrate front views of the drill bits 18300, 18302, and 18304, respectively, from FIGS. 183A-C. FIG. 185 is a perspective view of the drill bit 18300 shown in FIG. 183A.

FIG. 186 is another perspective view of the drill bit 18300 with the drill bit 18300 being spaced apart from its sheath 18309 in order to depict the traversal path of debris 18600 through an opening 18602 of the static casing/sheath 18309.

FIG. 187 illustrates a top perspective view of the sheath 18309 shown in FIG. 186. Referring to FIG. 187, the opening 18602 is defined at an end of the sheath 18309 that is nearest the drill bit (not shown). The opening 18602 includes sides notched areas 18700 and 18702 that are adjacent the main area that holds the shaft of the drill bit. These areas remain open when the shaft is in operational position such that the debris can be received into them for transport away from the work area and into the cutout region. Since the sheath translates into the cutting axis behind the leading edge of the drill bit there is significant debris relief provided by the side notched areas 18700 and 18702. This can help ensure proper surface finish, reduce heat generation, and increase precision of the drilling operation. One knowledgeable in the art can envision including any number of relevant cutouts of a given size/shape to meet the needs of the desired drilling/cutting application.

FIGS. 188A-188C illustrate side views of the drill bit 18300 (along with static casing/sheath 18309) drilling into material 18800 in accordance with embodiments of the present disclosure. Referring to FIG. 188A, this figure shows the drill bit 18300 at a position where it is close to the material 18800 for drilling. FIG. 188B shows the drill bit 18300 having drilled into the material 18800. FIG. 188C shows the drill bit 18300 at a position having drilled farther than the position shown in FIG. 188B. These figures demonstrate the ability of the sheath (or static casing) 18309 to translate into the material 18800 behind the leading edge of the drill bit 18300. Tapered edges on the static sheath/casing 18309 ensure the transition of the sheath 18309 into the cutting site behind the leading edge does not hang up on the material 18800. The presence of the sheath 18309 ensures stability is maintained throughout the drilling/cutting process. Typically, the deeper a drill goes into a cutting axis the more prone it is to inaccuracies, therefore, the ability of the static casing/sheath 18309 to support load after the initial engagement of the drill in the material 18800 works to reduce tip deflection and help maintain axial alignment.

FIGS. 189A-189C illustrate perspective views of drill device 18901 with drill bits 18300 having cut-away sections 18900 that extend a length of static rail/sheath 18902. As with other embodiments, this embodiment can be used to engage and transform (e.g. drill into) bone, soft tissue, or other material material (e.g. whether through end-cutting and/or side cutting edges). The drill bit 18300 has a shaft 18307 that is rotatable within the static rail/sheath 18302. One knowledgeable in the art can envision having any number of cutouts with a given size/shape to meet the needs of the desired drilling/cutting application. The cutouts could also run the entire length of the working shaft of the drill such that debris could migrate entirely out of the cutting axis. This embodiment provides the most effective method for providing debris relief by leveraging the large cutouts for any chips or other debris migrating backwards from the cutting end. The drill device 18901 can be attached to any type of mechanism that provides rotational motion (e.g. manual drilling handpieces, hand-held robotics, robotic arms, etc.) and the static rail/sheath 18309 would be rigidly attached to the housing of that mechanism to provide a static surface (mechanisms and housing not shown). FIGS. 190A-190C are front views of the drill bits 18300 of FIGS. 189A-189C, respectively. FIG. 191 is a perspective view of the drill bit 18300 shown in FIG. 190B.

FIG. 192 illustrates another perspective view of a drill device 19200 including the drill bit 18300 being spaced apart from its static rail/sheath 18309. Referring to FIG. 192, it can be seen that the cut-away section 18900 is defined by two notched portions 19200 and 19202 of the static rail/sheath 18309. The notched portions 19200 and 19202 are on opposing sides of the static rail/sheath 18309 but may be alternatively shaped and sized.

FIG. 193 illustrates a side view of a drill device 19301 including drill bit 18300 for depicting the traversal of fluids, debris, or particles through internal channels 19300A and 19300B in accordance with embodiments. Referring to FIG. 193, arrows 19302 show the direction of flow of fluids, etc. to the drill bit 18300 (e.g. this direction of flow could be used to cool the drilling operation and push out debris), and arrows 19304 show the direction of flow of fluids, etc. from the drill bit 18300 (e.g. this direction of flow could be used to provide an means of aspirating debris from the leading edge of the drill rather than for use with fluid/coolant). FIGS. 194A and 194B show opposing, perspective end views of the drill device 19301 for showing the traversal (indicated by arrows 19400) of fluid into the internal channels 19300 and to the drill bit 18300.

FIG. 195 illustrates a side view of a drill device 19501 including a drill bit 18300 for depicting the traversal of fluid, etc. along the shaft 18307 and through one or more openings, generally designated 19500, defined by the static casing/sheath 19502. Referring to FIG. 195, the direction of flow of fluid (or other material) is indicated by arrows 19504.

FIG. 196 illustrates a side view of a drill device 19601 including a drill bit 18300 with arrows 19600 for depicting the flow of fluid (this direction of fluid flow can be used to cool the drilling operation and/or push out debris) and arrows 19602 for depicting the flow of debris (this direction of flow could be used to provide a means of aspirating debris from the leading edge of the drill) within internal channels 19604 in accordance with embodiments of the present disclosure. The internal fluid channels reside within the static rail/casing 19606 to allow for direct translation to the leading edge of the device 19601. FIGS. 197A and 197B show opposing, perspective end views of the drill bit 18300 showing the traversal (indicated by arrows 19600) of fluid into the internal channels 19604 and to the drill bit 18300.

FIGS. 198A-198C illustrates perspective views of different drill devices 19801 including different drills bits 19800 that are each assembled with a static sheath 19802, and a sliding sheath 19804 in accordance with embodiments of the present disclosure. The sliding sheath 19804 can move with respect to the drill bit 19800 and its static sheath 19802 or vice versa (e.g. mechanism can drive either the sliding sheath and/or the combination of the static sheath/drill bit). The sliding sheath 19804 can be used to dynamically set depth of the drill bit 19800 and stabilize the cutting end prior to execution of the drilling process (e.g. to align axial position). This sliding sheath 19804 can "push" off of whatever surface it sits on to set depth of the end effector and can also be used to set feed rate. The sliding sheath 19804 in this embodiment has cutouts but may alternatively be a completely closed off sheath. Each of the embodiments can be scaled in length, diameter, and size depending on the application. FIGS. 199A-199C illustrate perspective views of the sliding sheath 19804 at different positions with respect to the drill bit 19800 and its static sheath 19802.

FIGS. 200A and 200B show a front view and side view, respectively, of the drills bit 19800, static sheath 19802, and sliding sheath 19804 shown in FIGS. 198A-199C.

FIGS. 201A-201C illustrate side views of the drill bit 19800 (along with sheath 19802) drilling into material 20100 in accordance with embodiments of the present disclosure. Referring to FIG. 201A, this figure shows the drill bit 19800 at a position where it is close to the material 20100 for drilling, and where the sliding sheath 19804 engages a surface of the material 20100. FIG. 201B shows the drill bit 19800 having drilled into the material 20100, but with the sliding sheath 19804 in the same position (e.g. allowing for translation of the cutting end into the material). FIG. 201C shows the drill bit 19800 at a position having drilled farther than the position shown in FIG. 201B. These figures demonstrate the ability of the static sheath 19802 to translate into the cutting site behind the leading edge of the cutting end while moving relative to the sliding sheath 19804. These figures also demonstrate the ability of the sliding sheath 19804 to "sit" on the surface of the material 20100 (e.g. bone) and set depth and/or cutting parameters such as feed rate.

FIG. 202 illustrates a side view of the drill bit 19800 side cutting into material 20100 in accordance with embodiments of the present disclosure. This figure demonstrates the ability of the sliding sheath mechanism to set the effective depth of the cutting end to allow for a side cutting configuration. The sliding sheath 19804 "sits" on the surface of the material 20100 and slides along the top surface while the end effector cuts from the side. One knowledgeable in the art can envision that the surface of the sliding sheath 19804 contacting the bone can be modified to provide a more stable surface if needed (e.g. adding a larger tab for increased engagement/stability).

FIGS. 203A and 203B illustrate perspective views of a drill bit 20300 assembled with a static sheath 20302 and sliding sheath 20304 in accordance with embodiments of the present disclosure. The drill bit 20300 and its static sheath 20302 can slide along a length of the interior of the sliding sheath 20304. Referring to FIG. 203A, this figure shows the drill bit 20300 and its static sheath 20304 with shield portion 20306 at a position within the sliding sheath 20304. FIG. 203B shows the end of the drill bit 20300 flush with the end of the sliding sheath 20304/shield portion 20306.

With continuing reference to FIGS. 203A and 203B, the sliding sheath 20304 defines a side specific shield portion 20306 at its end. This shield portion 20306 can be used to protect a material (e.g. bone or soft tissue) from being cut by the drill bit 20300 during operation. For example, the shield portion 20306 can protect the drill bit 20300 from cutting material on its side when positioned as shown in FIG. 203B and can be any size/shape to meet the desired cutting needs (e.g. longer shield to protect a larger tissue boundary).

FIGS. 204A and 204B show a front view and a side view, respectively, of the drill bit 20300 assembled with the static sheath 20302 and sliding sheath 20304 in the position shown in FIG. 203A.

FIG. 205 illustrates a side view depicting the drill bit 20300 cutting bone or other material 20500 while the shield portion 20306 is protecting a sensitive soft tissue 20502 on the other side. This half-casing sliding sheath provides a one-sided boundary relative to sensitive soft tissues during cutting.

FIGS. 206A and 206B illustrate perspective views of a drill bit 20600 assembled with a static sheath 20602 and sliding sheath 20604 having a partial end cap 20606 in accordance with embodiments of the present disclosure. The sliding sheath 20604 is similar to the sliding sheath 20304 shown in FIG. 205 except with the inclusion of the end cap 20606. The drill bit 20600 and its static sheath 20602 can slide along a length of the interior of the sliding sheath 20604. Referring to FIG. 206A, this figure shows the drill bit 20600 and its static sheath 20604 at a position within the sliding sheath 20604. FIG. 206B shows the end of the drill bit 20600 at the end of the sliding sheath 20604.

Referring to FIGS. 206A and 206B, the end cap 20606 can provide additional protection for areas near intended areas to be cut and can be any size/shape to meet the desired cutting needs. This is similar to the functionality of the shield portion 20306 except that end cap 20606 can protect additional space.

FIGS. 206C and 206D show a front view and a side view, respectively, of the drill bit 20600 assembled with the static sheath 20602 and sliding sheath 20604 in the position shown in FIG. 206A.

FIGS. 207A-207C illustrate perspective views of drill devices 20701 including different drill bits 20700 assembled with a static sheath 20702 and sliding sheath 20704 having a hook/end cap feature 20706 in accordance with embodiments of the present disclosure. The sliding sheath 20704 is similar to the sliding sheath 20604 shown in FIGS. 206A-206D except that the hook/end cap 20706 is shaped differently for protecting material from cutting at the opposing side of the drills leading edge. It can also provide a means of "pulling" the drill bit by hooking the feature under the opposing side of the desired material. The hook/end cap feature 20706 can be any relevant size/shape to meet the desired cutting needs. The sliding sheath 20704 can move relative to the drill bit 20700 and its static sheath 20702. One knowledgeable in the art can envision the use of a linear mechanism to drive the motion of the sliding sheath 20704 relative to the other components or vice versa (e.g. mechanism can drive either the sliding sheath and/or the combination of the static sheath/drill bit).

FIGS. 208A and 208B illustrate perspective views of the drill bit 20700, static sheath 20702, and sliding sheath 20704 of FIG. 207C. In FIGS. 208A and 208B, the drill bit 20700 is shown at different positions within the sliding sheath 20704. FIGS. 209A and 209B illustrate a front view and a side view, respectively, of the drill bit 20700, static sheath 20702, and sliding sheath 20704 of FIG. 207C.

FIGS. 210A-210C illustrate side views of the drill bit 20700 of FIGS. 208A-209B at different depths of drilling into a material 21000. The hook/end cap 20706 can assist with protecting areas other than portions of the material 21000 that the operator intends to cut. It also provides the added functionality of grabbing the opposing bottom surface of the material to be cut and effectively pull the drill bit 20700 towards the hook/end cap 20706. This functions as a stabilizer feature that prevents breaching through the opposite side of the material into sensitive soft tissues. FIG. 211 illustrates a side view of the drill bit 20700 of FIGS. 208A-209B being moved in the direction of arrow 21100 for side cutting material 21000. This figure demonstrates the ability of the hook/end cap 20706 to stabilize the cutting end to allow for a side cutting configuration. The hook/end cap 20706 "sits" on the bottom surface of the material 21100 and slides along the bottom surface while the end effector cuts from the side.

FIG. 212 illustrates a system for navigation of a drill bit 21200 due to linkage of its static sheath 21202 to a navigation array 21204 in accordance with embodiments of the present disclosure. Referring to FIG. 212, a navigation system 21206 can be operatively connected to the navigation array 21204. The connection of the navigation system 21206 can allow for linking navigation/3D locational data to the tip of the drill bit 21200. Further, rigid attachment directly to the static sheath 21202 (or casing) provides precise location tracking, since static rails are not rapidly rotating like the end effector they provide a stable surface. FIGS. 213A and 213B illustrates a side view and a top view, respectively, of the system shown in FIG. 212. The ability of the tracker array to be rigidly attached/integrated to the drilling system construct allows for more precise and relatively localized data of the drill itself since an array attached to the handpiece at a relatively further location away from the drilling end would increase errors due to any motion between modular junctions.

FIGS. 214A and 214B illustrate perspective views of a drill bit 19800 (along with static sheath/casing 19802) and sliding sheath 19804 in communication with a navigation system 21400 in accordance with embodiments of the present disclosure. Referring to FIGS. 214A and 214B, this configuration allows for linking navigation/3D locational data to inform on the position of the drill bit 19800 using a navigation array 21402 for communication with the linear sliding sheath mechanism 19804. Advantageously, this system provides the ability to set the relationship between the sliding sheath 19804 and drilling edge based on navigational data provided by the system to complete a given cutting task.

FIGS. 215A and 215B illustrate side views of the drill bit 19800 of FIGS. 214A and 214B drilling into the material 21500 in accordance with embodiments of the present disclosure. This depiction demonstrates the relative motion of the sliding sheath 19804 and drill bit 19800 (along with static sheath/casing 19802). Particularly, this is a clinical example of translating into bone set by sliding sheath 19804 and based on navigation data 21400. This navigation data 21400 provides linear sliding sheath 19804 information about its relative position to the material 21500 and sets cutting depth and relevant drilling parameters such as feed rate. Navigation data from the array 21402 and local bone can be used to help set a desired feed-rate to optimize cutting performance by dynamically controlling exposure of the cutting end (e.g. the sliding member 19804 pushes off of the surface of the adjacent bone 21500 at a specified feed rate).

FIG. 216 illustrates a flow diagram for control of a drilling device (whether manual, hand-held robotic, or robotic arm system configuration) having a linear sheath mechanism for a drill similar to those shown in FIGS. 198-215, and communication with sensors/navigation systems (similar to those shown in FIGS. 217-224) in accordance with embodiments of the present disclosure. There are multiple feedback loops that could be implemented including soft tissue safety mechanism, binding/kicking protection, initial bone engagement functionality, dynamic adjustment of drill stiffness during cutting, and real-time feed-rate adjustments. All feedback could be informed by the navigation system and/or sensor data originating from the surface of the static sheath components (e.g. deflection data generated from strain sensors on the rails) and received by the computing device to determine whether various thresholds are met to implement one or more actions (e.g. feed rate adjustments). Also, the computing device can control a user interface to indicate a current step or completion of a step in a procedure based on a given reading (e.g., bone drilling complete). The computing system can also leverage machine learning based on patterns recognized from the data (e.g. pre-operative, intra-operative, post-operative, historical data) to provide more actions based on the real-time data. This user interface could include an AR/VR head set that could allow for directly overlaying the drilling device within the drilling plane during use and/or simulating its geometry for increased visual feedback (e.g. drill is unable to be seen when inside a material and AR could virtually generate a visual of its location in 3D space using the navigation data).

FIG. 217 illustrates a top view of a drill bit 21700 and its static sheath 21702 with strain sensors 21704 attached thereto in accordance with embodiments of the present disclosure. The strain sensors 21704 are attached to the static sheath 21702 and can detect real-time strain data originating from the drilling site (whether its axial and/or side cutting). These strain sensors can be attached using any suitable method (e.g. adhesive, etc.) and on any surface available, and be setup in any configuration needed to detect the desired result (including to measure bending, flexing, torsion, etc. and/or using any set of strain sensor configurations like quarter bridge, half bridge, or full bridge setups). The strain sensors 21704 on the static sheath 21702 provide real-time feedback regarding the motion of the drill bit and/or any other rotational end-effector throughout the cutting operation as indicated by the arrows in FIG. 217. This is due to the fact that the end of the drill bit shaft 21706 is tightly captured by the static sheath 21702 while still allowing the drill bit 21700 to rotate. Therefore, any off-axis loading experienced by the two independent components (e.g. drill bit is rapidly spinning while static sheath remains relatively motionless) causes them to become coupled at the captured end and is detected by the strain sensors. One knowledgeable in the art can envision that there are other viable sensors that could measure strain such as fiber optics that could be used in a similar manner by positioning them along the surfaces of the static sheath 21702. It is important to note, strain sensors can be any relevant size/type (e.g. linear, rosettes, shear, chain, etc.), placed in any relevant configuration on the static components (e.g. quarter bridge, half-bridge, full-bridge, etc.), and leverage any relevant sensing principle (e.g. resistive) to meet the needs of the application/geometric constraints.

FIGS. 218A and 218B illustrate the drill bit 21700 and its static sheath 21702 with strain sensors 21704 shown in FIG. 217 at different positions with off-axis loading being detected in accordance with embodiments of the present disclosure. Particularly, FIG. 218A shows the drill bit 21700 and its static sheath 21702 prior to drilling. FIG. 218B shows the drill bit 21700 and its static sheath 21702 during drilling into material 21800. In FIG. 218B, the drill bit 21700 is off of a desired drilling trajectory. The acquired real-time strain data can be used to detect off-axis drilling and can allow for system adjustments and/or user feedback to ensure precision versus desired trajectory is maintained during drilling. This type of feedback could be integrated into any number of systems including manually held drilling devices, hand-held robotics, and/or robotic arm systems that can all communicate with the data provided at the drilling site.

FIG. 219 illustrates a flow diagram of an example method of sensor feedback for controlling a drilling device in accordance with embodiments of the present disclosure. Referring to FIG. 219, the flow diagram shows a strain feedback loop for a drilling device/robotic drilling platform (e.g. whether hand-held and/or robotic arm). The method includes acquiring strain sensors readings and using the readings to determine whether there is impermissible strain, excess axial strain, excess torsional strain, excess bending strain, excess shear strain, and whether there are permissible levels of strain of any type. The flow diagram shows example actions to implement based on these determinations. The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets, etc.) to provide feedback and output functionality. One knowledgeable in the art could envision the strain sensors working with an AR/VR headset to provide visual surface mapped feedback of real-time skiving relative to the desired trajectory as an overlay on top of the specific anatomic region of interaction/drilling axis.

FIG. 220 illustrates a side view of a drill bit 22000 with its static sheath or casing 22002 and an attached vibration sensor 22004 in accordance with embodiments of the present disclosure. Referring to FIG. 220, this configuration provides the ability to gather real-time vibration data in the drilling site based on the drilling performance of the drill bit 22000. This configuration with one or more vibration sensors can used with any embodiment of the static casings and attached using any suitable method (e.g. adhesive) on any surface available. Vibration sensors on the captured static casing around the drill bit allow for detecting bone type and optimizing drilling parameters throughout the operation. The ability of the static sheath 22002 to precisely capture the end of the drill bit 22000 is what allows for translation of vibrational data back to the sensors. It is important to note that vibration sensors can be any relevant size to meet the needs of the application and leverage any relevant sensing principle (e.g. piezoelectric, capacitive, accelerometer, gyroscope, eddy-current, strain gauge, wired, wireless, etc.).

FIGS. 221A-221C illustrate side views showing the drill bit 22000 of FIG. 220 at different stages for drilling a material 22100 (e.g. bone) having multiple layers of varying densities in accordance with embodiments of the present disclosure. Referring to FIG. 221A, the drill bit 22000 is at a position that detects initial cortical bone engagement as it begins drilling into the material 22100. Referring to FIG. 221B, the drill bit 22000 is detecting engagement with a cancellous layer of bone. Referring to FIG. 221C, the drill bit 22000 is detecting breaching through a layer of cortical bone (e.g. which could be used to stop operation of the device and prevent soft tissue damage). This configuration with the vibration sensor 22004 can be used to gather data on drilling properties and performance. This real-time vibration data can be used to detect bone type, breaching through layers, and provides insight into drilling performance (e.g. drilling feed rate) for system adjustments and/or user feedback.

FIG. 222 illustrates a flow diagram of an example method of vibration sensor feedback loops in accordance with embodiments of the present disclosure. Referring to FIG. 222, the flow diagram shows a vibration feedback loop for a drilling device/robotic drilling platform (e.g. whether hand-held and/or robotic arm). The method includes acquiring vibration sensors readings and using the readings to determine whether there are certain levels of vibration, to analyze vibration profiles during drilling, and characterize the vibration profiles of the material. The vibration sensor data provides a means of introducing safety measures during the procedure (e.g. to prevent hitting critical soft tissues when a cortical breach is detected), to help characterize bone type during drilling, and help optimize drilling performance. The flow diagram shows example actions to implement based on these determinations. The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets, etc.) to provide feedback and output functionality. One knowledgeable in the art could envision the vibration sensors working with an AR/VR headset to provide visual feedback of the desired drilling technique (e.g. adjusting feed rate) overlayed on the specific anatomic region of interest.

FIG. 223 illustrates a side view of a drill bit 22300 with its static sheath or casing 22302 and a temperature sensor 22304 in accordance with embodiments of the present disclosure. This configuration provides the ability to gather real time temperature data in the drilling site based on the drilling performance of the end effector. Further, the temperature sensor 22304 can be added to any embodiment of the static casings/sheaths and attached using any suitable method (e.g. adhesive) on any surface available. One or more temperature sensors can be attached to the captured static casing/sheath around the drill bit to allow for sensing temperature throughout the drilling process. It is important to note that temperature sensors can be of any relevant size and type (e.g. thermocouples, thermistors, resistance temperature detectors, semiconductor based sensors, etc.) to meet the needs of the application/geometric constraints.

FIG. 224 illustrates a flow diagram of an example method of temperature sensor feedback loops in accordance with embodiments of the present disclosure. The flow diagram shows a temperature feedback loop for a drilling device/robotic drilling platform (e.g. whether hand-held and/or robotic arm). Referring to FIG. 224, this figure depicts example steps implemented by a computing device for control based on measurements obtained by one or more temperature sensors, such as those shown in FIG. 223. Temperature measurements can be received by the computing device and used to determine whether threshold levels are met. The computing device can implement one or more actions based on whether threshold levels are met to influence the drilling process. The computing system can also leverage machine learning based on patterns recognized from the data (e.g. pre-operative, intra-operative, post-operative, historical data) to provide more actions based on the real-time sensor data. Data generated by the sensors can be more broadly used to communicate with any type of system (e.g. robotic arms, micro-robotic guides, hand-held robotics, AR/VR headsets, etc.) to provide feedback and output functionality. One knowledgeable in the art could envision the temperature sensors working with an AR/VR headset to overlay real-time drill temperatures onto a simulated static component/drill edge using temperature sensor data, or provides feedback on real-time bone temperatures (e.g. contour plot, heat map, etc.) locked on the specific anatomic region of interaction/cutting plane (e.g. VR/AR visual overlay on top of a proximal tibial drilling that was executed and uses a heat map to visually demonstrate temperature gradients on the patient bone).

The functional units described in this specification have been labeled as computing devices. A computing device may be implemented in programmable hardware devices such as processors, digital signal processors, central processing units, field programmable gate arrays, programmable array logic, programmable logic devices, cloud processing systems, or the like. The computing devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together but may comprise disparate instructions stored in different locations which, when joined logically together, comprise the computing device and achieve the stated purpose of the computing device. In another example, a computing device may be a mobile computing device such as, for example, but not limited to, a smart phone, a cell phone, a pager, a personal digital assistant (PDA), a mobile computer with a smart phone client, or the like. In another example, a cutting device or drill device can include an AR/VR headset for presenting operational and navigation information as described herein. In another example, a cutting device or drilling device can include a navigation tower. In another example, a computing device may be any type of wearable computer, such as a computer with a head-mounted display (IMD), or a smart watch or some other wearable smart device. Some of the computer sensing may be part of the fabric of the clothes the user is wearing. A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, smart watch, or the like) that is capable of sending and receiving data in a wireless manner using protocols like the Internet Protocol, or IP, and the wireless application protocol, or WAP. This allows users to access information via wireless devices, such as smart watches, smart phones, mobile phones, pagers, two-way radios, communicators, and the like. Wireless data access is supported by many wireless networks, including, but not limited to, Bluetooth, Near Field Communication, CDPD, CDMA, GSM, PDC, PHS, TDMA, FLEX, ReFLEX, iDEN, TETRA, DECT, DataTAC, Mobitex, EDGE and other 2G, 3G, 4G, 5G, and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone or smart watch that operates over GPRS (General Packet Radio Services), which is a data technology for GSM networks or operates over Near Field Communication e.g. Bluetooth. In addition to a conventional voice communication, a given mobile device can communicate with another such device via many different types of message transfer techniques, including Bluetooth, Near Field Communication, SMS (short message service), enhanced SMS (EMS), multi-media message (MMS), email WAP, paging, or other known or later-developed wireless data formats. Although many of the examples provided herein are implemented on smart phones, the examples may similarly be implemented on any suitable computing device, such as a computer.

An executable code of a computing device may be a single instruction, or many instructions, and may even be distributed over several different code segments, among different applications, and across several memory devices. Similarly, operational data may be identified and illustrated herein within the computing device, and may be embodied in any suitable form and organized within any suitable type of data structure. The operational data may be collected as a single data set, or may be distributed over different locations including over different storage devices, and may exist, at least partially, as electronic signals on a system or network.

In embodiments, systems described herein can use generative artificial intelligence (AI) for analysis of data described herein. Example data includes data acquired by sensors attached to a cutting device or drill device as described herein. The resulting AI analysis data can be subsequently used for controlling a device or providing feedback information as described herein.

The described features, structures, or characteristics may be combined in any suitable manner in one or more embodiments. In the following description, numerous specific details are provided, to provide a thorough understanding of embodiments of the disclosed subject matter. One knowledgeable in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

As used herein, the term “memory” is generally a storage device of a computing device. Examples include, but are not limited to, read-only memory (ROM) and random access memory (RAM).

The device or system for performing one or more operations on a memory of a computing device may be a software, hardware, firmware, or combination of these. The device or the system is further intended to include or otherwise cover all software or computer programs capable of performing the various heretofore-disclosed determinations, calculations, or the like for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PUP, Perl, or other suitable programming languages.

As referred to herein, the terms “computing device” and “entities” should be broadly construed and should be understood to be interchangeable. They may include any type of computing device, for example, a server, a desktop computer, a laptop computer, a smart phone, a cell phone, a pager, a personal digital assistant (PDA, e.g., with GPRS NIC), a mobile computer with a smartphone client, or the like.

As referred to herein, a user interface is generally a system by which users interact with a computing device. A user interface can include an input for allowing users to manipulate a computing device, and can include an output for allowing the system to present information and/or data, indicate the effects of the user’s manipulation, etc. An example of a user interface on a computing device (e.g. a mobile device) includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. A user interface can include an input for allowing users to manipulate a computing device, and can include an output for allowing the computing device to present information and/or data, indicate the effects of the user’s manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

The display object can be displayed on a display screen of a mobile device and can be selected by and interacted with by a user using the interface. In an example, the display of the mobile device can be a touch screen, which can display the display icon. The user can depress the area of the display screen at which the display icon is displayed for selecting the display icon. In another example, the user can use any other suitable interface of a mobile device, such as a keypad, to select the display icon or display object. For example, the user can use a track ball or times program instructions thereon for causing a processor to carry out aspects of the present disclosure.

As referred to herein, a computer network may be any group of computing systems, devices, or equipment that are linked together. Examples include, but are not limited to, local area networks (LANs) and wide area networks (WANs). A network may be categorized based on its design model, topology, or architecture. In an example, a network may be characterized as having a hierarchical internetworking model, which divides the network into three layers: access layer, distribution layer, and core layer. The access layer focuses on connecting client nodes, such as workstations to the network. The distribution layer manages routing, filtering, and quality-of-server (QoS) policies. The core layer can provide high-speed, highly-redundant forwarding services to move packets between distribution layer devices in different regions of the network. The core layer typically includes multiple routers and switches.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g. light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. A cutting device comprising:

a working blade body being configured for operable connection to a source of movement;

a static component being configured for operable connection to the source of movement, wherein the static component comprises at least one rail, wherein the at least one rail extends substantially a same length as the working blade body; and struts attached to the static component, wherein the struts and static component define an opening that holds a neck portion of the working blade body, and wherein the neck portion substantially fills the opening.

2. The cutting device of claim 1, wherein the static component supports the working blade body during loading.

3. The cutting device of claim 1, wherein the at least one rail comprises a first rail and a second rail that each define a distal end, and wherein the static component comprises a first strut and a second strut that are attached to the distal end of the first rail and the distal end of the second rail.

4. The cutting device of claim 1, wherein the at least one rail comprises a first rail and a second rail positioned on opposing sides of the working blade body.

5. The cutting device of claim 1, wherein the at least one rail comprises a first rail and a second rail that each define a distal end, and wherein the static component comprises a first strut and a second strut attached to the first rail and the second rail, wherein the first strut is positioned distal from the source of movement when the source of movement is operably connected, and wherein the second strut is positioned proximal to the source of movement when the source of movement is operably connected.

6. The cutting device of claim 1, wherein the working blade body comprises a blade edge.

7. The cutting device of claim 1, wherein the working blade body includes a cutting edge having a thickness equal to or greater than a thickness of the static component and a thickness of the working blade body.

8. The cutting device of claim 1, wherein the working blade body includes a first end and a second end, wherein the first end of the working blade body is operatively connected to the source of movement, and the second end of the working blade body is attached to a blade edge and extends beyond the static casing.

9. The cutting device of claim 1, wherein the working blade body and the static component define flat surfaces.

10. The cutting device of claim 1, wherein the working blade body is thinner or thicker than the static component.

11. The cutting device of claim 1, wherein the working blade body and the static component are substantially within a same plane.

12. The cutting device of claim 1, wherein the struts comprise a first strut and a second strut being attached to the at least one rail, and wherein the first strut and the second strut define an opening within which the working blade body is positioned.

13. The cutting device of claim 1, wherein the static component comprises a first rail and a second rail positioned on opposing sides of the working blade body, and wherein the struts, the first rail, and the second rail define an opening for the working blade body.

14. The cutting device of claim 1, wherein the static component defines a tapered tip that is sub-flush to a cutting edge of the working blade body.

15. The cutting device of claim 1, further comprising one or more tapered struts attached to the static component.

16. The cutting device of claim 1, wherein the struts and static component define an opening that holds a cutting blade of the working blade body, and wherein the cutting blade substantially fills the opening.

17. The cutting device of claim 1, wherein an end of the working blade body extends beyond the struts.

18. The cutting device of claim 1, wherein the static component comprises struts that have a width within a plane, wherein the working blade body is movable by the source of movement within the plane, and wherein a cutting blade edge of the working blade body is moveable along a pathway wider than the width of the struts.

19. The cutting device of claim 1, wherein the static component comprises rails that have a width within a plane, wherein the working blade body is movable by the source of movement within the plane, and wherein a cutting blade edge of the working blade body is moveable along a pathway wider than the width of the static components/rails.

20. The cutting device of claim 1, wherein the static component comprises rails that have a width within a plane, wherein the working blade body is movable by the source of movement within the plane, and wherein the working blade body is moveable along a pathway narrower than inner surfaces/width of the rails.

21. The cutting device of claim 1, wherein the working blade body defines at least one channel defined in the working blade body as a debris relief.

22. The cutting device of claim 21, wherein the at least one channel comprises a plurality of channels.

23. The cutting device of claim 1, wherein the struts comprise a first strut and a second strut, and wherein at least one channel extends from a side distal from the first and second strut to a side proximal the first and second strut.

24. The cutting device of claim 1, wherein the static component includes a first rail and a second rail that each have a distal end, and wherein the distal ends face each other and define a space therebetween.

25. The cutting device of claim 1, wherein the static component includes a first rail and a second rail, and wherein a distal end of the working blade body extends beyond the first rail and the second rail.

26. The cutting device of claim 1, wherein the static component includes a proximal strut that is adjacent to a proximal portion of the working blade body, wherein the proximal strut is thicker than the static component or a blade edge.

27. The cutting device of claim 1, wherein the static component includes a distal strut that is adjacent to a distal portion of the working blade body, wherein the distal strut is flush/thicker than the static component and flush/sub-flush to a blade edge.

28. The cutting device of claim 1, wherein the static component includes proximal struts that enclose a proximal portion of the working blade body, and wherein the proximal struts are thicker than the static component or a blade edge.

29. The cutting device of claim 1, wherein the static component includes distal struts that enclose a distal portion of the working blade body, and wherein the distal struts are flush/thicker than the static component and flush/sub-flush to a blade edge.

30. The cutting device of claim 1, wherein the static component includes a proximal strut that is adjacent to a proximal portion of the working blade body, wherein the proximal strut is flush/thicker than the static component and flush/subflush to a blade edge.

31. The cutting device of claim 1, wherein the static component includes proximal struts that enclose a proximal portion of the working blade body, and wherein the proximal struts are flush/thicker than the static component and flush/subflush to a blade edge.

32. The cutting device of claim 1, wherein the struts are attached to the at least one rail anywhere along a length of the at least one rail.

33. The cutting device of claim 1, wherein the struts attached to the at least one rail anywhere along a length of the at least one rail, and wherein the one or more struts are attached offset or aligned on the at least one rail.

34. The cutting device of claim 1, wherein the struts that have any thickness and proximal or distal on the static component.

35. The cutting device of claim 1, wherein the struts are positioned adjacent to a portion of the working blade body whether on the upper and/or lower surface and proximal or distal on the static component.

36. The cutting device of claim 1, wherein the struts are flush with the at least one rail.

37. The cutting device of claim 1, wherein the struts have a greater height than the static component and lower in height than a blade edge.

38. The cutting device of claim 1, wherein the struts have a greater height than the static component and a blade edge.

39. The cutting device of claim 1, wherein the working blade body defines a plurality of cutouts for providing clearance with one or more struts.

40. The cutting device of claim 1, wherein one or more struts span a working length in a substantially proximal-distal direction.

41. The cutting device of claim 1, further being configured for attachment to a handpiece.

42. The cutting device of claim 1, further being configured for attachment to a robotic handheld.

43. The cutting device of claim 1, further being configured for attachment to a robot arm.

44. The cutting device of claim 1, further being configured for attachment to a passive positioning arm.

45. A cutting device comprising:

a working blade body being configured for operable connection to a source of movement; and a static component being configured for operable connection to the source of movement, wherein the static component comprises at least one rail, wherein the at least one rail extends substantially a same length as the working blade body, wherein the static component comprises struts that have a width within a plane, wherein the working blade body is movable by the source of movement within the plane, and wherein the working blade body is moveable along a pathway narrower than the width of the struts.

* * * * *